US012457898B2

(12) United States Patent
Kim et al.

(10) Patent No.: US 12,457,898 B2
(45) Date of Patent: Oct. 28, 2025

(54) ORGANIC COMPOUND, COMPOSITION, ORGANIC OPTOELECTRONIC DEVICE, AND DISPLAY DEVICE

(71) Applicants: SAMSUNG SDI CO., LTD., Yongin-si (KR); SAMSUNG ELECTRONICS CO., LTD., Suwon-si (KR)

(72) Inventors: Byungku Kim, Suwon-si (KR); Giwook Kang, Suwon-si (KR); Hanill Lee, Suwon-si (KR); Kipo Jang, Suwon-si (KR); Sung-Hyun Jung, Suwon-si (KR); Min Seok Seo, Suwon-si (KR); Ji Hun Shin, Suwon-si (KR); Hyungyu Lee, Suwon-si (KR); Jinseok Jang, Suwon-si (KR); Ho Kuk Jung, Suwon-si (KR); Dalho Huh, Suwon-si (KR)

(73) Assignees: SAMSUNG SDI CO., LTD., Yongin-si (KR); SAMSUNG ELECTRONICS CO., LTD., Suwon-si (KR)

( * ) Notice: Subject to any disclaimer, the term of this patent is extended or adjusted under 35 U.S.C. 154(b) by 1107 days.

(21) Appl. No.: 16/630,893

(22) PCT Filed: Sep. 4, 2018

(86) PCT No.: PCT/KR2018/010304
§ 371 (c)(1),
(2) Date: Jan. 14, 2020

(87) PCT Pub. No.: WO2019/066282
PCT Pub. Date: Apr. 4, 2019

(65) Prior Publication Data

US 2020/0161564 A1 May 21, 2020

(30) Foreign Application Priority Data

Sep. 26, 2017 (KR) ........................ 10-2017-0124370

(51) Int. Cl.

| | |
|---|---|
| ***H01L 51/00*** | (2006.01) |
| ***C07D 491/048*** | (2006.01) |
| ***C07D 495/04*** | (2006.01) |
| ***H10K 85/60*** | (2023.01) |
| *H10K 50/11* | (2023.01) |
| *H10K 101/10* | (2023.01) |

(52) U.S. Cl.
CPC ..... *H10K 85/6572* (2023.02); *C07D 491/048* (2013.01); *C07D 495/04* (2013.01); *H10K 85/657* (2023.02); *H10K 50/11* (2023.02); *H10K 2101/10* (2023.02)

(58) Field of Classification Search
None
See application file for complete search history.

(56) References Cited

U.S. PATENT DOCUMENTS

| | | | |
|---|---|---|---|
| 9,502,656 B2 | 11/2016 | Joseph et al. | |
| 2015/0207082 A1 | 7/2015 | Dyatkin et al. | |
| 2016/0293853 A1 | 10/2016 | Zeng et al. | |
| 2017/0271610 A1 | 9/2017 | Takahashi | |
| 2020/0024282 A1 * | 1/2020 | Parham .............. | H10K 85/6576 |
| 2020/0028091 A1 * | 1/2020 | Parham .............. | H10K 85/6574 |

FOREIGN PATENT DOCUMENTS

| | | |
|---|---|---|
| CN | 106565433 A | 4/2017 |
| JP | 5589251 B2 | 8/2014 |
| JP | 5604848 B2 | 9/2014 |
| JP | 2015-134745 A | 7/2015 |
| KR | 10-2015-0083787 A | 7/2015 |
| KR | 10-2015-0084657 A | 7/2015 |
| KR | 10-2015-0100555 A | 9/2015 |
| KR | 10-2015-0133998 A | 12/2015 |
| KR | 10-2015-0134248 A | 12/2015 |
| KR | 10-2015-0136942 A | 12/2015 |
| KR | 10-2016-0017530 A | 2/2016 |
| KR | 10-2016-0026661 A | 3/2016 |
| KR | 10-2016-0046078 A | 4/2016 |
| KR | 10-2017-0103105 A | 9/2017 |
| TW | 201716382 A | 5/2017 |
| TW | 201735392 A | 10/2017 |
| TW | 201827438 A | 8/2018 |
| TW | 201829414 A | 8/2018 |
| WO | WO 2010/083359 A2 | 7/2010 |
| WO | WO 2013/077352 A1 | 5/2013 |
| WO | WO 2014/199637 A1 | 12/2014 |
| WO | WO 2015-037675 A1 | 3/2015 |

(Continued)

OTHER PUBLICATIONS

International Search Report dated Dec. 14, 2018 for PCT/KR2018/010304.

*Primary Examiner* — Po-Chih Chen
(74) *Attorney, Agent, or Firm* — Lee IP Law, P.C.

(57) ABSTRACT

Disclosed are an organic compound represented by Chemical Formula 1, a composition including the same, an organic optoelectronic device, and a display device.

[Chemical Formula 1]

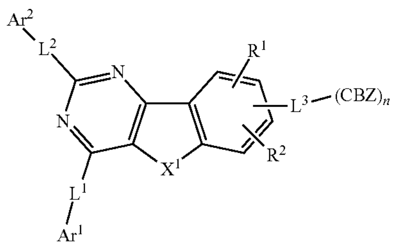

In Chemical Formula 1, $X^1$, $Ar^1$, $Ar^2$, $L^1$ to $L^3$, $R^1$, $R^2$, CBZ, and n are the same as described in the specification.

13 Claims, 1 Drawing Sheet

(56) References Cited

FOREIGN PATENT DOCUMENTS

| | | | | |
|---|---|---|---|---|
| WO | WO 2016-140497 | A2 | | 9/2016 |
| WO | WO 2016-153283 | A1 | | 9/2016 |
| WO | WO 2017-095054 | A1 | | 6/2017 |
| WO | WO 2017-109637 | A1 | | 6/2017 |
| WO | WO 2017/119654 | A1 | | 7/2017 |
| WO | WO2018060218 | | * | 4/2018 |
| WO | WO2018060307 | | * | 4/2018 |
| WO | WO 2018/060307 | A1 | | 5/2018 |

* cited by examiner

【FIG. 1】
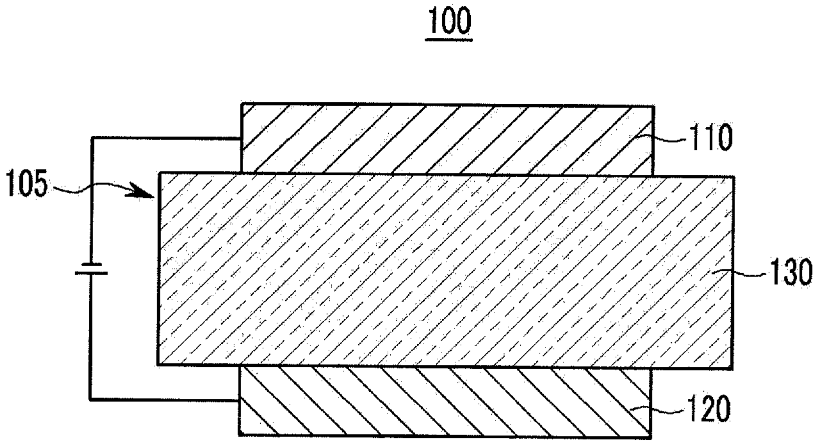
【FIG. 2】
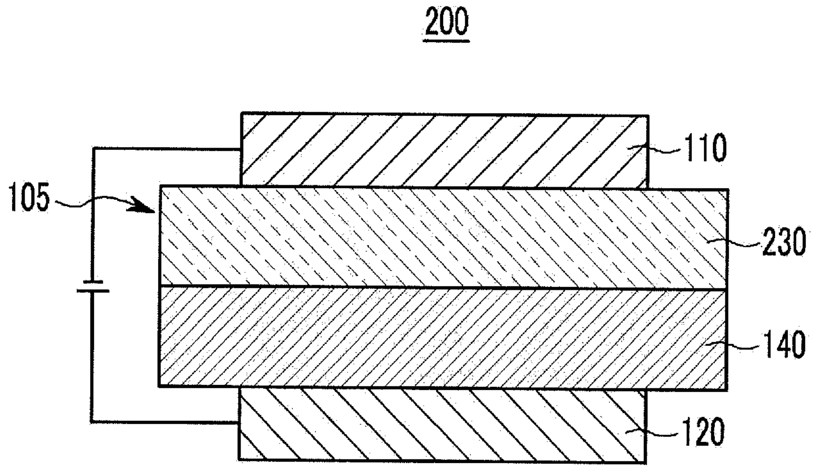

ORGANIC COMPOUND, COMPOSITION, ORGANIC OPTOELECTRONIC DEVICE, AND DISPLAY DEVICE

This is the U.S. national phase application based on PCT Application No. PCT/KR2018/010304, filed Sep. 4, 2018, which is based on Korean Patent Application No. 10-2017-0124370, filed Sep. 26, 2017.

BACKGROUND OF THE INVENTION

(a) Field of the Invention

An organic compound, a composition, an organic optoelectronic device, and a display device are disclosed.

(b) Description of the Related Art

An organic optoelectronic device (organic optoelectronic diode) is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and Performance of an organic light emitting diode may be affected by organic materials disposed between electrodes.

SUMMARY OF THE INVENTION

An embodiment provides an organic compound capable of realizing an organic optoelectronic device having high efficiency and a long life-span.

Another embodiment provides a composition capable of realizing an organic optoelectronic device having high efficiency and a long life-span.

Yet another embodiment provides an organic optoelectronic device including the organic compound or the composition.

Still another embodiment provides a display device including the organic optoelectronic device.

According to one embodiment, an organic compound represented by Chemical Formula 1 is provided.

[Chemical Formula 1]

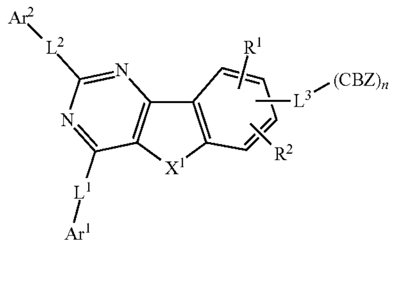

In Chemical Formula 1, $X^1$ is O or S, $Ar^1$ and $Ar^2$ are independently a substituted or unsubstituted C1 to C20 alkyl group, a substituted or unsubstituted C6 to C30 aryl group, a substituted or unsubstituted carbazolyl group, or a combination thereof, $L^1$ and $L^2$ are independently a single bond, a substituted or unsubstituted C1 to C20 alkylene group, a substituted or unsubstituted C6 to C30 arylene group, or a combination thereof, $L^3$ is a substituted or unsubstituted C1 to C20 alkylene group, a substituted or unsubstituted C6 to C30 arylene group, or a combination thereof, $R^1$ and $R^2$ are independently hydrogen, deuterium, a substituted or unsubstituted C1 to C20 alkyl group, a substituted or unsubstituted C6 to C30 aryl group, a substituted or unsubstituted C3 to C30 heterocyclic group, a cyano group, or a combination thereof, CBZ is a substituted or unsubstituted carbazolyl group (except a carbazolyl group substituted with a carbazolyl group), and n is an integer of 0 to 3, provided that when n is 0, at least one of $Ar^1$ and $Ar^2$ is a substituted or unsubstituted carbazolyl group.

According to another embodiment, a composition includes the first organic compound and a second organic compound including a carbazole moiety represented by Chemical Formula 4.

[Chemical Formula 4]

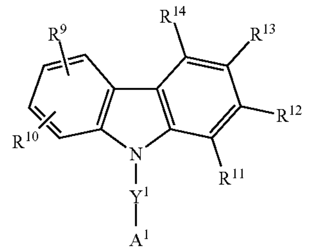

In Chemical Formula 4, $Y^1$ is a single bond, a substituted or unsubstituted C6 to C30 arylene group or divalent substituted or unsubstituted C2 to C30 heterocyclic group, $A^1$ is a substituted or unsubstituted C6 to C30 aryl group, or a substituted or unsubstituted C2 to C30 heterocyclic group, $R^9$ to $R^{14}$ are independently hydrogen, deuterium, a substituted or unsubstituted C1 to C20 alkyl group, a substituted or unsubstituted C6 to C30 aryl group, or a substituted or unsubstituted C2 to C30 heterocyclic group, $R^9$ and $R^{10}$ are independently present or fused to each other to form a ring, and $R^{11}$ to $R^{14}$ are independently present or adjacent groups of $R^{11}$ to $R^{14}$ are linked with each other to form a ring.

According to another embodiment, an organic optoelectronic device includes an anode and a cathode facing each other, and at least one organic layer disposed between the anode and the cathode, wherein the organic layer includes the organic compound or the composition.

According to yet another embodiment, a display device includes the organic optoelectronic device.

An organic optoelectronic device having a low driving voltage, high efficiency, and long life-span may be realized.

BRIEF DESCRIPTION OF THE DRAWINGS

FIGS. 1 and 2 are cross-sectional views showing organic light emitting diodes according to embodiments.

DETAILED DESCRIPTION OF THE EMBODIMENTS

Hereinafter, embodiments of the present invention are described in detail. However, these embodiments are exemplary, the present invention is not limited thereto and the present invention is defined by the scope of claims.

In the present specification, when a definition is not otherwise provided, the "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples of the present invention, the "substituted" refers to replacement of at least one hydrogen of a substituent or a compound by deuterium, a C1 to C20 alkyl group, a C6 to C30 aryl group, or a C2 to C30 heteroaryl group. In addition, in specific examples of the present invention, the "substituted" refers to replacement of at least one hydrogen of a substituent or a compound by deuterium, a C1 to C5 alkyl group, a C6 to C18 aryl group, a pyridinyl group, a quinolinyl group, an isoquinolinyl group, a dibenzofuranyl group, a dibenzothiophenyl group, or a carbazolyl group. In addition, in specific examples of the present invention, the "substituted" refers to replacement of at least one hydrogen of a substituent or a compound by deuterium, a C1 to C5 alkyl group, a C6 to C18 aryl group, a dibenzofuranyl group, or a dibenzothiophenyl group. In addition, in specific examples of the present invention, the "substituted" refers to replacement of at least one hydrogen of a substituent or a compound by deuterium, a methyl group, an ethyl group, a propanyl group, a butyl group, a phenyl group, a biphenyl group, a terphenyl group, a naphthyl group, a triphenyl group, a dibenzofuranyl group, or a dibenzothiophenyl group.

In the present specification, when a definition is not otherwise provided, "hetero" refers to one including one to three heteroatoms selected from N, O, S, P, and Si, and remaining carbons in one functional group.

In the present specification, the "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic or fused ring polycyclic (i.e., rings sharing adjacent pairs of carbon atoms) functional group.

In the present specification, the "heterocyclic group" is a generic concept of a heteroaryl group, and may include at least one hetero atom selected from N, O, S, P, and Si instead of carbon (C) in a cyclic compound such as aryl group, a cycloalkyl group, a fused ring thereof, or a combination thereof. When the heterocyclic group is a fused ring, the entire ring or each ring of the heterocyclic group may include one or more heteroatoms.

For example, a "heteroaryl group" may refer to an aryl group including at least one hetero atom selected from N, O, S, P, and Si instead of carbon (C). Two or more heteroaryl groups are linked by a sigma bond directly, or when the C2 to C60 heteroaryl group includes two or more rings, the two or more rings may be fused. When the heteroaryl group is a fused ring, each ring may include 1 to 3 hetero atoms.

Specific examples of the heterocyclic group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied, and that a hole formed in the anode may be easily injected into a light emitting layer, and a hole formed in a light emitting layer may be easily transported into an anode and transported in the light emitting layer due to conductive characteristics according to a highest occupied molecular orbital (HOMO) level.

In addition, electron characteristics refer to an ability to accept an electron when an electric field is applied, and that an electron formed in a cathode may be easily injected into a light emitting layer, and an electron formed in a light emitting layer may be easily transported into a cathode and transported in the light emitting layer due to conductive characteristics according to a lowest unoccupied molecular orbital (LUMO) level.

Hereinafter, an organic compound according to an embodiment is described.

An organic compound according to an embodiment is represented by Chemical Formula 1.

[Chemical Formula 1]

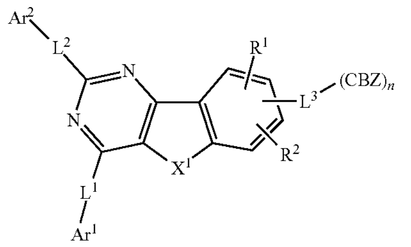

In Chemical Formula 1, $X^1$ is O or S, $Ar^1$ and $Ar^2$ are independently a substituted or unsubstituted C1 to C20 alkyl group, a substituted or unsubstituted C6 to C30 aryl group, a substituted or unsubstituted carbazolyl group, or a combination thereof, $L^1$ and $L^2$ are independently a single bond, a substituted or unsubstituted C1 to C20 alkylene group, a substituted or unsubstituted C6 to C30 arylene group, or a combination thereof, $L^3$ is a substituted or unsubstituted C1 to C20 alkylene group, a substituted or unsubstituted C6 to C30 arylene group, or a combination thereof, $R^1$ and $R^2$ are independently hydrogen, deuterium, a substituted or unsubstituted C1 to C20 alkyl group, a substituted or unsubstituted C6 to C30 aryl group, a substituted or unsubstituted C3 to C30 heterocyclic group, a cyano group, or a combination thereof, CBZ is a substituted or unsubstituted carbazolyl group (except a carbazolyl group substituted with a carbazolyl group), and n is an integer of 0 to 3, provided that when n is 0, at least one of $Ar^1$ and $Ar^2$ is a substituted or unsubstituted carbazolyl group.

In one example of the present invention, the "substituted" may refer to replacement of at least one hydrogen by a C1 to C5 alkyl group, a C6 to C18 aryl group, or a cyano group.

The organic compound represented by Chemical Formula 1 includes a fused ring in which a substituted pyrimidine ring is combined with benzofuran or benzothiophene and thus exhibits fast electron transport characteristics, and in addition, the electron transport characteristics become much faster, since a substituted or unsubstituted carbazolyl group is bonded with the benzofuran or benzothiophene of the fused ring. Accordingly, when the organic compound is applied to a device, the device may have a low driving voltage and high efficiency.

In addition, when the organic compound represented by Chemical Formula 1 has a relatively high glass transition temperature and thus is applied to a device, thermal stability of the device may be increased, and a life-span of the device may be improved by reducing or preventing degradation of the organic compound during the process or the operation. For example, the organic compound may have a glass transition temperature of about 50 to 300° C.

For example, $Ar^1$ and $Ar^2$ of Chemical Formula 1 may independently be a substituted or unsubstituted C6 to C30 aryl group, for example a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, a substituted or unsubstituted anthracenyl group, or a substituted or unsubstituted triphenylenyl group. Herein the "substituted" may refer to replacement of at least one hydrogen by deuterium, a C1 to C20 alkyl group, a C6 to C12 aryl group, or a cyano group.

For example, $L^1$ and $L^2$ of Chemical Formula 1 may independently be a single bond or a substituted or unsubstituted C6 to C30 arylene group. For example $L^1$ and $L^2$ are independently a single bond, a substituted or unsubstituted phenylene group, a substituted or unsubstituted biphenylene group, a substituted or unsubstituted terphenylene group, a substituted or unsubstituted naphthylene group, a substituted or unsubstituted phenanthrenylene group, or a substituted or unsubstituted anthracenylene group. For example, $L^1$ and $L^2$ may independently be a single bond, a substituted or unsubstituted m-phenylene group, a substituted or unsubstituted p-phenylene group, a substituted or unsubstituted m-biphenylene group, a substituted or unsubstituted p-biphenylene group, or a substituted or unsubstituted naphthylene group. Herein the "substituted" may refer to replacement of at least one hydrogen by deuterium, a C1 to C20 alkyl group, a C6 to C12 aryl group, or a cyano group.

For example, $L^3$ of Chemical Formula 1 may be a substituted or unsubstituted C6 to C30 arylene group. For example, $L^1$ may be a substituted or unsubstituted phenylene group, a substituted or unsubstituted biphenylene group, a substituted or unsubstituted terphenylene group, a substituted or unsubstituted naphthylene group, a substituted or unsubstituted phenanthrenylene group, or a substituted or unsubstituted anthracenylene group. For example, $L^3$ may be a substituted or unsubstituted m-phenylene group, a substituted or unsubstituted p-phenylene group, a substituted or unsubstituted m-biphenylene group, a substituted or unsubstituted p-biphenylene group, or a substituted or unsubstituted naphthylene group. Herein the "substituted" may refer to replacement of at least one hydrogen by deuterium, a C1 to C20 alkyl group, a C6 to C12 aryl group, or a cyano group.

For example, $R^1$ and $R^2$ of Chemical Formula 1 may independently be hydrogen, deuterium, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted fluorenyl group, a substituted or unsubstituted triphenylene group, a substituted or unsubstituted dibenzothiophenyl group, a substituted or unsubstituted dibenzofuranyl group, a cyano group, or a combination thereof.

For example, CBZ of Chemical Formula 1 may be a carbazolyl group or a carbazolyl group substituted with an aryl group, for example a carbazolyl group or a phenyl-substituted carbazolyl group.

For example, n of Chemical Formula 1 may be 1, 2, or 3.

For example, n of Chemical Formula 1 may be 1 or 2.

For example, n of Chemical Formula 1 may be 0 and one of $Ar^1$ and $Ar^2$ may be a substituted or unsubstituted carbazolyl group.

For example, n of Chemical Formula 1 may be 1 or 2 and $Ar^1$ and $Ar^2$ may independently be a C6 to C30 aryl group.

The organic compound may be for example represented by Chemical Formula 2 or 3.

[Chemical Formula 2]

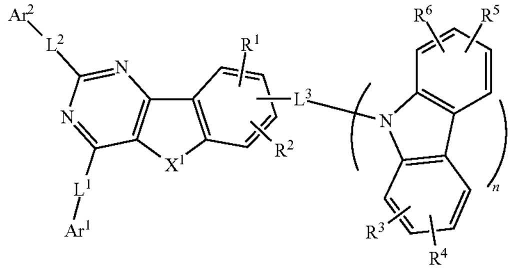

[Chemical Formula 3]

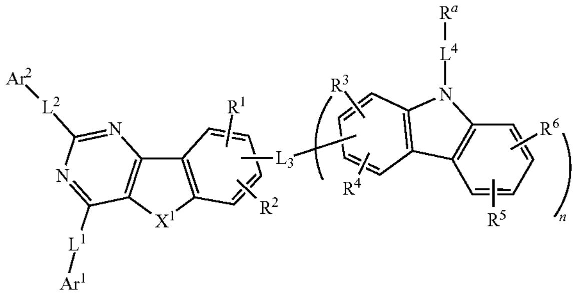

In Chemical Formula 2 or 3, $X^1$ is O or S, $Ar^1$ and $Ar^2$ are independently a substituted or unsubstituted C1 to C20 alkyl group, a substituted or unsubstituted C6 to C30 aryl group, a substituted or unsubstituted carbazolyl group, or a combination thereof, $L^1$ and $L^2$ are independently a single bond, a substituted or unsubstituted C1 to C20 alkylene group, a substituted or unsubstituted C6 to C30 arylene group, or a combination thereof, $L^3$ is a substituted or unsubstituted C1 to C20 alkylene group, a substituted or unsubstituted C6 to C30 arylene group, or a combination thereof, $L^4$ is a single bond, a substituted or unsubstituted C1 to C20 alkylene group, a substituted or unsubstituted C6 to C30 arylene group, a divalent substituted or unsubstituted C2 to C30 heterocyclic group (except a carbazolylene group), or a combination thereof, $R^1$ to $R^6$ and $R^a$ are independently hydrogen, deuterium, a substituted or unsubstituted C1 to C20 alkyl group, a substituted or unsubstituted C6 to C30 aryl group, a substituted or unsubstituted C3 to C30 heterocyclic group (except a carbazolyl group), a cyano group, or a combination thereof, and n is an integer of 0 to 3, provided that when n is 0, at least one of $Ar^1$ and $Ar^2$ is a substituted or unsubstituted carbazolyl group.

For example, $Ar^1$ and $Ar^2$ of Chemical Formula 2 or 3 may independently be a substituted or unsubstituted C6 to C30 aryl group, for example a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, a substituted or unsubstituted anthracenyl group, or a substituted or unsubstituted triphenylenyl group. Herein, the "substituted" may refer to replacement of at least one hydrogen by deuterium, a C1 to C20 alkyl group, a C6 to C12 aryl group, or a cyano group.

For example, $L^1$, $L^2$, and $L^4$ of Chemical Formula 2 or 3 may independently be a single bond or a substituted or unsubstituted C6 to C30 arylene group. For example, $L^1$, $L^2$, and $L^4$ may independently be a single bond, a substituted or unsubstituted phenylene group, a substituted or unsubstituted biphenylene group, a substituted or unsubstituted terphenylene group, a substituted or unsubstituted naphthylene group, a substituted or unsubstituted phenanthrenylene group, or a substituted or unsubstituted anthracenylene group. For example $L^1$, $L^2$, and $L^4$ may independently be a single bond, a substituted or unsubstituted m-phenylene group, a substituted or unsubstituted p-phenylene group, a substituted or unsubstituted m-biphenylene group, a substituted or unsubstituted p-biphenylene group, or a substituted or unsubstituted naphthylene group. Herein the "substituted" may refer to replacement of at least one hydrogen by deuterium, a C1 to C20 alkyl group, a C6 to C12 aryl group, or a cyano group.

For example, $L^3$ of Chemical Formula 2 or 3 may be a substituted or unsubstituted C6 to C30 arylene group. For example, $L^3$ of Chemical Formula 2 or 3 may be a substituted or unsubstituted phenylene group, a substituted or unsubstituted biphenylene group, a substituted or unsubstituted terphenylene group, a substituted or unsubstituted naphthylene group, or a substituted or unsubstituted anthracenylene group. For example, $L^3$ of Chemical Formula 2 or 3 may be a substituted or unsubstituted m-phenylene group, a substituted or unsubstituted p-phenylene group, a substituted or unsubstituted m-biphenylene group, a substituted or unsubstituted p-biphenylene group, or a substituted or unsubstituted naphthylene group. Herein, the "substituted" may refer to replacement of at least one hydrogen by deuterium, a C1 to C20 alkyl group, a C6 to C12 aryl group, or a cyano group.

For example, $R^1$ to $R^6$ of Chemical Formula 2 or 3 may independently be hydrogen, deuterium, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenylene group, a substituted or unsubstituted fluorenyl group, a substituted or unsubstituted triphenylene group, a substituted or unsubstituted dibenzothiophenyl group, a substituted or unsubstituted dibenzofuranyl group, a cyano group, or a combination thereof.

For example, $R^a$ of Chemical Formula 3 may be hydrogen, deuterium, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenylene group, a substituted or unsubstituted fluorenyl group, a substituted or unsubstituted triphenylene group, a substituted or unsubstituted dibenzothiophenyl group, a substituted or unsubstituted dibenzofuranyl group, a cyano group, or a combination thereof. For example, $R^a$ may be hydrogen or a substituted or unsubstituted phenyl group.

For example, the organic compound represented by Chemical Formula 2 may be for example represented by Chemical Formulae 2a to 2d depending on bonding positions.

[Chemical Formula 2a]

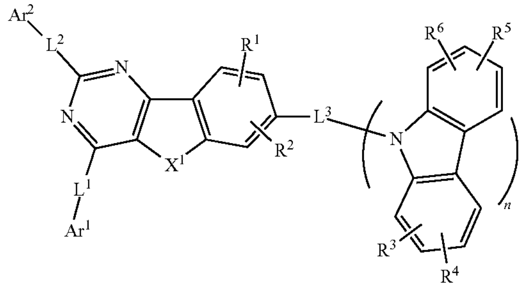

[Chemical Formula 2b]

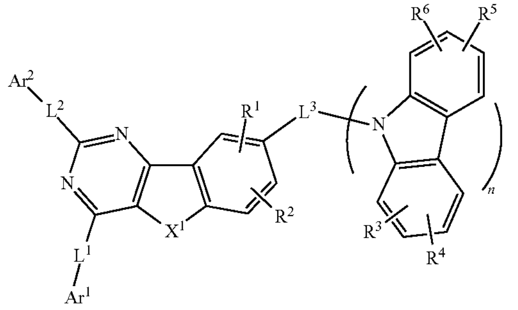

[Chemical Formula 2c]

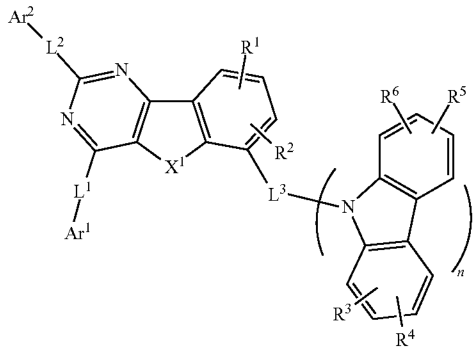

-continued

[Chemical Formula 2d]

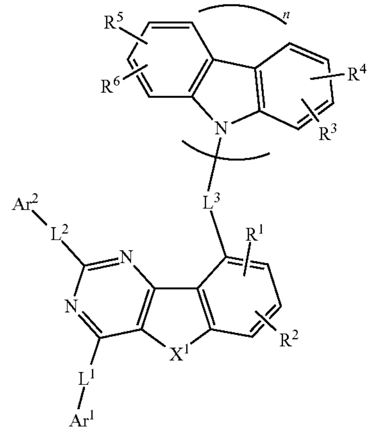

In Chemical Formulae 2a to 2d, $X^1$, $Ar^1$, $Ar^2$, $L^1$ to $L^3$, $R^1$ to $R^6$, and n are the same as described above.

For example, the organic compound represented by Chemical Formula 3 may be for example represented by Chemical Formulae 3a to 3d depending on bonding positions.

[Chemical Formula 3a]

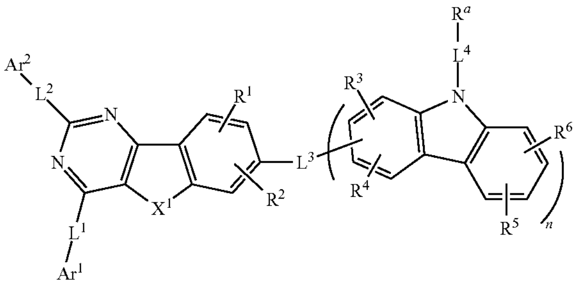

[Chemical Formula 3b]

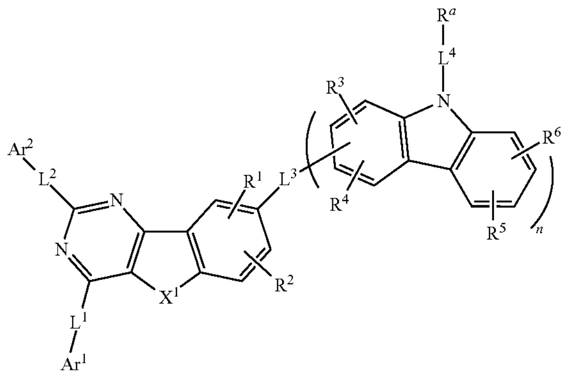

-continued

[Chemical Formula 3c]

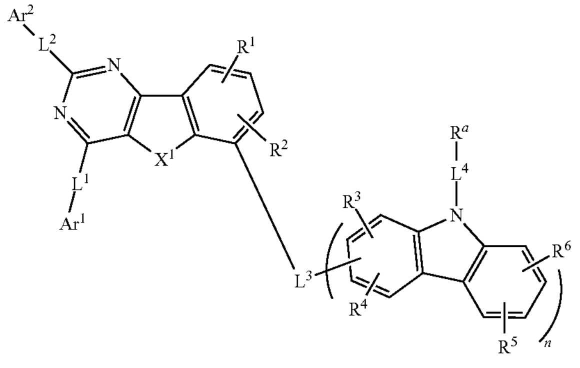

[Chemical Formula 3d]

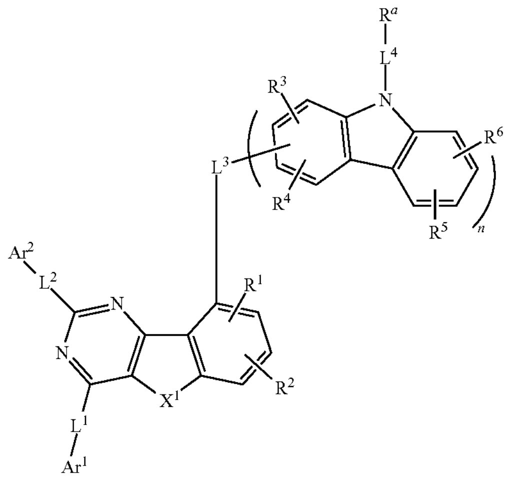

In Chemical Formulae 3a to 3d, $X^1$, $Ar^1$, $Ar^2$, $L^1$ to $L^4$, $R^1$ to $R^6$, and $R^a$ are the same as described above.

For example, the organic compound represented by Chemical Formula 3a may be for example represented by Chemical Formulae 3a-I to 3a-IV depending on bonding positions.

[Chemical Formula 3a-I]

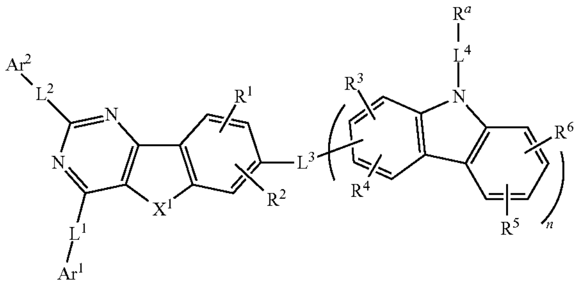

-continued

[Chemical Formula 3a-II]

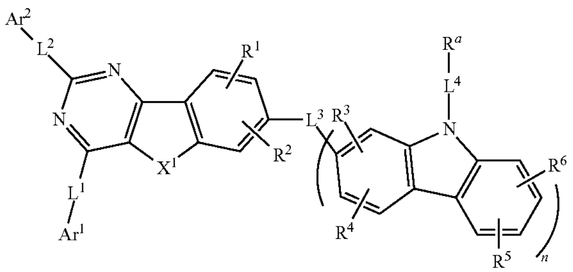

[Chemical Formula 3a-III]

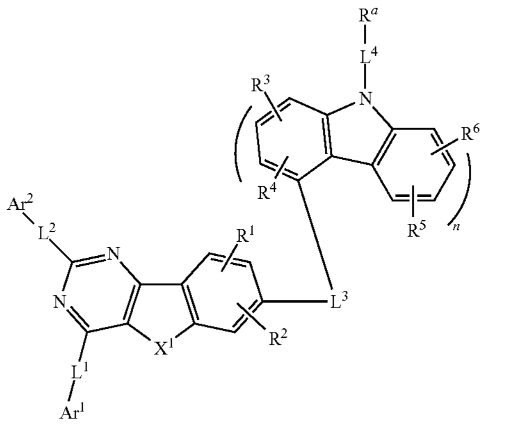

[Chemical Formula 3a-IV]

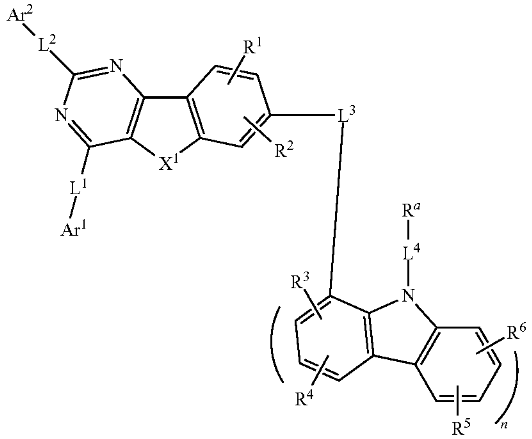

For example, the organic compound represented by Chemical Formula 3b may be for example represented by Chemical Formulae 3b-I to 3b-IV depending on bonding positions.

[Chemical Formula 3b-I]

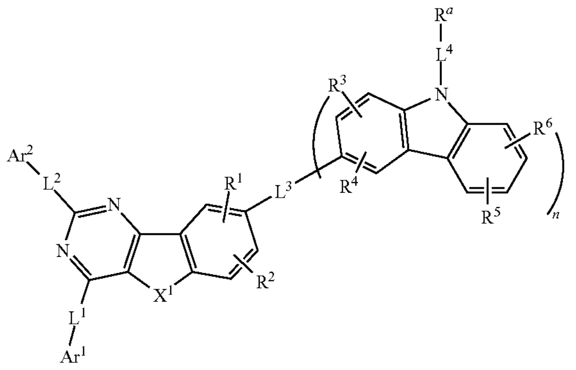

[Chemical Formula 3b-II]

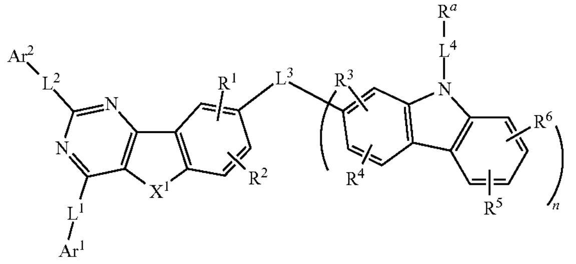

[Chemical Formula 3b-III]

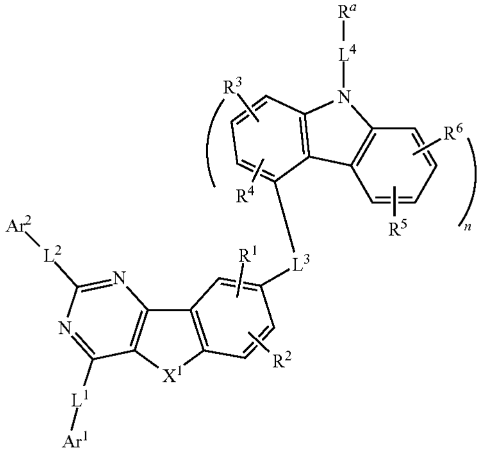

[Chemical Formula 3b-IV]

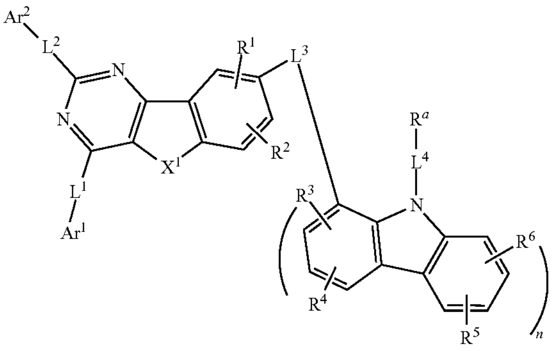

[Chemical Formula 3c-I]

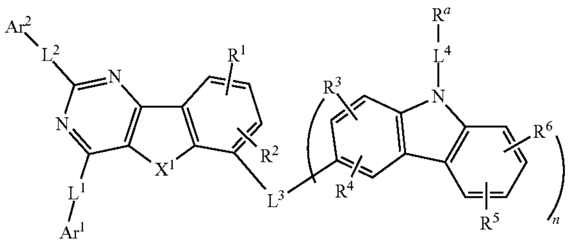

[Chemical Formula 3c-II]

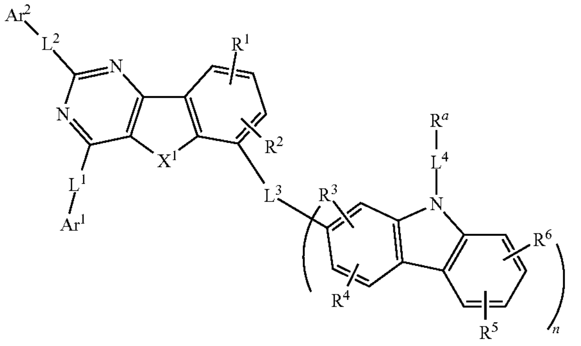

[Chemical Formula 3c-III]

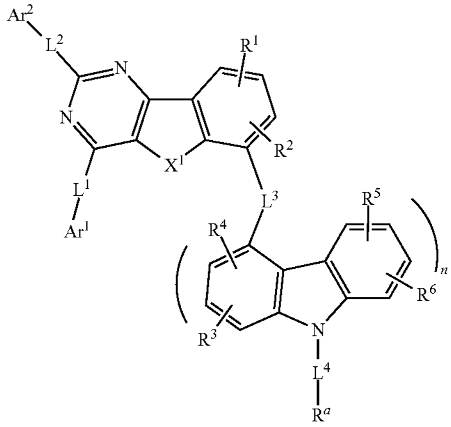

[Chemical Formula 3c-IV]

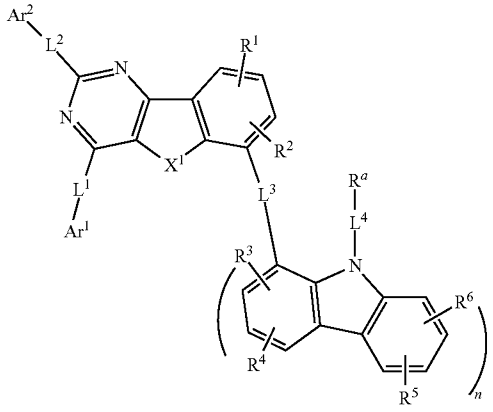

For example, the organic compound represented by Chemical Formula 3c may be for example represented by Chemical Formulae 3c-I to 3c-IV depending on bonding positions.

For example, the organic compound represented by Chemical Formula 3d may be for example represented by Chemical Formulae 3d-I to 3d-IV depending on bonding positions.

[Chemical Formula 3d-I]
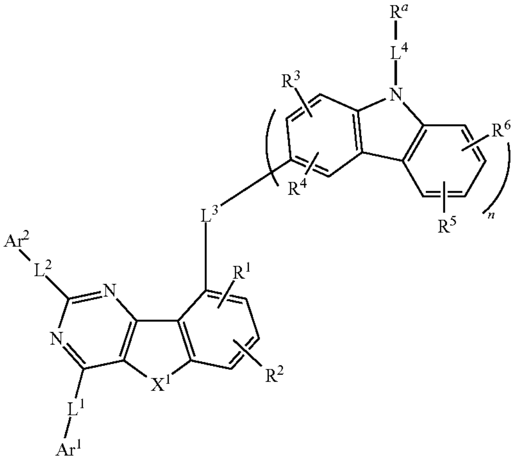
[Chemical Formula 3d-II]
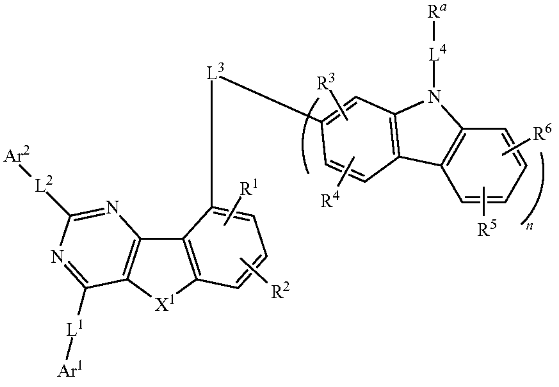
[Chemical Formula 3d-III]
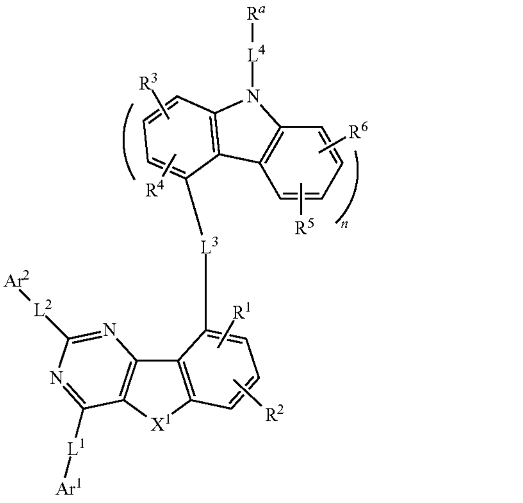
-continued
[Chemical Formula 3d-IV]
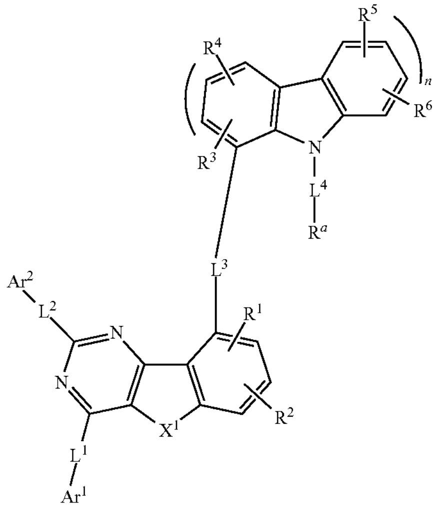
In Chemical Formulae 3a-I to 3a-IV, 3b-I to 3b-IV, 3c-I to 3c-IV, and 3d-I to 3d-IV, $X^1$, $Ar^1$, $Ar^2$, $L^1$ to $L^4$, $R^1$ to $R^6$, and $R^a$ are the same as described above.
The organic compound may be for example selected from compounds of Group 1, but is not limited thereto.
[Group 1]
1
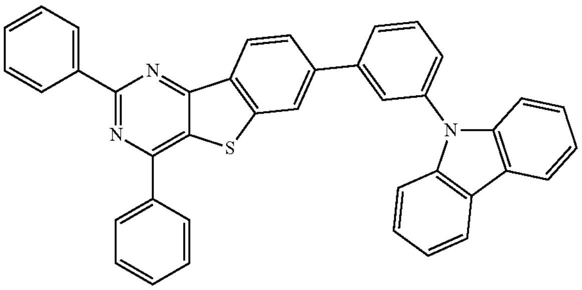
2
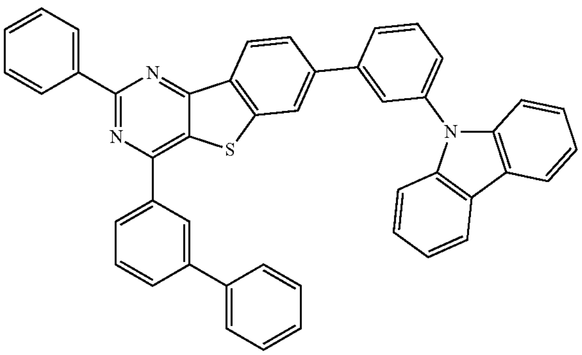

-continued
3
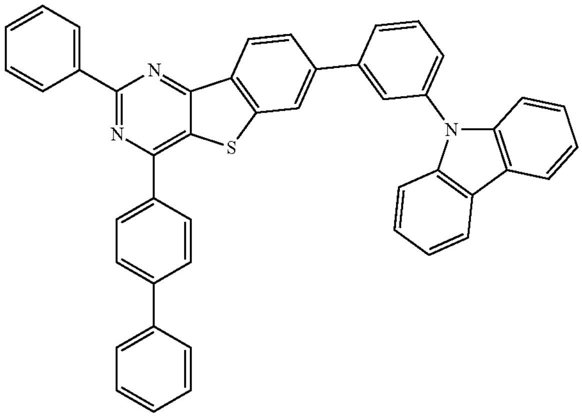
4
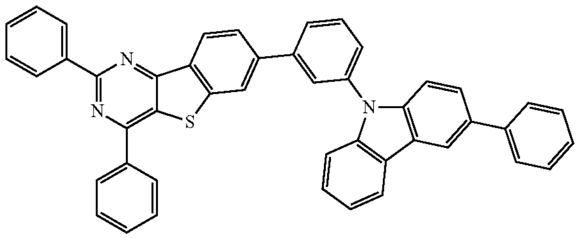
5
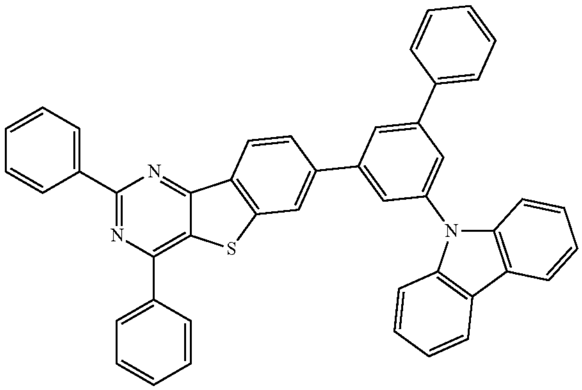
6
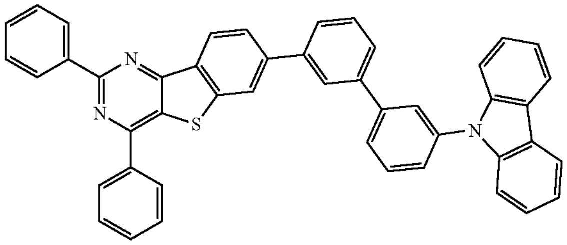
-continued
7
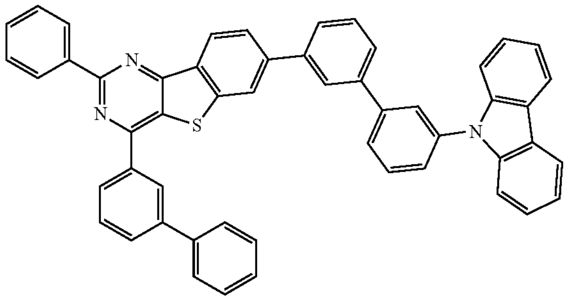
8
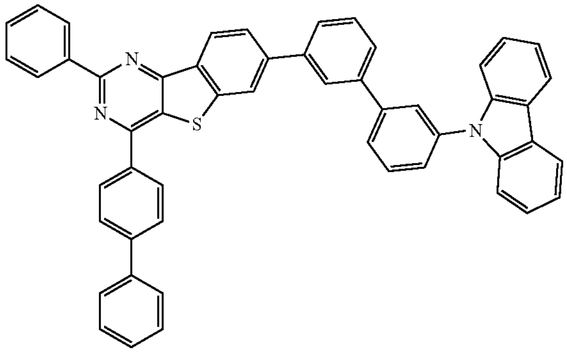
9
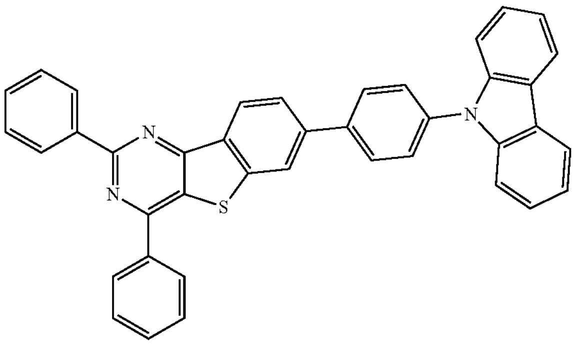
10
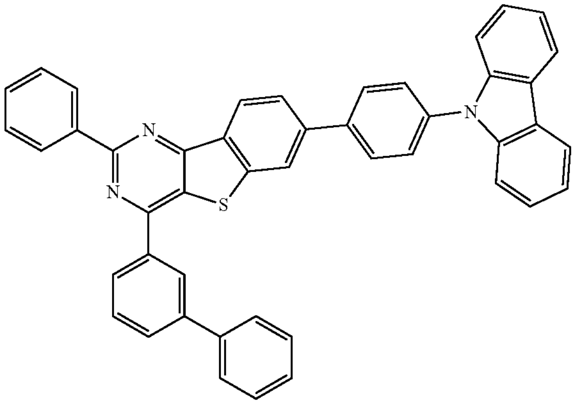

-continued
11
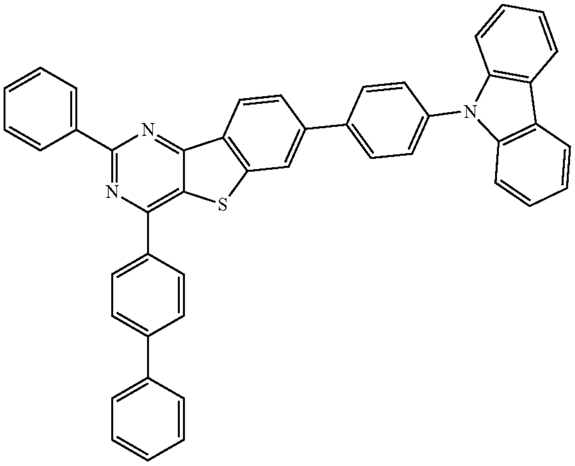
12
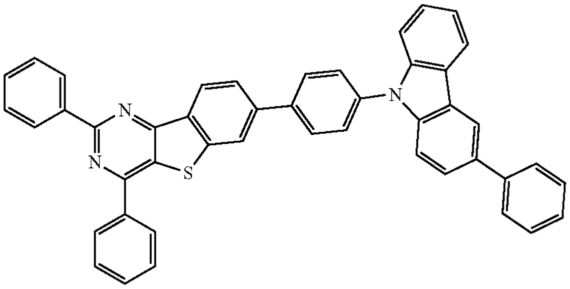
13
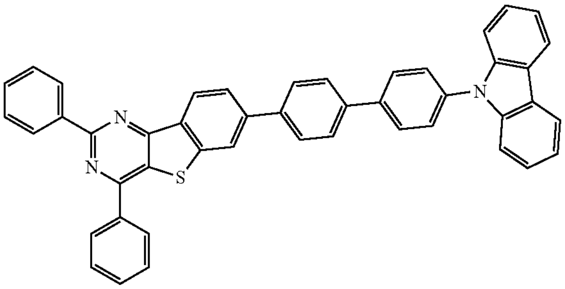
14
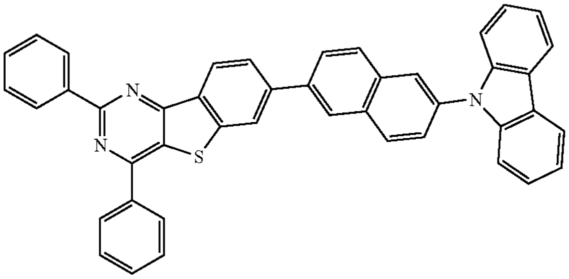
-continued
15
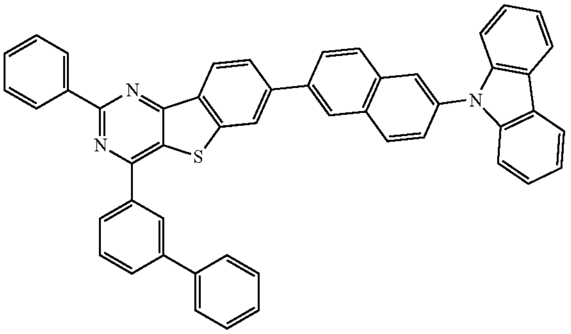
16
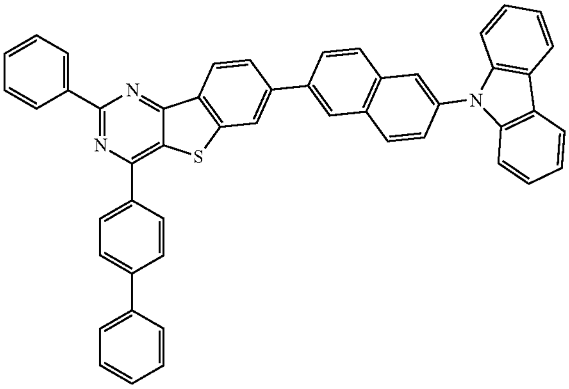
17
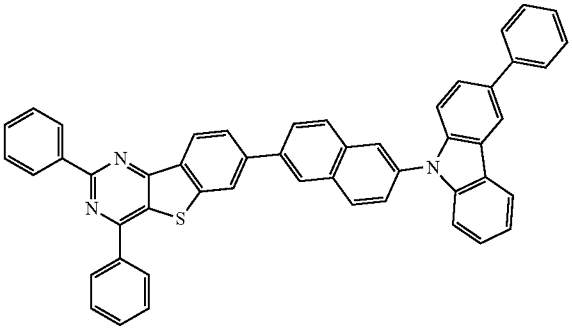
18
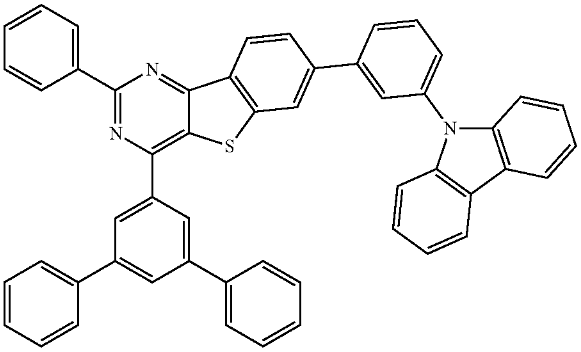

-continued
19
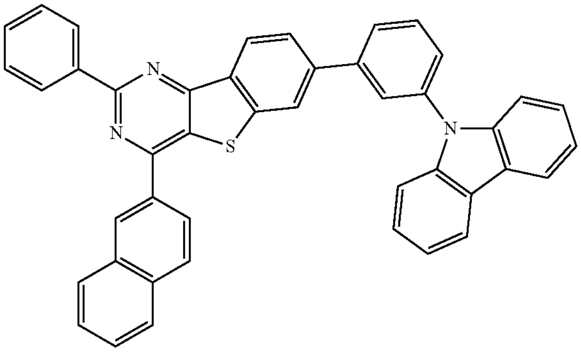
20
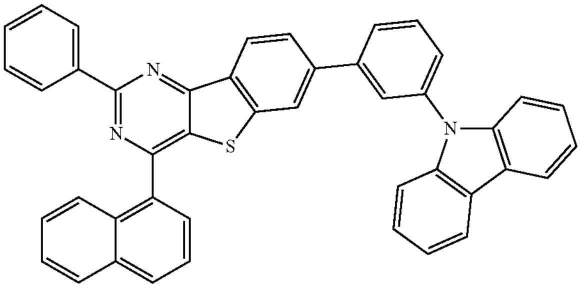
21
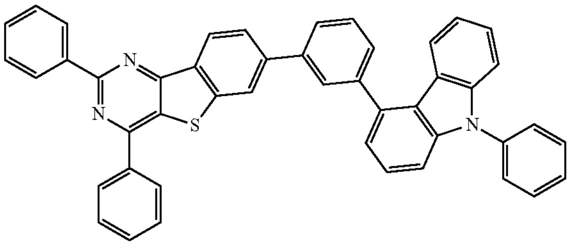
22
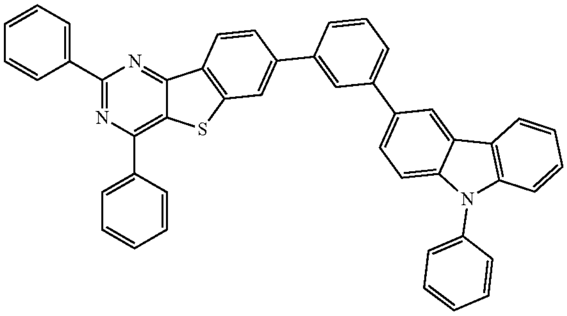
23
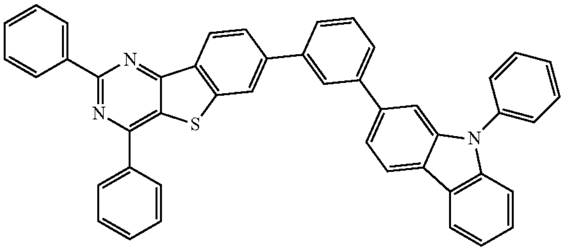
-continued
24
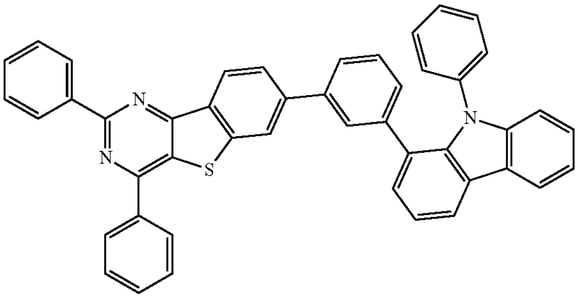
25
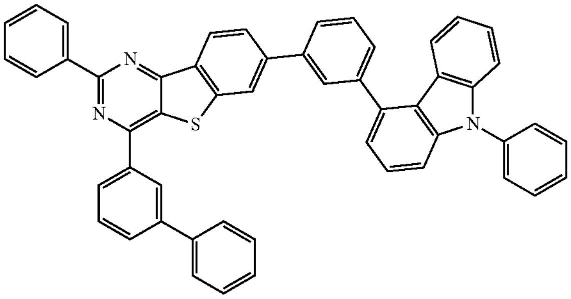
26
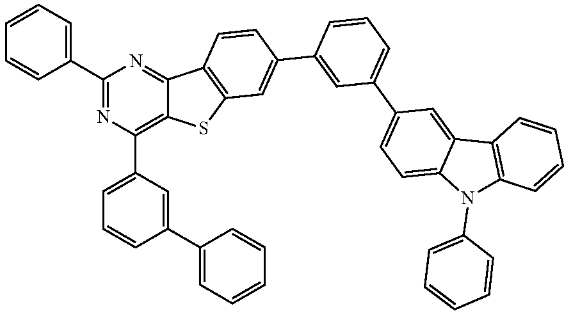
27
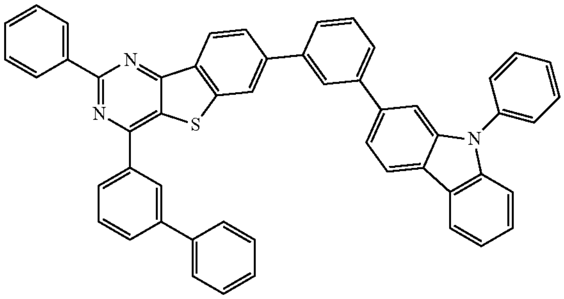

-continued
28
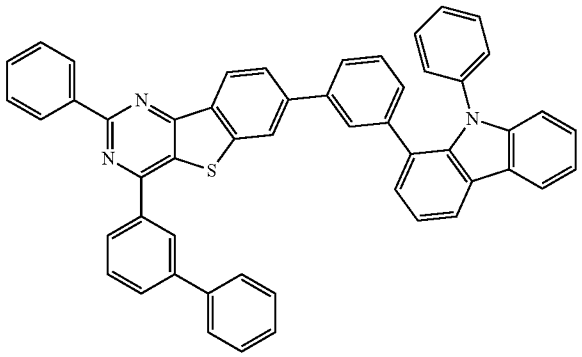
29
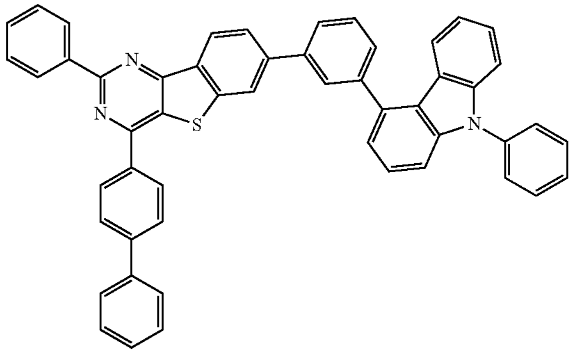
30
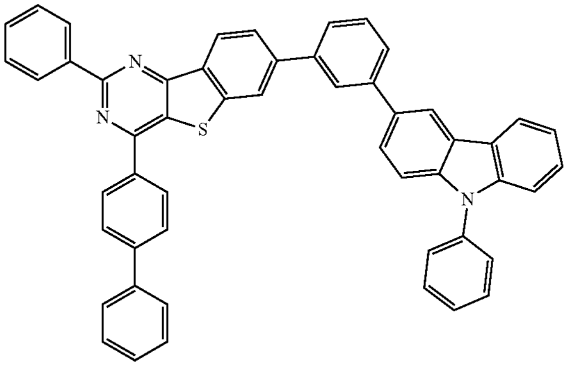
31
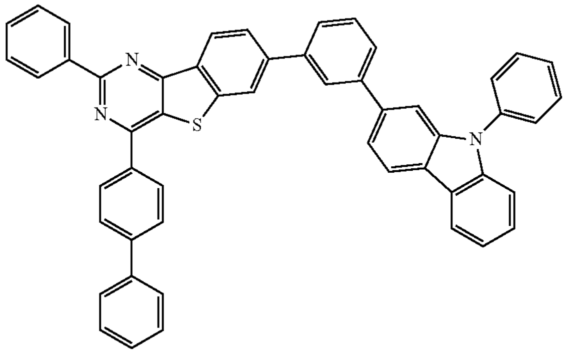
-continued
32
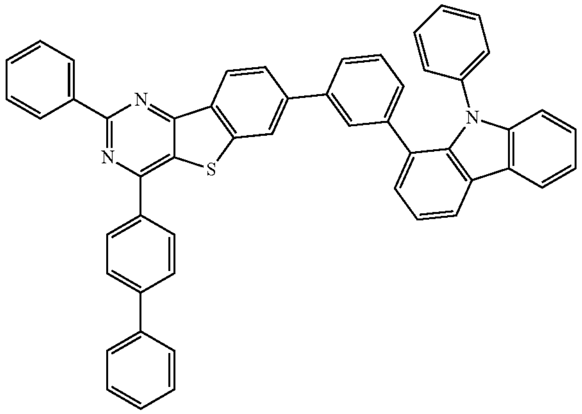
33
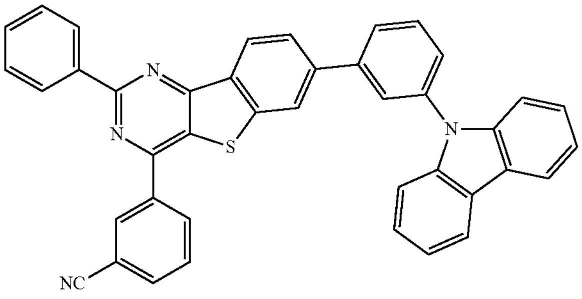
34
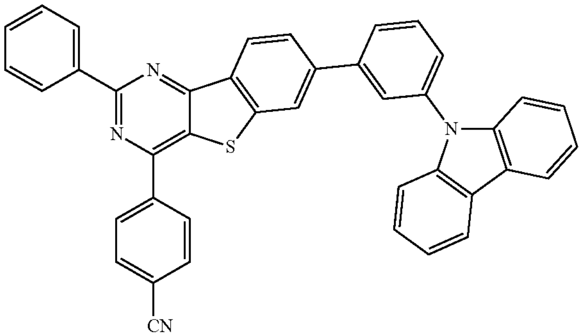
35
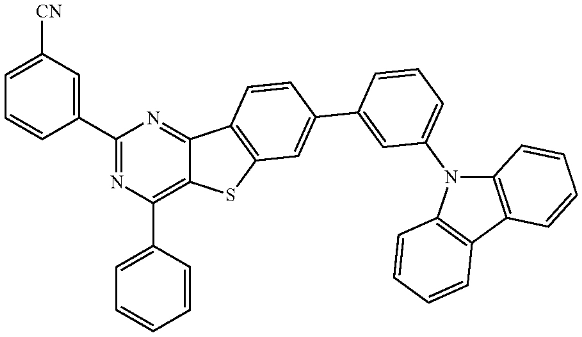

-continued
36
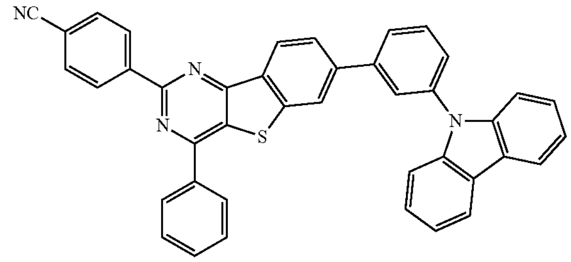
37
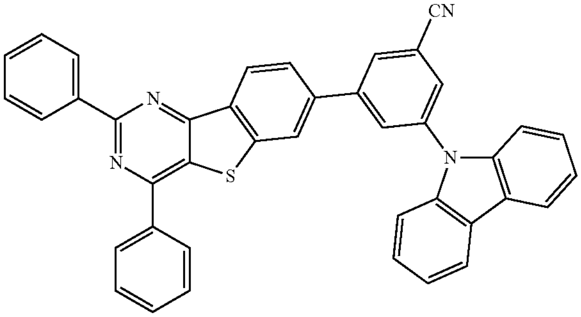
38
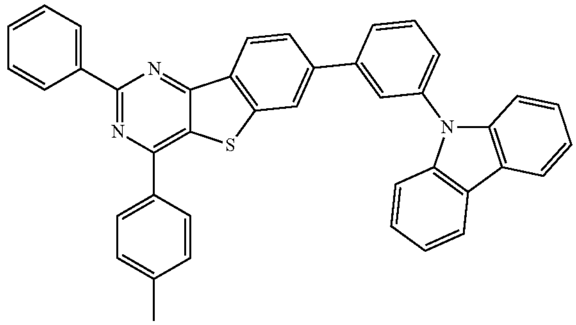
39
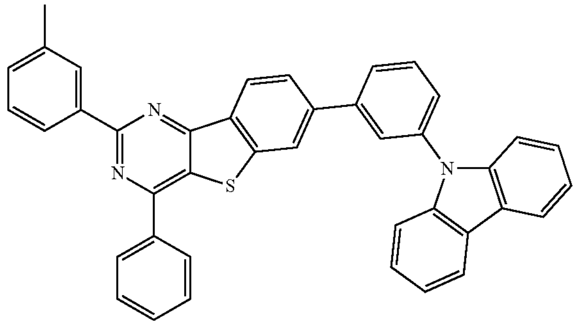
-continued
40
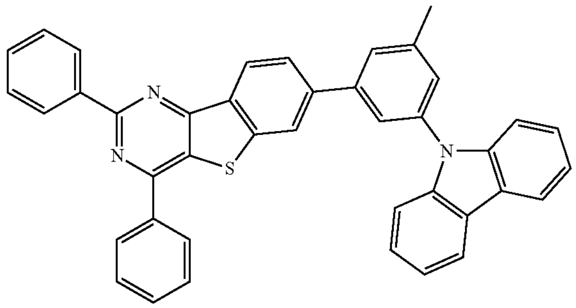
41
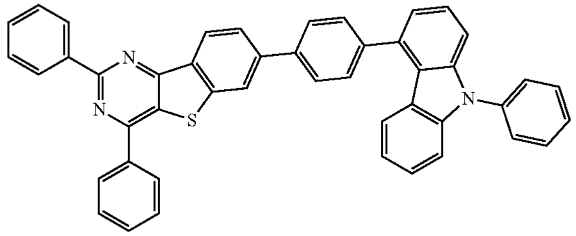
42
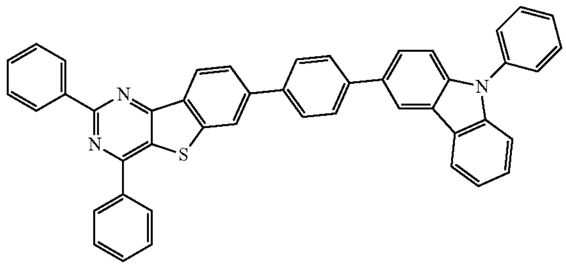
43
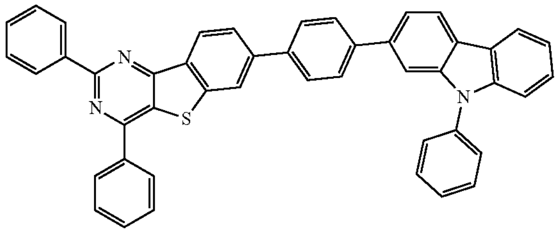
44
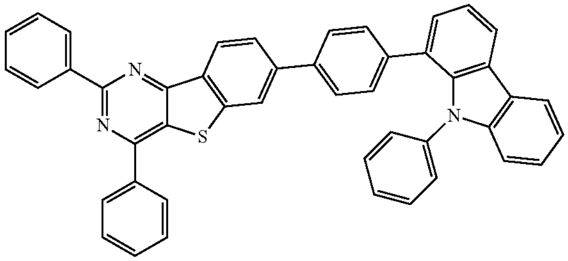

-continued
45
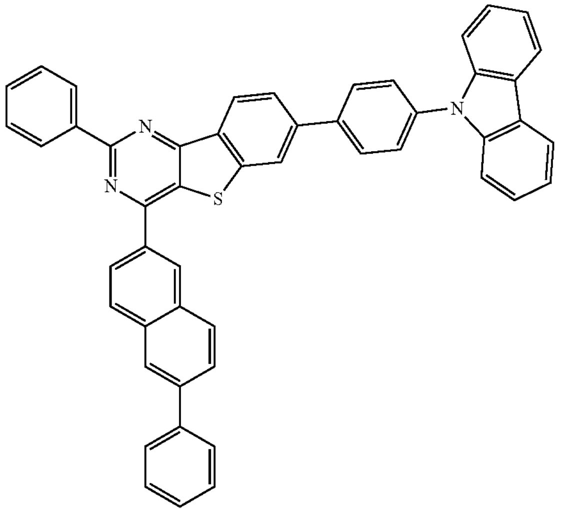
46
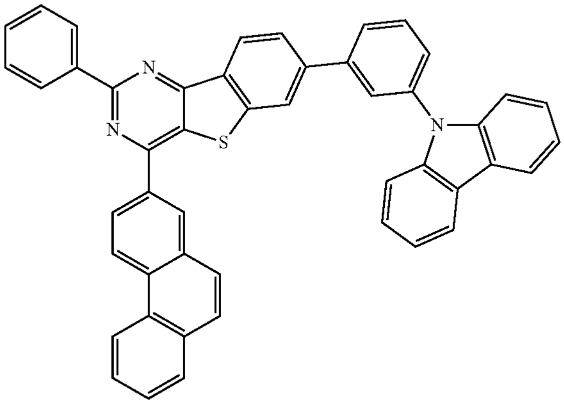
47
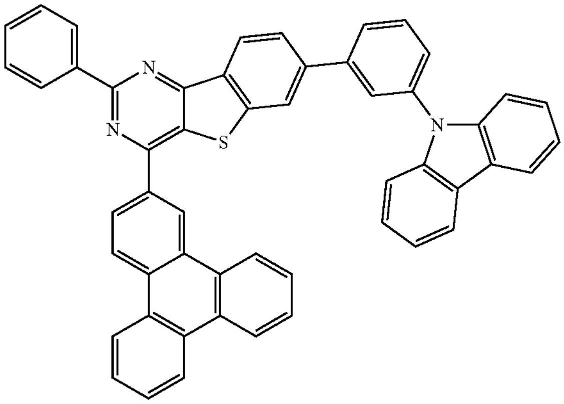
-continued
48
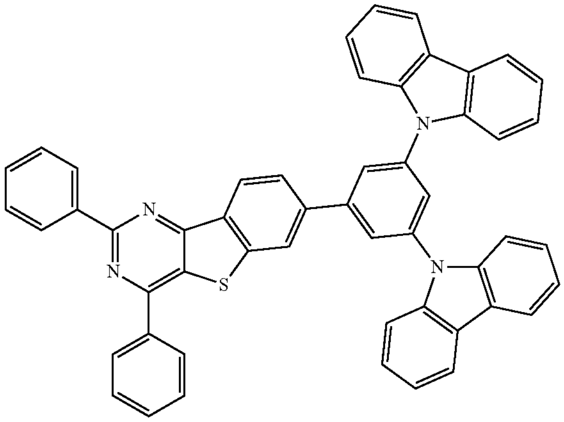
49
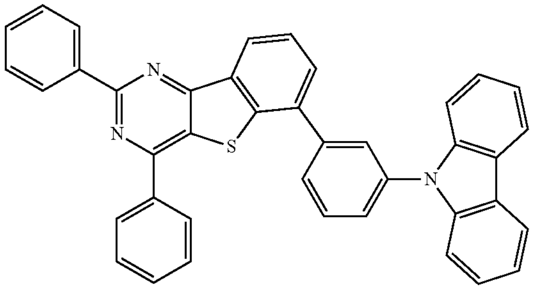
50
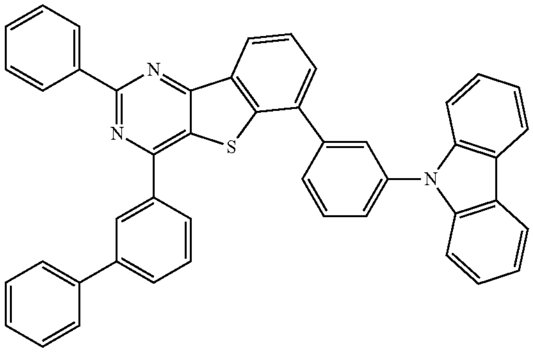
51
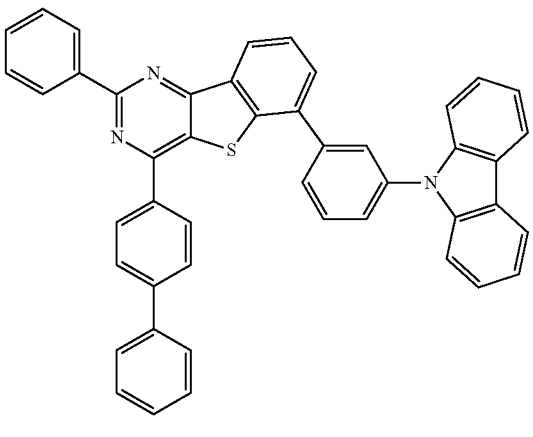

-continued
52
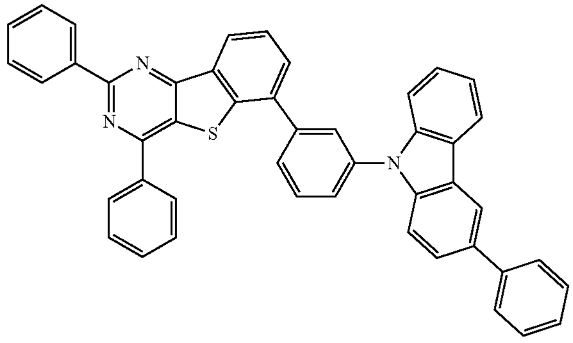
53
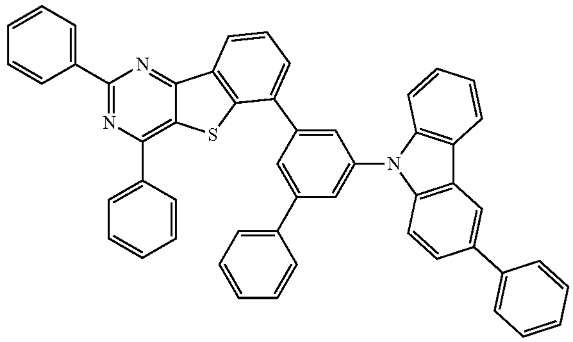
54
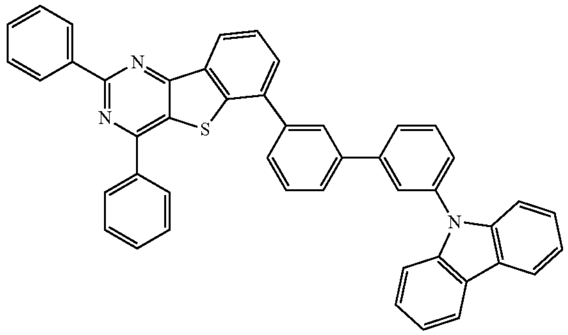
55
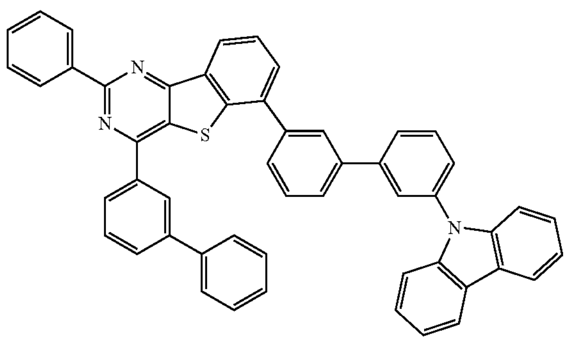
-continued
56
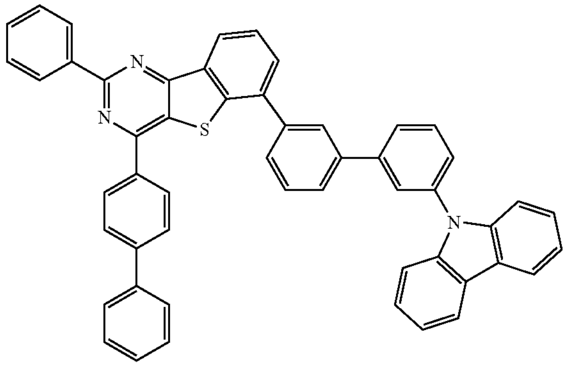
57
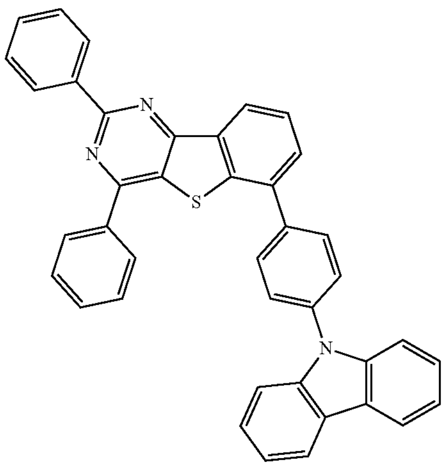
57
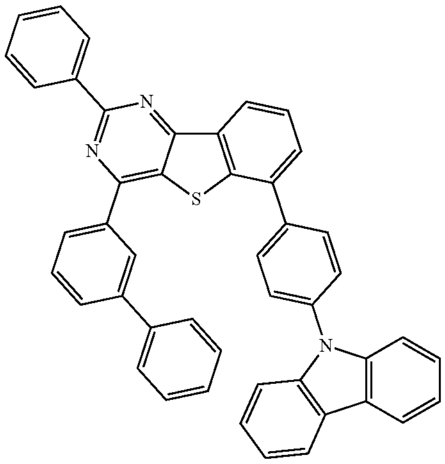

-continued
59
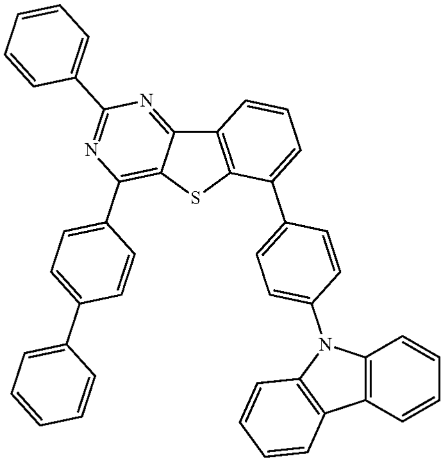
60
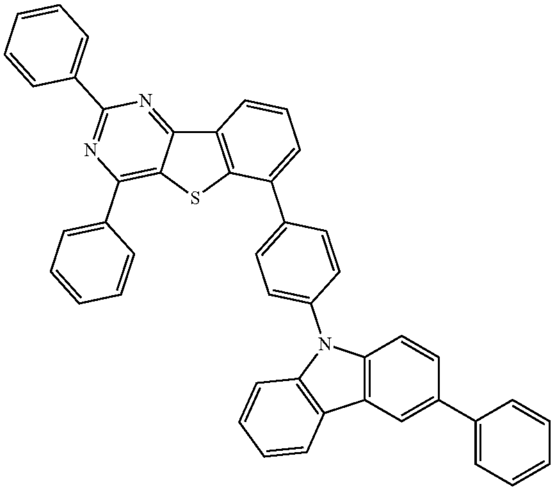
61
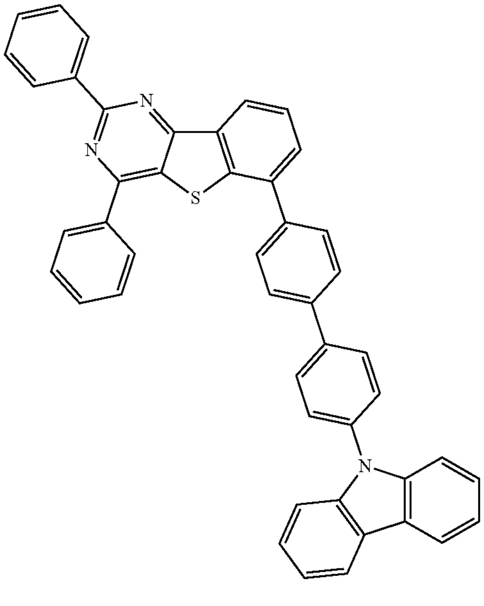
-continued
62
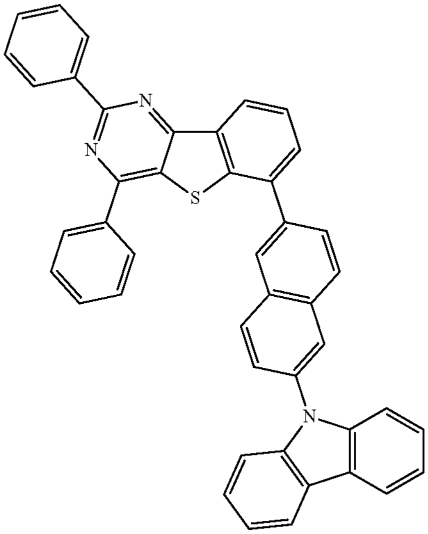
63
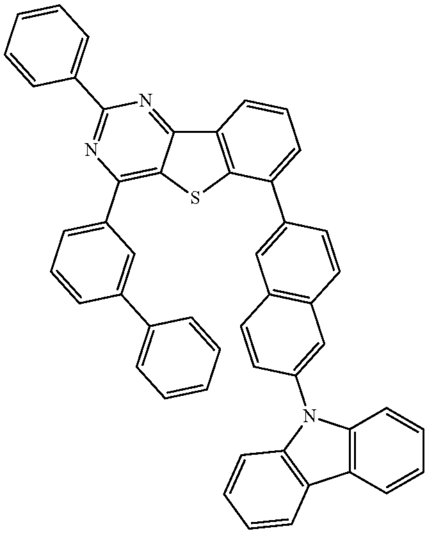
64
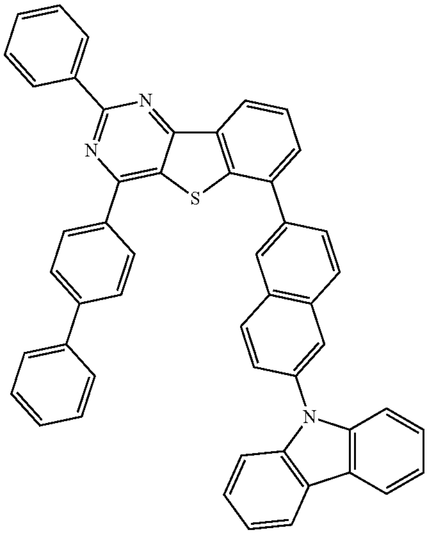

-continued
65
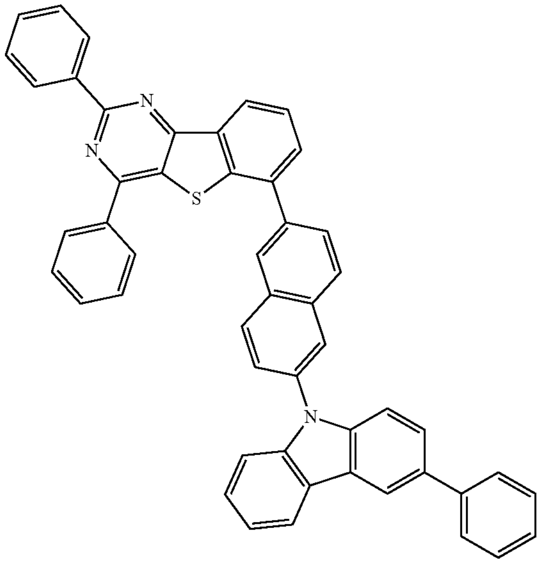
66
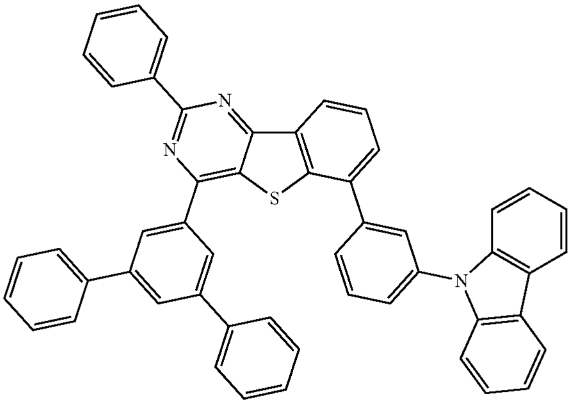
67
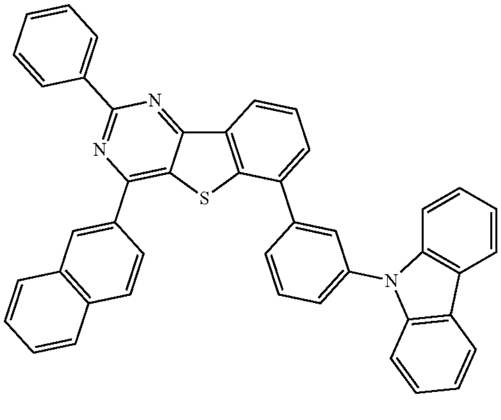
-continued
68
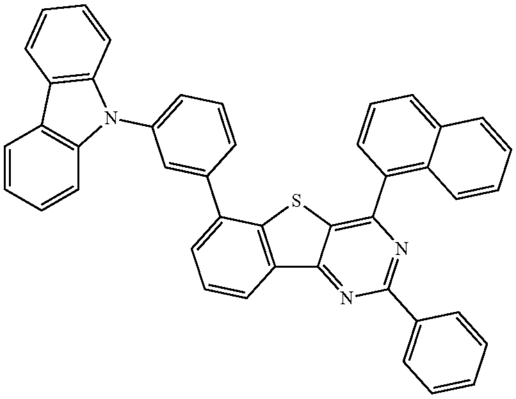
69
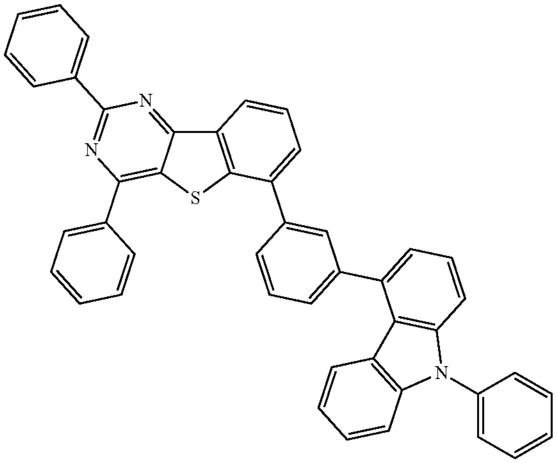
70
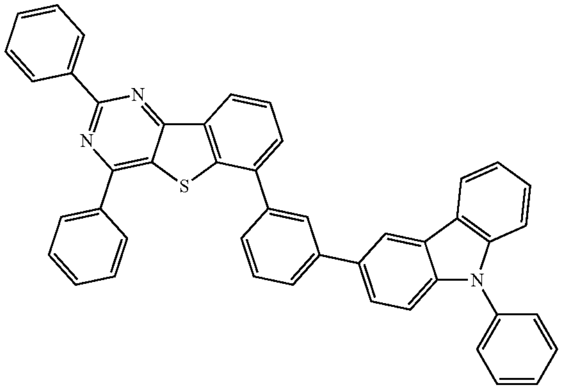
71
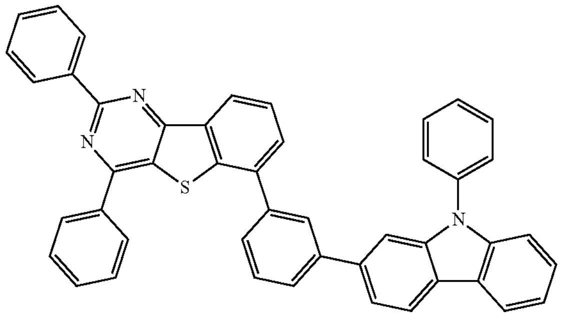

-continued
72
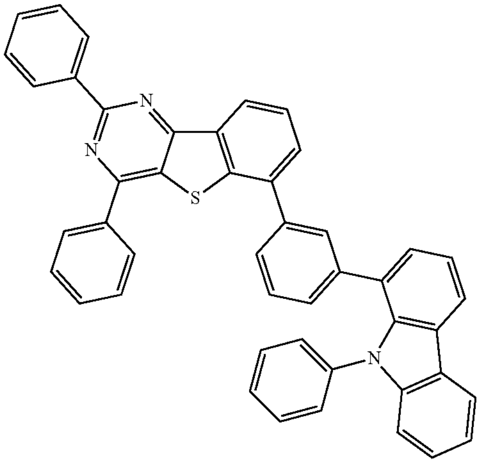
73
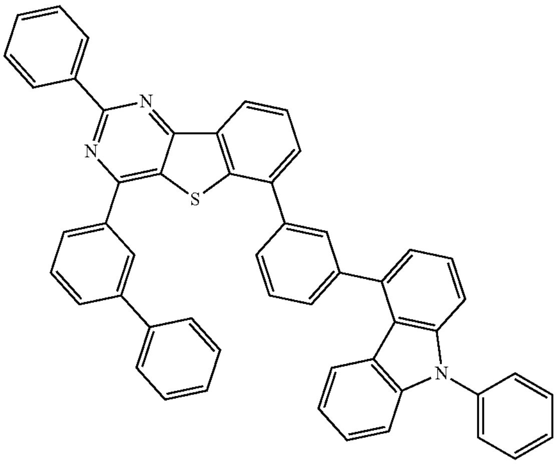
74
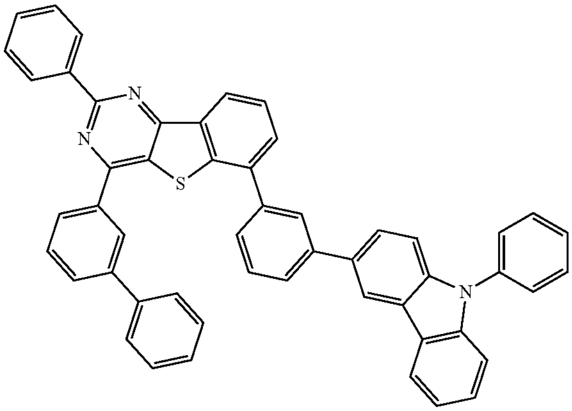
-continued
75
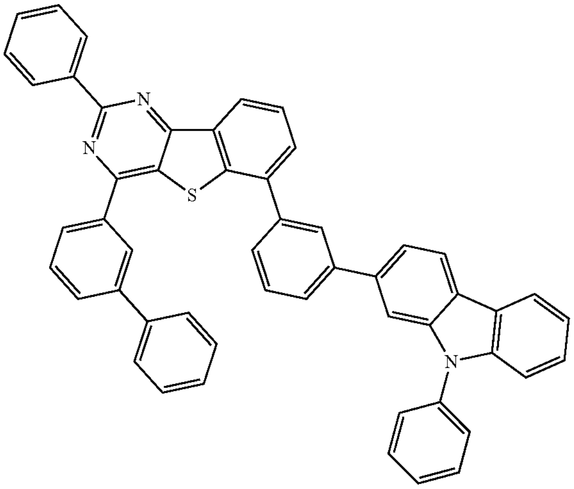
76
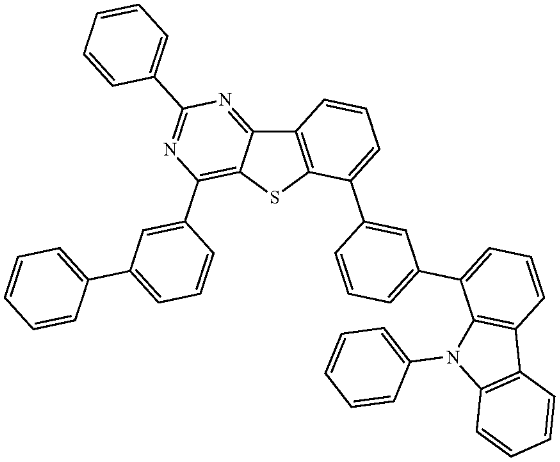
77
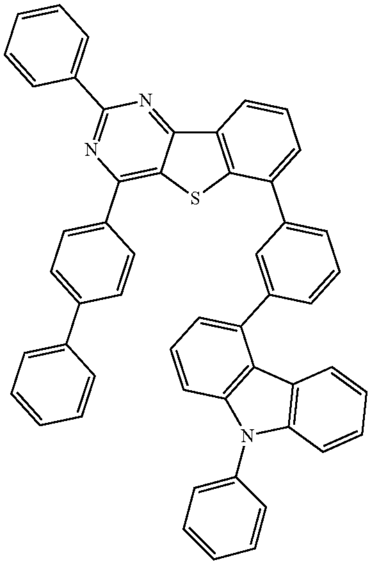

-continued
78
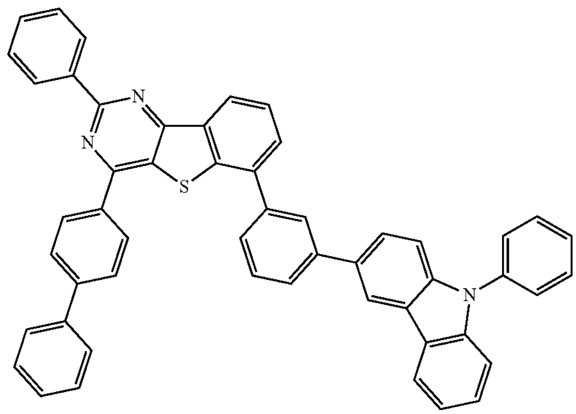
79
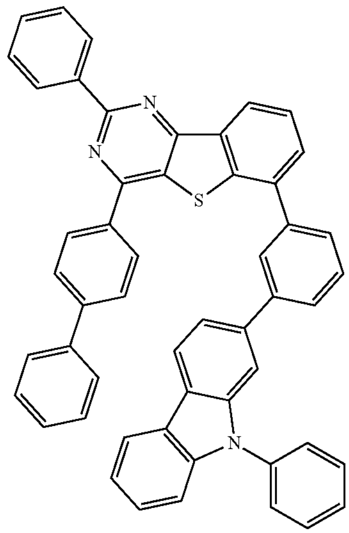
80
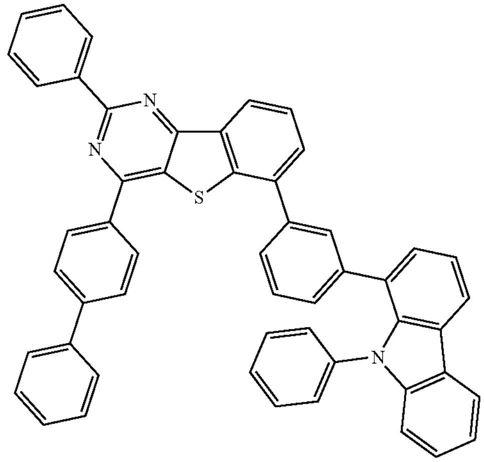
-continued
81
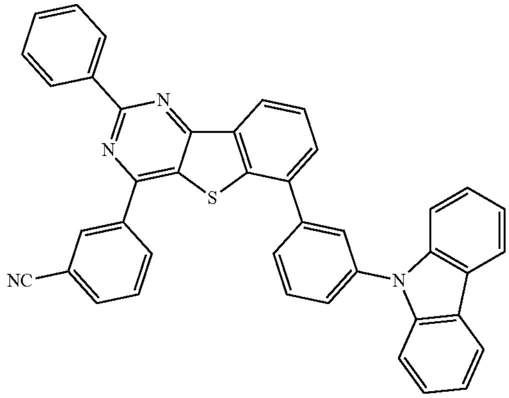
82
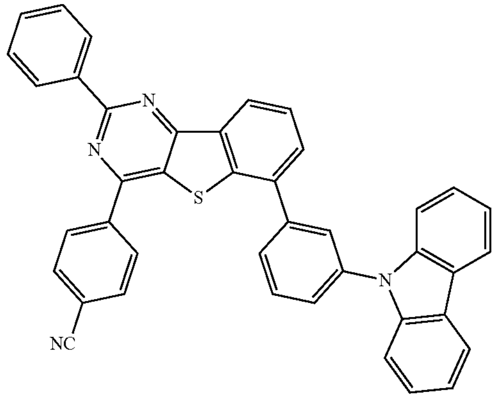
83
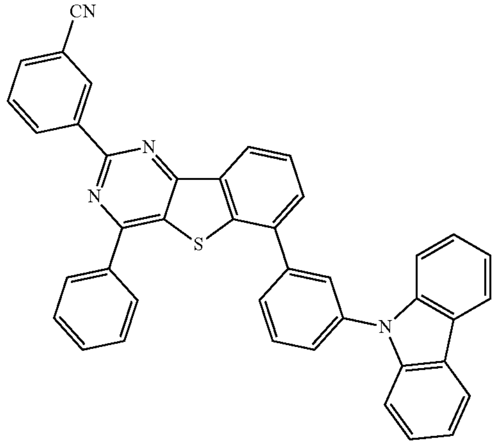

-continued
84
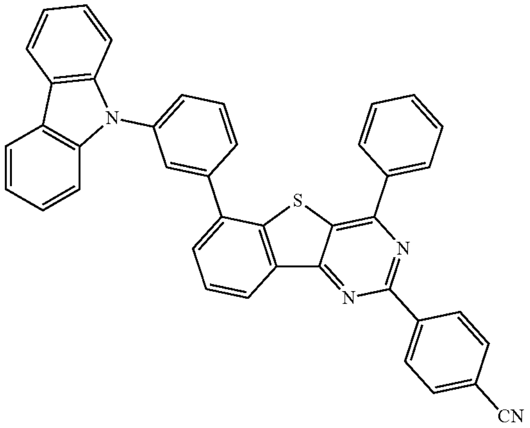
85
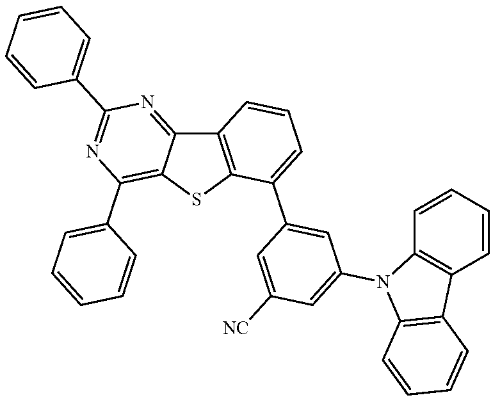
86
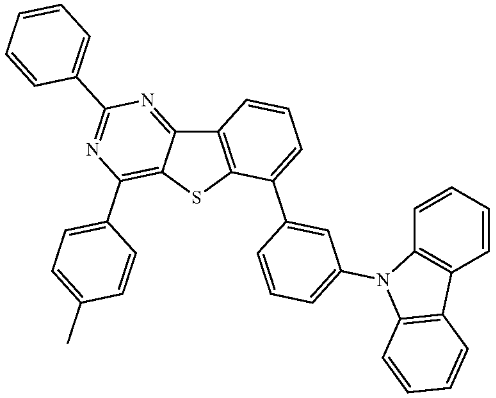
-continued
87
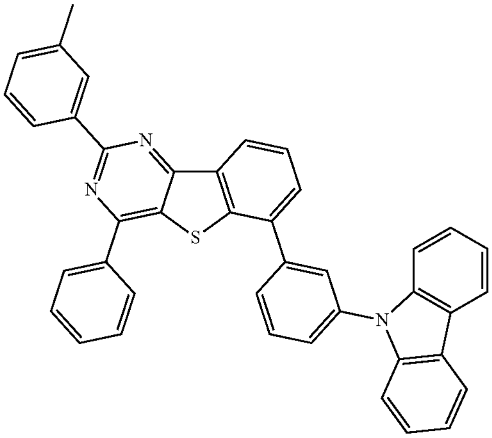
88
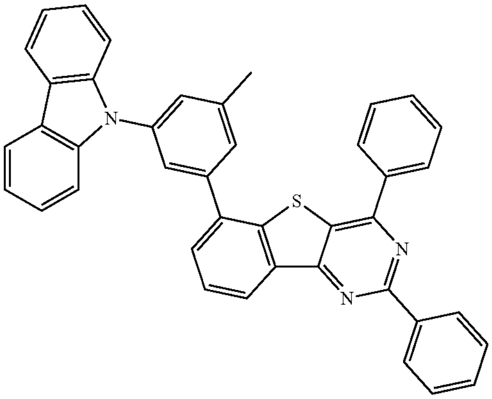
89
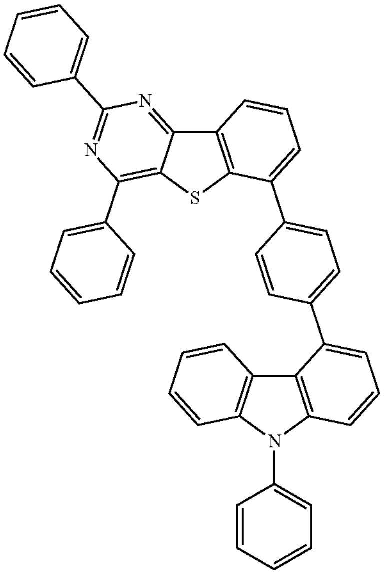

-continued
90
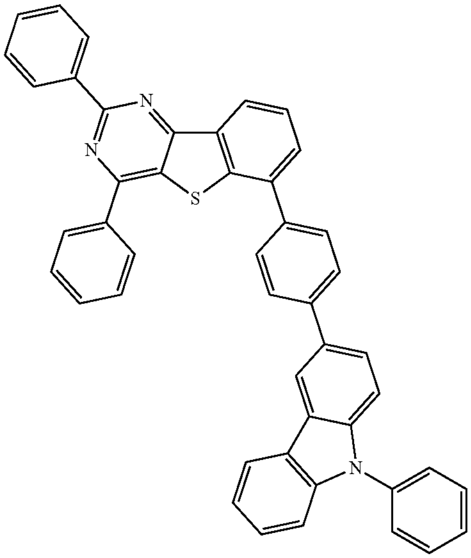
91
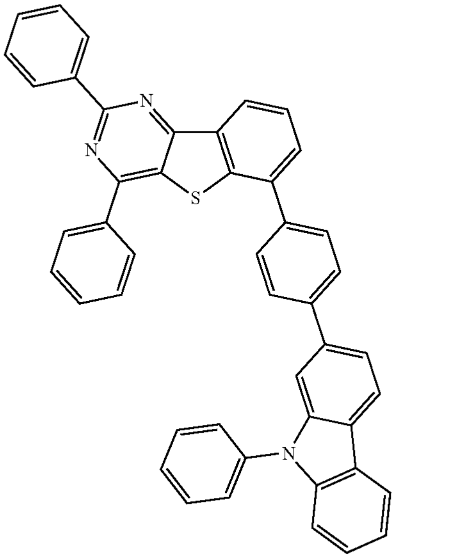
92
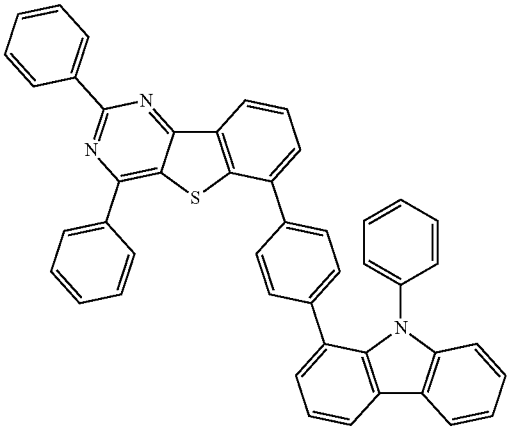
-continued
93
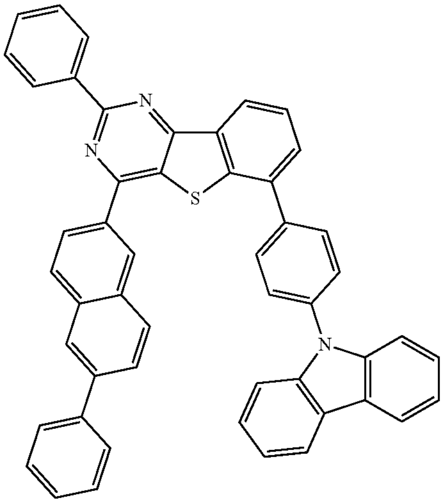
94
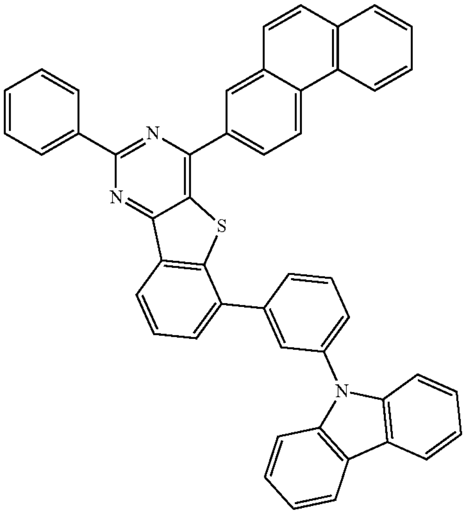
95
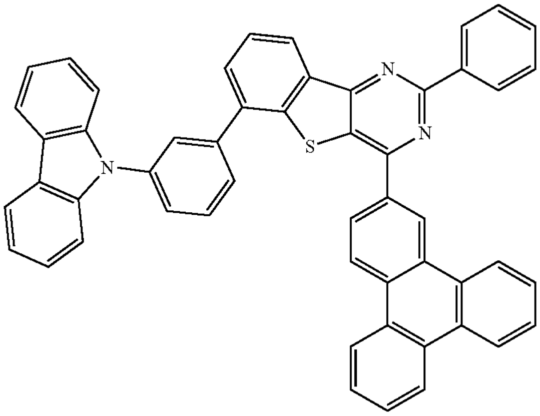

-continued
96
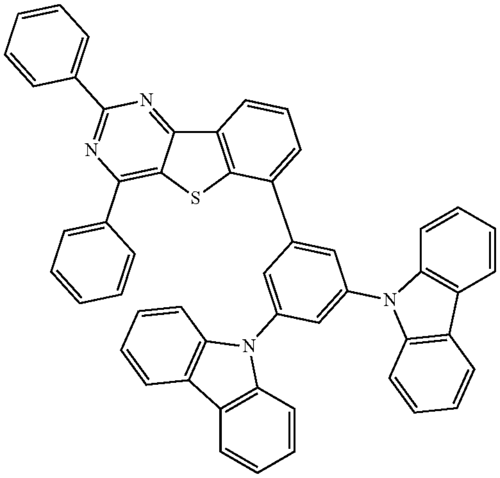
97
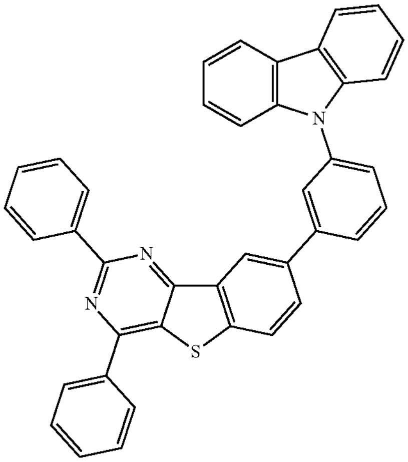
98
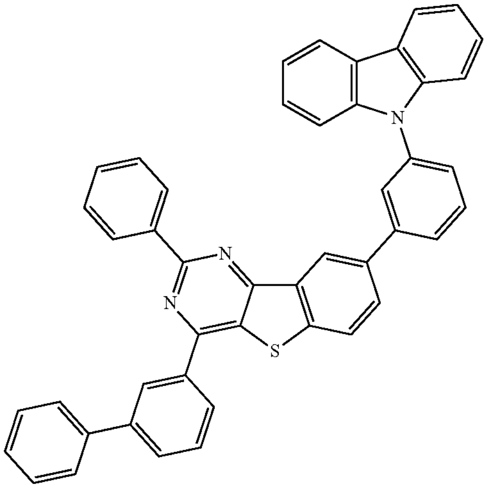
-continued
99
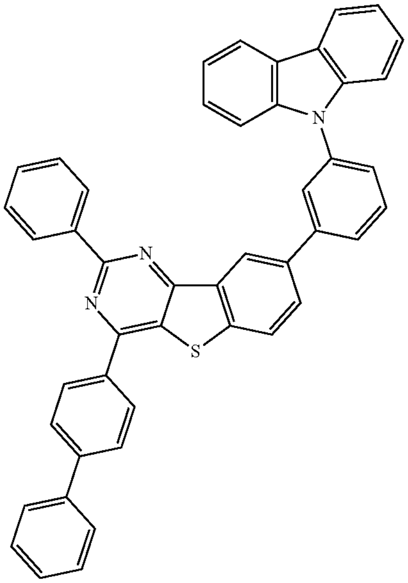
100
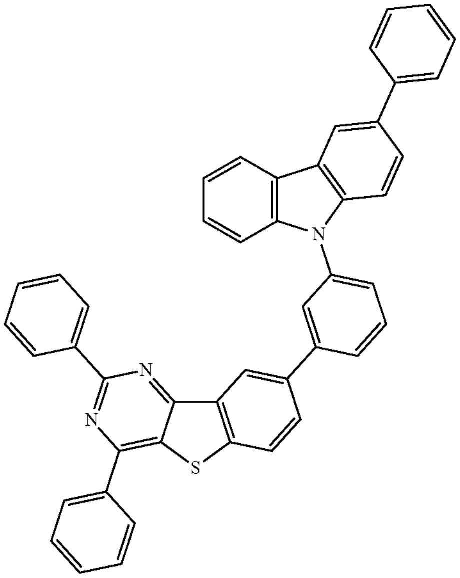
101
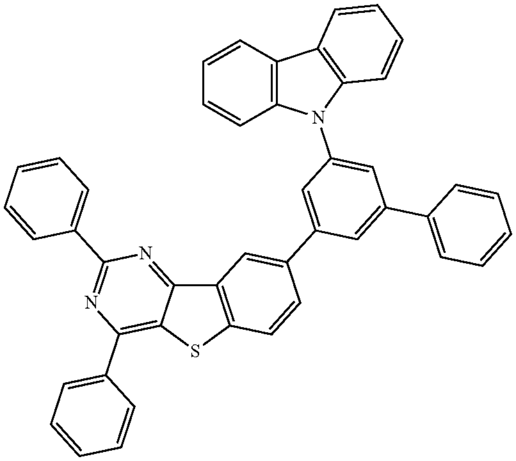

-continued
102
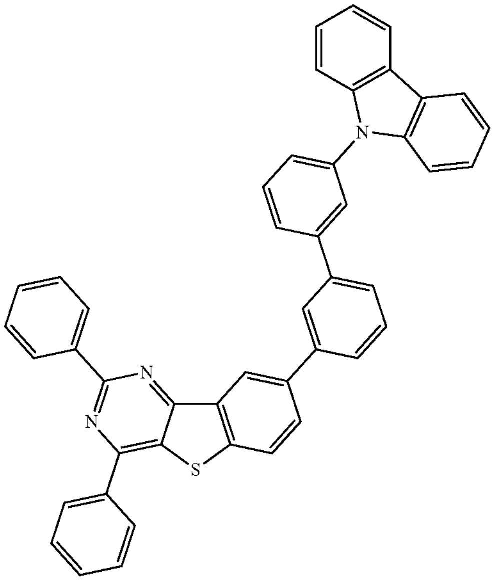
103
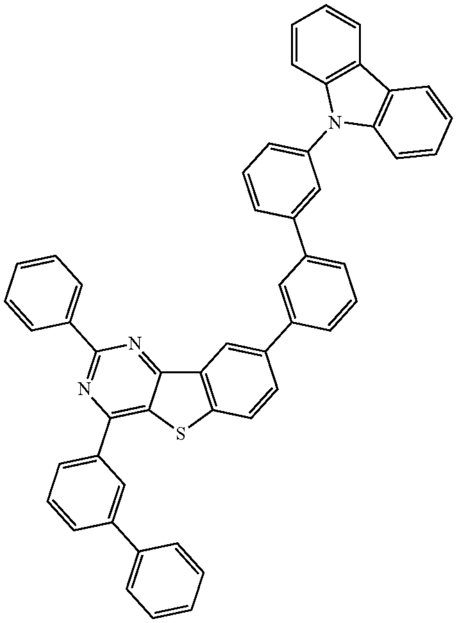
-continued
104
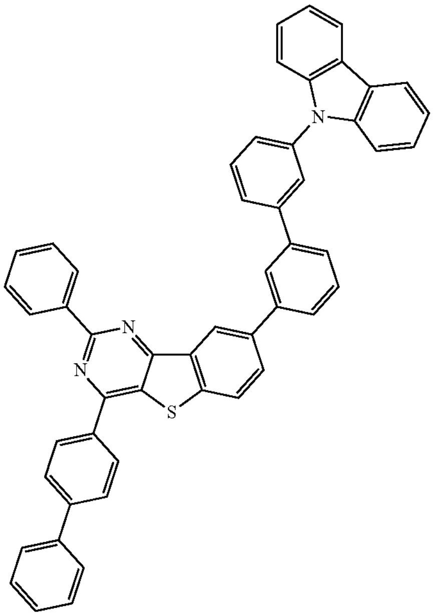
105
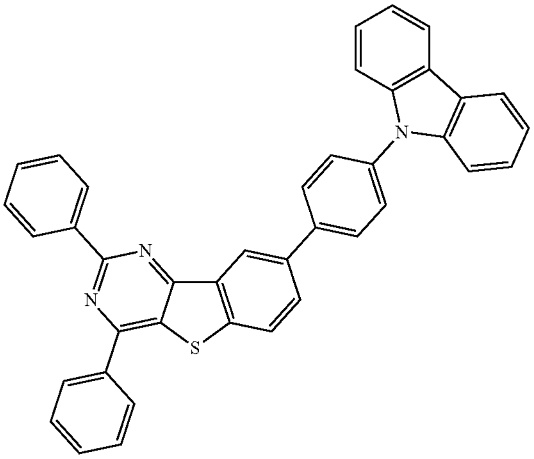
106
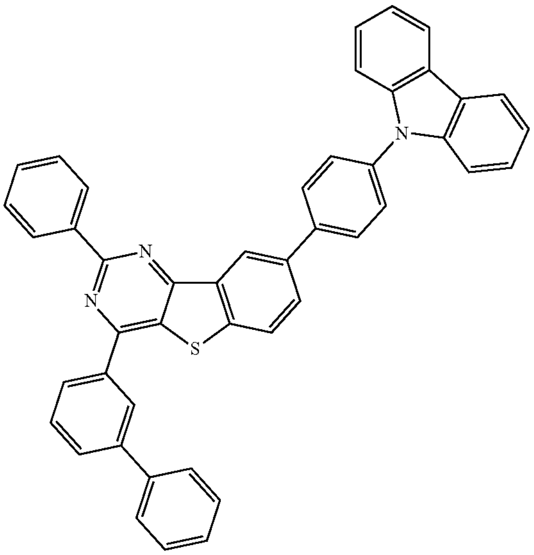

-continued
107
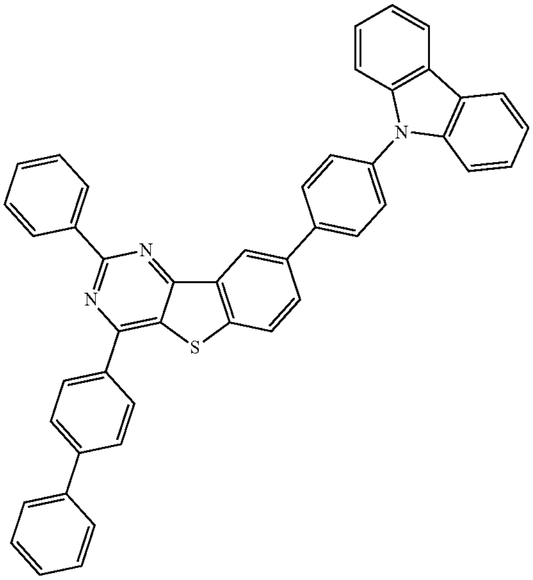
108
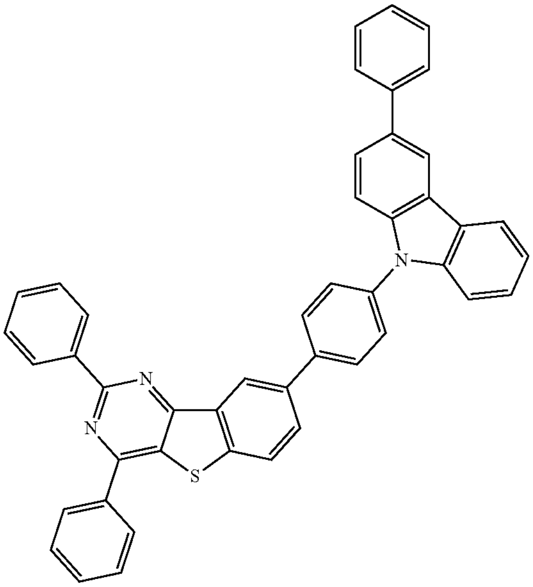
-continued
109
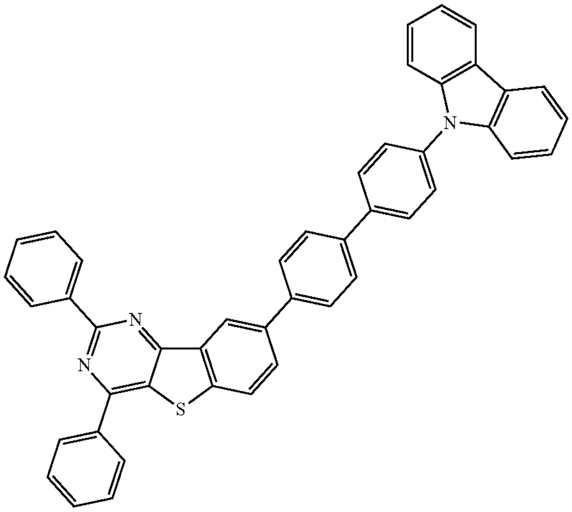
110
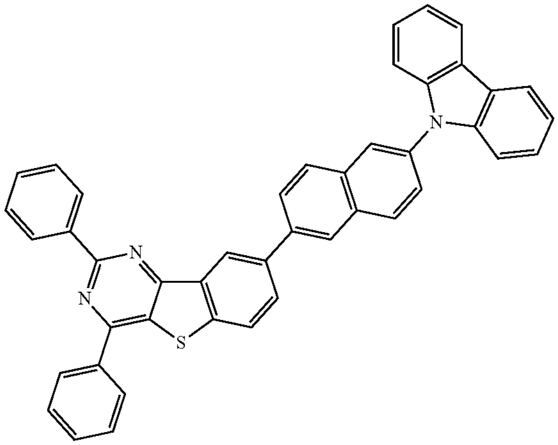
111
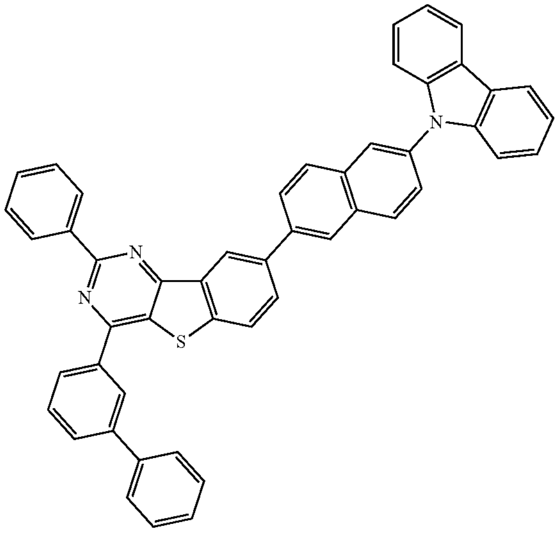

-continued
112
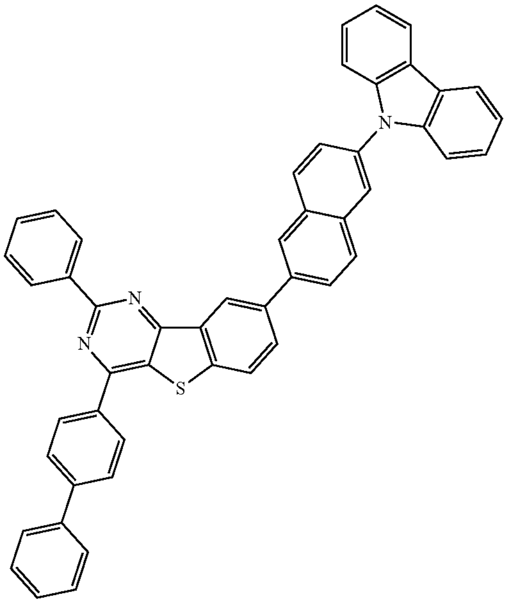
113
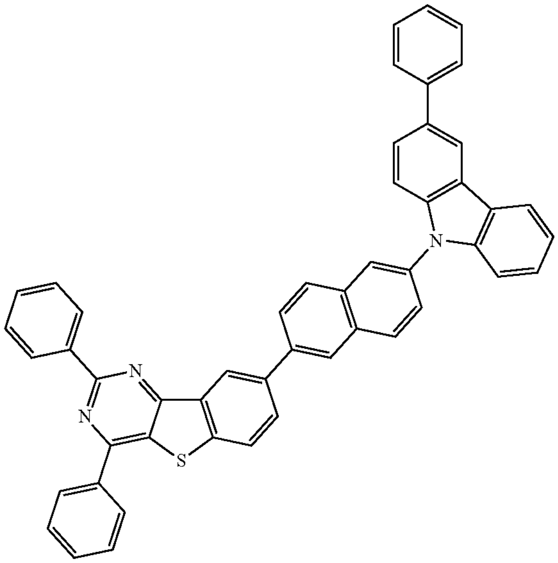
-continued
114
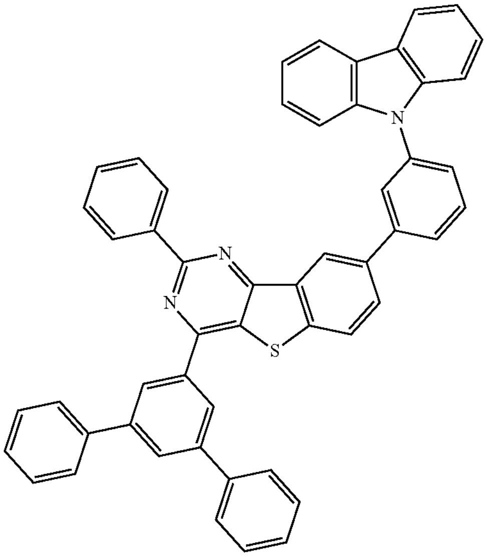
115
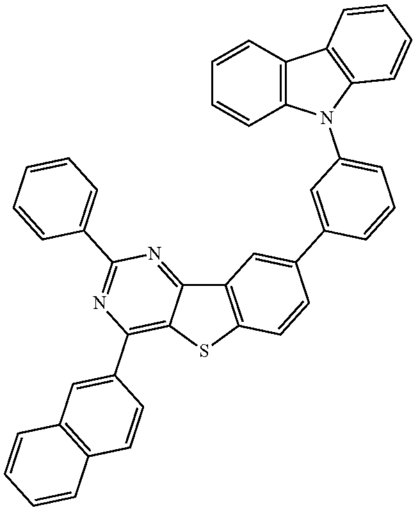
116
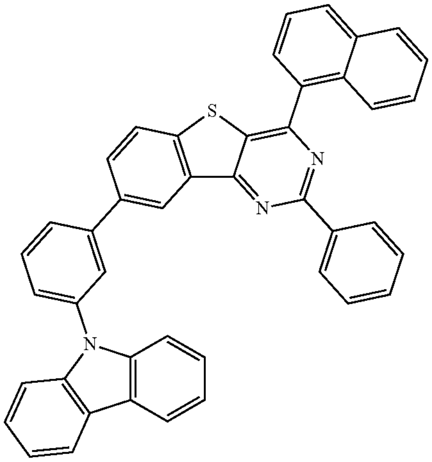

-continued
117
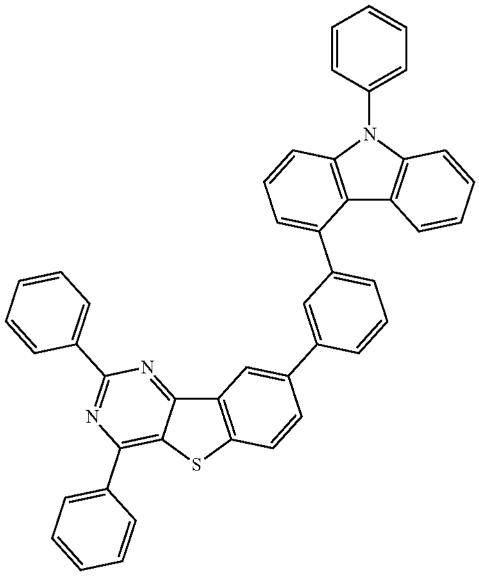
118
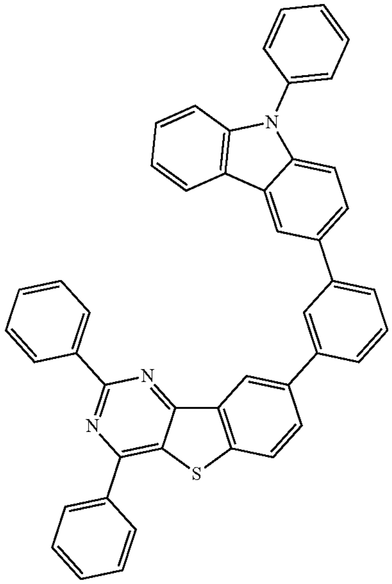
-continued
119
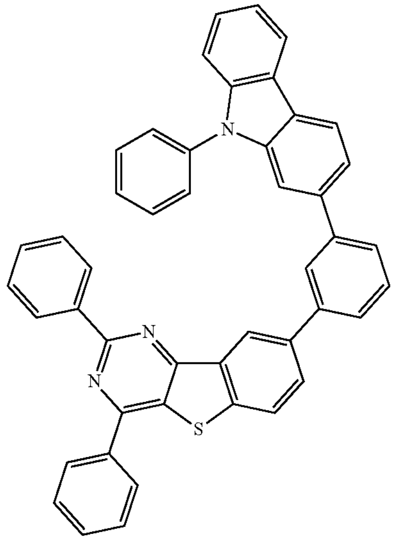
120
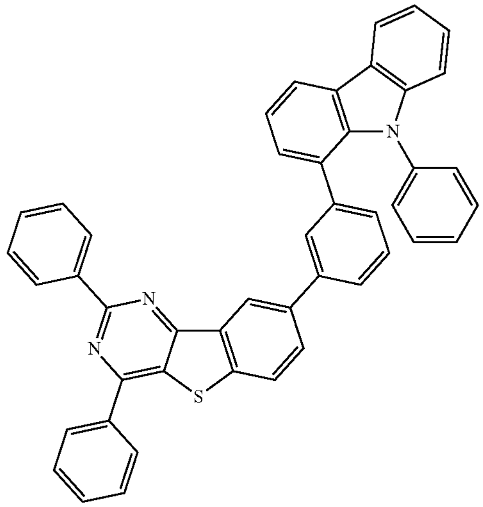
121
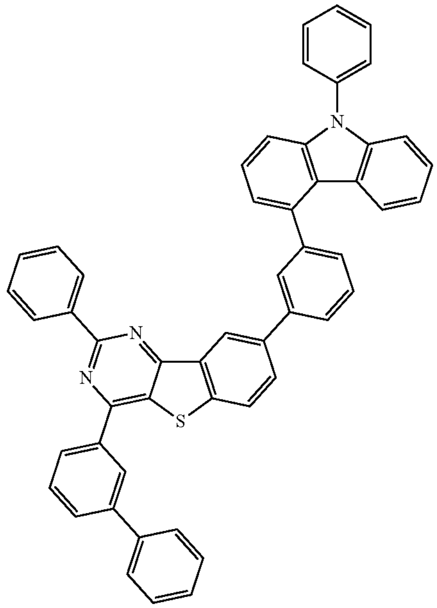

-continued
122
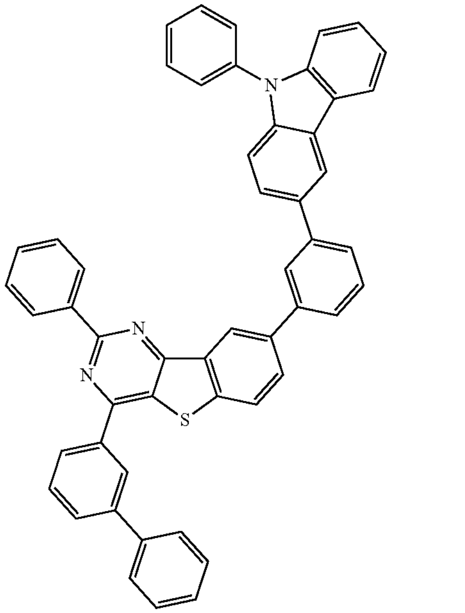
-continued
124
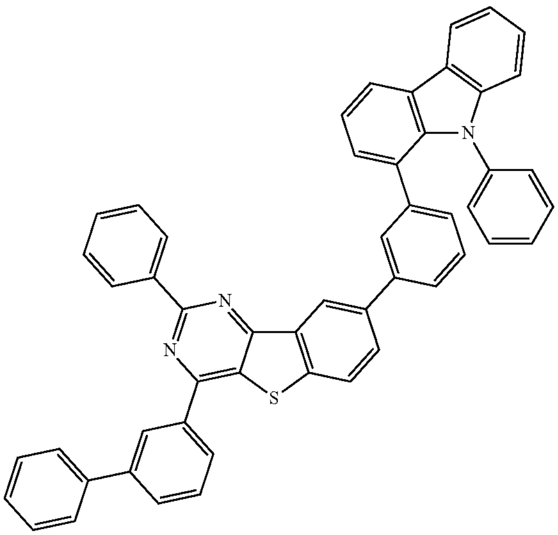
125
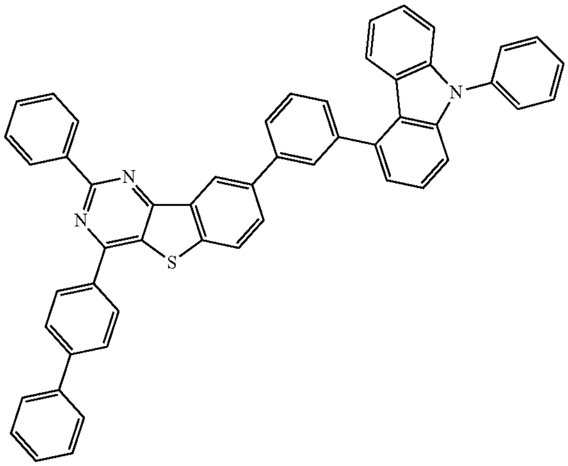
123
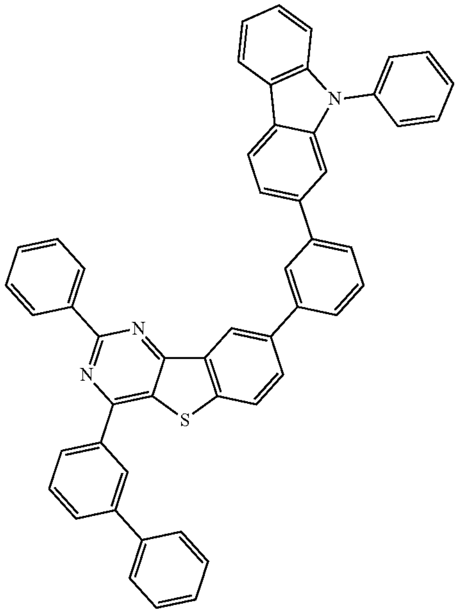
126
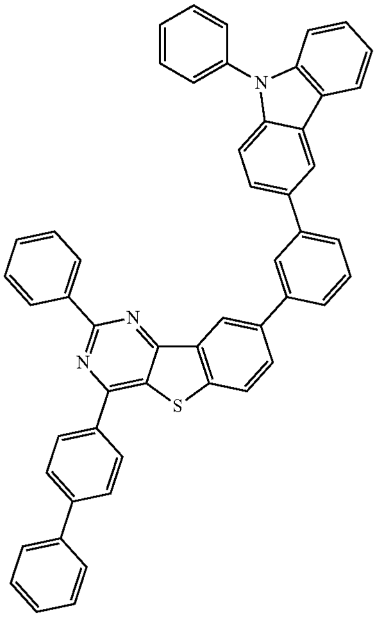

-continued
127
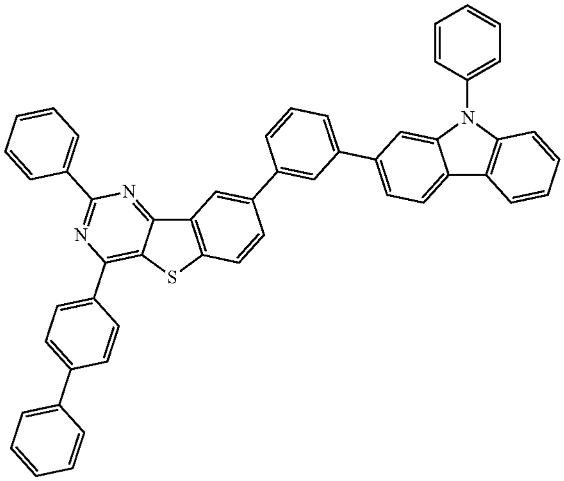
128
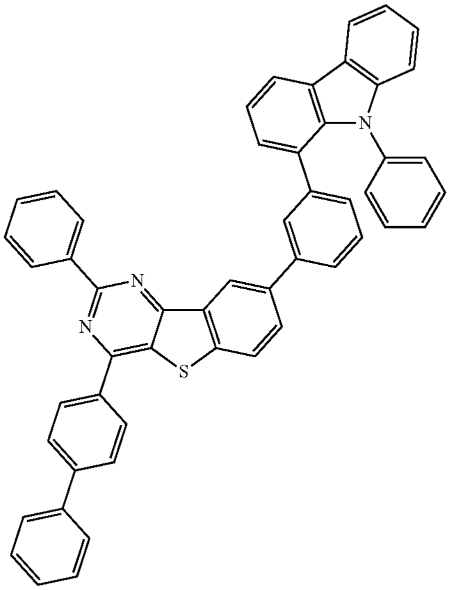
129
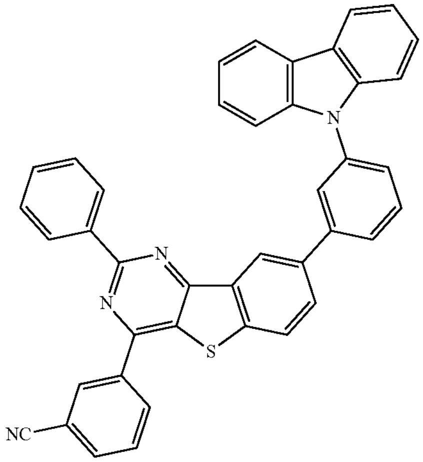
-continued
130
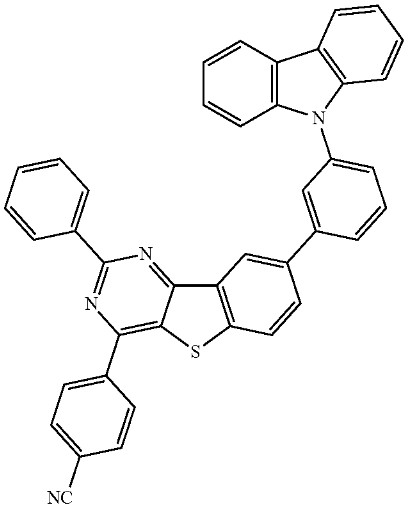
131
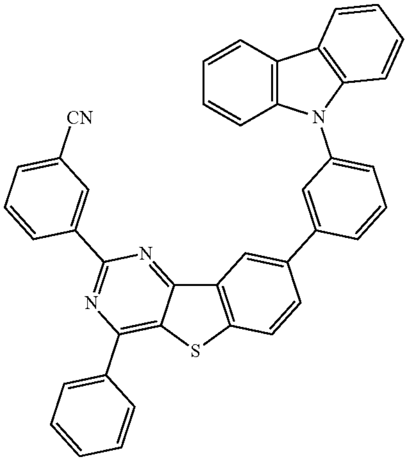
132
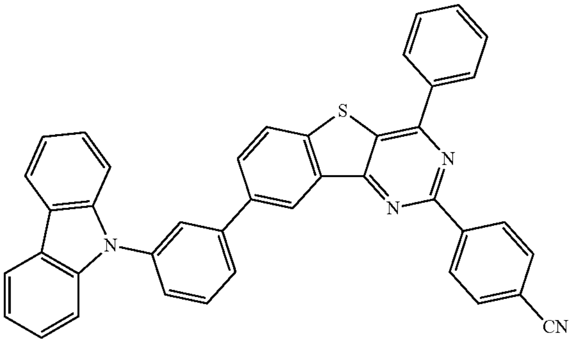

-continued
133
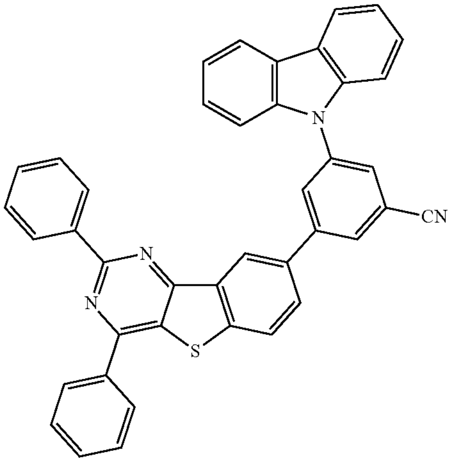
134
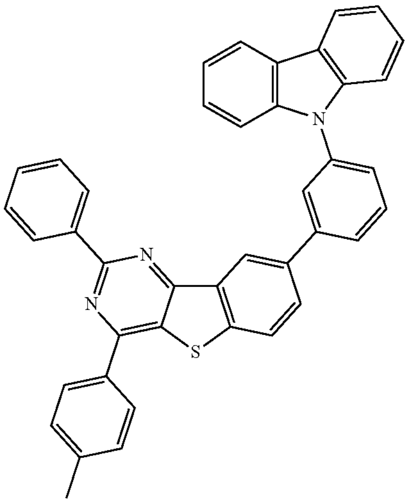
135
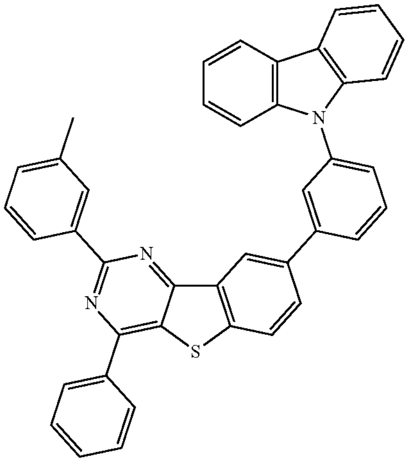
-continued
136
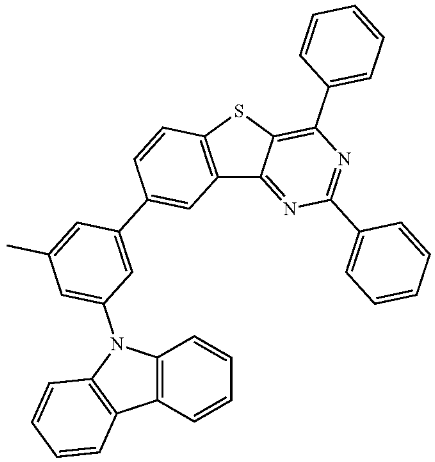
137
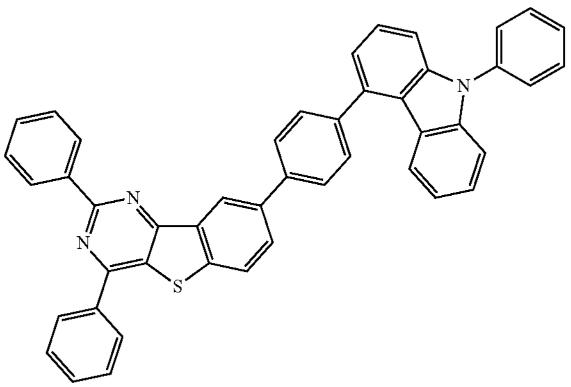
138
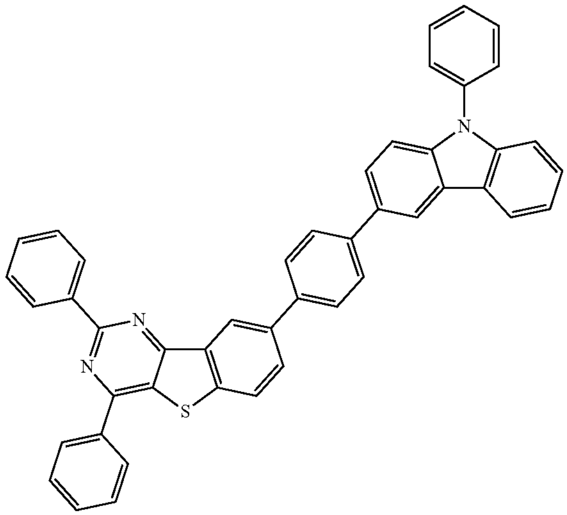

-continued
139
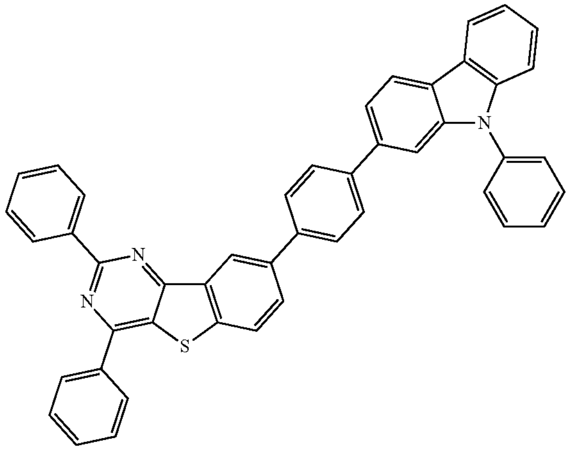
140
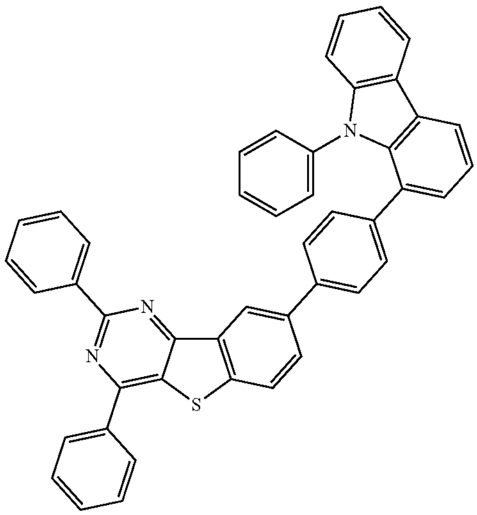
141
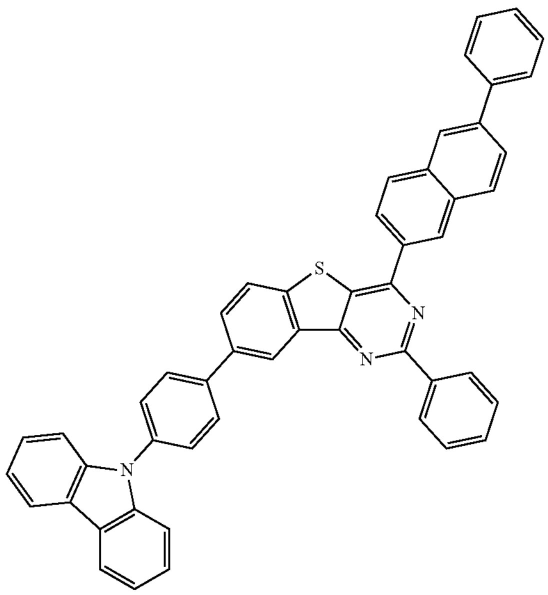
-continued
142
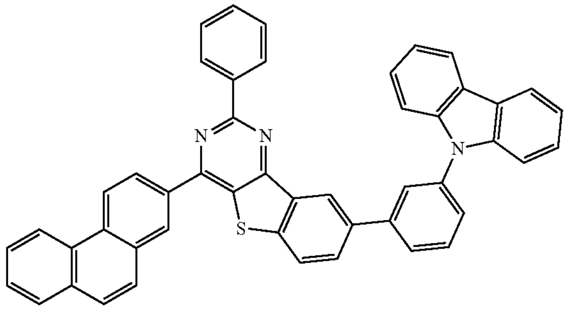
143
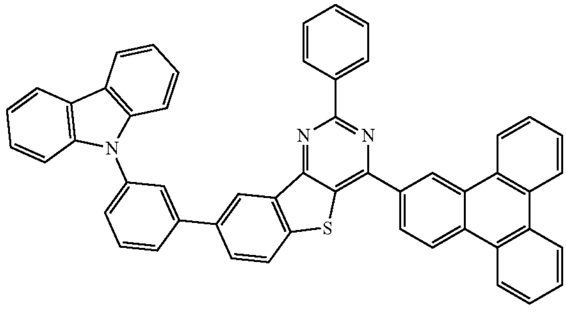
144
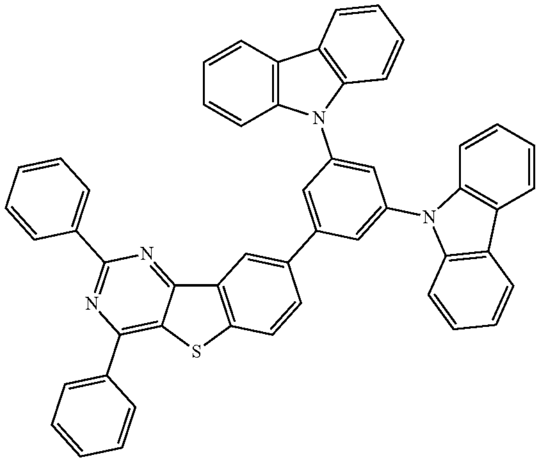
145
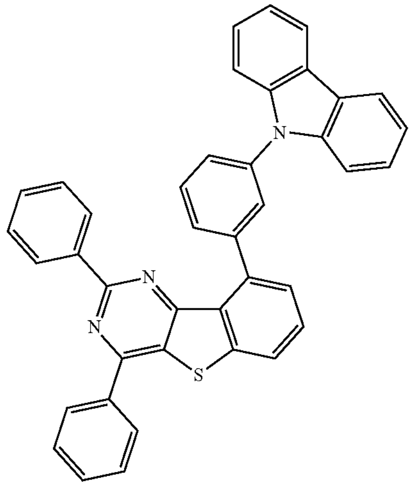

-continued
146
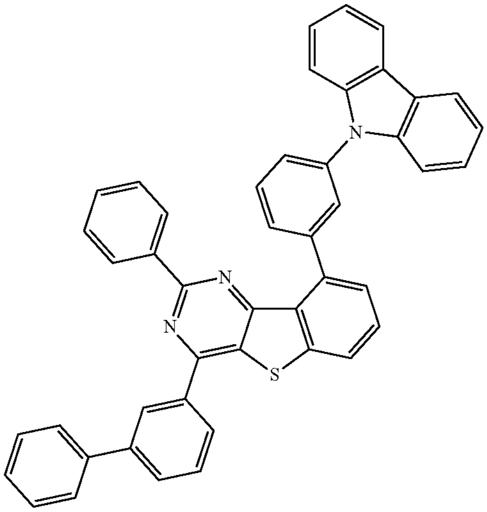
147
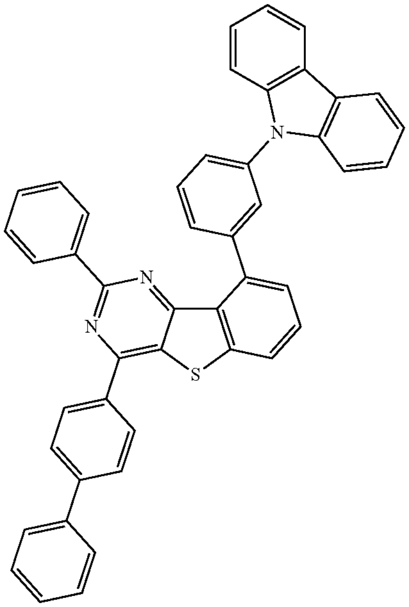
148
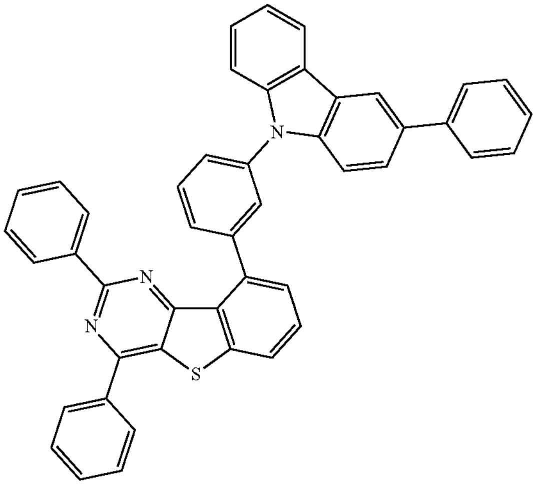
-continued
149
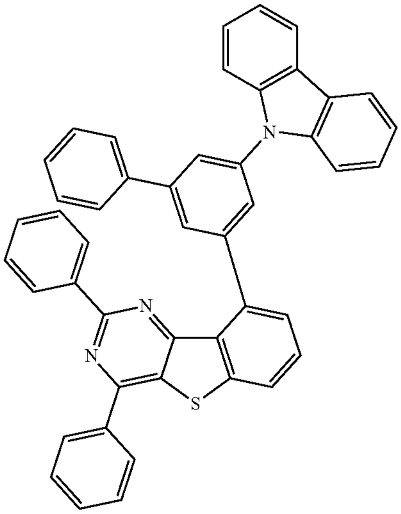
150
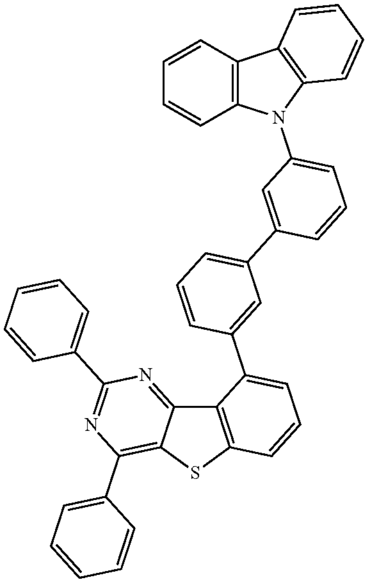

-continued
151
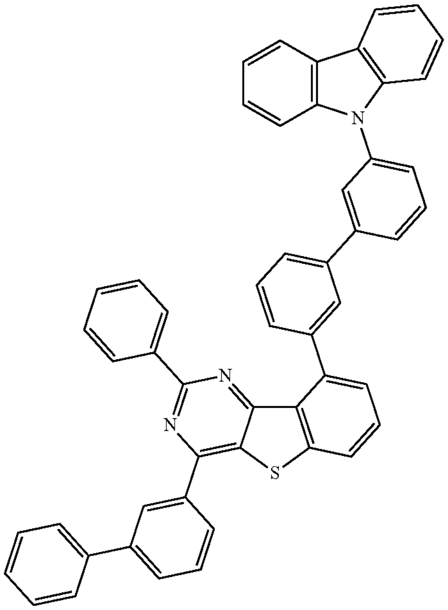
152
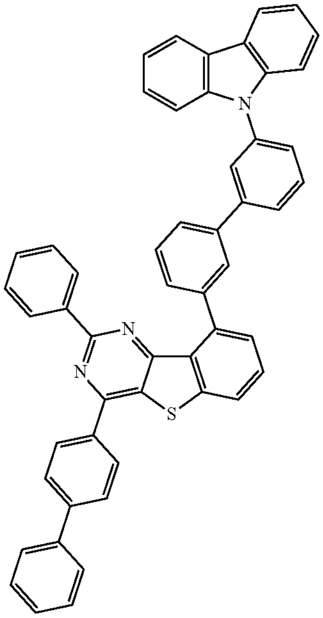
-continued
153
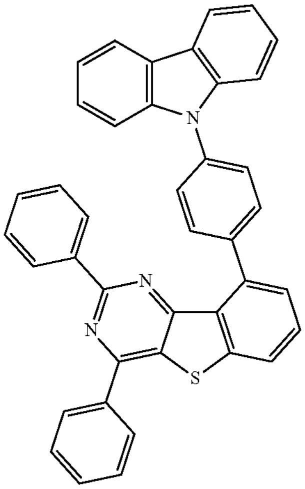
154
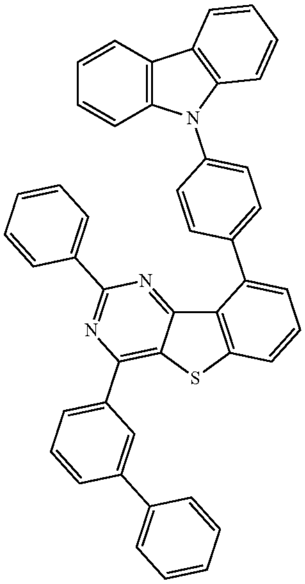

-continued
155
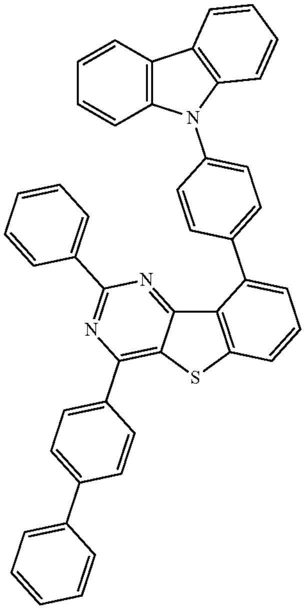
157
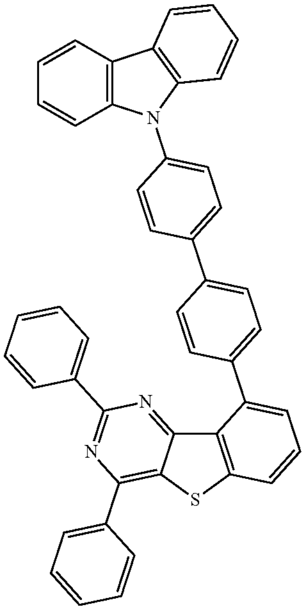
156
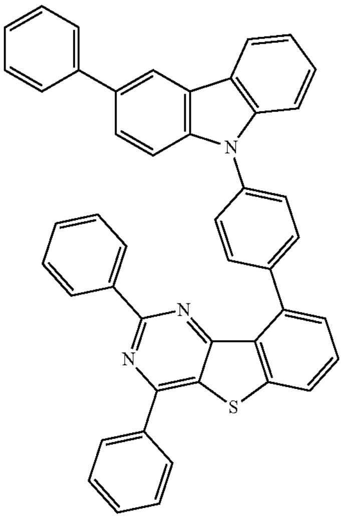
158
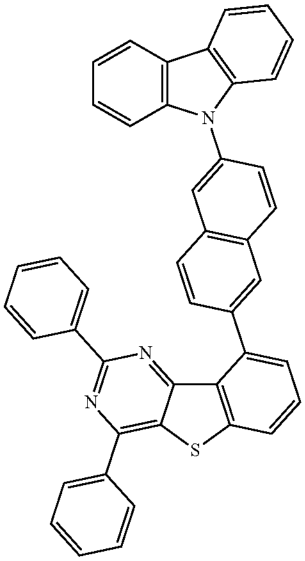

-continued
159
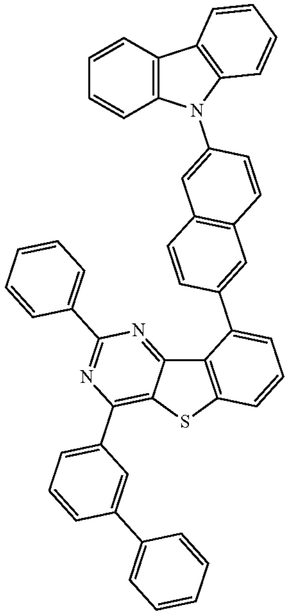
160
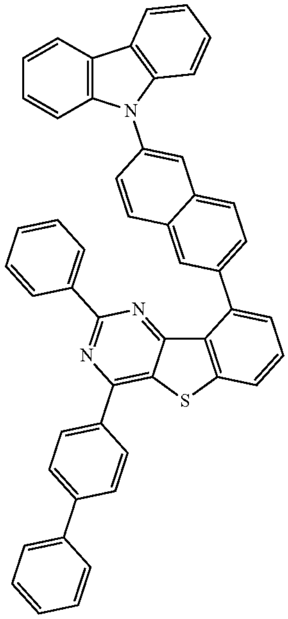
-continued
161
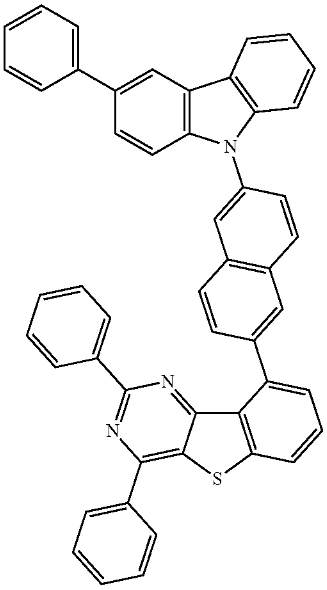
162
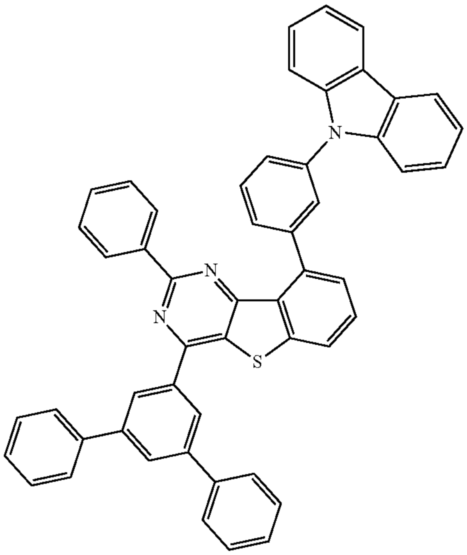

163
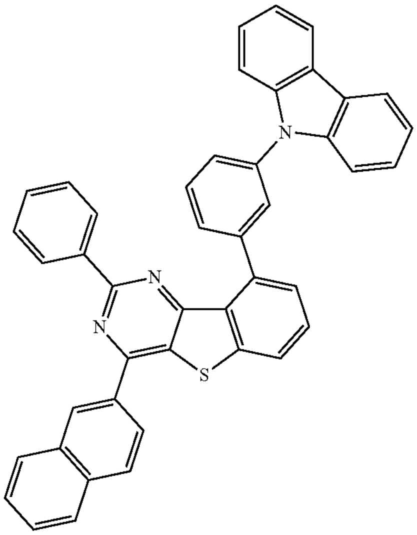
164
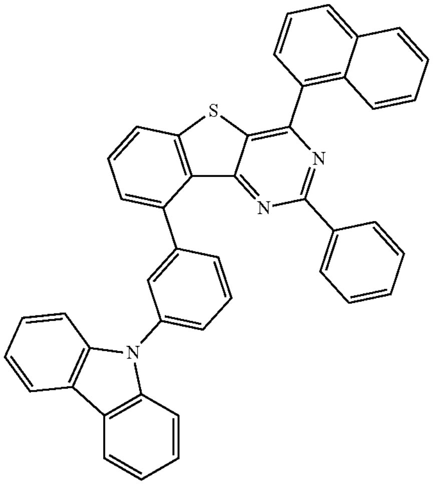
165
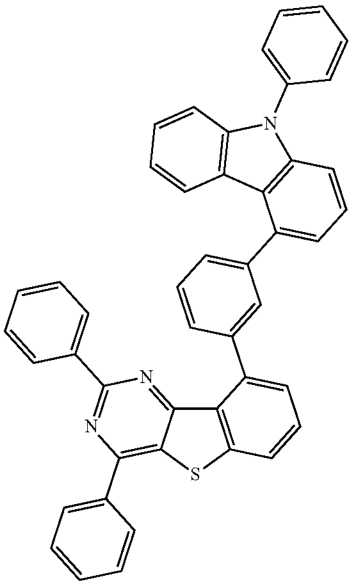
166
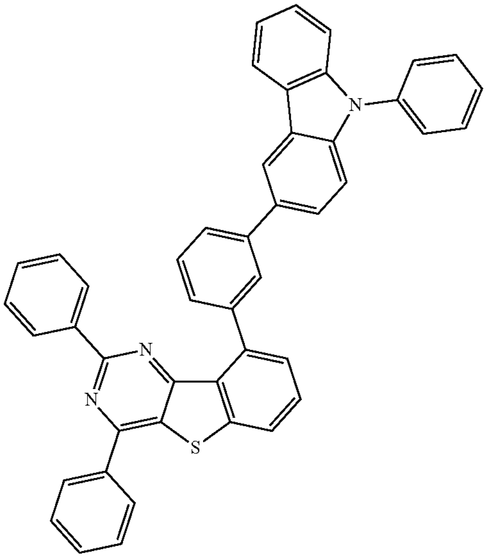
167
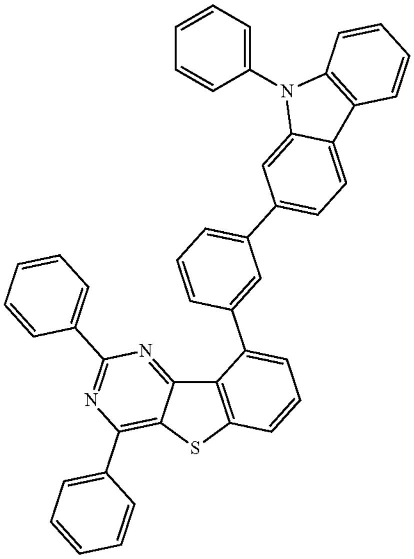
168
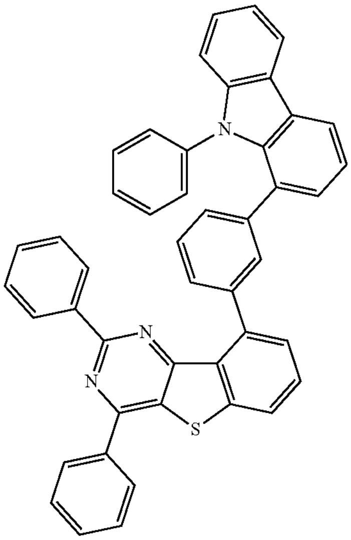

169
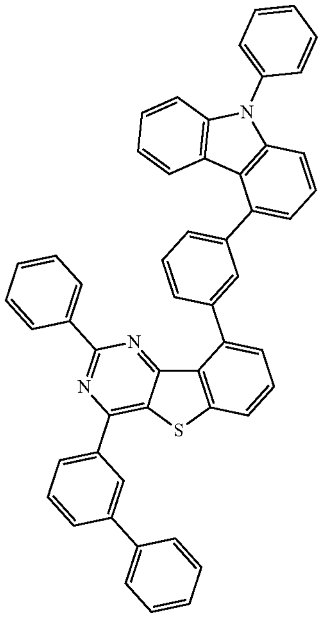
170
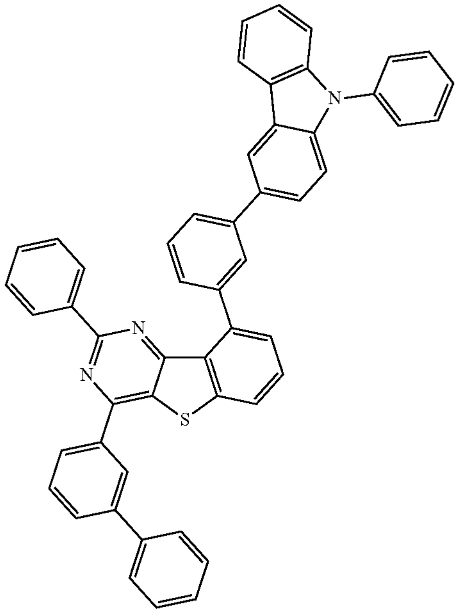
171
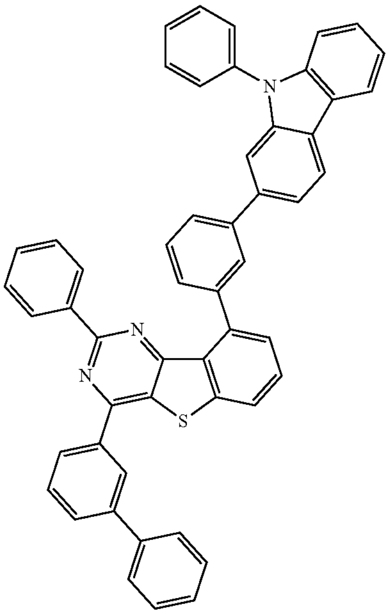
172
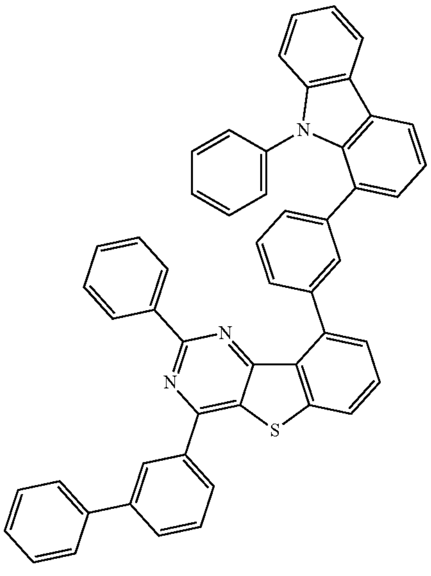

-continued
173
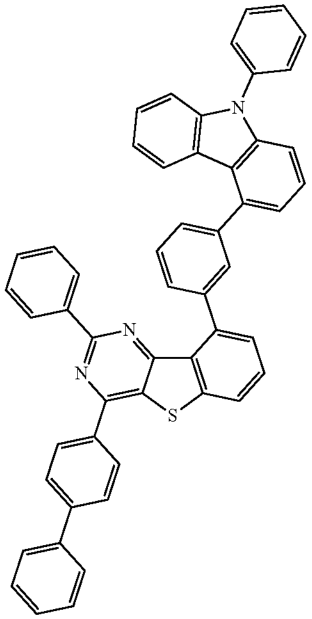
174
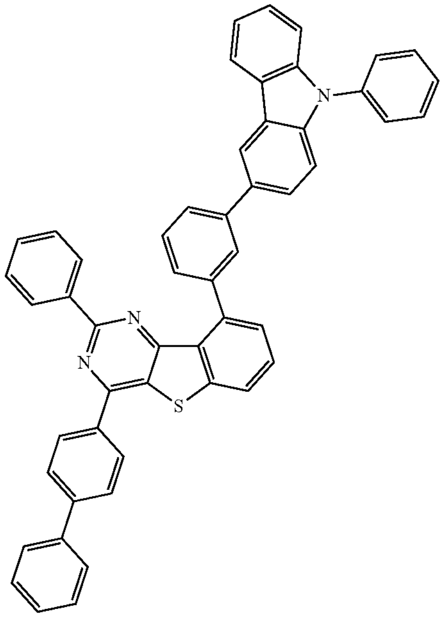
-continued
175
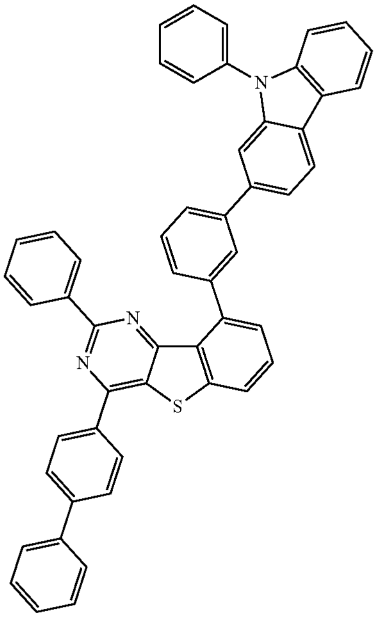
176
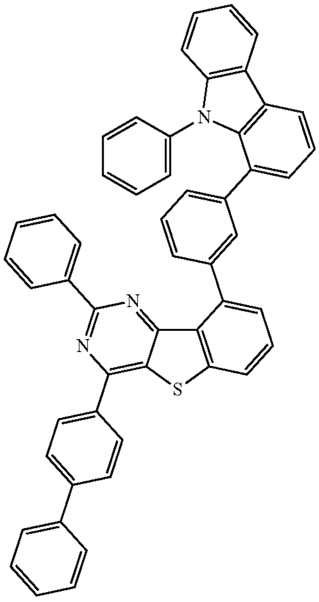

-continued
177
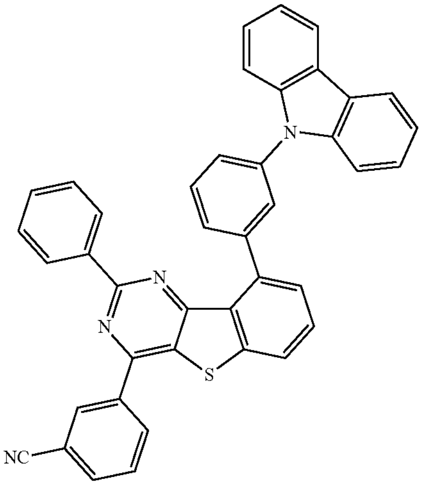
178
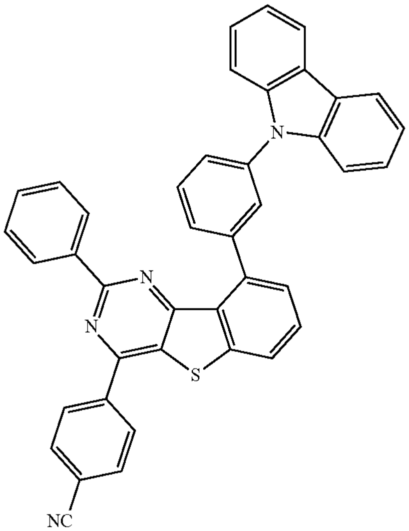
179
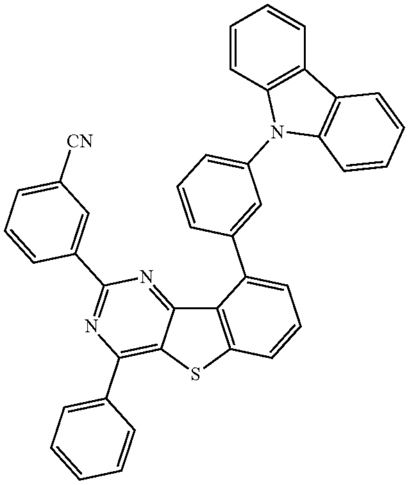
-continued
180
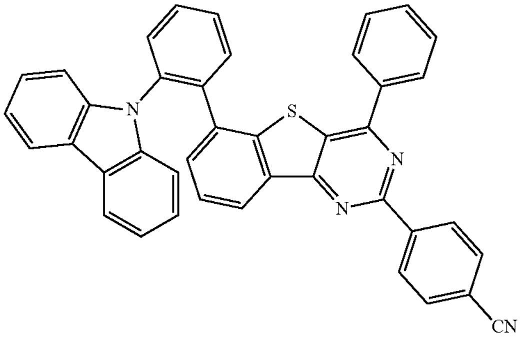
181
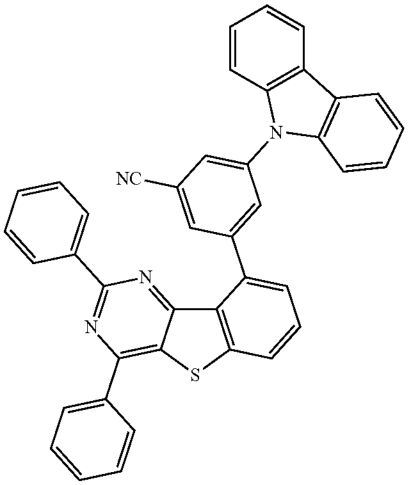
182
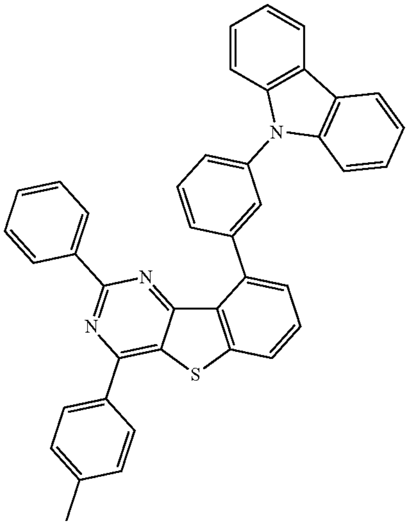

-continued
183
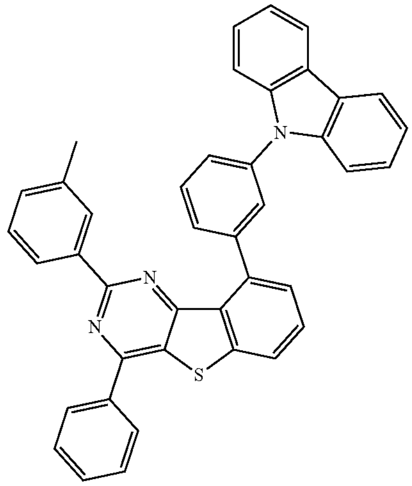
184
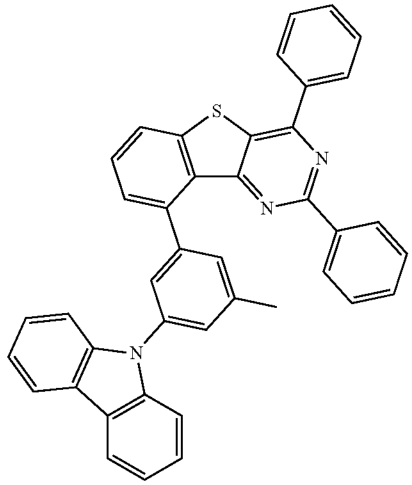
185
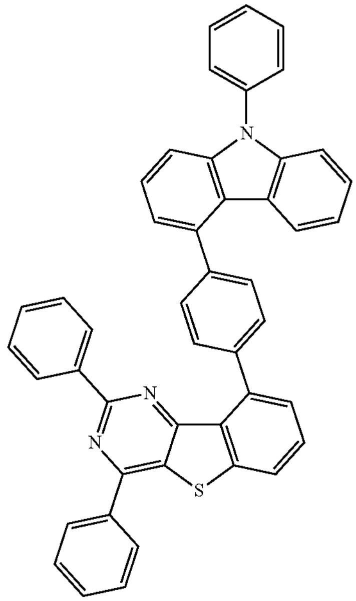
-continued
186
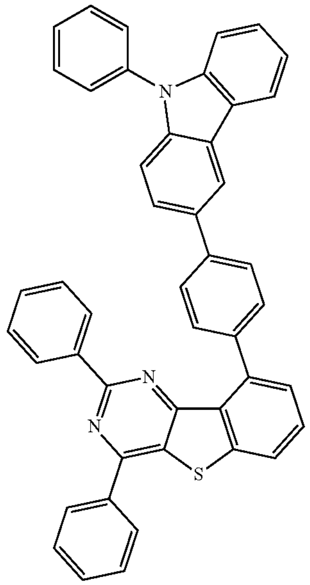
187
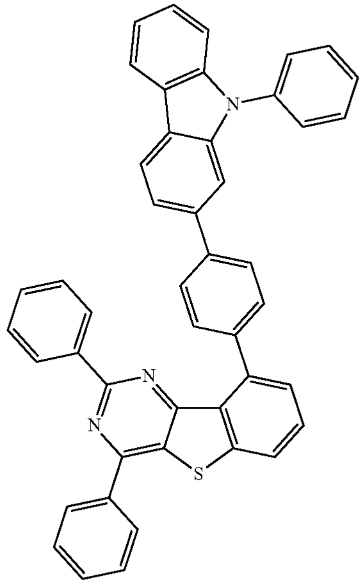

-continued
188
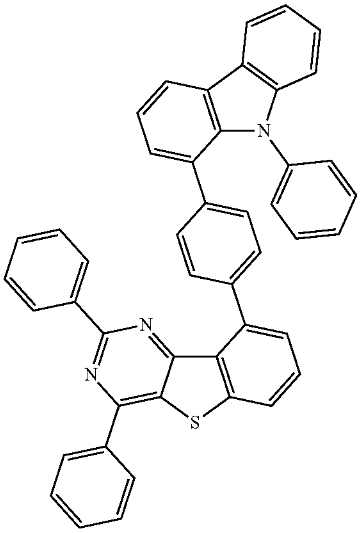
189
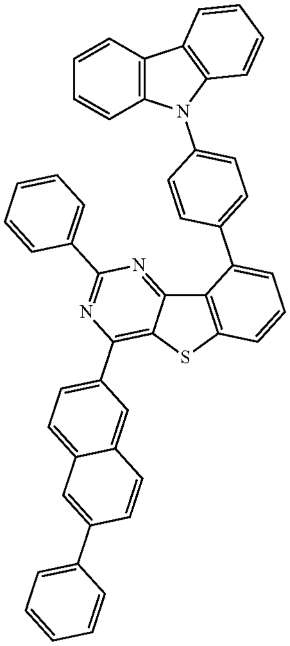
-continued
190
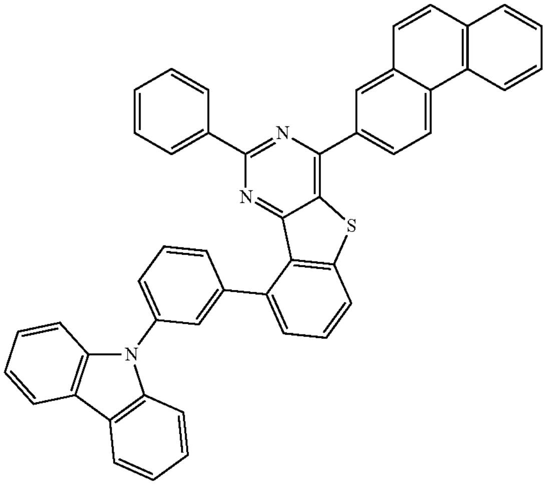
191
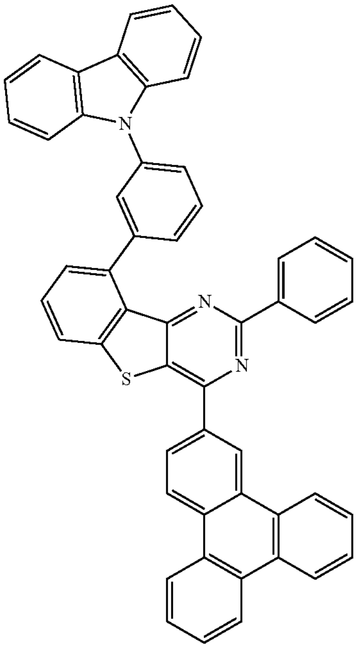

-continued
192
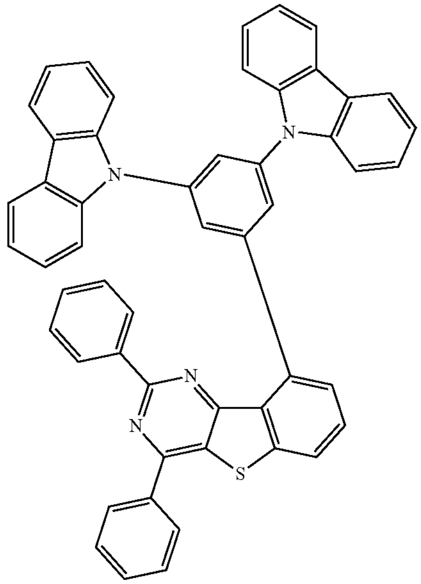
193
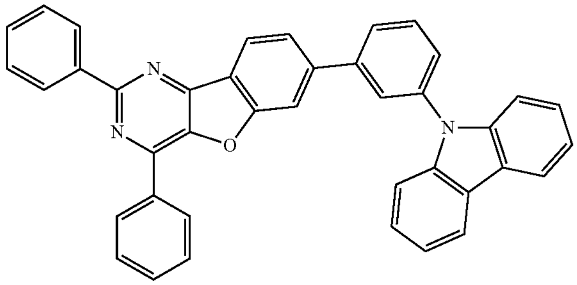
194
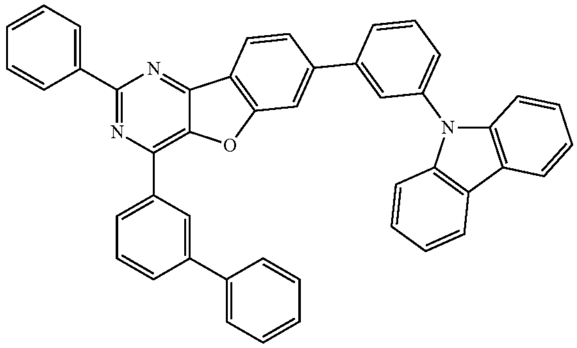
-continued
195
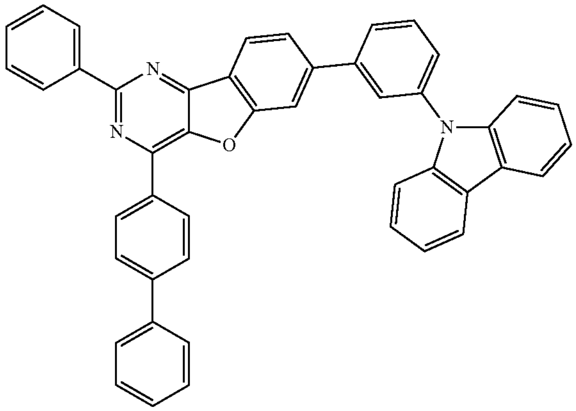
196
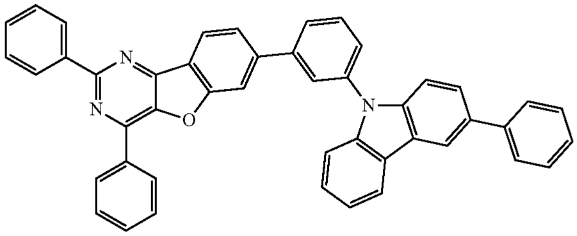
197
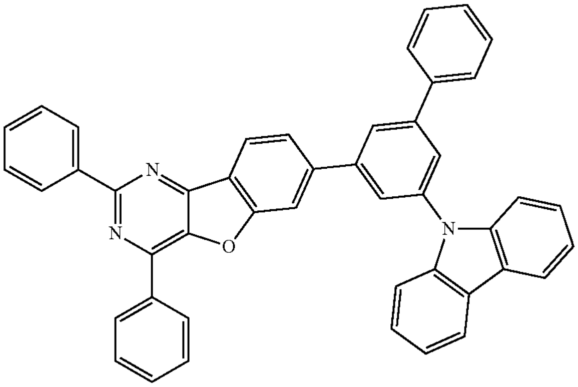
198
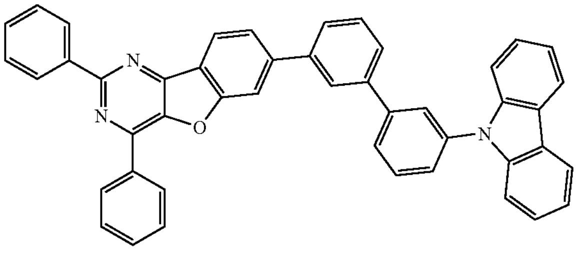

-continued
199
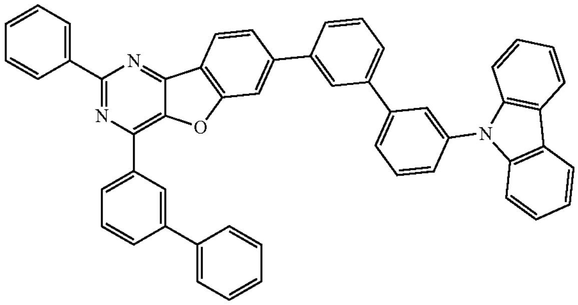
200
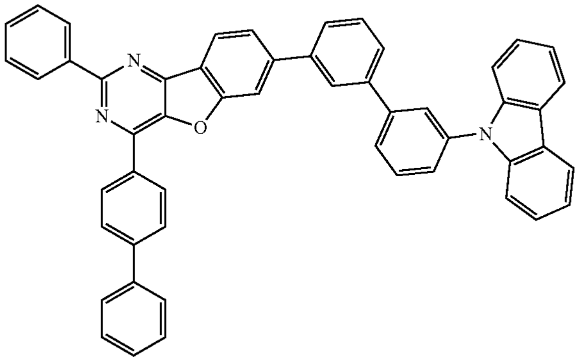
201
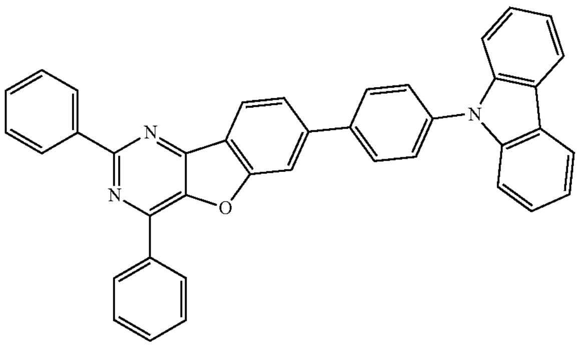
202
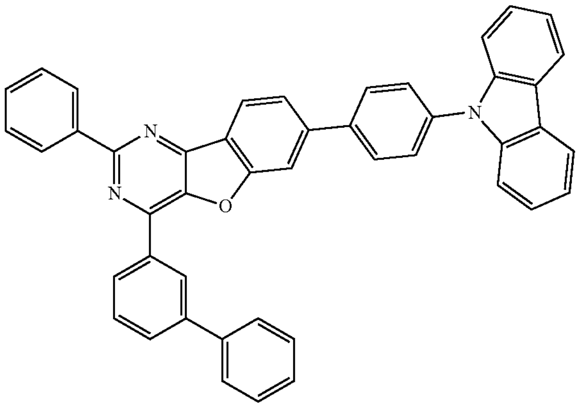
-continued
203
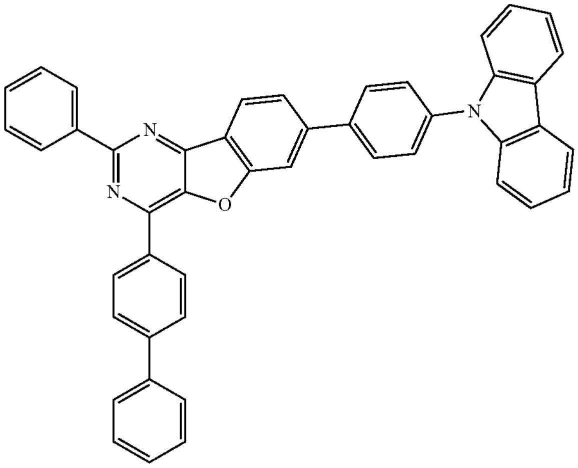
204
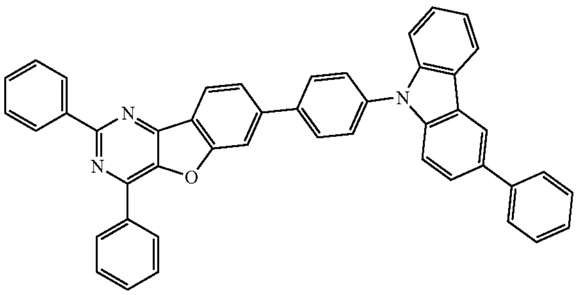
205
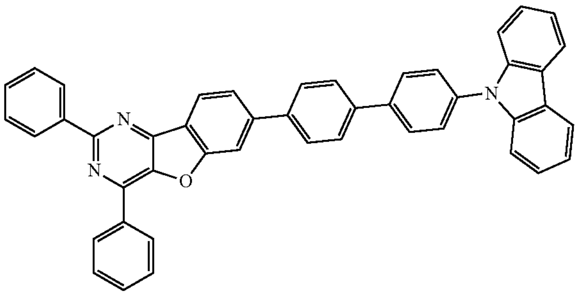
206
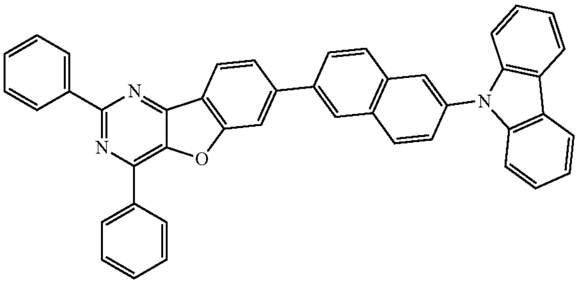

-continued
207
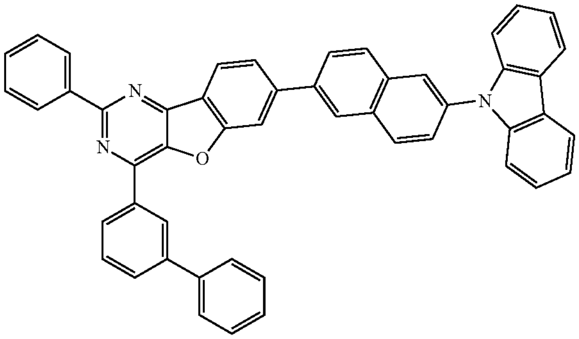
208
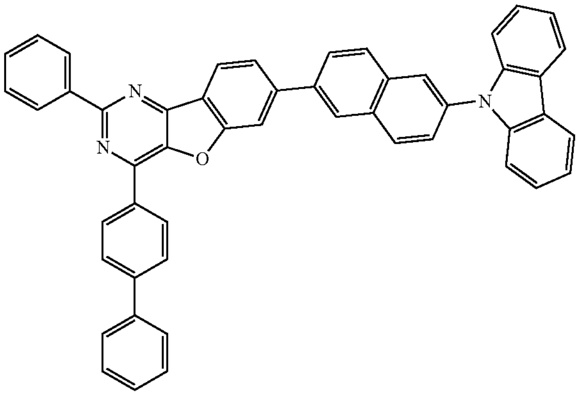
209
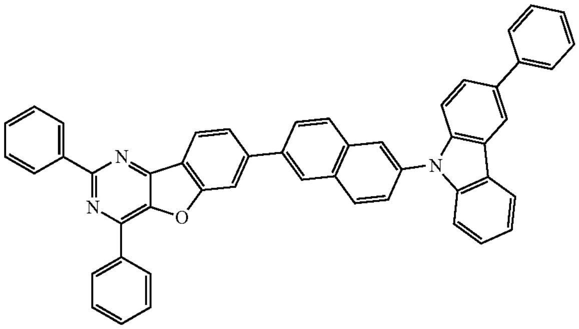
210
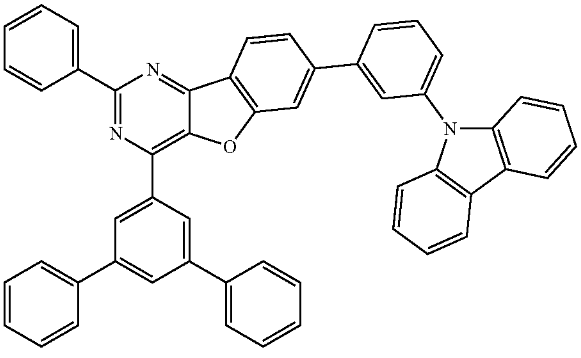
-continued
211
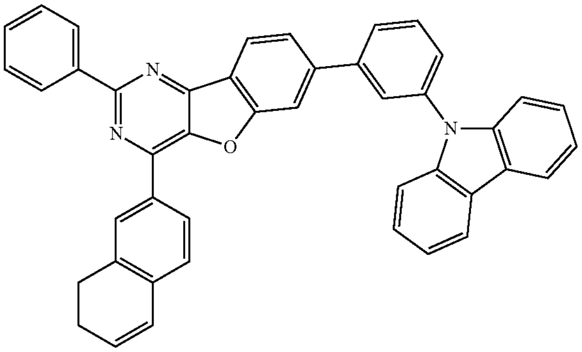
212
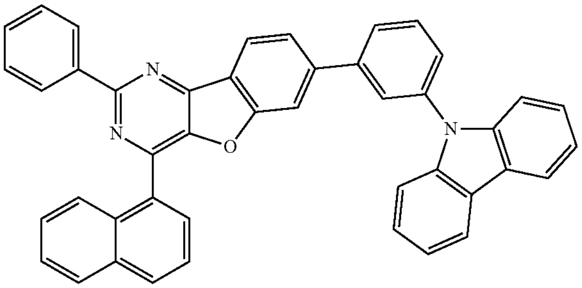
213
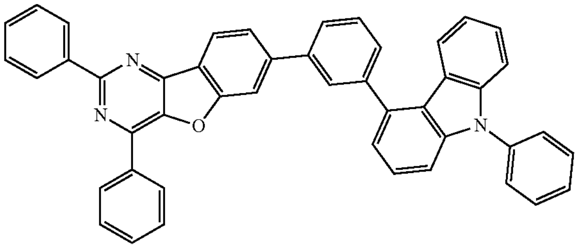
214
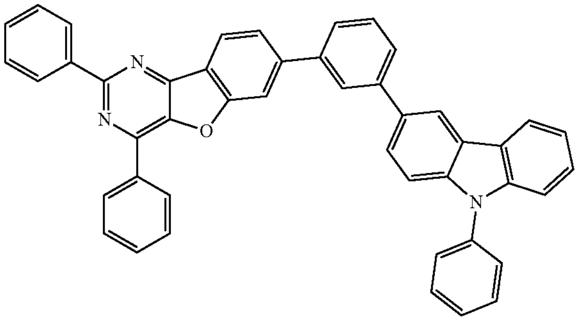
215
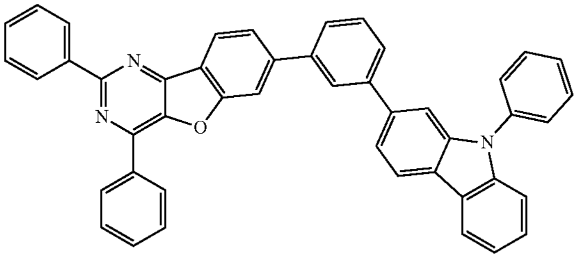

-continued
216
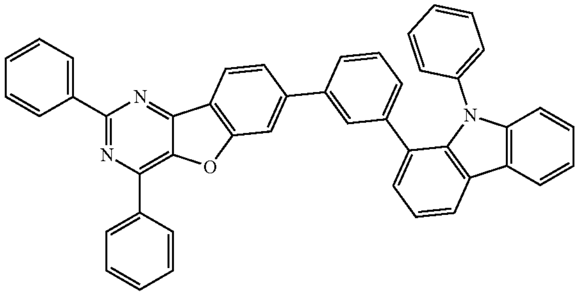
217
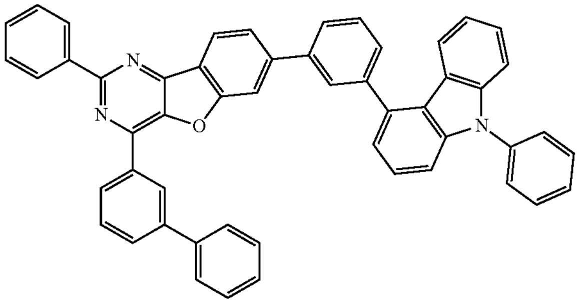
218
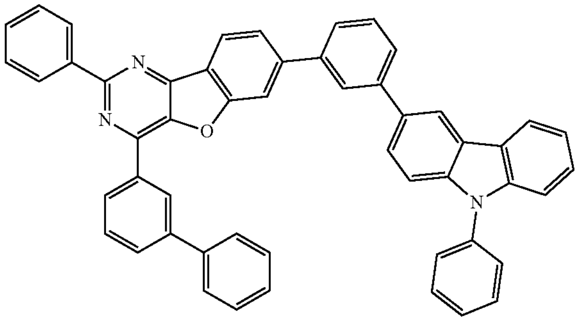
219
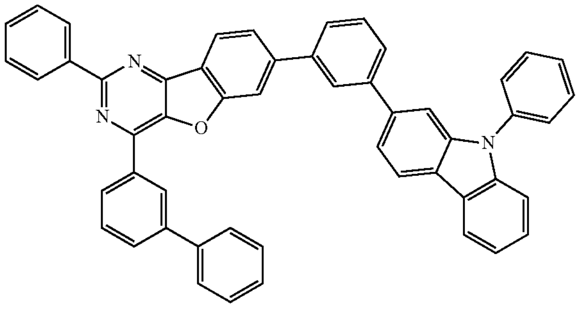
-continued
220
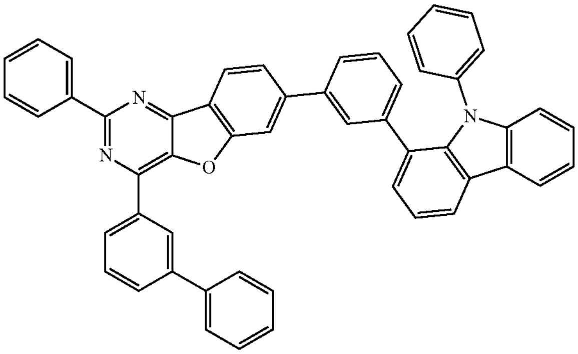
221
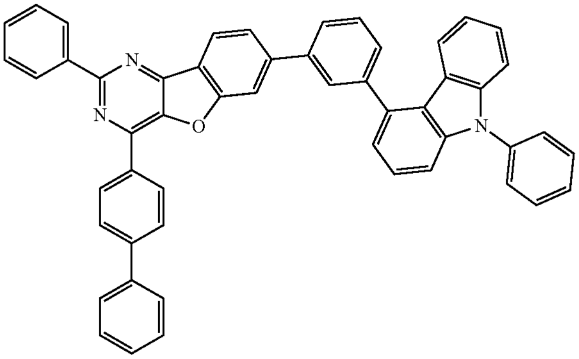
222
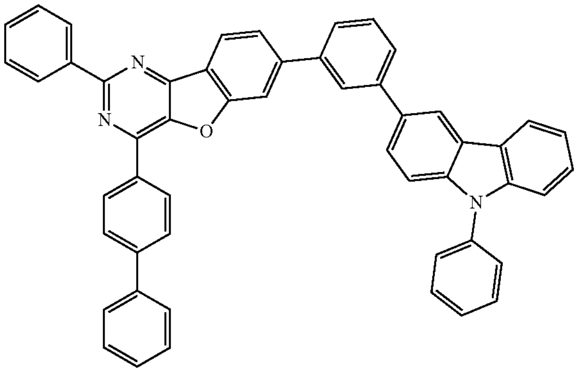
223
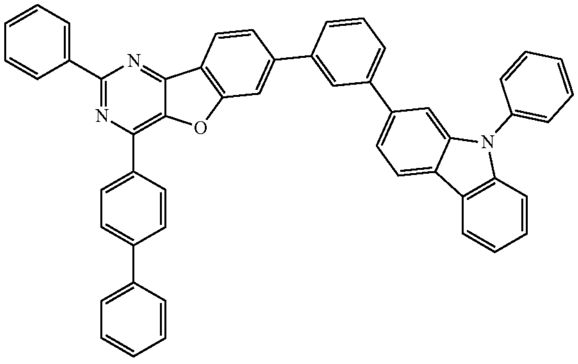

224
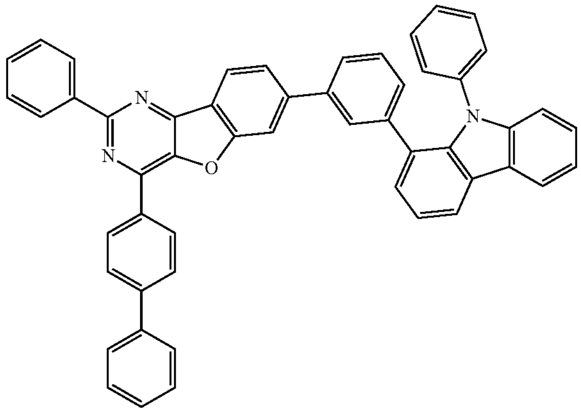
225
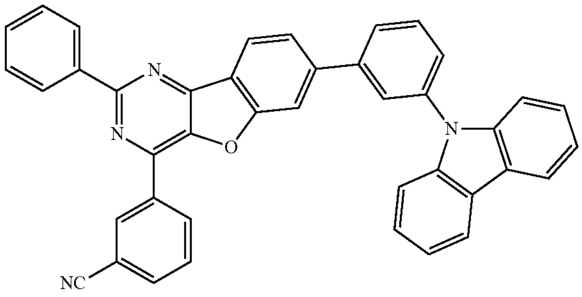
226
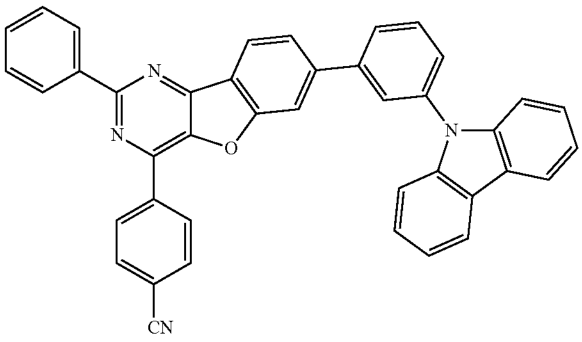
227
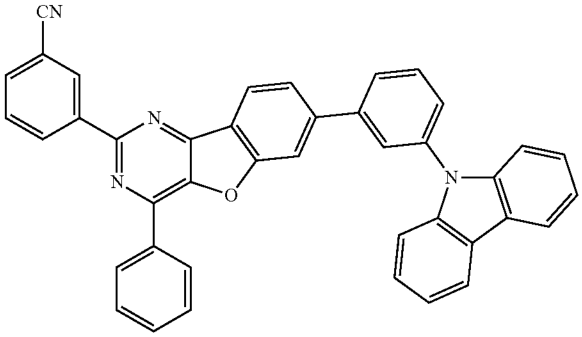
228
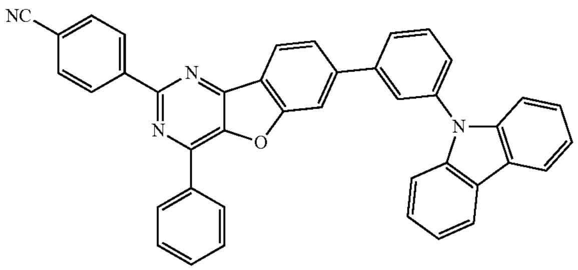
229
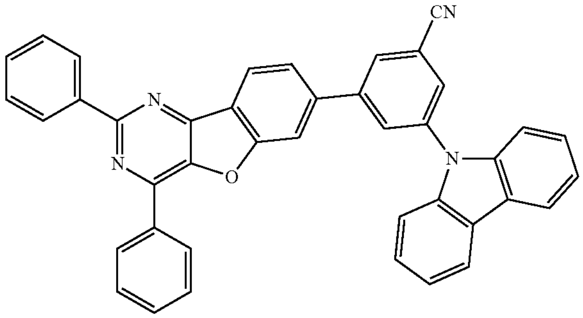
230
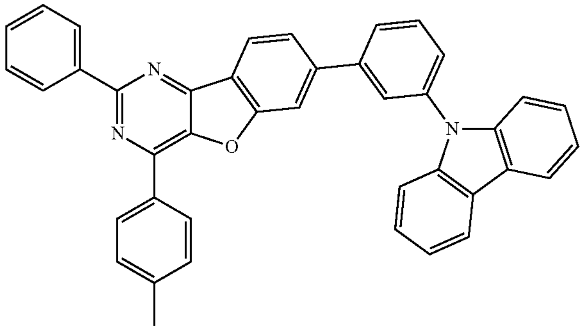
231
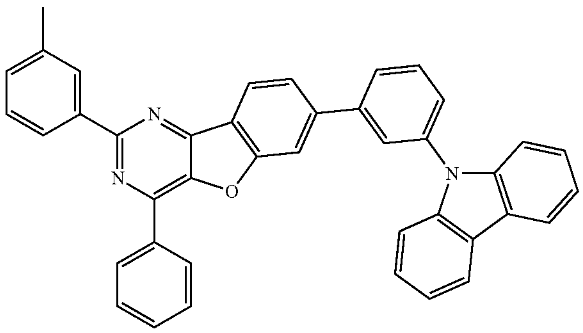

-continued
232
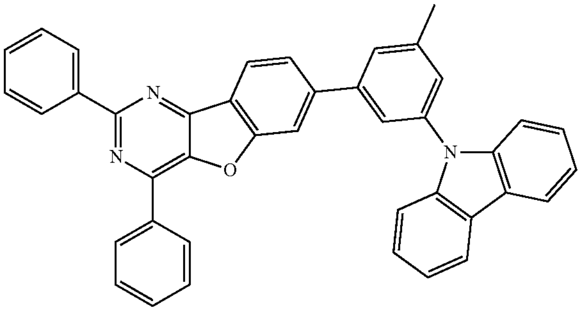
233
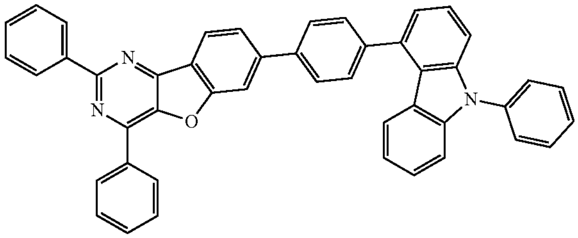
234
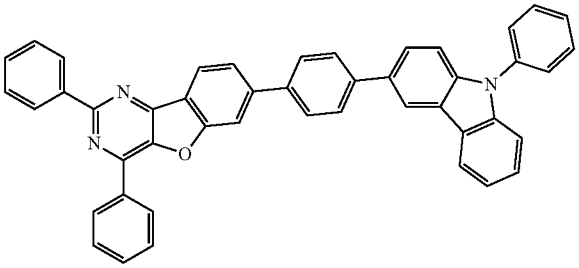
235
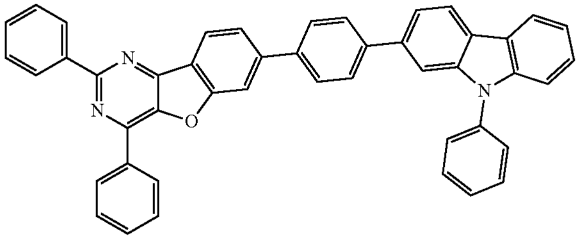
236
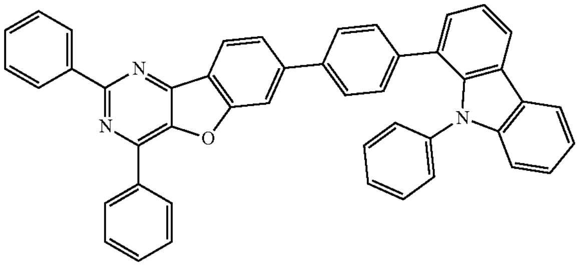
-continued
237
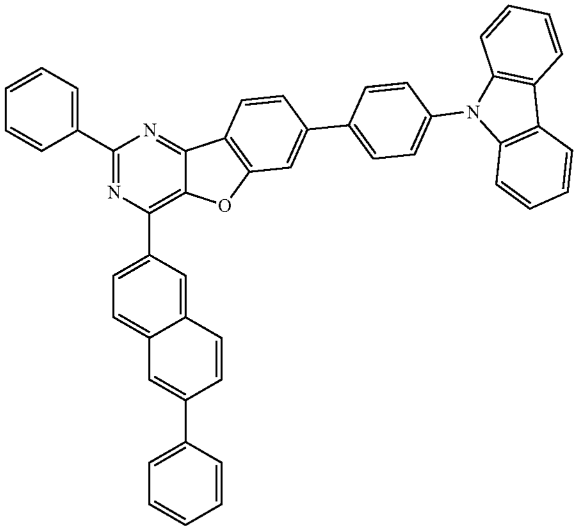
238
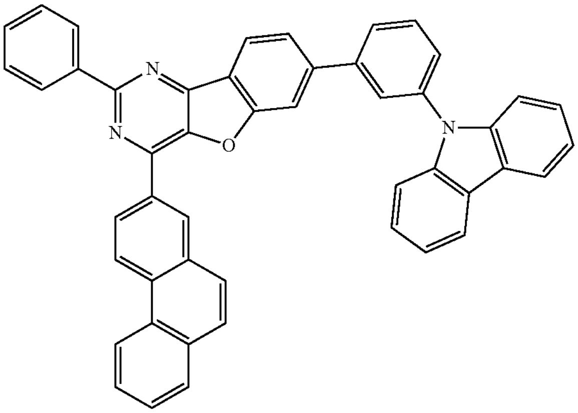
239
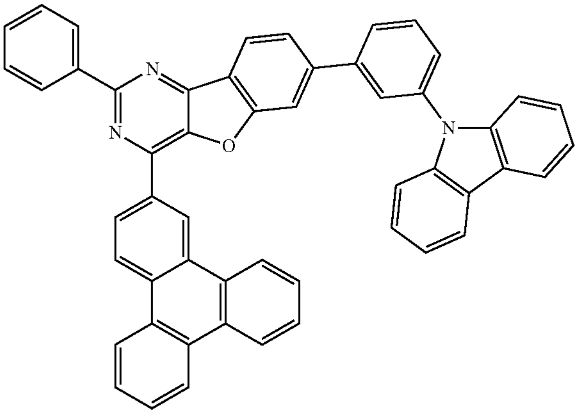

-continued
240
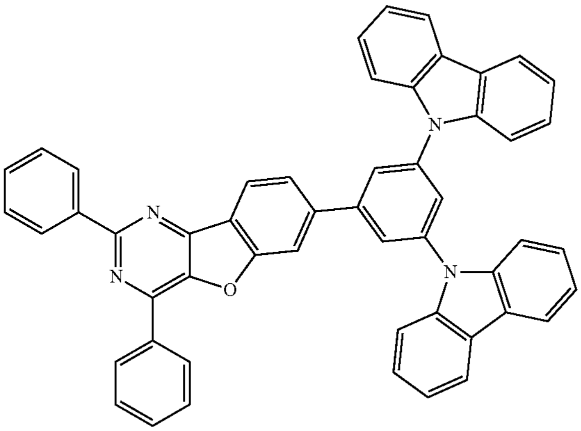
241
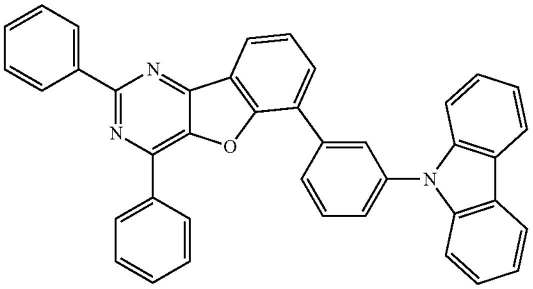
242
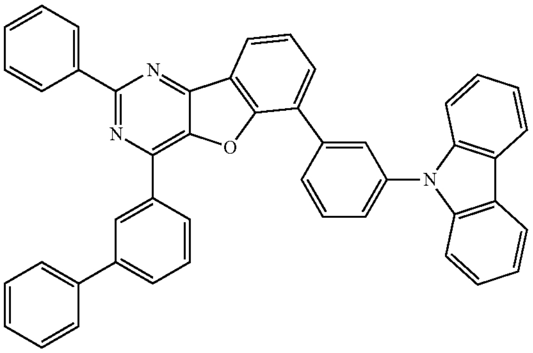
243
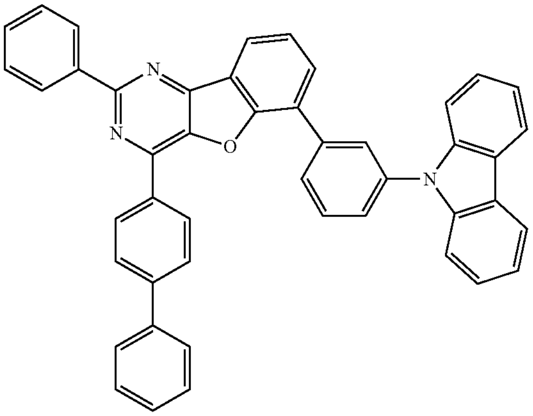
-continued
244
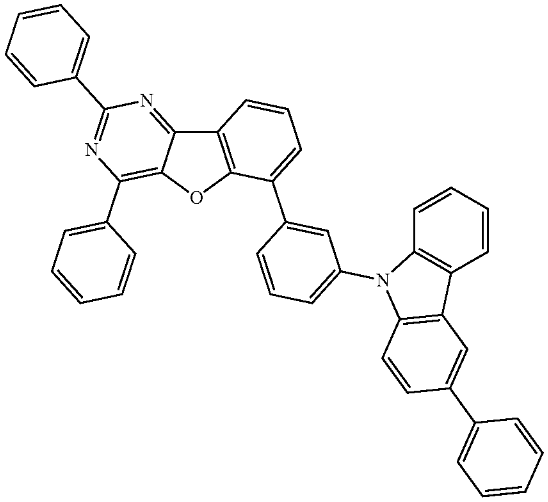
245
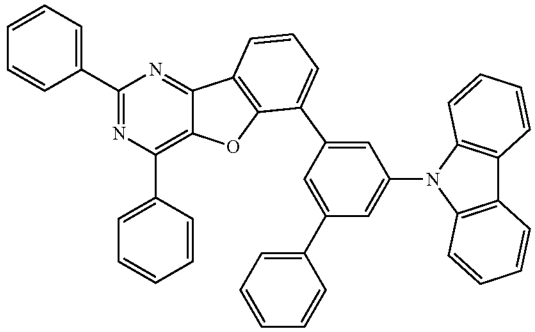
246
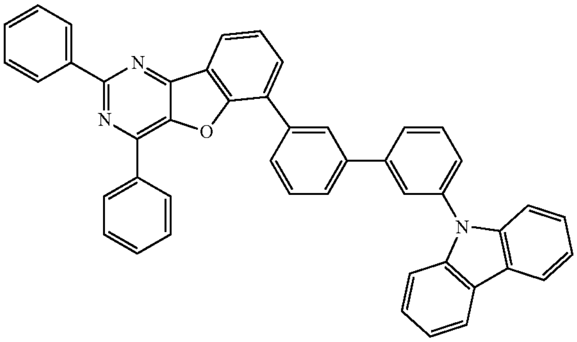
247
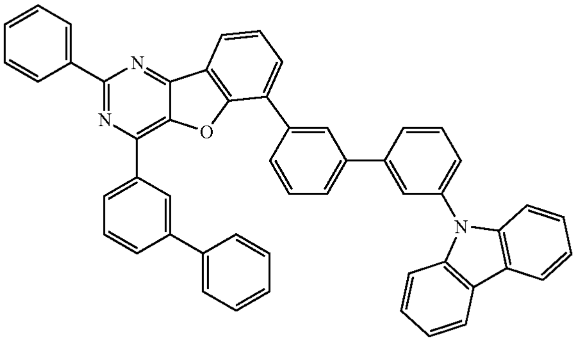

-continued
248
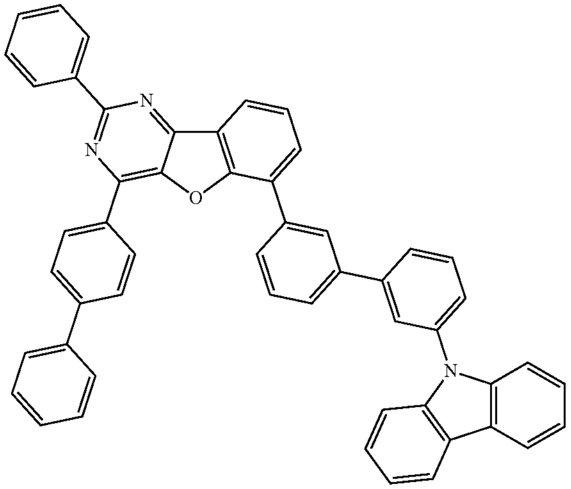
249
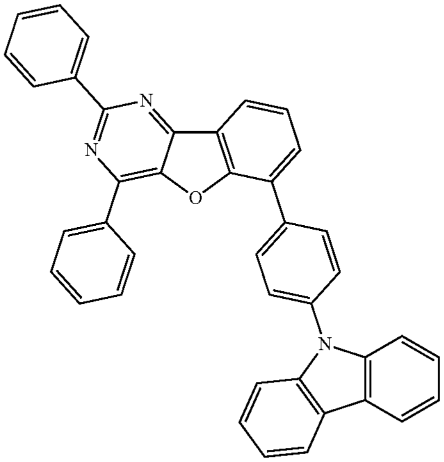
250
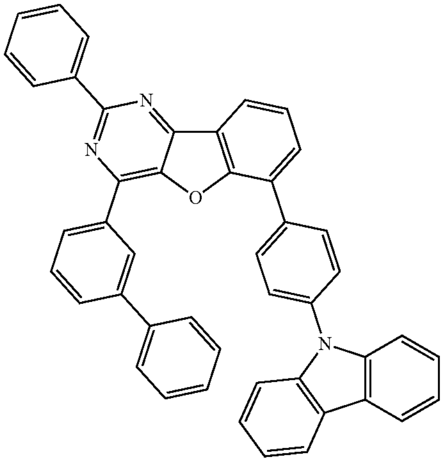
-continued
251
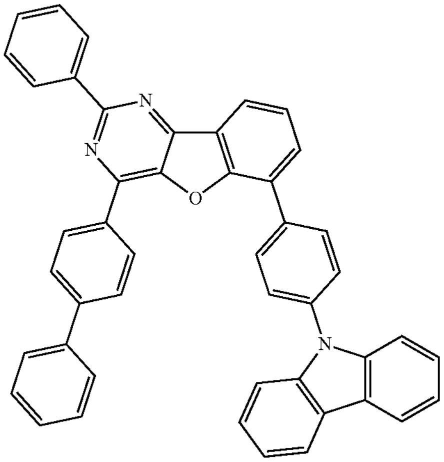
252
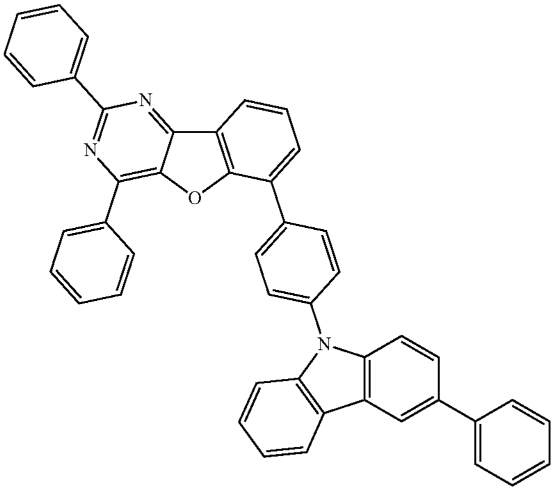
253
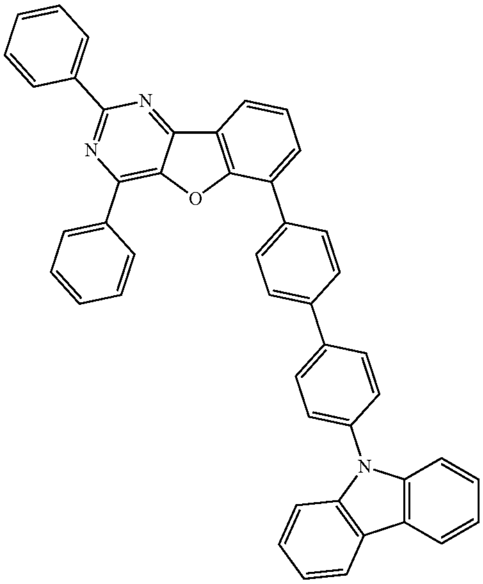

-continued
254
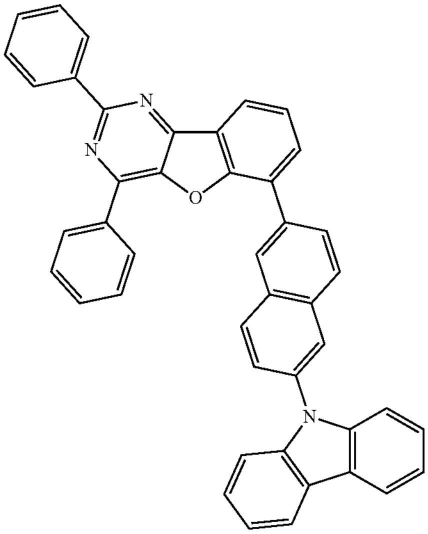
255
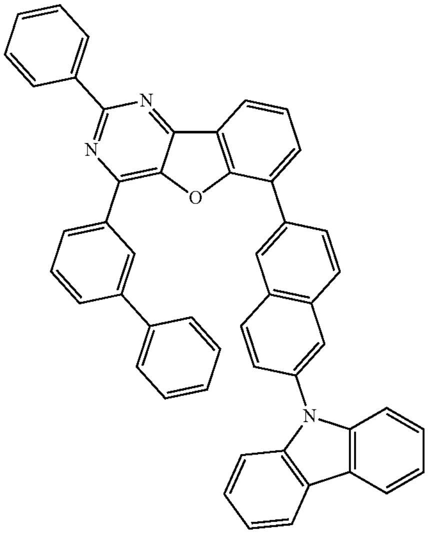
256
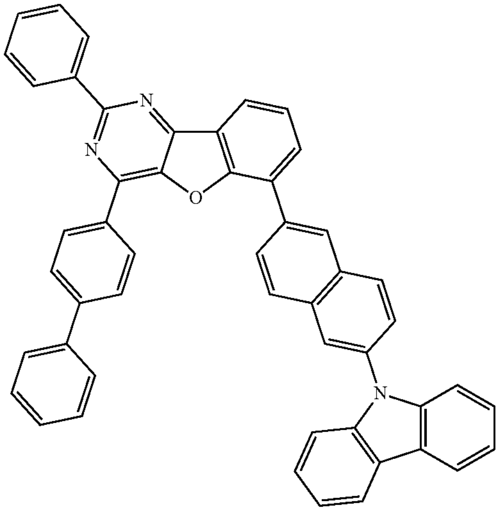
-continued
257
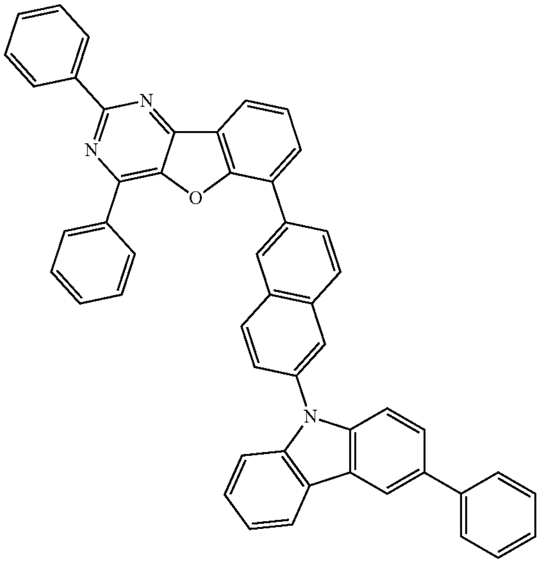
258
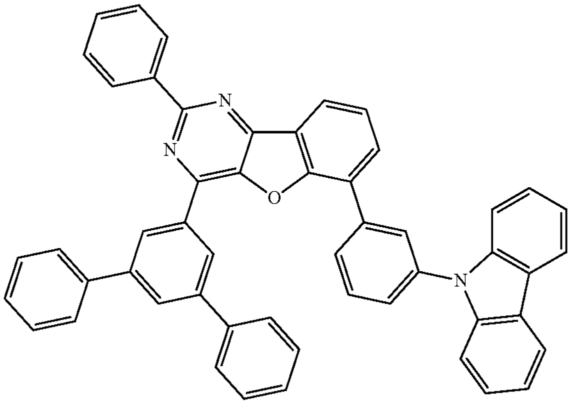
259
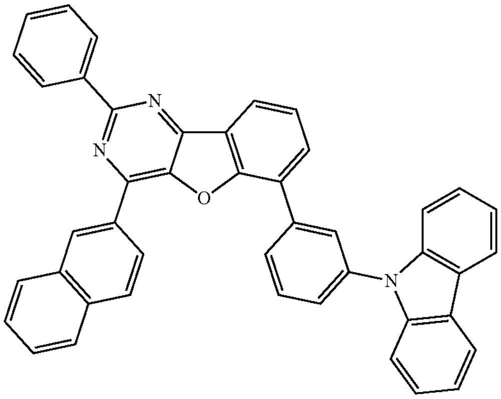

-continued
260
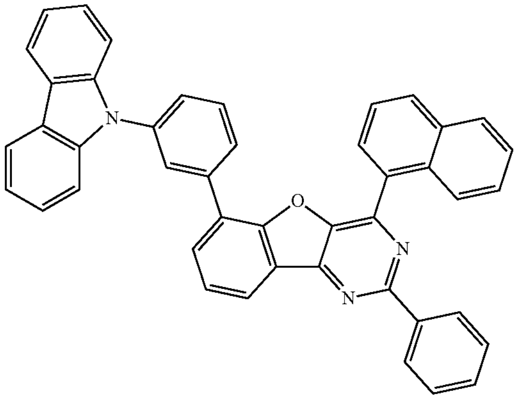
261
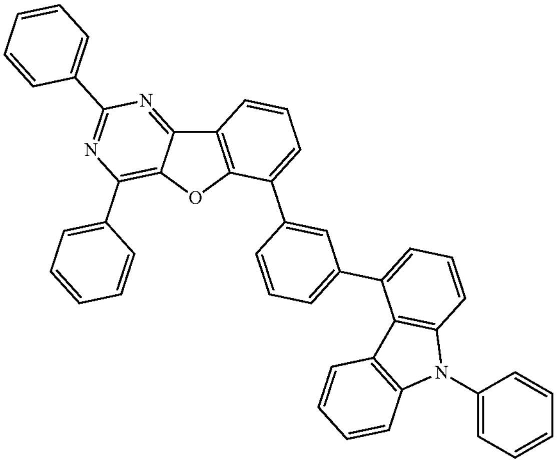
262
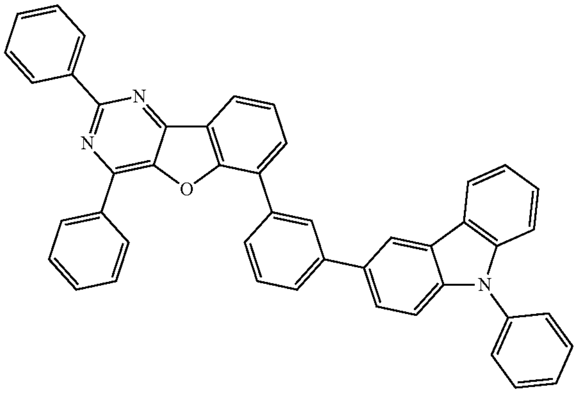
-continued
263
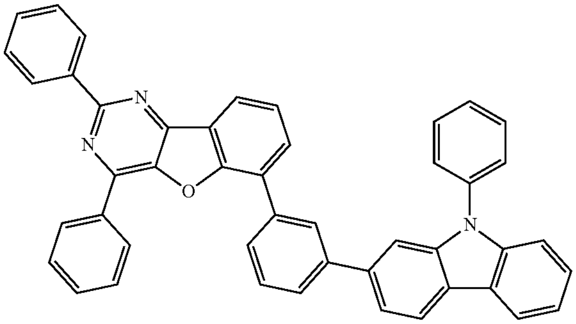
264
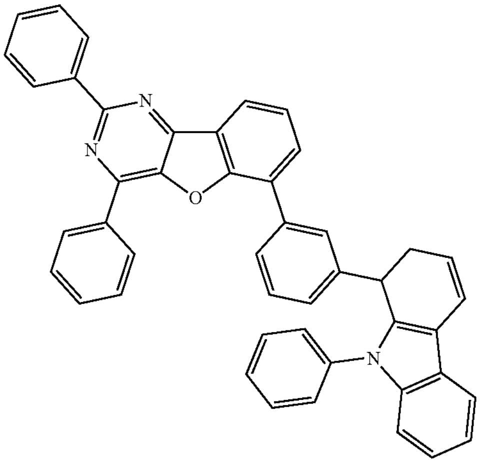
265
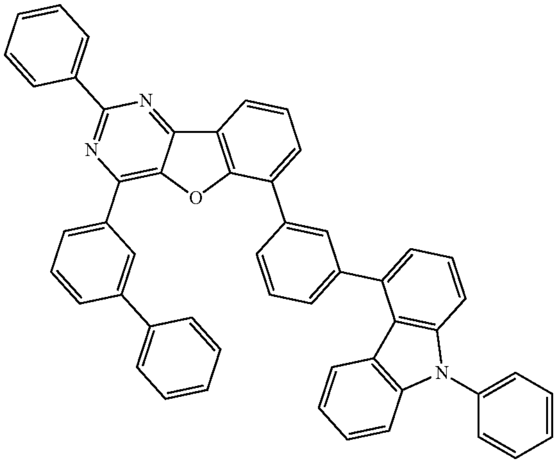

-continued
266
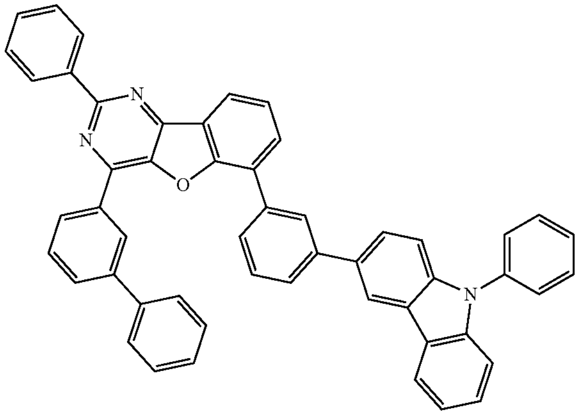
267
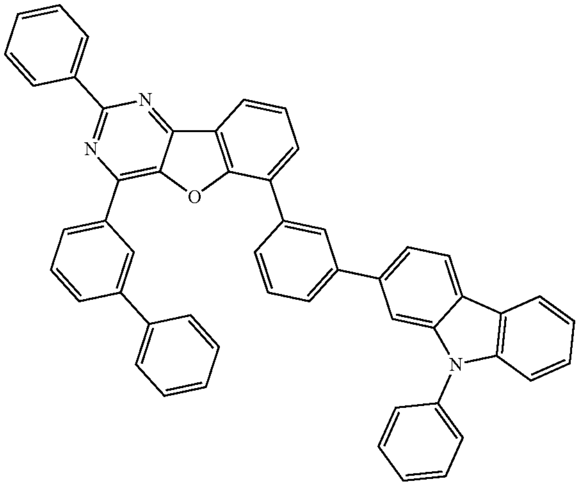
268
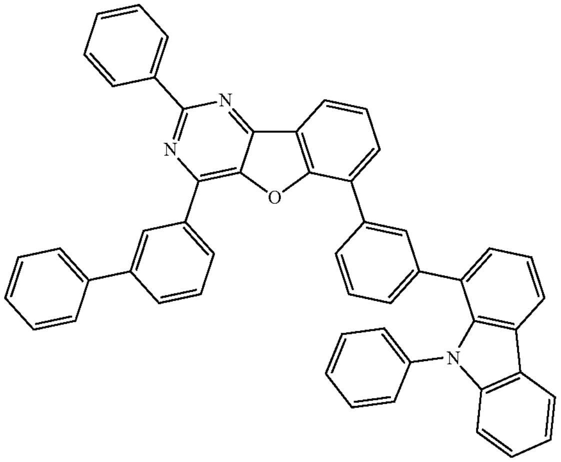
-continued
269
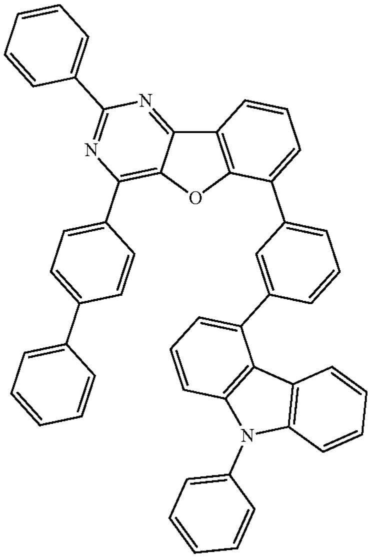
270
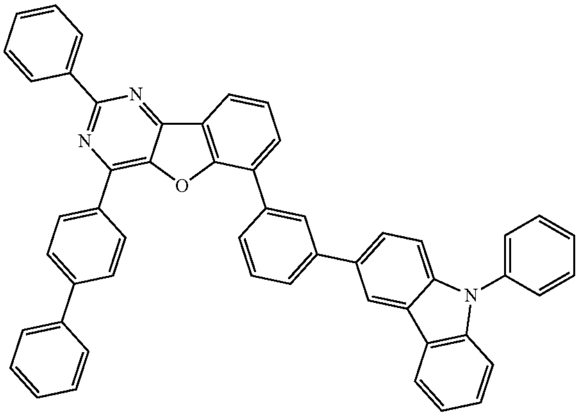
271
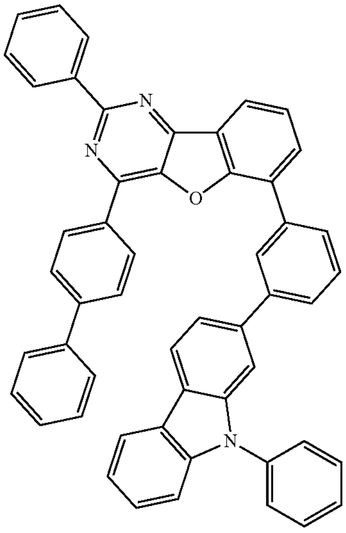

-continued
272
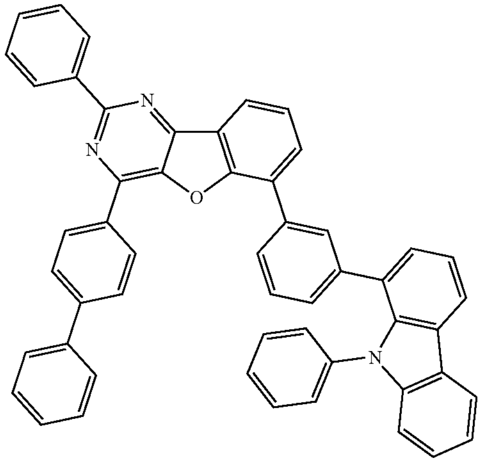
273
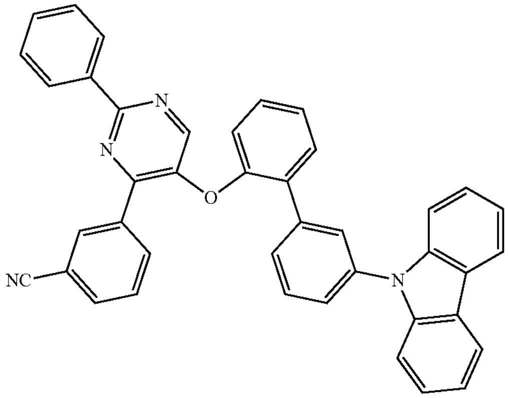
274
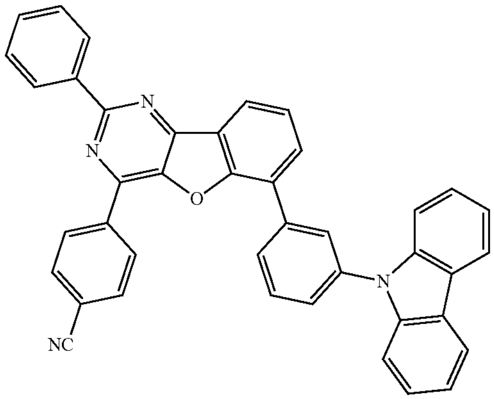
-continued
275
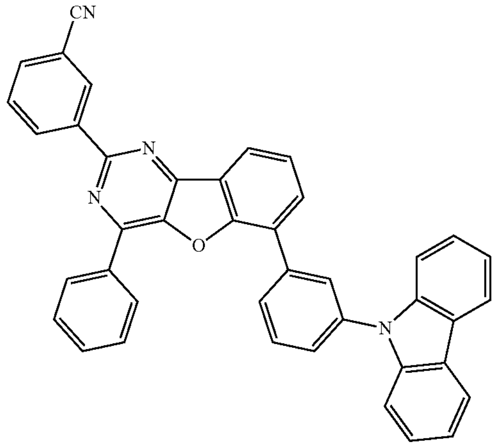
276
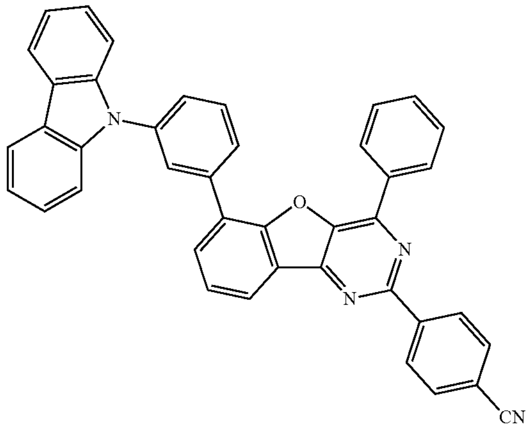
277
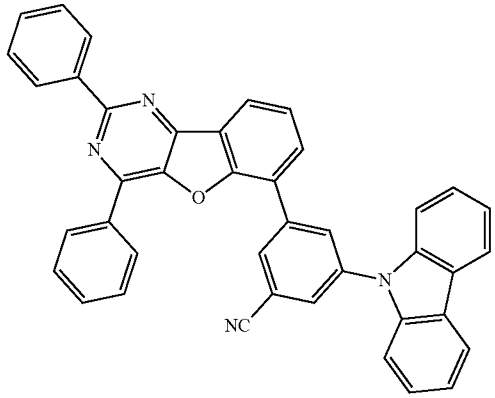

278
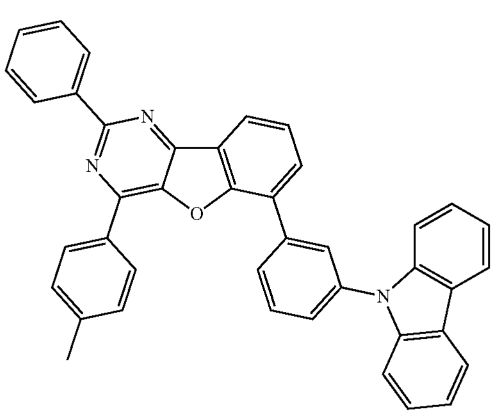
279
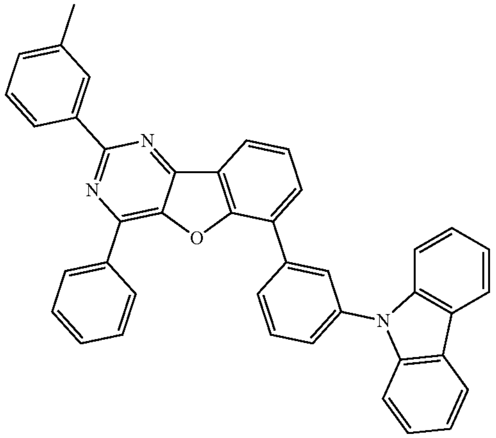
280
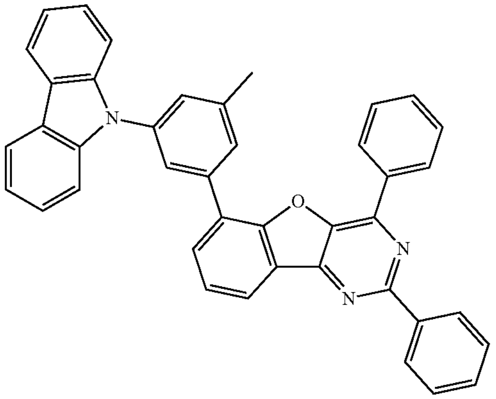
281
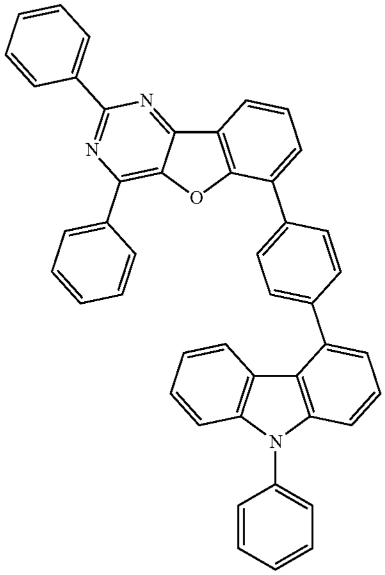
282
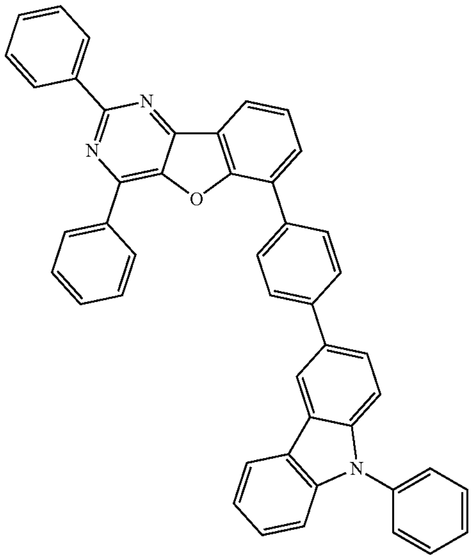

-continued
283
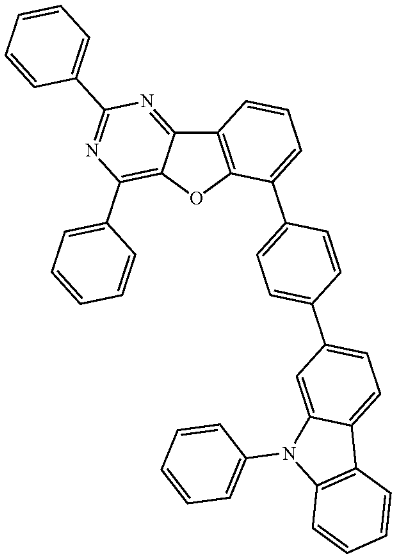
284
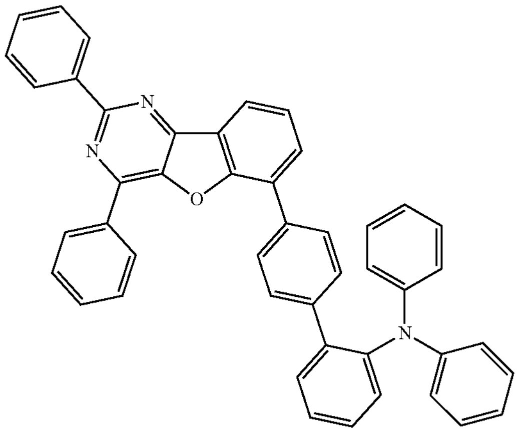
285
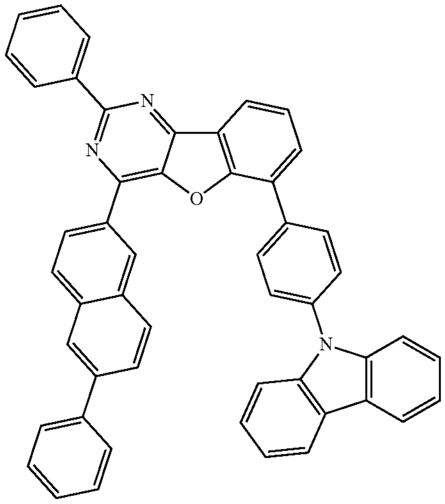
-continued
286
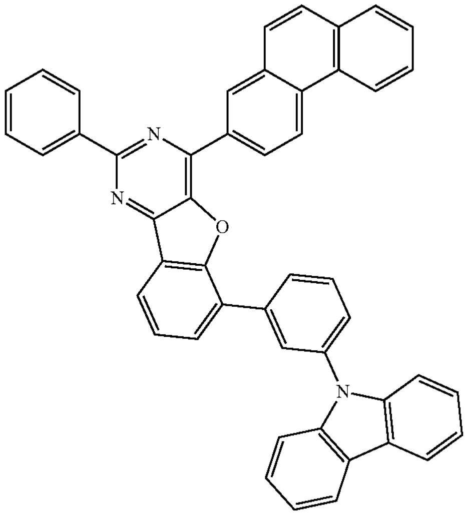
287
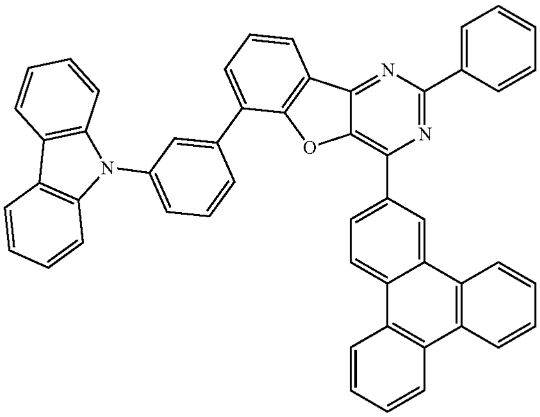
288
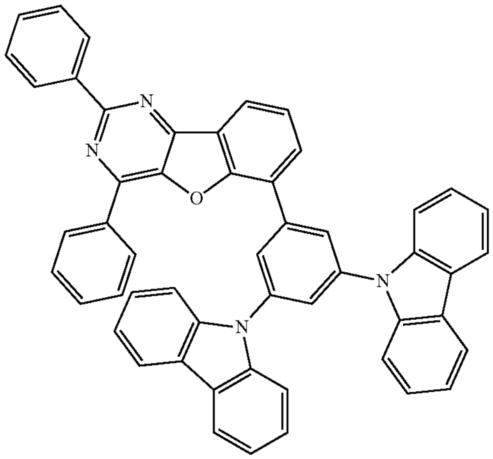

-continued
289
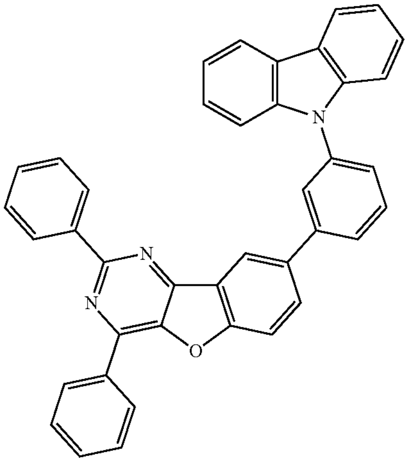
290
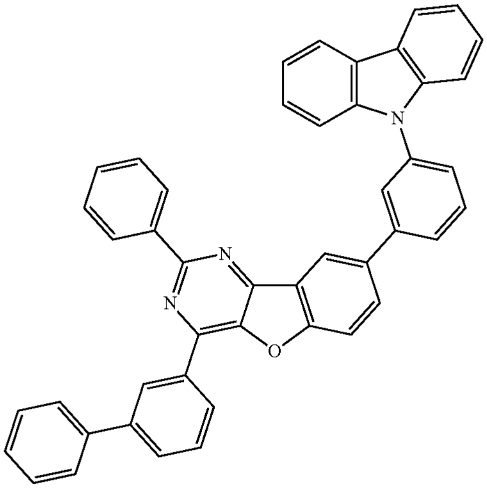
291
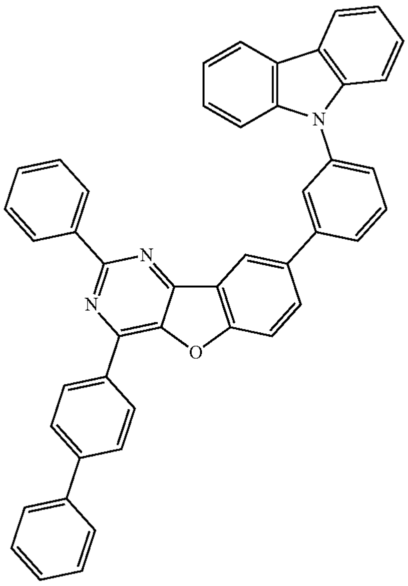
-continued
292
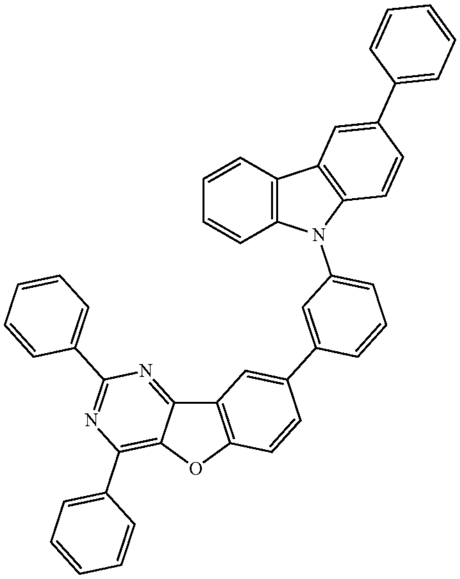
293
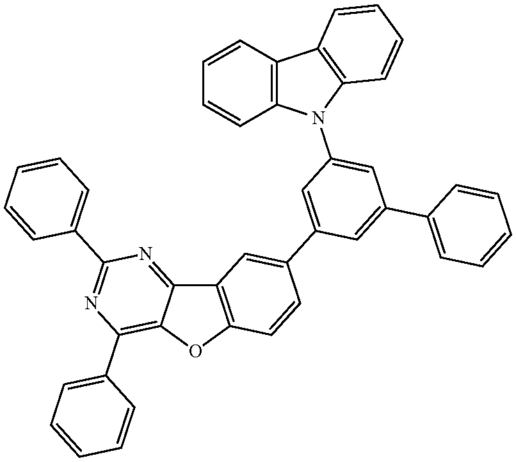
294
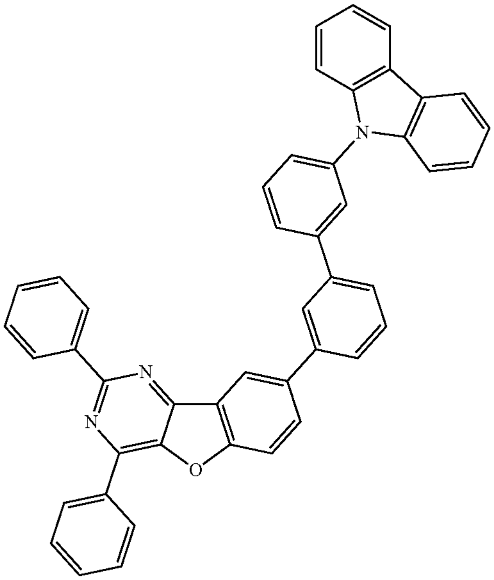

-continued
295
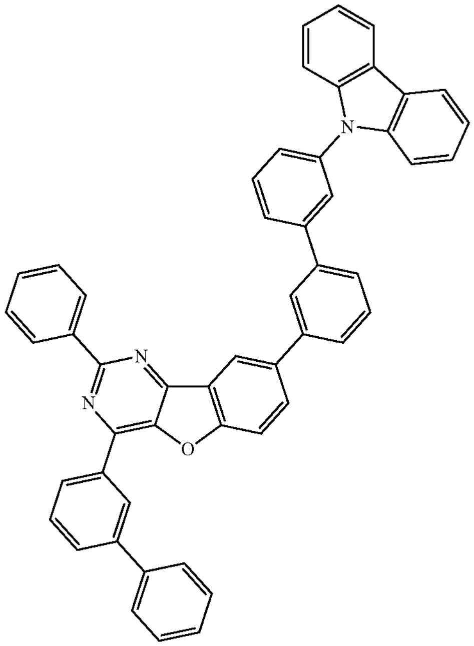
296
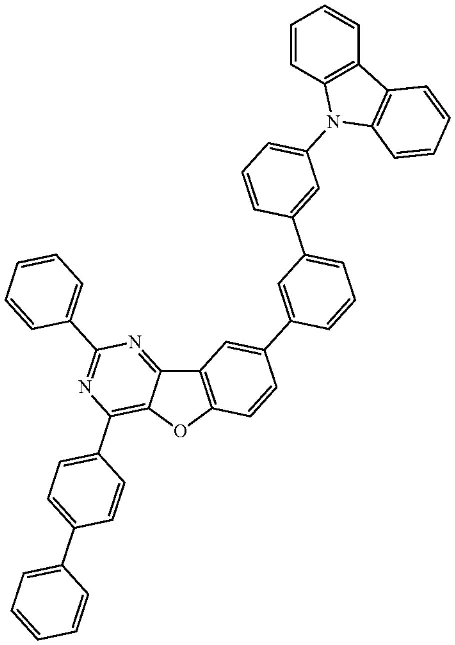
-continued
297
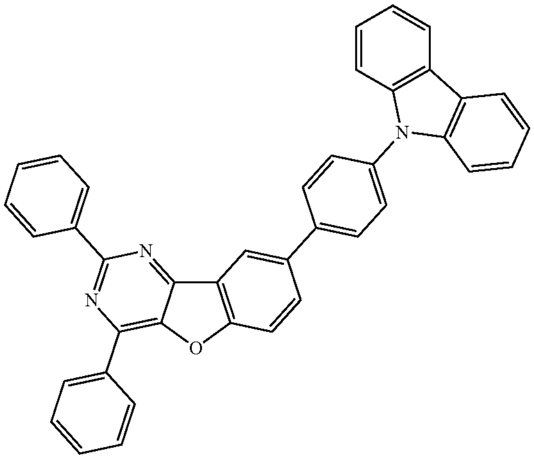
298
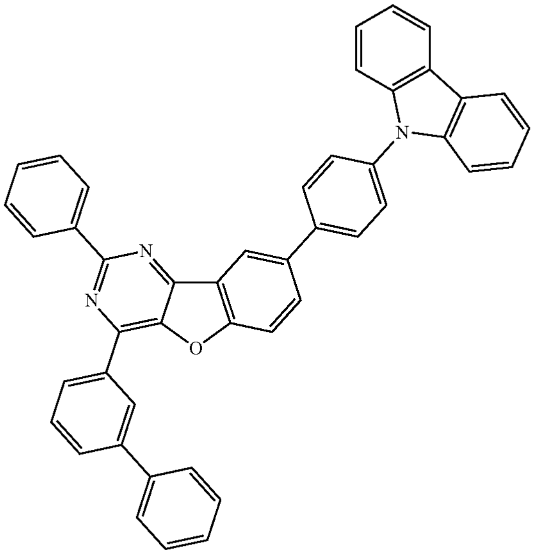
299
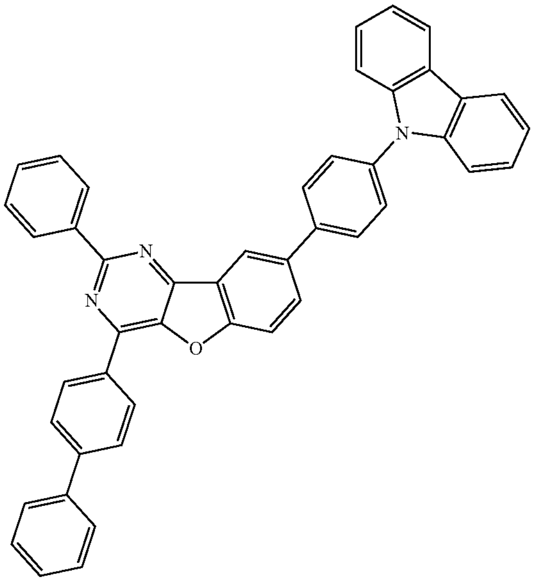

-continued
300
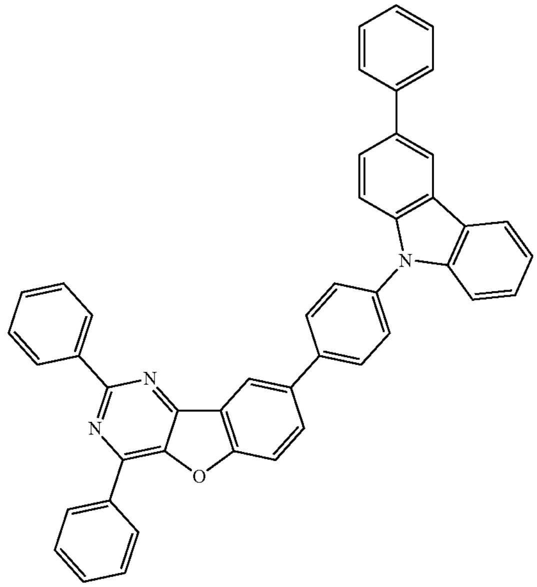
301
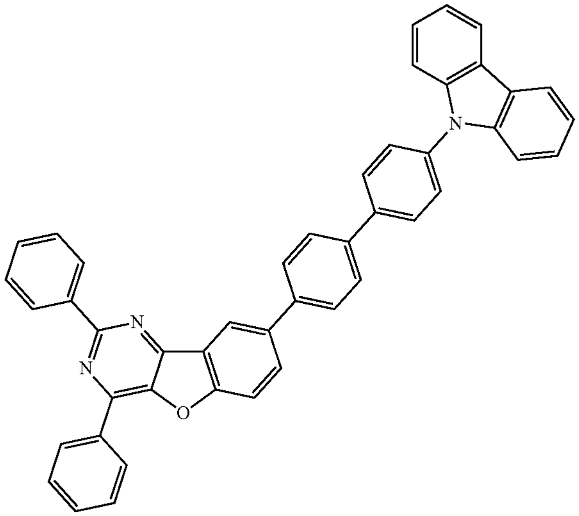
302
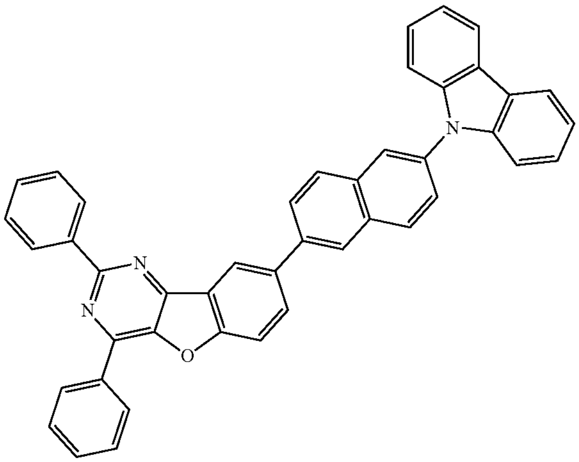
-continued
303
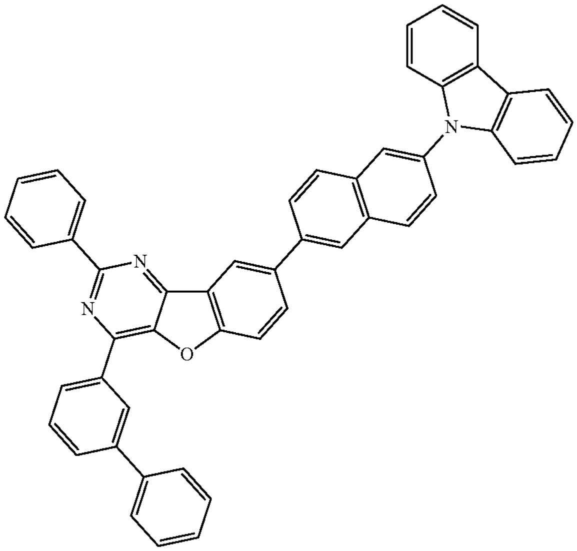
304
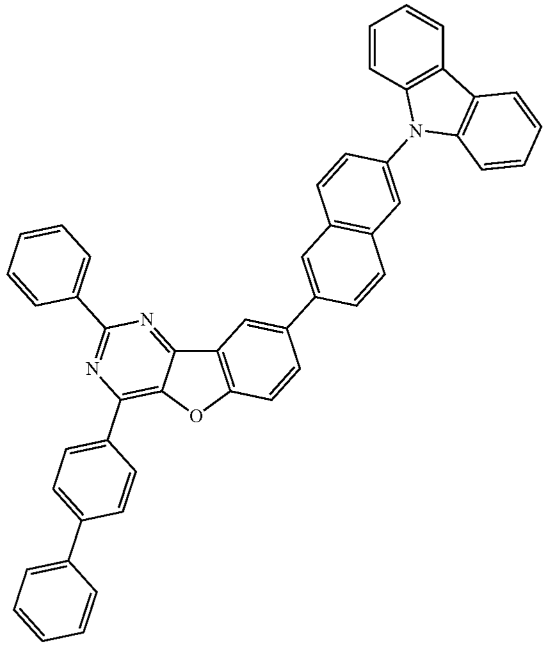

-continued
305
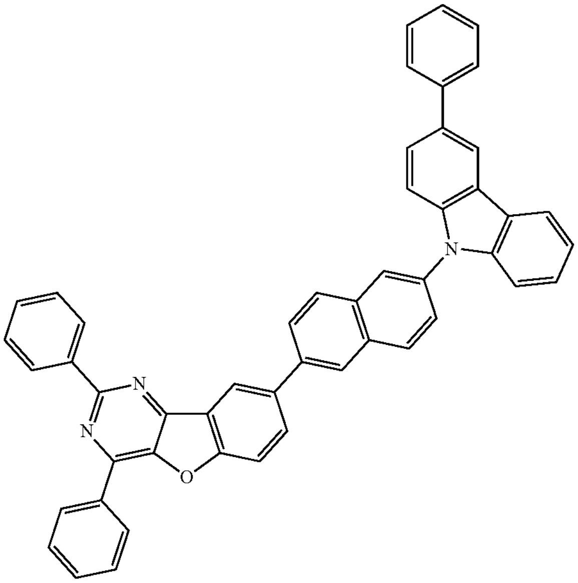
306
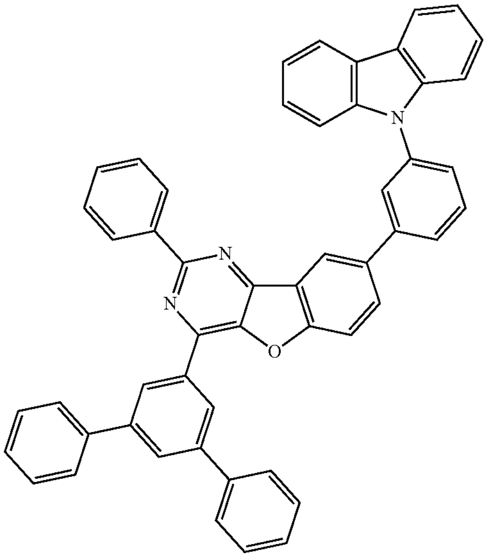
307
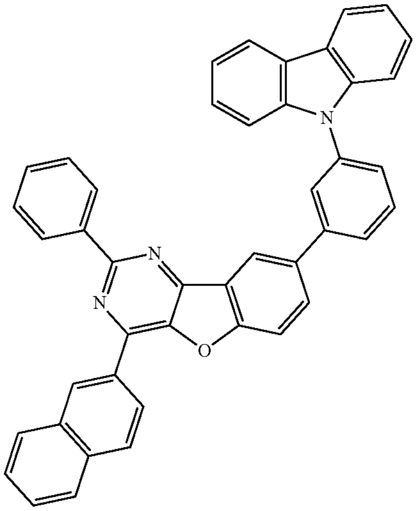
-continued
308
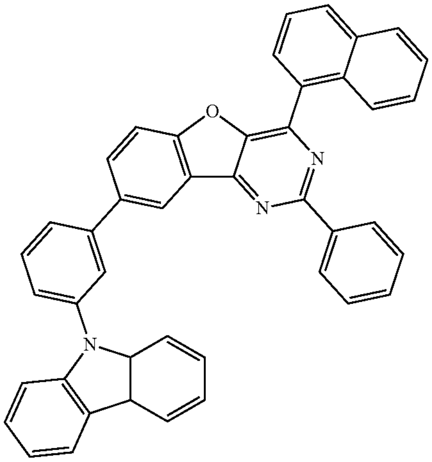
309
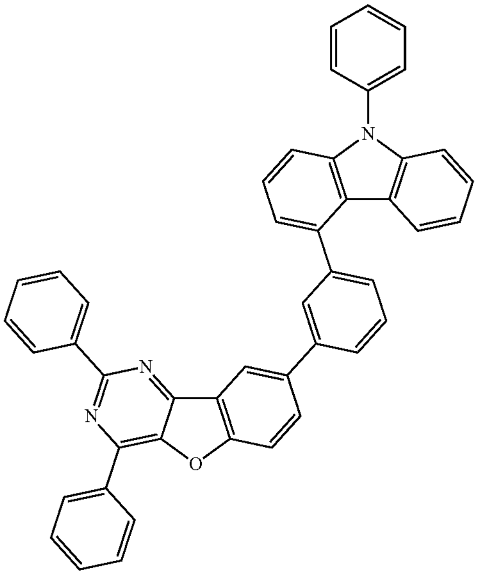
310
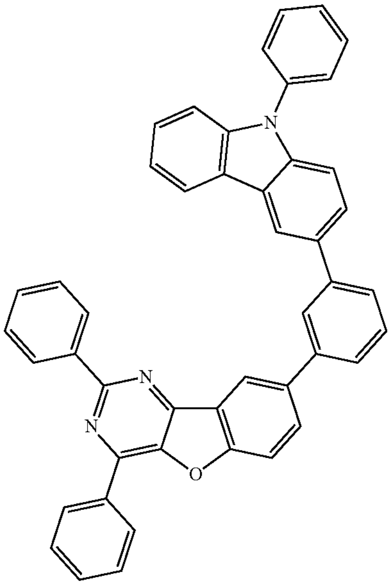

-continued
311
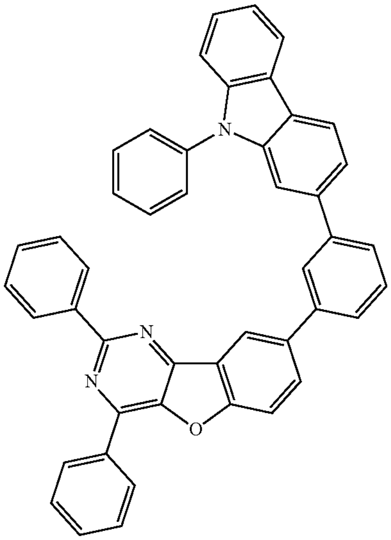
312
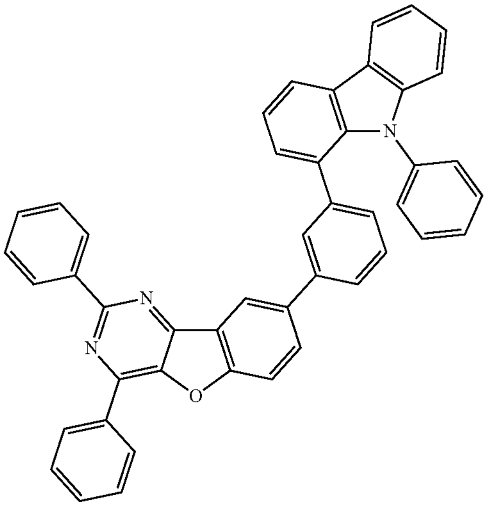
-continued
313
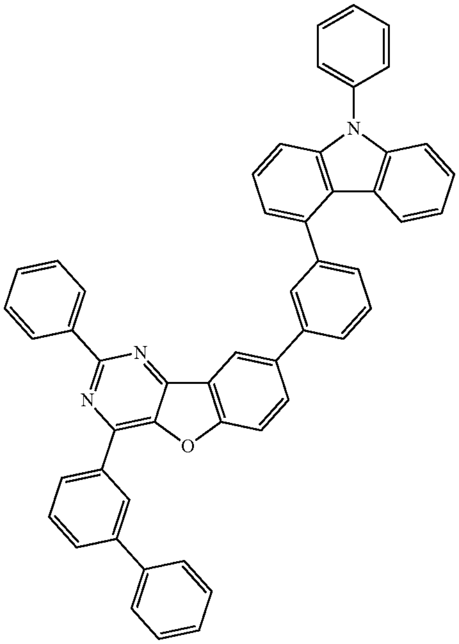
314
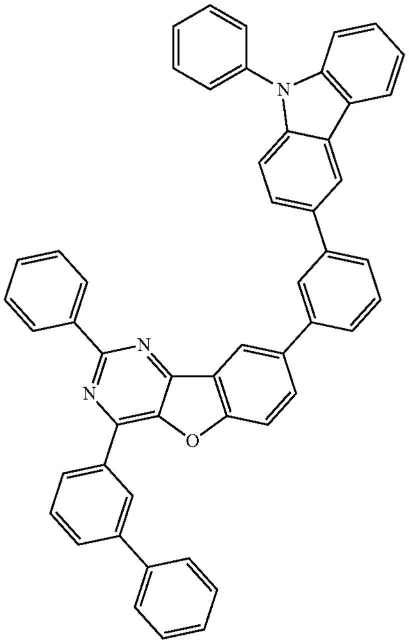

-continued
315
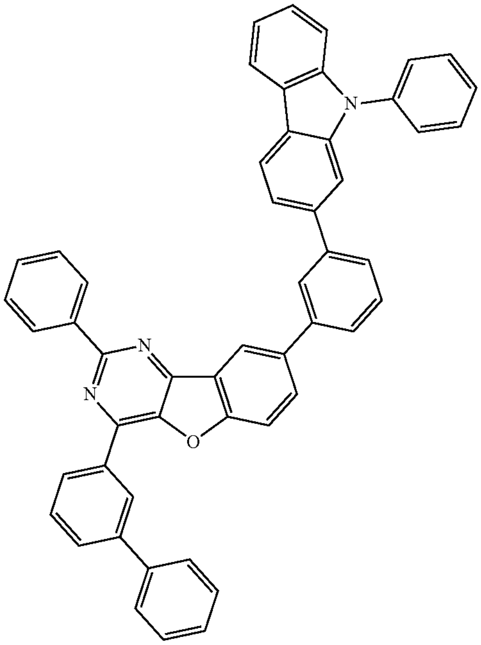
316
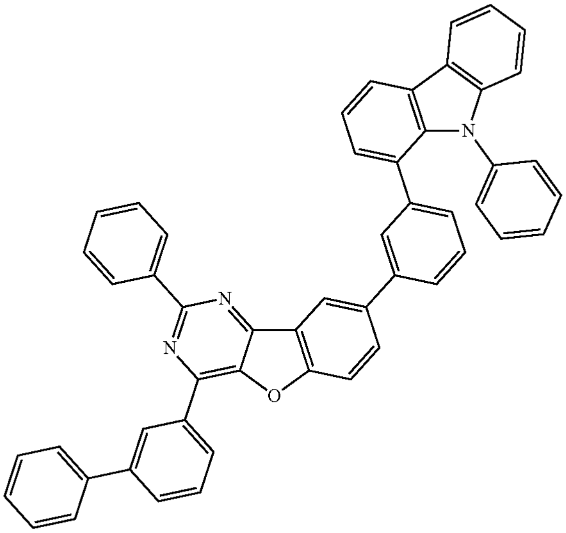
-continued
317
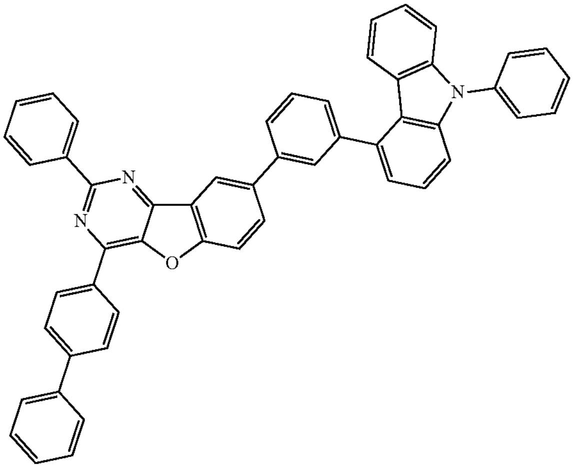
318
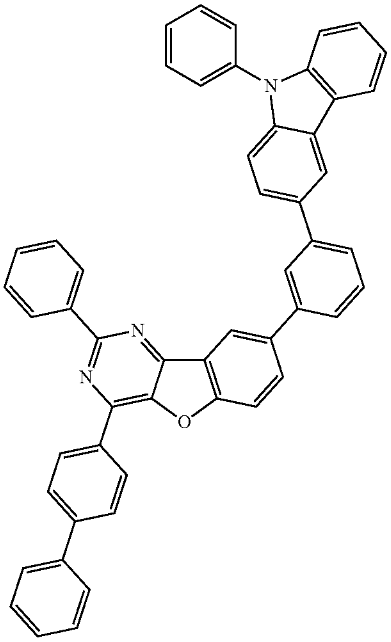
319
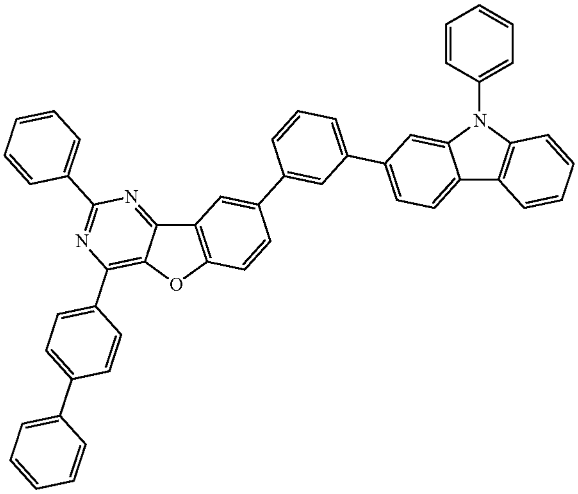

-continued
320
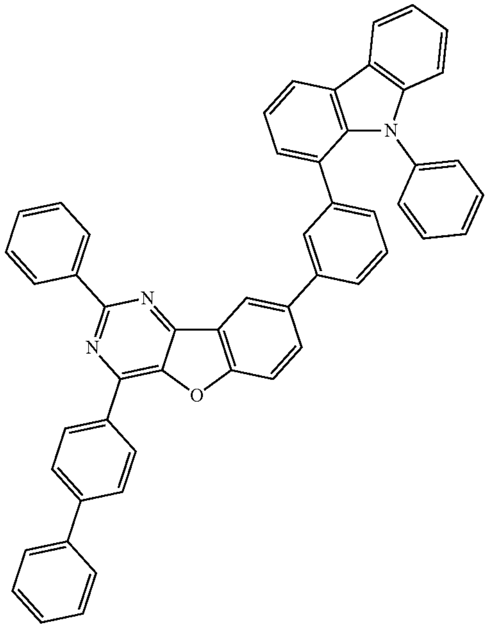
321
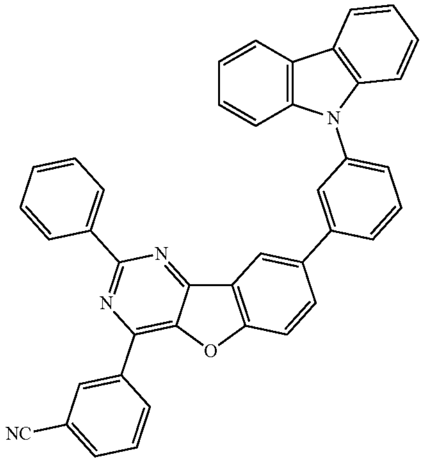
322
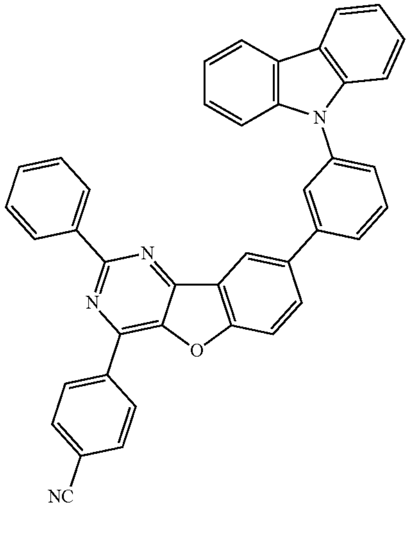
-continued
323
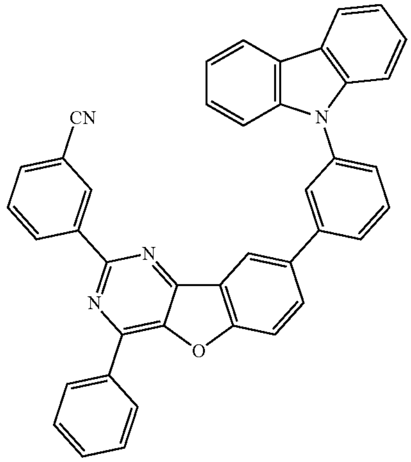
324
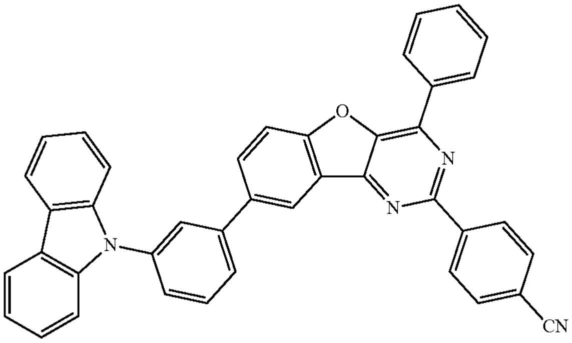
325
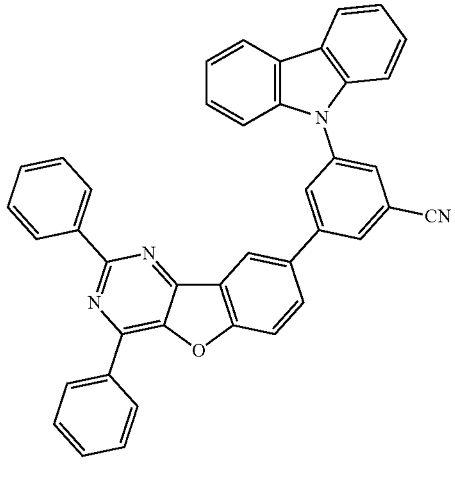

-continued
326
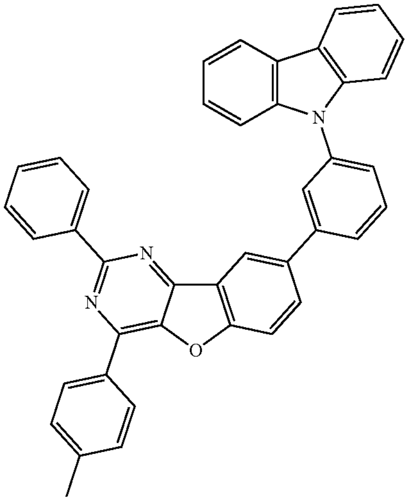
327
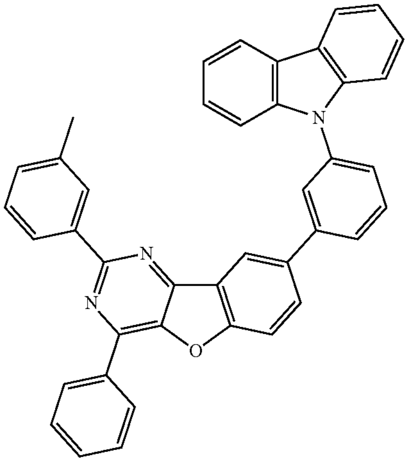
328
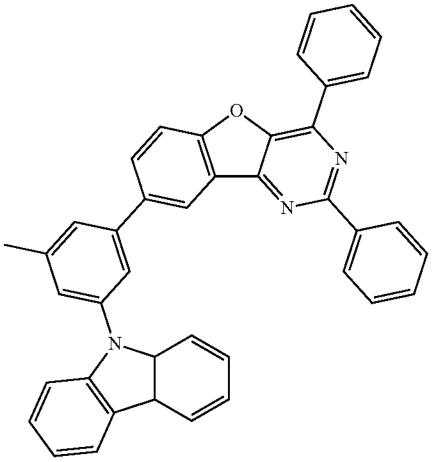
-continued
329
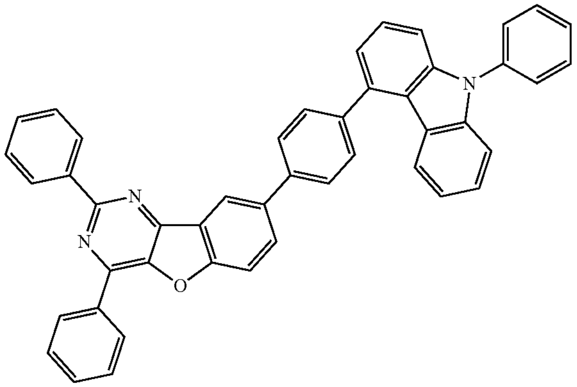
330
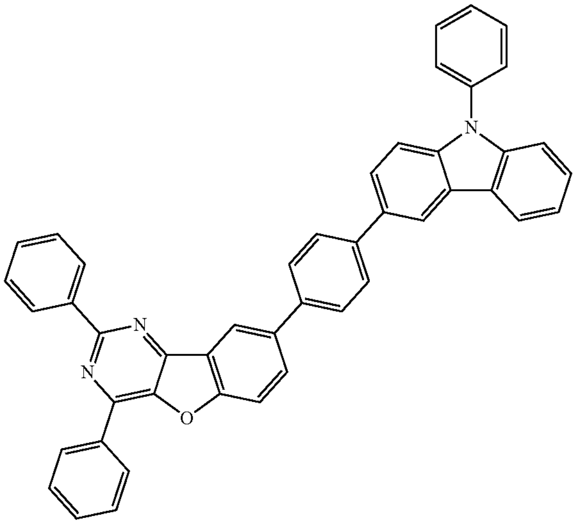
331
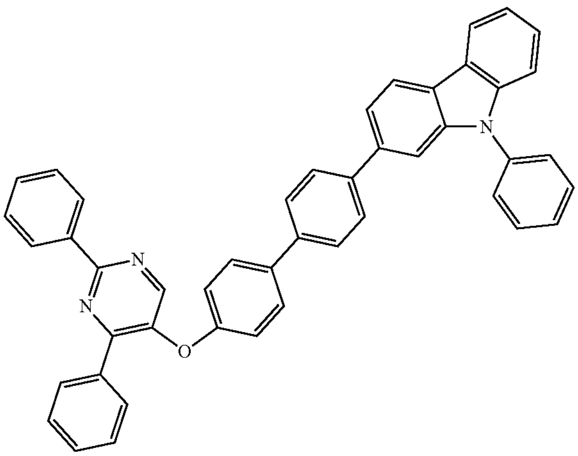

-continued
332
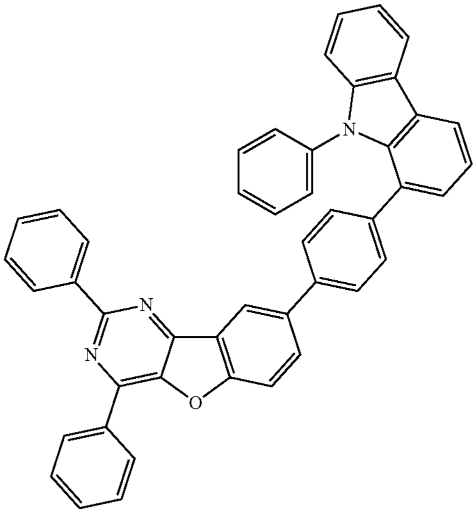
333
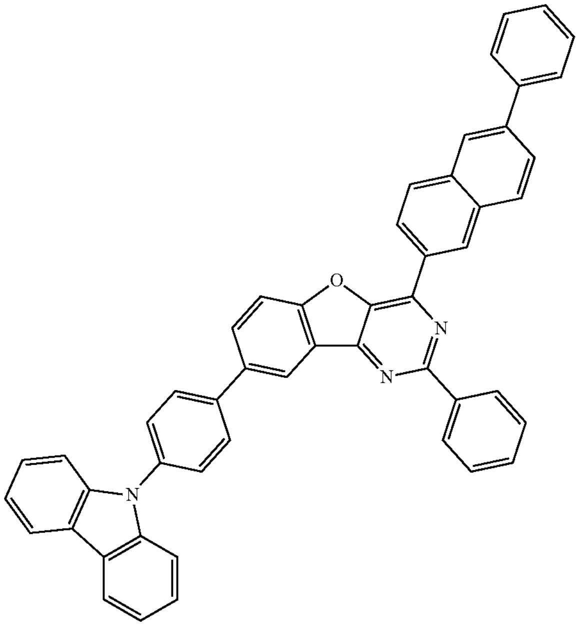
334
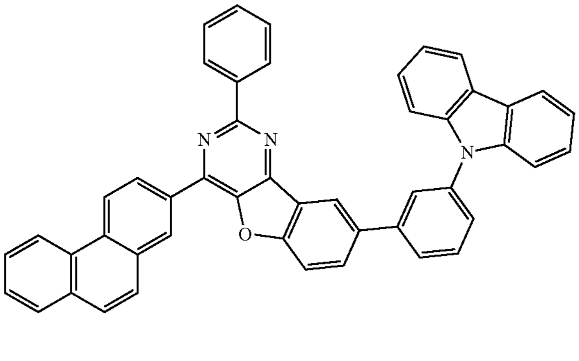
-continued
335
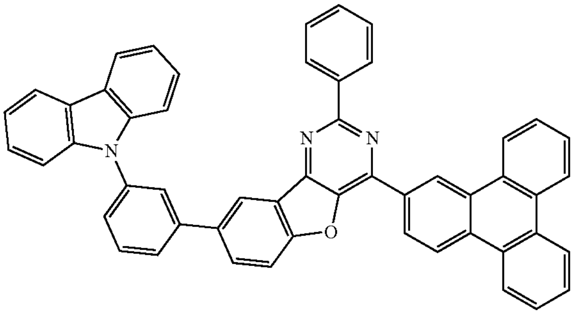
336
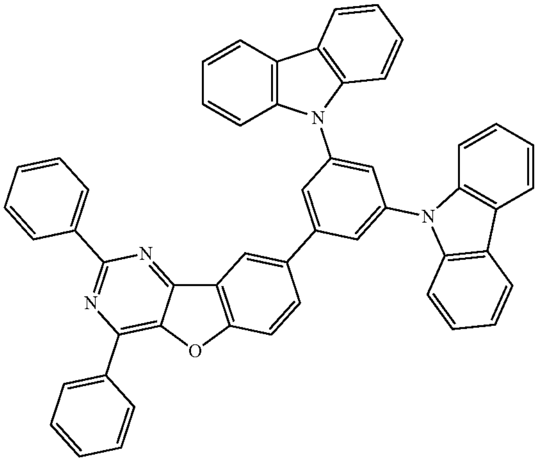
337
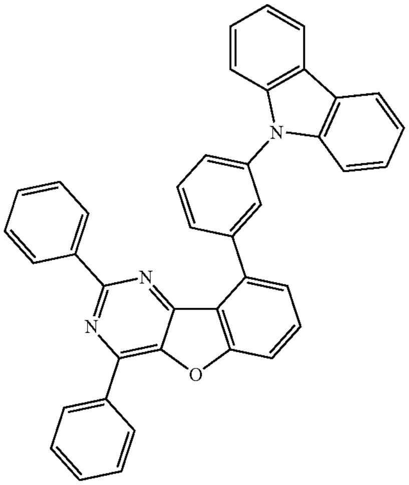

-continued
338
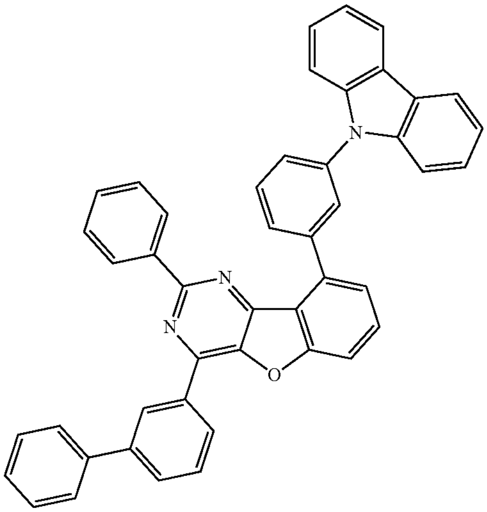
339
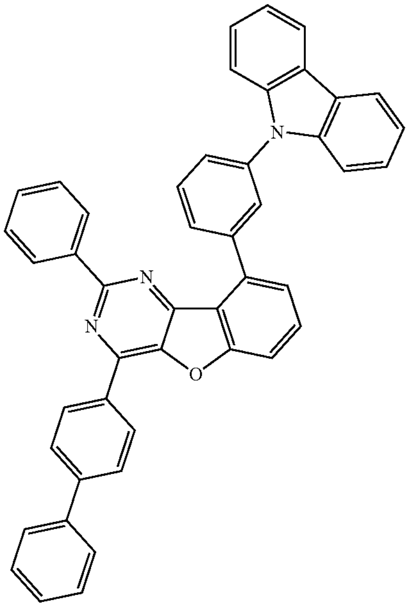
340
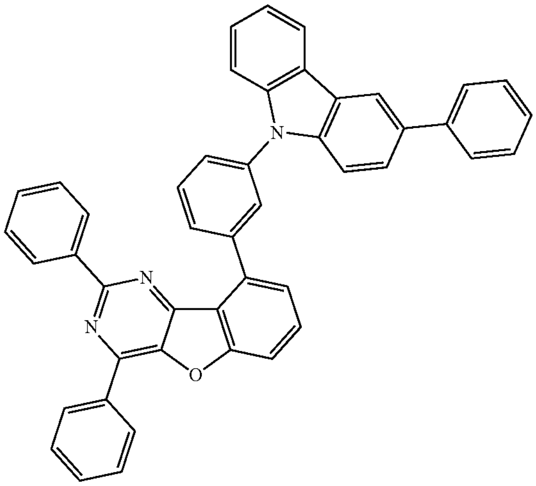
-continued
341
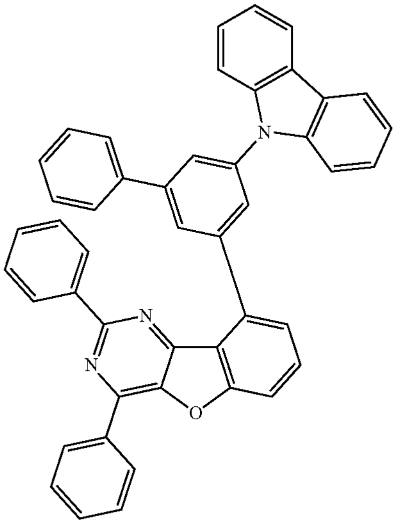
342
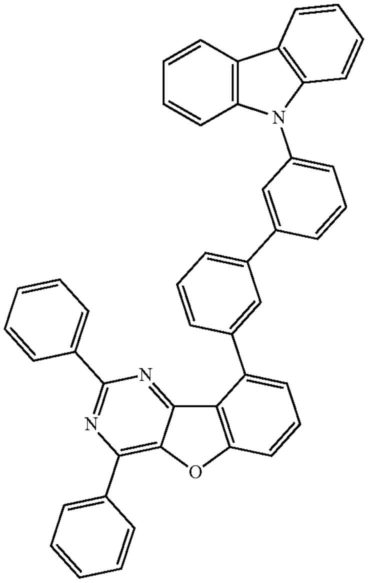

-continued
343
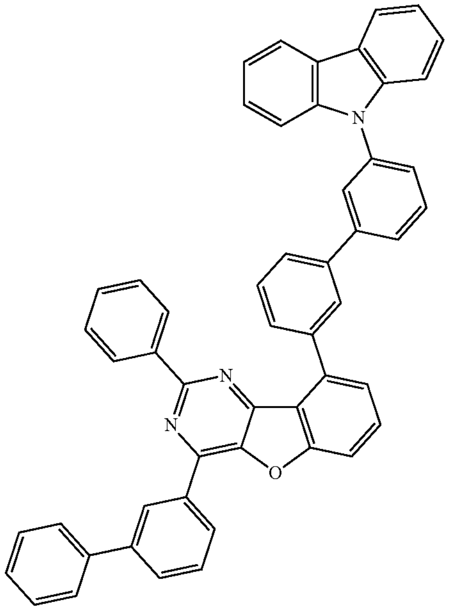
344
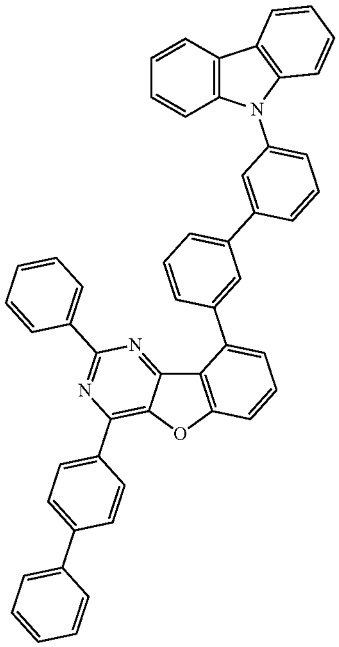
-continued
345
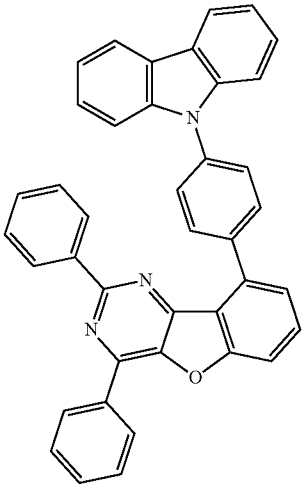
346
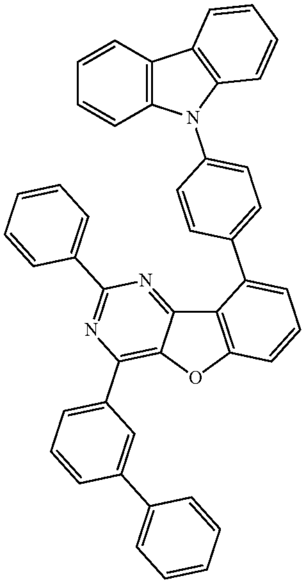

-continued
347
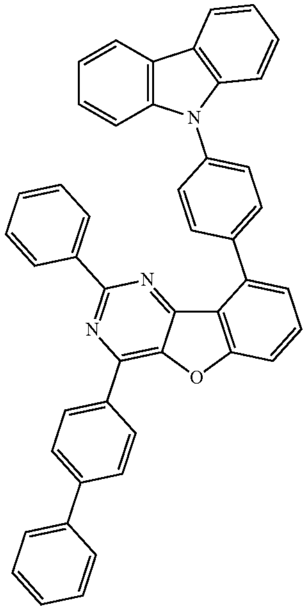
348
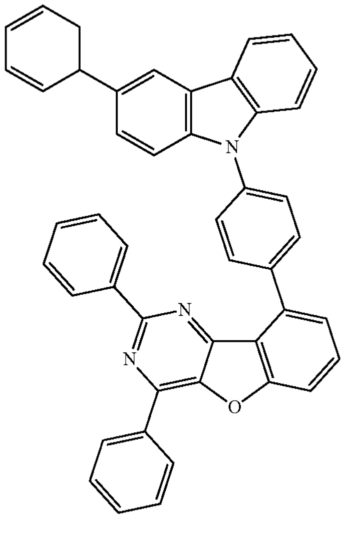
-continued
349
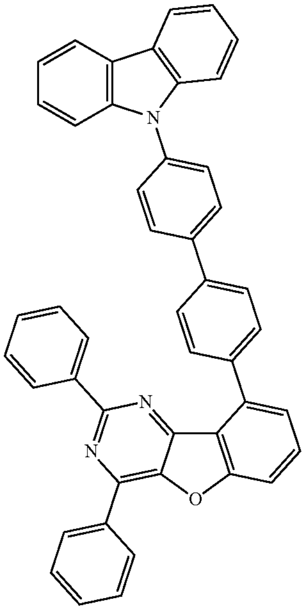
350
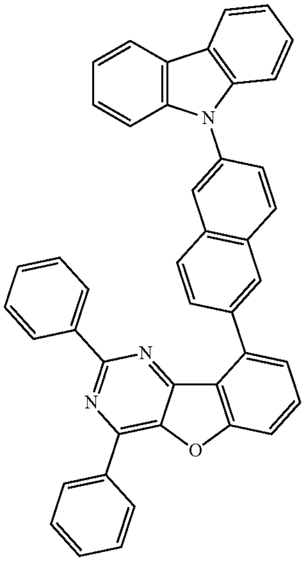

-continued
351
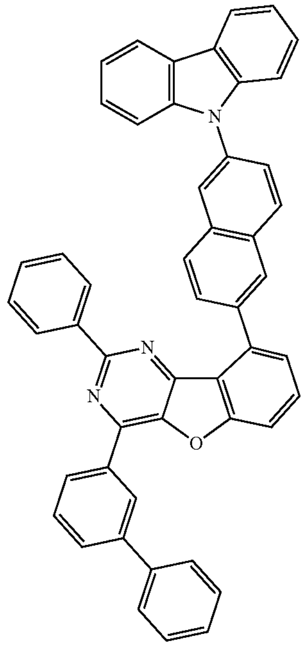
352
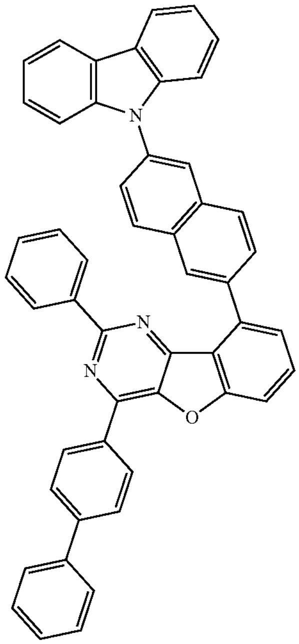
-continued
353
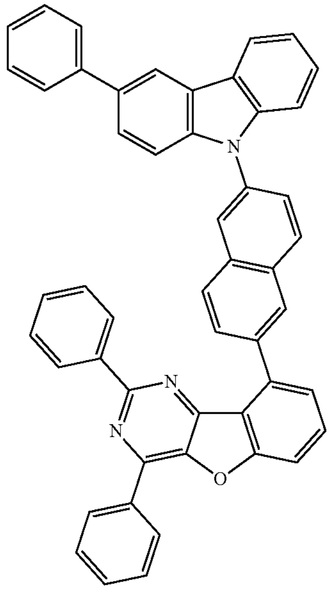
354
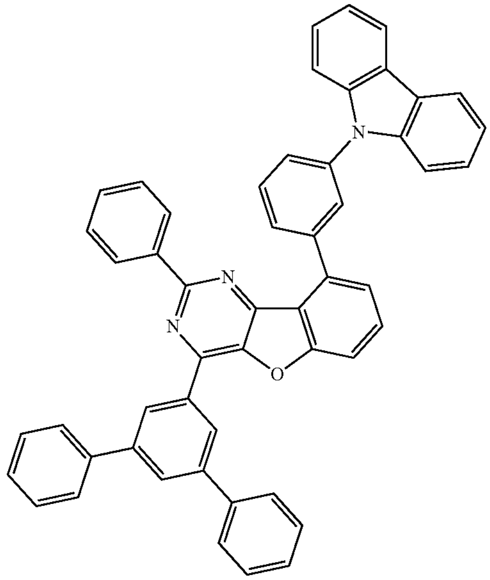

-continued
355
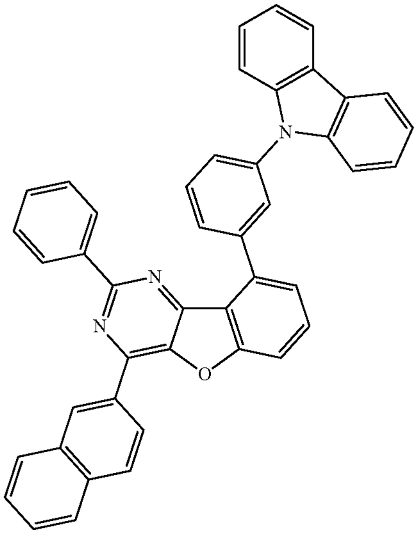
356
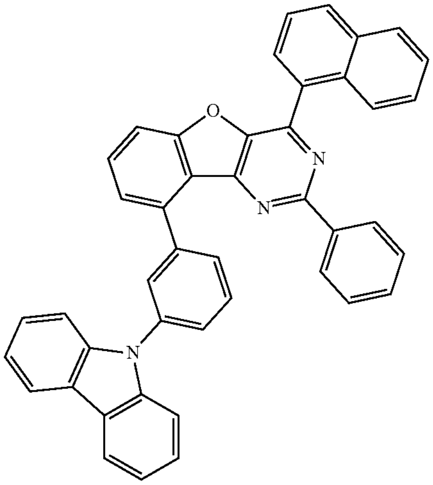
357
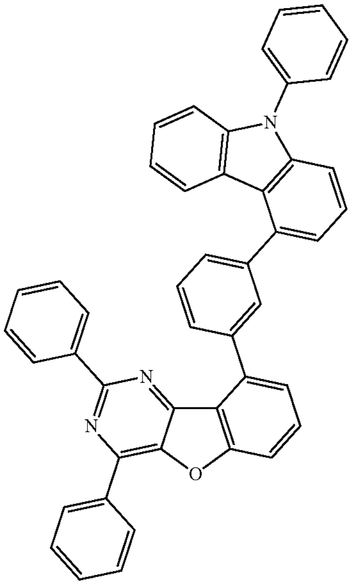
-continued
358
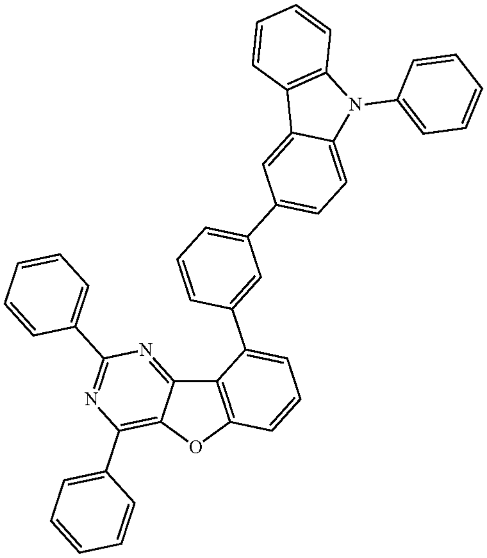
359
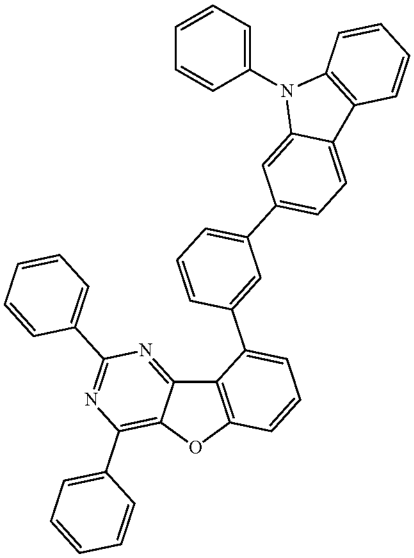
360
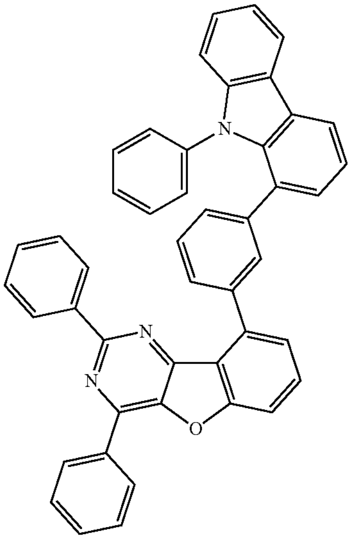

-continued
361
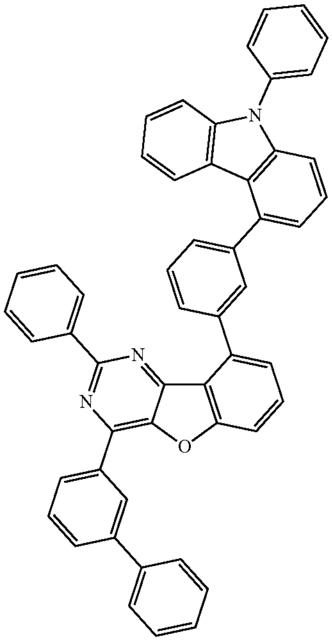
362
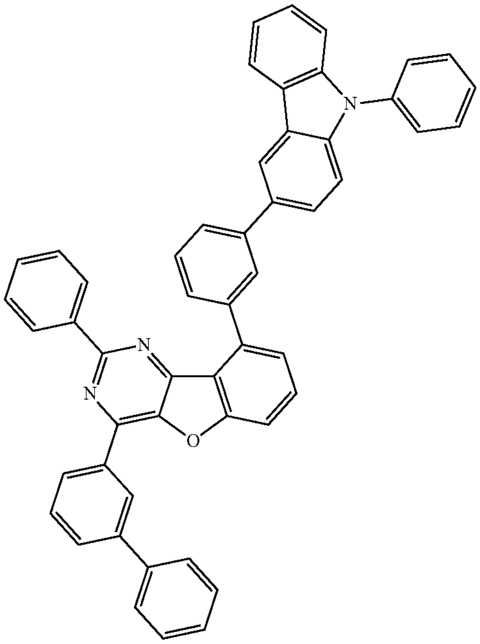
-continued
363
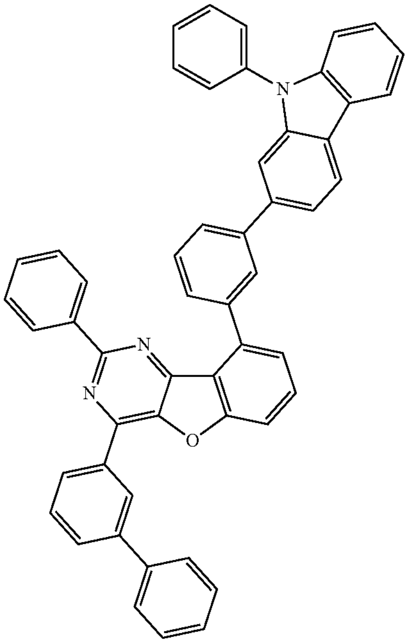
364
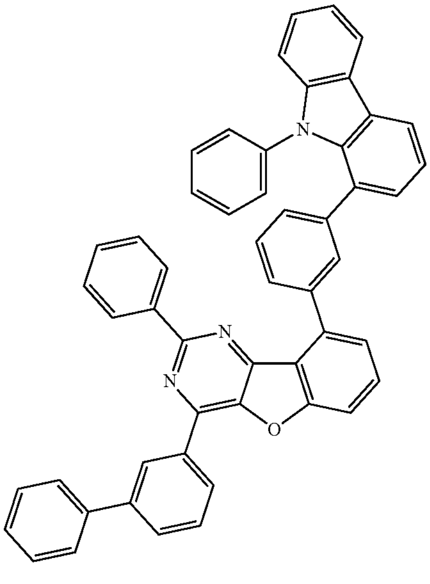

-continued
365
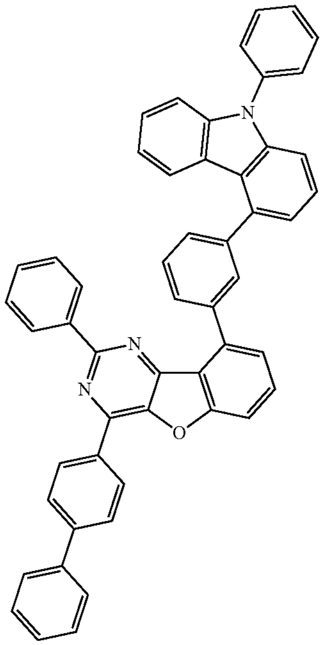
366
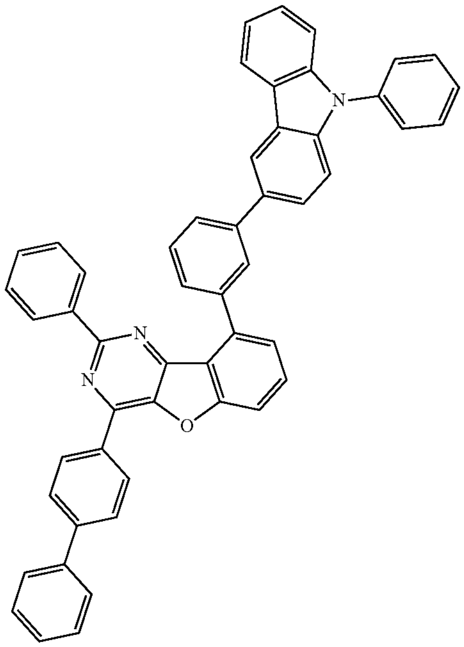
-continued
367
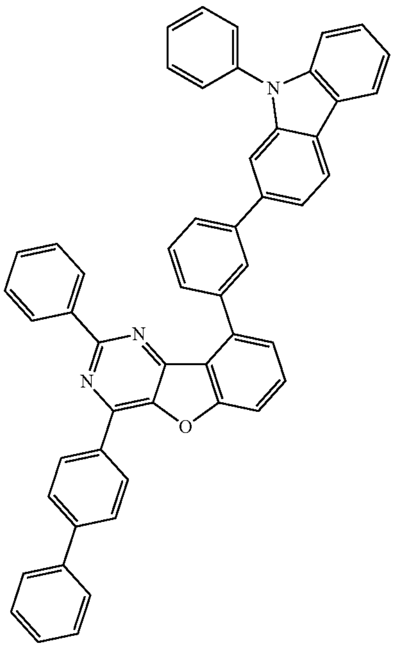
368
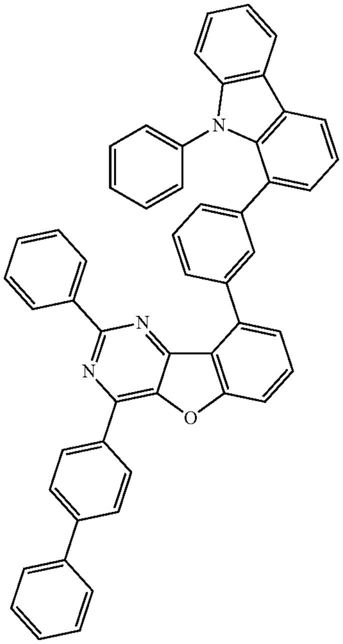

-continued
369
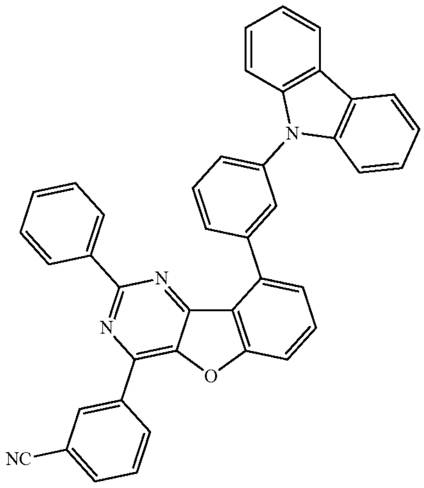
370
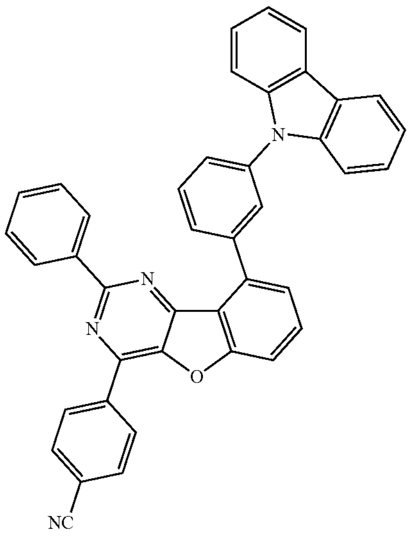
371
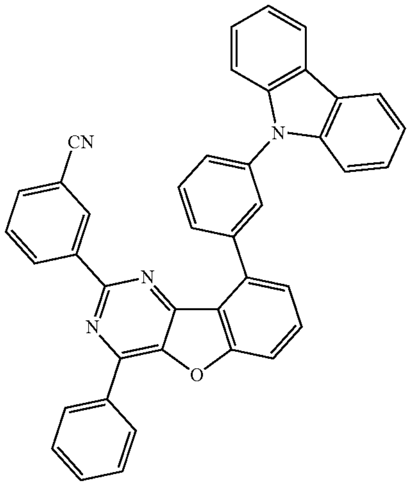
-continued
372
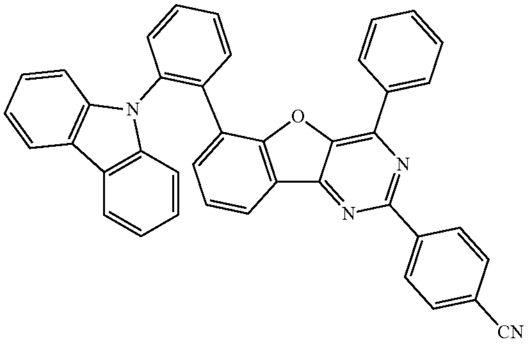
373
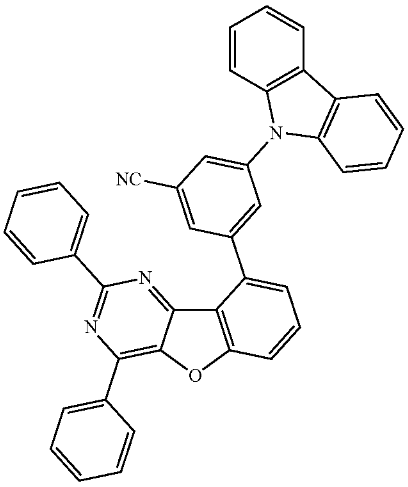
374
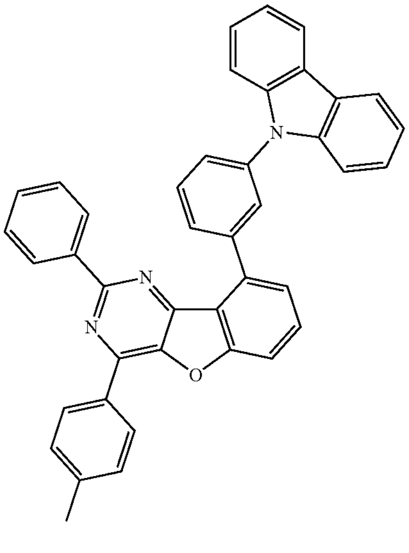

-continued
375
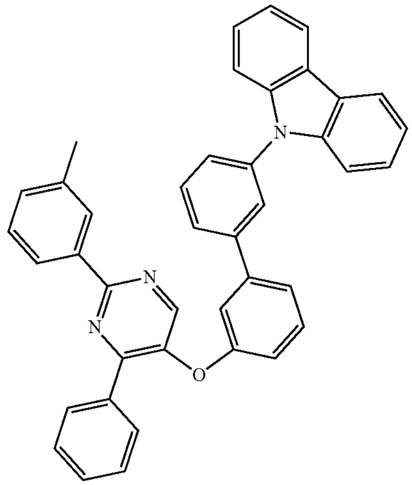
376
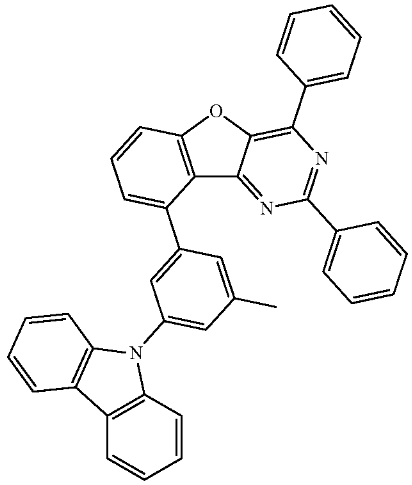
377
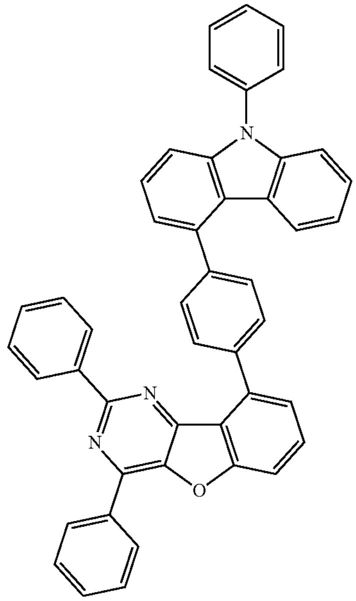
-continued
378
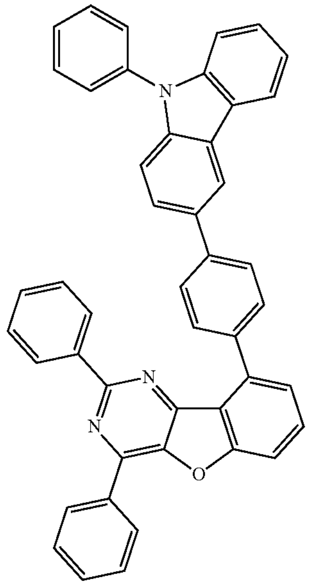
379
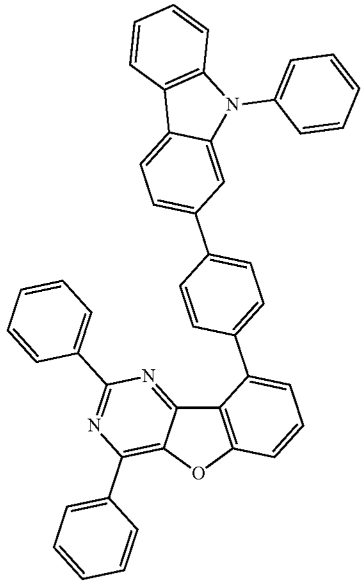

380
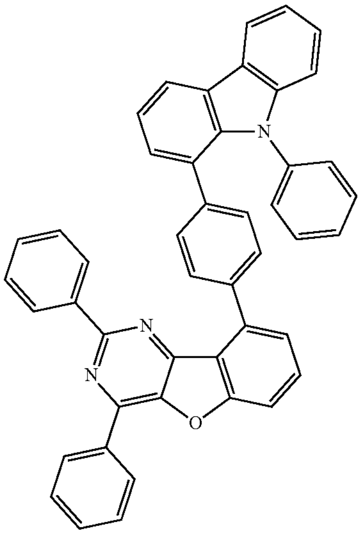
381
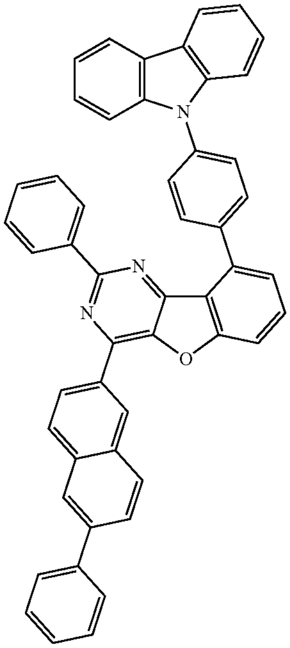
382
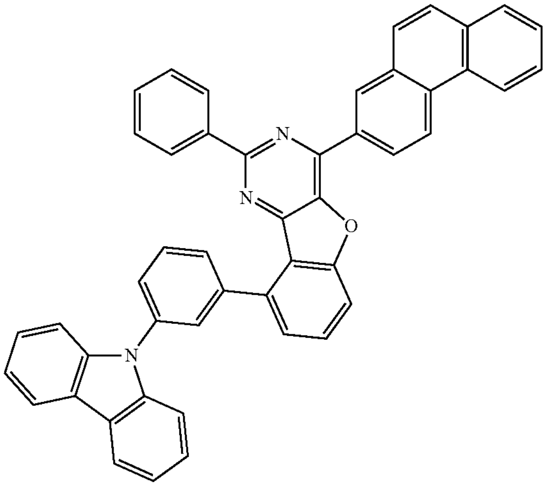
383
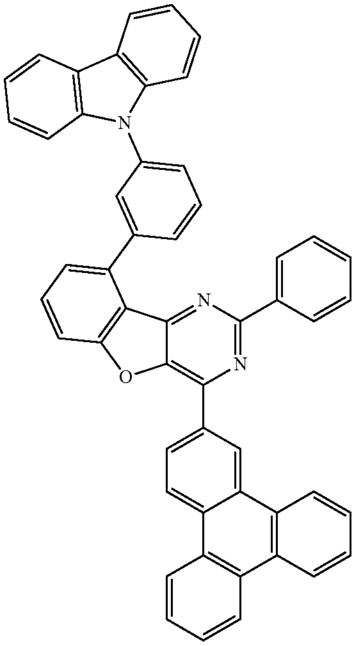

-continued

384

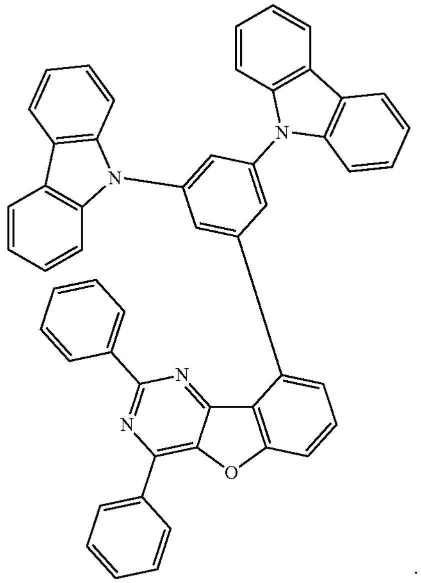

The organic compound may be applied to an organic optoelectronic device alone or with other organic compound. When the organic compound is used with other organic compound, they may be applied in a form of a composition.

Hereinafter, a composition according to another embodiment is described.

A composition according to an embodiment may include the organic compound (hereinafter, referred to as "a first organic compound") and an organic compound having hole characteristics (hereinafter, referred to as "a second organic compound").

The second organic compound may include for example a carbazole moiety, for example a substituted or unsubstituted carbazole compound, a substituted or unsubstituted biscarbazole compound, or a substituted or unsubstituted indolocarbazole compound, but is not limited thereto.

For example, the second organic compound may include for example a carbazole moiety represented by Chemical Formula 4.

[Chemical Formula 4]

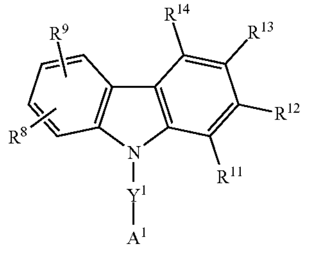

In Chemical Formula 4, $Y^1$ is a single bond, a substituted or unsubstituted C6 to C30 arylene group or divalent substituted or unsubstituted C2 to C30 heterocyclic group, $A^1$ is a substituted or unsubstituted C6 to C30 aryl group, or a substituted or unsubstituted C2 to C30 heterocyclic group, $R^9$ to $R^{14}$ are independently hydrogen, deuterium, a substituted or unsubstituted C1 to C20 alkyl group, a substituted or unsubstituted C6 to C30 aryl group, or a substituted or unsubstituted C2 to C30 heterocyclic group, $R^9$ and $R^{10}$ are independently present or fused to each other to form a ring, and $R^{11}$ to $R^{14}$ are independently present or adjacent groups of $R^{11}$ to $R^{14}$ are linked with each other to form a ring.

For example, in the definitions of Chemical Formula 4, the substituted may refer to replacement of at least one hydrogen by deuterium, a C1 to C10 alkyl group, a C6 to C12 aryl group, or a C2 to C10 heteroaryl group, for example replacement of at least one hydrogen by deuterium, a phenyl group, an ortho-biphenyl group, a meta-biphenyl group, a para-biphenyl group, a terphenyl group, a naphthyl group, a dibenzofuranyl group, or a dibenzothiophenyl group.

For example, the second organic compound may be a compound represented by Chemical Formula 4A.

[Chemical Formula 4A]

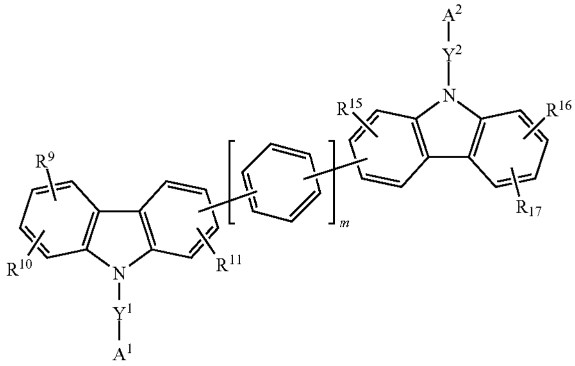

In Chemical Formula 4A, $Y^1$ and $Y^2$ are independently a single bond, a substituted or unsubstituted C6 to C30 arylene group, a divalent substituted or unsubstituted C2 to C30 heterocyclic group, or a combination thereof, $A^1$ and $A^2$ are independently a substituted or unsubstituted C6 to C30 aryl group, a substituted or unsubstituted C2 to C30 heterocyclic group, or a combination thereof, $R^9$ to $R^{11}$ and $R^{15}$ to $R^{17}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and m is an integer of 0 to 2.

For example, $Y^1$ and $Y^2$ of Chemical Formula 4A may independently be a single bond, a substituted or unsubstituted phenylene group, or a substituted or unsubstituted biphenylene group, for example a single bond, a meta-phenylene group, a para-phenylene group, a meta-biphenylene group, or a para-biphenylene group.

For example, $A^1$ and $A^2$ of Chemical Formula 4A may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, or a substituted or unsubstituted triphenylene group, a substituted or unsubstituted pyridinyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof. For example, $A^1$ and $A^2$ of Chemical Formula 4A may independently be a substituted or unsubstituted phenyl group, a substituted or unsubstituted biphenyl group, a substituted or unsubstituted dibenzothiophenyl group, a substituted or unsubstituted dibenzofuranyl group, or a substituted or unsubstituted carbazolyl group.

For example, $R^9$ to $R^{11}$ and $R^{15}$ to $R^{17}$ of Chemical Formula 4A may be hydrogen, a substituted or unsubstituted C6 to C30 aryl group, or a substituted or unsubstituted C2 to C30 heterocyclic group, and may be for example all hydrogen.

For example, m of Chemical Formula 4A may be 0 or 1, and m may be for example 0.

For example, in Chemical Formula 4A, bonds of two carbazole groups may be a 2,3-bond, a 3,3-bond, or a 2,2-bond, and may be for example a 3,3-bond.

For example, the compound represented by Chemical Formula 4A may be represented by Chemical Formula 4A-1.

[Chemical Formula 4A-1]

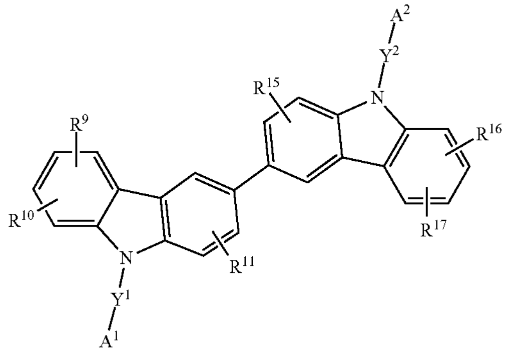

In Chemical Formula 4A-1, $Y^1$, $Y^2$, $A^1$, $A^2$, $R^9$ to $R^{11}$, and $R^{15}$ to $R^{17}$ are the same as described above.

For example, the compound represented by Chemical Formula 4A may be a compound formed by combining one of carbazole cores listed in Group 2 and substituents (*—$Y^1$-$A^1$ and *—$Y^2$-$A^2$) listed in Group 3, but is not limited thereto.

[Group 2]

C-1

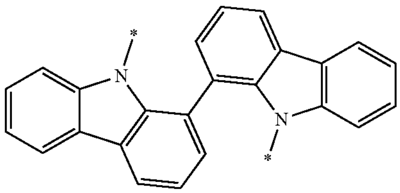

C-2

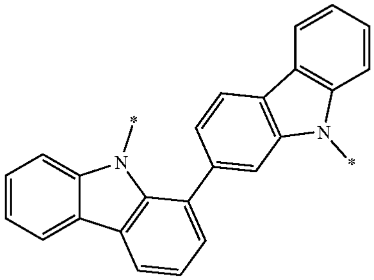

-continued

C-3

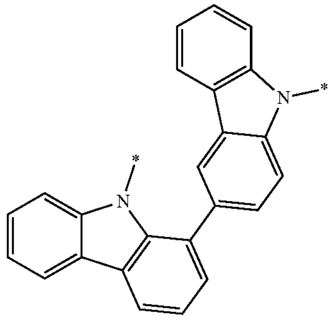

C-4

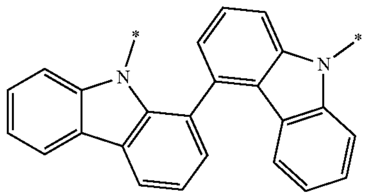

C-5

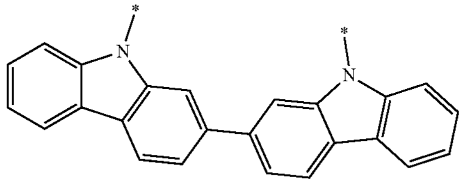

C-6

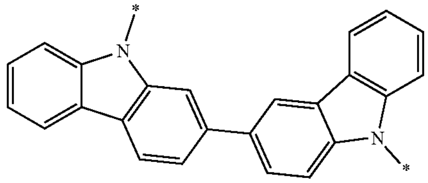

C-7

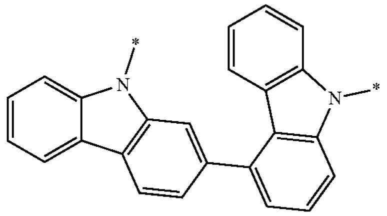

C-8

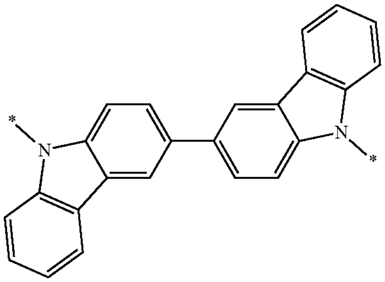

-continued
C-9
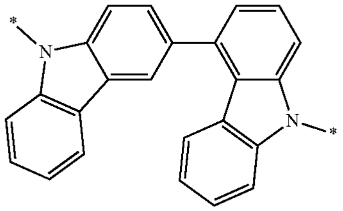
C-10
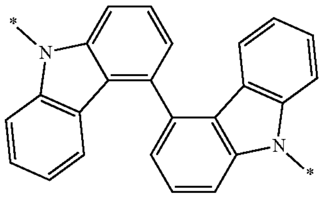
C-11
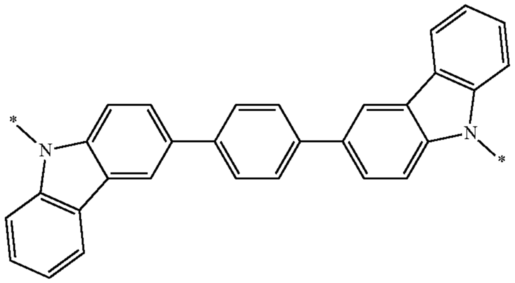
C-12
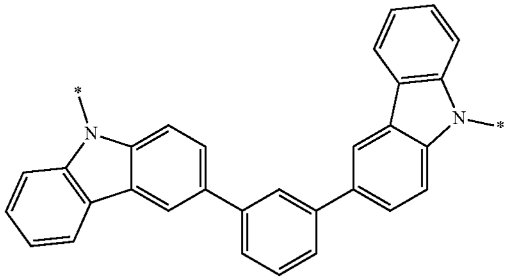
C-13
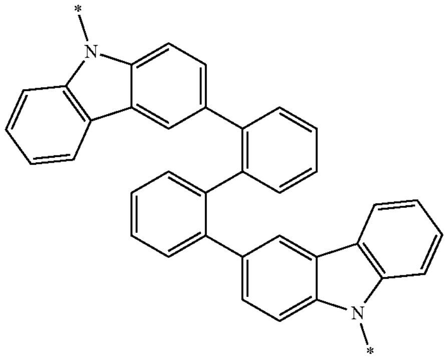
-continued
C-14
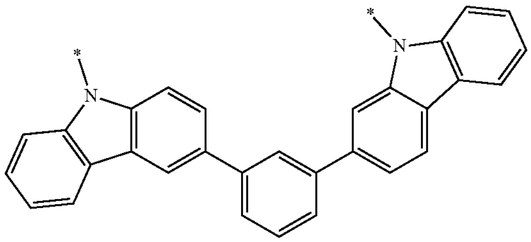
C-15
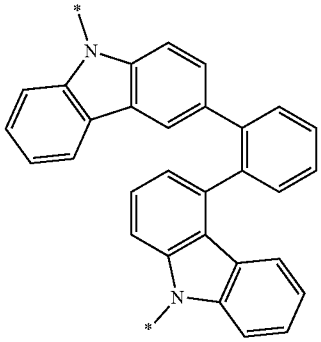
C-16
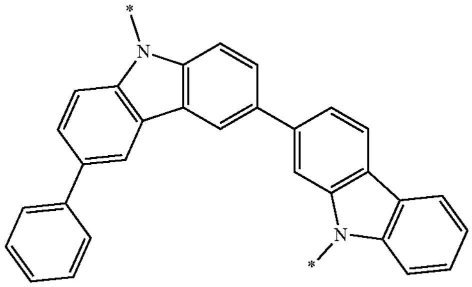
C-17
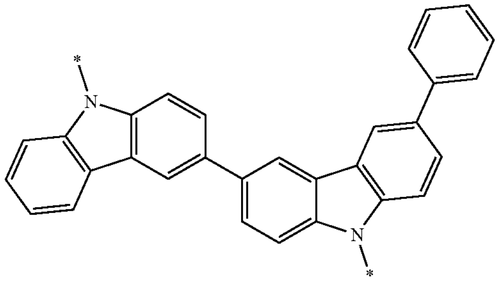
C-18
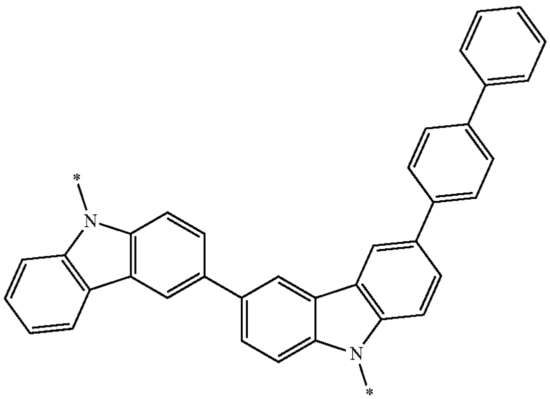

-continued
[Group 3]
B-1
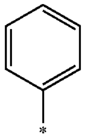
B-2
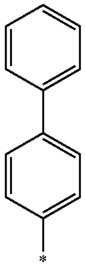
B-3
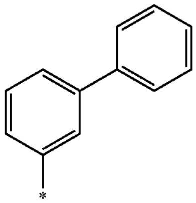
B-4
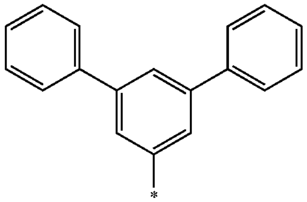
B-5
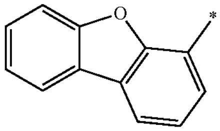
B-6
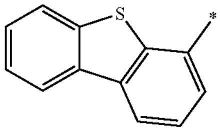
B-7
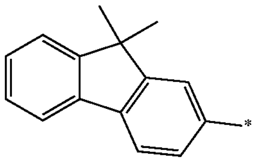
B-8
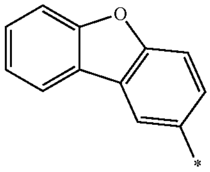
-continued
B-9
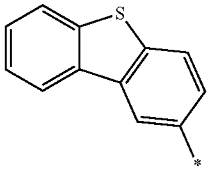
B-10
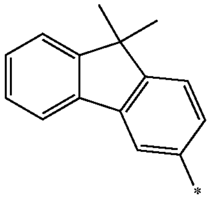
B-11
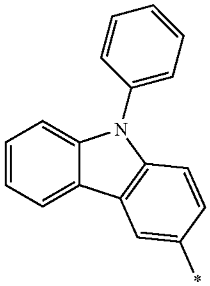
B-12
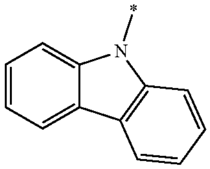
B-13
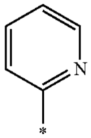
B-14
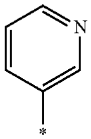
B-15
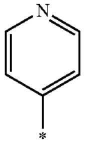
B-16
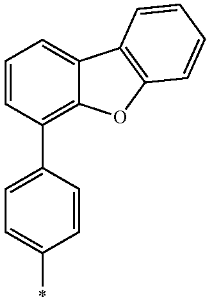

-continued
B-17
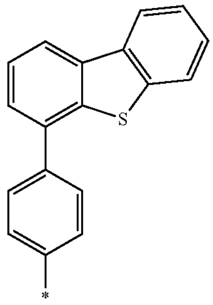
B-18
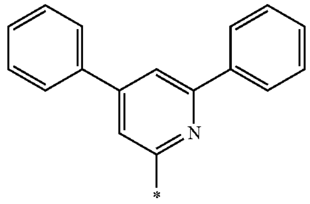
B-19
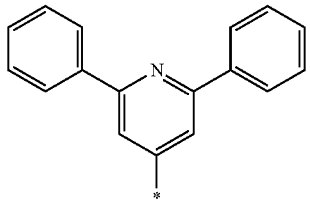
B-20
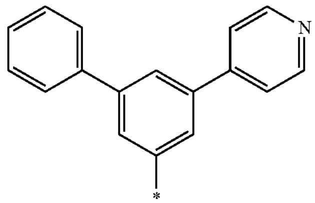
B-21
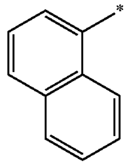
B-22
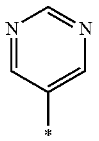
B-23
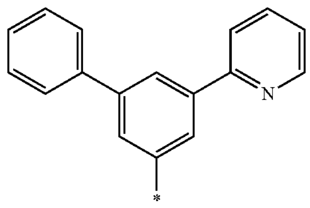
-continued
B-24
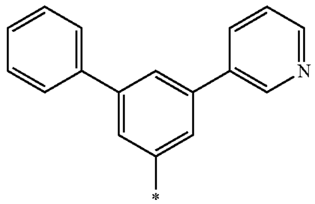
B-25
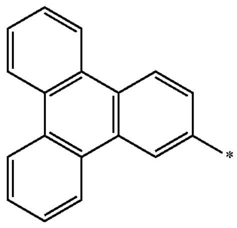
B-26
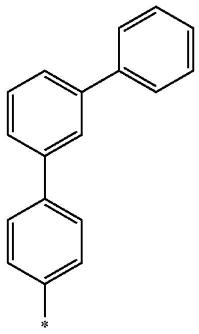
B-27
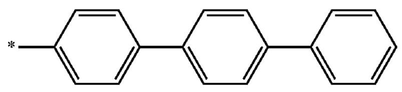
B-28
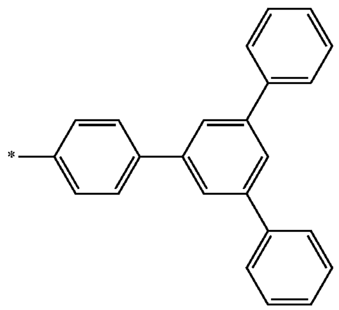
In Groups 2 and 3, * is a linking point.
For example, the compound represented by Chemical Formula 4A may be for example one of compounds of Group 4, but is not limited thereto.

[Group 4]
[E-1]
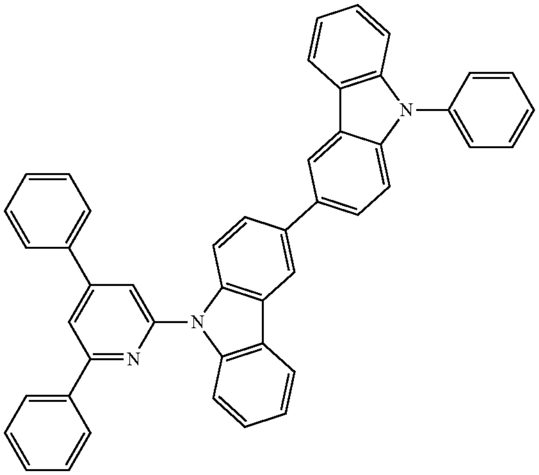
[E-2]
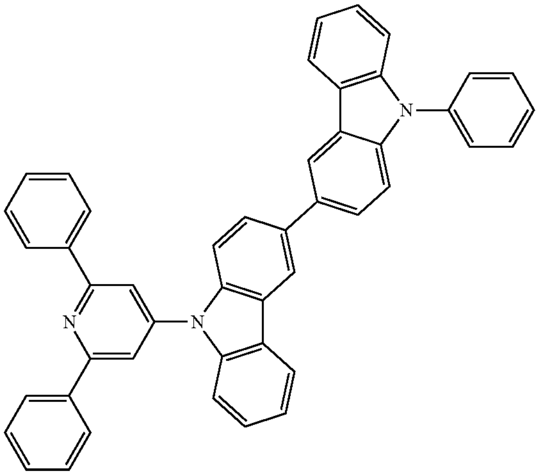
[E-3]
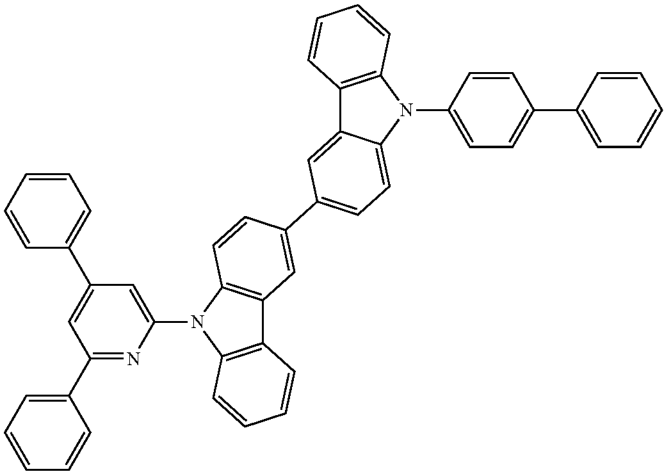

-continued
[E-4]
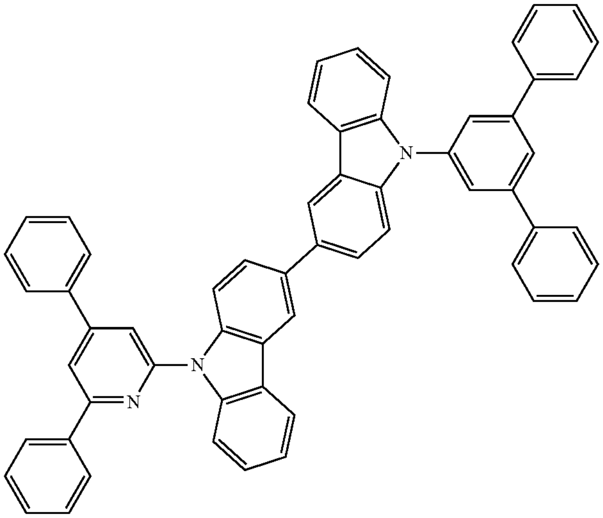
[E-5]
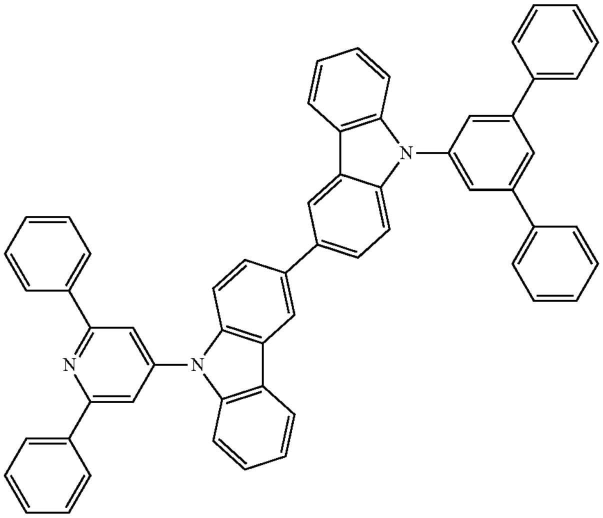
[E-6]
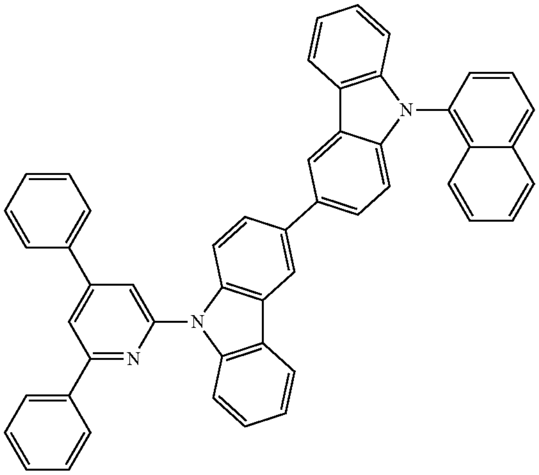

-continued
[E-7]
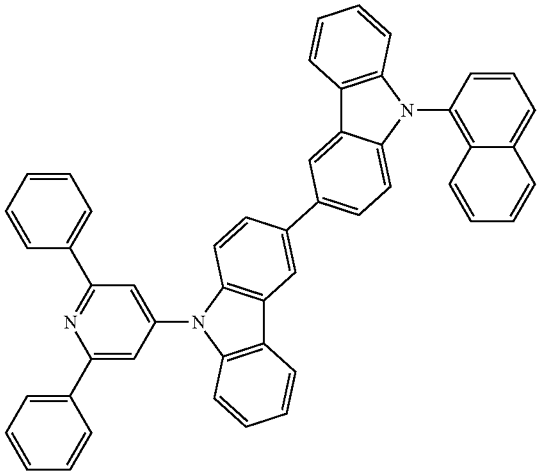
[E-8]
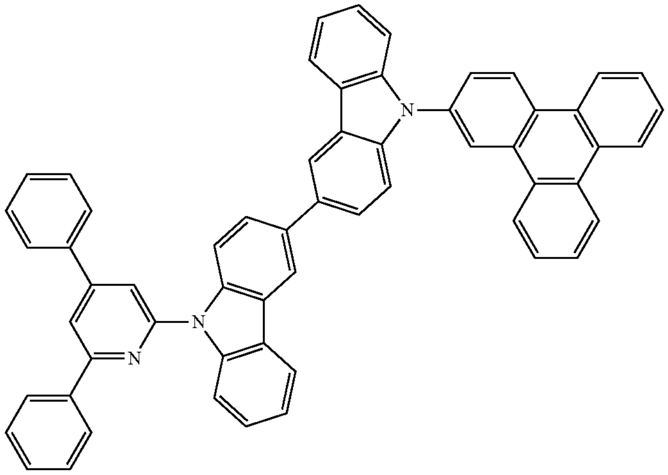
[E-9]
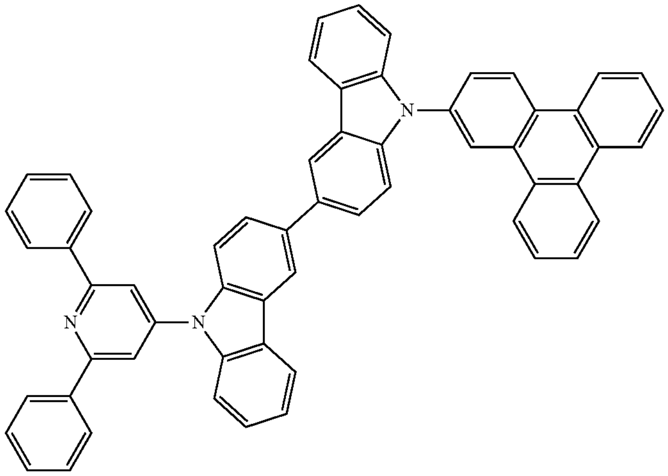

-continued
[E-10]
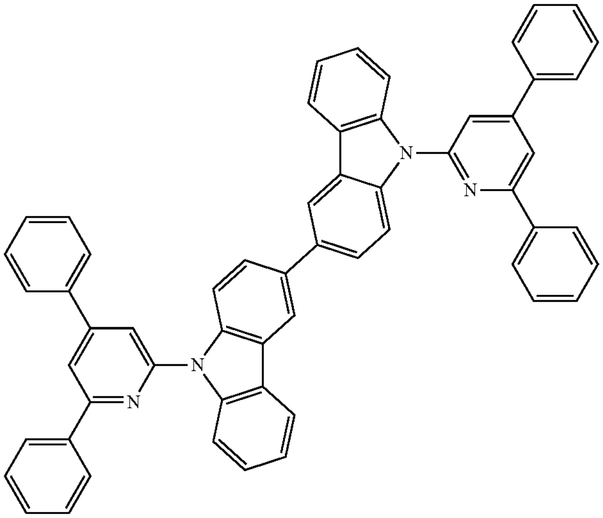
[E-11]
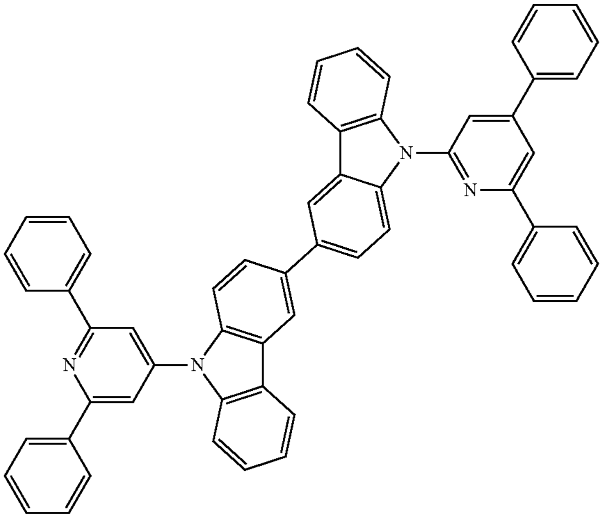
[E-12]
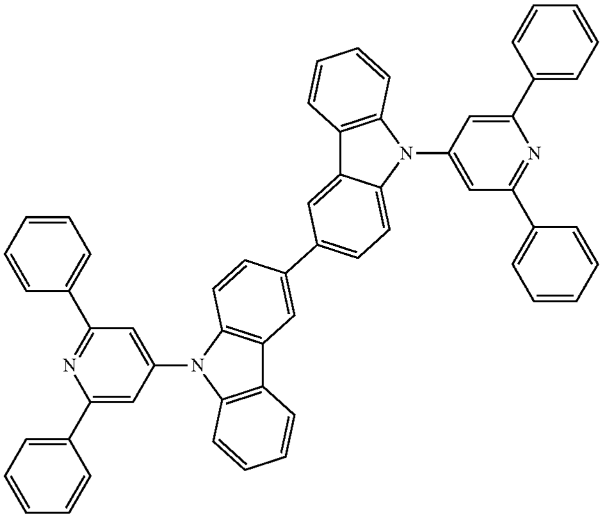

-continued
[E-13]
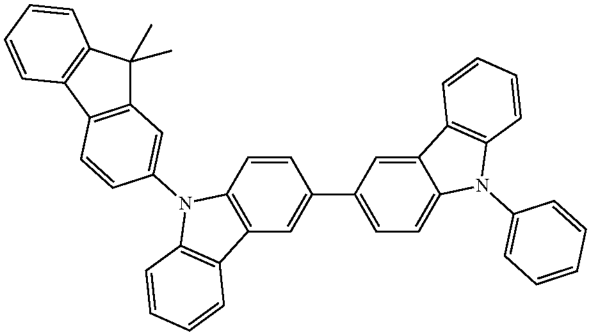
[E-14]
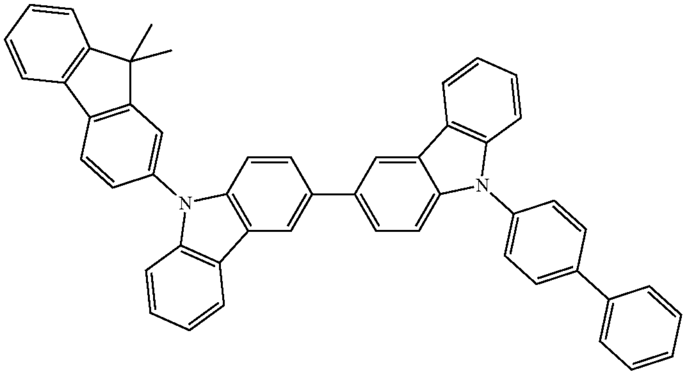
[E-15]
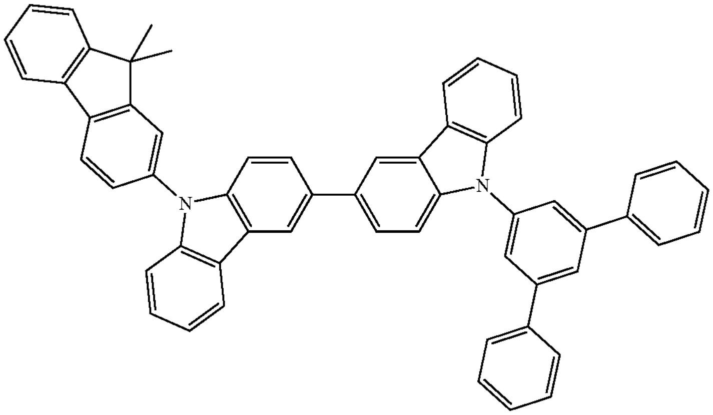
[E-16]
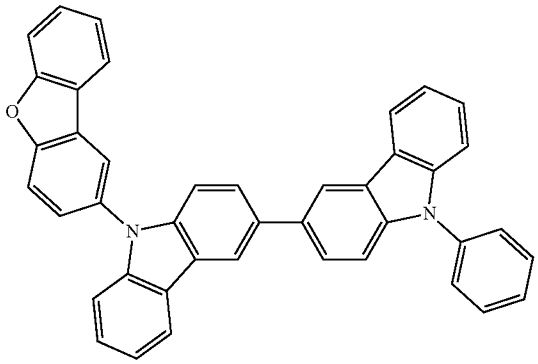

-continued
[E-17]
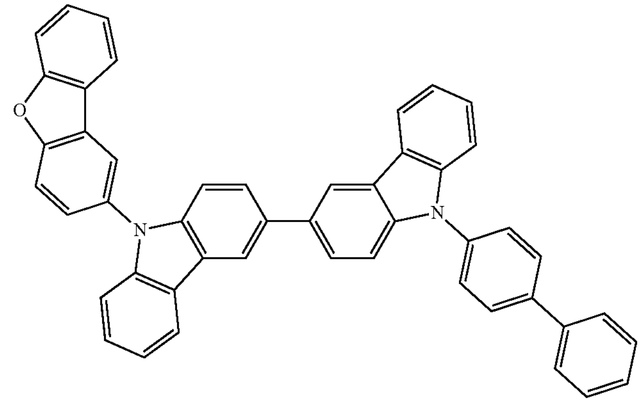
[E-18]
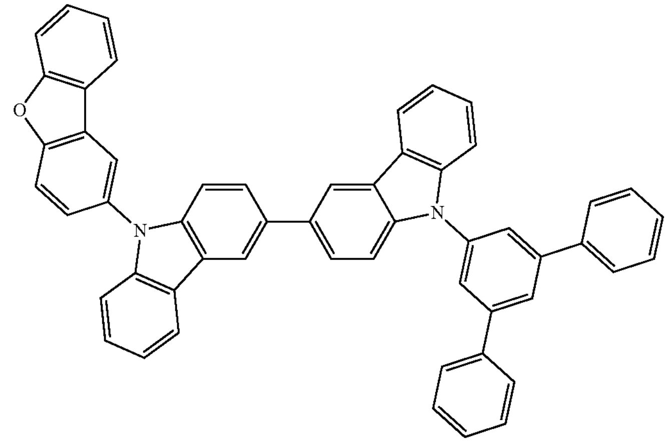
[E-19]
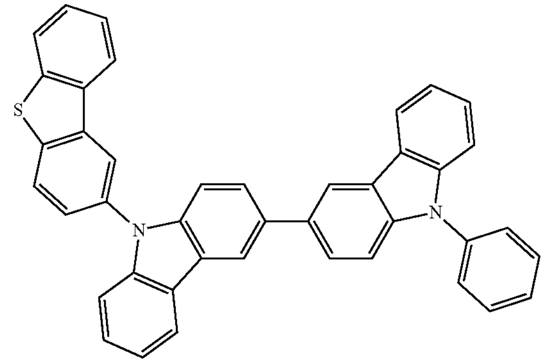
[E-20]
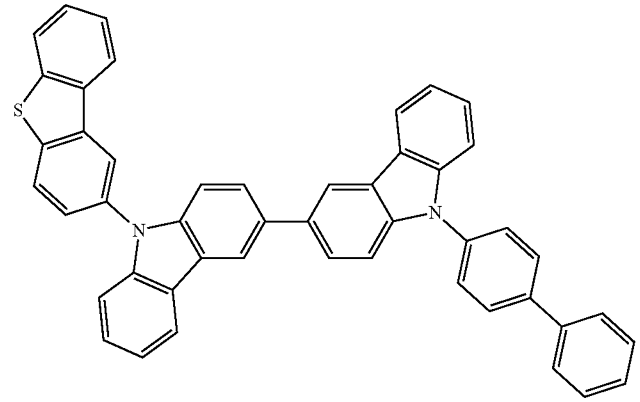

-continued
[E-21]
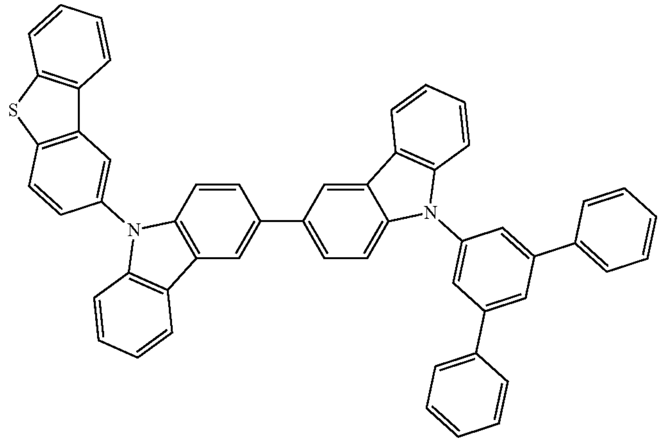
[E-22]
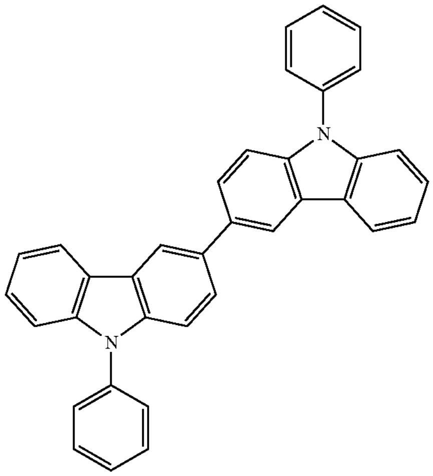
[E-23]
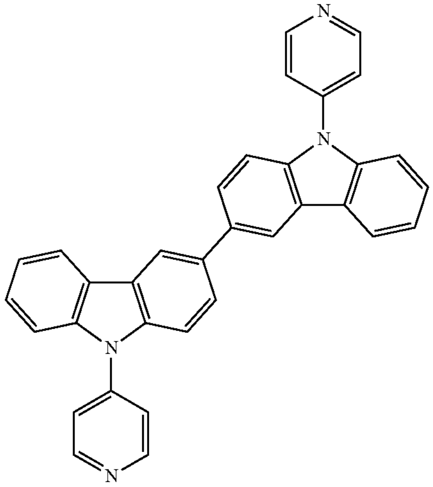

-continued
[E-24]
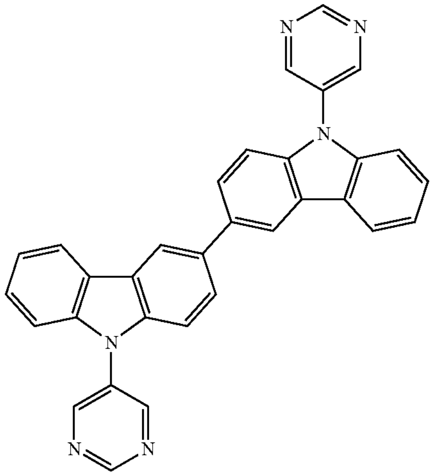
[E-25]
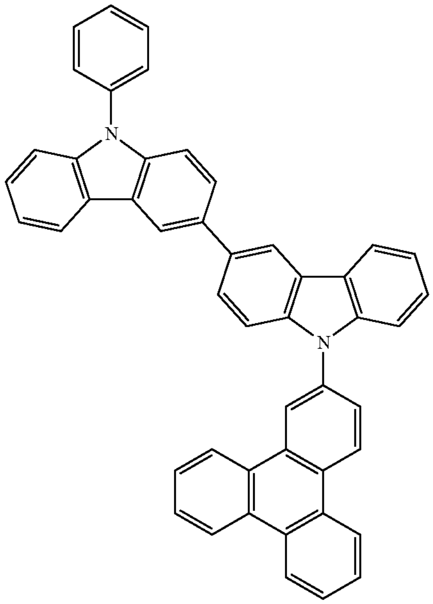

-continued
[E-26]
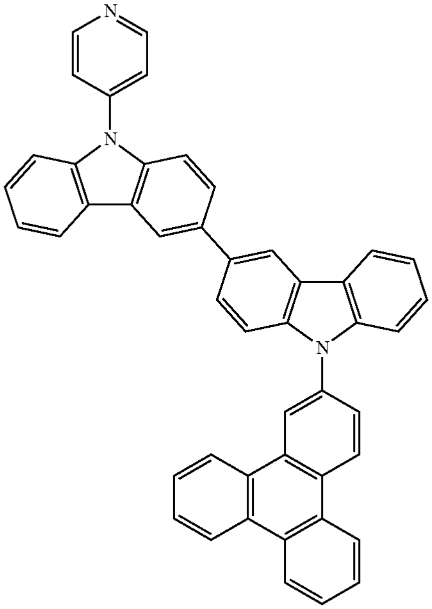
[E-27]
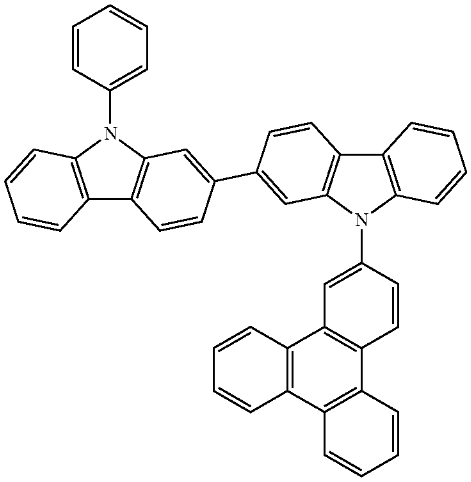
[E-28]
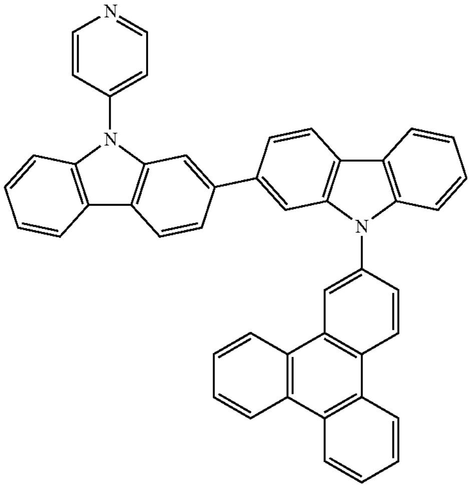

-continued
[E-29]
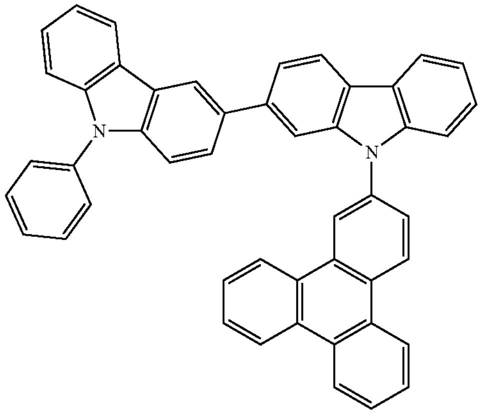
[E-30]
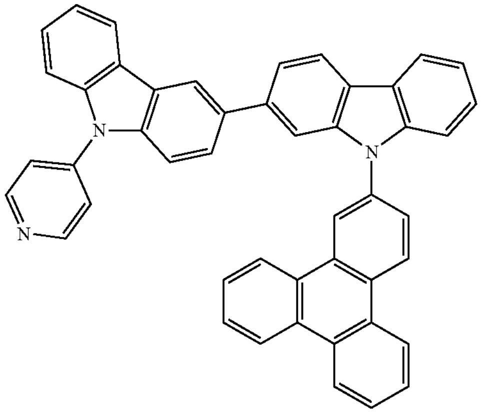
[E-31]
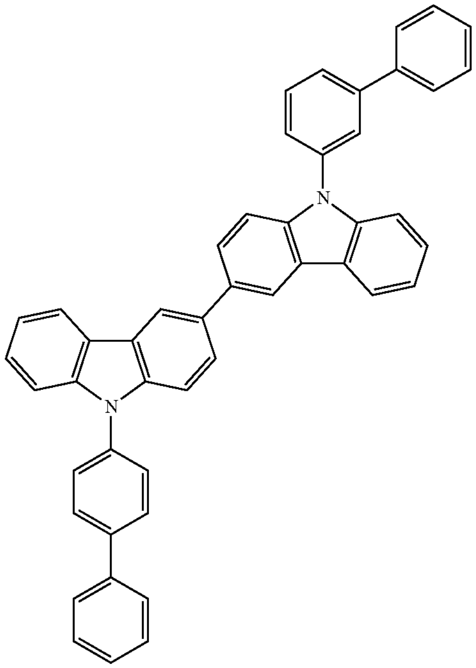

-continued
[E-32]
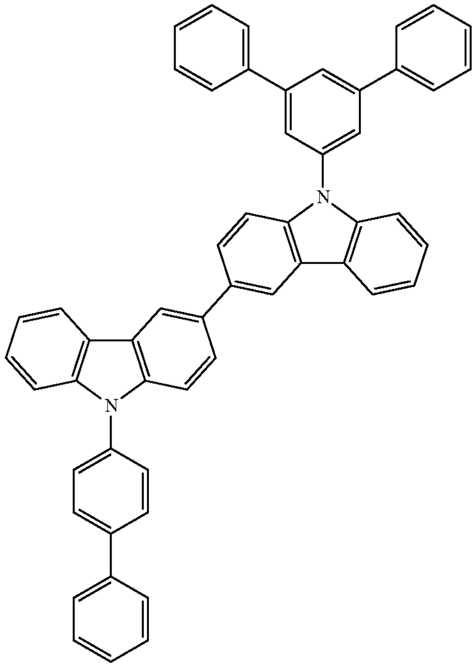
[E-33]
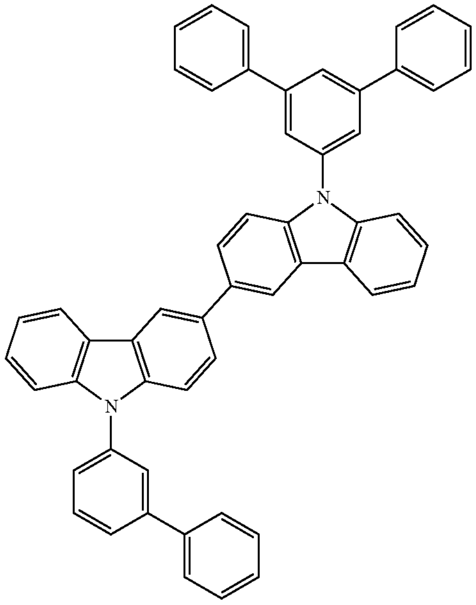

-continued
[E-34]
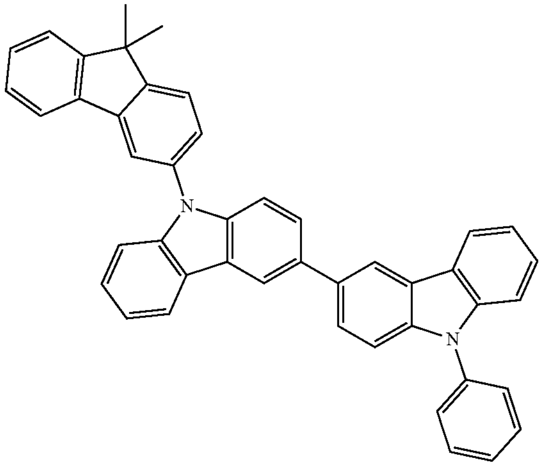
[E-35]
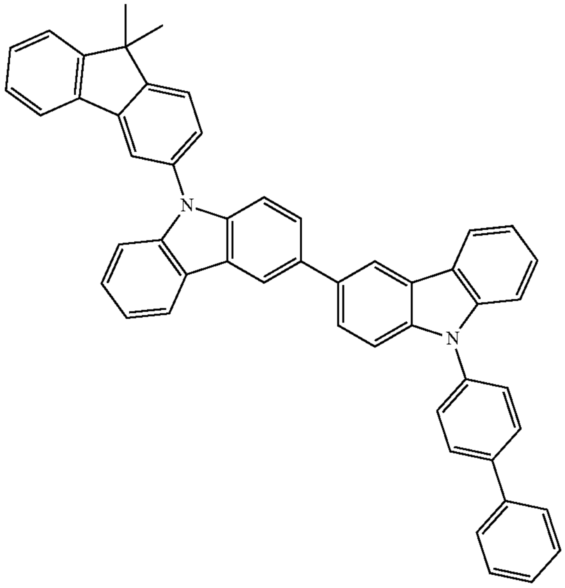
[E-36]
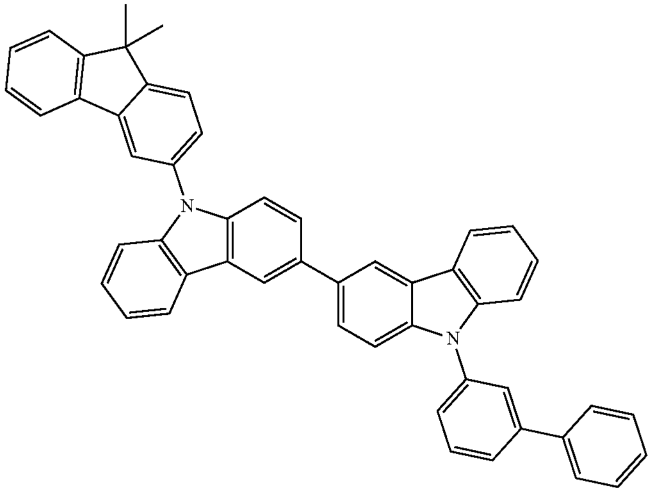

-continued
[E-37]
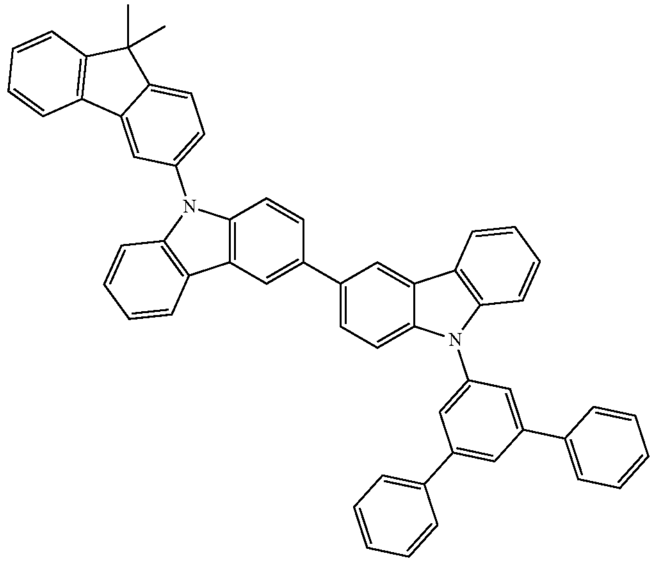
[E-38]
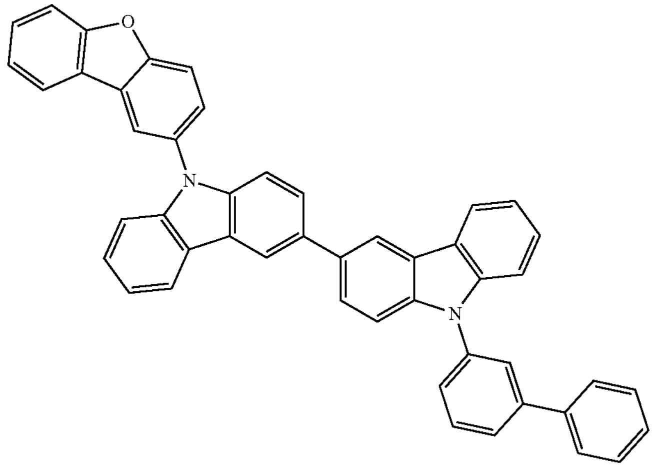
[E-39]
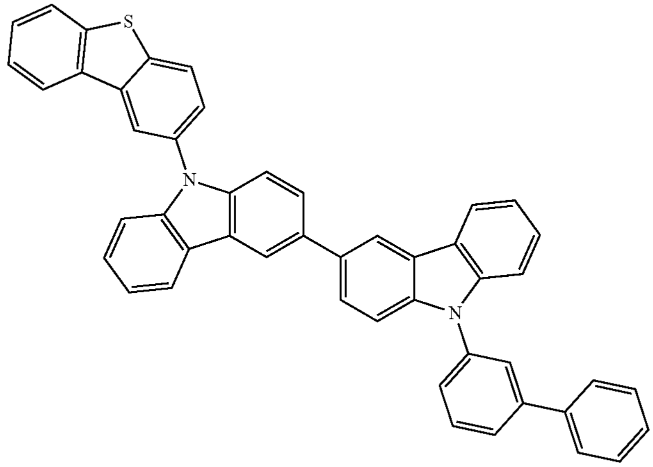

-continued
[E-40]
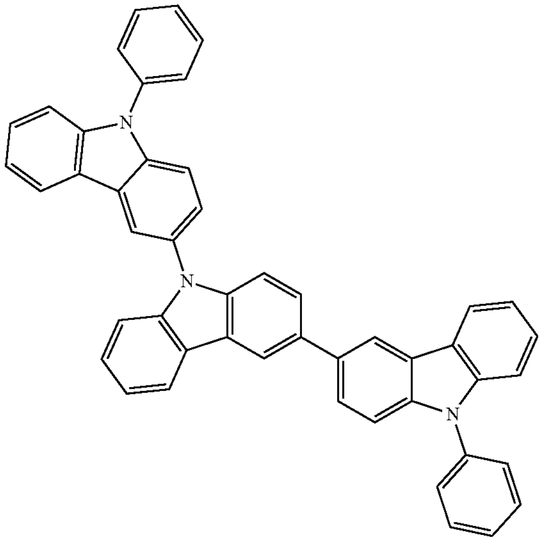
[E-41]
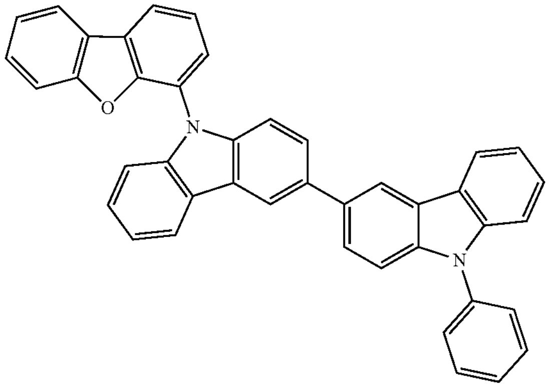
[E-42]
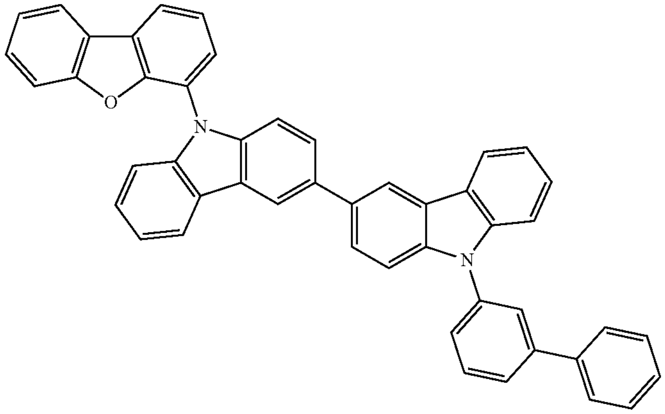

-continued
[E-43]
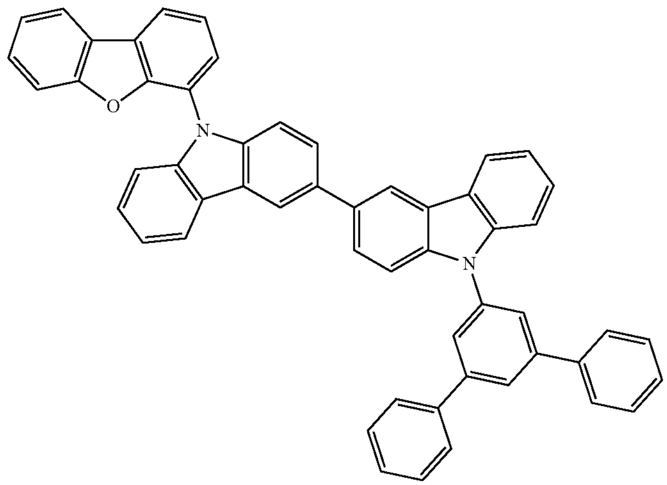
[E-44]
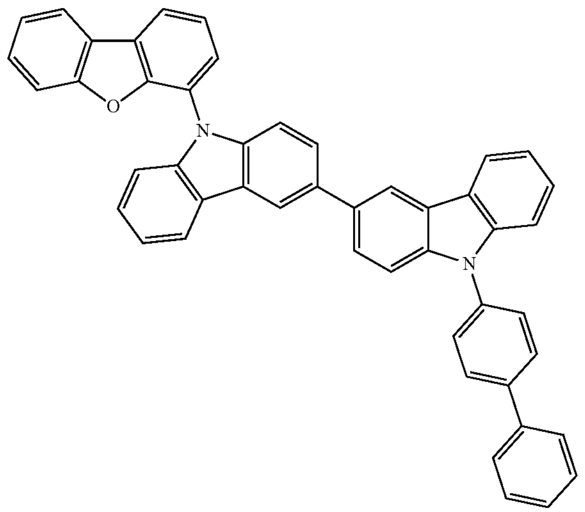
[E-45]
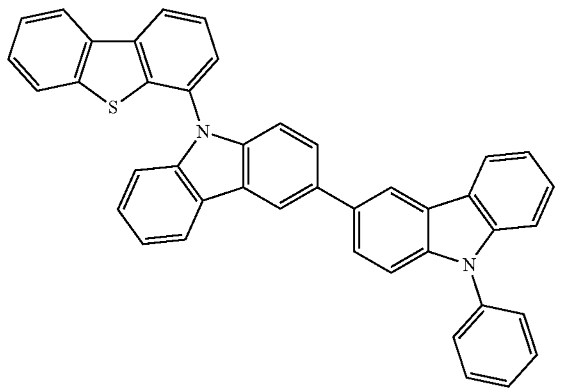

-continued
[E-46]
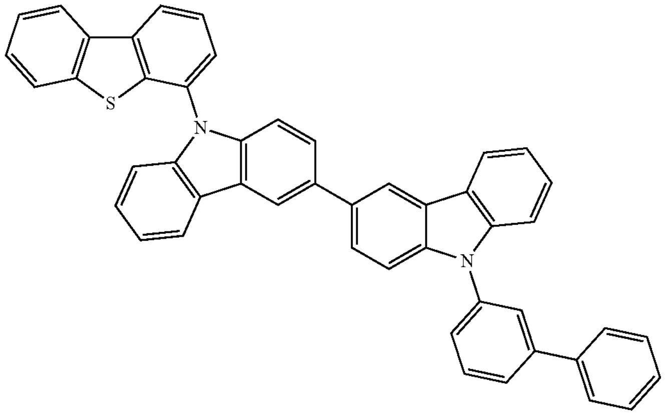
[E-47]
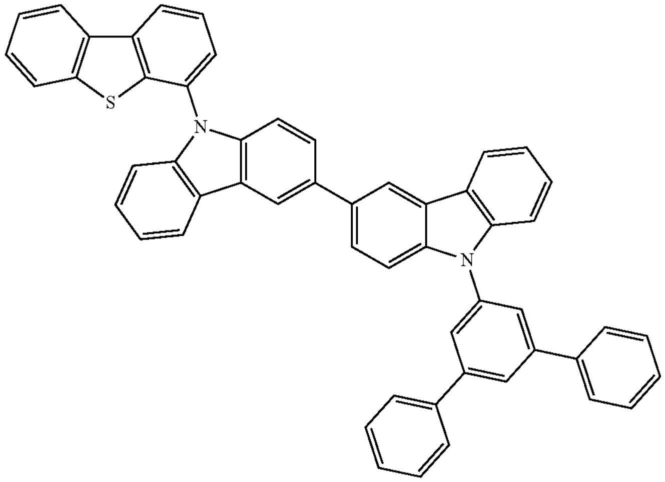
[E-48]
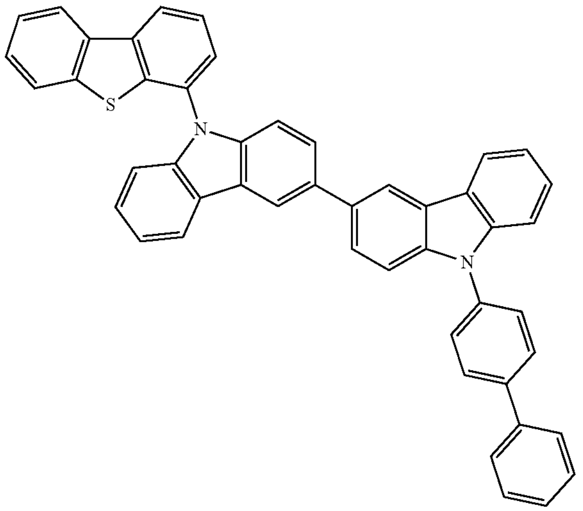

-continued
[E-49]
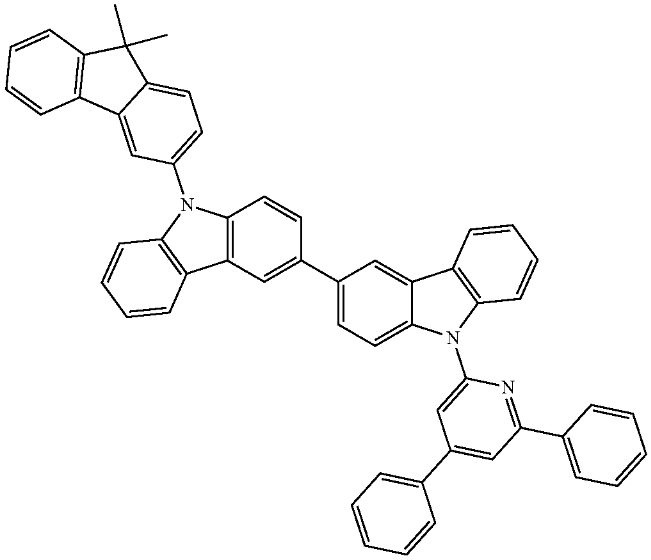
[E-50]
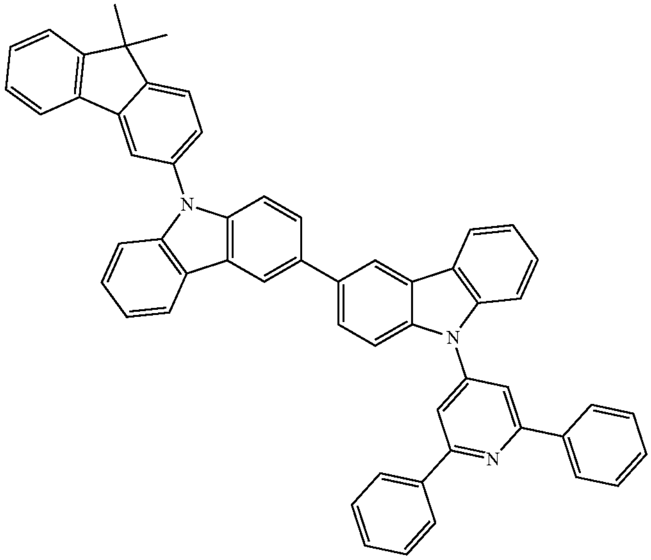

-continued
[E-51]
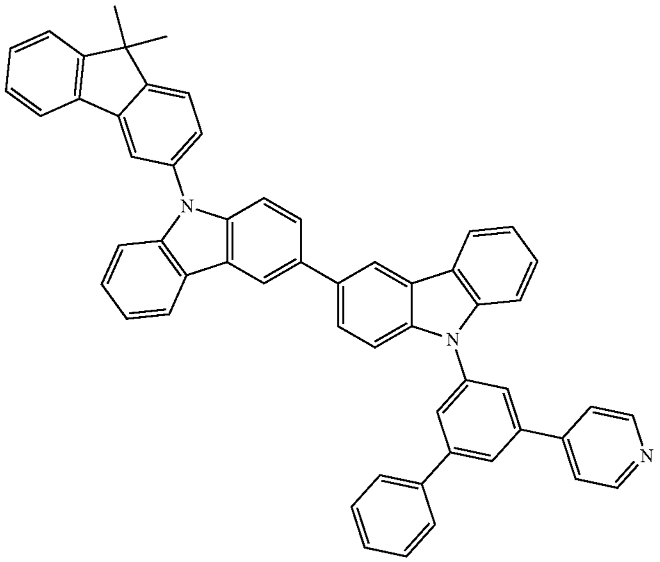
[E-52]
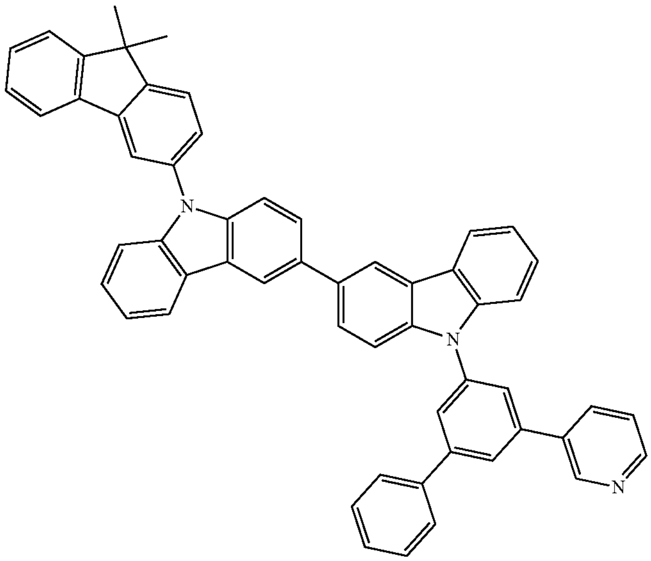

-continued
[E-53]
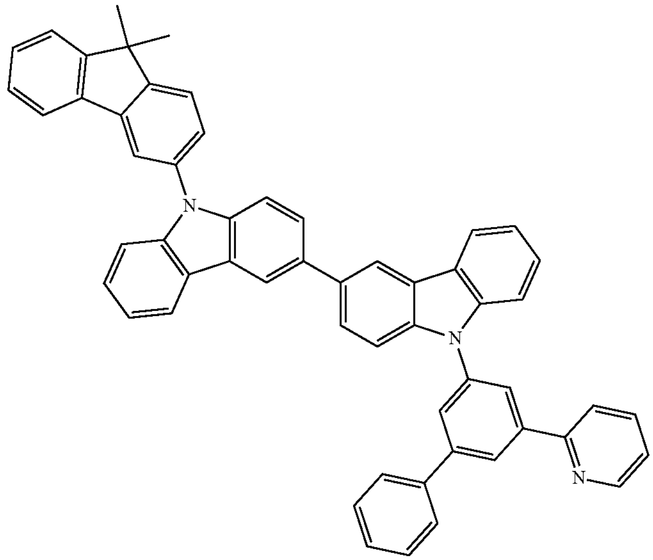
[E-54]
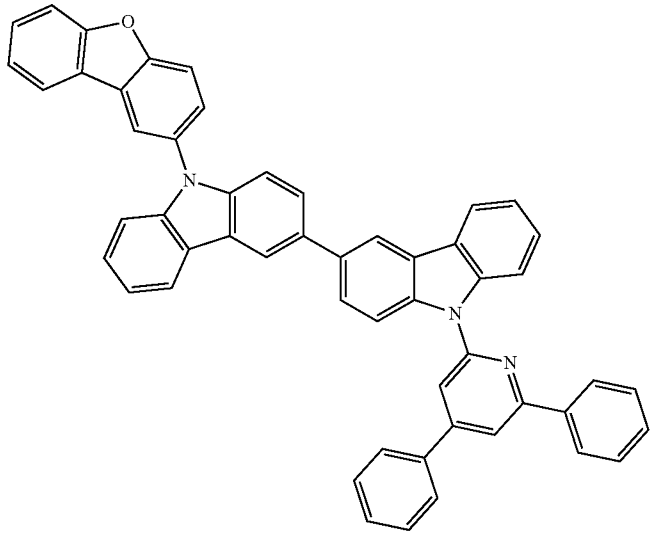
[E-55]
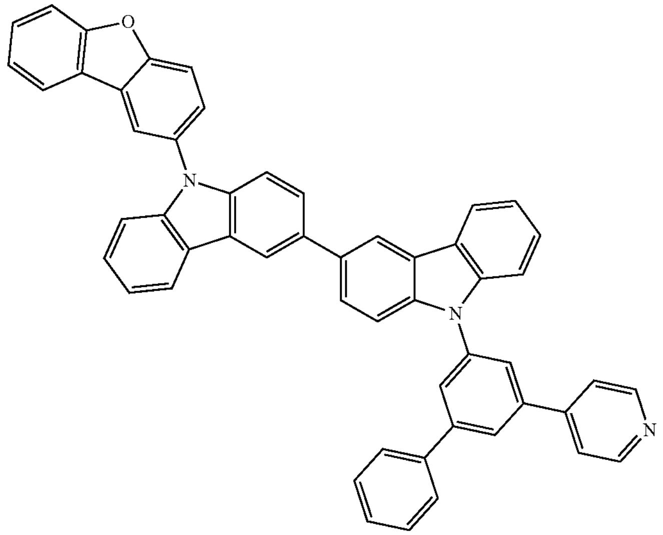

-continued
[E-56]
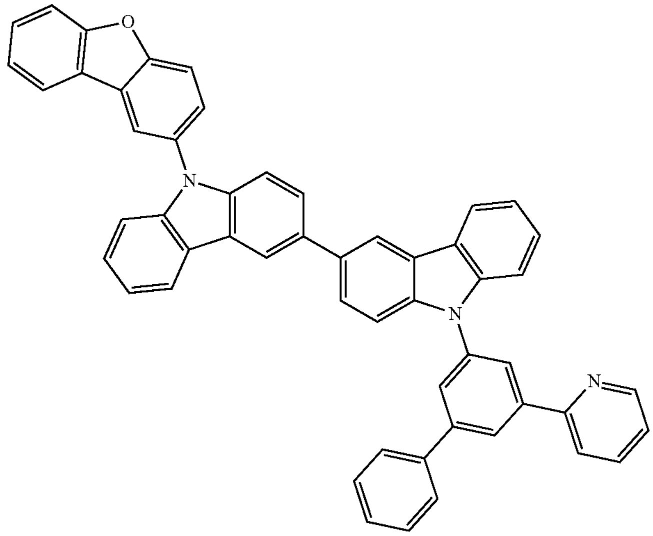
[E-57]
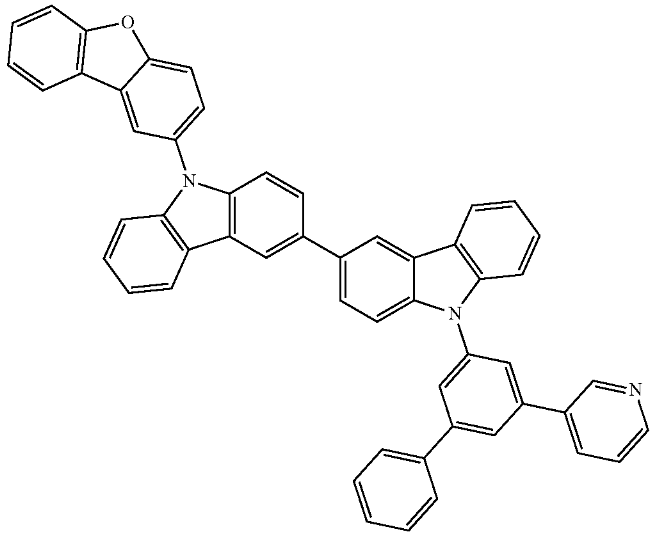
[E-58]
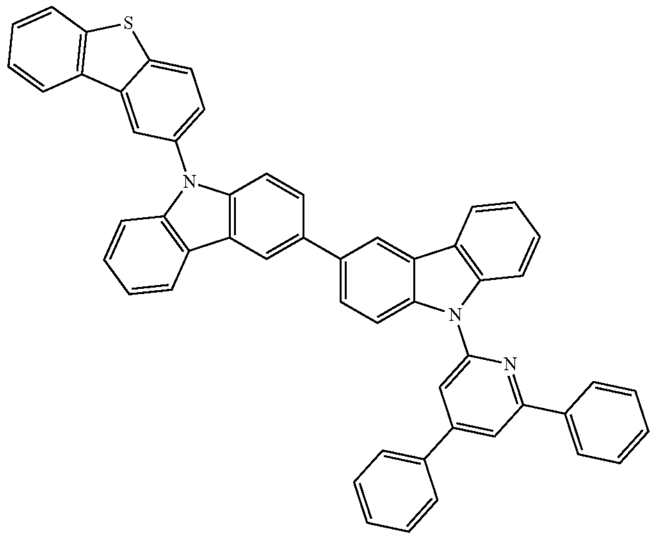

-continued
[E-59]
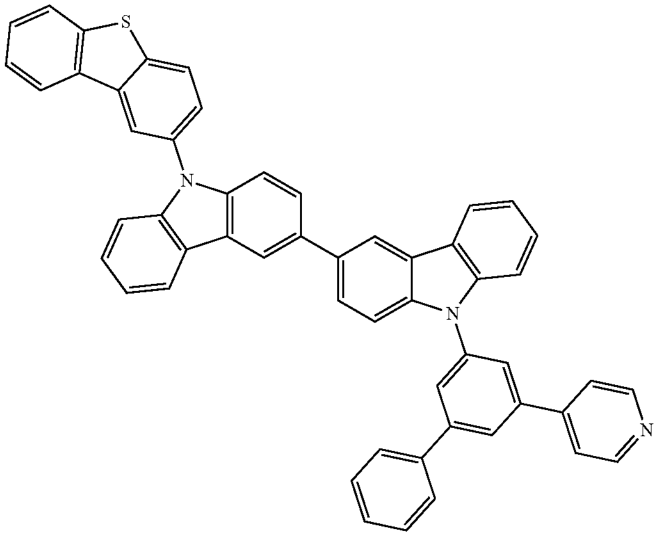
[E-60]
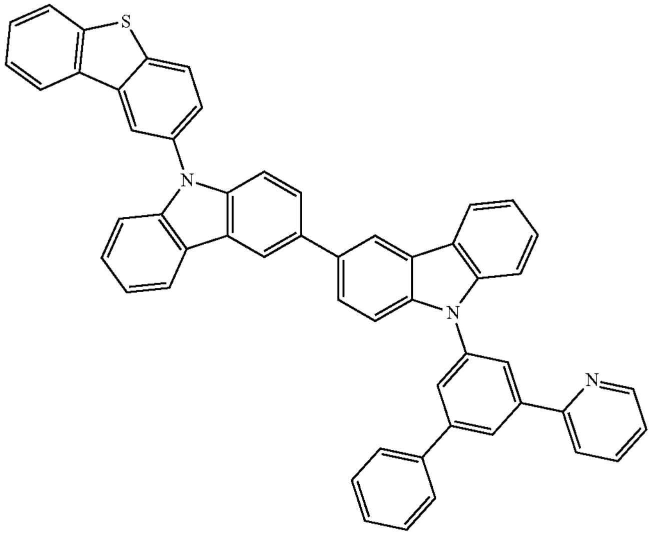
[E-61]
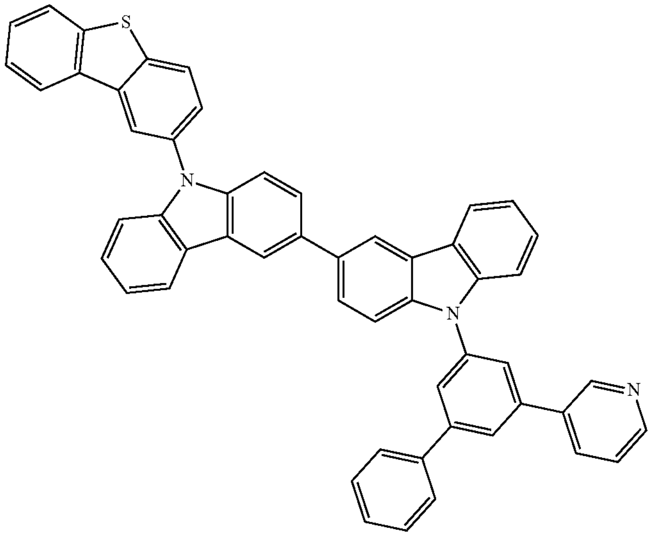

-continued
[E-62]
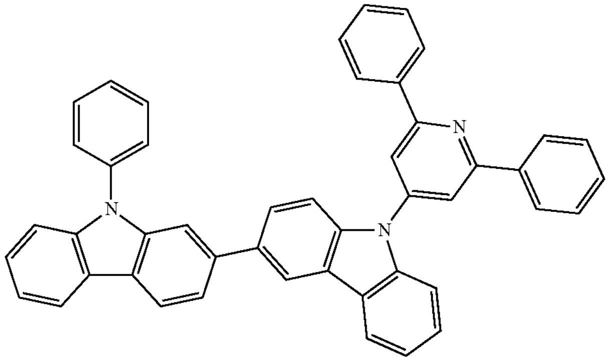
[E-63]
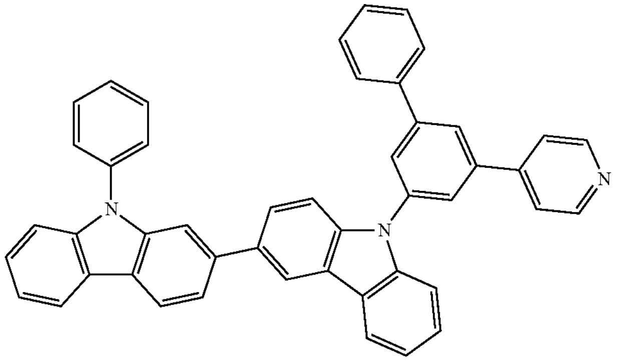
[E-64]
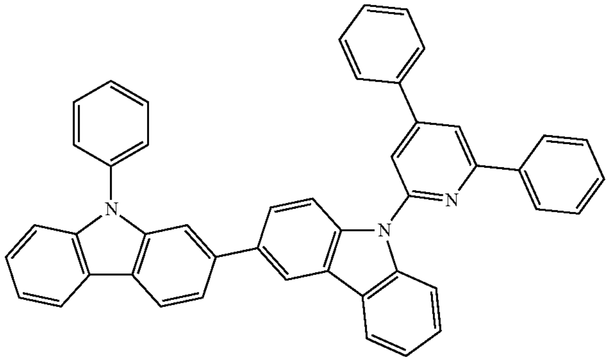
[E-65]
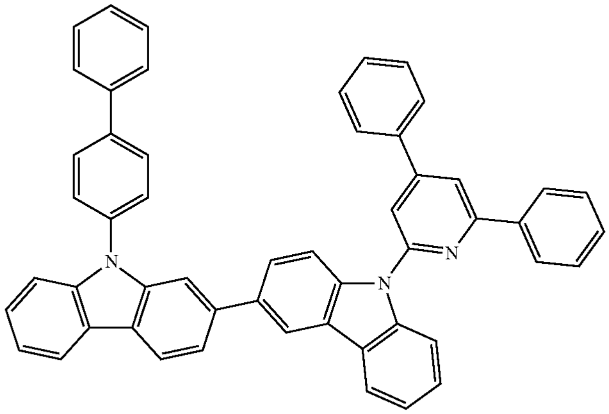

-continued
[E-66]
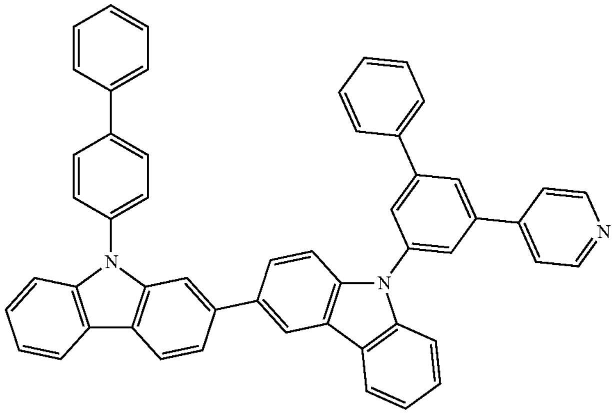
[E-67]
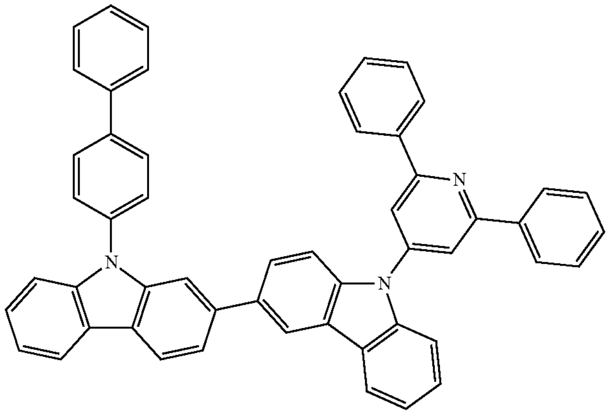
[E-68]
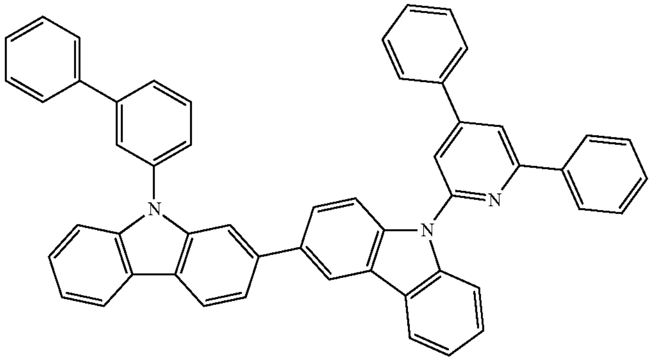
[E-69]
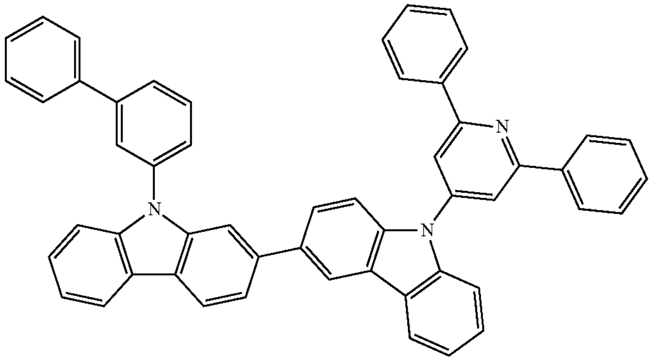

-continued
[E-70]
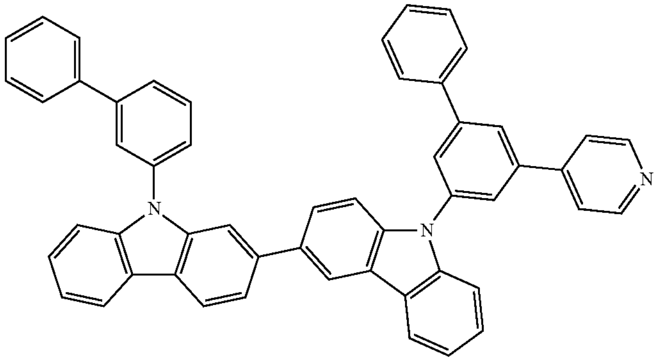
[E-71]
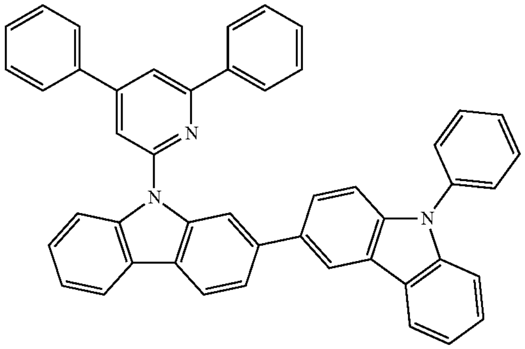
[E-72]
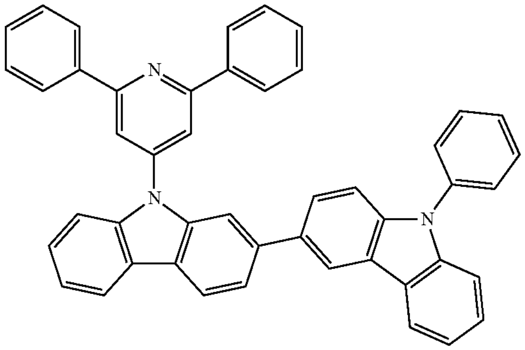
[E-73]
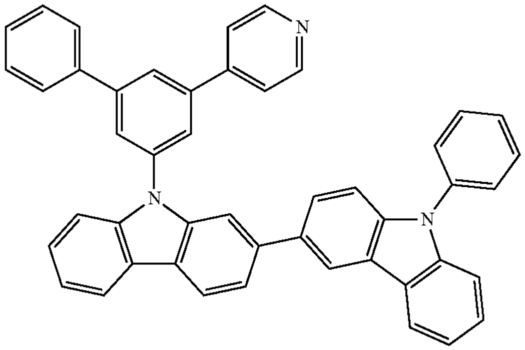

-continued
[E-74]
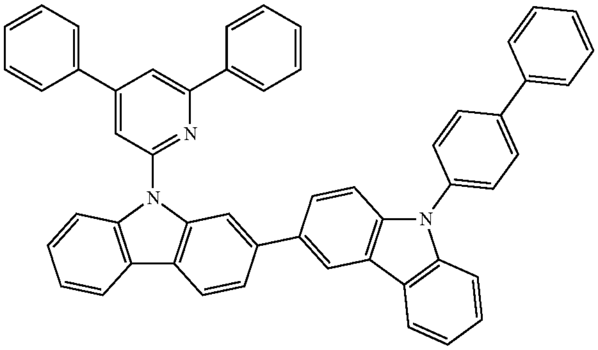
[E-75]
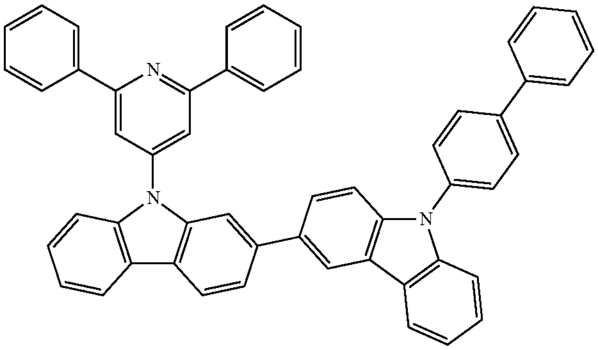
[E-76]
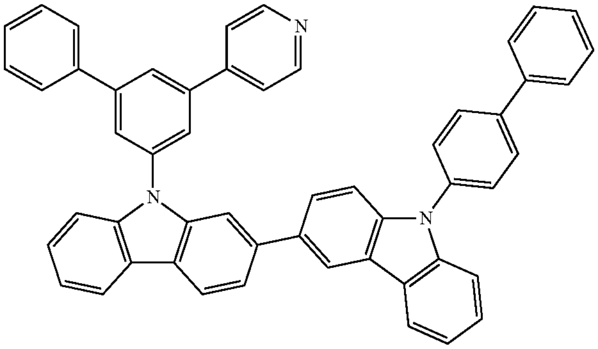
[E-77]
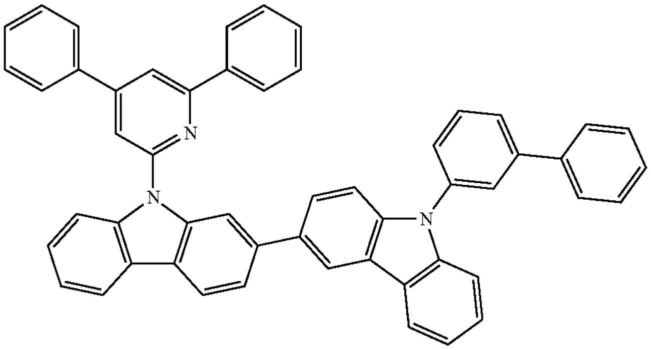

-continued
[E-78]
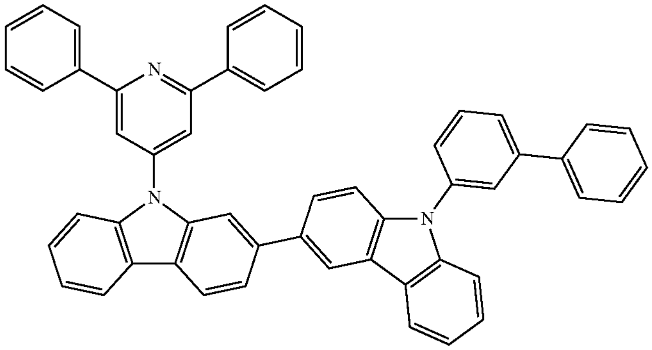
[E-79]
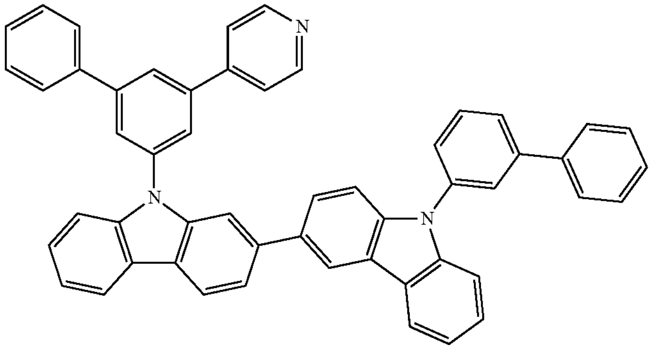
[E-80]
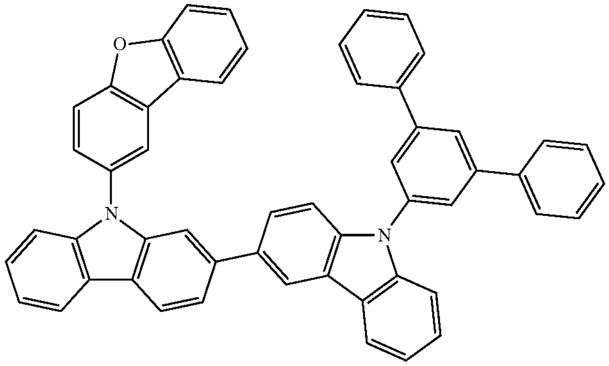
[E-81]
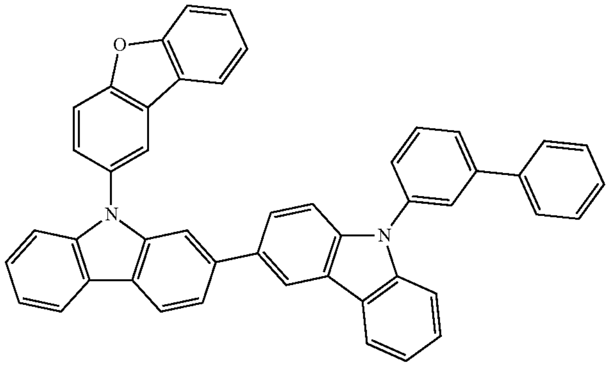

-continued
[E-82]
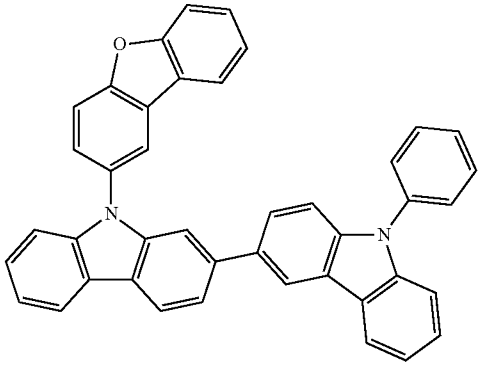
[E-83]
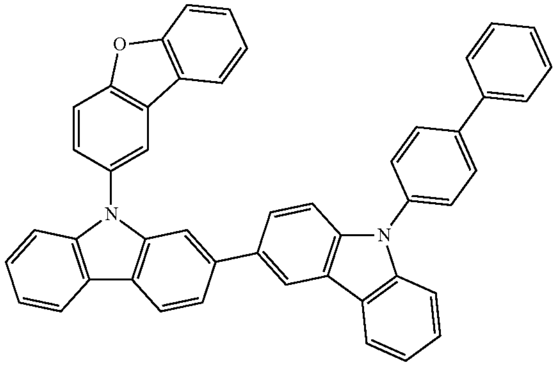
[E-84]
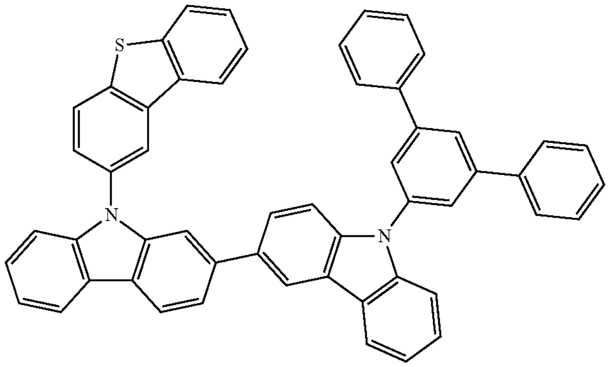
[E-85]
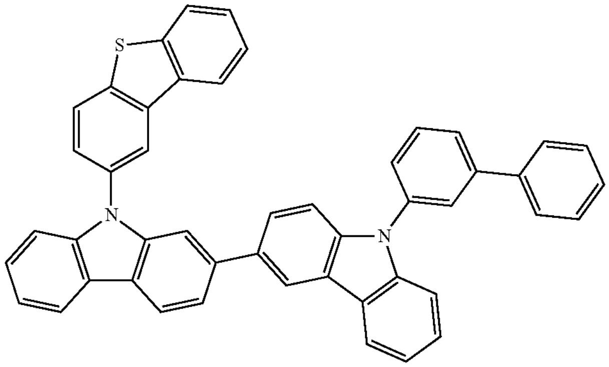

-continued
[E-86]
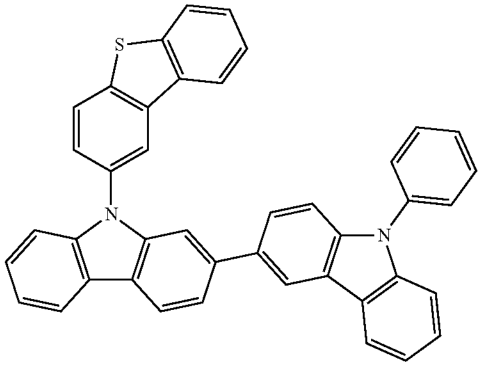
[E-87]
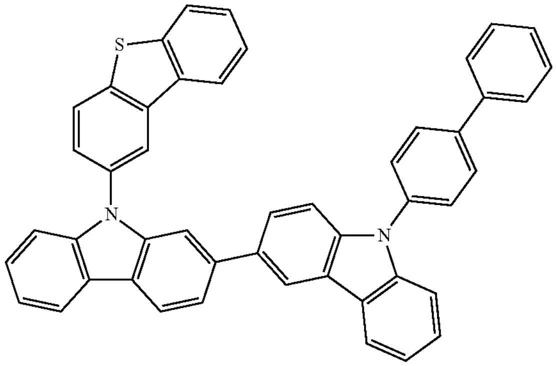
[E-88]
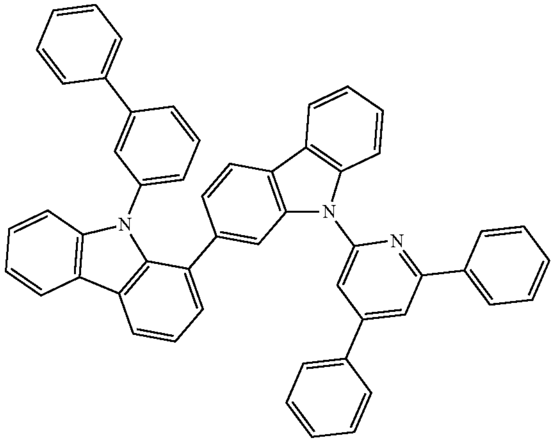
[E-89]
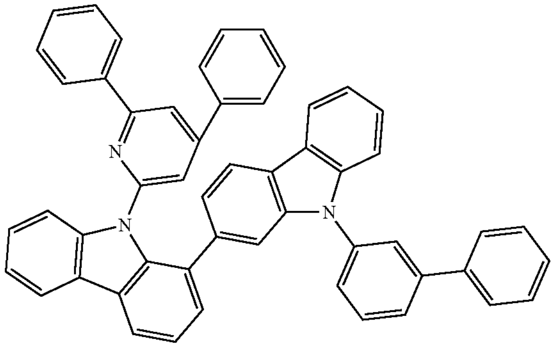

-continued
[E-90]
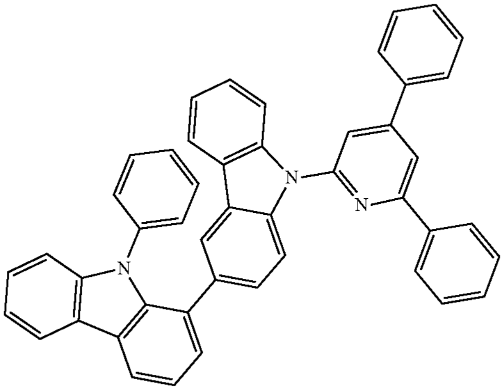
[E-91]
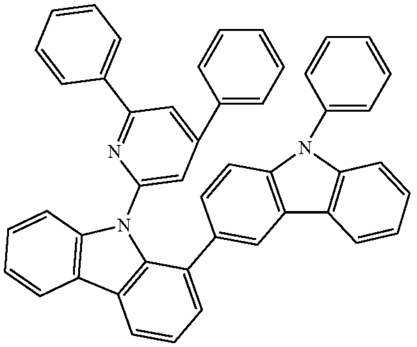
[E-92]
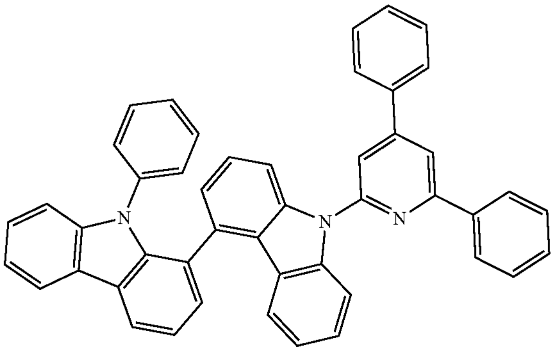
[E-93]
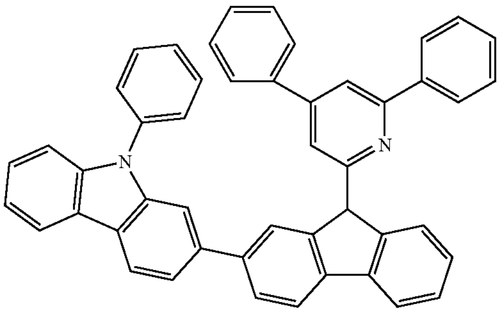

-continued
[E-94]
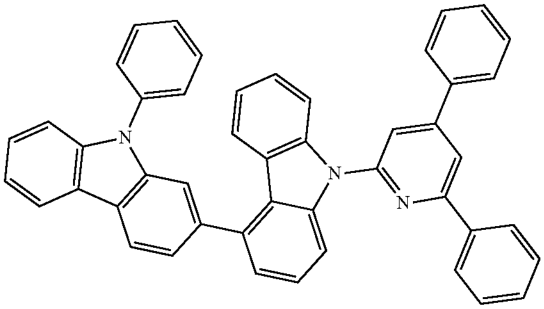
[E-95]
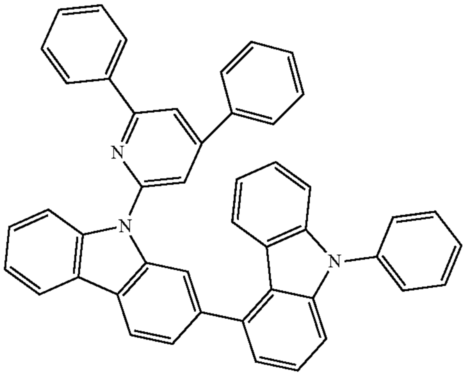
[E-96]
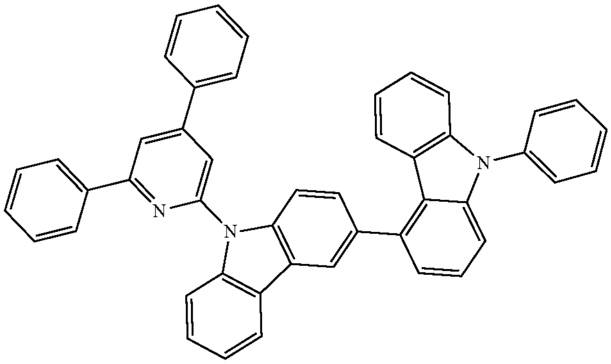
[E-97]
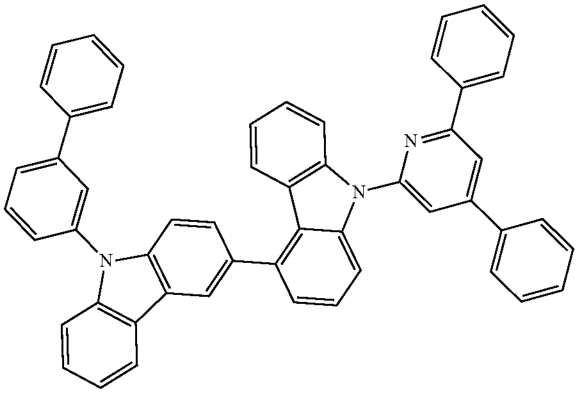

-continued
[E-98]
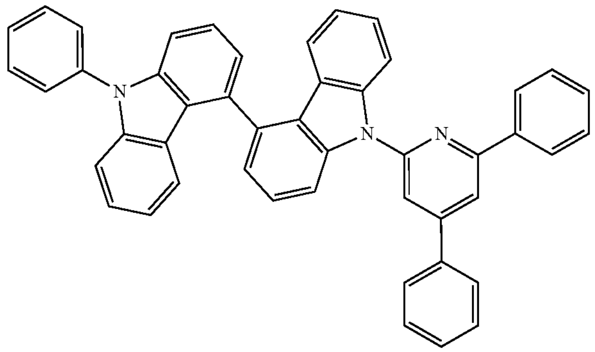
[E-99]
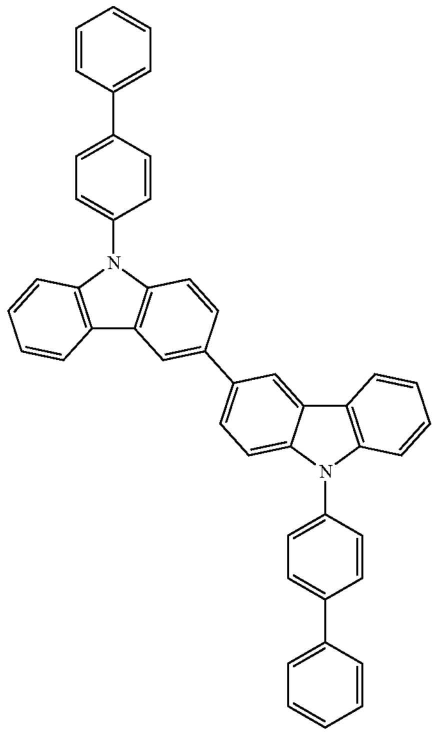

-continued
[E-100]
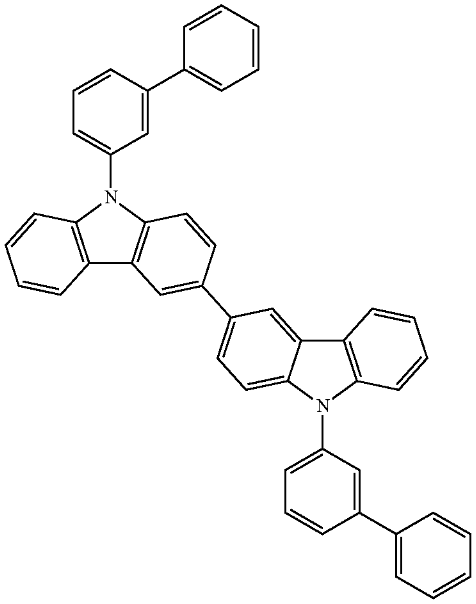
[E-101]
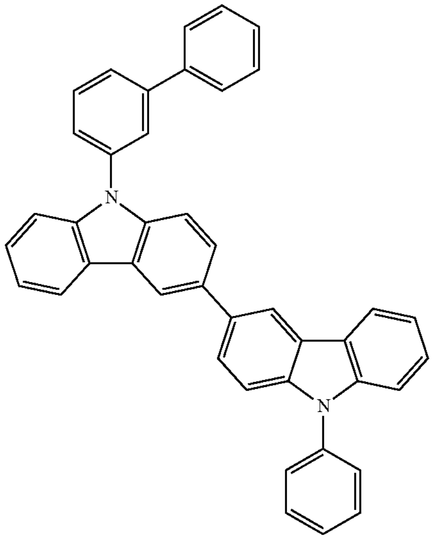
[E-102]
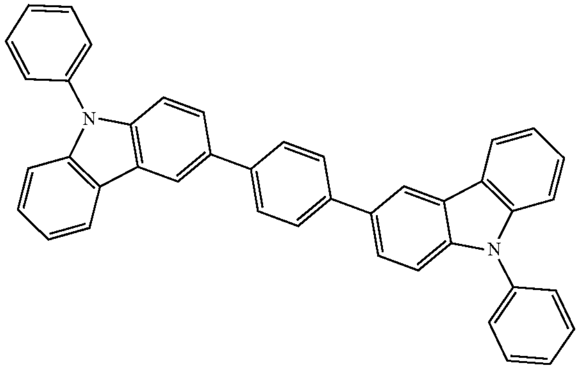

-continued
[E-103]
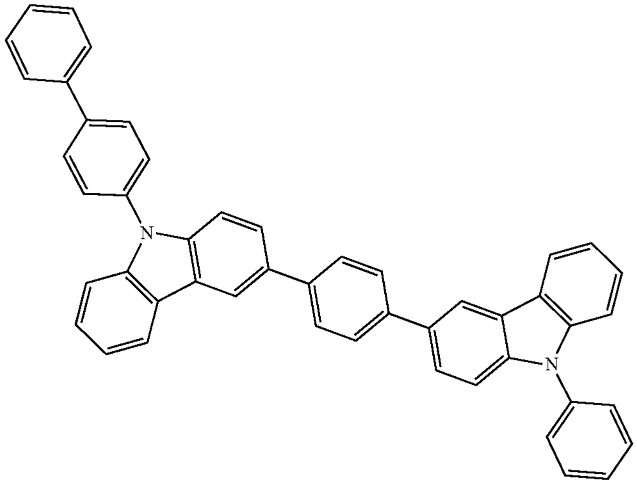
[E-104]
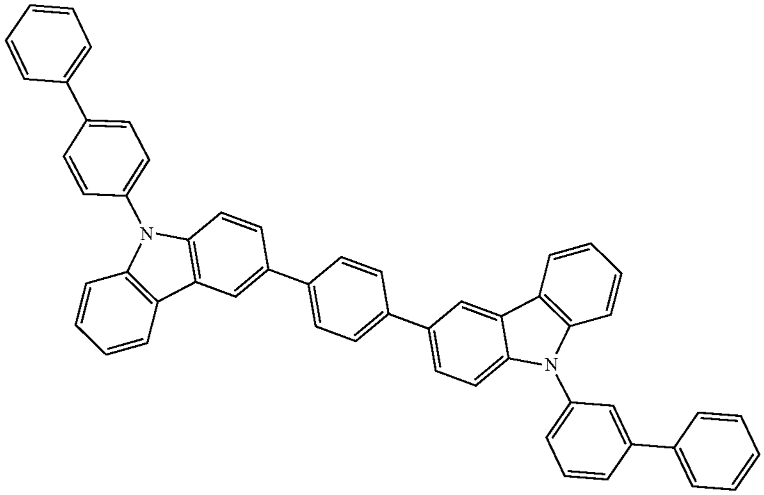
[E-105]
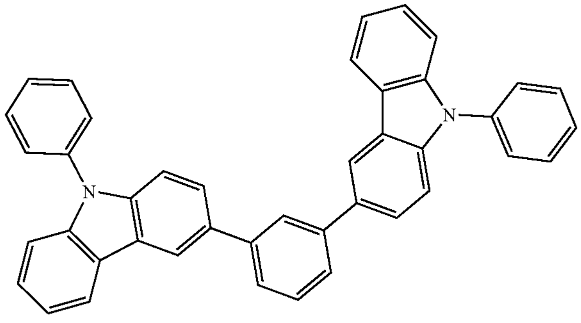
[E-106]
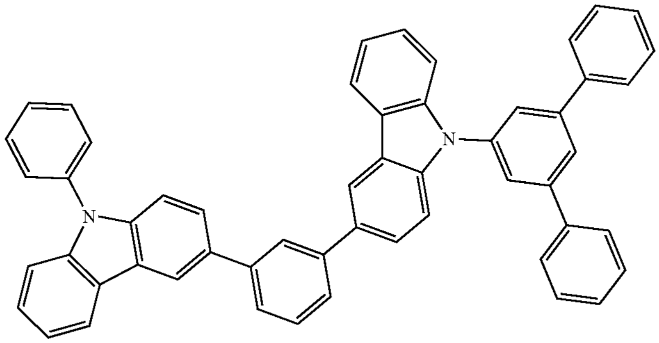

-continued
[E-107]
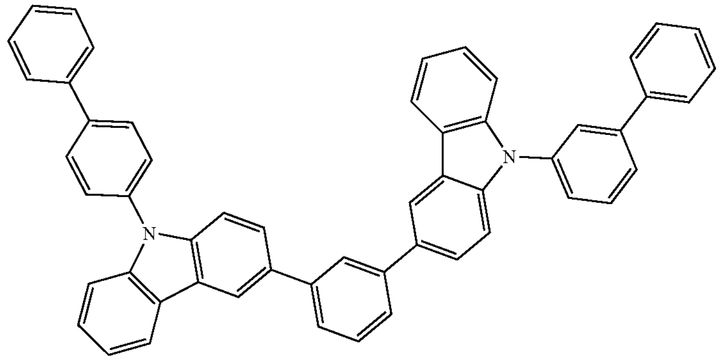
[E-108]
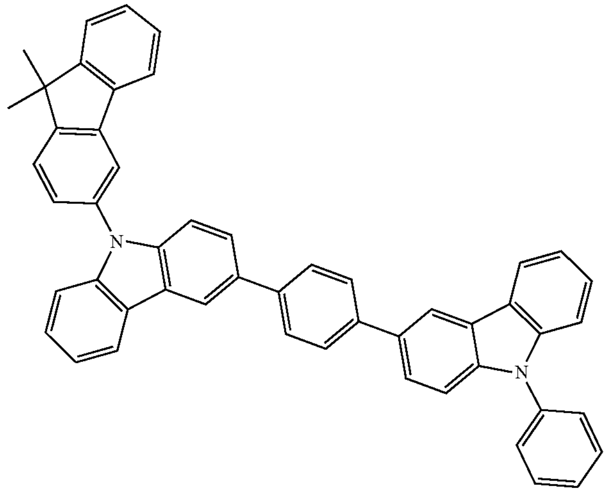
[E-109]
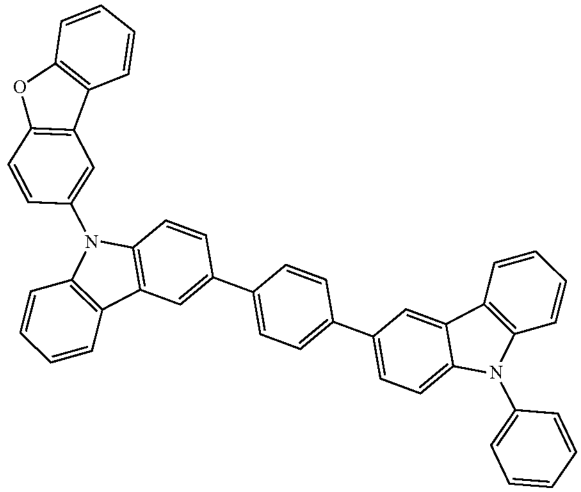

-continued
[E-110]
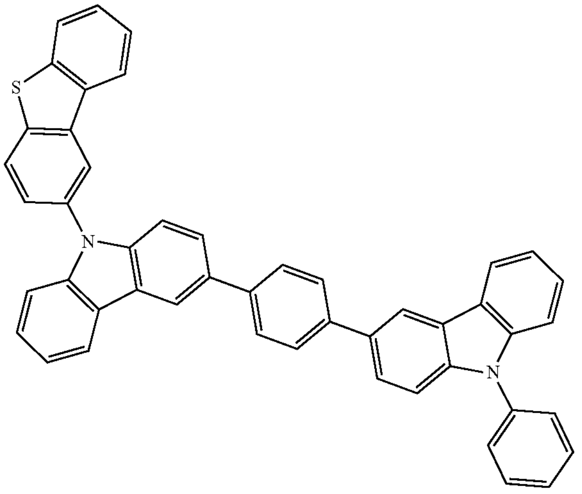
[E-111]
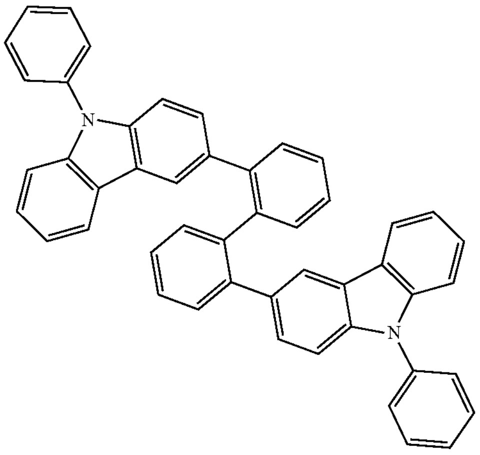
[E-112]
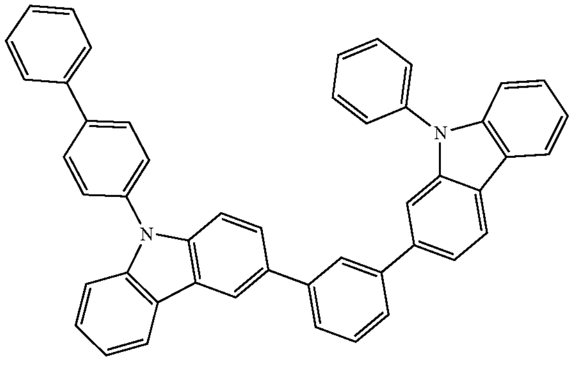

-continued
[E-113]
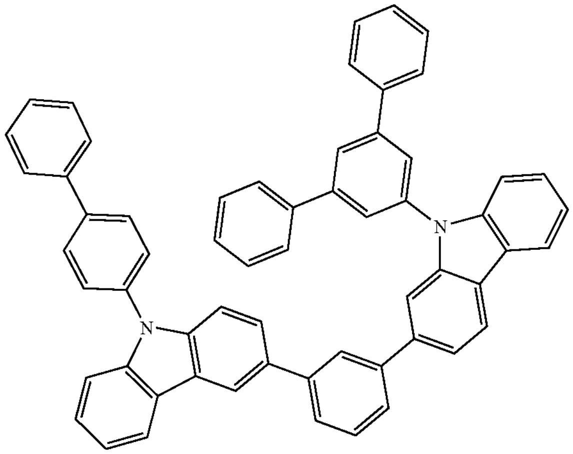
[E-114]
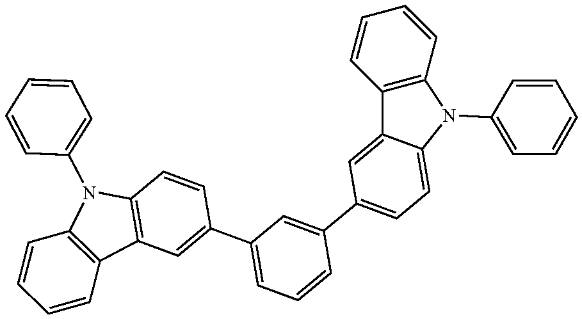
[E-115]
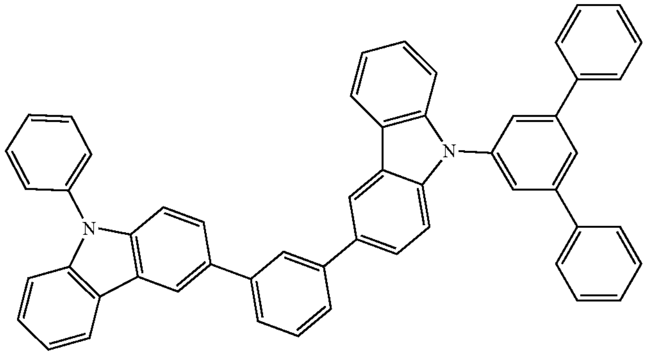
[E-116]
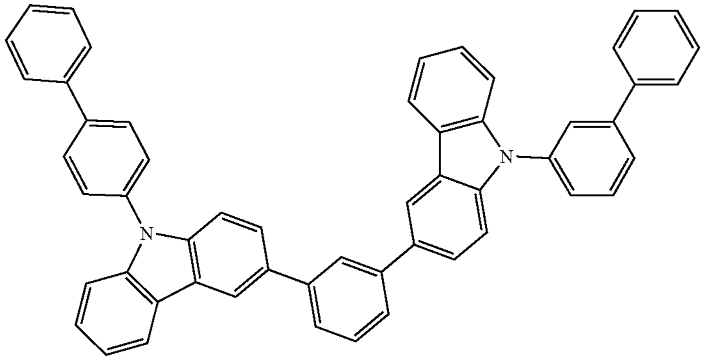

-continued
[E-117]
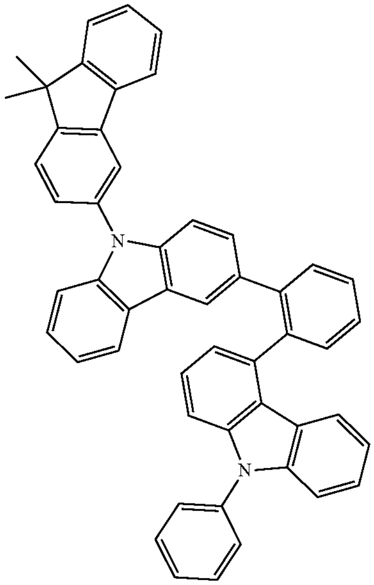
[E-118]
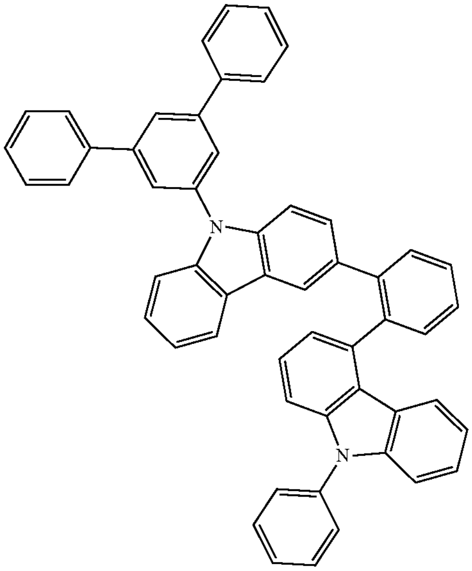

-continued
[E-119]
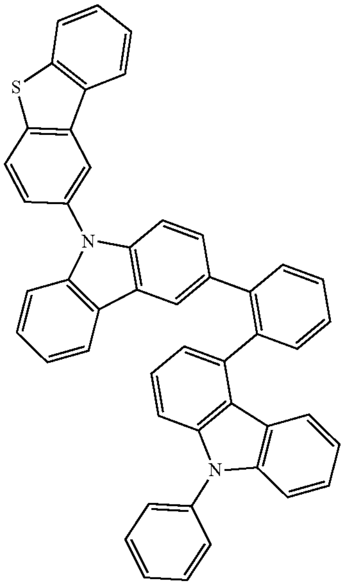
[E-120]
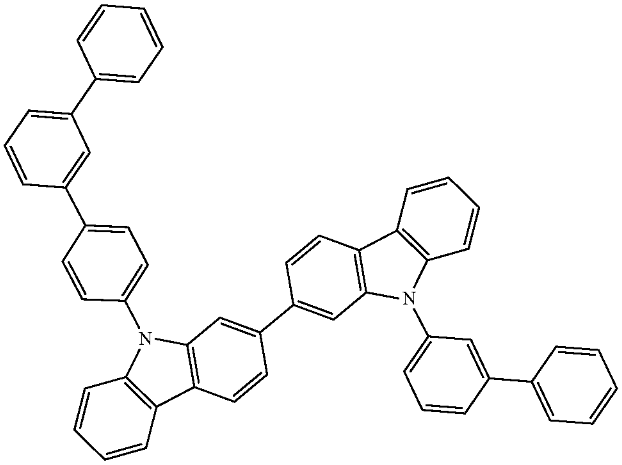
[E-121]
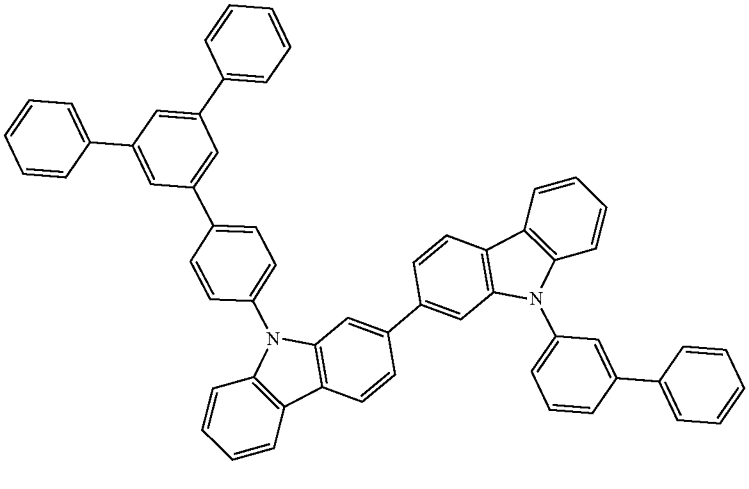

-continued
[E-122]
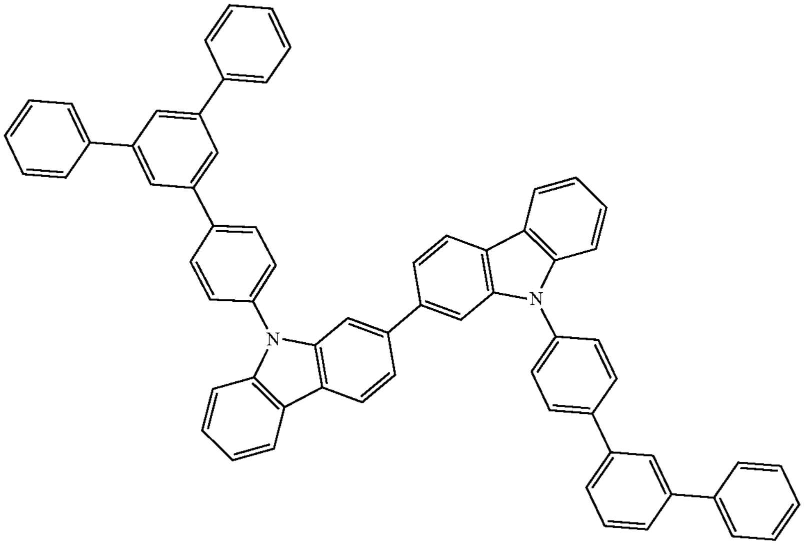
[E-123]
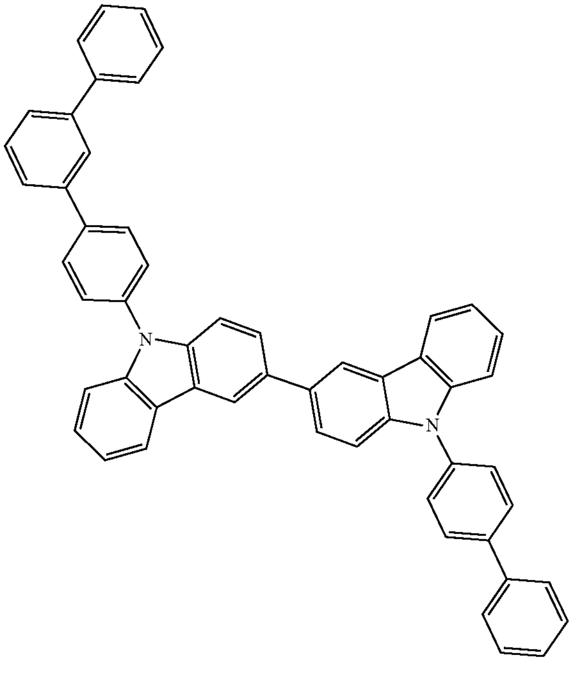

-continued
[E-124]
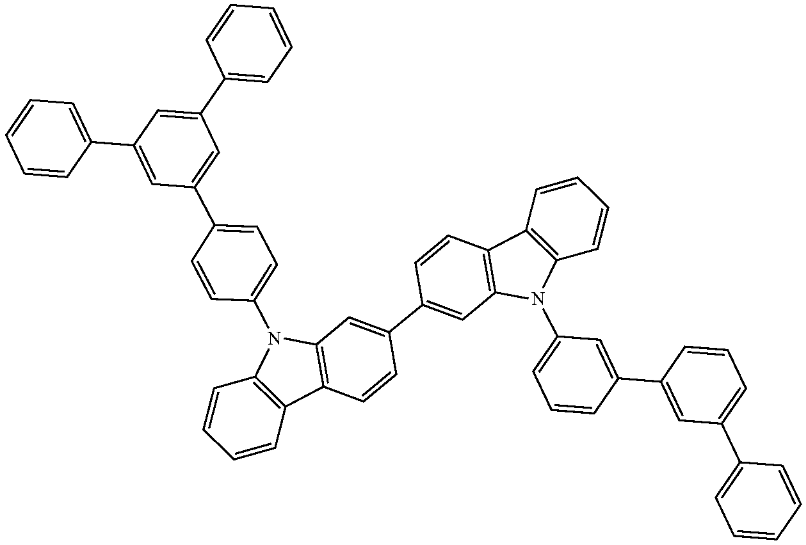
[E-125]
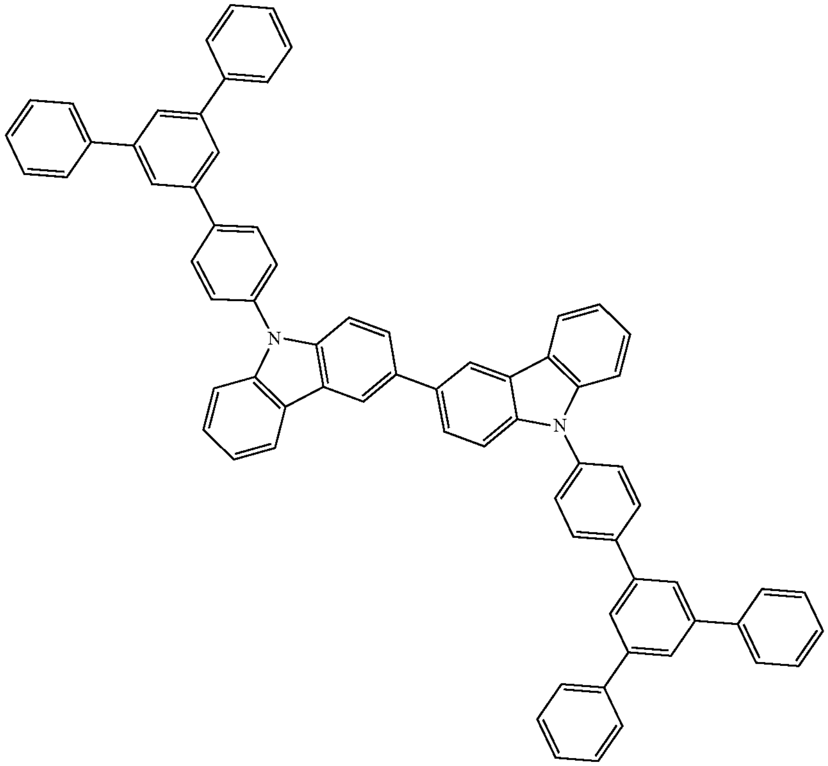

-continued
[E-126]
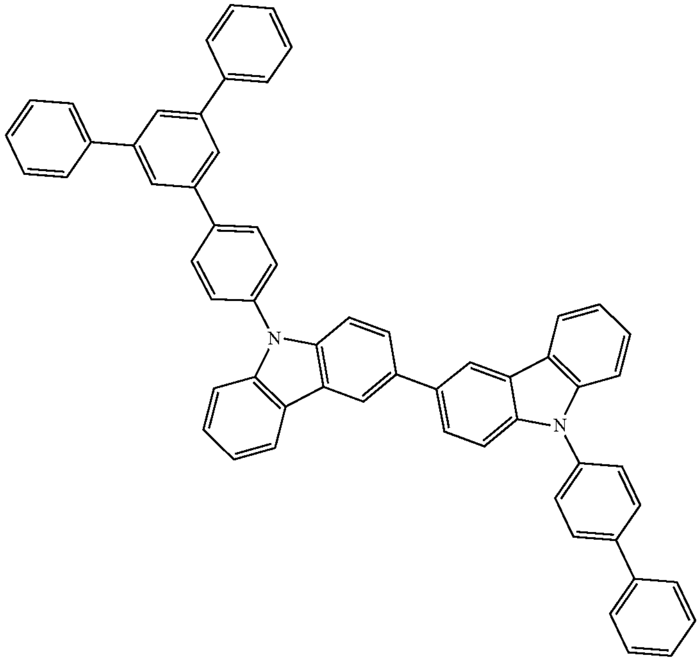
[E-127]
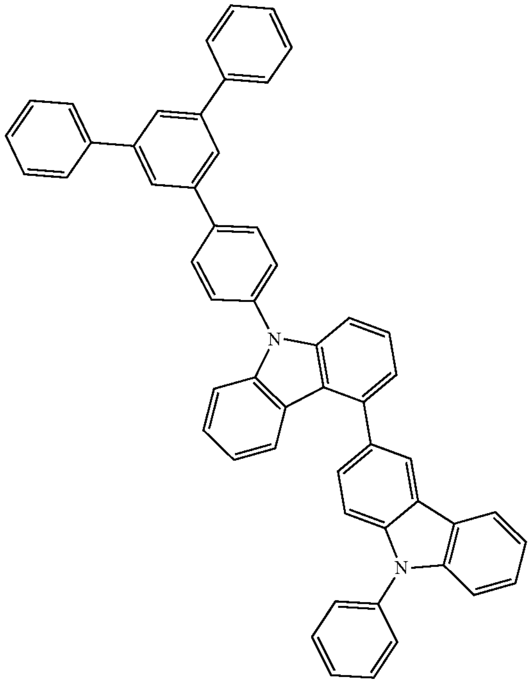

-continued
[E-128]
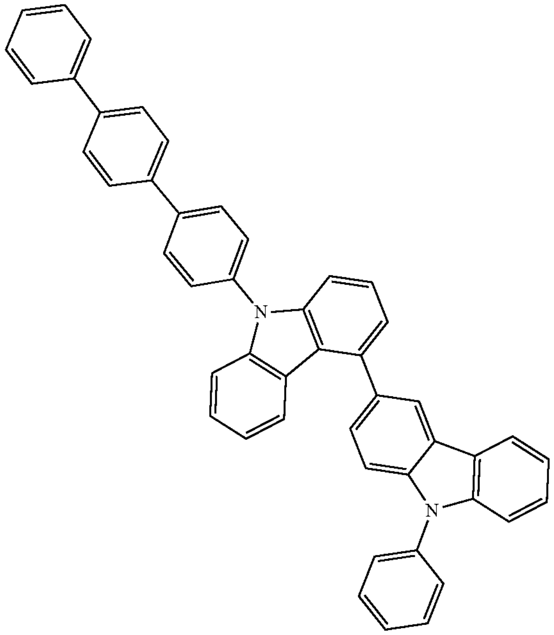
[E-129]
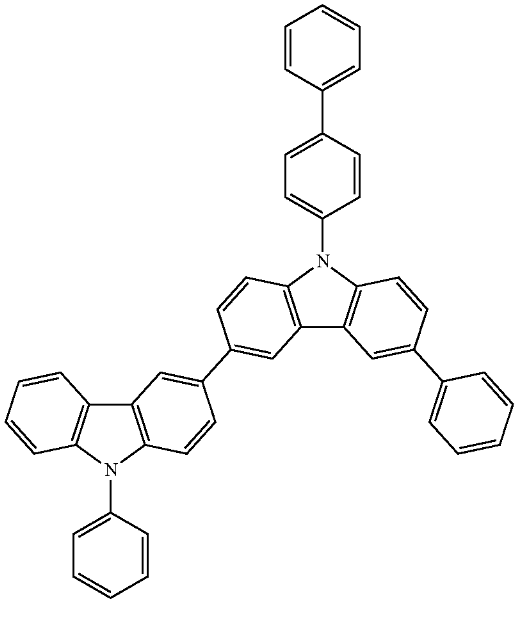

-continued
[E-130]
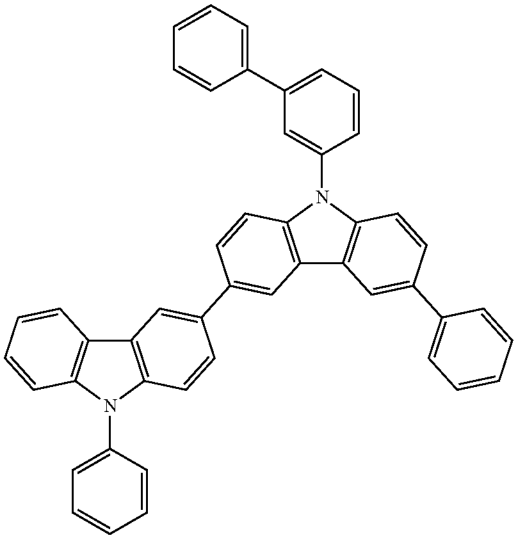
[E-131]
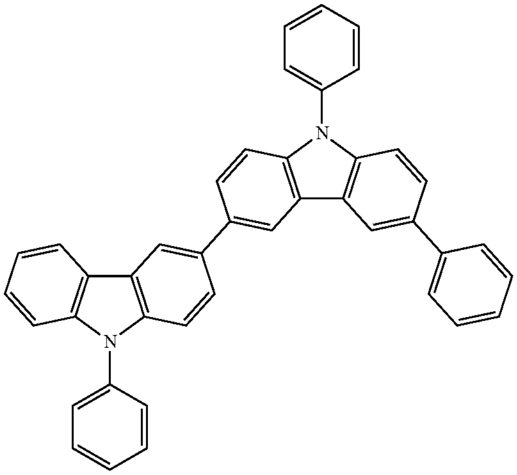
[E-132]
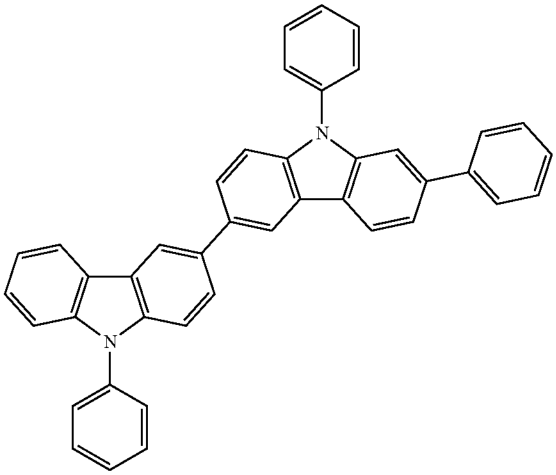

-continued
[E-133]
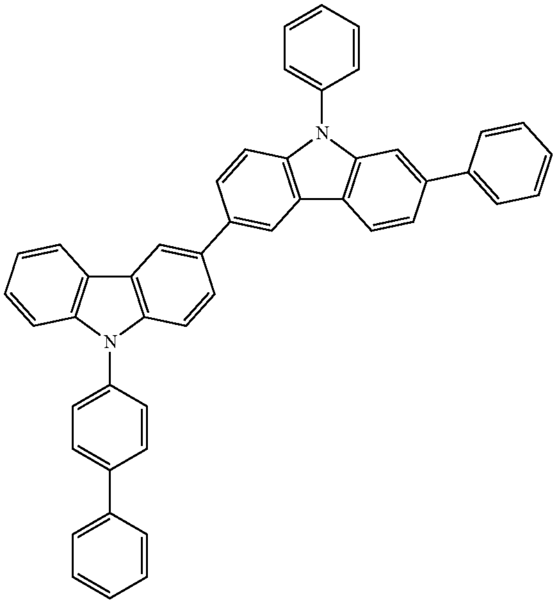
[E-134]
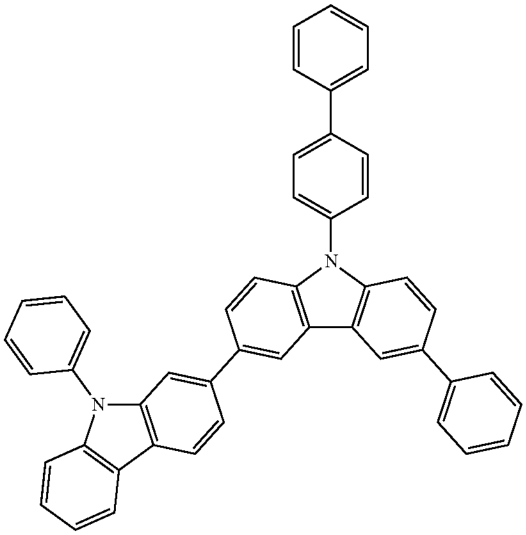
[E-135]
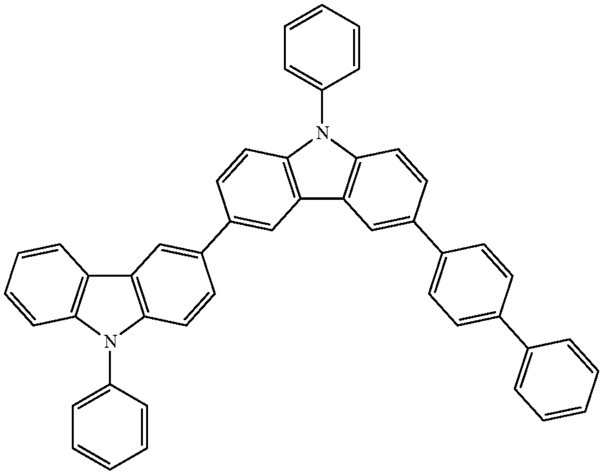

-continued
[E-136]
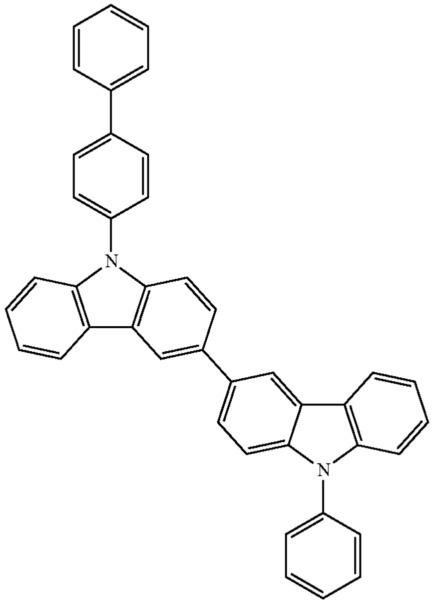
[E-137]
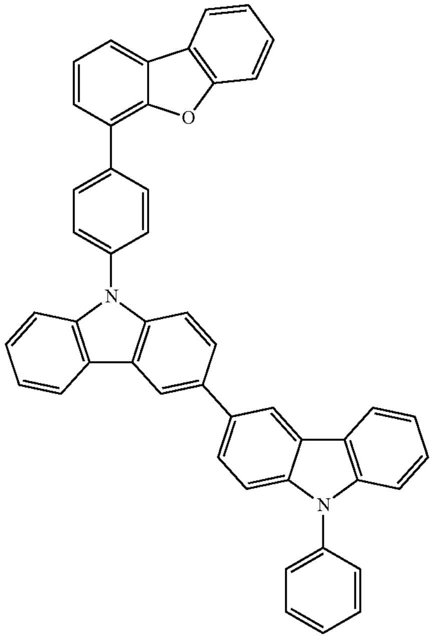

-continued

[E-138]

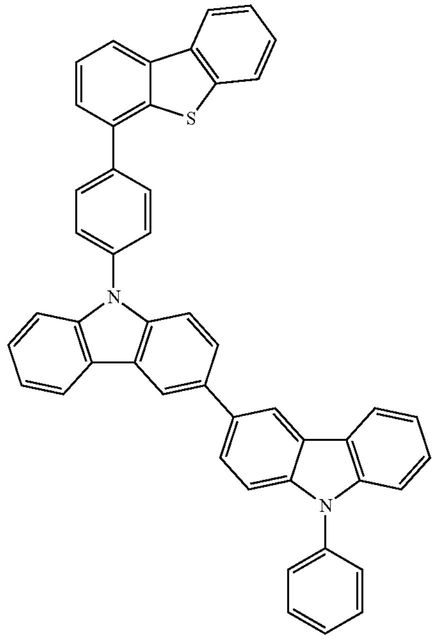

For example, the second organic compound may be an indolocarbazole compound represented by a combination of Chemical Formulae 4B-1 and 4B-2.

[Chemical Formula 4B-1]

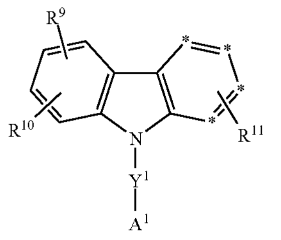

[Chemical Formula 4B-2]

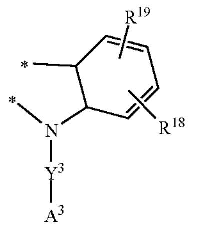

In Chemical Formulae 4B-1 and 4B-2, $Y^1$ and $Y^3$ are independently a single bond, a substituted or unsubstituted C6 to C30 arylene group, a divalent substituted or unsubstituted C2 to C30 heterocyclic group, or a combination thereof, $A^1$ and $A^3$ are independently a substituted or unsubstituted C6 to C30 aryl group, a substituted or unsubstituted C2 to C30 heterocyclic group, or a combination thereof, adjacent two *'s of Chemical Formula 4B-1 are bonded with two *'s of Chemical Formula 4B-2, the remaining two *'s of Chemical Formula 4B-1 are independently $CR^{11}$, wherein $R^{11}$ is the same or different, and $R^9$ to $R^{11}$, $R^{18}$, and $R^{19}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof.

For example, $Y^1$ and $Y^3$ of Chemical Formulae 4B-1 and 4B-2 may independently be a single bond, a substituted or unsubstituted phenylene group, or a substituted or unsubstituted biphenylene group.

For example, $A^1$ and $A^3$ of Chemical Formulae 4B-1 and 4B-2 may independently be a substituted or unsubstituted C6 to C30 aryl group and for example the aryl group may be a phenyl group, a biphenyl group, a naphthyl group, a terphenyl group, an anthracenyl group, or a phenanthrenyl group, and more preferably a biphenyl group, a naphthyl group, a terphenyl group, or a phenyl group. For example, $A^1$ and $A^3$ of Chemical Formulae 4B-1 and 4B-2 may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted pyridinyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof.

For example, the indolocarbazole compound represented by a combination of Chemical Formulae 4B-1 and 4B-2 may be represented by one of Chemical Formulae 4B-a to 4B-e.

[Chemical Formula 4B-a]

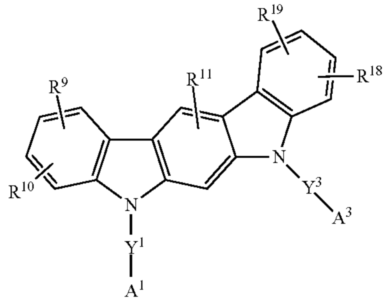

[Chemical Formula 4B-b]

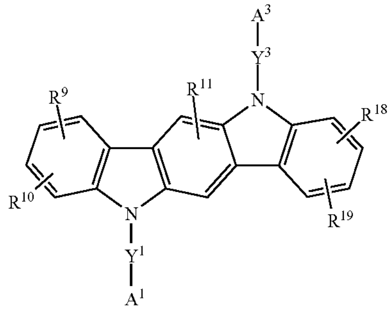

[Chemical Formula 4B-c]

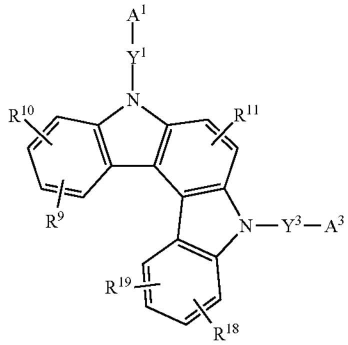

[Chemical Formula 4B-d]

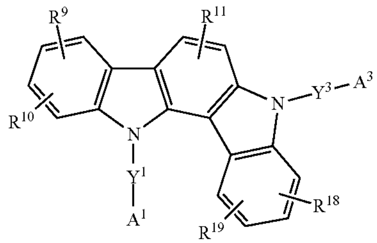

[Chemical Formula 4B-e]

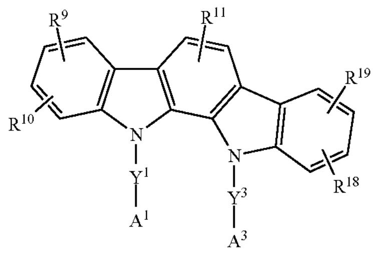

In Chemical Formulae 4B-a to 4B-e, $Y^1$, $Y^3$, $A^1$, $A^3$, $R^9$ to $R^{11}$, $R^{18}$, and $R^{19}$ are the same as described above.

For example, the indolocarbazole compound represented by a combination of Chemical Formulae 4B-1 and 4B-2 may be represented by Chemical Formula 4B-c or 4B-d.

For example, the indolocarbazole compound represented by a combination of Chemical Formulae 4B-1 and 4B-2 may be represented by Chemical Formula 4B-c.

For example, the indolocarbazole compound represented by a combination of Chemical Formulae 4B-1 and 4B-2 may be for example one of compounds of Group 5, but is not limited thereto.

[Group 5]

[F-1]

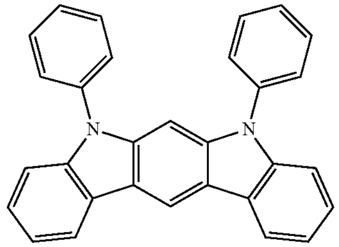

[F-2]

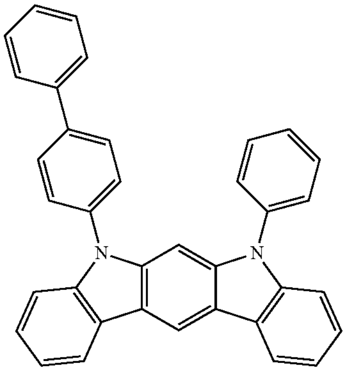

[F-3]

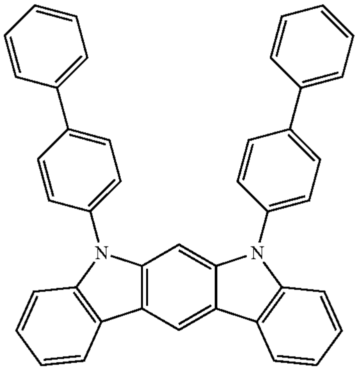

[F-4]

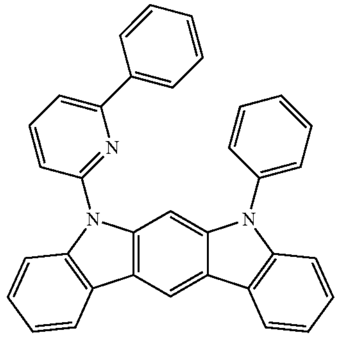

-continued
[F-5]
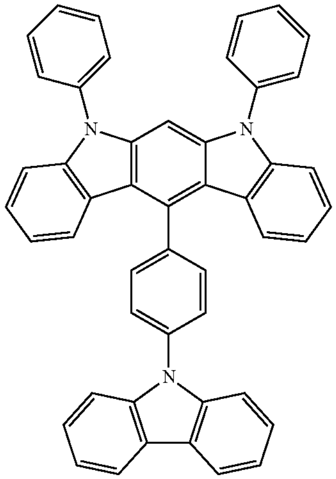
[F-6]
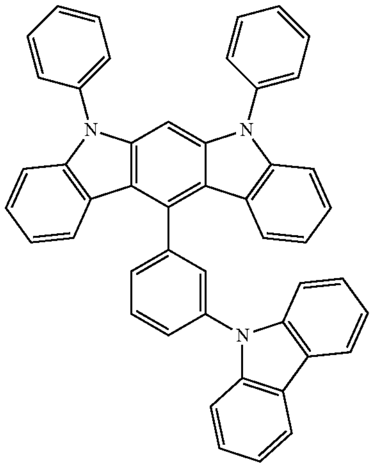
[F-7]
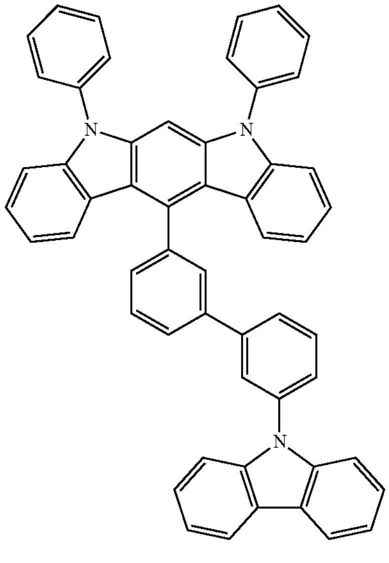
-continued
[F-8]
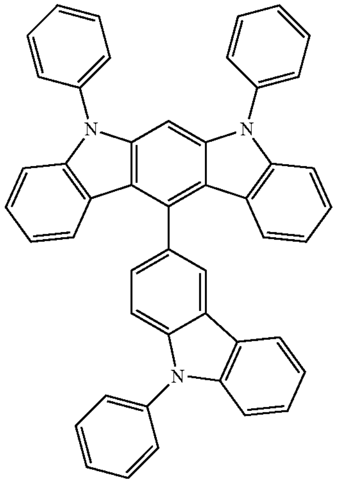
[F-9]
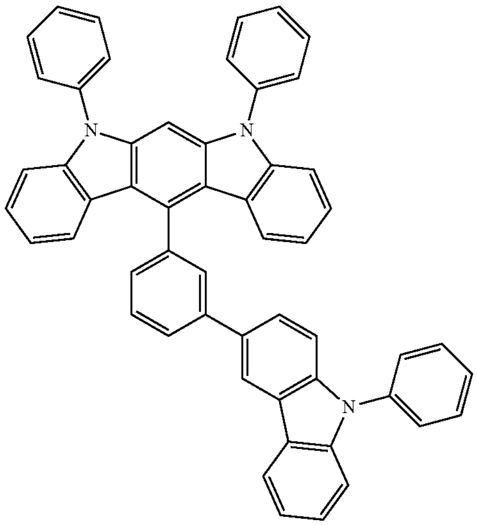
[F-10]
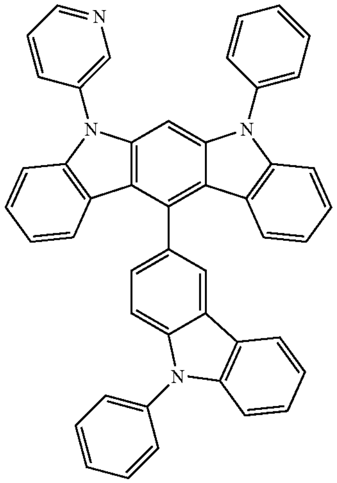

-continued
[F-11]
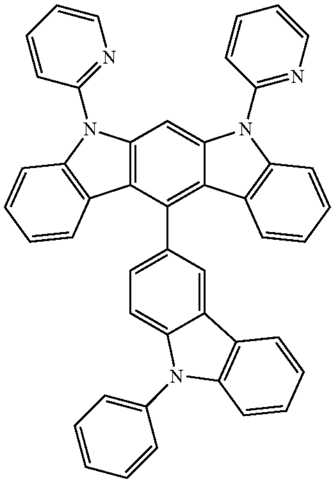
[F-12]
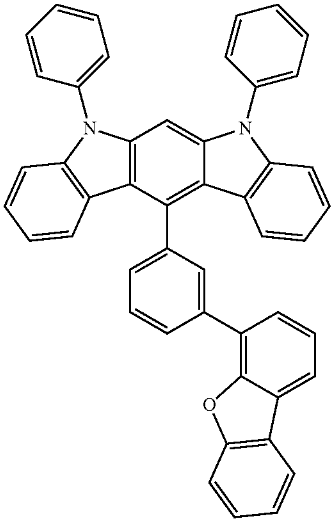
[F-13]
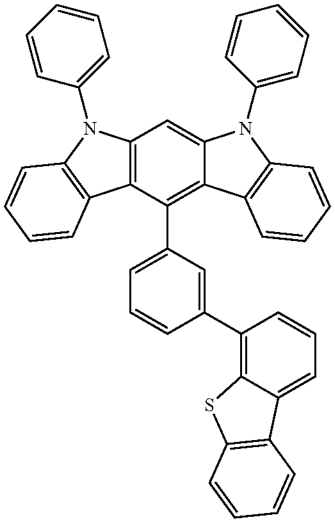
-continued
[F-14]
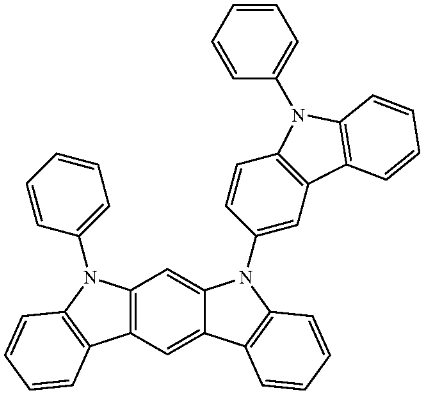
[F-15]
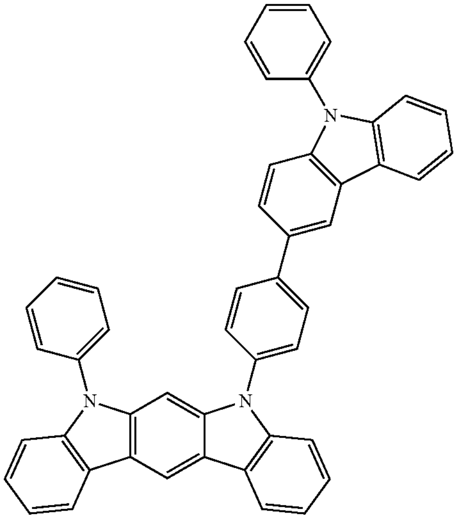
[F-16]
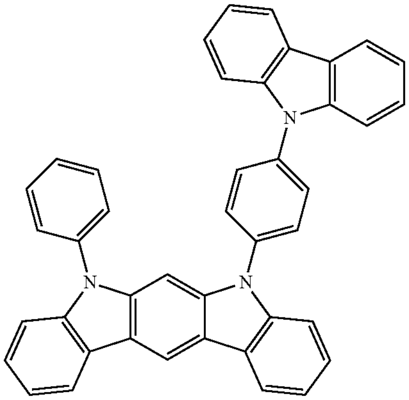

-continued
[F-17]
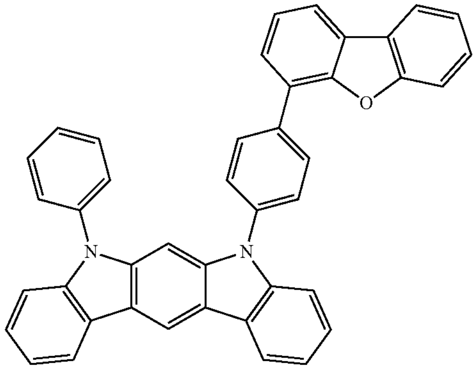
[F-18]
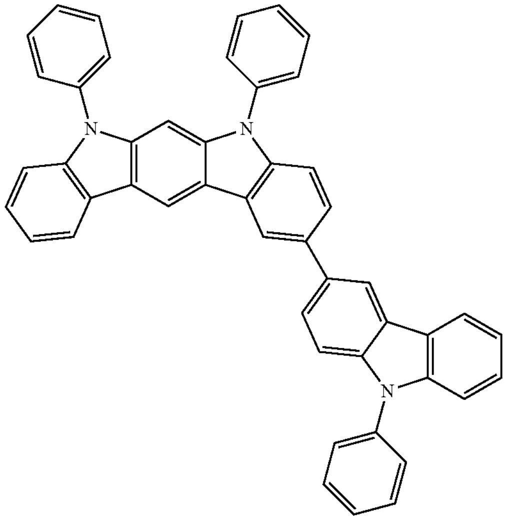
[F-19]
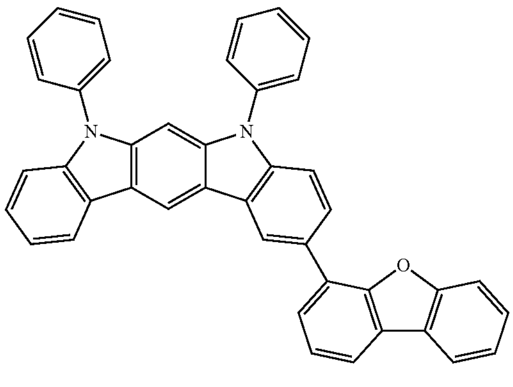
-continued
[F-20]
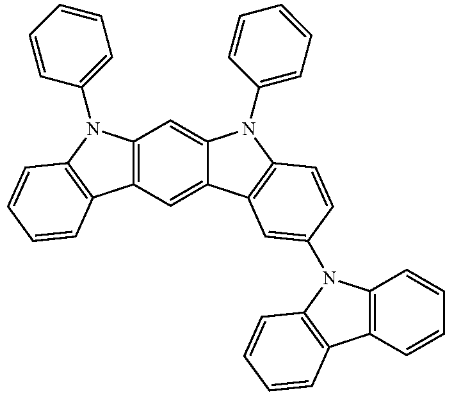
[F-21]
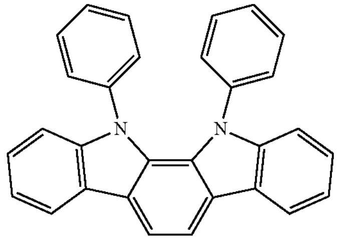
[F-22]
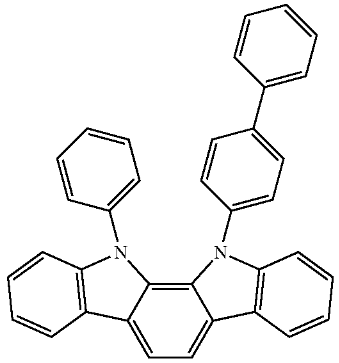
[F-23]
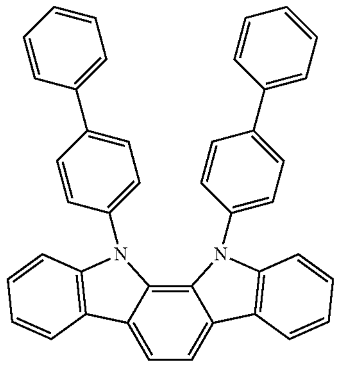

-continued
[F-24]
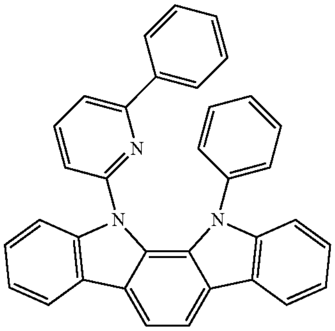
[F-25]
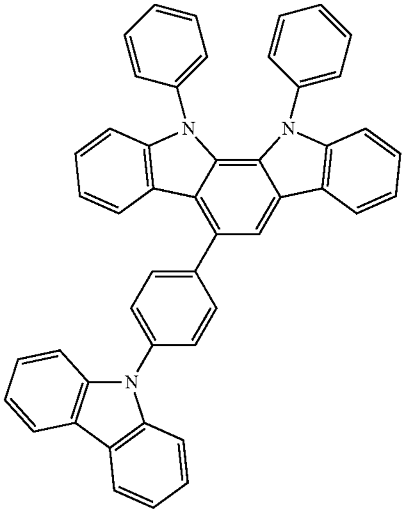
[F-26]
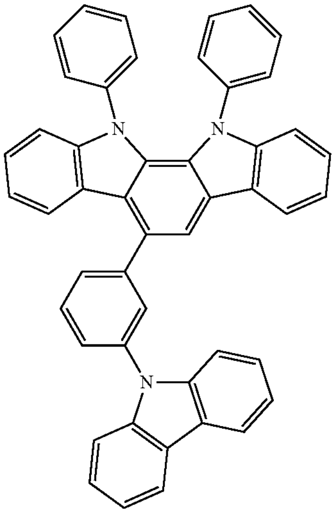
-continued
[F-27]
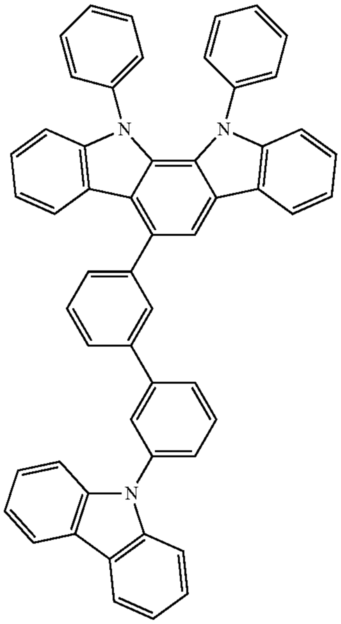
[F-28]
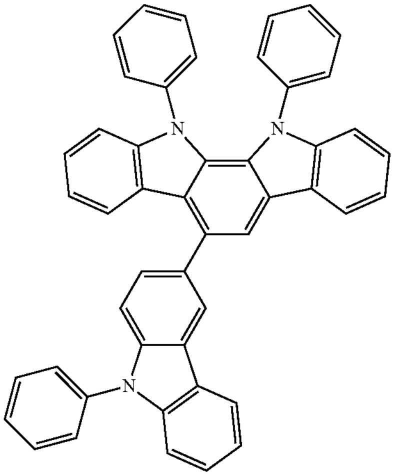

-continued
[F-29]
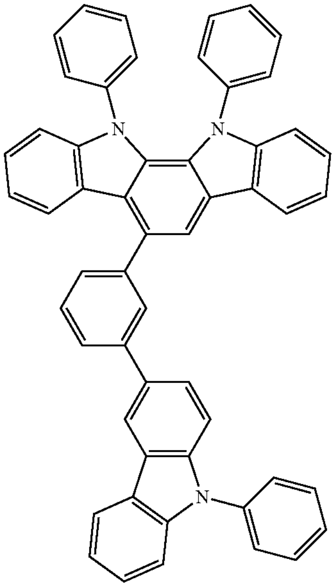
[F-30]
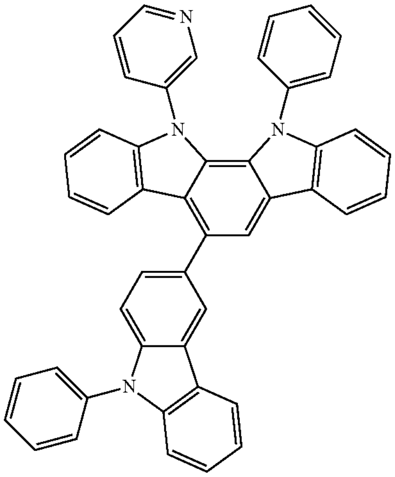
[F-31]
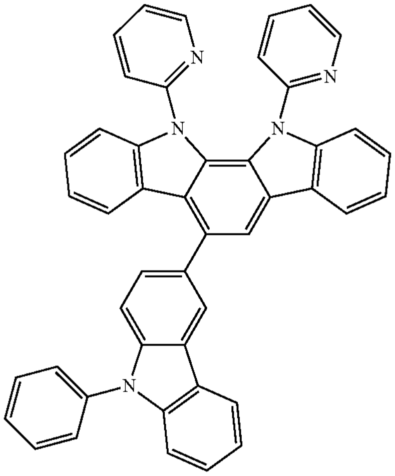
-continued
[F-32]
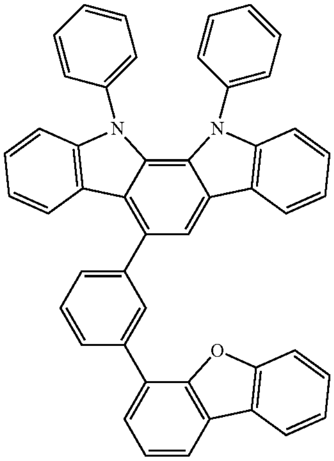
[F-33]
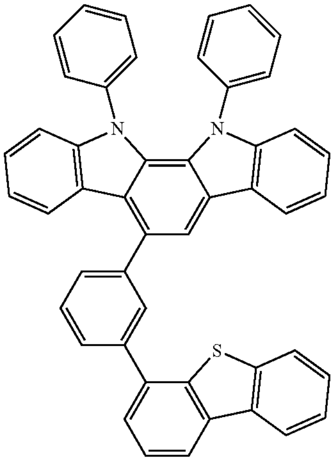
[F-34]
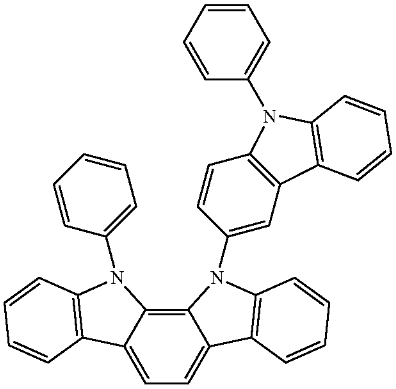

-continued
[F-35]
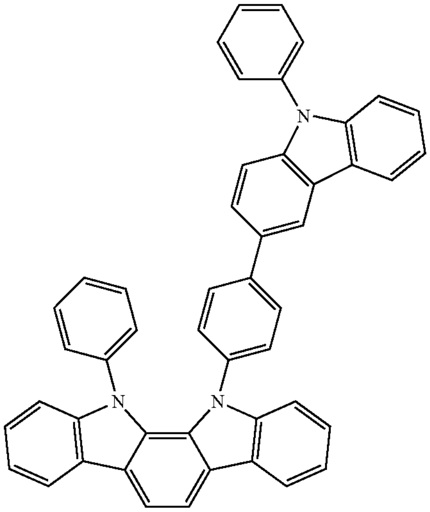
[F-36]
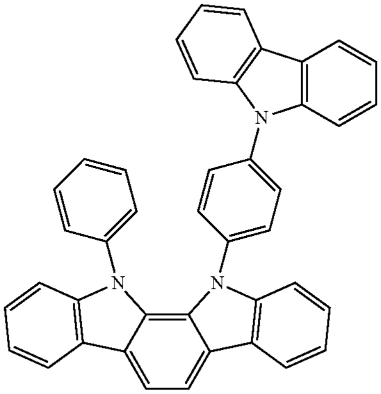
[F-37]
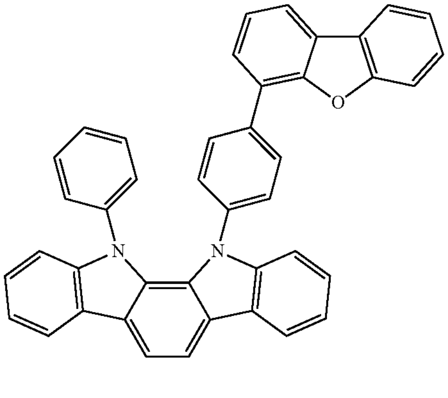
-continued
[F-38]
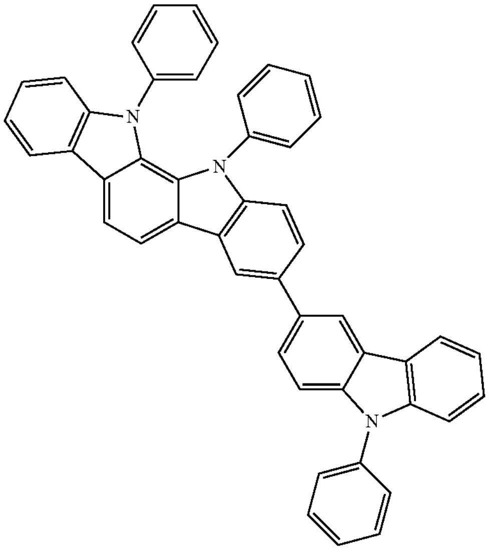
[F-39]
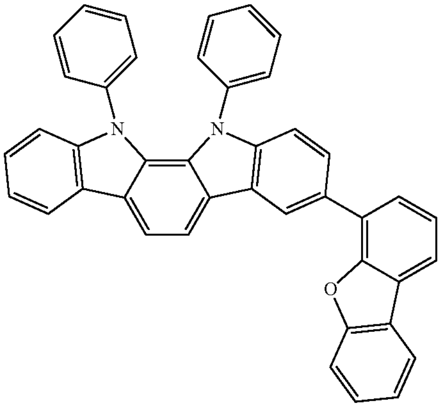
[F-40]
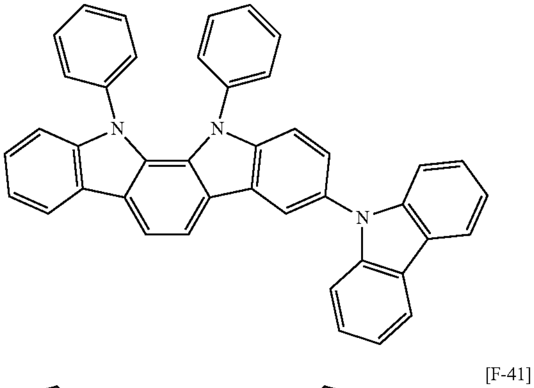
[F-41]
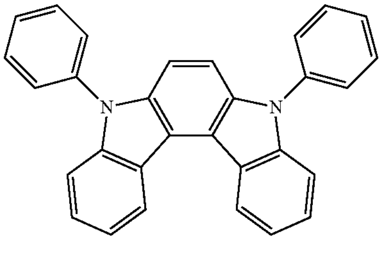

-continued
[F-42]
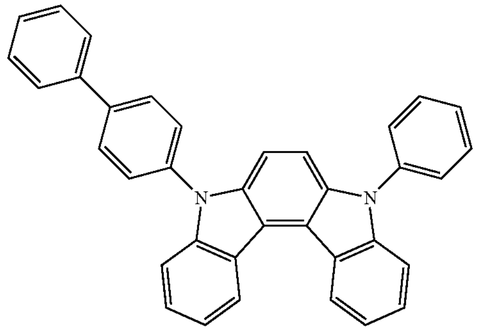
[F-43]
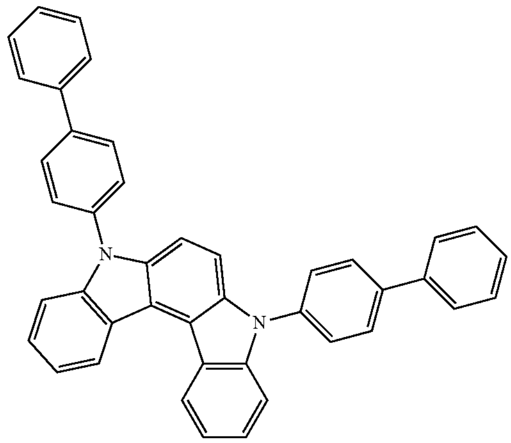
[F-44]
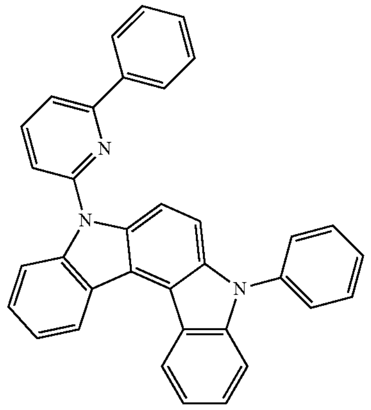
-continued
[F-45]
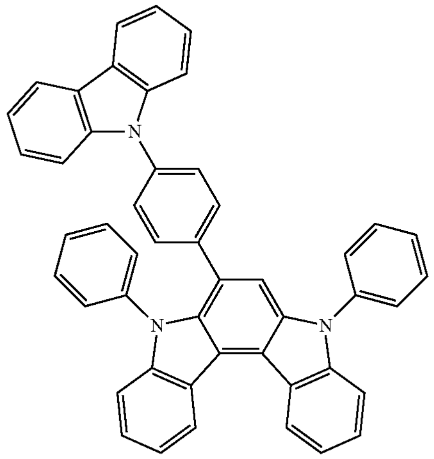
[F-46]
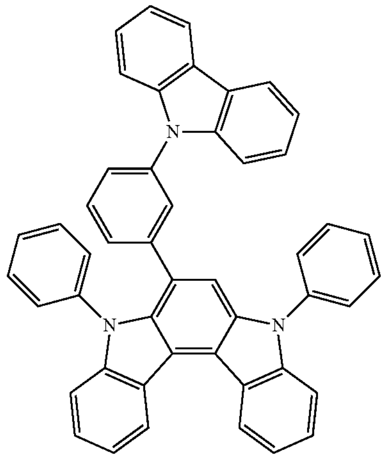
[F-47]
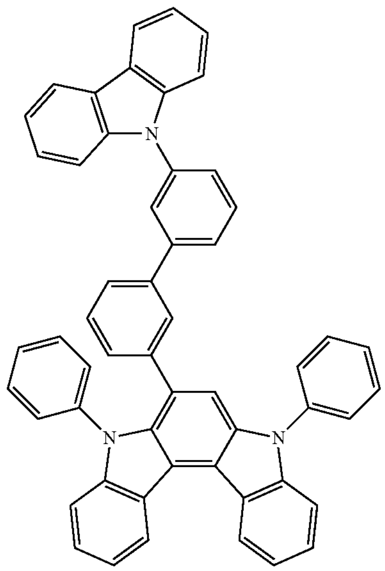

-continued
[F-48]
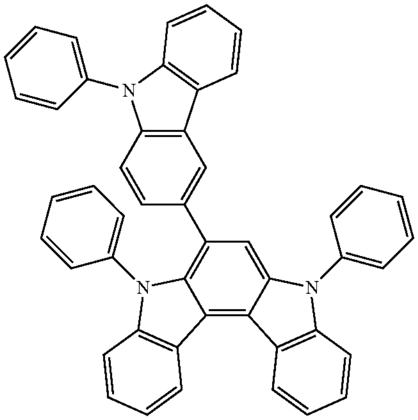
[F-49]
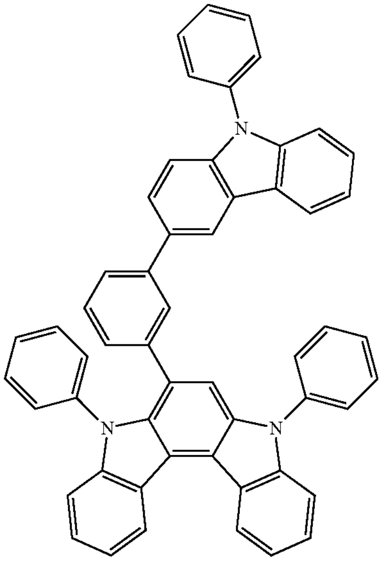
[F-50]
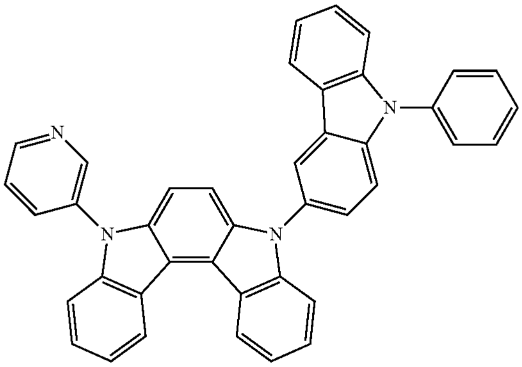
-continued
[F-51]
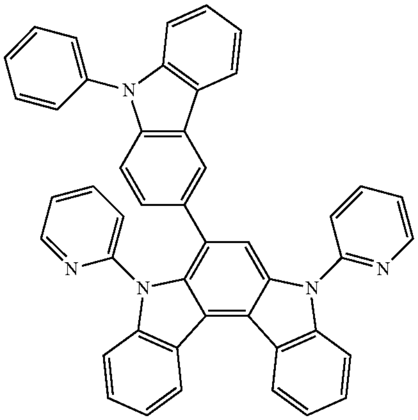
[F-52]
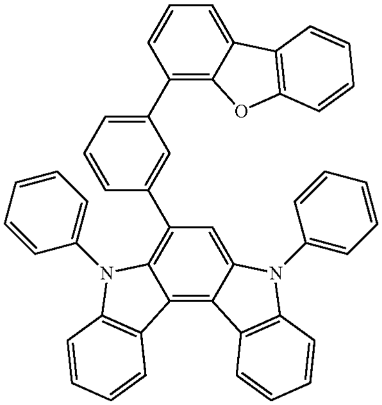
[F-53]
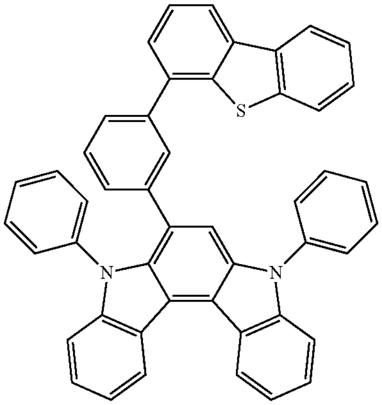
[F-54]
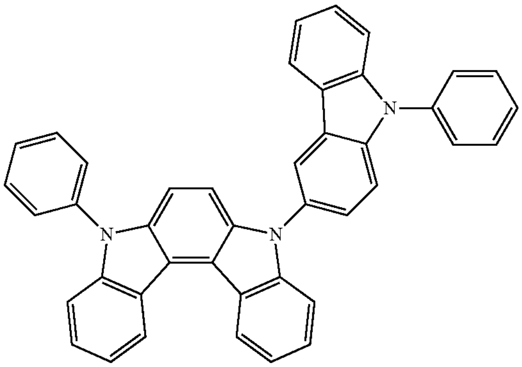

[F-55]
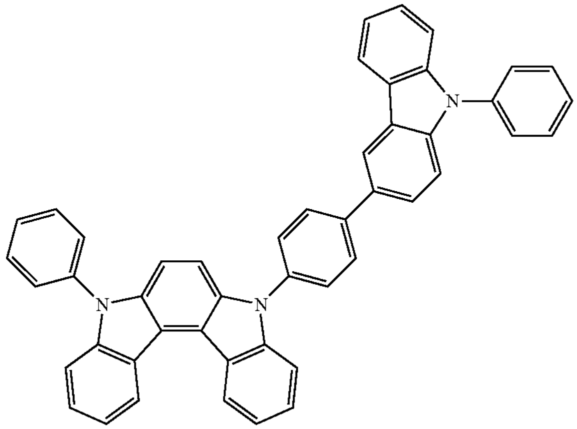
[F-56]
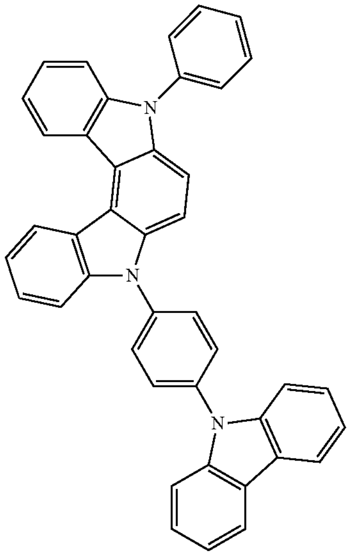
[F-57]
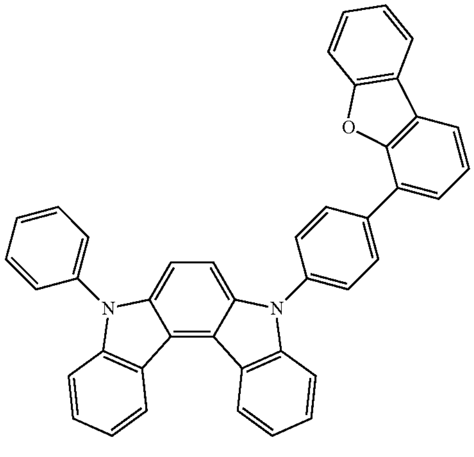
[F-58]
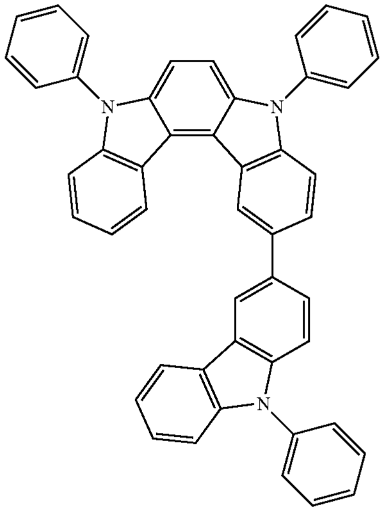
[F-59]
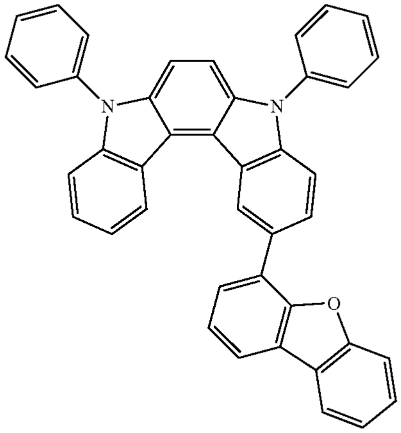
[F-60]
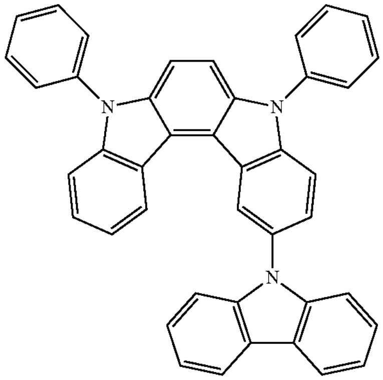

-continued
[F-61]
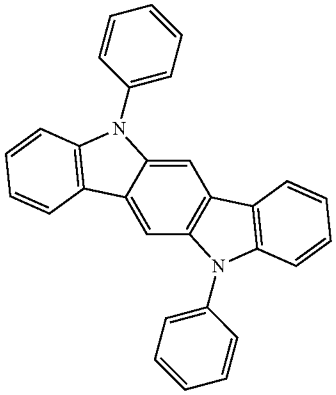
[F-62]
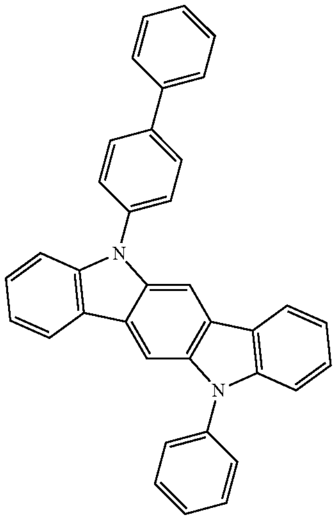
[F-63]
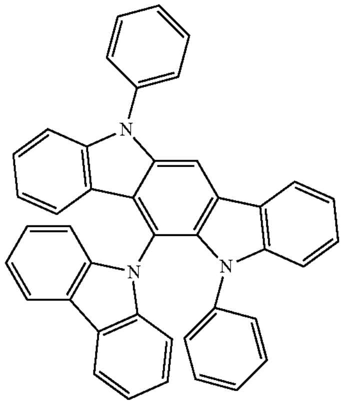
-continued
[F-64]
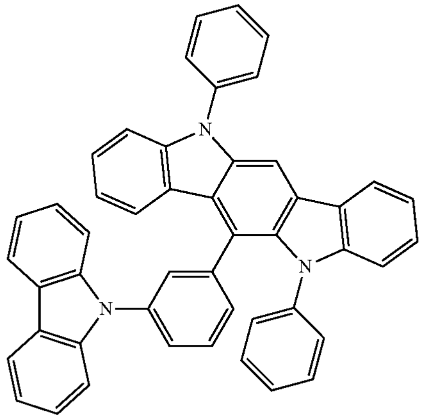
[F-65]
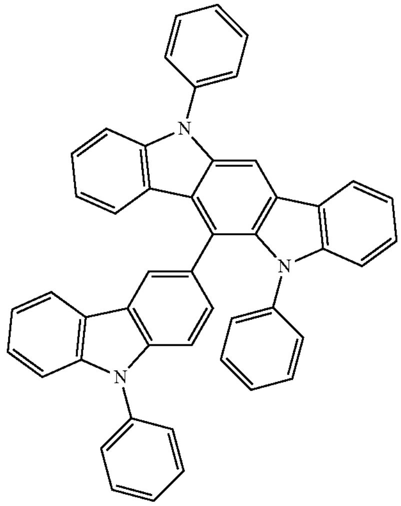
[F-66]
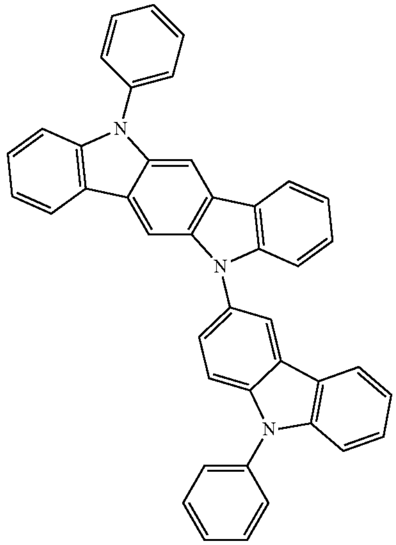

[F-67]
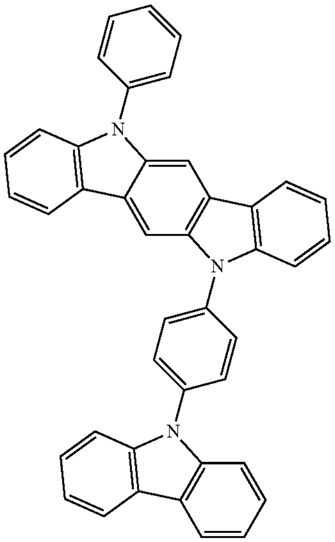
[F-68]
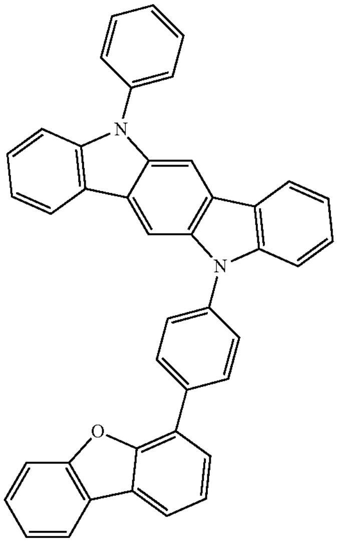
[F-69]
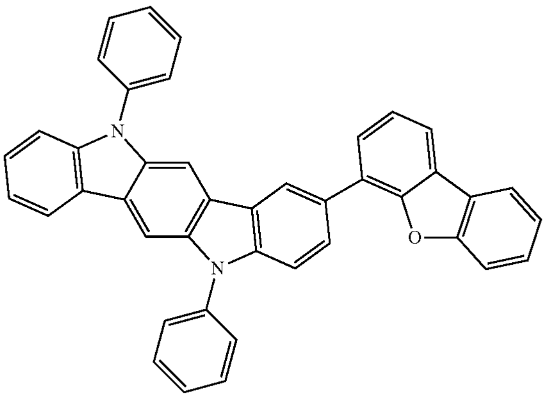
[F-70]
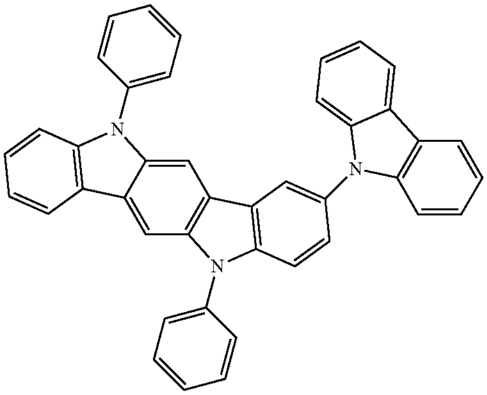
[F-71]
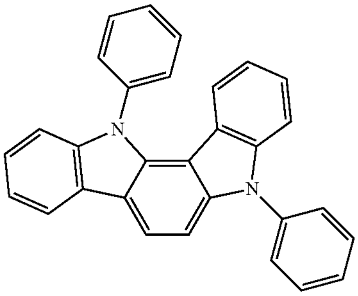
[F-72]
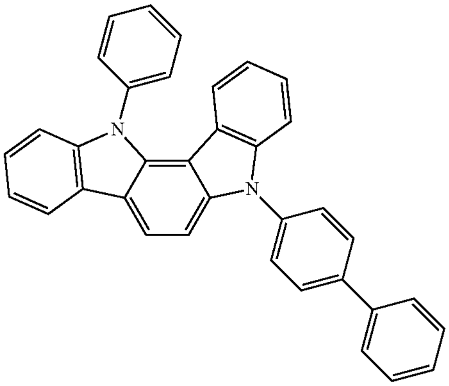
[F-73]
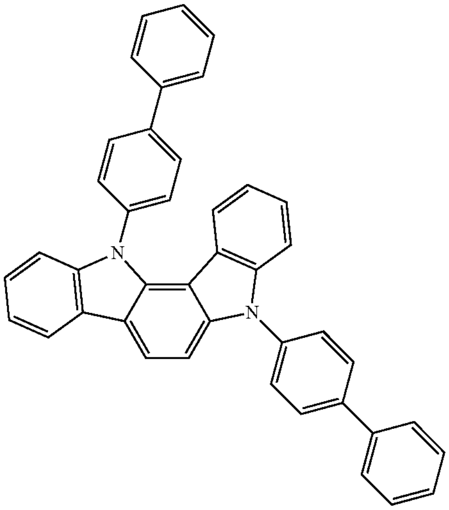

-continued
[F-74]
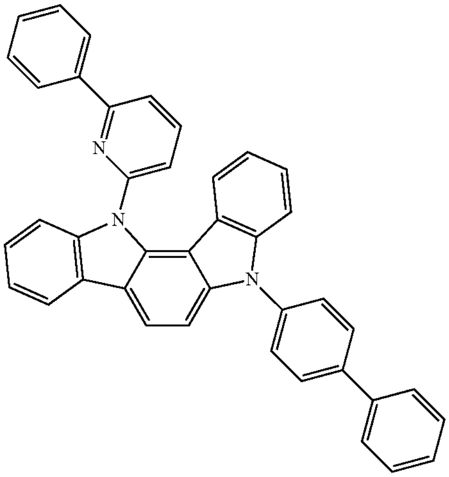
[F-75]
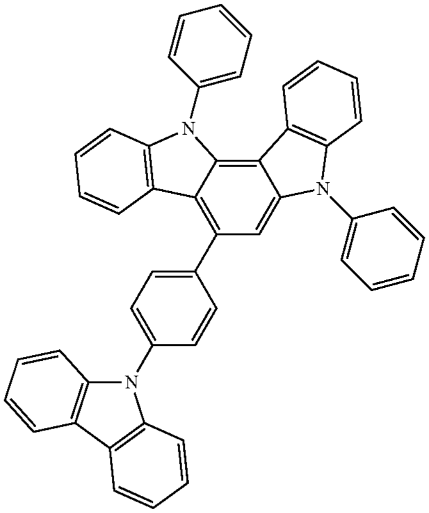
[F-76]
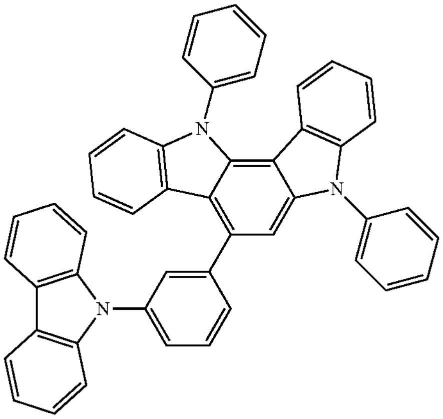
-continued
[F-77]
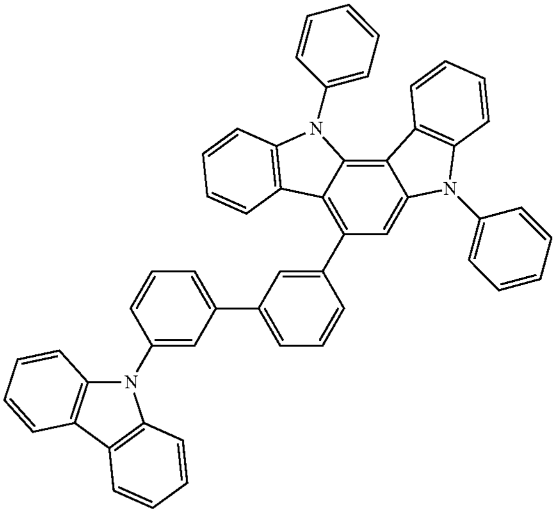
[F-78]
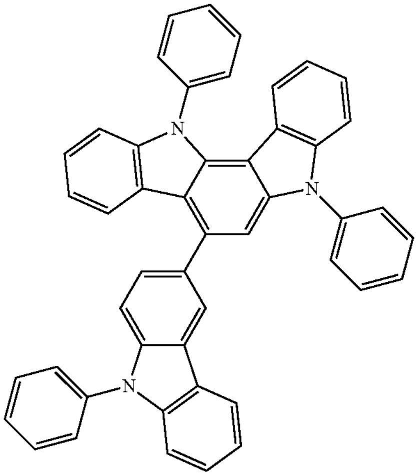
[F-79]
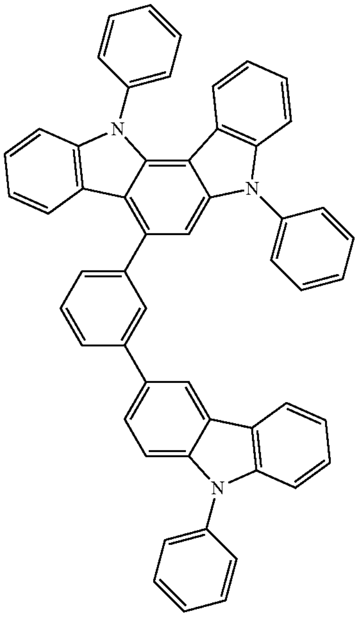

-continued
[F-80]
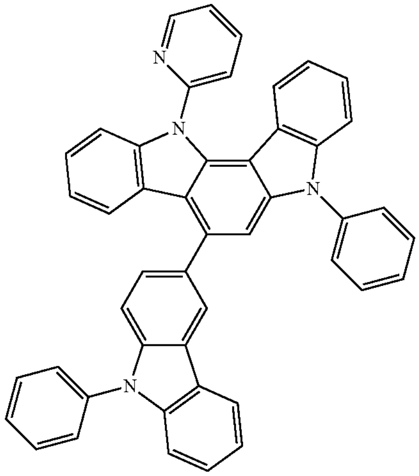
[F-81]
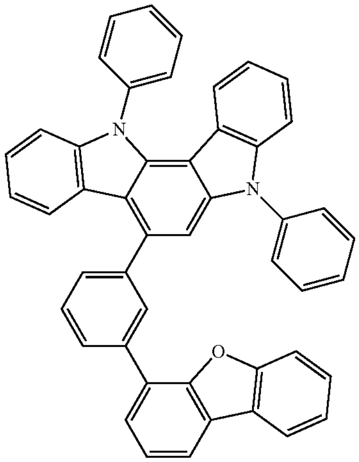
[F-82]
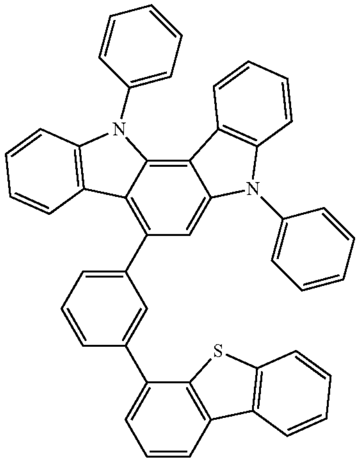
-continued
[F-83]
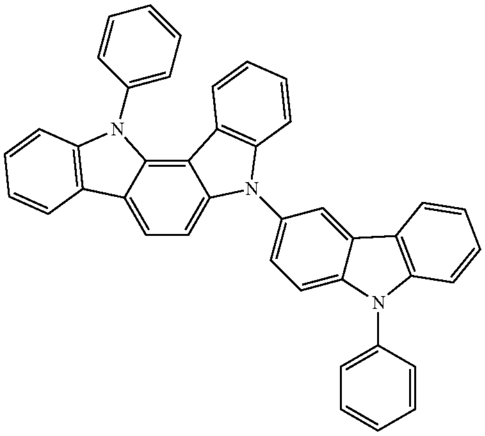
[F-84]
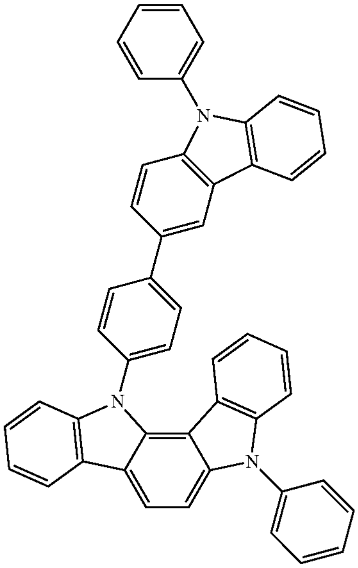
[F-85]
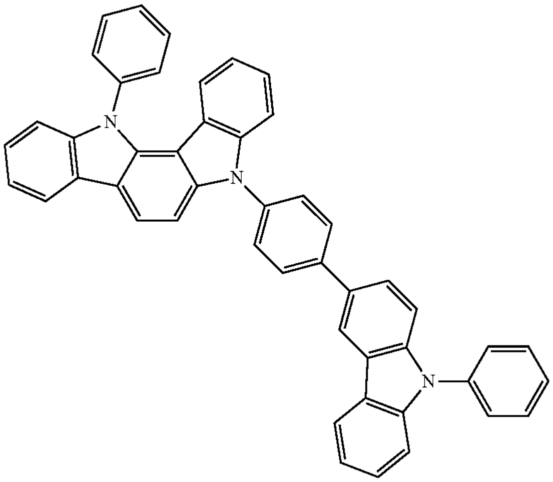

-continued
[F-86]
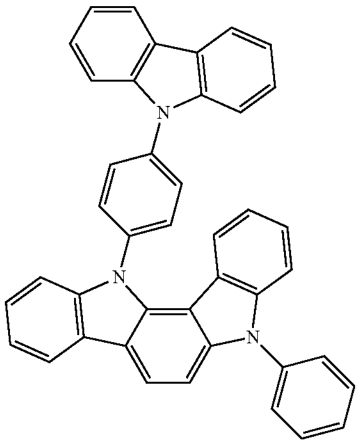
[F-87]
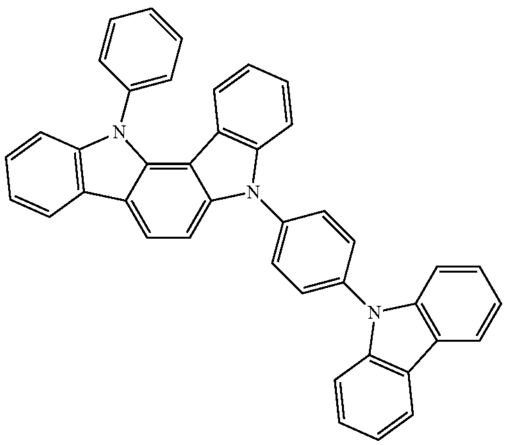
[F-88]
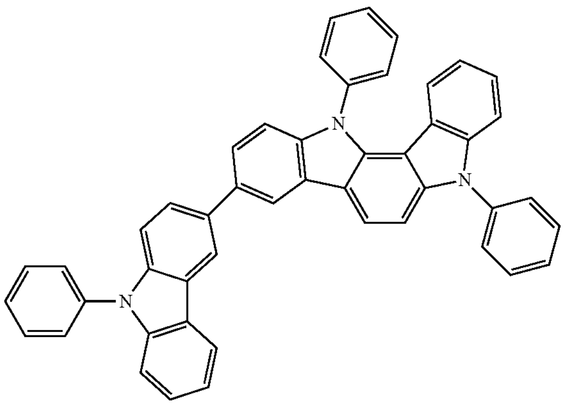
-continued
[F-89]
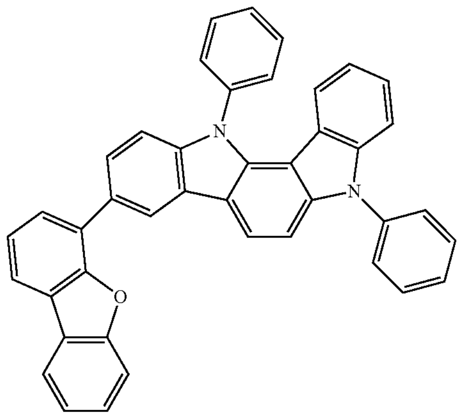
[F-90]
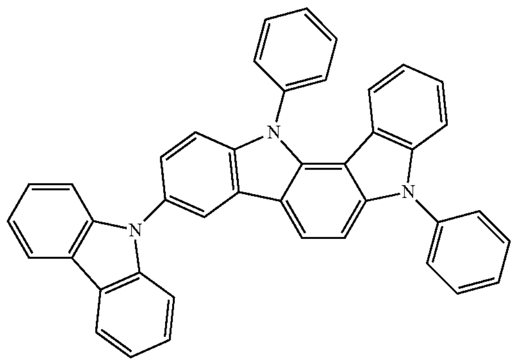
[F-91]
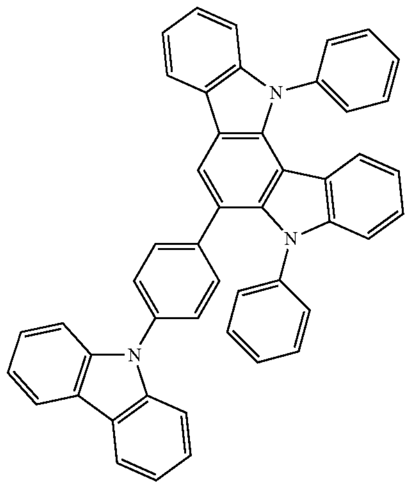

-continued
[F-92]
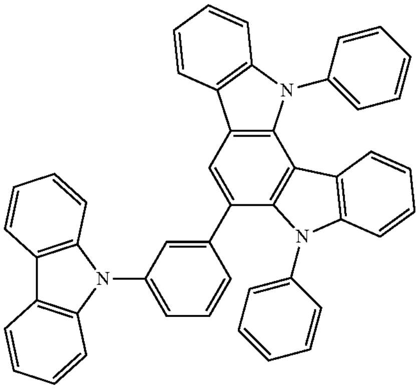
[F-93]
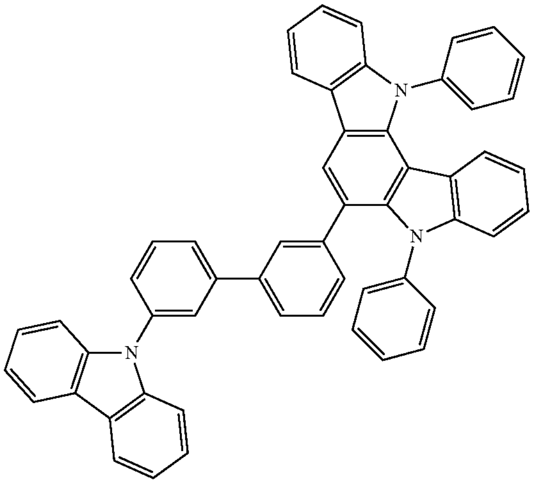
[F-94]
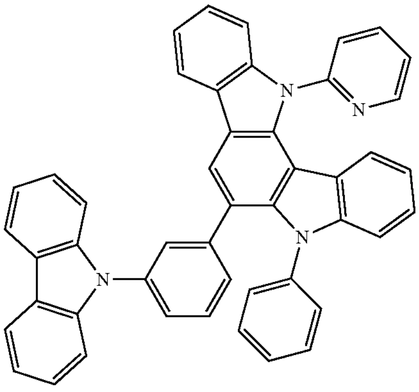
-continued
[F-95]
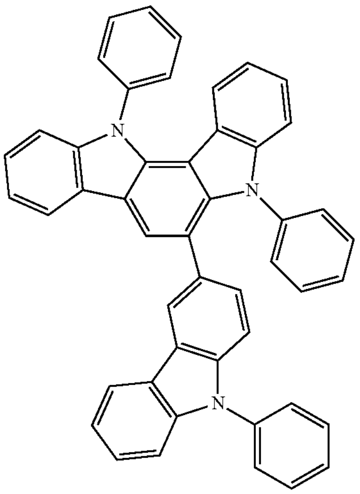
[F-96]
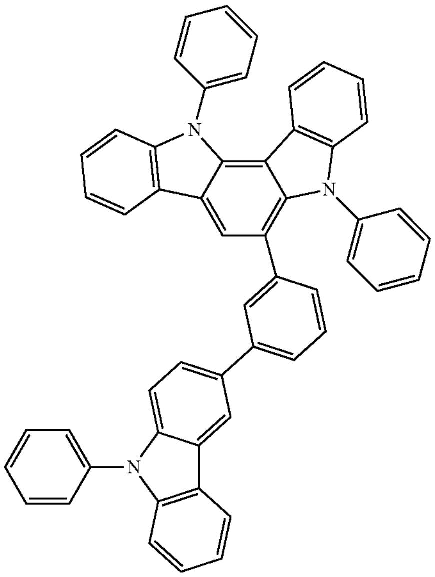
[F-97]
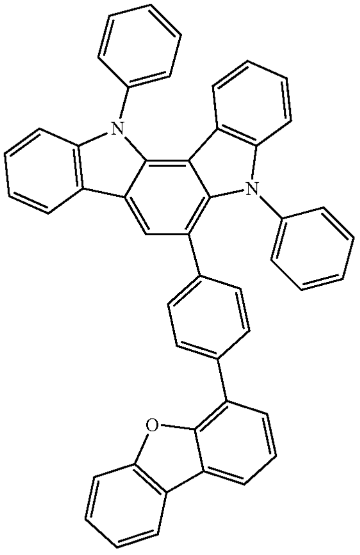

-continued
[F-98]
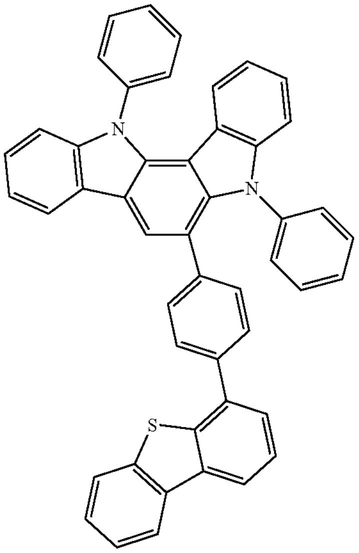
[F-99]
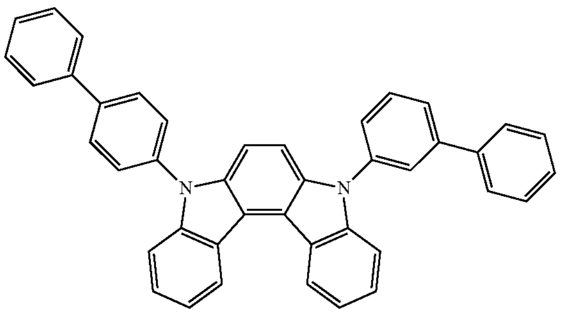
[F-100]
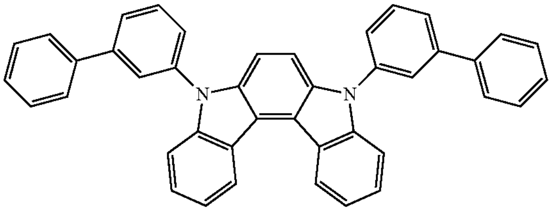
[F-101]
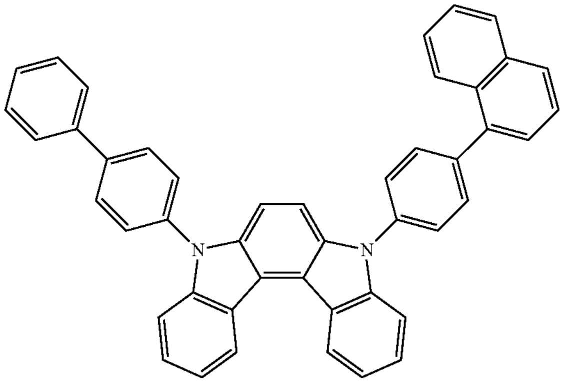
-continued
[F-102]
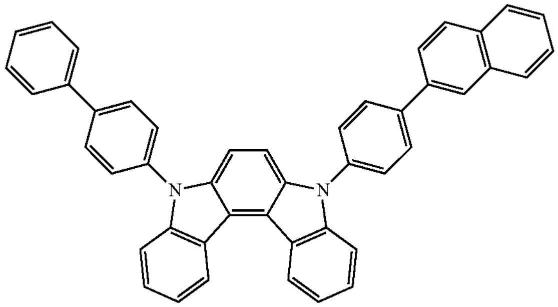
[F-103]
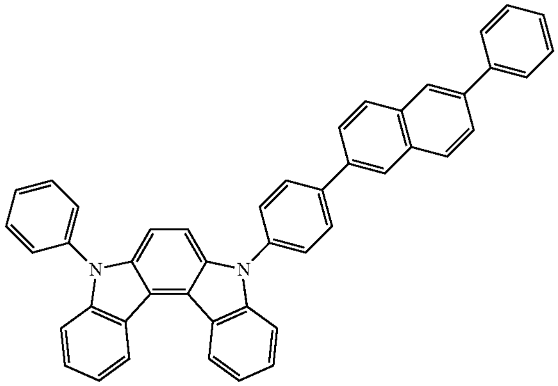
[F-104]
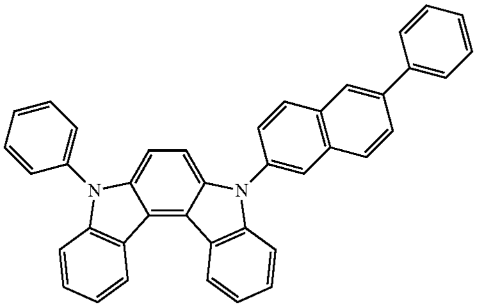
[F-105]
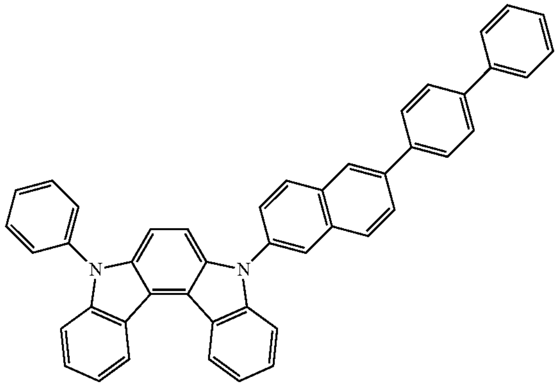

-continued

[F-106]

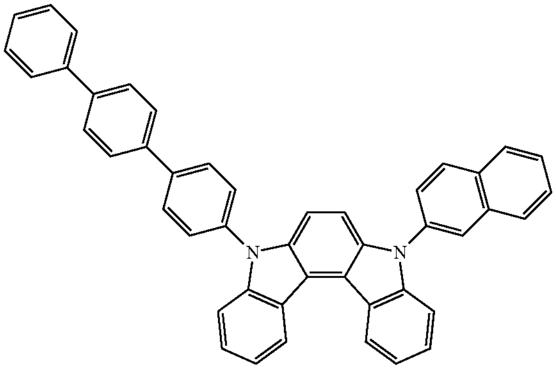

[F-107]

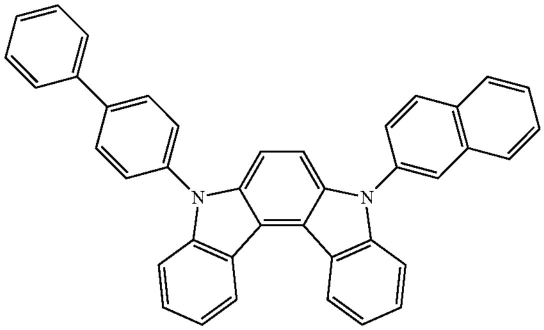

[F-108]

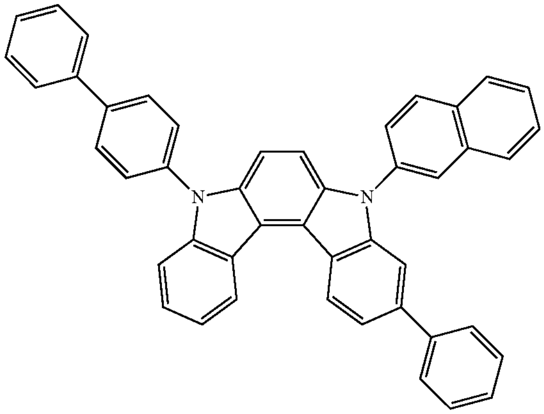

[F-109]

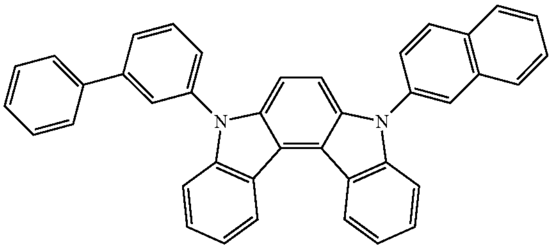

-continued

[F-110]

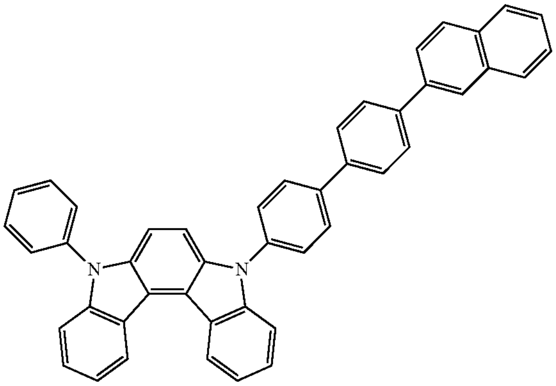

[F-111]

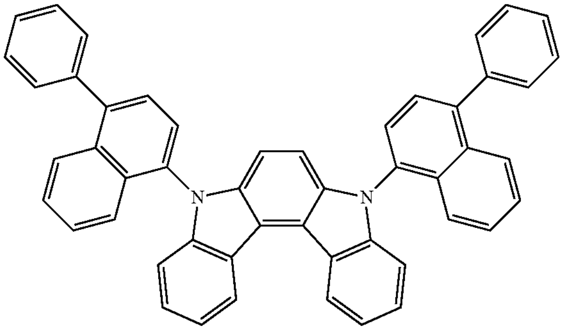

[F-112]

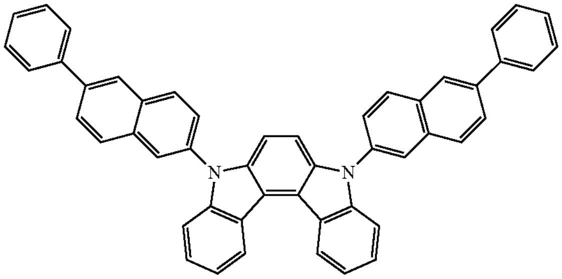

The first organic compound and the second organic compound may variously be combined to prepare various compositions. The composition may include the first organic compound and the second compound in a weight ratio of about 1:99 to 99:1, for example about 10:90 to 90:10, about 20:80 to 80:20, about 30:70 to 70:30, about 40:60 to 60:40 or about 50:50.

The composition may further include at least one organic compound in addition to the first organic compound and the second organic compound.

The composition may further include a dopant. The dopant may be a red, green, or blue dopant. The dopant is mixed in a small amount to cause light emission, and may be generally a material such as a metal complex that emits light by multiple excitation into a triplet or more. The dopant may be for example an inorganic, organic, or organic/inorganic compound, and one or more kinds thereof may be used. The dopant may be included in an amount of about 0.1 to 20 wt % based on a total amount of the composition.

Examples of the dopant may be a phosphorescent dopant and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$L_2MX$ [Chemical Formula Z]

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof, and the L and X may be, for example a bidendate ligand.

Hereinafter, an organic optoelectronic device including the organic compound or the composition is described.

The organic optoelectronic device may be for example an organic light emitting diode, an organic photoelectric device, or an organic solar cell. Examples of the organic optoelectronic device may be an organic light emitting diode.

The organic optoelectronic device includes an anode and a cathode facing each other and an organic layer disposed between the anode and the cathode, wherein the organic layer includes the organic compound or the composition.

The organic layer may include an active layer such as a light emitting layer or a light absorbing layer and the organic compound or the composition may be included in the active layer.

The organic layer may include an auxiliary layer between the anode and the active layer and/or between the cathode and the active layer, and the organic compound or the composition may be included in the auxiliary layer.

FIG. 1 is a cross-sectional view showing an embodiment of an organic light emitting diode as one example of an organic optoelectronic device.

Referring to FIG. 1, an organic light emitting diode 100 according to an embodiment includes an anode 110 and a cathode 120 facing each other and an organic layer 105 between the anode 110 and the cathode 120.

The anode 110 may be made of a conductor having a large work function to help hole injection, and may be for example a metal, a metal oxide and/or a conductive polymer. The anode 110 may be for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 120 may be made of a conductor having a small work function to help electron injection, and may be for example a metal, a metal oxide and/or a conductive polymer. The cathode 120 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al, and $BaF_2$/Ca, but is not limited thereto.

The organic layer 105 may include the organic compound or the composition.

The organic layer 105 may include a light emitting layer 130.

The light emitting layer 130 may include the organic compound or the composition as a host. The light emitting layer 130 may further include another organic compound. The light emitting layer 130 may further include a dopant and the dopant may be for example a phosphorescent dopant.

The organic layer 105 may further include an auxiliary layer (not shown) between the anode 110 and the light emitting layer 130 and/or between the cathode 120 and the light emitting layer 130. The auxiliary layer may be a hole injection layer (HIL), a hole transport layer (HTL), an electron blocking layer, an electron injection layer, an electron transport layer, a hole blocking layer, or a combination thereof. The auxiliary layer may include the organic compound or the composition.

FIG. 2 is a cross-sectional view of an organic light emitting diode according to another embodiment.

Referring to FIG. 2, an organic light emitting diode 200 according to an embodiment includes an anode 110 and a cathode 120 facing each other and an organic layer 105 disposed between the anode 110 and the cathode 120.

The organic layer 105 includes an electron auxiliary layer 140 between the light emitting layer 230 and the cathode 120. The electron auxiliary layer 140 may be for example an electron injection layer, an electron transport layer, and/or a hole blocking layer, and may help injection and transport of electrons between the cathode 120 and the light emitting layer 230.

For example, the organic compound or the composition may be included in the light emitting layer 230. The light emitting layer 230 may further include another organic compound as a host. The light emitting layer 230 may further include a dopant and the dopant may be for example a phosphorescent dopant.

For example, the organic compound may be included in the electron auxiliary layer 140. The electron auxiliary layer 140 may include the organic compound alone, a mixture of at least two kinds of the organic compounds, or a mixture of the organic compound and another organic compound.

In FIG. 2, at least one hole auxiliary layer (not shown) may be further included between the anode 110 and the light emitting layer 230 as the organic layer 105.

The organic light emitting diode may be applied to an organic light emitting display device.

Hereinafter, the embodiments are illustrated in more detail with reference to examples. However, these examples are exemplary, and the present scope is not limited thereto.

Hereinafter, starting materials and reaction materials used in Examples and Synthesis Examples may commercially be available from Sigma-Aldrich Co. Ltd., or TCI Inc., or are synthesized by known methods.

(Preparation of Compound for Organic Optoelectronic Device)

The compound as one specific examples of the present invention was synthesized through the following steps.

(First Compound for Organic Optoelectronic Device)

Synthesis Example 1: Synthesis of Intermediate A

[Reaction Scheme 1]

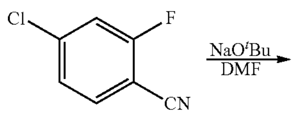

-continued

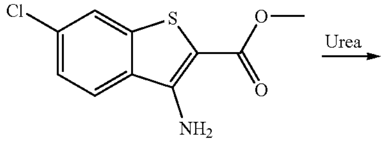

Intermediate A-1

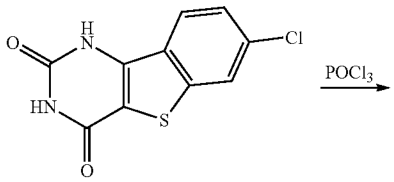

Intermediate A-2

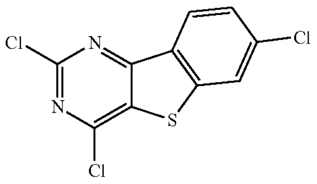

Intermediate A

Synthesis of Intermediate A-1

4-chloro-2-fluorobenzonitrile (100 g, 0.64 mol), methyl thioglycolate (70.0 ml, 0.77 mol), and 1.2 L of N,N-dimethylformamide were put in a 3 L round flask, and its internal temperature was decreased down to −5° C. Sodium tert-butoxide (93.67 g, 0.96 mol) was slowly added thereto, and herein, the internal temperature was controlled to be 0° C. or lower. The obtained mixture was stirred at room temperature for 2 hours, and the reactant was slowly added to cold water in a dropwise fashion. A solid produced therein was stirred at room temperature, filtered, and dried to obtain Intermediate A-1. (142.9 g, 92%).

Synthesis of Intermediate A-2

A mixture of Intermediate A-1 (140.0 g, 0.58 mol) and urea (173.9 g, 2.90 mol) was stirred at 200° C. for 2 hours in a 2 L round flask. The reaction mixture at a high temperature was cooled down to room temperature and poured into a sodium hydroxide solution, impurities therein were filtered and removed, the reactant is acidized (HCl, 2N) to obtain a precipitate, and the precipitate was dried to obtain Intermediate A-2 (114.17 g, 78%).

Synthesis of Intermediate A

A mixture of Intermediate A-2 (114 g, 0.45 mol) and phosphorus oxychloride (1000 mL) was stirred and refluxed in a 2000 mL round flask for 8 hours. The reaction mixture was cooled down to room temperature, and a precipitate was produced by pouring ice/water thereinto, while fervently stirred. A reactant obtained therefrom was filtered to obtain Intermediate A (a white solid, 122.8 g, 94%). An element analysis result of Intermediate A is as follows.

calcd. C10H3Cl3N2S: C, 41.48; H, 1.04; Cl, 36.73; N, 9.67; S, 11.07; found: C, 41.48; H, 1.04; Cl, 36.73; N, 9.67; S, 11.07.

Synthesis Example 2: Synthesis of Intermediates B, C, and D

[Reaction Scheme 2]

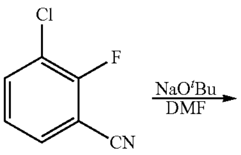

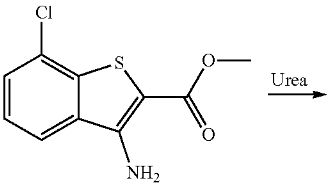

Intermediate B-1

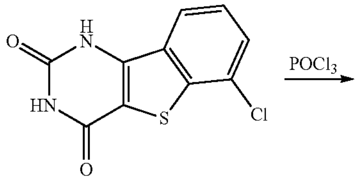

Intermediate B-2

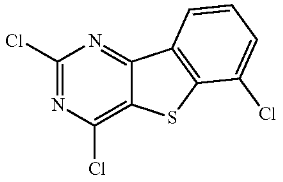

Intermediate B

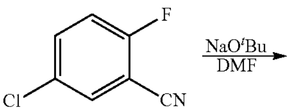

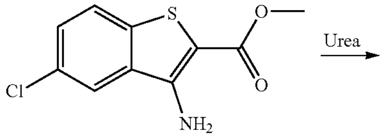

Intermediate C-1

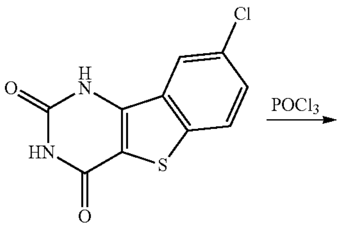

Intermediate C-2

-continued

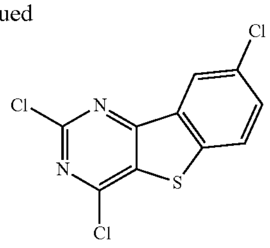

Intermediate C

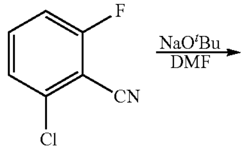

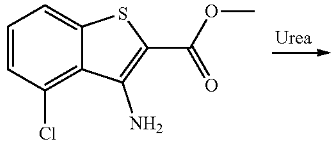

Intermediate D-1

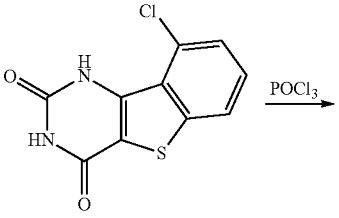

Intermediate D-2

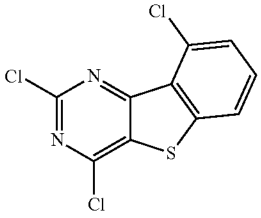

Intermediate D

Synthesis of Intermediates B, C, and D

Intermediates B, C, and D were synthesized according to the same method as Synthesis Example 1 except for changing a starting material as shown in Reaction Scheme 2.

Synthesis Example 3: Synthesis of Intermediate E

[Reaction Scheme 3]

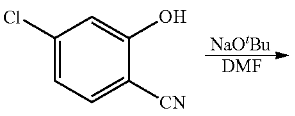

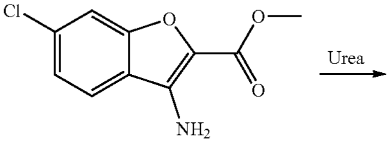

Intermediate E-1

-continued

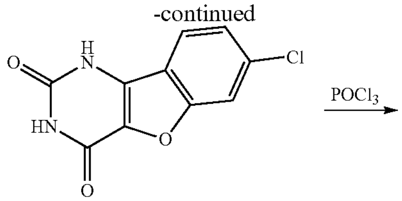

Intermediate E-2

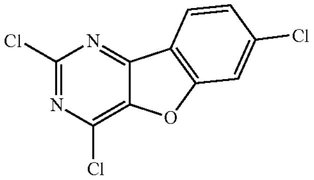

Intermediate E

Synthesis of Intermediate E-1

4-chloro-2-hydroxybenzonitrile (100 g, 0.65 mol), ethylbromoacetate (130.5 g, 0.78 mol), and 1.3 L of N,N-dimethylformamide were put in a 3 L round flask, and its internal temperature was decreased down to −5° C. Sodium tert-butoxide (93.88 g, 0.98 mol) was slowly added thereto, and the obtained mixture was controlled not to be higher than 0° C. The obtained mixture was stirred at room temperature for 2 hours, and the reactant was slowly added thereto in a dropwise fashion. A solid produced therein was stirred at room temperature, filtered, and dried to obtain Intermediate E-1. (132.2 g, 90%).

Synthesis of Intermediate E-2 and Intermediate E

Intermediate E was synthesized according to the same method as Intermediate A-2 and Intermediate A according to Synthesis Example 1.

Synthesis Example 4: Synthesis of Intermediates F, G, and H

[Reaction Scheme 4]

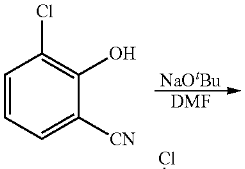

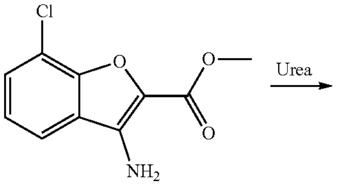

Intermediate F-1

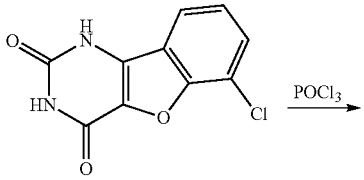

Intermediate F-2

-continued

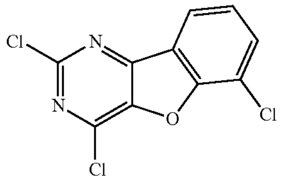

Intermediate F

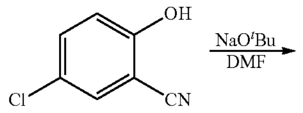

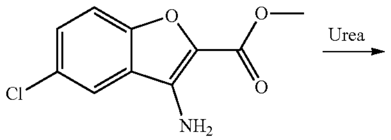

Intermediate G-1

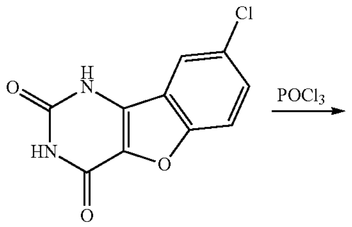

Intermediate G-2

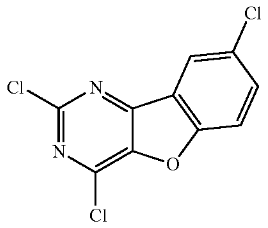

Intermediate G

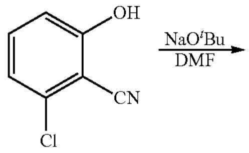

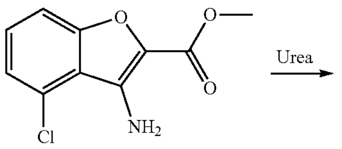

Intermediate H-1

-continued

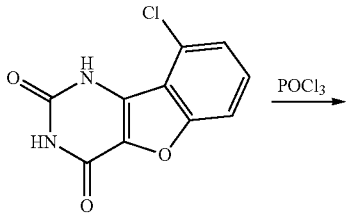

Intermediate H-2

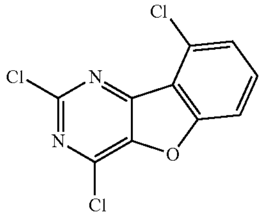

Intermediate H

Synthesis of Intermediate F, Intermediate G, and Intermediate H

Intermediate F, G, and H were synthesized according to the same method as Synthesis Example 3 except for changing a starting material as shown in Reaction Scheme 4.

Synthesis Example 5: Synthesis of Compound 2

[Reaction Scheme 5]

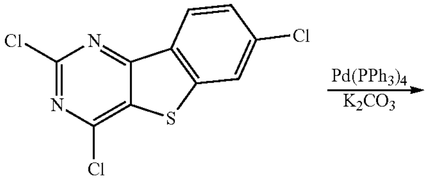

Intermediate A

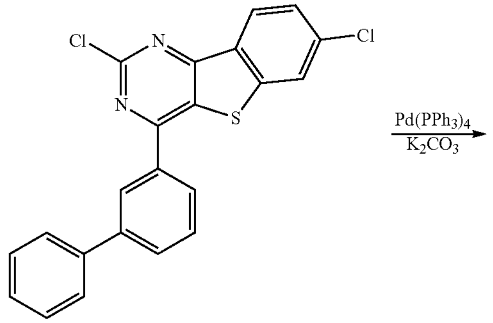

Intermediate 1-1

-continued

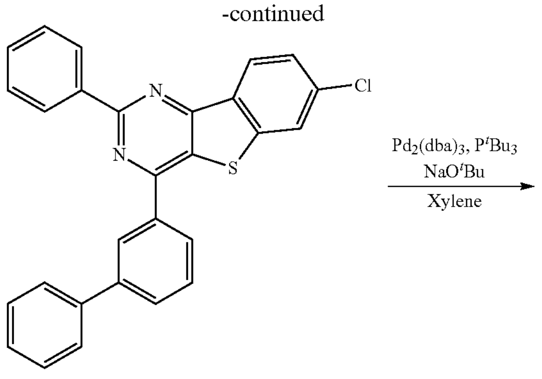

Intermediate 1-2

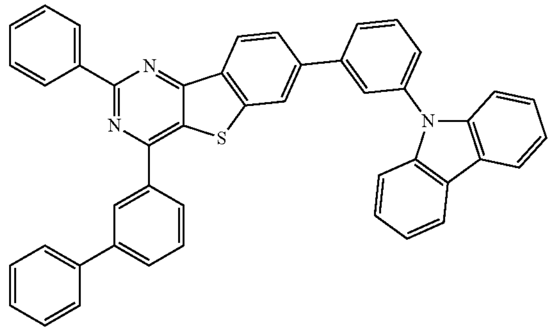

2

Synthesis of Intermediate 1-1

Intermediate A (10.0 g, 34.1 mmol), 3-biphenyl boronic acid (7.83 g, 34.53 mmol), potassium carbonate (11.93 g, 86.33 mmol) tetrakis(triphenylphosphine) palladium (0) (1.2 g, 1.04 mmol), 80 mL of 1,4-dioxane, and 40 mL of water were put in a 250 mL flask and then, heated at 65° C. for 12 hours under a nitrogen flow. An organic layer was separated therefrom and added to 240 mL of methanol, and a solid crystallized therein was dissolved in monochlorobenzene, filtered through silica gel/Celite, and then, recrystallized with monochlorobenzene after removing an organic solvent in an appropriate amount to obtain Intermediate 1-1 (10.83 g, a yield of 77%).

Synthesis of Intermediate 1-2

Intermediate 1-1 (10.5 g, 25.78 mmol), phenylboronic acid (3.14 g, 25.78 mmol), potassium carbonate (8.91 g, 64.45 mmol), and tetrakis (triphenylphosphine) palladium (0) (0.89 g, 0.77 mmol) were added to 70 mL of 1,4-dioxane and 35 mL of water in a 250 mL flask, and the mixture was heated at 70° C. under a nitrogen flow for 12 hours. An organic layer was separated therefrom and added to 210 mL of methanol, and a solid crystallized therein was dissolved in monochlorobenzene, filtered through silica gel/Celite, and after removing an organic solvent in an appropriate amount, recrystallized with monochlorobenzene to obtain Intermediate 1-2 (8.44 g, a yield of 79%).

Synthesis of Compound 2

8.00 g (17.83 mmol) of Intermediate 1-2, 6.58 g (17.83 mmol) of 9-(3-(4,4,5,5-tetramethyl-1,3,2-dioxaborane-2-yl) phenyl)-9H-carbazole, 3.43 g (35.65 mmol) of sodium t-butoxide, 1.03 g (1.78 mmol) of tris(dibenzylideneacetone) dipalladium, and 3.57 mL of tri t-butylphosphine (50% in toluene) were mixed with 120 mL of xylene in a 250 mL round flask, and the mixture was heated and refluxed under a nitrogen flow for 12 hours. The obtained mixture was added to 500 mL of methanol, a solid crystallized therein was filtered, dissolved in dichlorobenzene, filtered through silica gel/Celite, and after removing an organic solvent in an appropriate amount, recrystallized with methanol to obtain Compound 2 (8.5 g, a yield of 73%).

calcd. C46H29N3S: C, 84.25; H, 4.46; N, 6.41; S, 4.89; found: C, 84.25; H, 4.46; N, 6.41; S, 4.89.

Synthesis Examples 6 to 36

Each final compound was synthesized according to the same method as Synthesis Example 5 except for respectively using the compounds shown in Table 1 as a starting material.

TABLE 1

| Synthesis Example | Starting material | Final Product | Amount (yield) | Data of Final Products |
|---|---|---|---|---|
| Synthesis Example 6 | Interme-diate A | 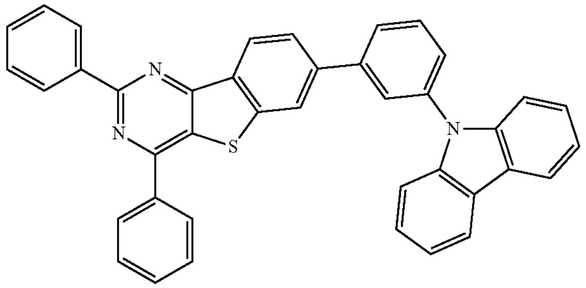 1 | 5.32 g, (75%) | calcd. C40H25N3S: C, 82.87; H, 4.35; N, 7.25; S, 5.53; found: C, 82.87; H, 4.36; N, 7.25; S, 5.53 |

TABLE 1-continued
| Synthesis Example | Starting material | Final Product | Amount (yield) | Data of Final Products |
|---|---|---|---|---|
| Synthesis Example 7 | Interme-diate A | 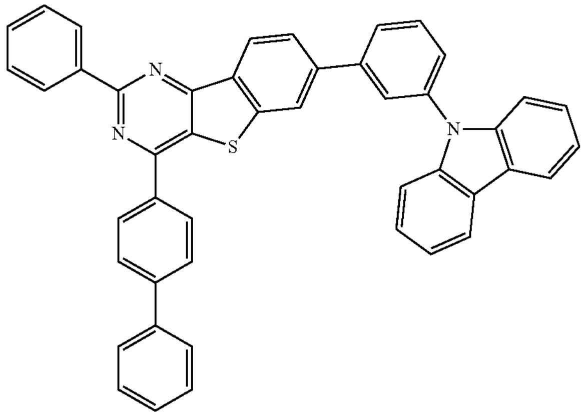 3 | 4.33 g, (79%) | calcd. C46H29N3S: C, 84.25; H, 4.46; N, 6.41; S, 4.89; found: C, 84.25; H, 4.46; N, 6.41; S, 4.89 |
| Synthesis Example 8 | Interme-diate A | 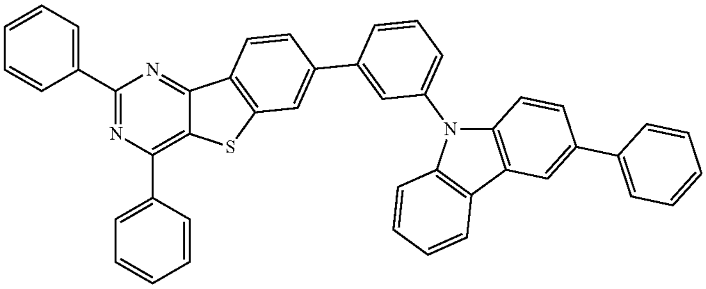 4 | 5.98 g, (75%) | calcd. C46H29N3S: C, 84.25; H, 4.46; N, 6.40; S, 4.89; found: C, 84.25; H, 4.46; N, 6.41; S, 4.89 |
| Synthesis Example 9 | Interme-diate A | 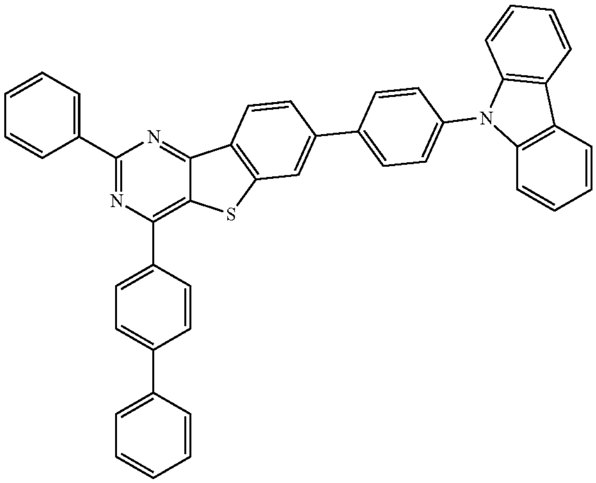 11 | 4.25 g, (70%) | calcd. C46H29N3S: C, 84.25; H, 4.46; N, 6.40; S, 4.89; found: C, 84.25; H, 4.46; N, 6.41; S, 4.89 |

TABLE 1-continued
| Synthesis Example | Starting material | Final Product | Amount (yield) | Data of Final Products |
|---|---|---|---|---|
| Synthesis Example 10 | Interme-diate A | 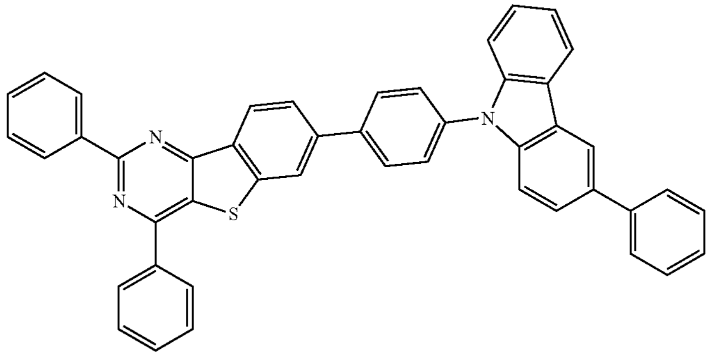 12 | 5.92 g, (72%) | calcd. C46H29N3S: C, 84.25; H, 4.46; N, 6.40; S, 4.89; found: C, 84.25; H, 4.46; N, 6.41; S, 4.89 |
| Synthesis Example 11 | Interme-diate A | 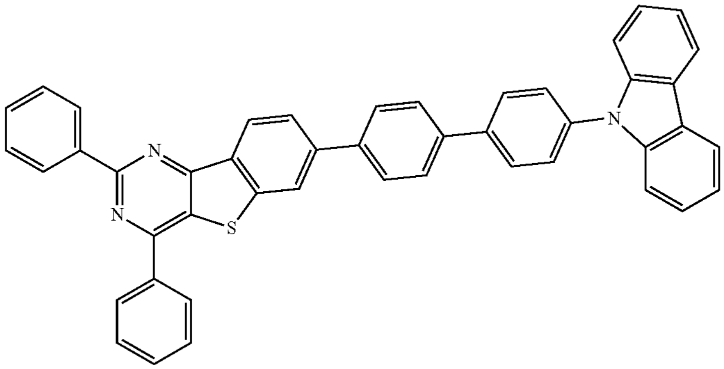 13 | 5.49 g, (70%) | calcd. C46H29N3S: C, 84.25; H, 4.46; N, 6.40; S, 4.89; found: C, 84.25; H, 4.46; N, 6.41; S, 4.89 |
| Synthesis Example 12 | Interme-diate A | 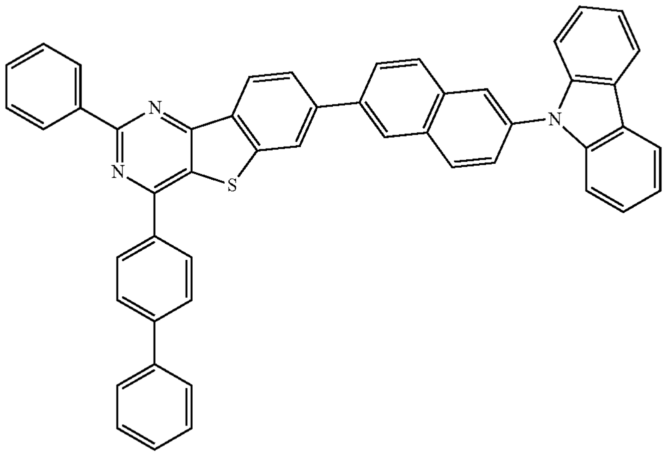 16 | 5.91 g, (77%) | calcd. C50H31N3S: C, 85.08; H, 4.43; N, 5.95; S, 4.54; found: C, 85.08; H, 4.43; N, 5.95; S, 4.54 |

TABLE 1-continued
| Synthesis Example | Starting material | Final Product | Amount (yield) | Data of Final Products |
|---|---|---|---|---|
| Synthesis Example 13 | Interme-diate A | 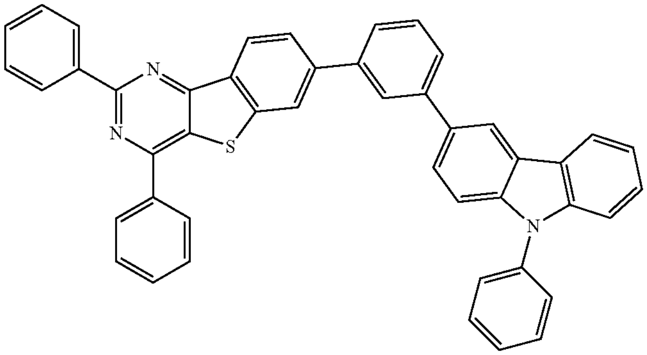 22 | 4.16 g, (75%) | calcd. C46H29N3S: C, 84.25; H, 4.46; N, 6.40; S, 4.89; found: C, 84.25; H, 4.46; N, 6.41; S, 4.89 |
| Synthesis Example 14 | Interme-diate A | 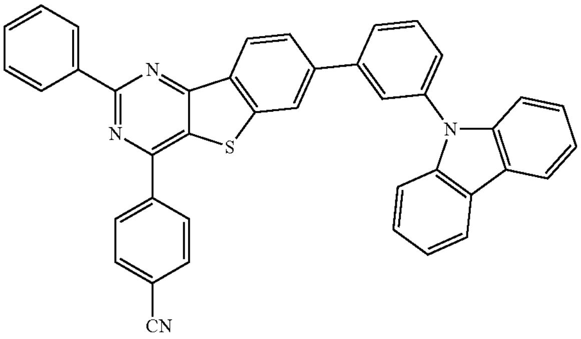 34 | 5.45 g, (70%) | calcd. C41H24N4S: C, 81.43; H, 4.00; N, 9.26; S, 5.30; found: C, 81.43; H, 4.00; N, 9.26; S, 5.30 |
| Synthesis Example 15 | Interme-diate A | 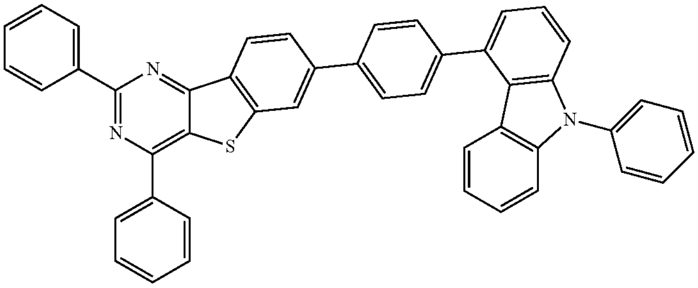 41 | 4.41 g, (78%) | calcd. C46H29N3S: C, 84.25; H, 4.46; N, 6.40; S, 4.89; found: C, 84.25; H, 4.46; N, 6.41; S, 4.89 |

TABLE 1-continued
| Synthesis Example | Starting material | Final Product | Amount (yield) | Data of Final Products |
|---|---|---|---|---|
| Synthesis Example 16 | Intermediate A | 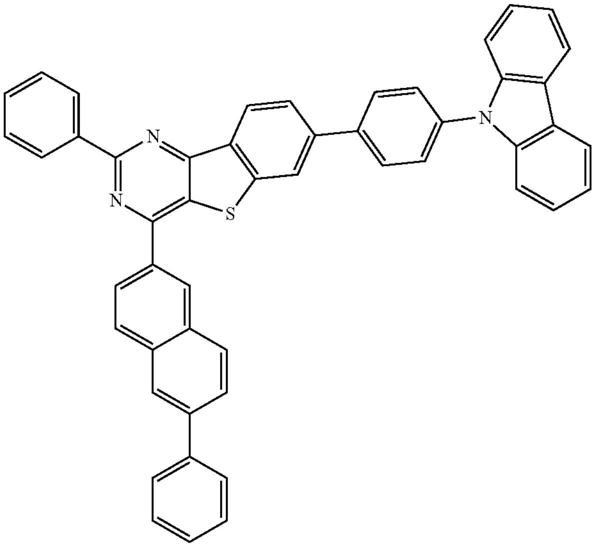 45 | 6.50 g, (69%) | calcd. C50H31N3S: C, 85.08; H, 4.43; N, 5.95; S, 4.54; found: C, 85.08; H, 4.43; N, 5.95; S, 4.54 |
| Synthesis Example 17 | Intermediate B | 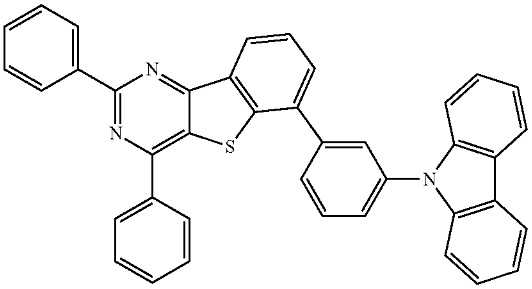 49 | 9.30 g, (78%) | calcd. C40H25N3S: C, 82.87; H, 4.35; N, 7.25; S, 5.53; found: C, 82.87; H, 4.36; N, 7.25; S, 5.53 |
| Synthesis Example 18 | Intermediate B | 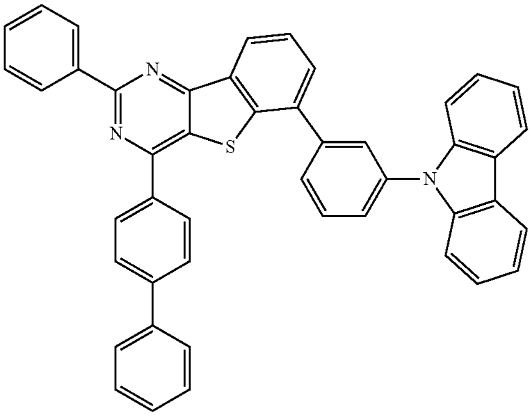 51 | 7.55 g, (74%) | calcd. C46H29N3S: C, 84.25; H, 4.46; N, 6.41; S, 4.89; found: C, 84.25; H, 4.46; N, 6.41; S, 4.89 |

TABLE 1-continued
| Synthesis Example | Starting material | Final Product | Amount (yield) | Data of Final Products |
|---|---|---|---|---|
| Synthesis Example 19 | Interme-diate B | 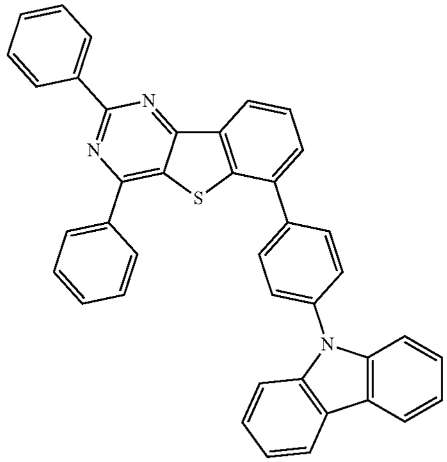 51 | 5.59 g, (76%) | calcd. C40H25N3S; C, 82.87; H, 4.35; N, 7.25; S, 5.53; found: C, 82.87; H, 4.36; N, 7.25; S, 5.53 |
| Synthesis Example 20 | Interme-diate C | 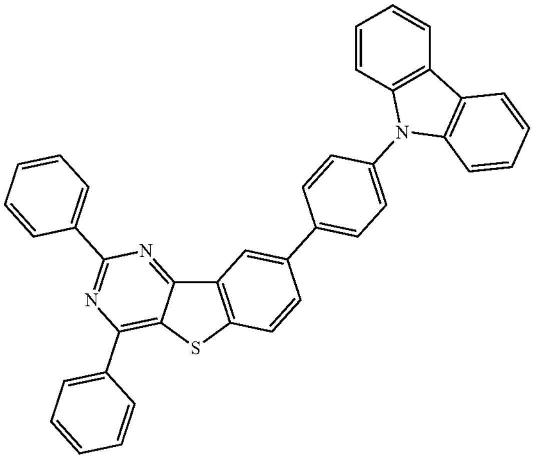 105 | 6.60 g, (79%) | calcd. C40H25N3S: C, 82.87; H, 4.35; N, 7.25; S, 5.53; found: C, 82.87; H, 4.36; N, 7.25; S, 5.53 |
| Synthesis Example 21 | Interme-diate C | 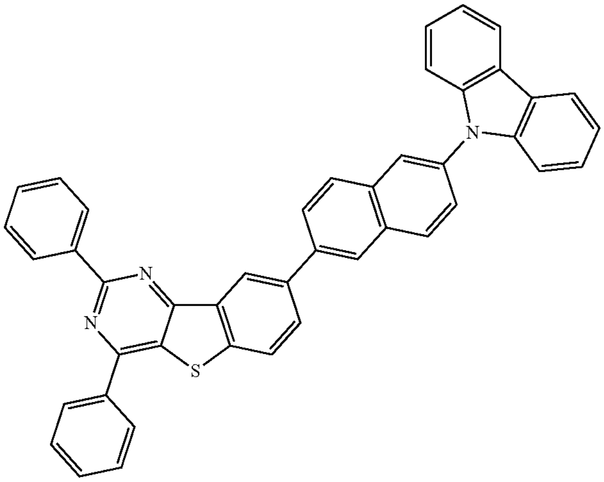 110 | 4.25 g, (74%) | calcd. C44H27N3S: C, 83.91; H, 4.32; N, 6.67; S, 5.09; found: C, 83.91; H, 4.32; N, 6.67; S, 5.09 |

TABLE 1-continued
| Synthesis Example | Starting material | Final Product | Amount (yield) | Data of Final Products |
|---|---|---|---|---|
| Synthesis Example 22 | Interme-diate C | 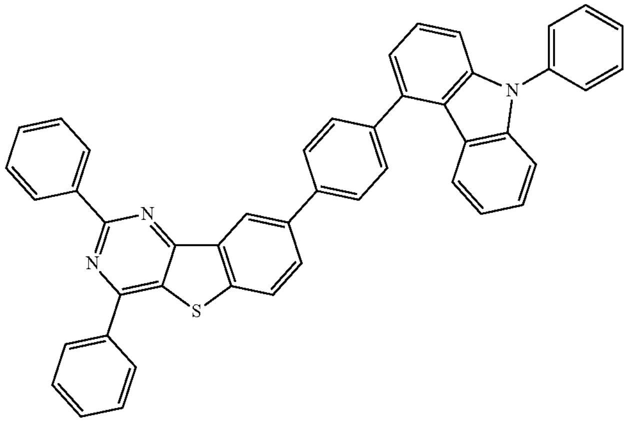 137 | 5.88 g, (77%) | calcd. C46H29N3S: C, 84.25; H, 4.46; N, 6.41; S, 4.89; found: C, 84.25; H, 4.46; N, 6.41; S, 4.89 |
| Synthesis Example 23 | Interme-diate D | 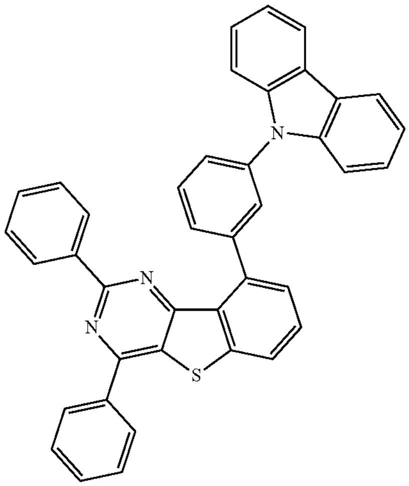 145 | 6.47 g, (76%) | calcd. C40H25N3S: C, 82.87; H, 4.35; N, 7.25; S, 5.53; found: C, 82.87; H, 4.36; N, 7.25; S, 5.53 |
| Synthesis Example 24 | Interme-diate D | 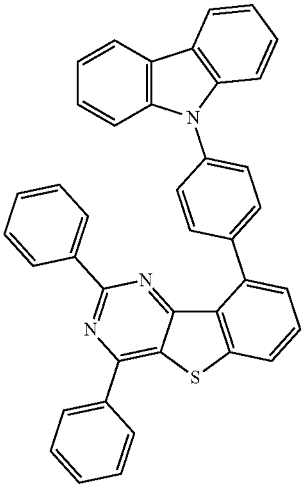 153 | 6.05 g, (68%) | calcd. C40H25N3S: C, 82.87; H, 4.35; N, 7.25; S, 5.53; found: C, 82.87; H, 4.36; N, 7.25; S, 5.53 |

TABLE 1-continued
| Synthesis Example | Starting material | Final Product | Amount (yield) | Data of Final Products |
|---|---|---|---|---|
| Synthesis Example 25 | Interme-diate D | 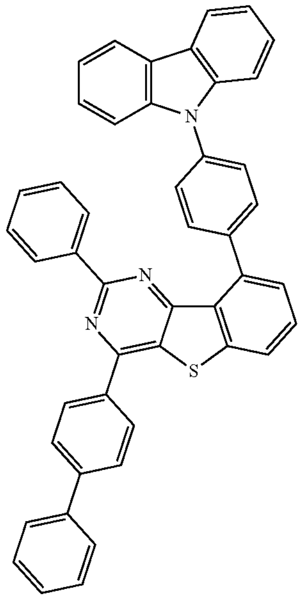 155 | 5.31 g, (75%) | calcd. C46H29N3S: C, 84.25; H, 4.46; N, 6.41; S, 4.89; found: C, 84.25; H, 4.46; N, 6.41; S, 4.89 |
| Synthesis Example 26 | Interme-diate D | 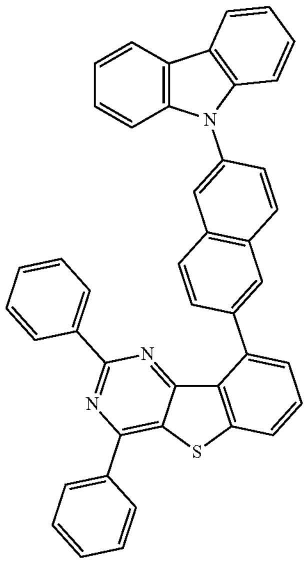 158 | 7.11 g, (75%) | calcd. C44H27N3S: C, 83.91; H, 4.32; N, 6.67; S, 5.09; found: C, 83.91; H, 4.32; N, 6.67; S, 5.09 |

TABLE 1-continued
| Synthesis Example | Starting material | Final Product | Amount (yield) | Data of Final Products |
|---|---|---|---|---|
| Synthesis Example 27 | Interme-diate E | 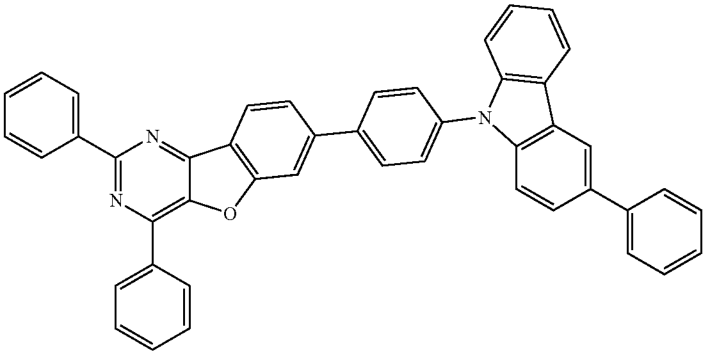 204 | 6.73 g, (73%) | calcd. C46H29N3O; C, 86.36; H, 4.57; N, 6.57; O, 2.50; found: C, 86.36; H, 4.57; N, 6.57; O, 2.49 |
| Synthesis Example 28 | Interme-diate E | 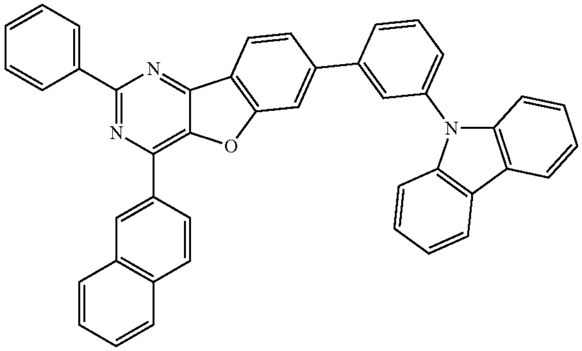 211 | 5.19 g, (72%) | calcd. C44H27N3O; C, 86.11; H, 4.43; N, 6.85; O, 2.61; found: C, 86.11; H, 4.43; N, 6.85; O, 2.61 |
| Synthesis Example 29 | Interme-diate F | 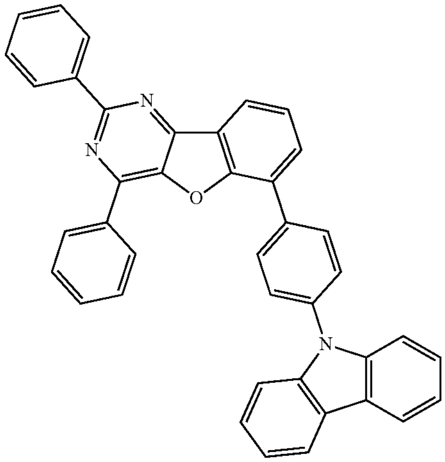 249 | 5.60 g, (76%) | calcd. C40H25N3O; C, 85.24; H, 4.47; N, 7.46; O, 2.84; found: C, 85.24; H, 4.47; N, 7.46; O, 2.84 |

TABLE 1-continued
| Synthesis Example | Starting material | Final Product | Amount (yield) | Data of Final Products |
|---|---|---|---|---|
| Synthesis Example 30 | Interme-diate F | 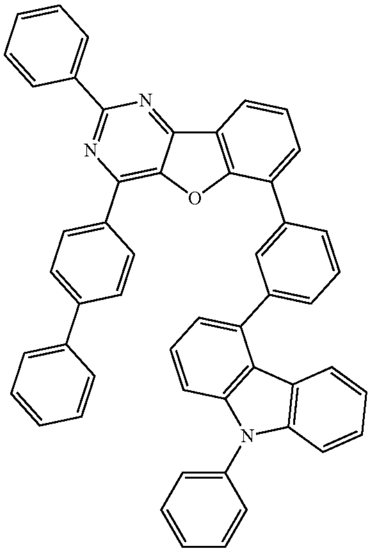 269 | 7.24 g, (73%) | calcd. C52H33N3O; C, 87.25; H, 4.65; N, 5.87; O, 2.24; found: C, 87.25; H, 4.65; N, 5.87; O, 2.24 |
| Synthesis Example 31 | Interme-diate G | 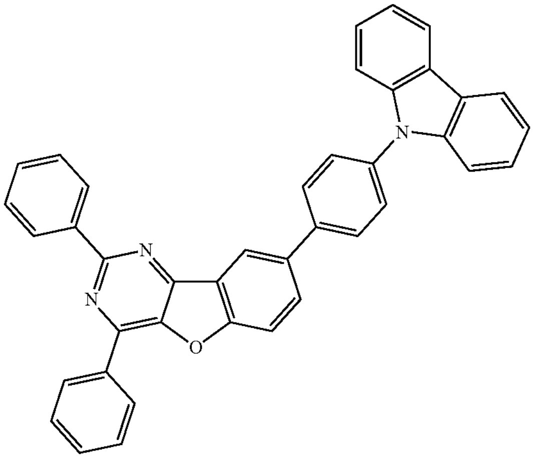 297 | 5.76 g, (77%) | calcd. C40H25N3O; C, 85.24; H, 4.47; N, 7.46; O, 2.84; found: C, 85.24; H, 4.47; N, 7.46; O, 2.84 |

TABLE 1-continued
| Synthesis Example | Starting material | Final Product | Amount (yield) | Data of Final Products |
|---|---|---|---|---|
| Synthesis Example 32 | Interme-diate G | 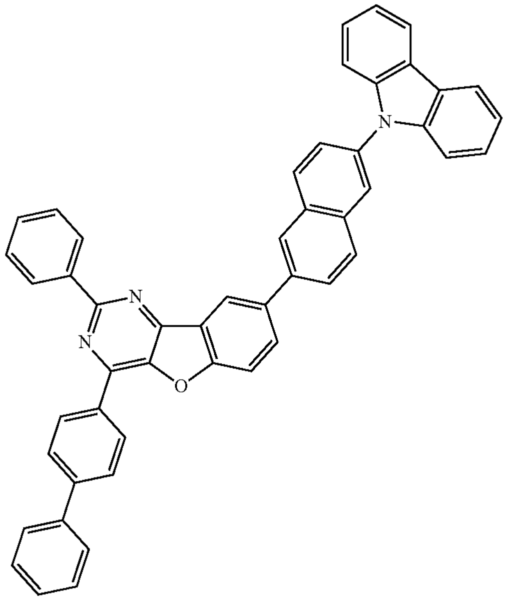 304 | 8.35 g, (74%) | calcd. C50H31N3O; C, 87.06; H, 4.53; N, 6.09; O, 2.32; found: C, 87.05; H, 4.53; N, 6.09; O, 2.32 |
| Synthesis Example 33 | Interme-diate H | 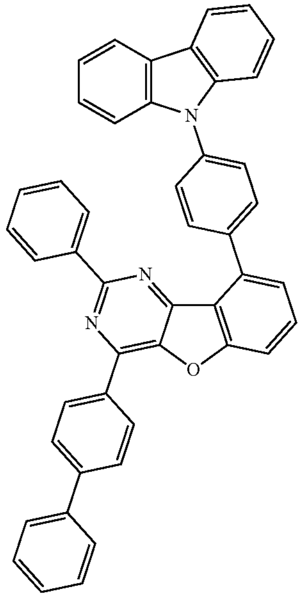 347 | 5.02 g, (75%) | calcd. C46H29N3O; C, 86.36; H, 4.57; N, 6.57; O, 2.50; found: C, 86.36; H, 4.57; N, 6.57; O, 2.49 |

TABLE 1-continued
| Synthesis Example | Starting material | Final Product | Amount (yield) | Data of Final Products |
|---|---|---|---|---|
| Synthesis Example 34 | Interme-diate H | 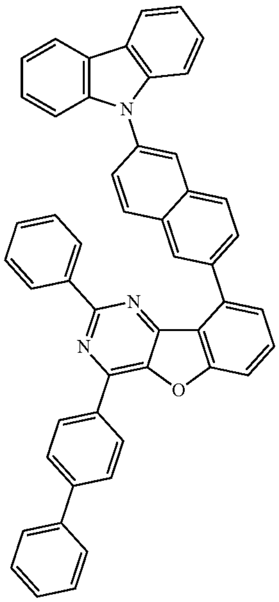 352 | 4.66 g, (74%) | calcd. C50H31N3O; C, 87.06; H, 4.53; N, 6.09; O, 2.32; found: C, 87.05; H, 4.53; N, 6.09; O, 2.32 |
| Synthesis Example 35 | Interme-diate H | 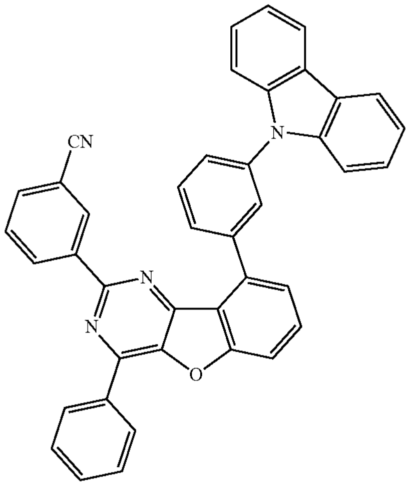 371 | 6.60 g, (71%) | calcd. C41H24N4O; C, 83.65; H, 4.11; N, 9.52; O, 2.72; found: C, 83.65; H, 4.11; N, 9.52; O, 2.72 |

TABLE 1-continued
| Synthesis Example | Starting material | Final Product | Amount (yield) | Data of Final Products |
| --- | --- | --- | --- | --- |
| Synthesis Example 36 | Interme-diate H | 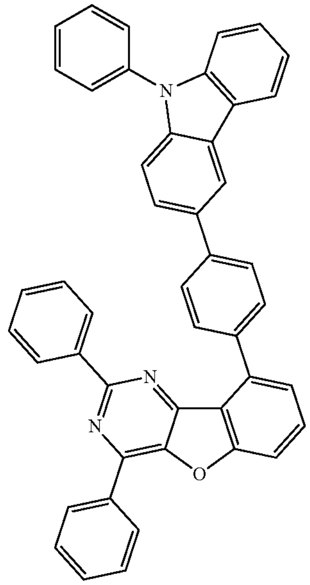 378 | 5.53 g, (78%) | calcd. C46H29N3O; C, 86.36; H, 4.57; N, 6.57; O, 2.50; found: C, 86.36; H, 4.57; N, 6.57; O, 2.49 |
(Second Compound for Organic Optoelectronic Device)
Synthesis Example 37: Synthesis of Intermediate I
[Reaction Scheme 6]
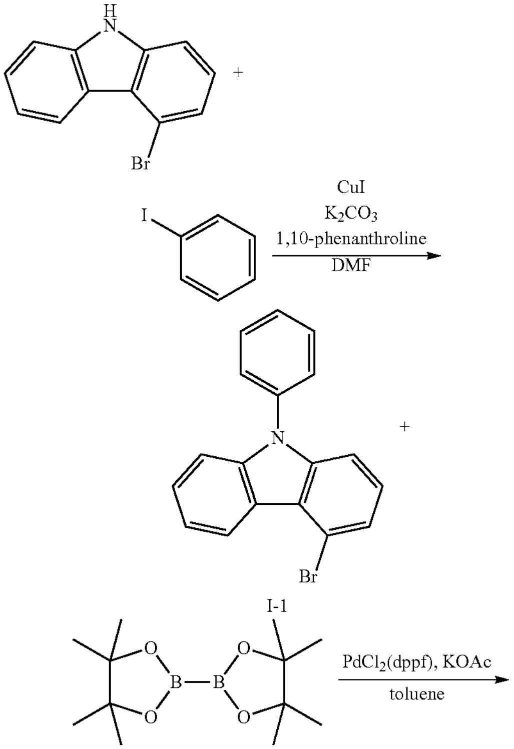
-continued
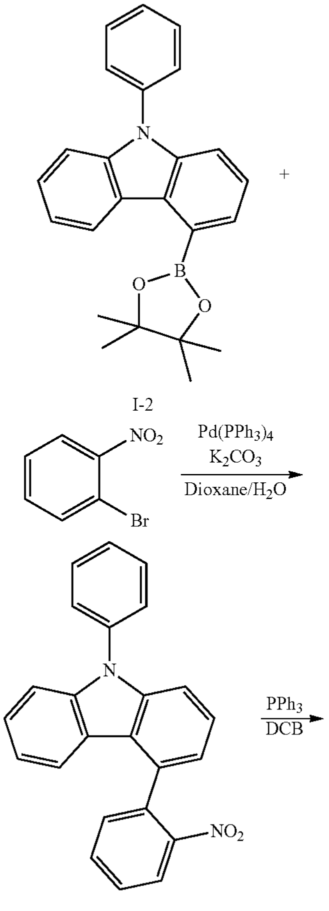

-continued

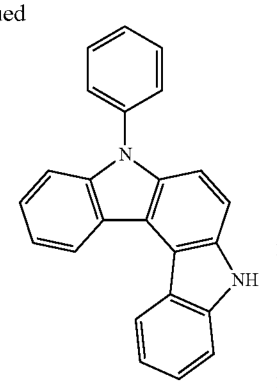

I

Synthesis of Intermediate I-1

200.0 g (0.8 mol) of Intermediate of 4-bromo-9H-carbazole, 248.7 g (1.2 mol) of iodo benzene, 168.5 g (1.2 mol) of potassium carbonate, 31.0 g (0.2 mol) of copper iodide (I), and 29.3 g (0.2 mol) of 1,10-phenanthroline were added to 2.5 L of N,N-dimethylformamide in a 5 L flask, and the mixture was refluxed under a nitrogen flow for 24 hours. The obtained mixture was added to 4 L of distilled water, and a solid crystallized therein was filtered and washed with water, methanol, and hexane. After removing moisture from an organic layer obtained by extracting the solid with water and dichloromethane by using magnesium sulfate, the organic layer was concentrated and purified through column chromatography to obtain Intermediate 1-1 as a white solid (216.2 g, a yield of 83%).

calcd. C27H18C1N3: C, 67.10; H, 3.75; Br, 24.80; N, 4.35; found: C C, 67.12; H, 3.77; Br, 24.78; N, 4.33.

Synthesis of Intermediate I-2

Intermediate I-1 (216.0 g, 0.7 mol), 4,4,4', 4', 5,5,5', 5'-octamethyl-2,2'-bi(1,3,2-dioxaborolane (212.8 g, 0.8 mol), potassium acetate (KOAc, 197.4 g, 2.0 mol), 1,1'-bis (diphenylphosphino) ferrocene-palladium(II)dichloride (21.9 g, 0.03 mol), and tricyclohexylphosphine (45.1 g, 0.2 mol) were added to 3 L of N,N-dimethylformamide in a 5 L flask, and the mixture was stirred at 130° C. for 12 hours. When a reaction was complete, an organic layer obtained by extracting the reaction solution with water and EA was concentrated after removing moisture therefrom by using magnesium sulfate and then, purified through column chromatography to obtain Intermediate 1-2 as a white solid (205.5 g, a yield of 83%).

calcd. C26H25BN2O2: C, 78.06; H, 6.55; B, 2.93; N, 3.79; O, 8.67; found: C, 78.08; H, 6.57; B, 2.91; N, 3.77; O, 8.67.

Synthesis of Intermediate 1-3

150.0 g (0.4 mol) of Intermediate I-2, 164.1 g (0.8 mol) of Intermediate of 1-bromo-2-nitro benzene, 278.1 g (2.01 mol) of potassium carbonate, and 23.5 g (0.02 mol) of tetrakis(triphenylphosphine) palladium (0) were added to 2 L of 1,4-dioxane and 1 L of water in a 5 L flask and then, heated at 90° C. under a nitrogen flow for 16 hours. After removing a reaction solvent therefrom, the rest thereof was dissolved in dichloromethane, filtered through silica gel/Celite, and after removing an organic solvent in an appropriate amount, recrystallized with methanol to obtain Intermediate 1-3 as a yellow solid (86.3 g, a yield of 58%).

calcd. C18H12N2O2: C, 79.11; H, 4.43; N, 7.69; O, 8.78; found: C, 79.13; H, 4.45; N, 7.67; O, 8.76.

Synthesis of Intermediate I

Intermediate 1-3 (86.0 g, 0.23 mol) and triphenyl phosphine (309.5 g, 1.18 mol) were mixed with 600 mL of dichloro benzene in a 1000 ml flask, and after substituted with nitrogen, the mixture was stirred at 160° C. for 12 hours. When a reaction was complete, the resultant was purified through column chromatography with hexane after removing a solvent therefrom to obtain Intermediate I as a yellow solid (57.3 g, a yield of 73%).

Calcd. C18H12N2: C, 86.72; H, 4.85; N, 8.43; found: C, 86.70; H, 4.83; N, 8.47.

Synthesis Examples 38 to 50

Each final compound was synthesized according to the same method as Synthesis Example 37 except for using the compound shown in Table 2 as a starting material.

TABLE 2

| Synthesis Example | Starting material | Final Product | Amount (yield) | Data of Final Products |
|---|---|---|---|---|
| Synthesis Example 38 | 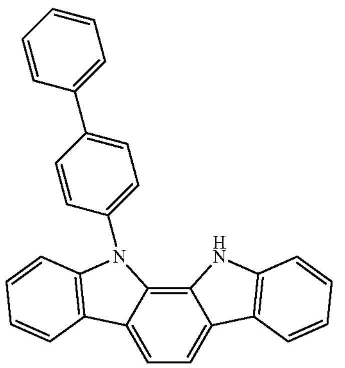 | 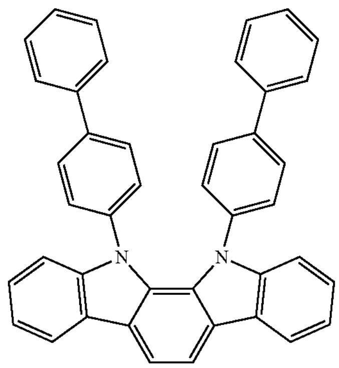 F-23 | 10.23 g, (45%) | calcd. C42H28N2: C, 89.97; H, 5.03; N, 5.00; found: C, 89.97; H, 5.03; N, 5.00 |

TABLE 2-continued
| Synthesis Example | Starting material | Final Product | Amount (yield) | Data of Final Products |
|---|---|---|---|---|
| Synthesis Example 39 | 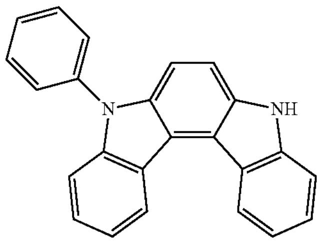 | 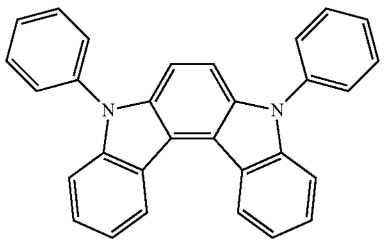 F-41 | 7.31 g, (77%) | calcd. C30H20N2: C, 88.21; H, 4.93; N, 6.86; found: C, 88.21; H, 4.93; N, 6.86 |
| Synthesis Example 40 | 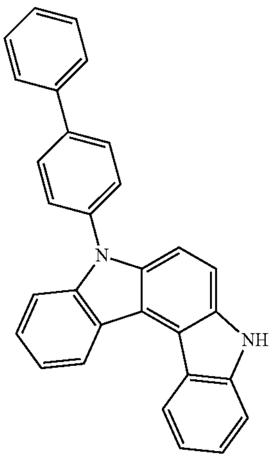 | 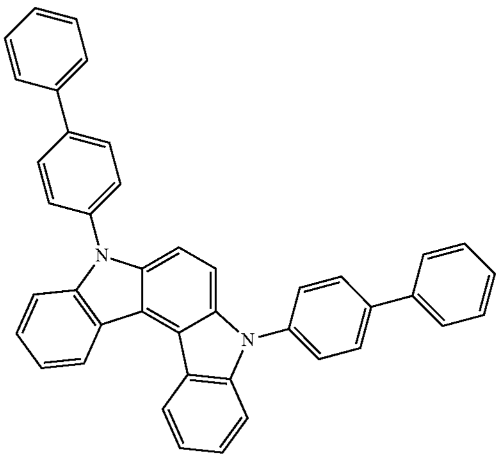 F-43 | 6.33 g, (76%) | calcd. C42H28N2: C, 89.97; H, 5.03; N, 5.00; found: C, 89.97; H, 5.03; N, 5.00 |
| Synthesis Example 41 | 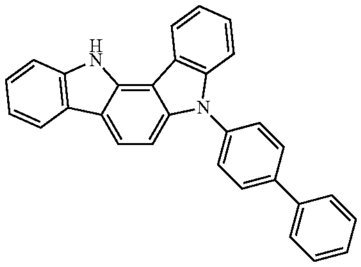 | 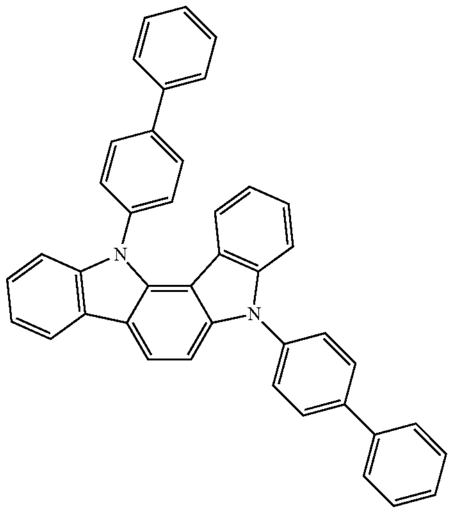 F-73 | 8.33 g, (74%) | calcd. C42H28N2: C, 89.97; H, 5.03; N, 5.00; found: C, 89.97; H, 5.03; N, 5.00 |

TABLE 2-continued
| Synthesis Example | Starting material | Final Product | Amount (yield) | Data of Final Products |
|---|---|---|---|---|
| Synthesis Example 42 | 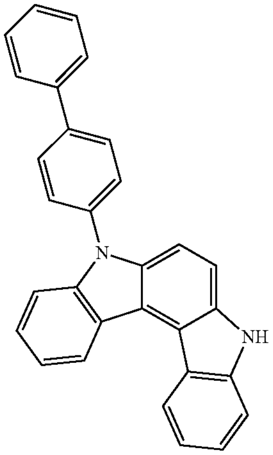 | 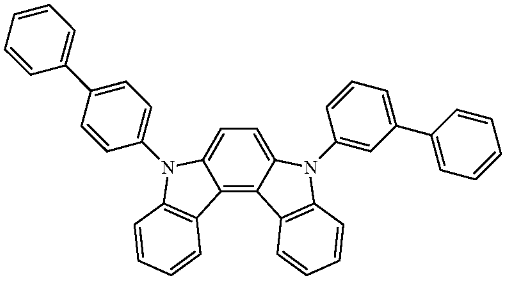 F-99 | 5.53 g, (79%) | calcd. C42H28N2: C, 89.97; H, 5.03; N, 5.00; found: C, 89.97; H, 5.03; N, 5.00 |
| Synthesis Example 43 | 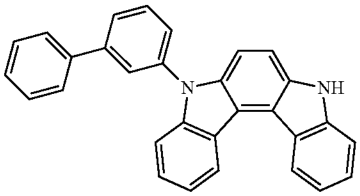 | 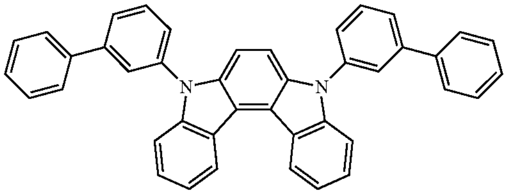 F-100 | 7.41 g, (73%) | calcd. C42H28N2: C, 89.97; H, 5.03; N, 5.00; found: C, 89.97; H, 5.03; N, 5.00 |
| Synthesis Example 44 | 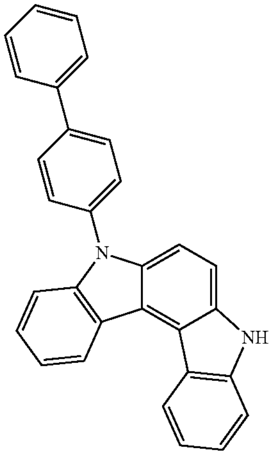 | 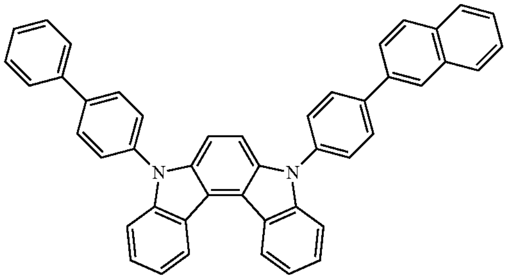 F-102 | 5.94 g, (76%) | calcd. C46H30N2: C, 90.46; H, 4.95; N, 4.59; found: C, 90.46; H, 4.95; N, 4.59 |
| Synthesis Example 45 | 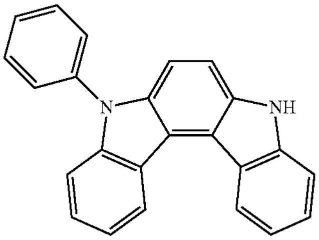 | 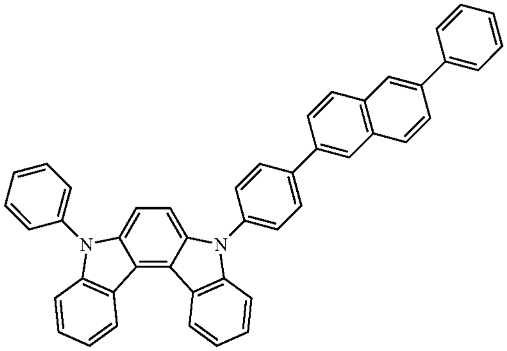 F-103 | 6.37 g, (76%) | calcd. C46H30N2: C, 90.46; H, 4.95; N, 4.59; found: C, 90.46; H, 4.95; N, 4.59 |

TABLE 2-continued
| Synthesis Example | Starting material | Final Product | Amount (yield) | Data of Final Products |
|---|---|---|---|---|
| Synthesis Example 46 | 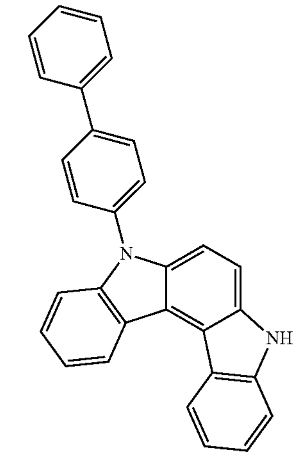 | 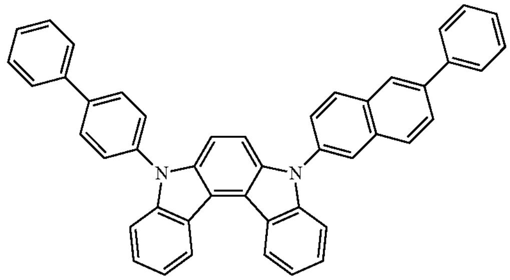 F-104 | 10.39 g, (79%) | calcd. C46H30N2: C, 90.46; H, 4.95; N, 4.59; found: C, 90.46; H, 4.95; N, 4.59 |
| Synthesis Example 47 | 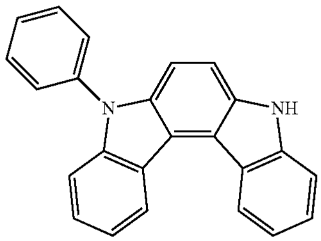 | 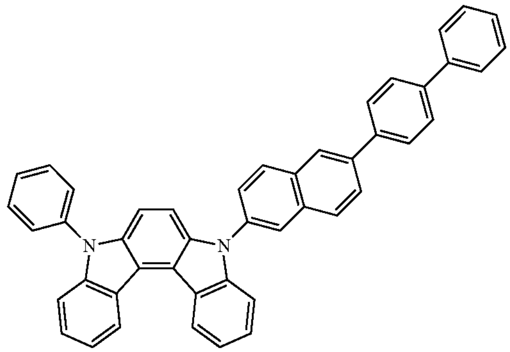 F-105 | 5.33 g, (69%) | calcd. C46H30N2: C, 90.46; H, 4.95; N, 4.59; found: C, 90.46; H, 4.95; N, 4.59 |
| Synthesis Example 48 | 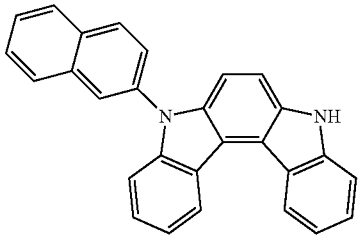 | 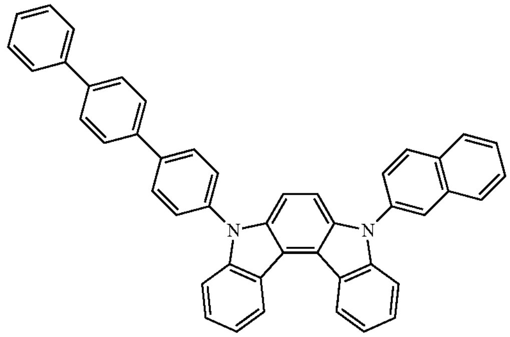 F-106 | 6.96 g, (77%) | calcd. C46H30N2: C, 90.46; H, 4.95; N, 4.59; found: C, 90.46; H, 4.95; N, 4.59 |

TABLE 2-continued

| Synthesis Example | Starting material | Final Product | Amount (yield) | Data of Final Products |
|---|---|---|---|---|
| Synthesis Example 49 | 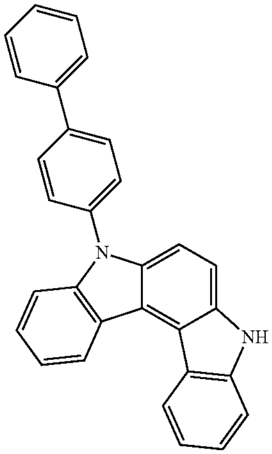 | 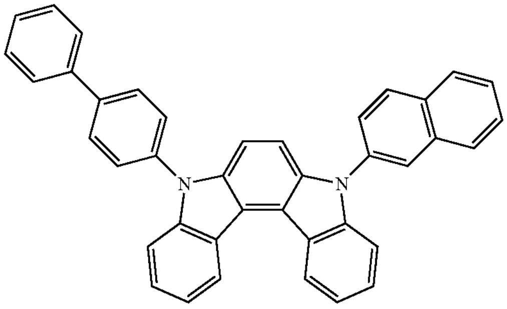 F-107 | 6.11 g, (77%) | calcd. C40H26N2: C, 89.86; H, 4.90; N, 5.24; found: C, 89.86; H, 4.90; N, 5.24 |
| Synthesis Example 50 | 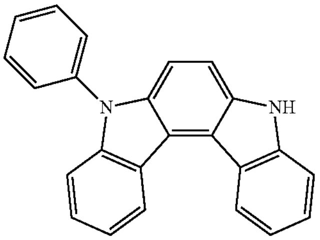 | 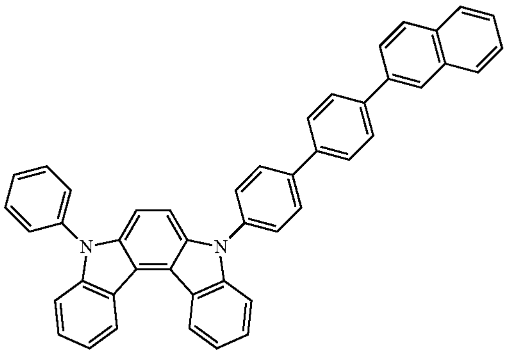 F-110 | 9.44 g, (75%) | calcd. C46H30N2: C, 90.46; H, 4.95; N, 4.59; found: C, 90.46; H, 4.95; N, 4.59 |

Manufacture of Organic Light Emitting Diode I

Example 1

A glass substrate disposed with ITO electrode was cut into a size of 50 mm×50 mm×0.5 mm and then, ultrasonic wave cleaned with acetone isopropyl alcohol and pure water respectively for 15 minutes and UV ozone cleaned for 30 minutes.

On the ITO electrode, m-MTDATA was vacuum-deposited at 1 Å/sec to form a 600 Å-thick hole injection layer, and on the hole injection layer, α-NPB was vacuum-deposited at a deposition rate of 1 Å/sec to form a 300 Å thick hole transport layer. Subsequently, on the hole transport layer, $Ir(ppy)_3$ (Dopant 1) and Compound 2 were codeposited at each deposition rate of 0.1 Å/sec and 1 Å/sec to form a 400 Å-thick light emitting layer. On the light emitting layer, BAlq was vacuum-deposited at a deposition rate of 1 Å/sec to form a hole blocking layer and on the hole blocking layer, $Alq_3$ was vacuum-deposited to form an electron transport layer. On the electron transport layer, LiF 10 Å (an electron injection layer (EIL)) and Al 2000 Å (a cathode) were sequentially vacuum-deposited to manufacture an organic light emitting diode.

Examples 2 to 25

Each organic light emitting diode was manufactured according to the same method as Example 1 except for respectively using the compounds shown in Table 1 instead of Compound 2 as a host to form a light emitting layer.

Comparative Examples 1 to 6

Each organic light emitting diode was manufactured according to the same method as Example 1 except for respectively using Comparative Compounds A to F instead of Compound 2 as a host to form a light emitting layer.

A

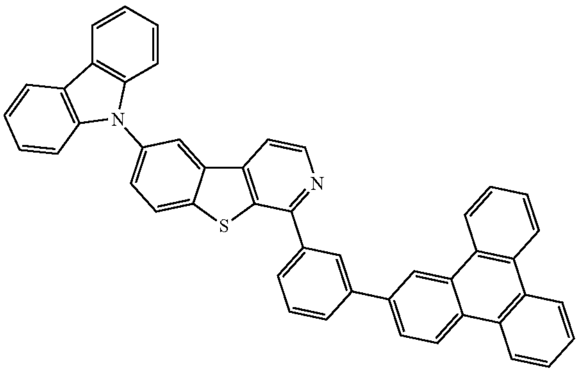

-continued

B

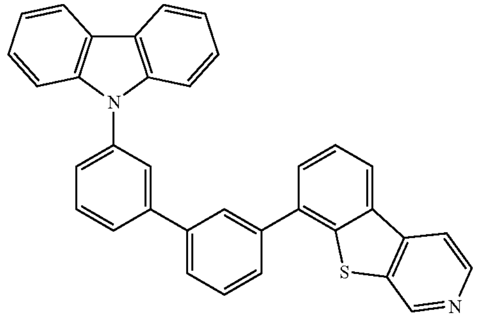

C

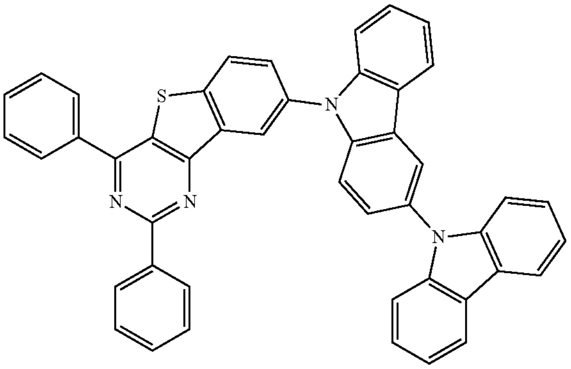

D

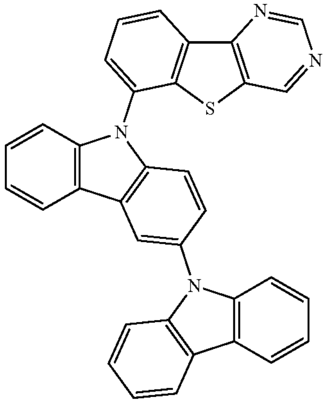

-continued

E

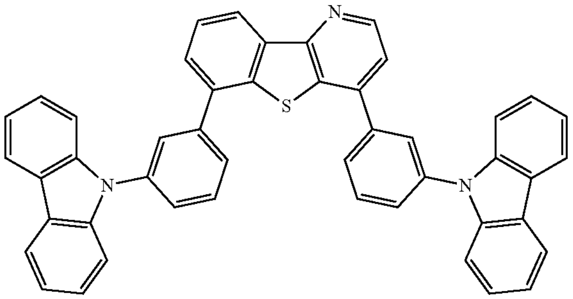

F

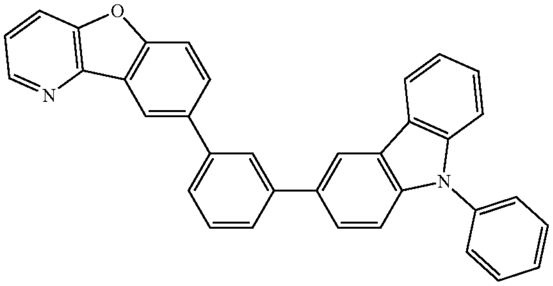

Evaluation Example I

Driving voltages, efficiency, and luminance of organic light emitting diodes according to Examples 1 to 25 and Comparative Examples 1 to 6 were measured using a luminance meter, PR650 Spectroscan Source Measurement Unit. (made by PhotoResearch Inc.) by supplying power from a current voltage meter (Kethley SMU 236).

The results are shown in Table 3.

Specific measurement methods are as follows.

(1) Measurement of Current Density Change Depending on Voltage Change

The organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/$cm^2$) were calculated by using the luminance, current density, and voltages (V) from the items (1) and (2).

(4) Measurement of Life-Span

A $T_{95}$ life-span was evaluated as time (hr) taken until 95% of luminance relative to 100% of initial luminance was obtained.

TABLE 3

| Examples | Host | Dopant | Driving Voltage (V) | Current efficiency (cd/A) | Luminance (cd/$m^2$) | $T_{95}$ life-span (hr) |
|---|---|---|---|---|---|---|
| Example1 | Compound 2 | Dopant 1 | 4.4 | 43 | 6000 | 77 |
| Example2 | Compound 1 | Dopant 1 | 4.3 | 44 | 6000 | 79 |

TABLE 3-continued

| Examples | Host | Dopant | Driving Voltage (V) | Current efficiency (cd/A) | Luminance ($cd/m^2$) | $T_{95}$ life-span (hr) |
|---|---|---|---|---|---|---|
| Example3 | Compound 3 | Dopant 1 | 4.2 | 46 | 6000 | 80 |
| Example4 | Compound 4 | Dopant 1 | 4.4 | 43 | 6000 | 77 |
| Example5 | Compound 11 | Dopant 1 | 4.2 | 46 | 6000 | 80 |
| Example6 | Compound 12 | Dopant 1 | 4.4 | 44 | 6000 | 76 |
| Example7 | Compound 13 | Dopant 1 | 4.3 | 44 | 6000 | 77 |
| Example8 | Compound 22 | Dopant 1 | 4.6 | 43 | 6000 | 75 |
| Example9 | Compound 34 | Dopant 1 | 4.4 | 46 | 6000 | 83 |
| Example10 | Compound 41 | Dopant 1 | 4.6 | 44 | 6000 | 74 |
| Example11 | Compound 49 | Dopant 1 | 4.6 | 44 | 6000 | 76 |
| Example12 | Compound 51 | Dopant 1 | 4.2 | 47 | 6000 | 79 |
| Example13 | Compound 57 | Dopant 1 | 4.3 | 46 | 6000 | 78 |
| Example14 | Compound 105 | Dopant 1 | 4.3 | 46 | 6000 | 79 |
| Example15 | Compound 137 | Dopant 1 | 4.7 | 43 | 6000 | 72 |
| Example16 | Compound 145 | Dopant 1 | 4.3 | 46 | 6000 | 78 |
| Example17 | Compound 153 | Dopant 1 | 4.7 | 44 | 6000 | 72 |
| Example18 | Compound 155 | Dopant 1 | 4.2 | 46 | 6000 | 80 |
| Example19 | Compound 204 | Dopant 1 | 4.4 | 45 | 6000 | 69 |
| Example20 | Compound 249 | Dopant 1 | 4.3 | 47 | 6000 | 75 |
| Example21 | Compound 269 | Dopant 1 | 4.4 | 44 | 6000 | 70 |
| Example22 | Compound 297 | Dopant 1 | 4.2 | 48 | 6000 | 74 |
| Example23 | Compound 347 | Dopant 1 | 4.2 | 48 | 6000 | 75 |
| Example24 | Compound 371 | Dopant 1 | 4.3 | 46 | 6000 | 71 |
| Example25 | Compound 378 | Dopant 1 | 4.4 | 45 | 6000 | 70 |
| Comparative Example 1 | Comparative Compound A | Dopant 1 | 5.7 | 37 | 6000 | 34 |
| Comparative Example 2 | Comparative Compound B | Dopant 1 | 6.3 | 39 | 6000 | 30 |
| Comparative Example 3 | Comparative Compound C | Dopant 1 | 4.4 | 42 | 6000 | 52 |
| Comparative Example 4 | Comparative Compound D | Dopant 1 | 4.3 | 41 | 6000 | 39 |
| Comparative Example 5 | Comparative Compound E | Dopant 1 | 6.0 | 40 | 6000 | 31 |
| Comparative Example 6 | Comparative Compound F | Dopant 1 | 6.7 | 43 | 6000 | 25 |

Referring to Table 3, the organic light emitting diodes according to Examples 1 to 25 exhibited a low driving voltage, high efficiency, and/or a long life-span compared with the organic light emitting diodes according to Comparative Examples 1 to 6. Accordingly, a host used in a light emitting layer for the organic light emitting diodes according to Examples 1 to 25 had excellent charge transport characteristics as a phosphorescent host material and simultaneously, a light emitting wavelength region overlapped with an absorption spectrum of a dopant and accordingly, improved performance such as increasing efficiency and decreasing an equivalent or excellent driving voltage and thus showed maximized capability as an OLED material. Above all, a driving voltage and a life-span turned out to be superbly improved.

On the contrary, the comparative compounds used as a host in the organic light emitting diodes according to Comparative Examples 1 to 6 had extremely weak electron transport capability and thus hardly accomplished a balance between hole and electron transports or had a structure that carbon adjacent to N of pyridine, pyrimidine, and quinoxaline in a fused ring was unsubstituted, that is, a structure having CH and thus might weaken thermal stability and electric stability of a light emitting layer of an organic light emitting diode when applied thereto and accordingly, turned out to much decrease driving voltages and life-span characteristics of the organic light emitting diodes according to Comparative Examples using them as a host of a light emitting layer.

Manufacture of Organic Light Emitting Diode II

Examples 26 to 52 and Comparative Examples 7 to 10

Each organic light emitting diode was manufactured according to the same method as Example 1 except for using a first host and a second host shown in Table 4 as a host for a light emitting layer. Herein, the dopant:the first host:the second host were codeposited in a weight ratio of 10:45:45.

Evaluation Example II

Driving voltages, efficiency, luminance, and life-span of organic light emitting diodes according to Examples 26 to 51 and Comparative Examples 7 to 10 were measured using a luminance meter, PR650 Spectroscan Source Measurement Unit. (made by PhotoResearch Inc.) by supplying power from a current voltage meter (Kethley SMU 236).

The results are shown in Table 4.

TABLE 4

| Example | First host | Second host | Dopant | Driving Voltage (V) | Current Efficiency (cd/A) | Luminance ($cd/m^2$) | $T_{95}$ life-span (hr) |
|---|---|---|---|---|---|---|---|
| 26 | Compound 3 | E-31 | Dopant 1 | 4.0 | 50 | 6000 | 87 |
| 27 | Compound 34 | E-31 | Dopant 1 | 4.3 | 47 | 6000 | 89 |
| 28 | Compound 51 | E-31 | Dopant 1 | 4.0 | 49 | 6000 | 87 |
| 29 | Compound 57 | E-31 | Dopant 1 | 4.2 | 48 | 6000 | 84 |
| 30 | Compound 105 | E-31 | Dopant 1 | 4.2 | 48 | 6000 | 85 |
| 31 | Compound 145 | E-31 | Dopant 1 | 4.2 | 47 | 6000 | 85 |
| 32 | Compound 155 | E-31 | Dopant 1 | 4.0 | 49 | 6000 | 87 |
| 33 | Compound 249 | E-31 | Dopant 1 | 4.0 | 48 | 6000 | 83 |
| 34 | Compound 297 | E-31 | Dopant 1 | 3.9 | 49 | 6000 | 84 |
| 35 | Compound 347 | E-31 | Dopant 1 | 4.1 | 49 | 6000 | 82 |
| 36 | Compound 3 | E-99 | Dopant 1 | 4.0 | 50 | 6000 | 86 |
| 37 | Compound 34 | E-99 | Dopant 1 | 4.2 | 48 | 6000 | 88 |
| 38 | Compound 51 | E-99 | Dopant 1 | 3.9 | 50 | 6000 | 88 |
| 39 | Compound 57 | E-99 | Dopant 1 | 4.1 | 48 | 6000 | 86 |
| 40 | Compound 155 | E-99 | Dopant 1 | 3.9 | 50 | 6000 | 88 |
| 41 | Compound 347 | E-99 | Dopant 1 | 3.9 | 49 | 6000 | 84 |
| 42 | Compound 3 | F-43 | Dopant 1 | 3.7 | 49 | 6000 | 87 |
| 43 | Compound 34 | F-43 | Dopant 1 | 4.0 | 48 | 6000 | 87 |
| 44 | Compound 155 | F-43 | Dopant 1 | 3.9 | 49 | 6000 | 87 |
| 45 | Compound 347 | F-43 | Dopant 1 | 3.8 | 49 | 6000 | 85 |
| 46 | Compound 3 | F-99 | Dopant 1 | 3.8 | 51 | 6000 | 90 |
| 47 | Compound 34 | F-99 | Dopant 1 | 3.9 | 49 | 6000 | 88 |
| 48 | Compound 155 | F-99 | Dopant 1 | 3.8 | 50 | 6000 | 91 |
| 49 | Compound 347 | F-99 | Dopant 1 | 3.7 | 49 | 6000 | 87 |
| 50 | Compound 3 | F-73 | Dopant 1 | 4.2 | 49 | 6000 | 84 |
| 51 | Compound 155 | F-73 | Dopant 1 | 4.2 | 48 | 6000 | 84 |
| Comparative Example 7 | Comparative Compound C | E-31 | Dopant 1 | 4.3 | 44 | 6000 | 61 |
| Comparative Example 8 | Comparative Compound D | E-31 | Dopant 1 | 4.2 | 43 | 6000 | 49 |
| Comparative Example 9 | Comparative Compound C | E-99 | Dopant 1 | 4.2 | 45 | 6000 | 57 |
| Comparative Example 10 | Comparative Compound D | E-99 | Dopant 1 | 4.1 | 44 | 6000 | 47 |

Referring to Table 4, the organic light emitting diodes according to Examples 26 to 51 showed improved efficiency in equivalent or low driving voltages and an excellent long life-span compared with the organic light emitting diodes according to Comparative Examples 7 to 10.

Manufacture of Organic Light Emitting Diode III

Example 52

An organic light emitting diode was manufactured by using Compound 11 obtained in Synthesis Example 9 as a host and $(piq)_2Ir(acac)$ (Dopant 2) as a dopant.

As for an anode, 1000 Å-thick ITO was used, and as for a cathode, 1000 Å-thick aluminum was used. Specifically, illustrating a method of manufacturing the organic light emitting diode, the anode was manufactured by cutting an ITO glass substrate having 15 $\Omega/cm^2$ of a sheet resistance into a size of 50 mm×50 mm×0.7 mm, ultrasonic wave-cleaning them in each acetone, isopropyl alcohol, and pure water for 15 minutes respectively, and UV ozone cleaning them for 30 minutes.

On the substrate, an 800 Å-thick hole transport layer was formed by depositing N4,N4'-di(naphthalene-1-yl)-N4,N4'-diphenylbiphenyl-4,4'-diamine (NPB) (80 nm) under a vacuum degree of $650\times10^{-7}$ Pa at a deposition rate of 0.1 to 0.3 nm/s. Subsequently, a 300 Å-thick light emitting layer was formed by using Compound 11 of Synthesis Example 9 under the same vacuum deposition condition, and a phosphorescent dopant of $(piq)_2Ir(acac)$ (Dopant 2) was simultaneously deposited. Herein, the phosphorescent dopant was deposited to be 3 wt % based on 100 wt % of a total weight of the light emitting layer by adjusting the deposition rate.

On the light emitting layer, a 50 Å-thick hole blocking layer was formed by depositing bis(2-methyl-8-quinolinolate)-4-(phenylphenolato)aluminium (BAlq) under the same vacuum deposition condition. Subsequently, a 200 Å-thick electron transport layer was formed by depositing Alq3 under the same vacuum deposition condition. On the electron transport layer, a cathode was formed by sequentially depositing LiF and Al to manufacture an organic light emitting diode.

A structure of the organic light emitting diode was ITO/NPB (80 nm)/EML (Compound 11 (97 wt %)+$(piq)_2Ir(acac)$ (3 wt %), 30 nm)/Balq (5 nm)/Alq3 20 nm/LiF (1 nm)/Al (100 nm).

Examples 53 to 57

Each organic light emitting diode was manufactured according to the same method as Example 52 except for respectively using Compounds 16, 45, 110, 204, and 304 instead of Compound 11 as a host for a light emitting layer.

Comparative Examples 11 and 12

Each organic light emitting diode was manufactured according to the same method as Example 52 except for respectively using Comparative Compounds G and C instead of Compound 11 as a host for a light emitting layer.

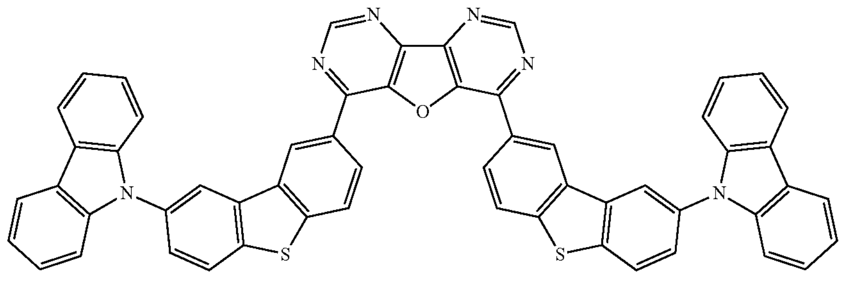

G

Evaluation Example III

Luminous efficiency and life-span characteristics of the organic light emitting diodes according to Examples 52 to 57 and Comparative Examples 11 and 12 were evaluated.

Specific measurement methods are as follows, and the results are shown in Table 5.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 $mA/cm^2$) were calculated by using the luminance, current density, and voltages (V) from the items (1) and (2).

(4) Measurement of Life-Span

The results were obtained by measuring a time when current efficiency (cd/A) was decreased down to 90%, while luminance ($cd/m^2$) was maintained to be 5000 $cd/m^2$.

(5) Roll-Off

An efficiency drop was calculated according to (Max measurement—measurement as 5000 $cd/m^2$/Max measurement) from the characteristic measurements of the (3).

TABLE 5

| | First host | Driving voltage (V) | Photo-luminescence efficiency (cd/A) | Roll-off (%) | Life-spanT90 (h) |
|---|---|---|---|---|---|
| Example 52 | Compound 11 | 4.37 | 15.4 | 14.0 | 140 |
| Example 53 | Compound 16 | 4.30 | 15.6 | 13.8 | 143 |
| Example 54 | Compound 45 | 4.29 | 15.8 | 14.1 | 140 |
| Example 55 | Compound 110 | 4.41 | 14.8 | 14.9 | 136 |
| Example 56 | Compound 204 | 4.45 | 15.0 | 14.4 | 132 |
| Example 57 | Compound 304 | 4.38 | 16.0 | 14.6 | 135 |
| Comparative Example 11 | Comparative Compound G | 5.71 | 12.4 | 12.0 | 73 |
| Comparative Example 12 | Comparative Compound C | 4.61 | 13.9 | 10.5 | 110 |

Referring to Table 5, the organic light emitting diodes according to Examples 52 to 57 showed equivalent or low driving voltages, high efficiency, and a long life-span compared with the organic light emitting diodes according to Comparative Examples 11 and 12.

Accordingly, a host used in a light emitting layer for the organic light emitting diodes according to Examples 52 to 57 as a phosphorescent host material had excellent charge transport characteristics and simultaneously, a light emitting wavelength region overlapped with an absorption spectrum of a dopant and accordingly, turned out to improve performance such as increasing efficiency and decreasing a driving voltage and particularly, a long life-span and thus have maximized capability as an OLED material.

Manufacture of Organic Light Emitting Diode IV

Examples 58 to 73 and Comparative Examples 13 to 16

An organic light emitting diode was manufactured according to the same method as Example 52 except for using the first and second hosts shown in Table 7 as a host for a light emitting layer. Herein, the dopant:the first host:the second host were codeposited in a weight ratio of 3:48.5:48.5.

Evaluation Example IV

Driving voltages, efficiency, luminance, and life-span of organic light emitting diodes according to Examples 58 to 72 and Comparative Examples 13 to 16 were measured using a luminance meter, PR650 Spectroscan Source Measurement Unit. (made by PhotoResearch Inc.) by supplying power from a current voltage meter (Kethley SMU 236).

The results are shown in Table 6.

TABLE 6

| | First host | Second host | Driving Voltage (V) | Photoluminescence efficiency (cd/A) | Roll-off (%) | Life-spanT 90 (h) |
|---|---|---|---|---|---|---|
| Example 58 | Compound 11 | E-31 | 4.26 | 17.8 | 10.4 | 166 |
| Example 59 | Compound 11 | E-99 | 4.23 | 18.2 | 10.2 | 162 |
| Example 60 | Compound 11 | F-104 | 3.95 | 19.3 | 10.0 | 185 |
| Example 61 | Compound 11 | F-106 | 3.89 | 19.5 | 10.1 | 187 |
| Example 62 | Compound 11 | F-107 | 3.99 | 18.9 | 10.0 | 179 |
| Example 63 | Compound 11 | F-110 | 4.03 | 18.7 | 10.2 | 175 |
| Example 64 | Compound 16 | F-104 | 3.93 | 19.6 | 10.3 | 189 |
| Example 65 | Compound 45 | F-104 | 3.85 | 19.8 | 10.1 | 190 |
| Example 66 | Compound 110 | F-104 | 3.97 | 18.9 | 10.2 | 182 |
| Example 67 | Compound 204 | F-104 | 3.99 | 18.8 | 10.0 | 180 |
| Example 68 | Compound 304 | F-104 | 3.85 | 19.5 | 10.4 | 180 |
| Example 69 | Compound 16 | F-106 | 3.91 | 19.7 | 10.0 | 191 |
| Example 70 | Compound 45 | F-106 | 3.84 | 19.8 | 10.0 | 194 |
| Example 71 | Compound 110 | F-106 | 3.94 | 19.2 | 9.9 | 186 |
| Example 72 | Compound 204 | F-106 | 3.96 | 19.1 | 10.1 | 185 |
| Example 73 | Compound 304 | F-106 | 3.83 | 19.7 | 10.6 | 183 |
| Comparative Example 13 | Comparative Compound G | F-104 | 4.51 | 16.7 | 12.0 | 105 |
| Comparative Example 14 | Comparative Compound C | F-104 | 4.21 | 17.6 | 10.5 | 139 |
| Comparative Example 15 | Comparative Compound G | F-106 | 4.46 | 17.2 | 11.2 | 120 |
| Comparative Example 16 | Comparative Compound C | F-106 | 4.16 | 17.8 | 10.2 | 145 |

Referring to Table 6, each organic light emitting diode according to Examples 58 to 73 showed equivalent or low driving voltages, equivalent or high efficiency, and a long life-span compared with the organic light emitting diodes according to Comparative Examples 13 to 16.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

What is claimed is:

1. A composition, comprising:

a first organic compound, the first organic compound being represented by Chemical Formula 1, and a second organic compound having a carbazole moiety represented by Chemical Formula 4,

[Chemical Formula 1]

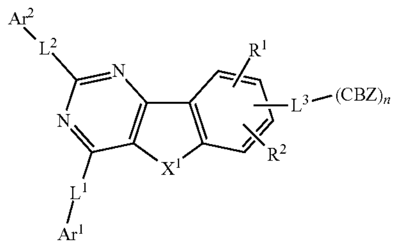

wherein, in Chemical Formula 1, $X^1$ is O or S, $Ar^1$ and $Ar^2$ are independently a substituted or unsubstituted C1 to C20 alkyl group, a substituted or unsubstituted C6 to C30 aryl group, a substituted or unsubstituted carbazolyl group, or a combination thereof, $L^1$ and $L^2$ are independently a single bond, a substituted or unsubstituted C1 to C20 alkylene group, a substituted or unsubstituted C6 to C30 arylene group, or a combination thereof, $L^3$ is a substituted or unsubstituted C1 to C20 alkylene group, a substituted or unsubstituted C6 to C30 arylene group, or a combination thereof, $R^1$ and $R^2$ are independently hydrogen, deuterium, a substituted or unsubstituted C1 to C20 alkyl group, a substituted or unsubstituted C6 to C30 aryl group, a substituted or unsubstituted C3 to C30 heterocyclic group, a cyano group, or a combination thereof, CBZ is a substituted or unsubstituted carbazolyl group that is not a carbazolyl group substituted with a carbazolyl group, and n is an integer of 1 to 3,

[Chemical Formula 4]

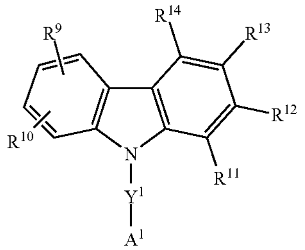

wherein, in Chemical Formula 4, $Y^1$ is a single bond, a substituted or unsubstituted C6 to C30 arylene group or divalent substituted or unsubstituted C2 to C30 heterocyclic group, $A^1$ is a substituted or unsubstituted C6 to C30 aryl group, or a substituted or unsubstituted C2 to C30 heterocyclic group, $R^9$ to $R^{14}$ are independently hydrogen, deuterium, a substituted or unsubstituted C1 to C20 alkyl group, a substituted or unsubstituted C6 to C30 aryl group, or a substituted or unsubstituted C2 to C30 heterocyclic group, and $R^{11}$ to $R^{14}$ are independently present or adjacent groups of $R^{11}$ to $R^{14}$ are linked with each other to form a ring.

2. The composition of claim 1, wherein the second organic compound is represented by Chemical Formula 4A or a combination of Chemical Formulae 4B-1 and 4B-2:

[Chemical Formula 4A]

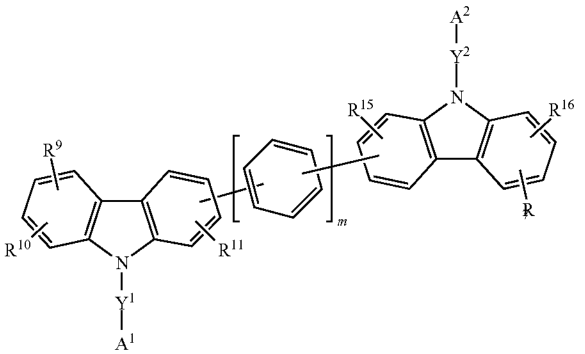

[Chemical Formula 4B-1]

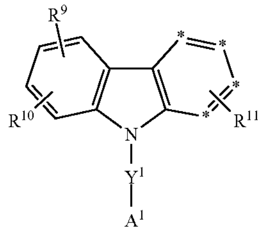

[Chemical Formula 4B-2]

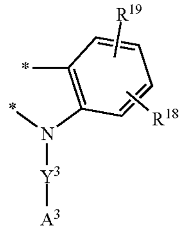

wherein, in Chemical Formula 4A, Chemical Formula 4B-1, Chemical Formula 4B-2, $Y^1$ to $Y^3$ are independently a single bond, a substituted or unsubstituted C6 to C30 arylene group, or a divalent substituted or unsubstituted C2 to C30 heterocyclic group, $A^1$ to $A^3$ are independently a substituted or unsubstituted C6 to C30 aryl group or a substituted or unsubstituted C2 to C30 heterocyclic group, adjacent two *'s of Chemical Formula 4B-1 are bonded with two *'s of Chemical Formula 4B-2, the remaining two *'s of Chemical Formula 4B-1 are independently $CR^{11}$, wherein $R^{11}$ is the same or different, $R^9$ to $R^{11}$ and $R^{15}$ to $R^{19}$ are independently hydrogen, deuterium, a substituted or unsubstituted C1 to C20 alkyl group, a substituted or unsubstituted C6 to C30 aryl group, or a substituted or unsubstituted C2 to C30 heterocyclic group, and m is an integer of 0 to 2.

3. The composition of claim 2, wherein $A^1$ of Chemical Formula 4A, $A^1$ of the combination of Chemical Formula 4B-1 and Chemical Formula 4B-2, $A^2$ of Chemical Formula 4A, and $A^3$ of the combination of Chemical Formulae 4B-1 and 4B-2 are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted pyridinyl group, a substituted or unsubstituted dibenzothiophenyl group, a substituted or unsubstituted dibenzofuranyl group, a substituted or unsubstituted carbazolyl group, or a substituted or unsubstituted fluorenyl group.

4. The composition of claim 2, wherein the second organic compound is represented by Chemical Formula 4A-1 or 4B-c:

[Chemical Formula 4A-1]

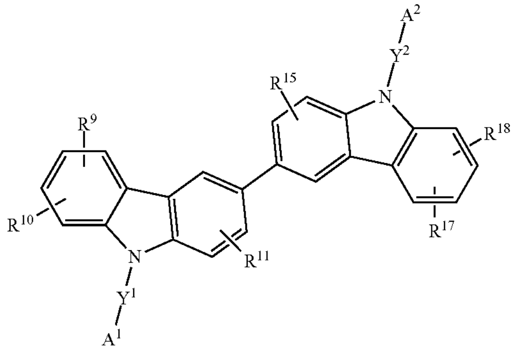

[Chemical Formula 4B-c]

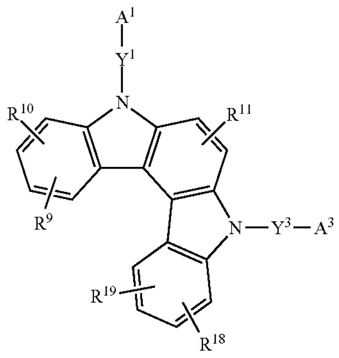

wherein, in Chemical Formula 4A-1 and Chemical Formula 4B-c, $Y^1$ to $Y^3$ are independently a single bond, a substituted or unsubstituted C6 to C30 arylene group, or a divalent substituted or unsubstituted C2 to C30 heterocyclic group, $A^1$ to $A^3$ are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted pyridinyl group, a substituted or unsubstituted dibenzothiophenyl group, a substituted or unsubstituted dibenzofuranyl group, a substituted or unsubstituted carbazolyl group, or a substituted or unsubstituted fluorenyl group, and $R^9$ to $R^{11}$ and $R^{15}$ to $R^{19}$ are independently hydrogen, deuterium, a substituted or unsubstituted C1 to C20 alkyl group, a substituted or unsubstituted C6 to C30 aryl group, or a substituted or unsubstituted C2 to C30 heterocyclic group.

5. The composition of claim 1, wherein the first organic compound is represented by Chemical Formula 2 or 3:

[Chemical Formula 2]

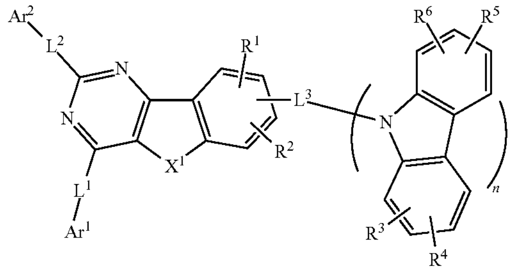

[Chemical Formula 3]

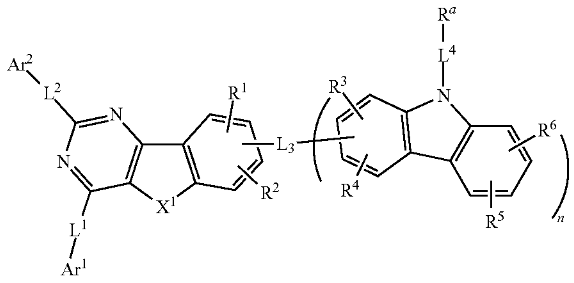

wherein, in Chemical Formula 2 or 3, $X^1$ is O or S, $Ar^1$ and $Ar^2$ are independently a substituted or unsubstituted C1 to C20 alkyl group, a substituted or unsubstituted C6 to C30 aryl group, a substituted or unsubstituted carbazolyl group, or a combination thereof, $L^1$ and $L^2$ are independently a single bond, a substituted or unsubstituted C1 to C20 alkylene group, a substituted C6 to C30 arylene group, or a combination thereof, $L^3$ is a substituted or unsubstituted C1 to C20 alkylene group, a substituted or unsubstituted C6 to C30 arylene group, or a combination thereof, $L^4$ is a single bond, a substituted or unsubstituted C1 to C20 alkylene group, a substituted or unsubstituted C6 to C30 arylene group, divalent substituted or unsubstituted C2 to C30 heterocyclic group that is not a carbazolylene group, or a combination thereof, $R^1$ to $R^6$ and $R^a$ are independently hydrogen, deuterium, a substituted or unsubstituted C1 to C20 alkyl group, a substituted or unsubstituted C6 to C30 aryl group, a substituted or unsubstituted C3 to C30 heterocyclic group that is not a carbazolyl group, a cyano group, or a combination thereof, and n is an integer of 1 to 3.

6. The composition of claim 5, wherein the first organic compound represented by Chemical Formula 2 is represented by one of Chemical Formulae 2a to 2d:

[Chemical Formula 2a]

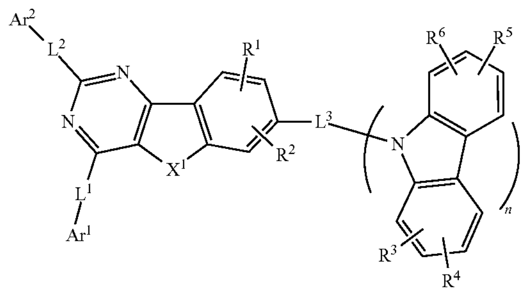

[Chemical Formula 2b]

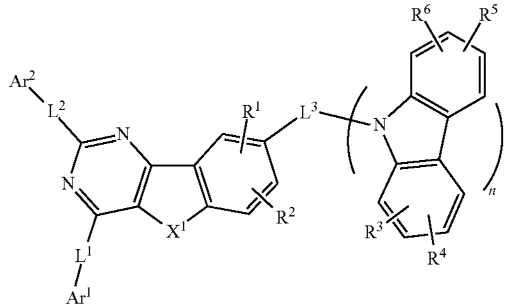

[Chemical Formula 2c]

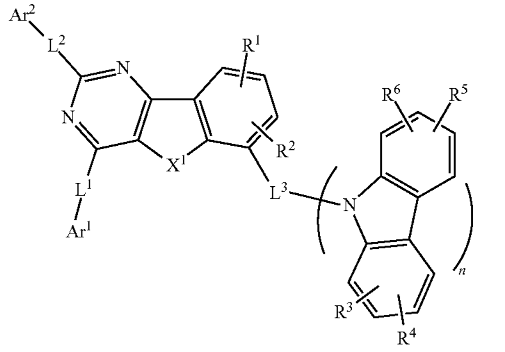

[Chemical Formula 2d]

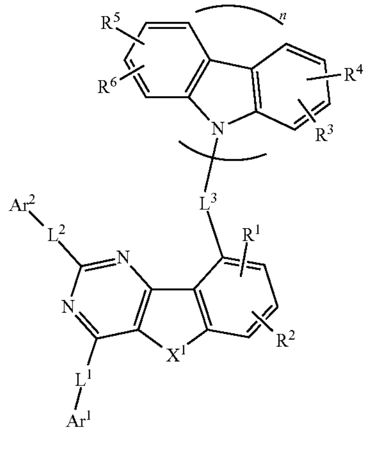

wherein, in Chemical Formulae 2a to 2d, $X^1$ is O or S, $Ar^1$ and $Ar^2$ are independently a substituted or unsubstituted C1 to C20 alkyl group, a substituted or unsubstituted C6 to C30 aryl group, a substituted or unsubstituted carbazolyl group, or a combination thereof, $L^1$ and $L^2$ are independently a single bond, a substituted or unsubstituted C1 to C20 alkylene group, a substituted or unsubstituted C6 to C30 arylene group, or a combination thereof, $L^3$ is a substituted or unsubstituted C1 to C20 alkylene group, a substituted or unsubstituted C6 to C30 arylene group, or a combination thereof, $R^1$ to $R^6$ are independently hydrogen, deuterium, a substituted or unsubstituted C1 to C20 alkyl group, a substituted or unsubstituted C6 to C30 aryl group, a substituted or unsubstituted C3 to C30 heterocyclic group that is not a carbazolyl group, a cyano group, or a combination thereof, and n is an integer of 1 to 3.

7. The composition of claim 5, wherein the first organic compound represented by Chemical Formula 3 is represented by one of Chemical Formulae 3a to 3d:

[Chemical Formula 3a]

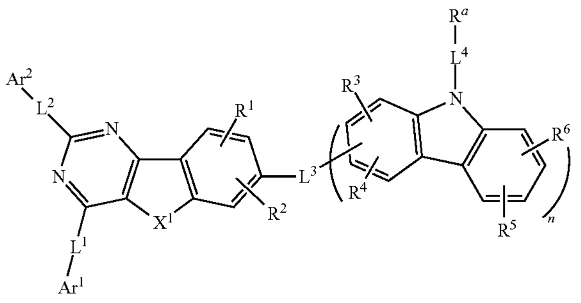

[Chemical Formula 3b]

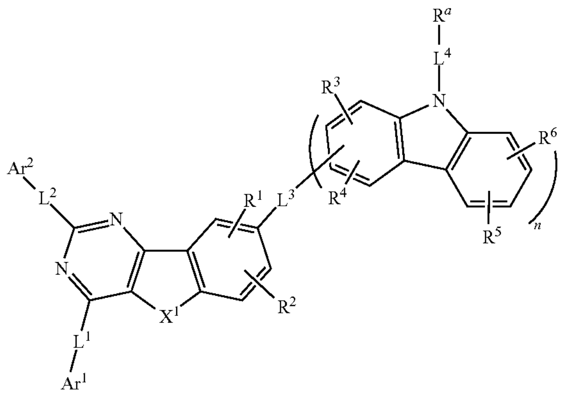

[Chemical Formula 3c]

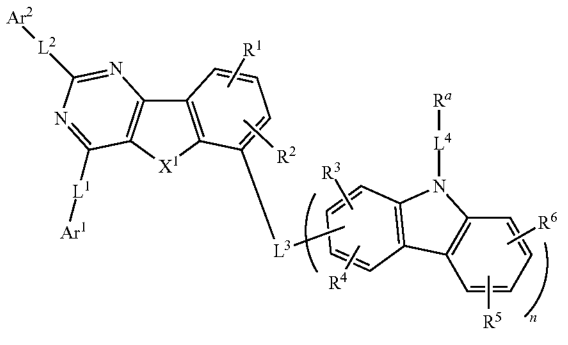

-continued

[Chemical Formula 3d]

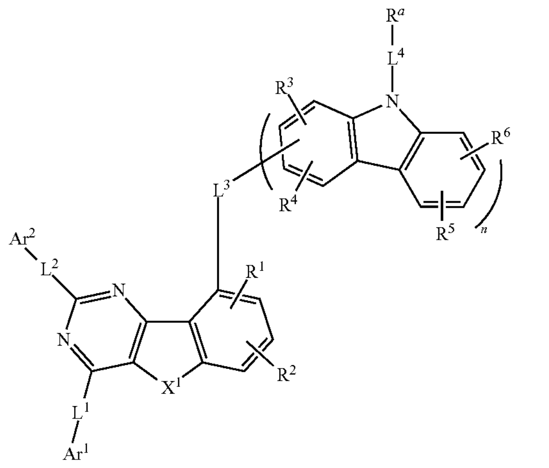

wherein, in Chemical Formulae 3a to 3d, $X^1$ is O or S, $Ar^1$ and $Ar^2$ are independently a substituted or unsubstituted C1 to C20 alkyl group, a substituted or unsubstituted C6 to C30 aryl group, a substituted or unsubstituted carbazolyl group, or a combination thereof, $L^1$ and $L^2$ are independently a single bond, a substituted or unsubstituted C1 to C20 alkylene group, a substituted or unsubstituted C6 to C30 arylene group, or a combination thereof, $L^3$ is a substituted or unsubstituted C1 to C20 alkylene group, a substituted or unsubstituted C6 to C30 arylene group, or a combination thereof, $L^4$ is a single bond, a substituted or unsubstituted C1 to C20 alkylene group, a substituted or unsubstituted C6 to C30 arylene group, a divalent substituted or unsubstituted C2 to C30 heterocyclic group that is not a carbazolylene group, or a combination thereof, $R^1$ to $R^6$ and $R^a$ are independently hydrogen, deuterium, a substituted or unsubstituted C1 to C20 alkyl group, a substituted or unsubstituted C6 to C30 aryl group, a substituted or unsubstituted C3 to C30 heterocyclic group that is not a carbazolyl group, a cyano group, or a combination thereof, and n is an integer of 1 to 3.

8. The composition of claim 1, wherein $Ar^1$ and $Ar^2$ are independently a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, a substituted or unsubstituted anthracenyl group or a substituted or unsubstituted triphenylenyl group, wherein the "substituted" refers to replacement of at least one hydrogen by deuterium, a C1 to C20 alkyl group, a C6 to C12 aryl group, or a cyano group.

9. The composition of claim 5, wherein $R^1$ to $R^6$ and $R^a$ are independently hydrogen, deuterium, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted fluorenyl group, a substituted or unsubstituted triphenylene group, a substituted or unsubstituted dibenzothiophenyl group, a substituted or unsubstituted dibenzofuranyl group, or a combination thereof.
10. The composition of claim 1, wherein the first organic compound is one of compounds listed in Group 1:
[Group 1]
1
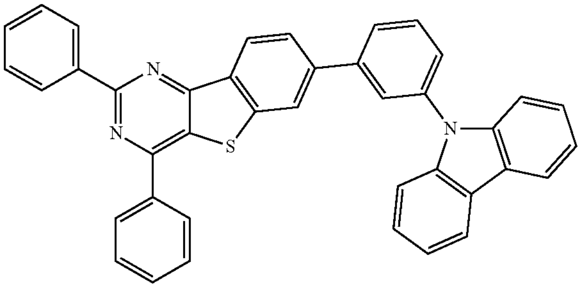
2
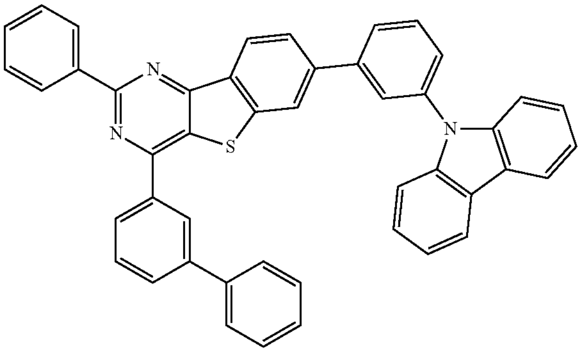
3
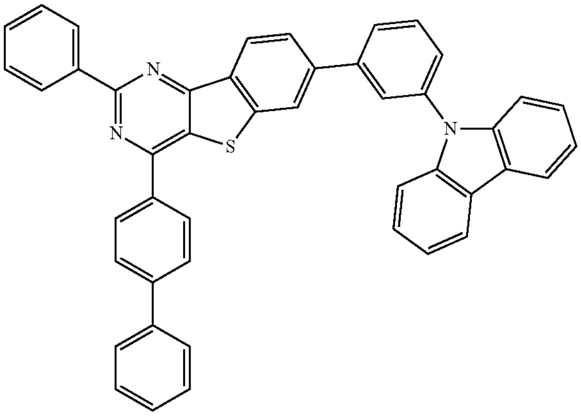
4
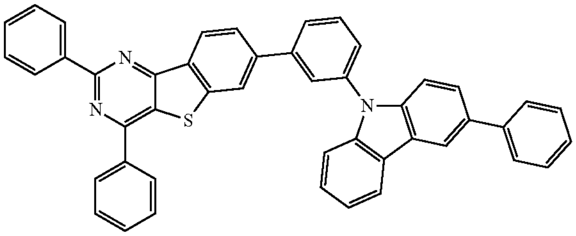
-continued
5
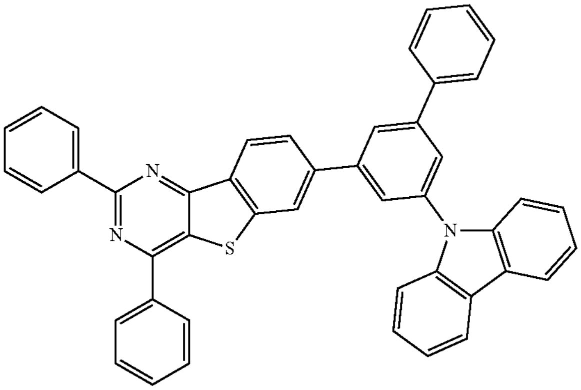
6
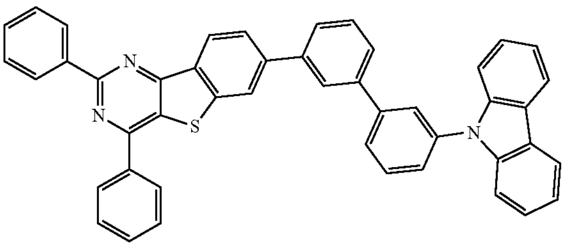
7
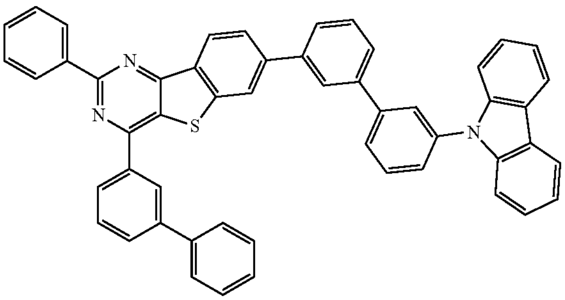
8
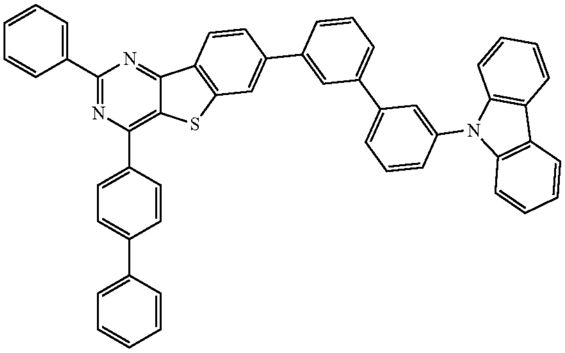

-continued
9
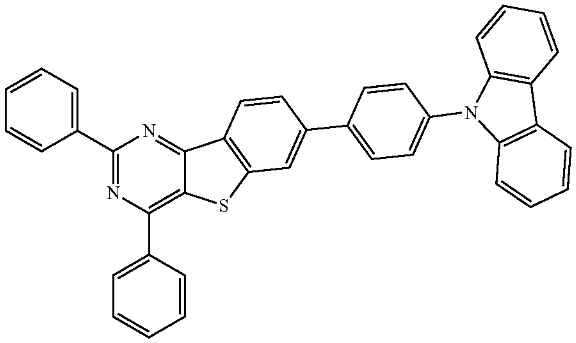
10
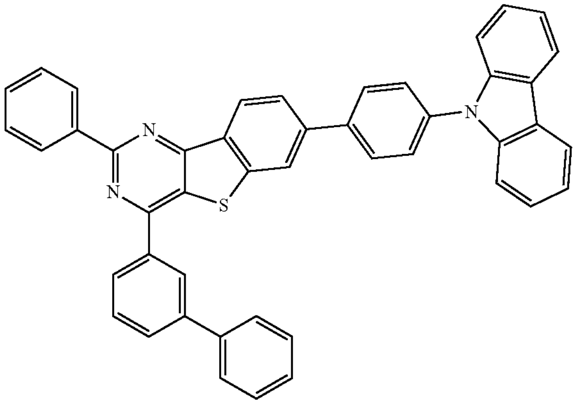
11
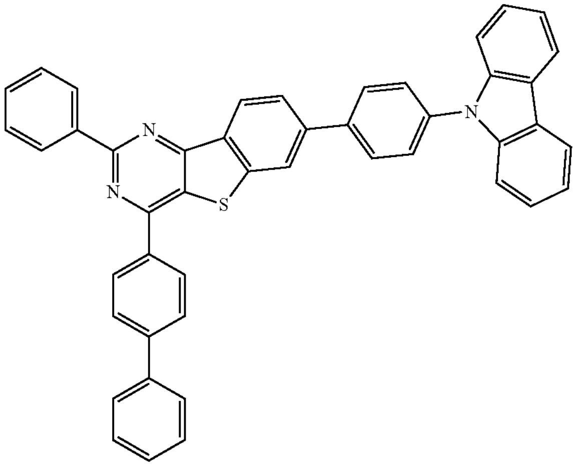
12
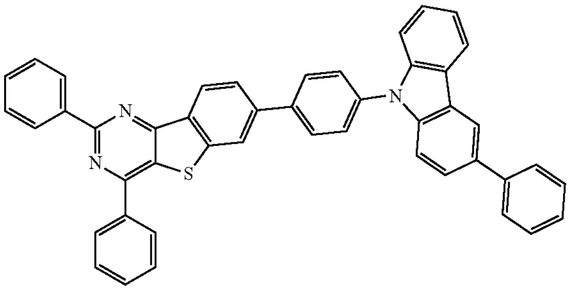
-continued
13
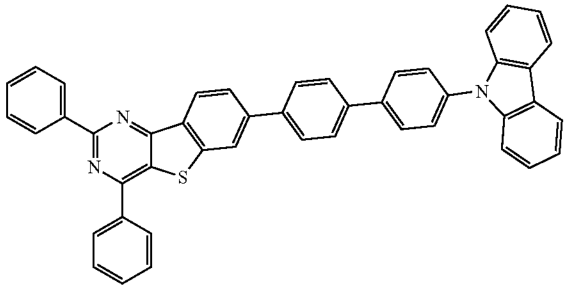
14
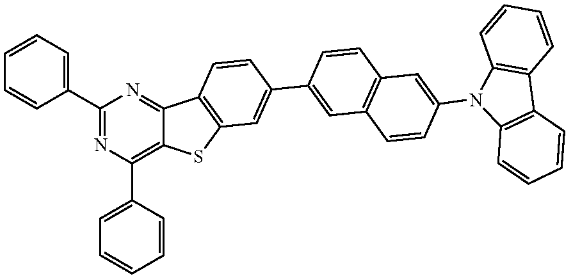
15
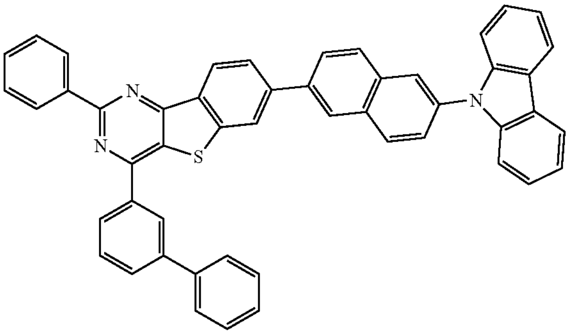
16
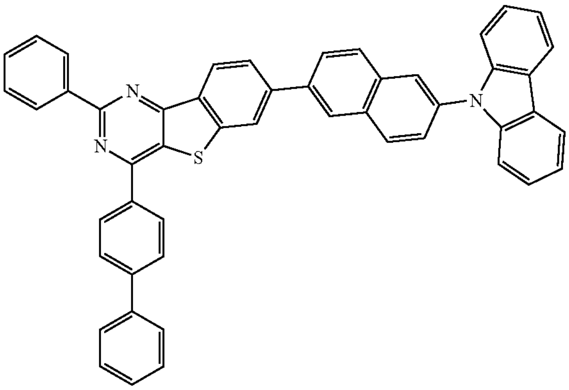

-continued
17
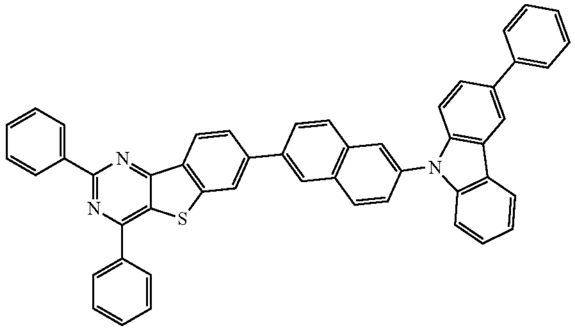
18
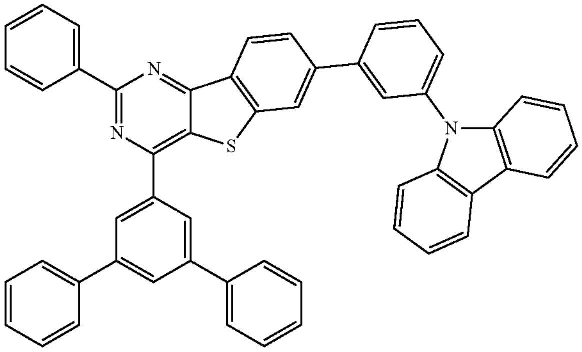
19
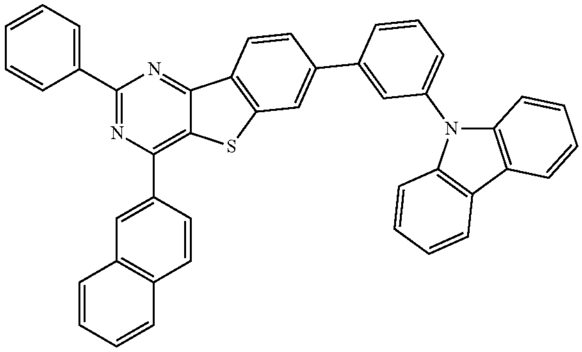
20
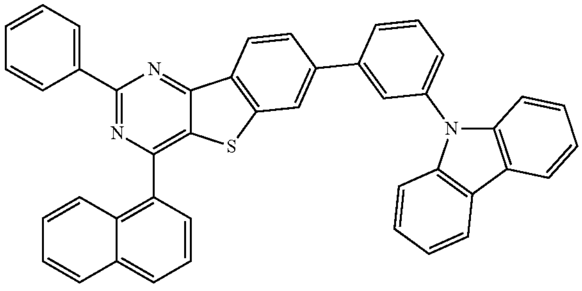
-continued
21
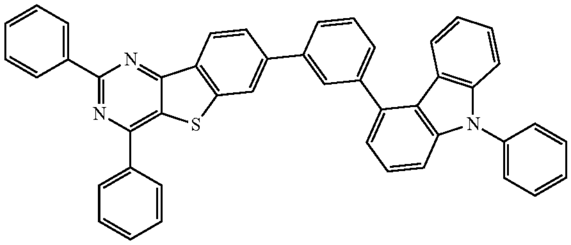
22
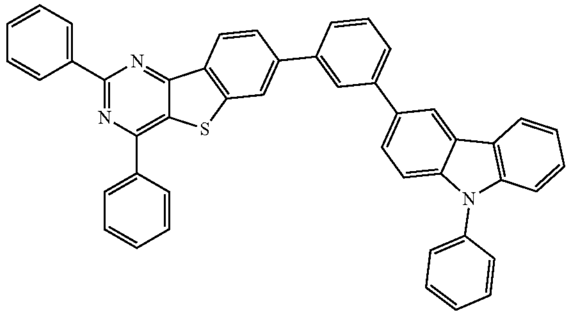
23
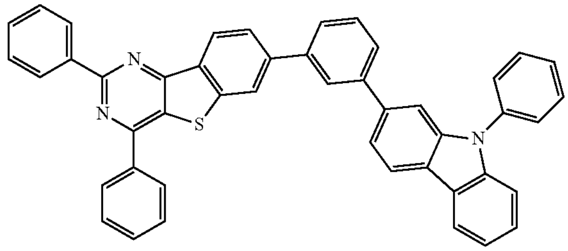
24
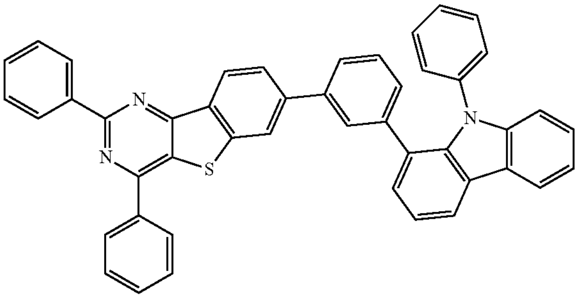
25
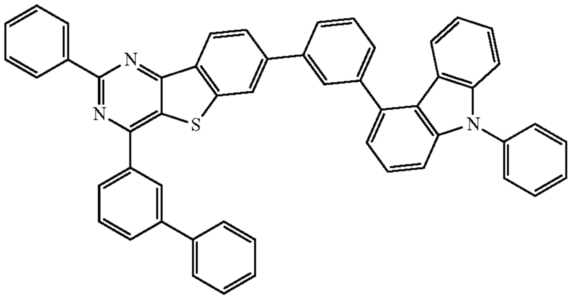

-continued
26
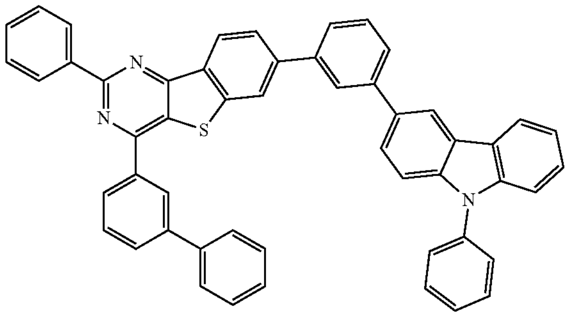
27
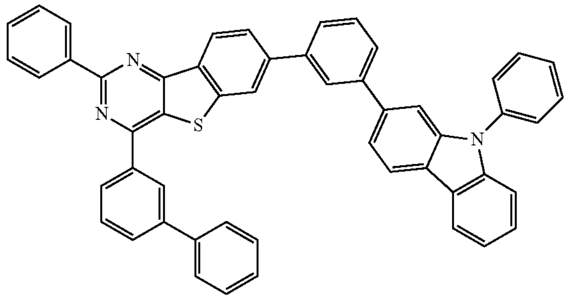
28
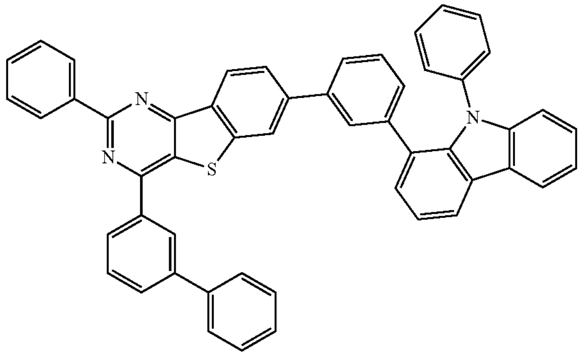
29
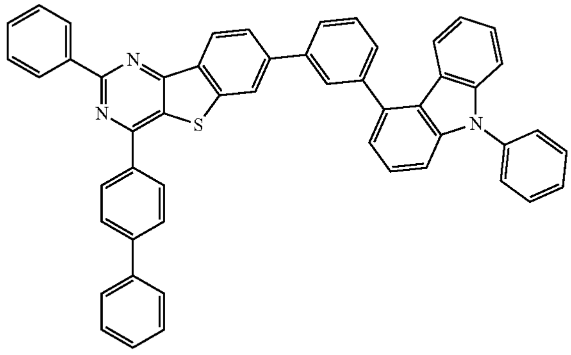
-continued
30
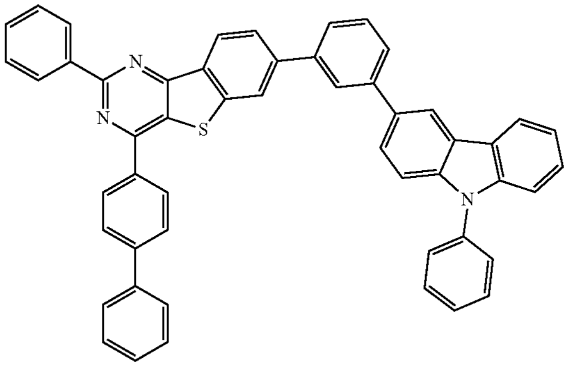
31
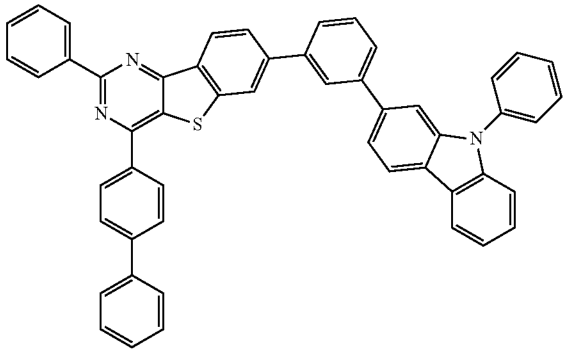
32
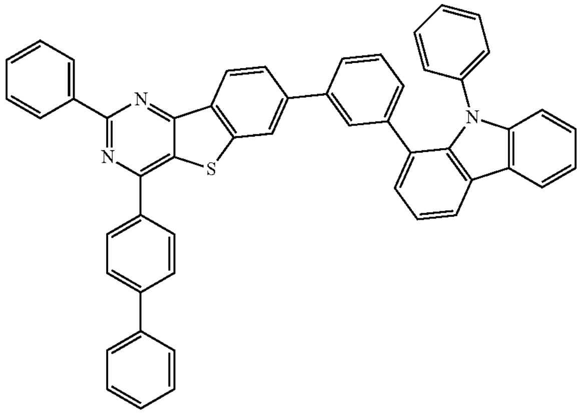
33
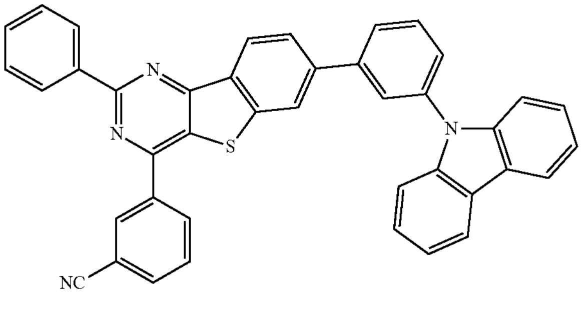

-continued
34
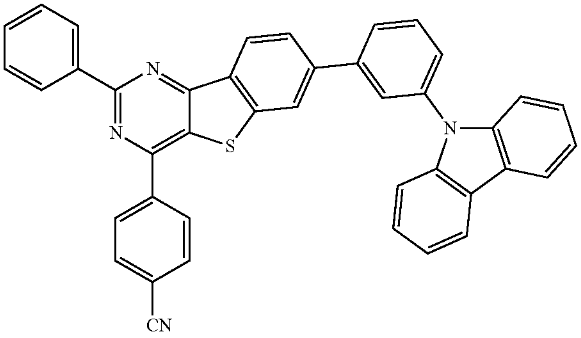
35
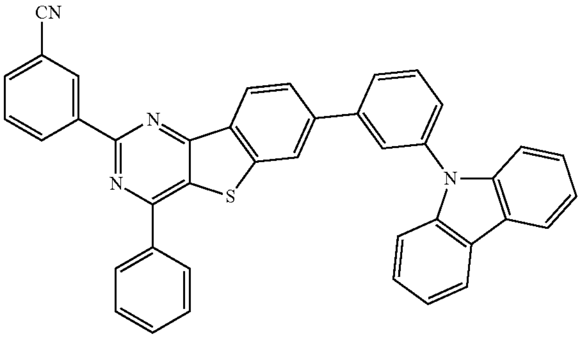
36
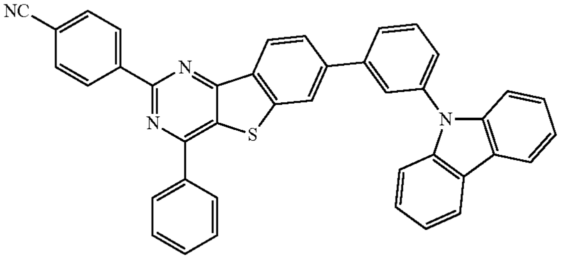
37
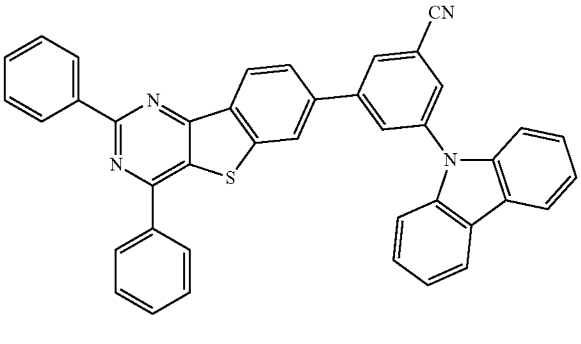
-continued
38
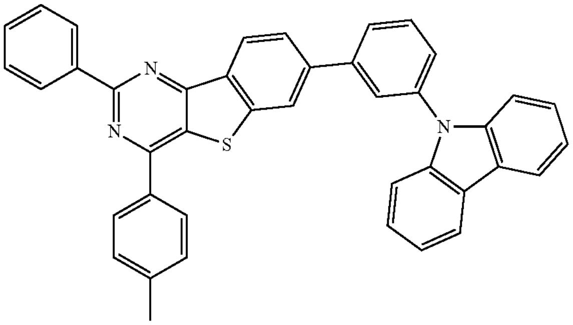
39
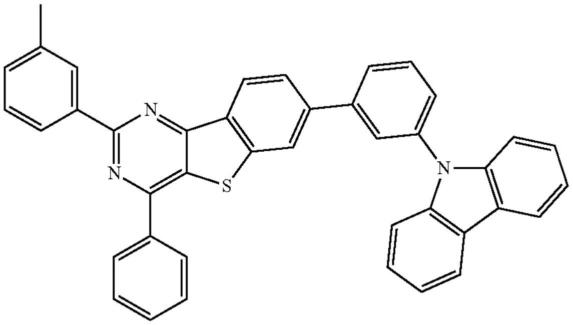
40
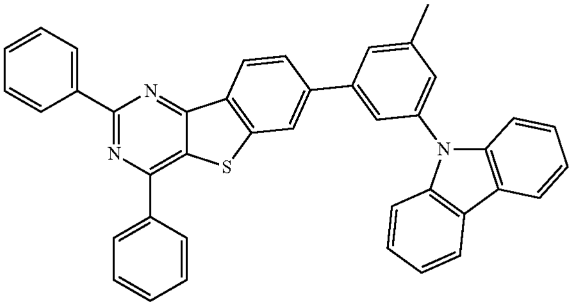
41
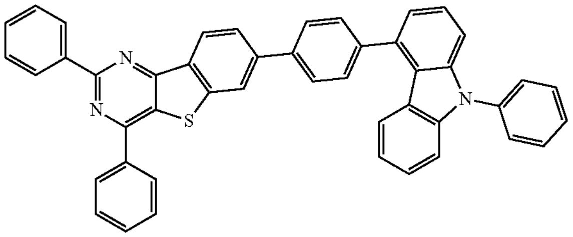
42
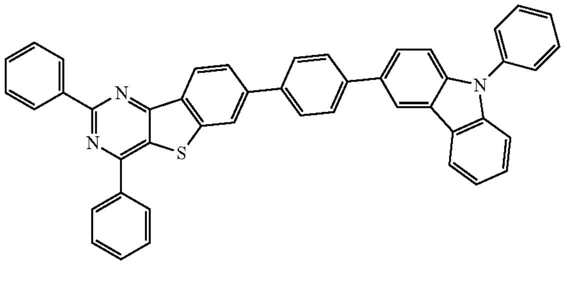

-continued
43
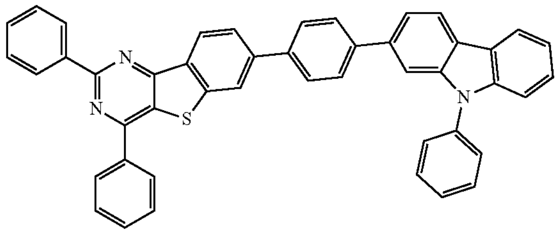
44
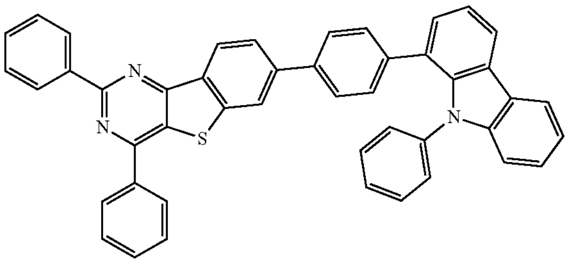
45
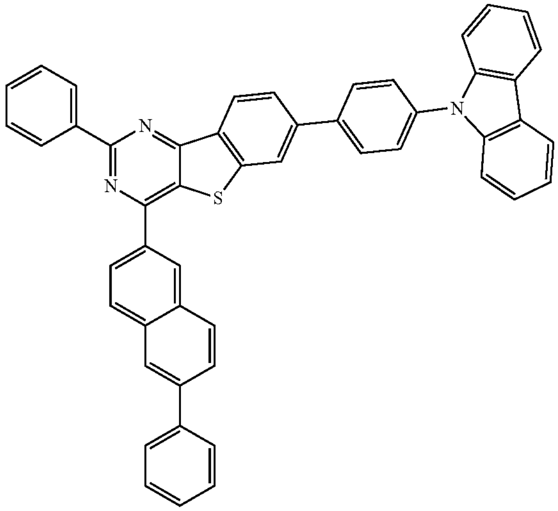
46
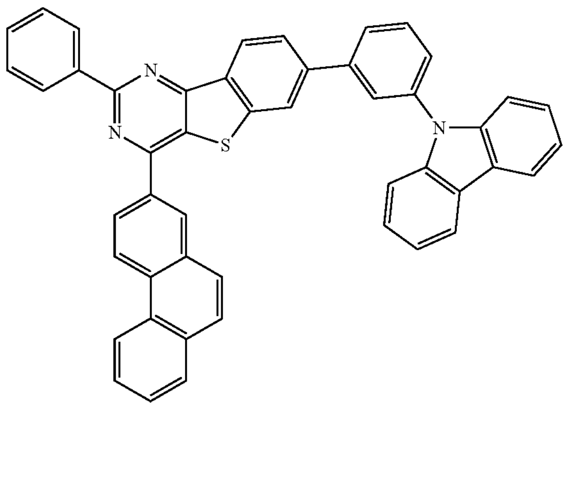
-continued
47
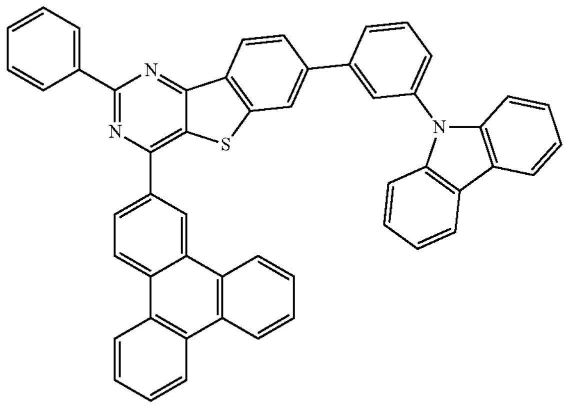
48
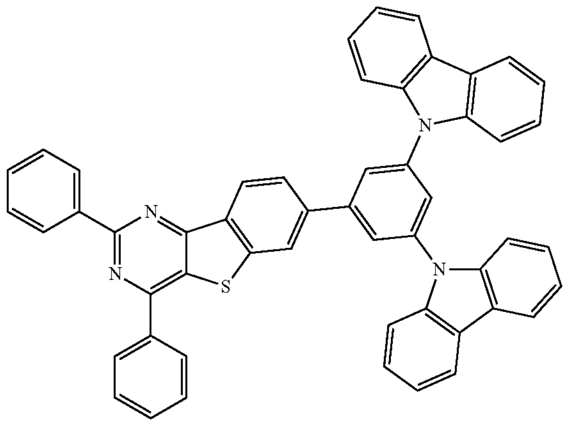
49
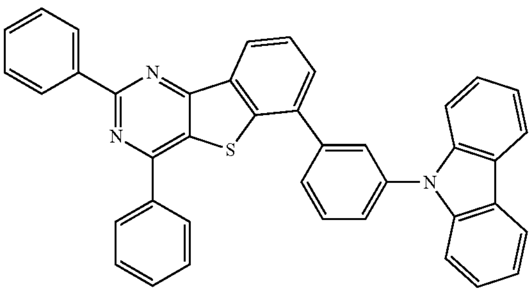
50
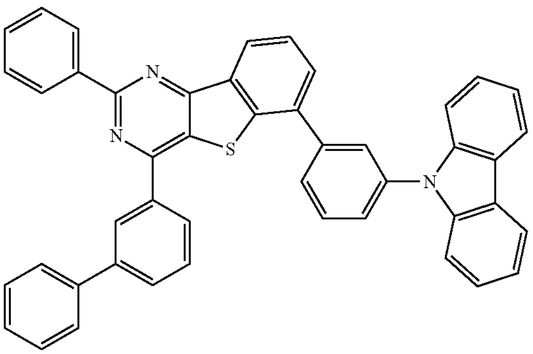

-continued
51
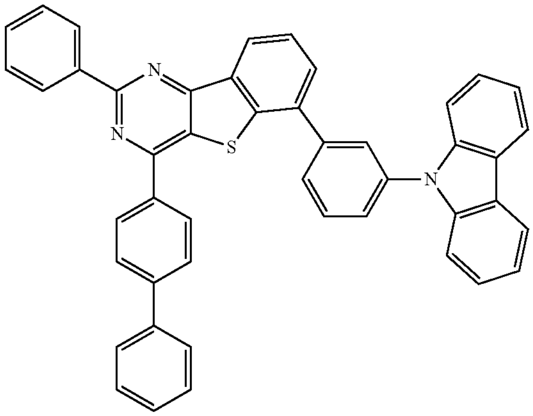
52
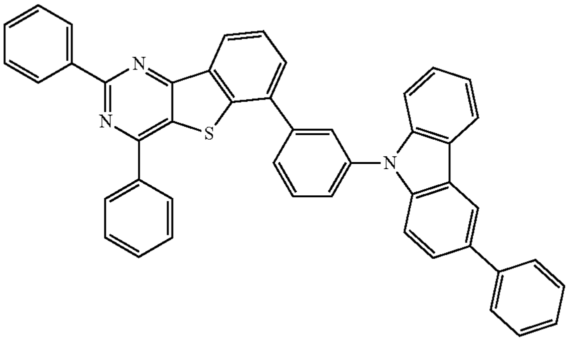
53
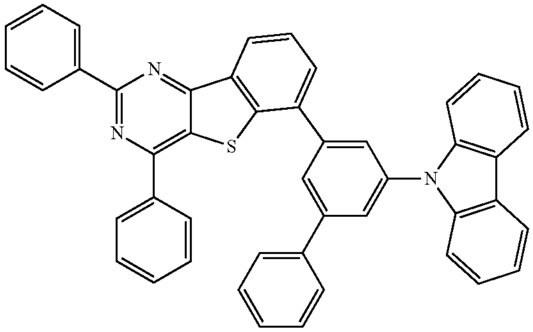
54
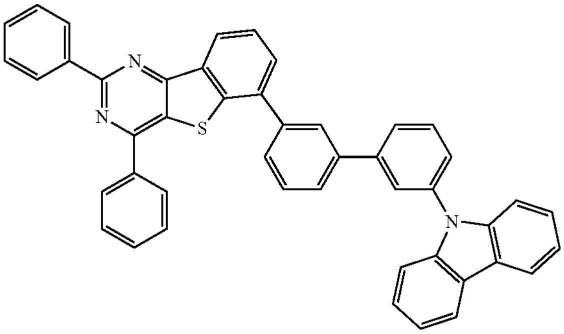
-continued
55
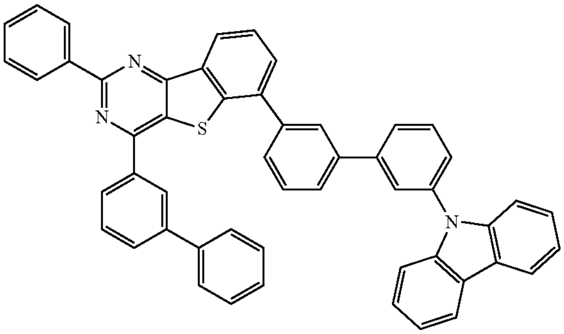
56
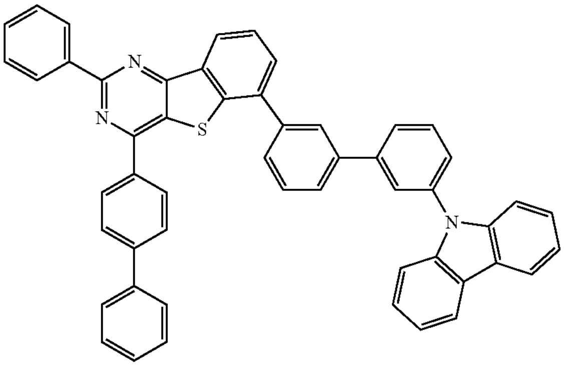
57
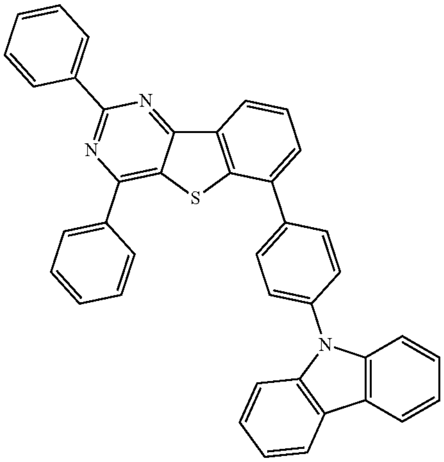

-continued
58
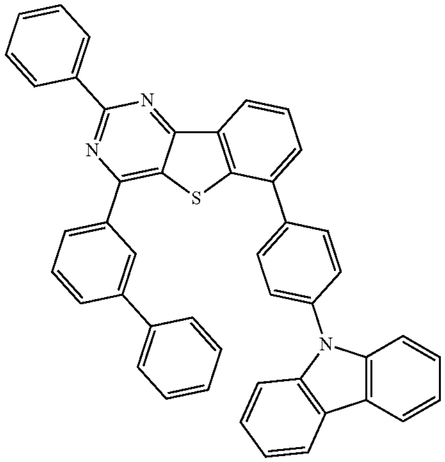
59
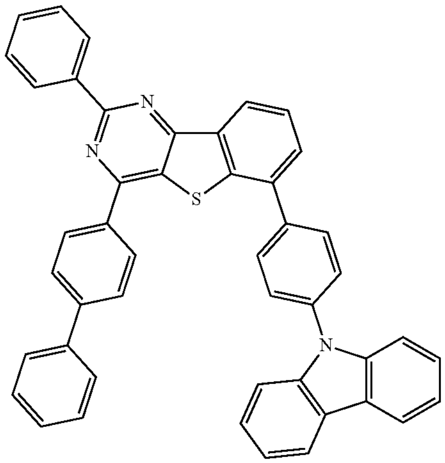
60
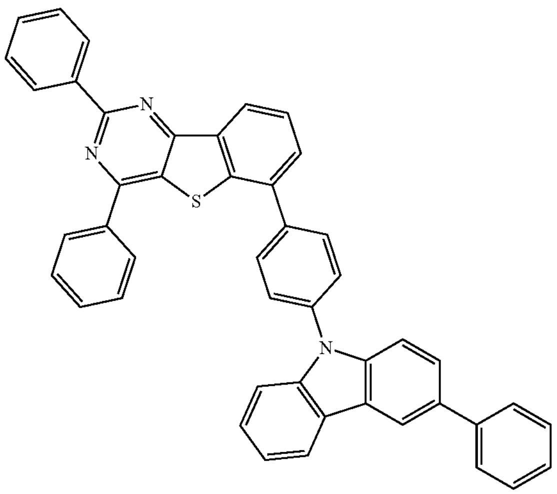
-continued
61
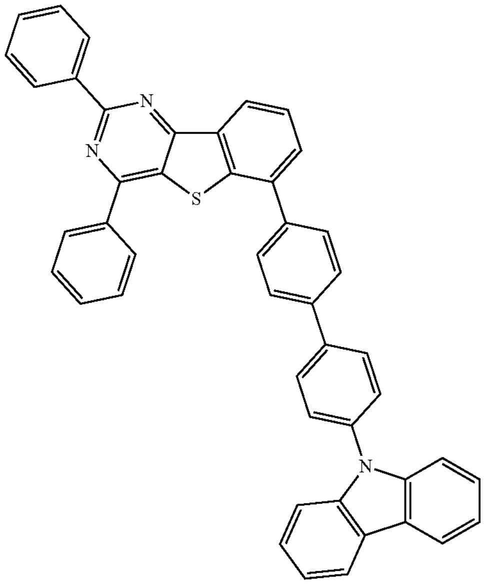
62
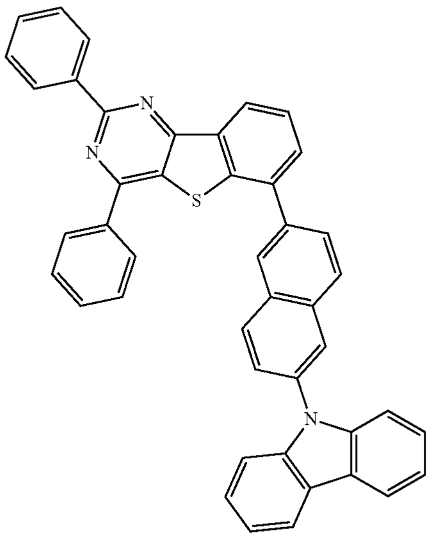
63
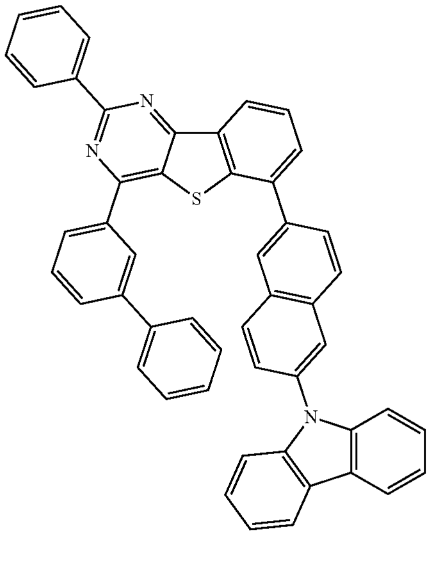

-continued
64
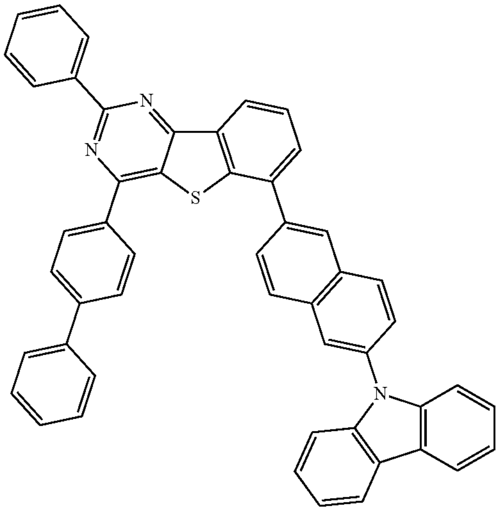
65
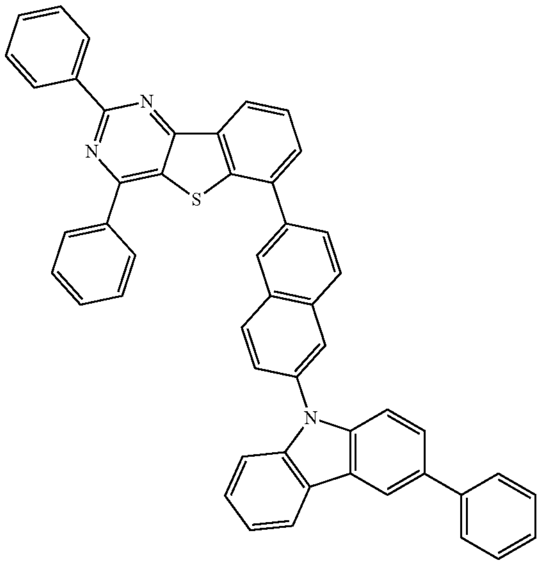
66
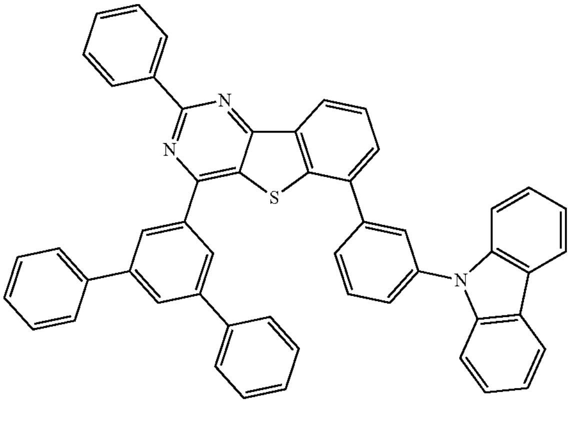
-continued
67
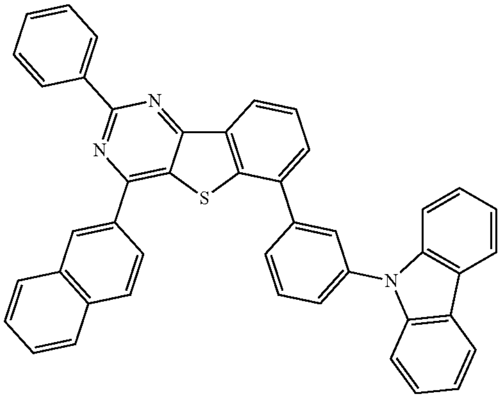
68
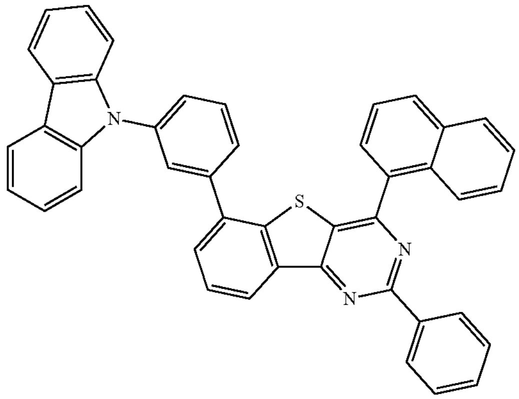
69
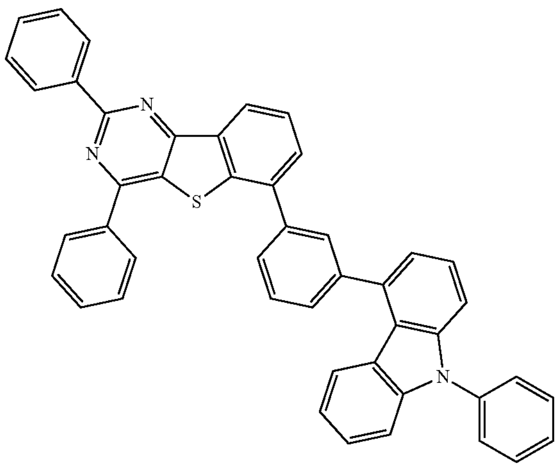

-continued
70
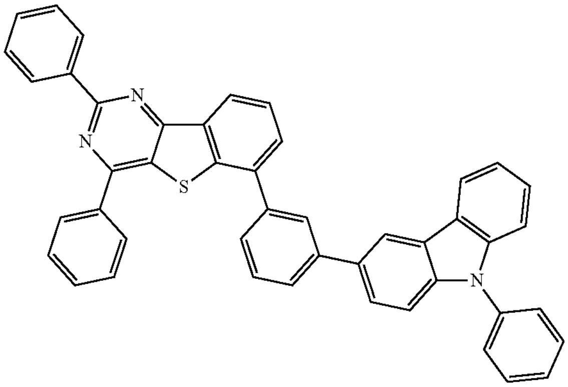
71
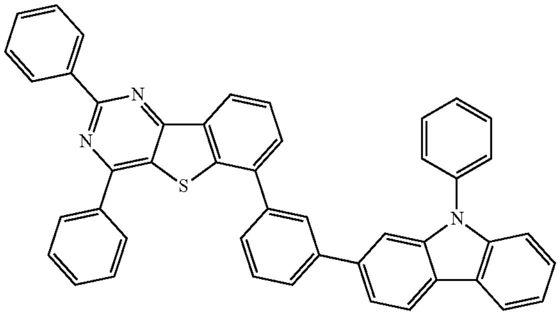
72
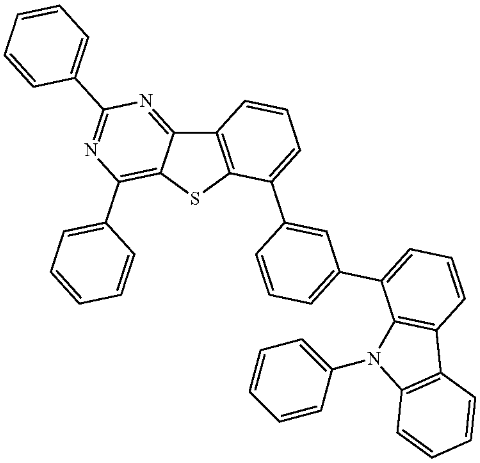
-continued
73
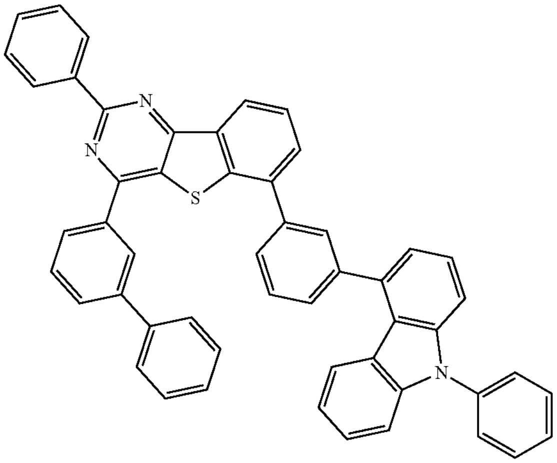
74
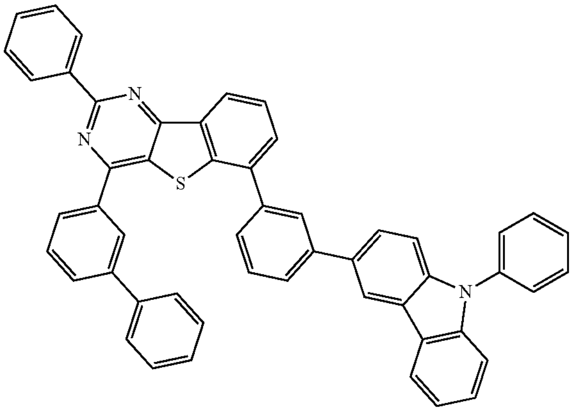
75
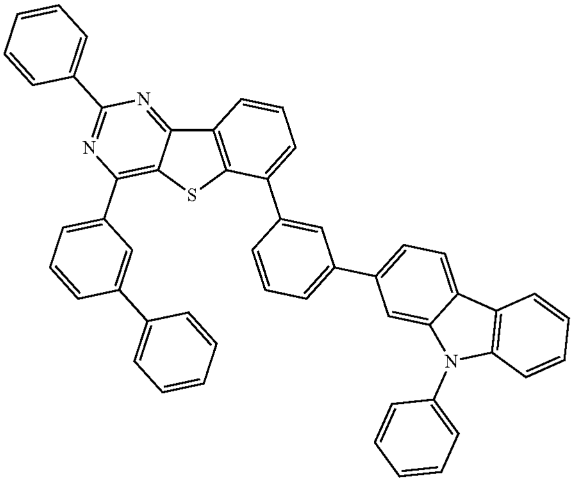

-continued
76
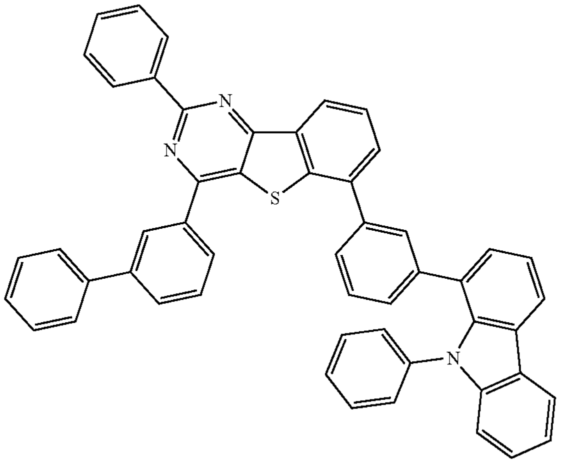
77
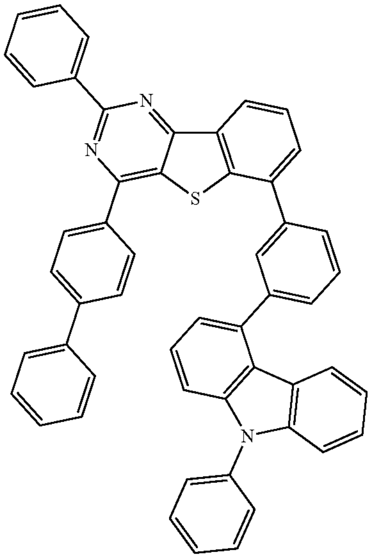
78
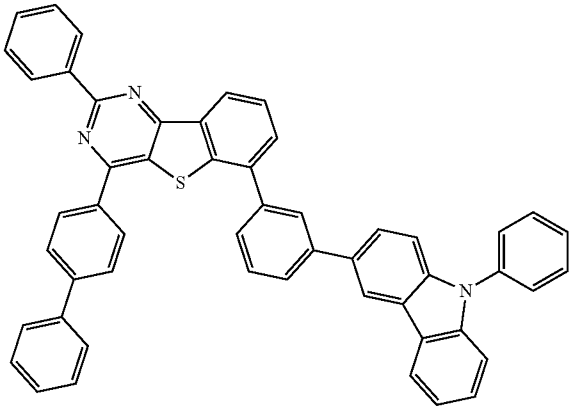
-continued
79
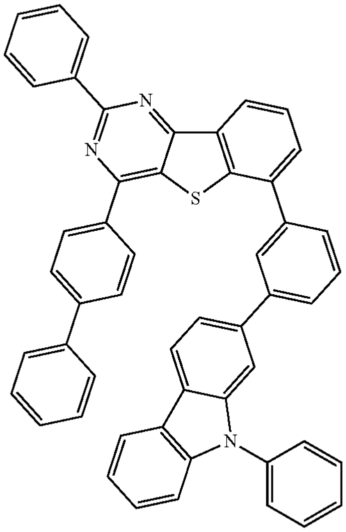
80
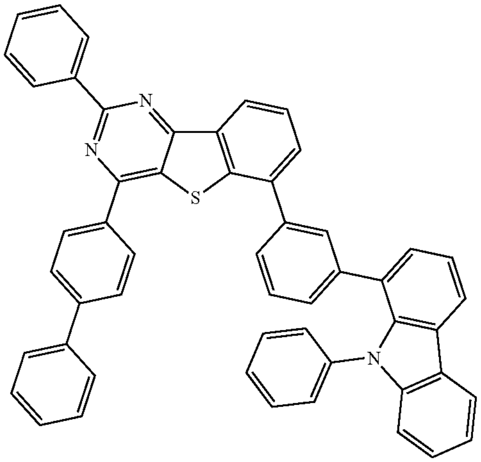
81
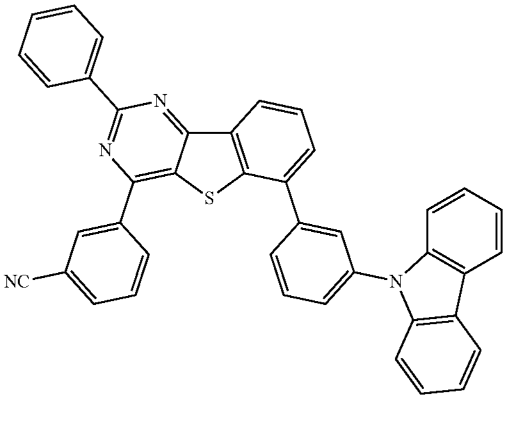

-continued
82
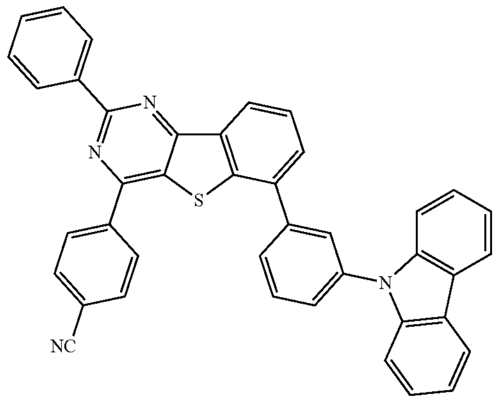
83
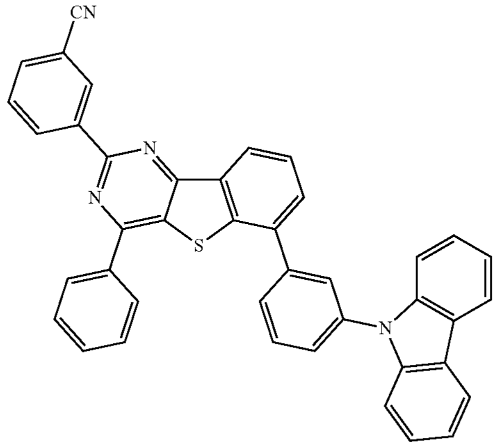
84
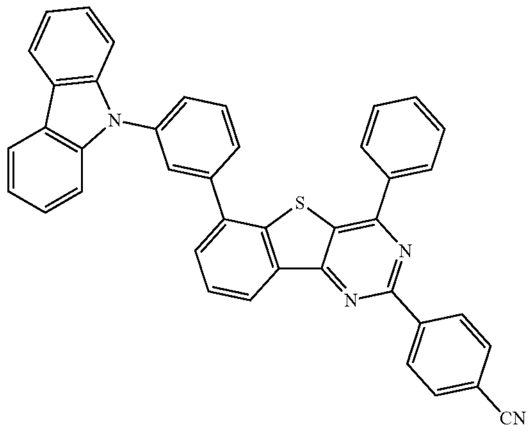
-continued
85
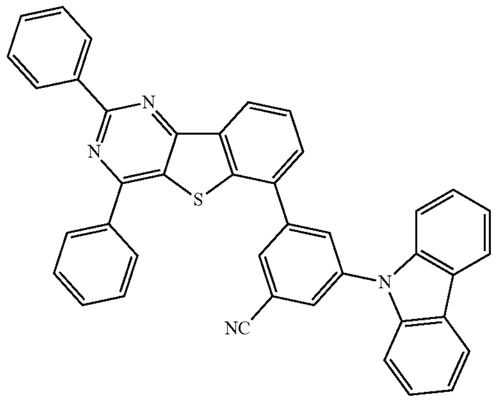
86
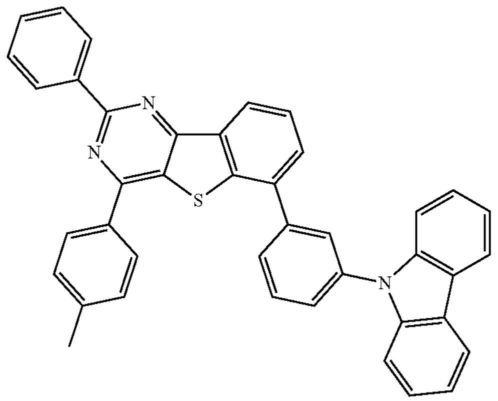
87
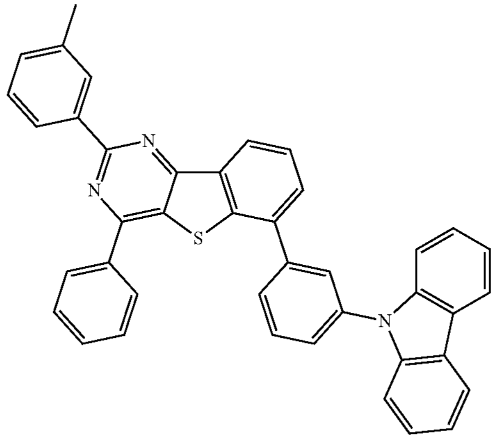
88
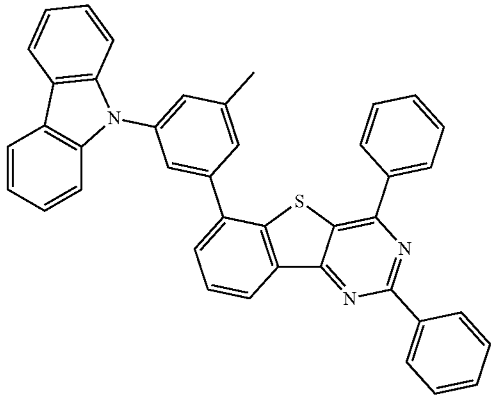

-continued
89
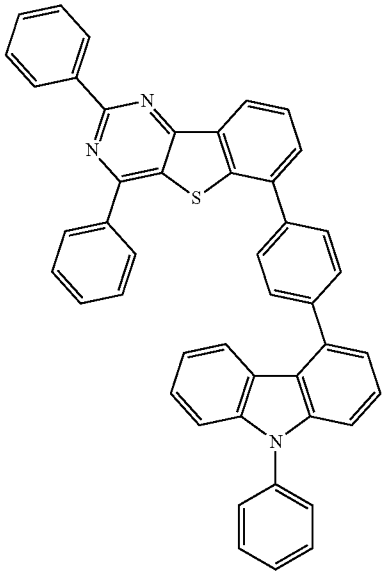
90
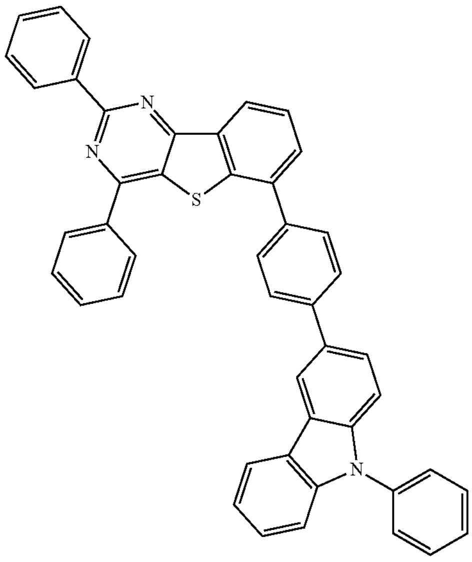
-continued
91
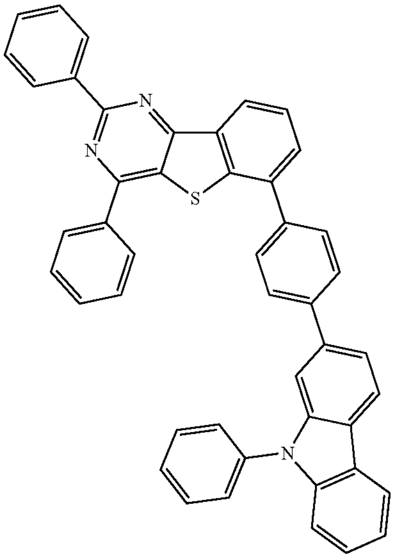
92
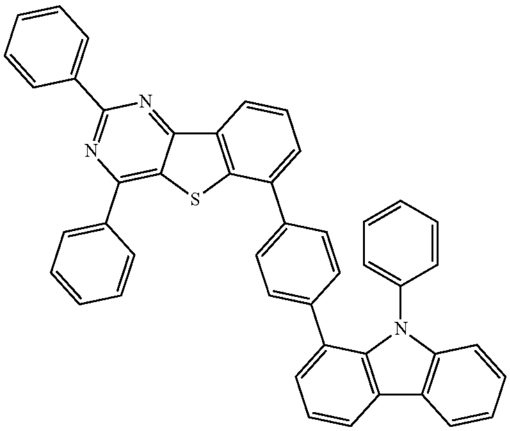
93
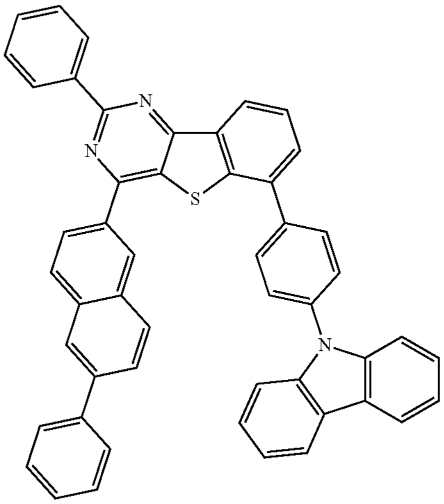

-continued
94
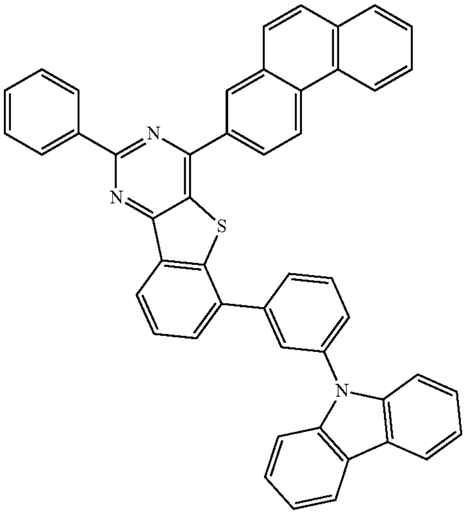
95
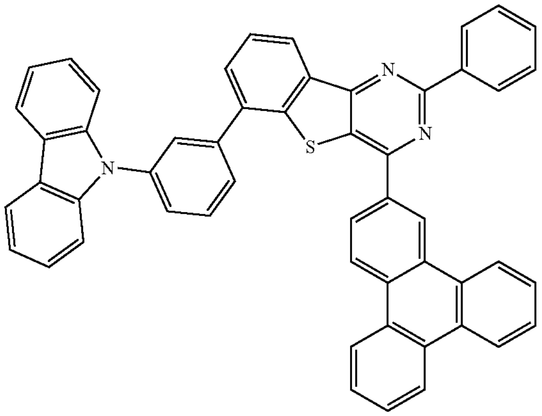
96
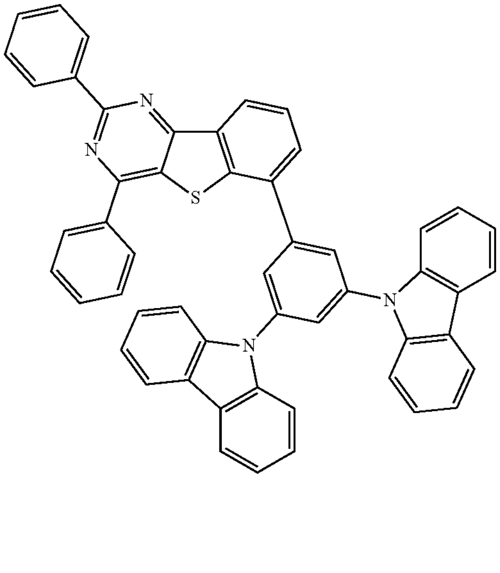
-continued
97
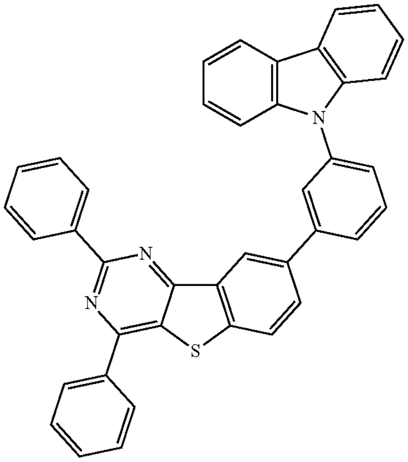
98
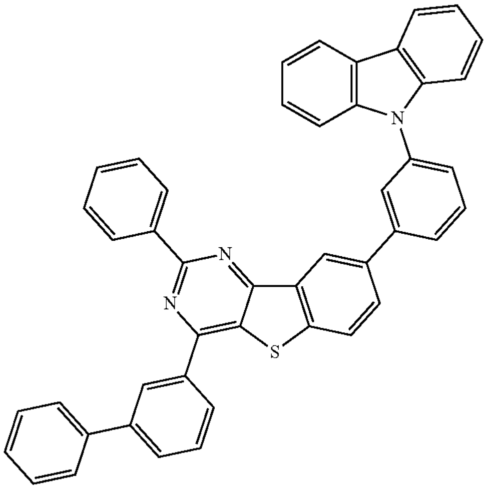
99
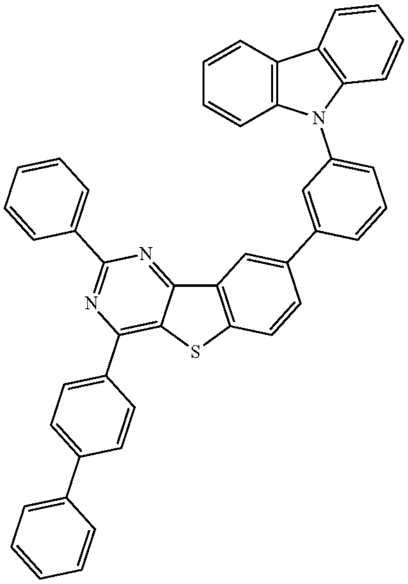

-continued
100
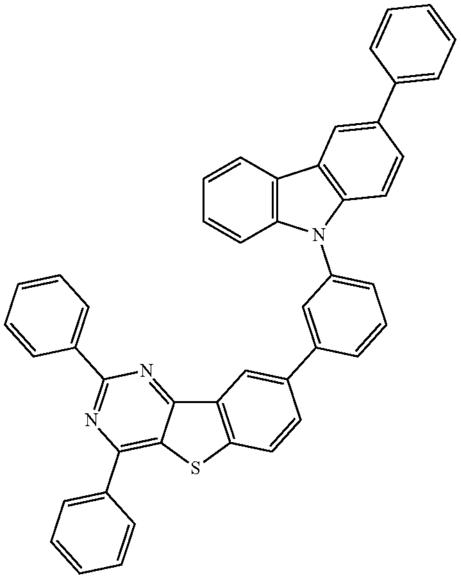
101
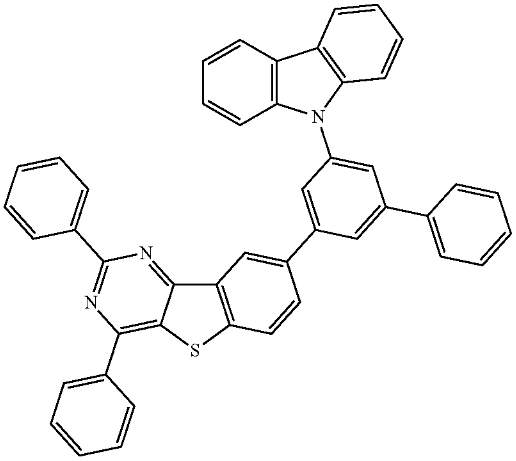
102
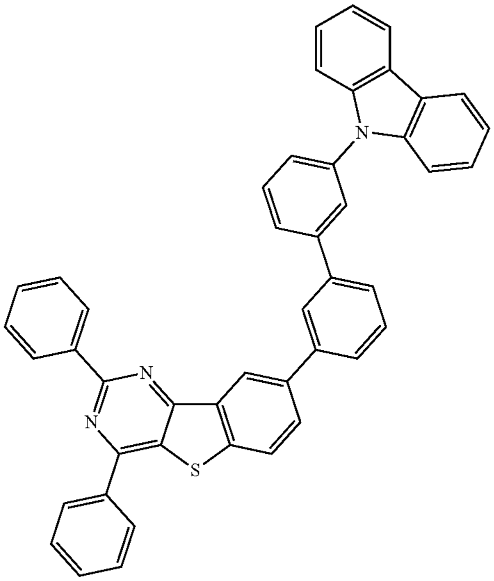
-continued
103
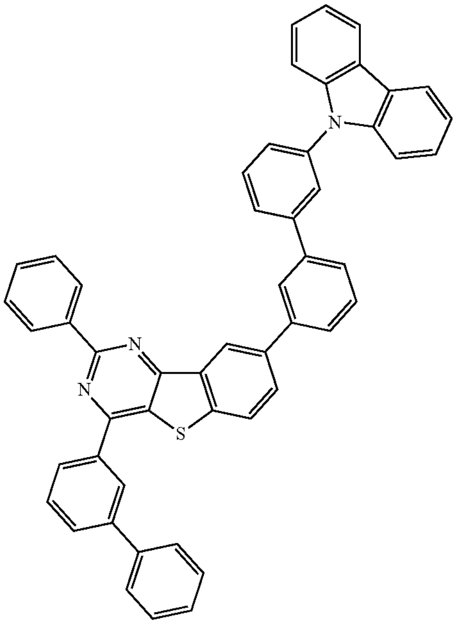
104
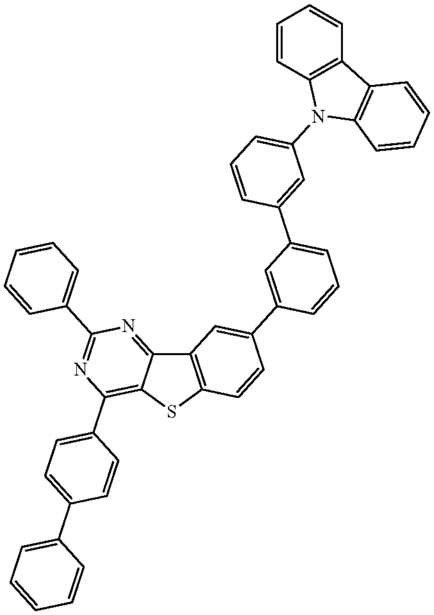

-continued
105
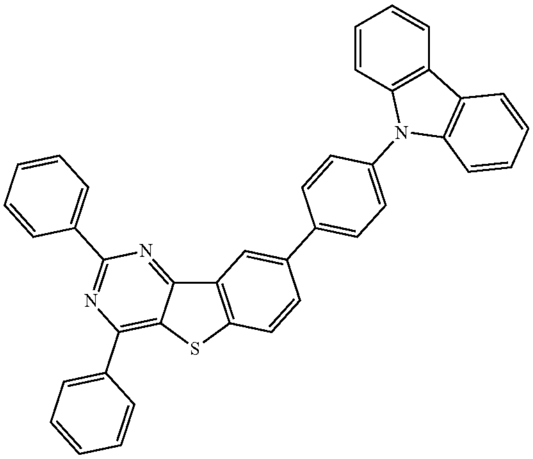
106
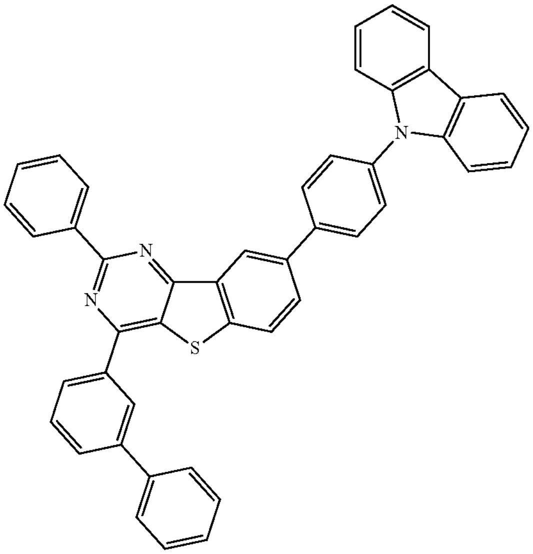
107
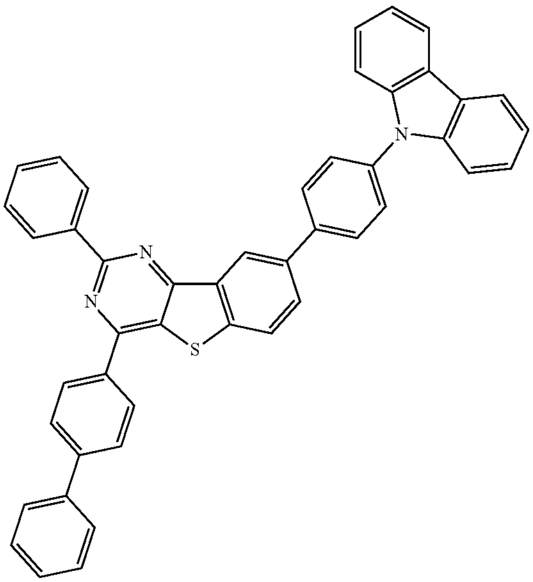
-continued
108
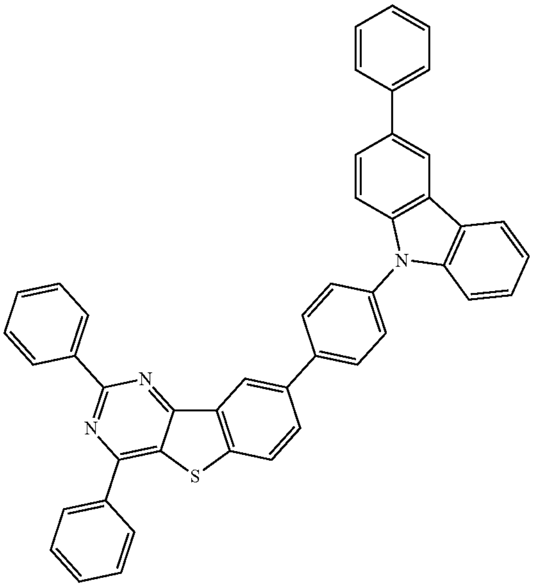
109
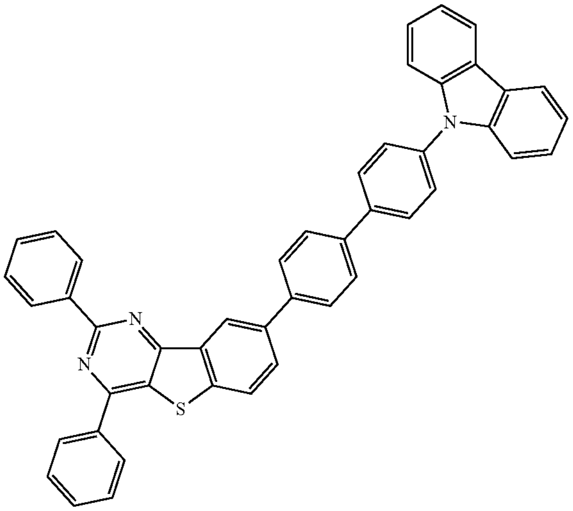
110
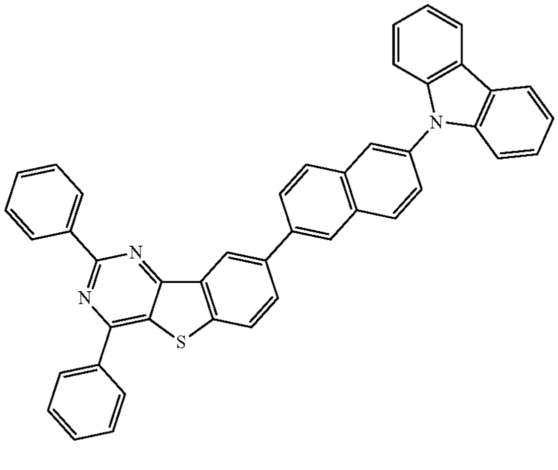

-continued
111
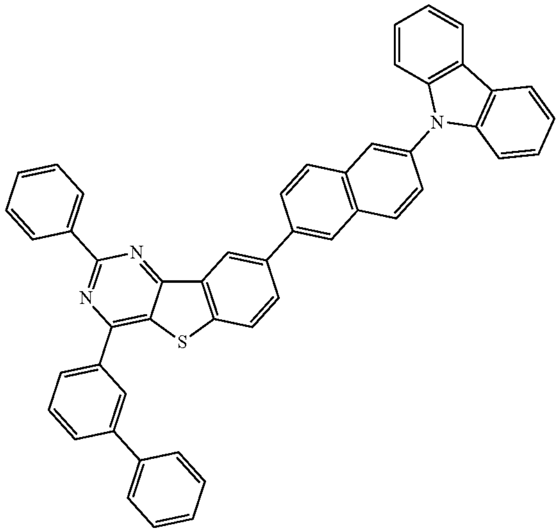
112
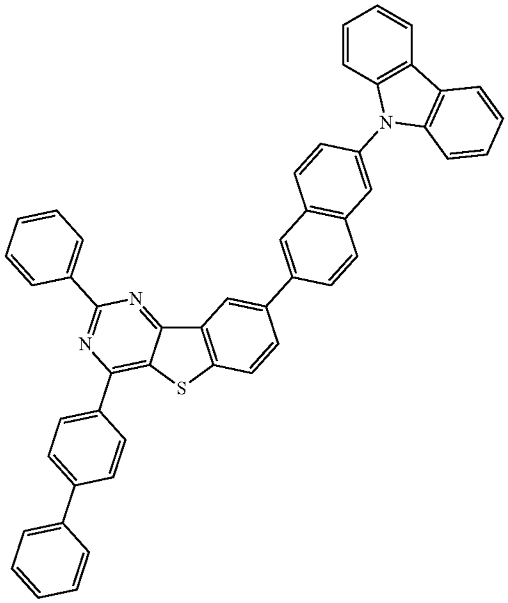
-continued
113
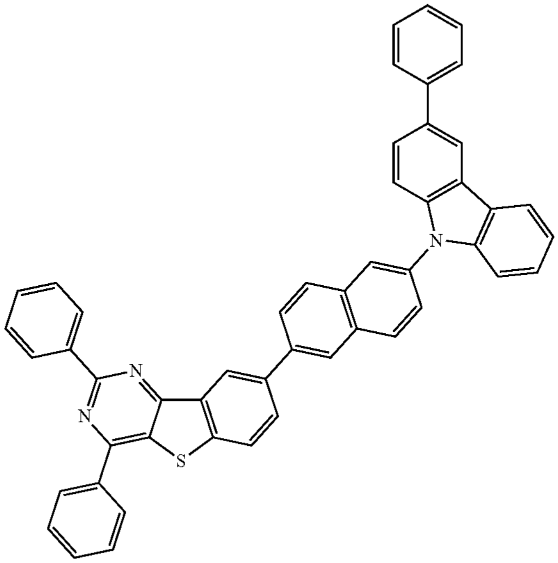
114
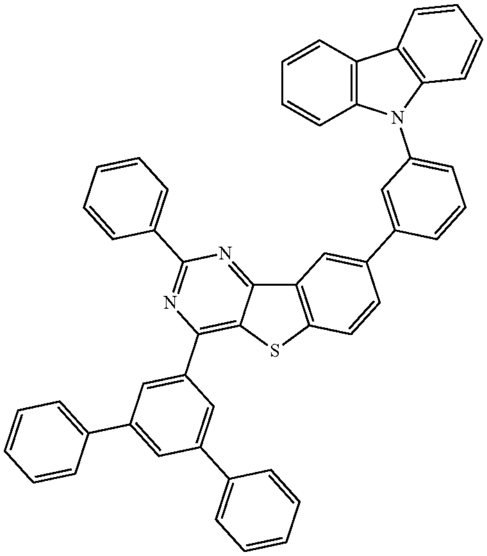
115
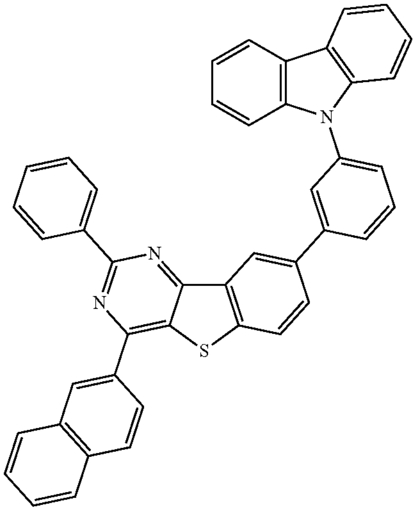

-continued
116
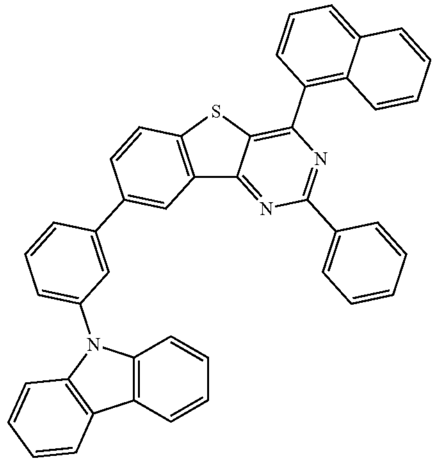
117
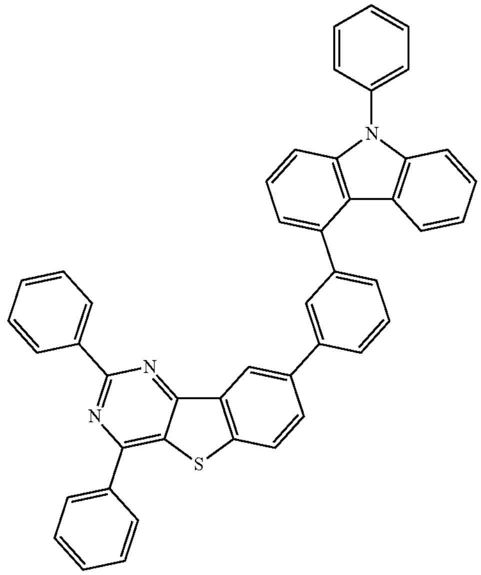
118
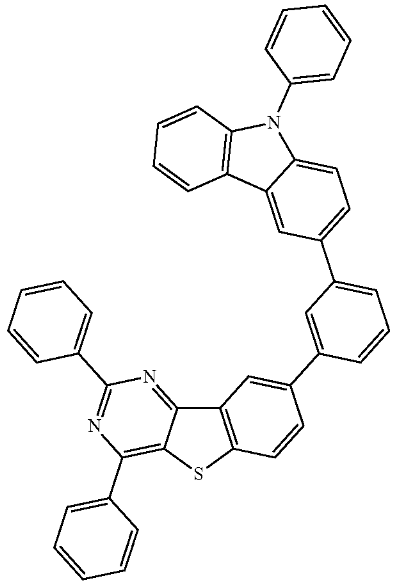
-continued
119
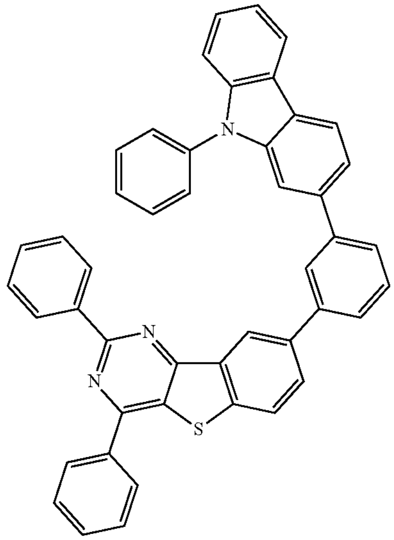
120
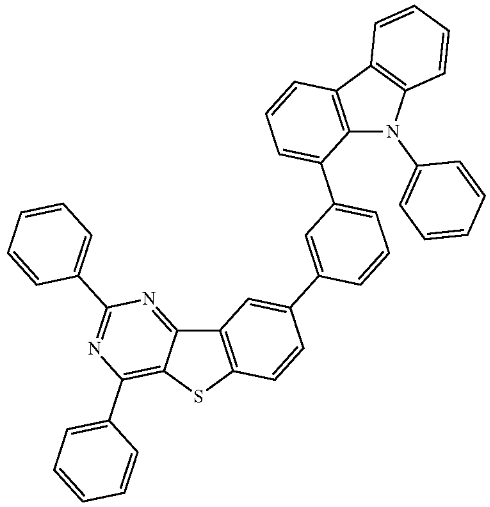
121
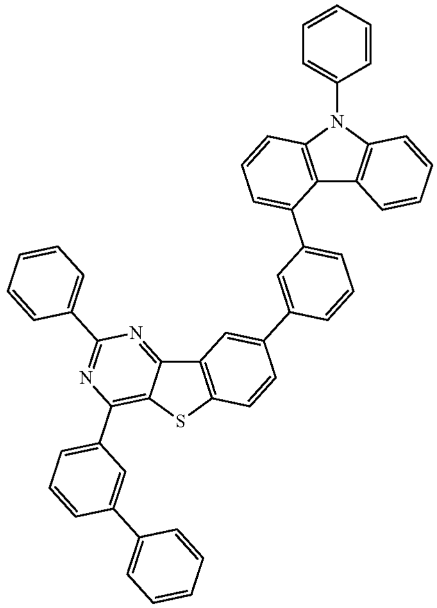

-continued
122
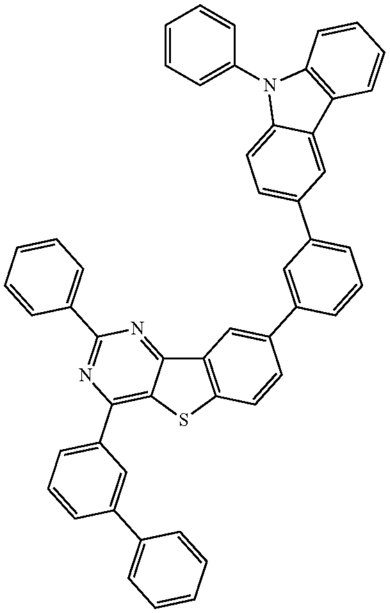
123
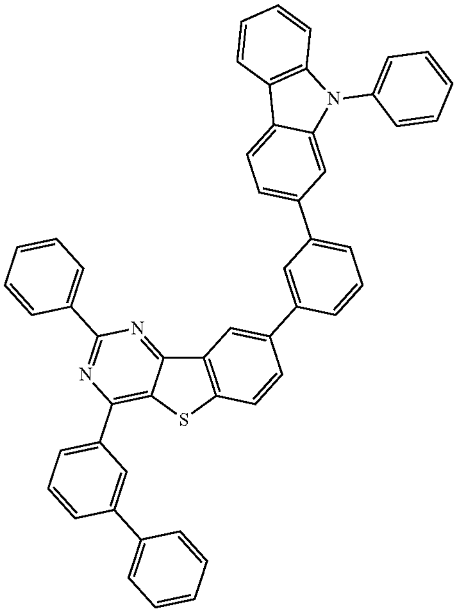
-continued
124
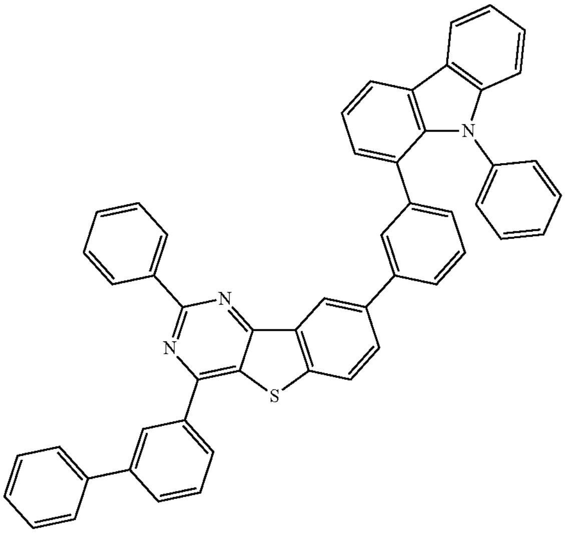
125
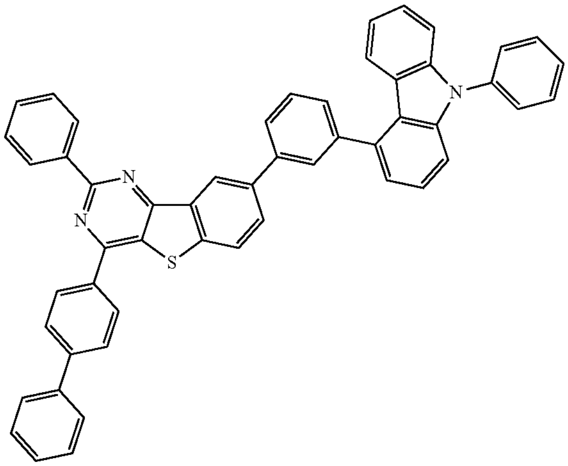
126
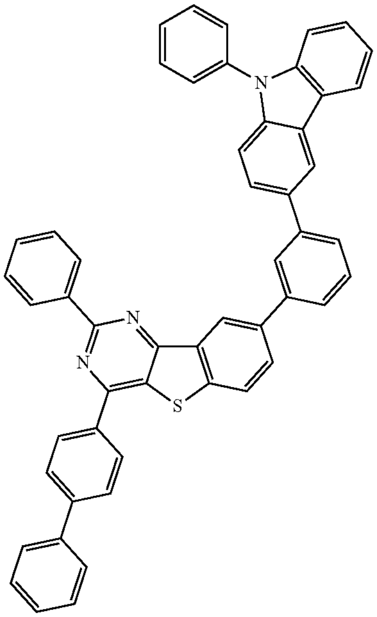

-continued
127
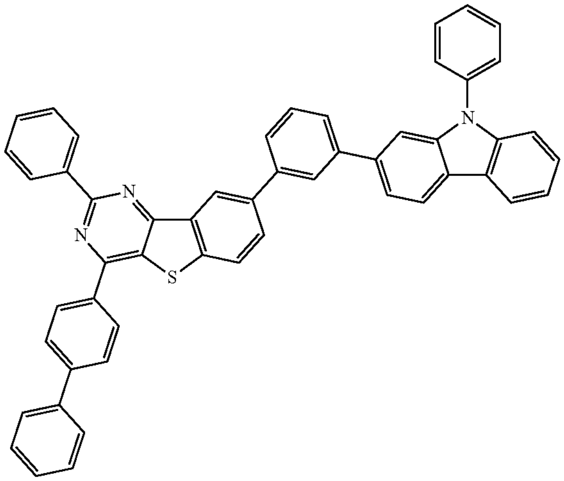
128
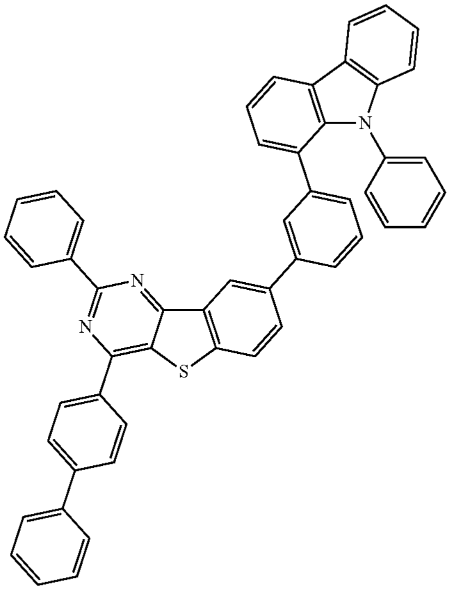
129
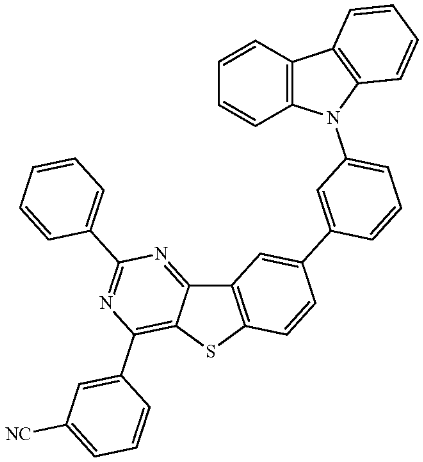
-continued
130
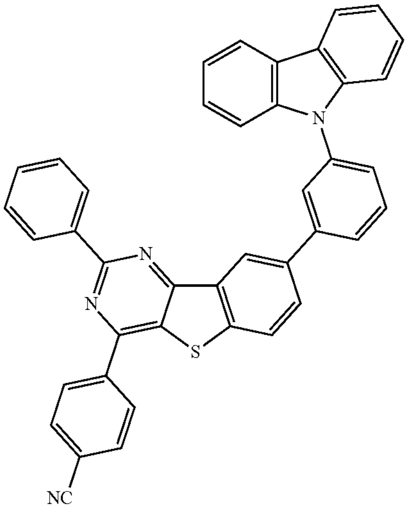
131
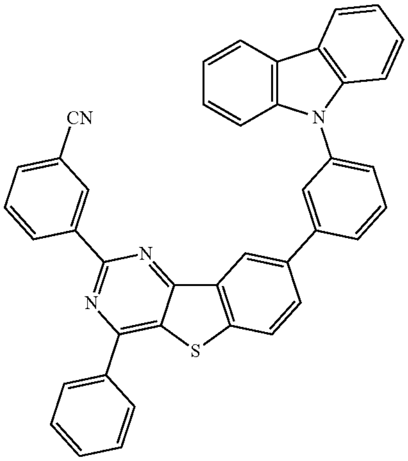
132
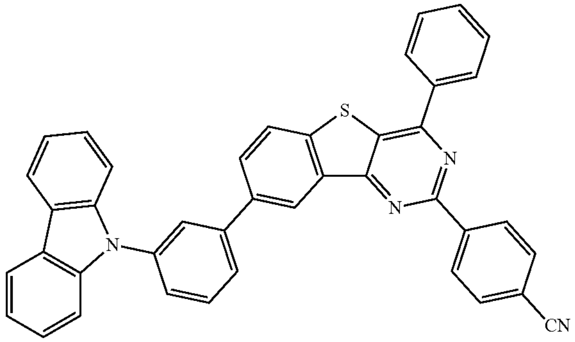

-continued
133
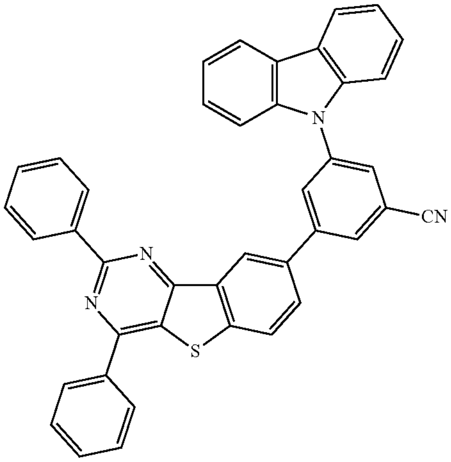
134
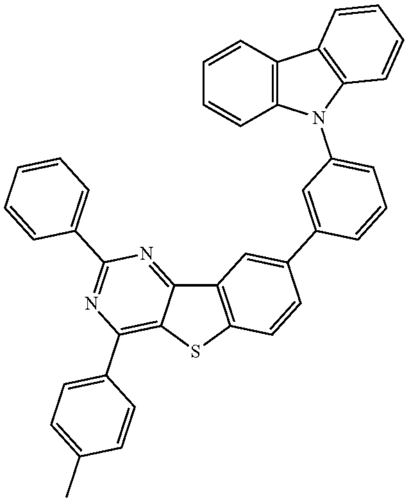
135
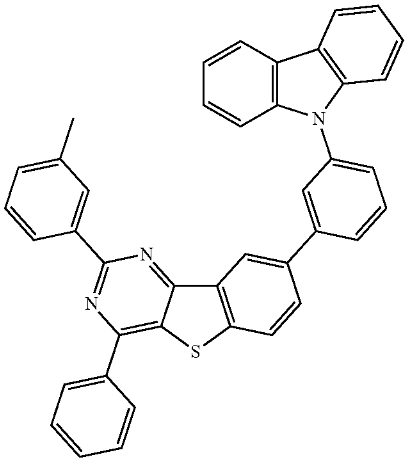
-continued
136
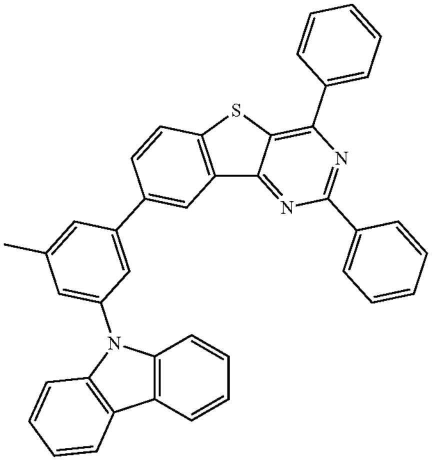
137
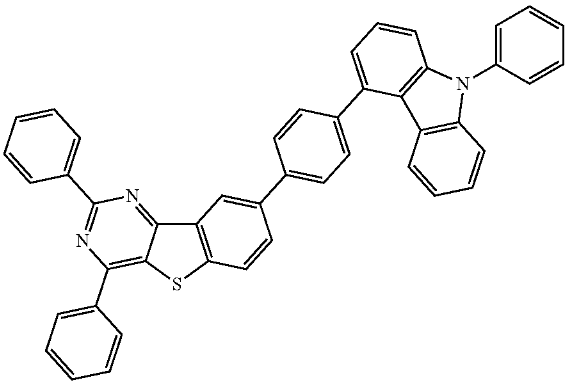
138
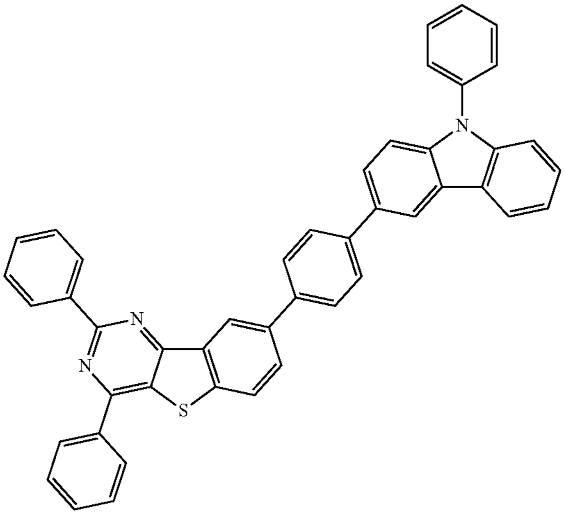

-continued
139
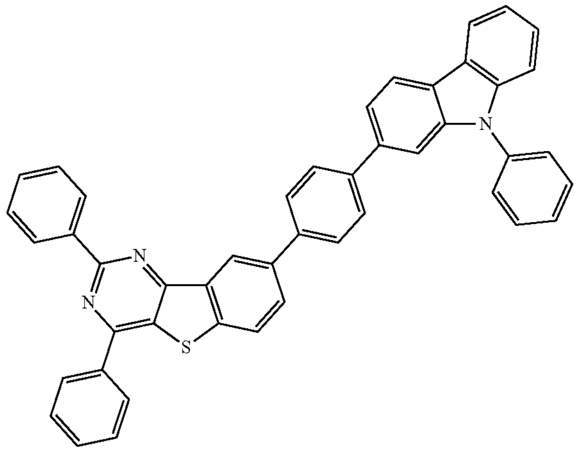
141
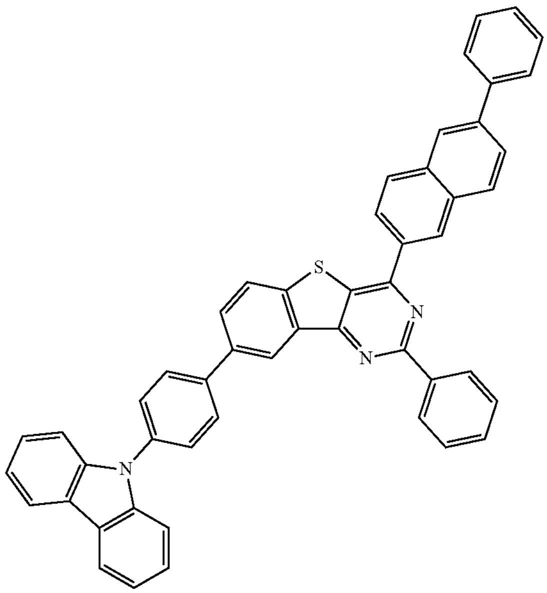
140
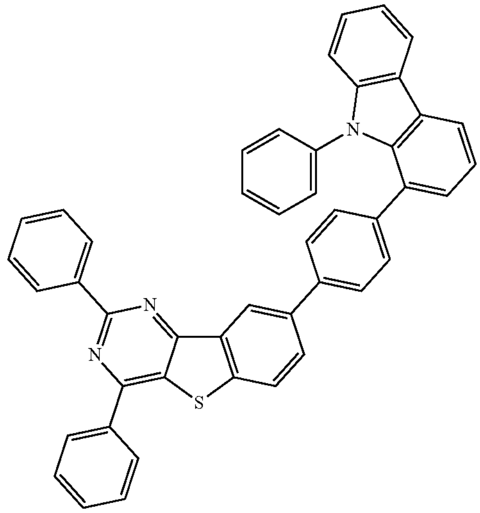
142
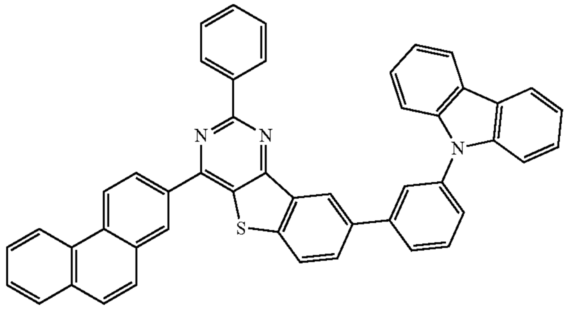
143
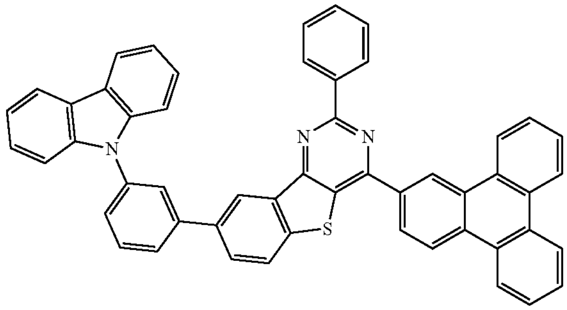

144
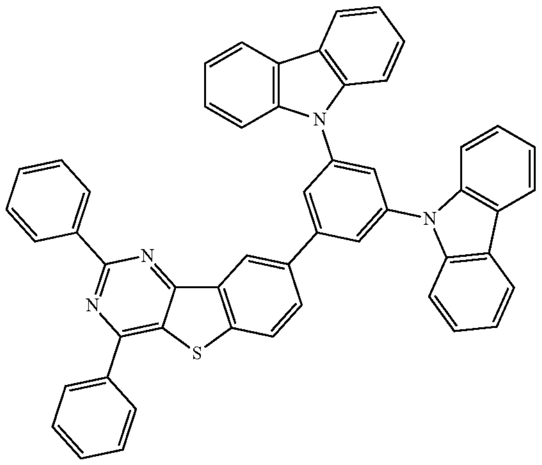
145
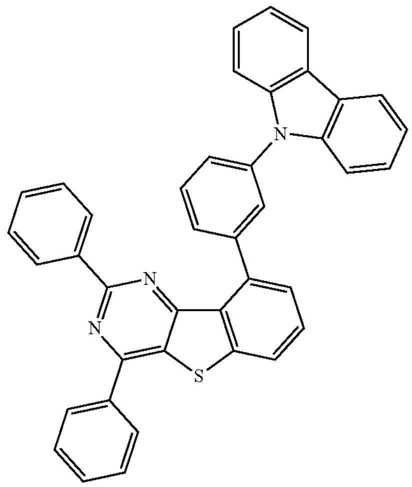
146
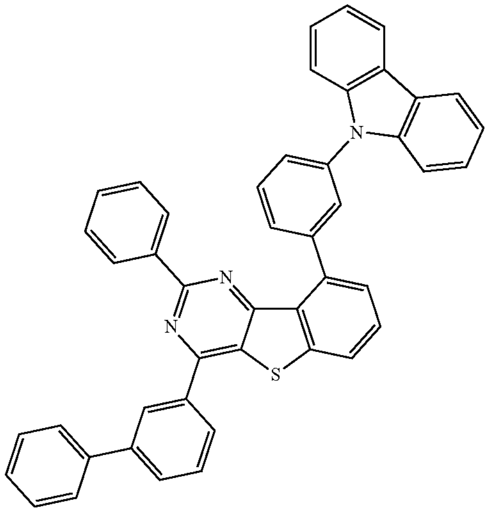
147
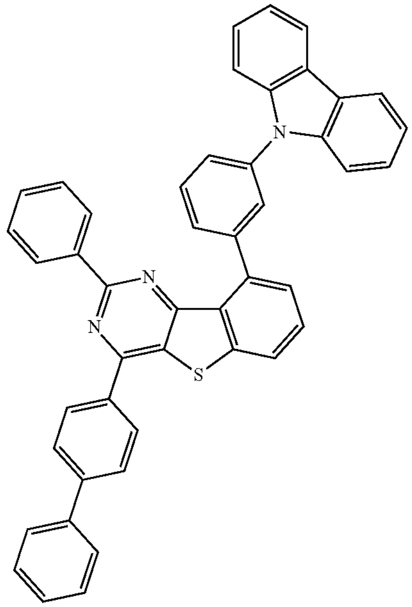
148
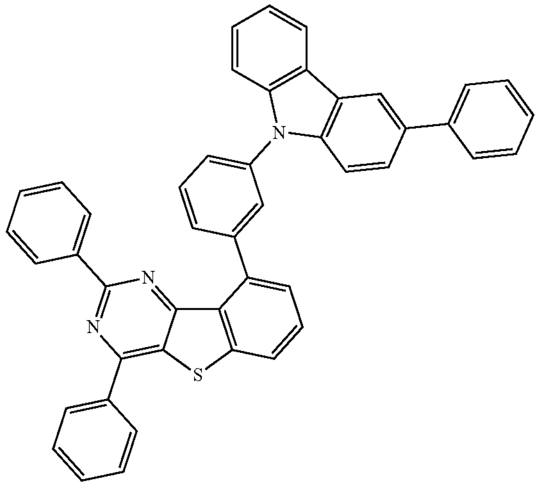
149
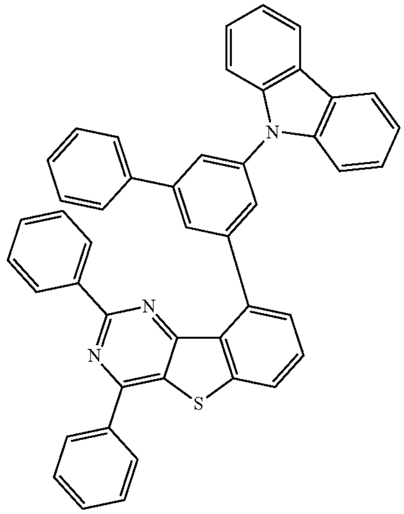

-continued
150
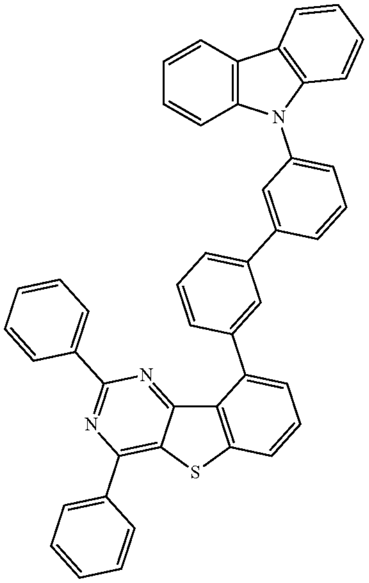
151
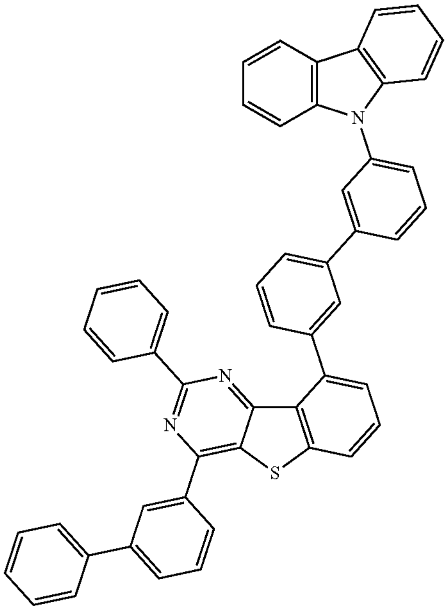
-continued
152
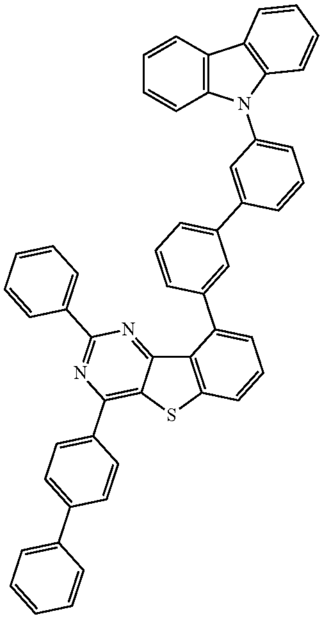
153
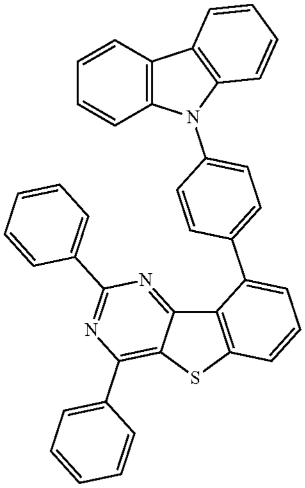

154
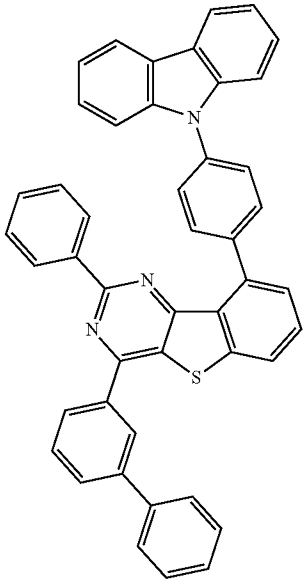
155
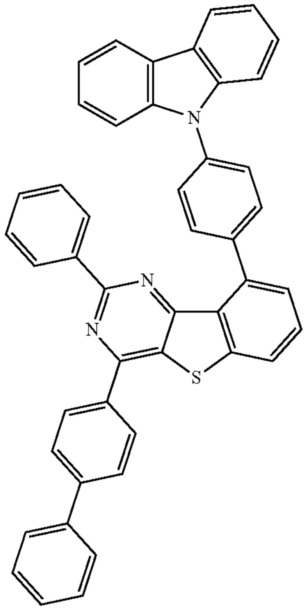
156
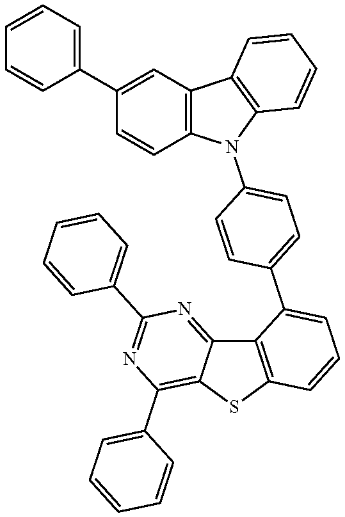
157
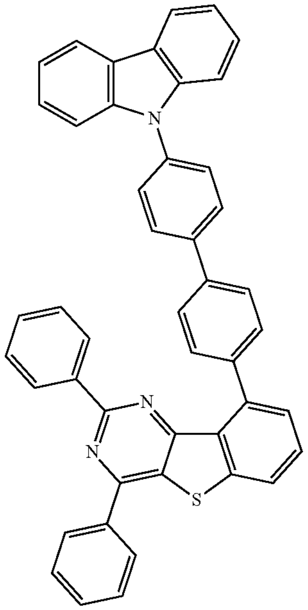

-continued
158
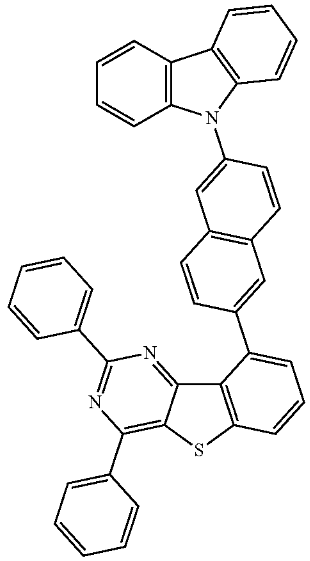
160
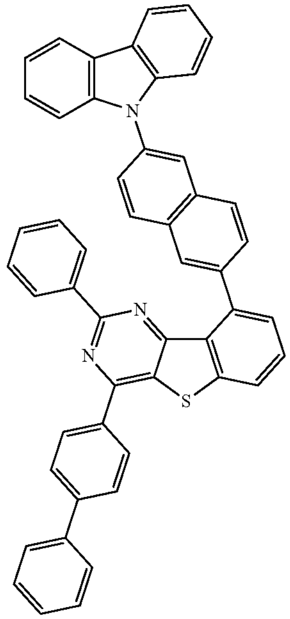
159
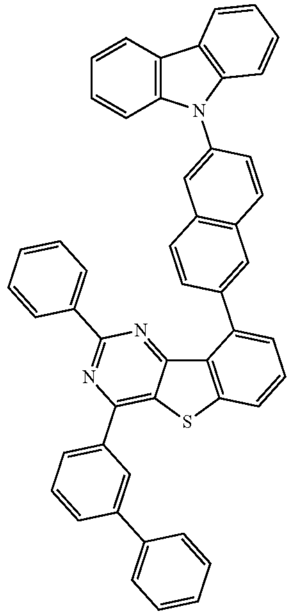
161
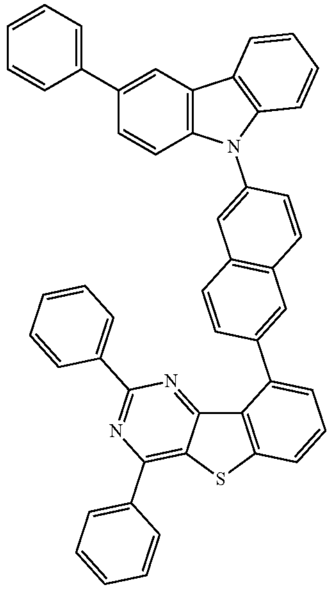

-continued
162
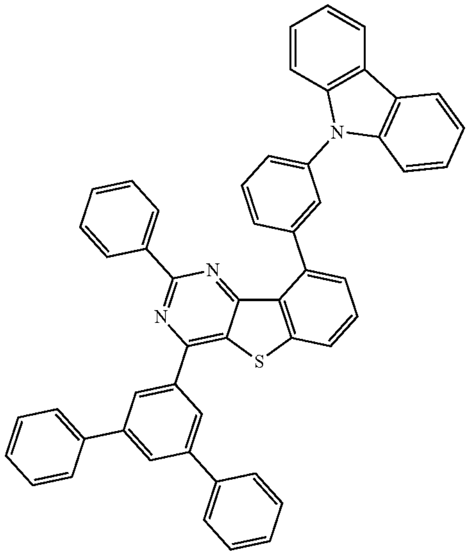
163
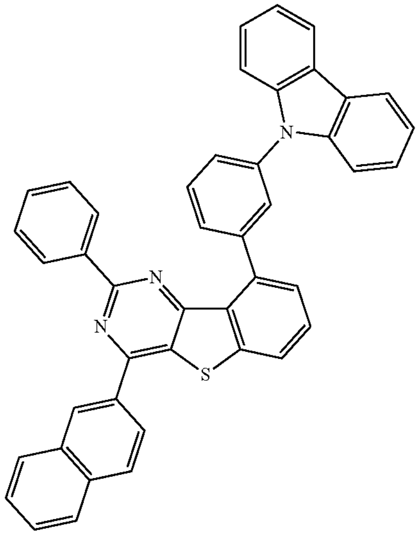
164
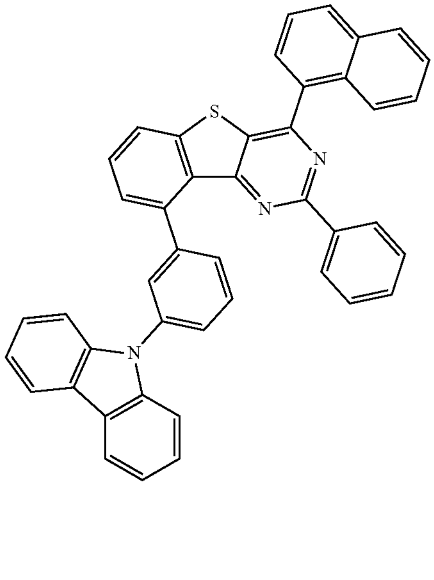
-continued
165
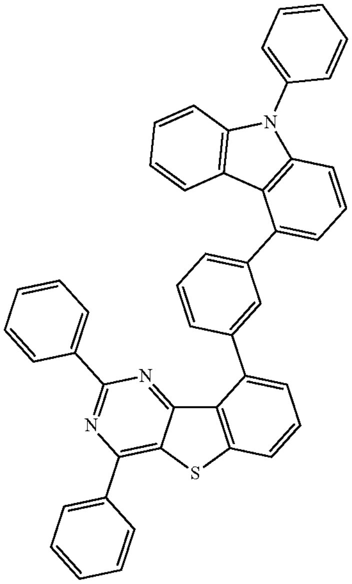
166
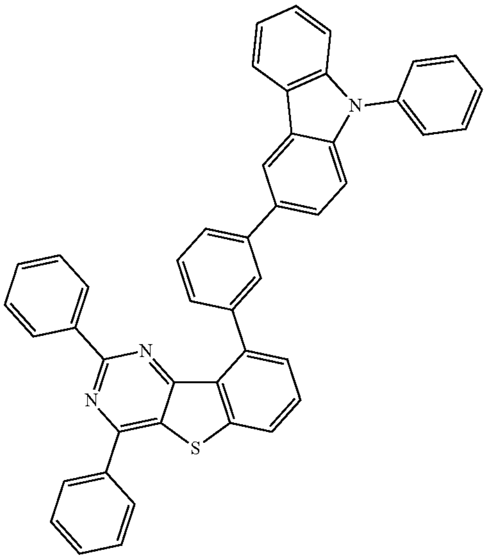

-continued
167
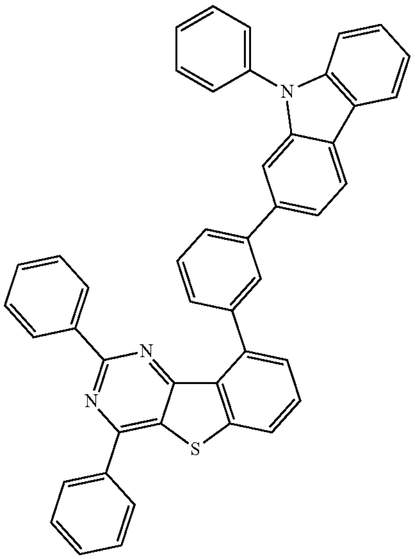
169
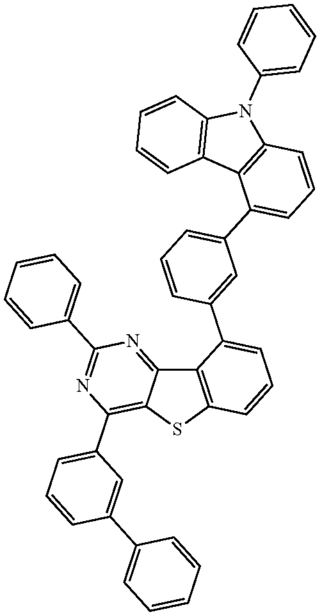
168
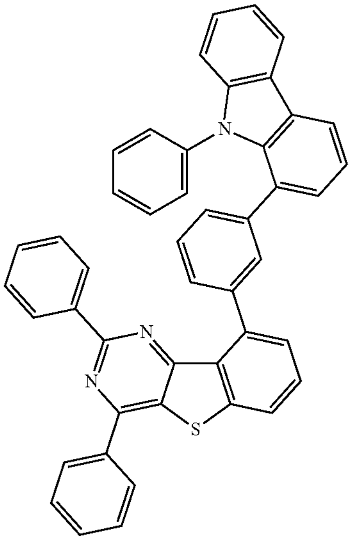
170
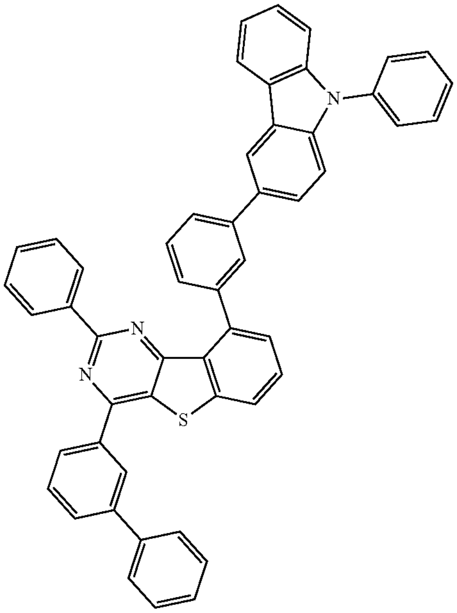

171
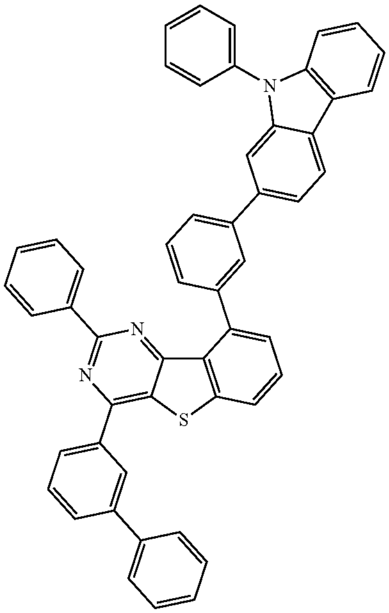
172
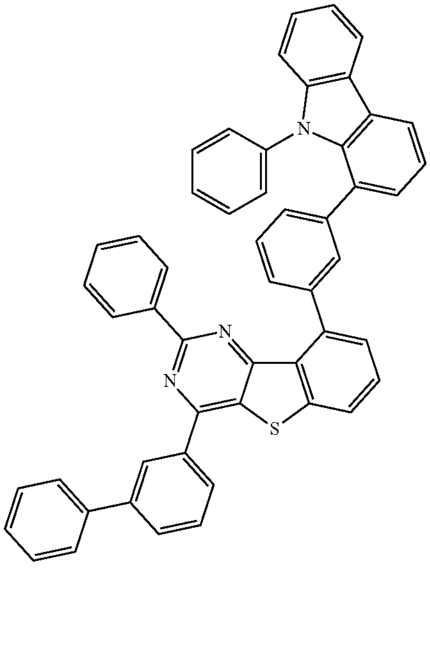
173
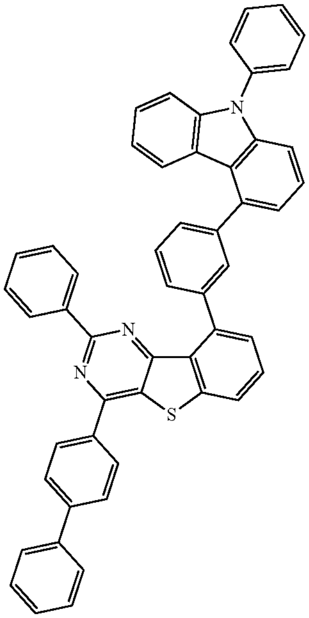
174
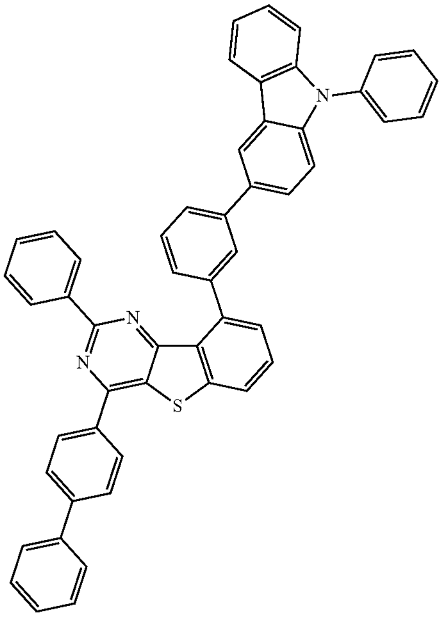

-continued
175
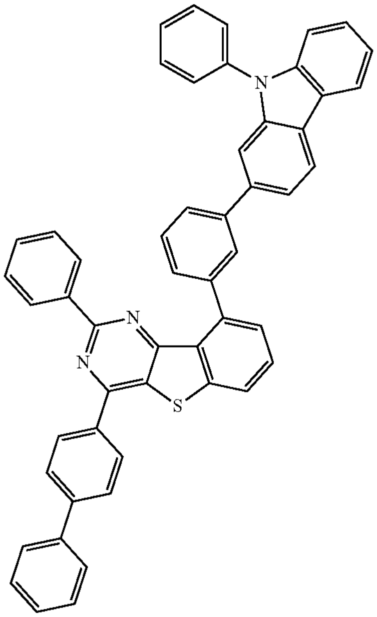
176
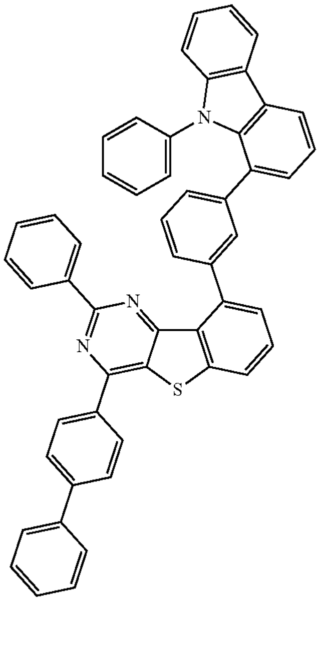
-continued
177
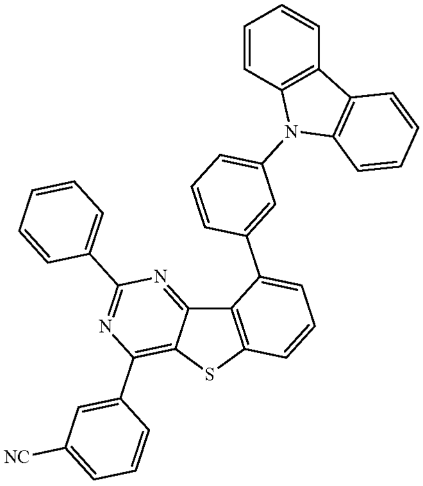
178
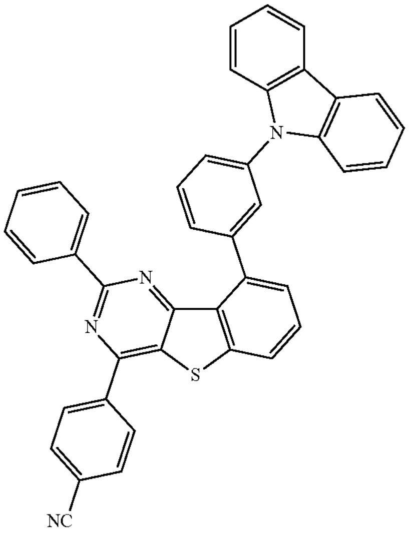
179
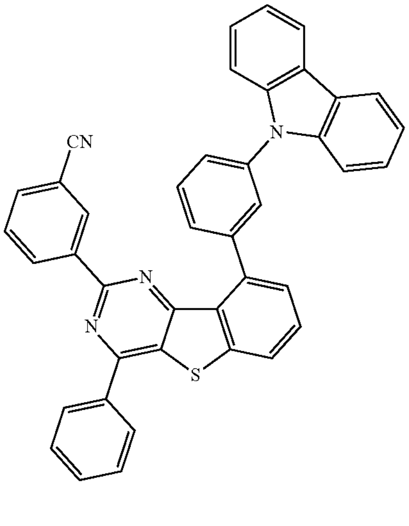

-continued
180
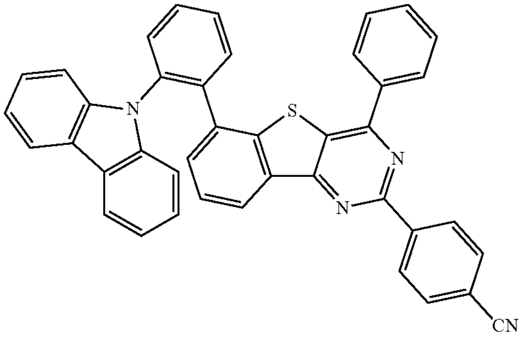
181
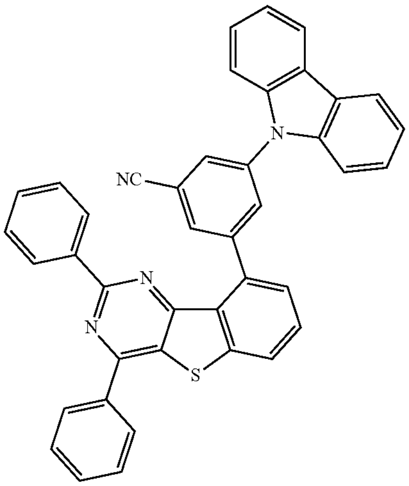
182
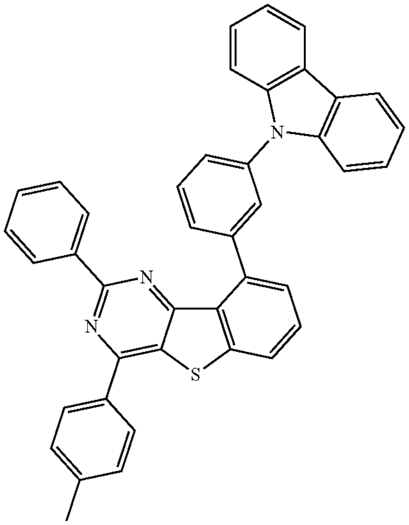
-continued
183
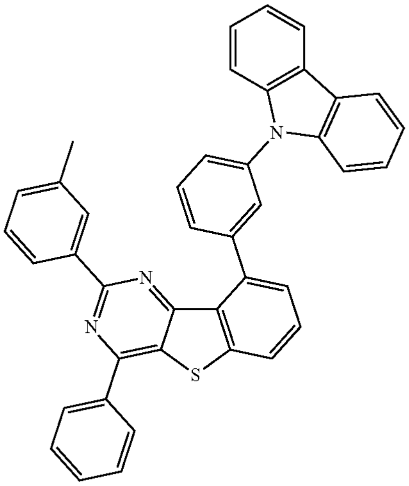
184
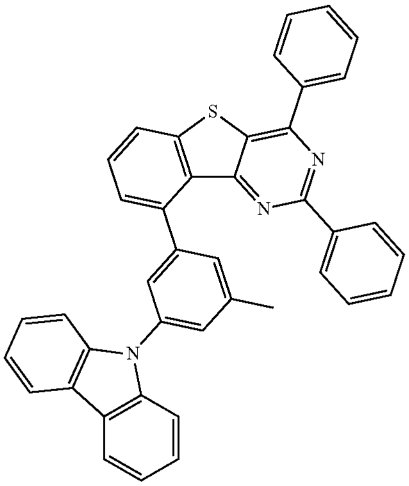
185
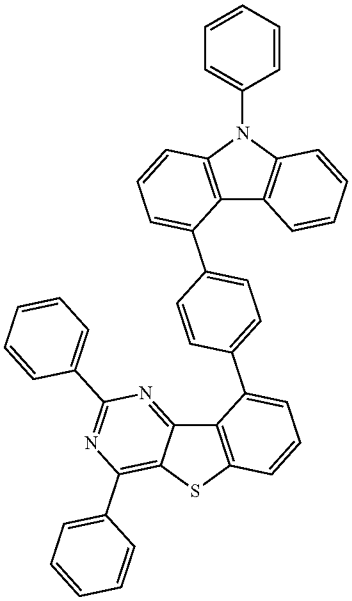

-continued
186
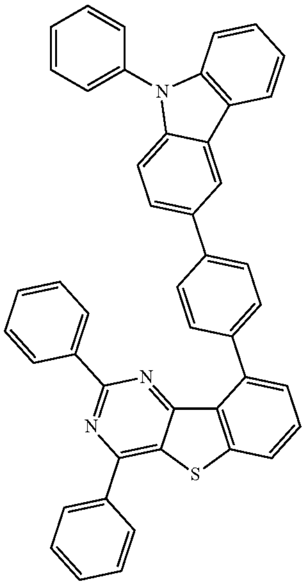
187
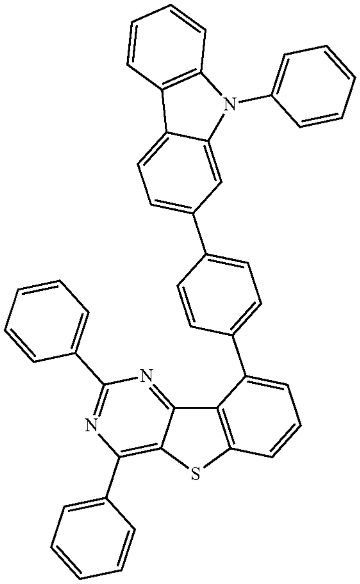
-continued
188
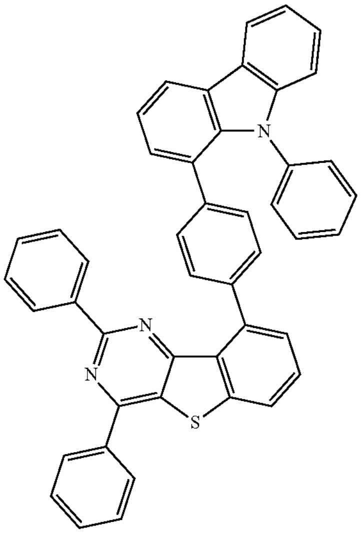
189
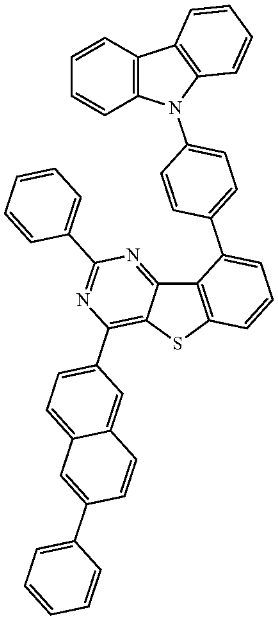
190
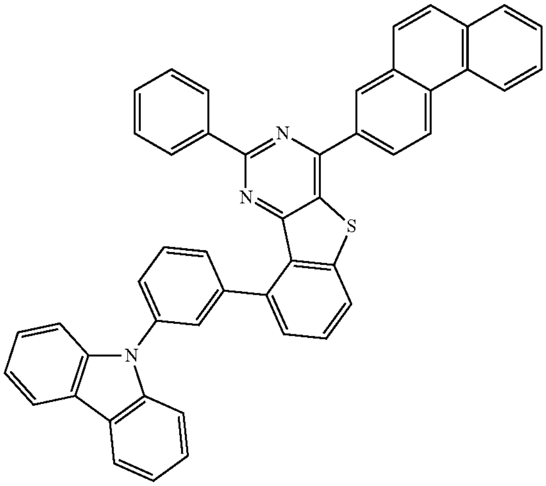

-continued
191
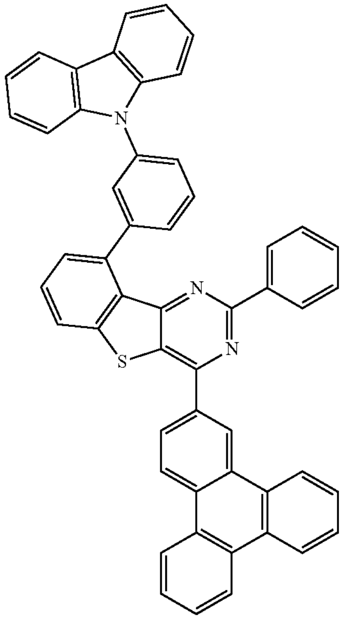
192
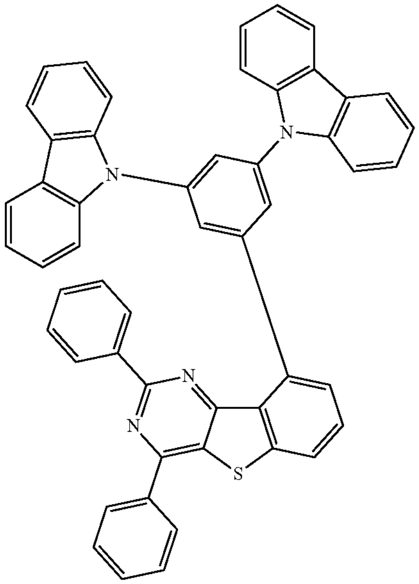
193
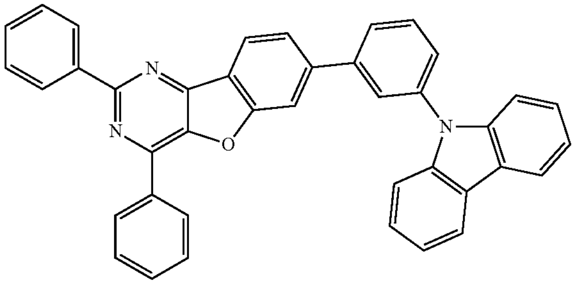
-continued
194
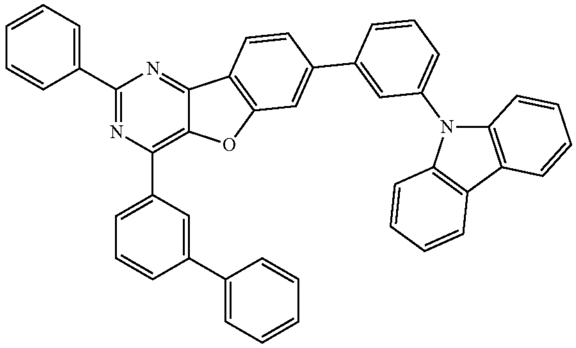
195
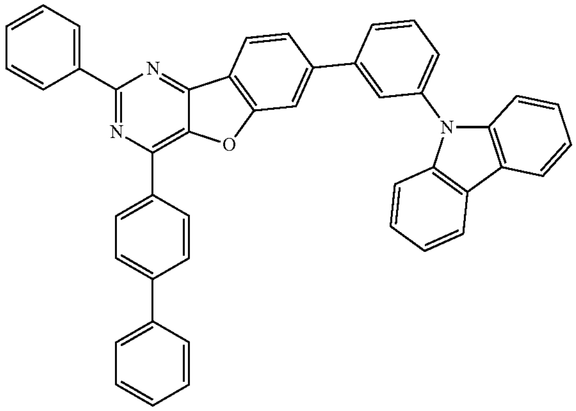
196
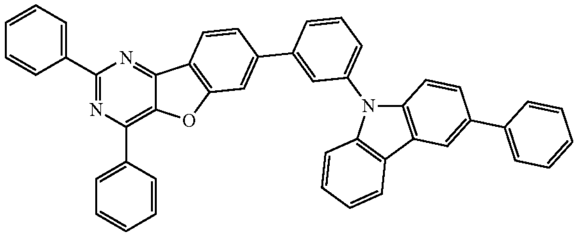
197
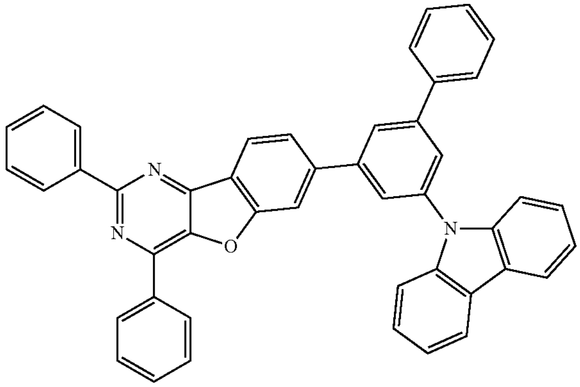

-continued
198
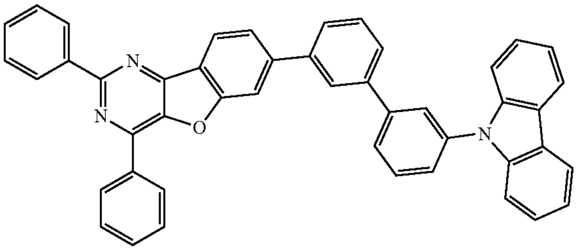
199
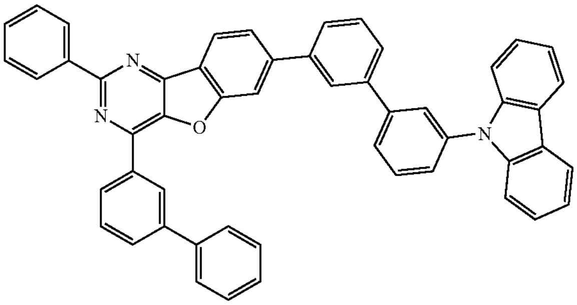
200
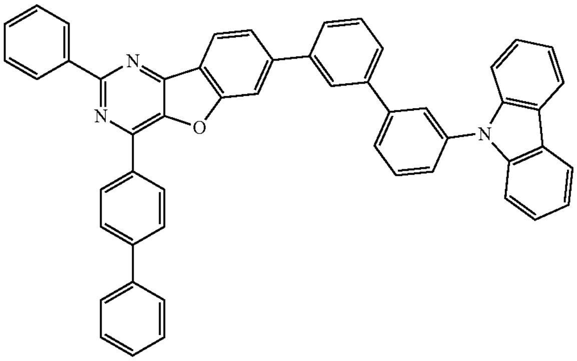
201
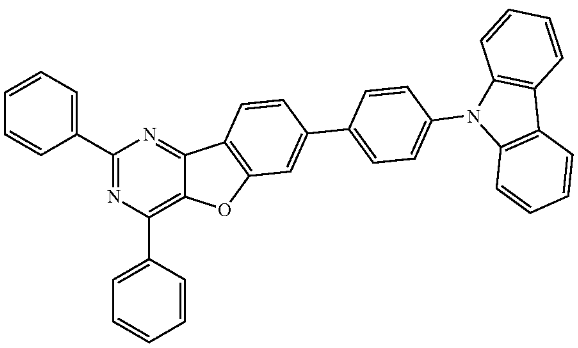
-continued
202
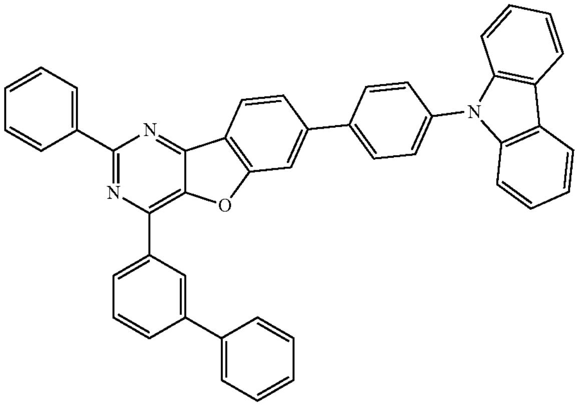
203
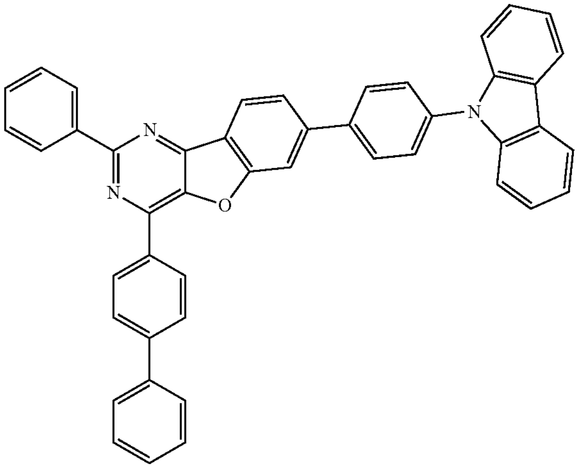
204
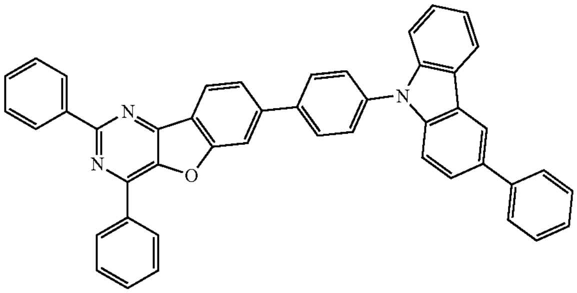
205
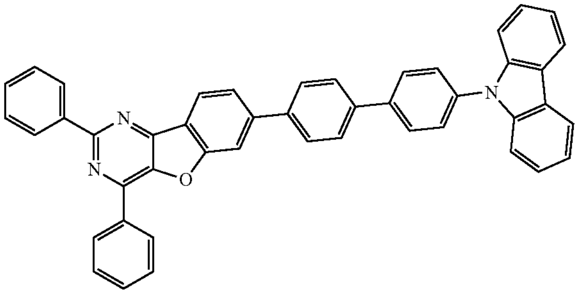

-continued
206
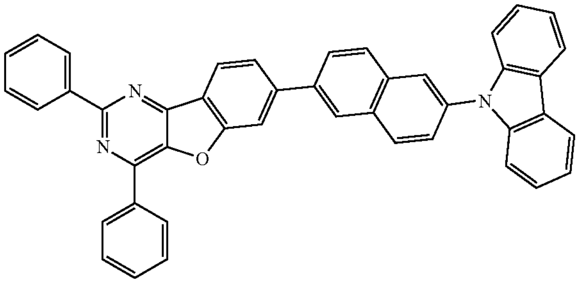
207
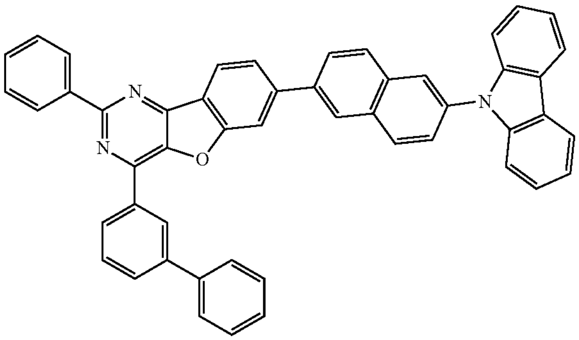
208
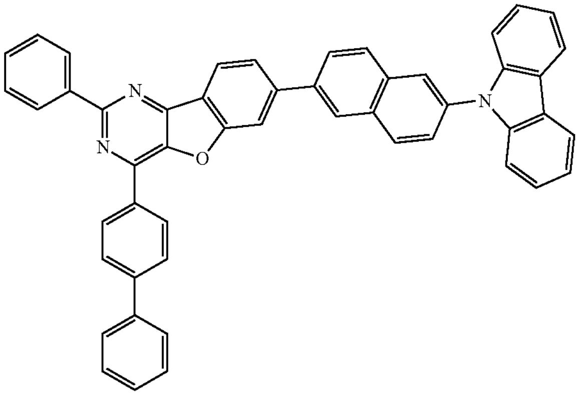
209
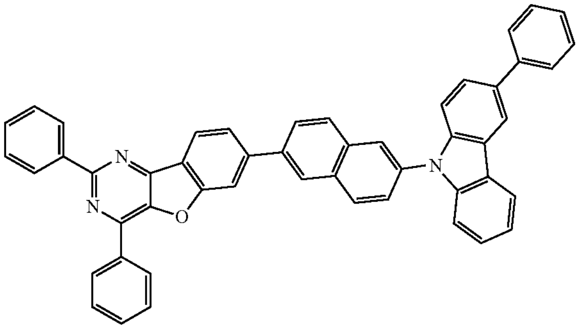
-continued
210
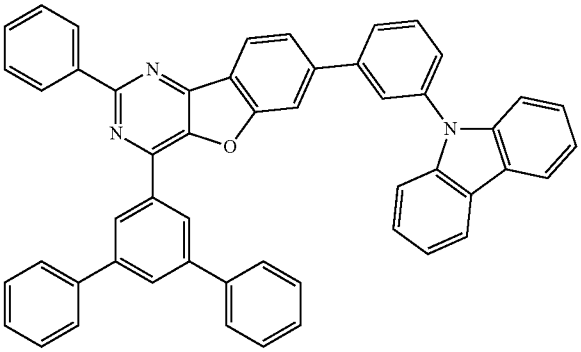
211
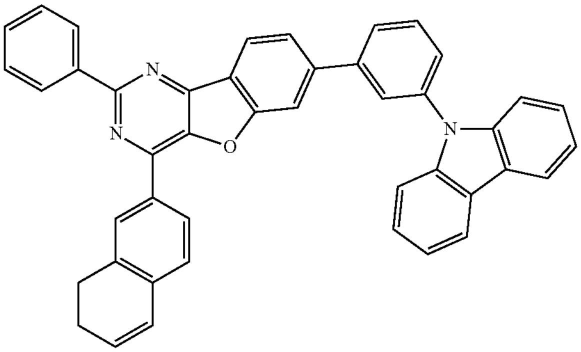
212
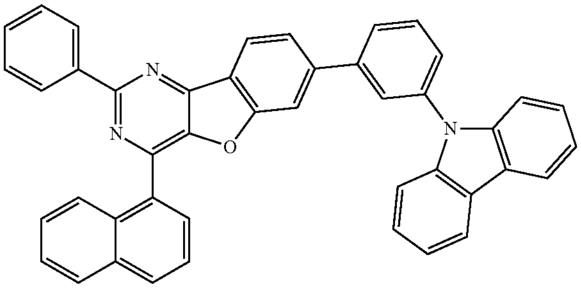
213
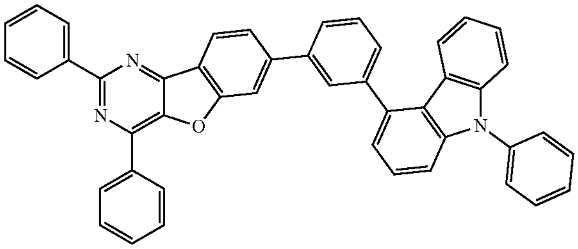

-continued
214
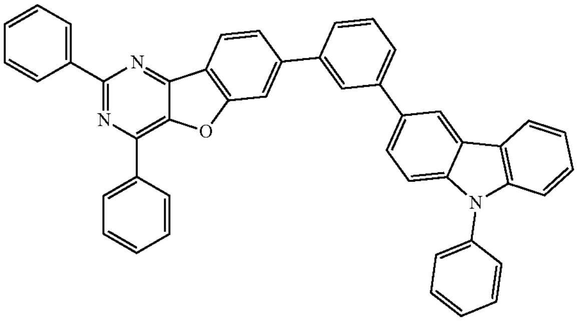
215
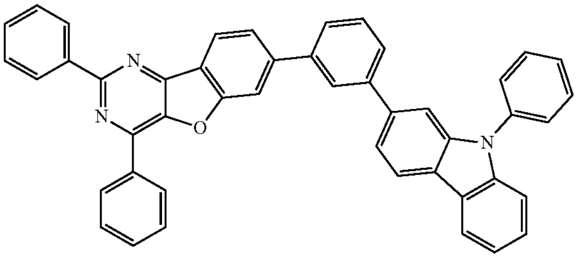
216
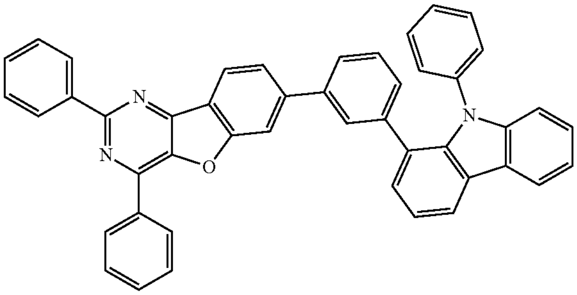
217
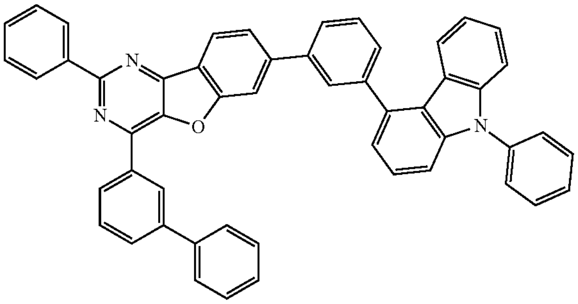
218
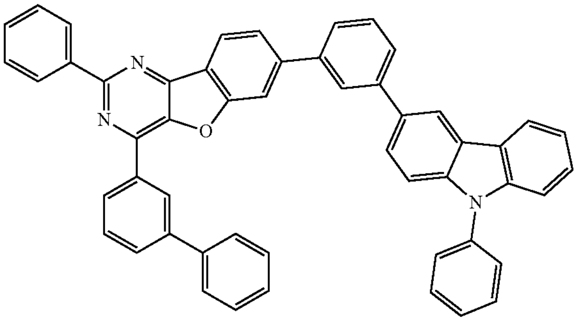
-continued
219
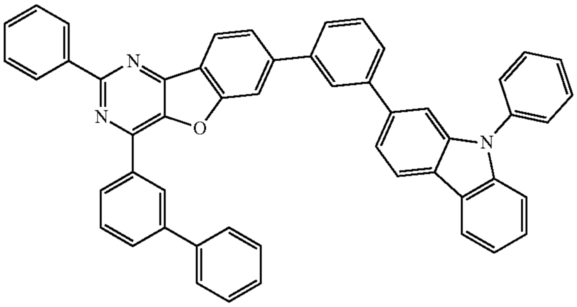
220
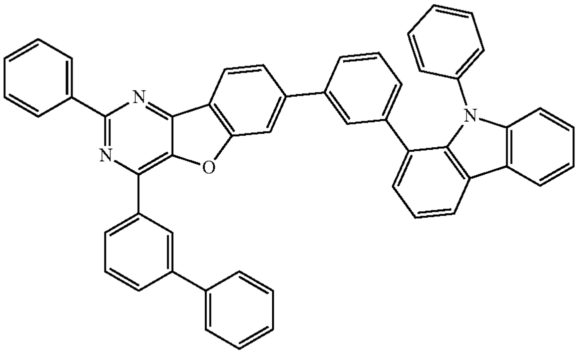
221
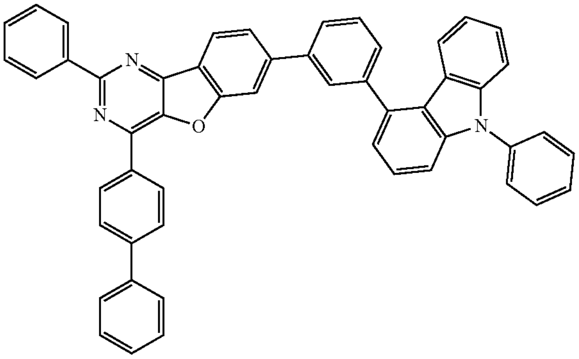
222
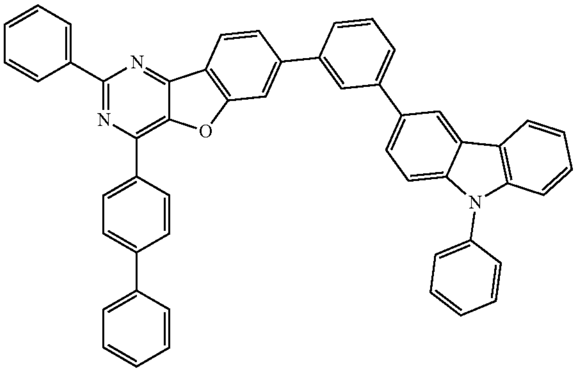

-continued
223
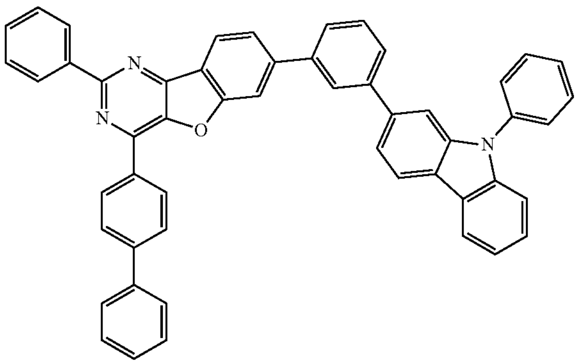
224
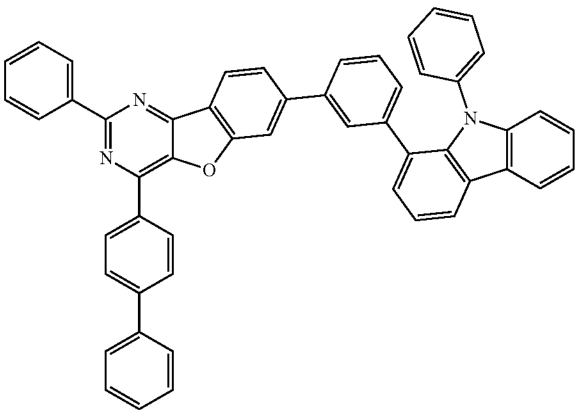
225
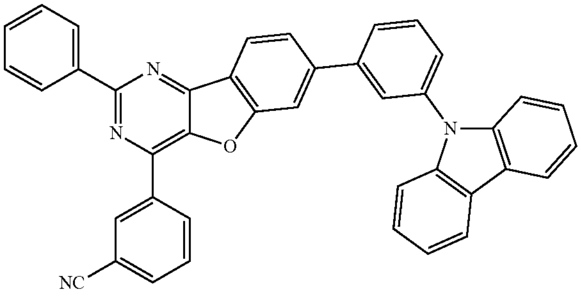
226
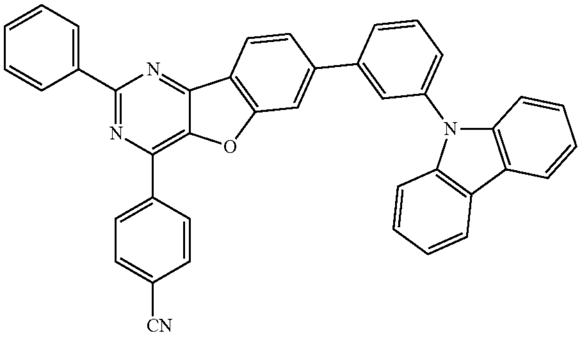
-continued
227
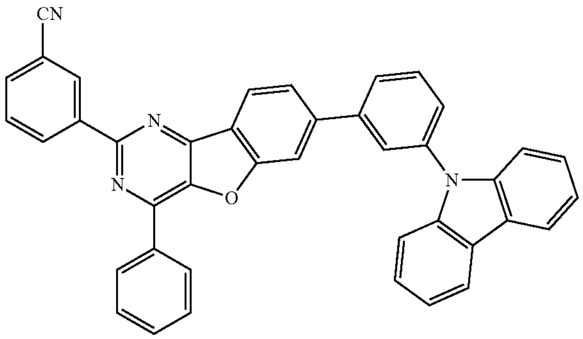
228
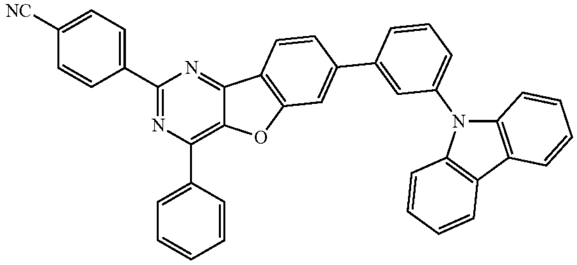
229
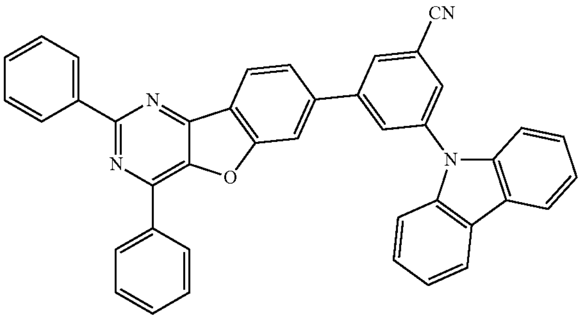
230
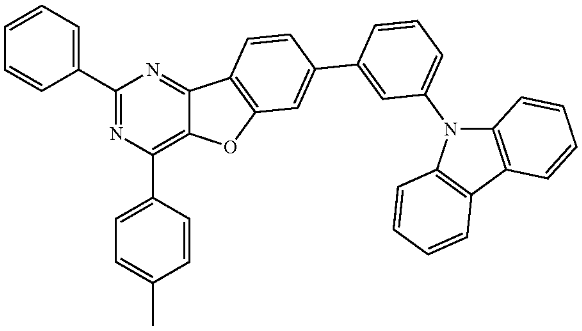

-continued
231
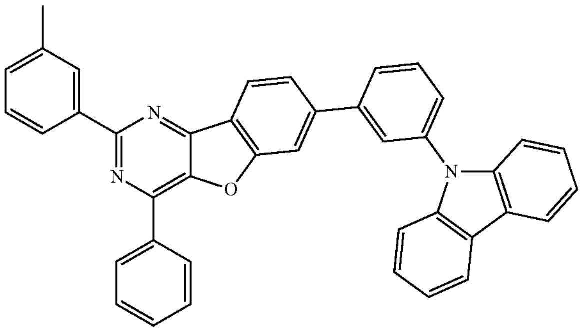
232
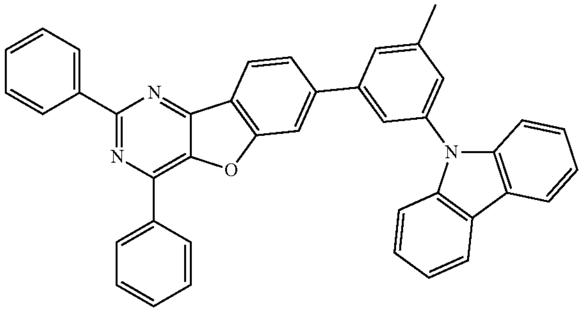
233
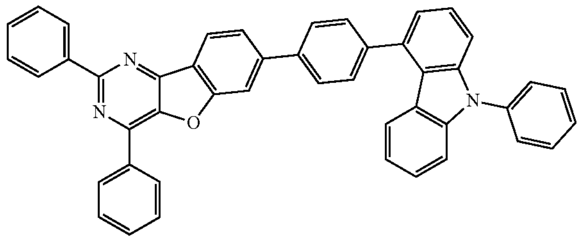
234
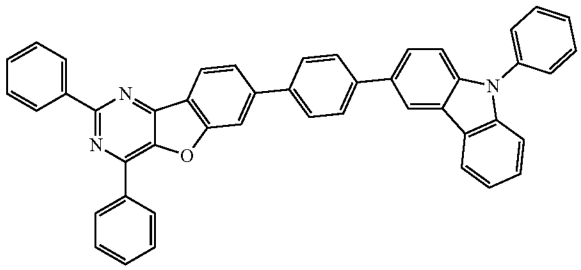
235
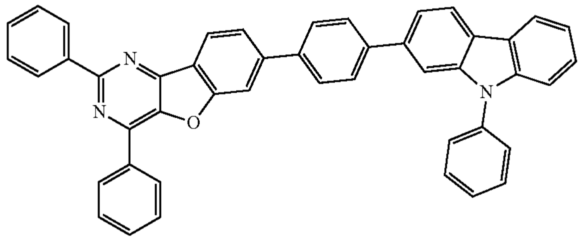
-continued
236
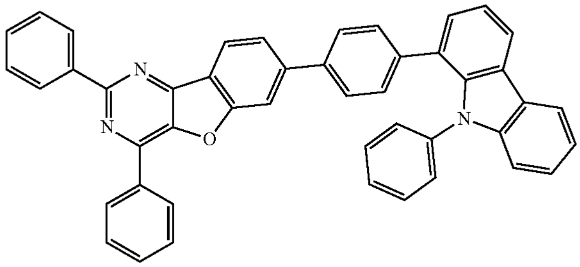
237
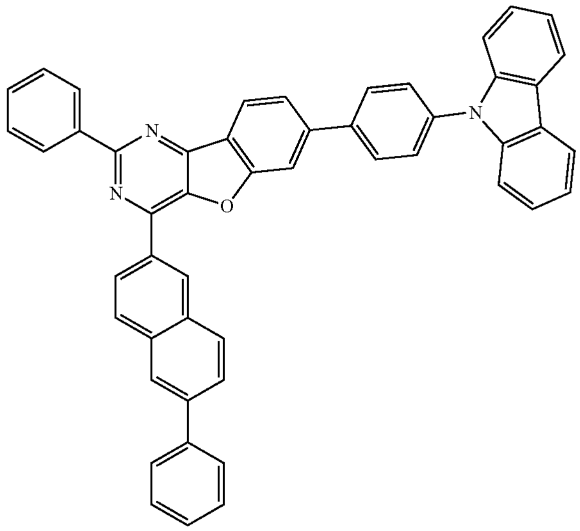
238
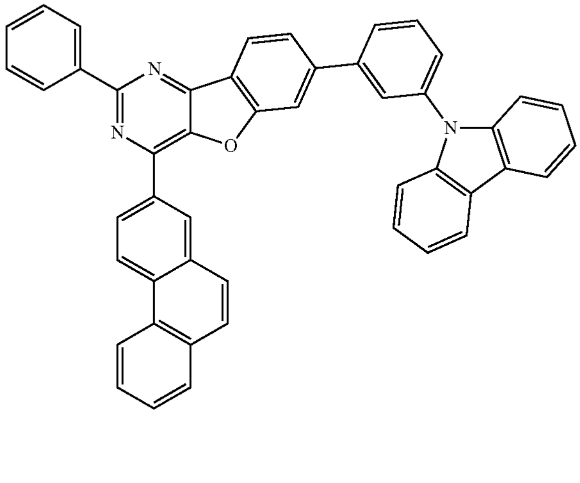

-continued
239
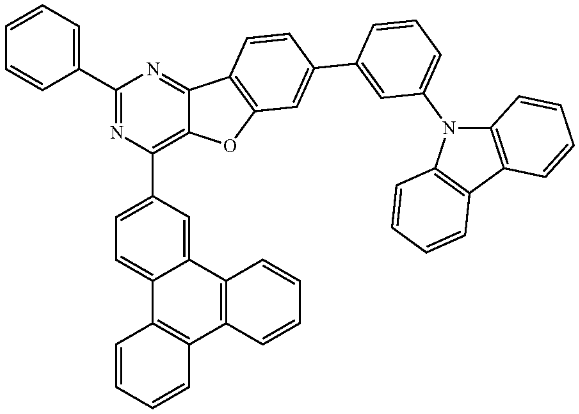
240
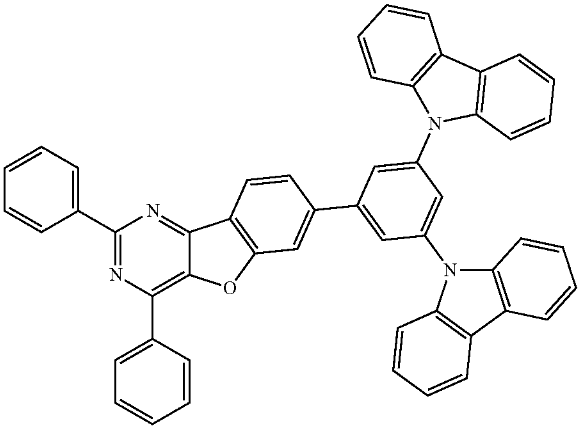
241
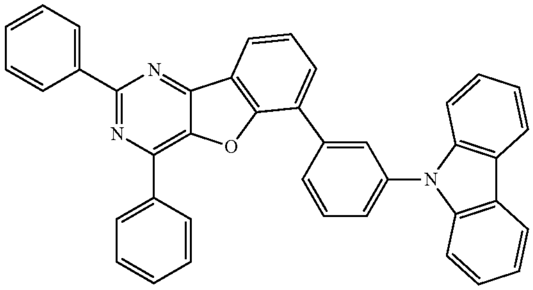
242
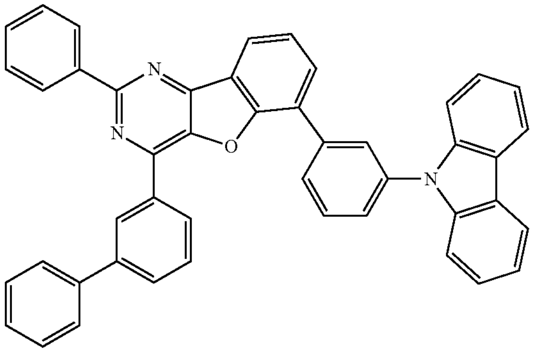
-continued
243
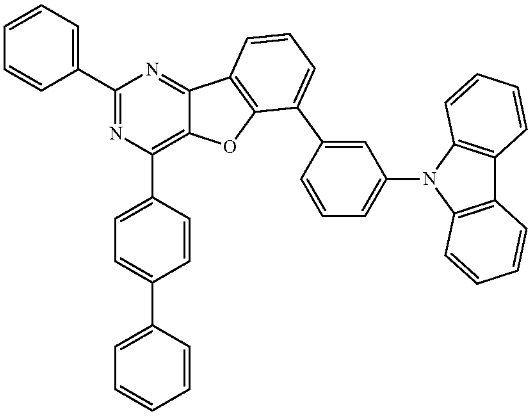
244
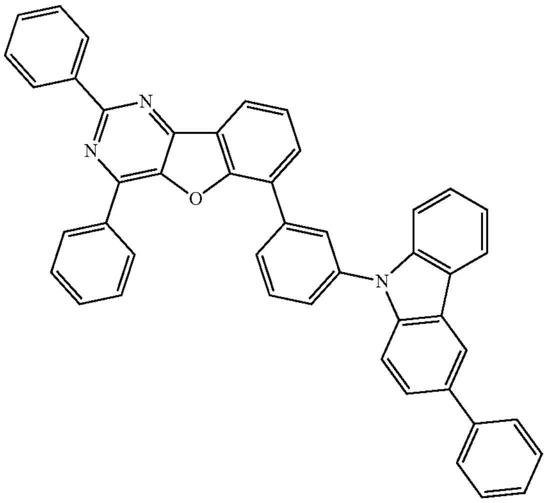
245
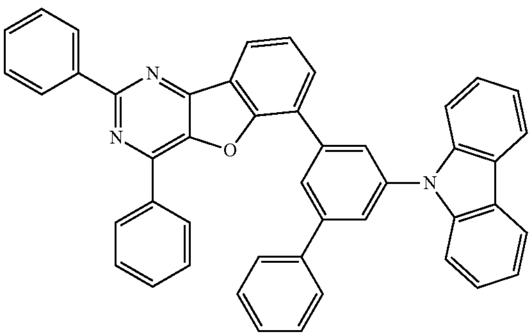

-continued
246
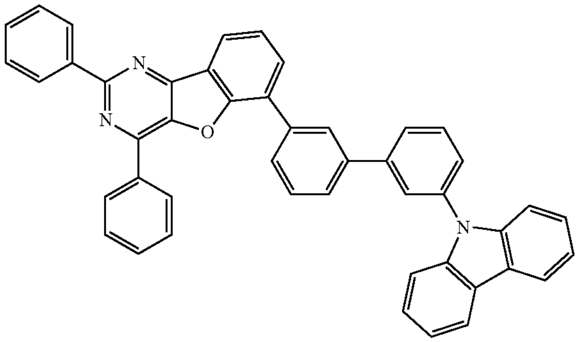
247
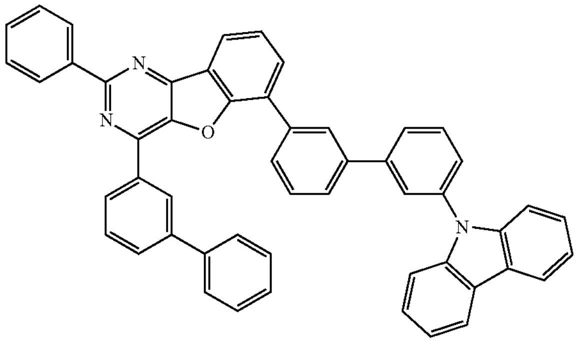
248
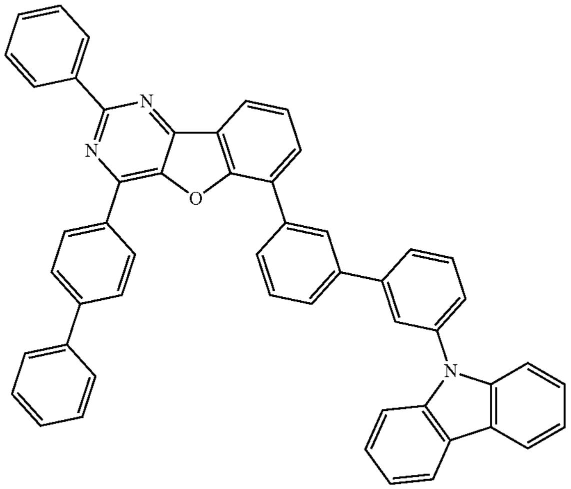
-continued
249
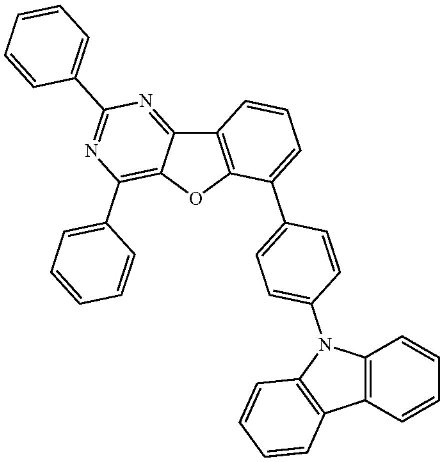
250
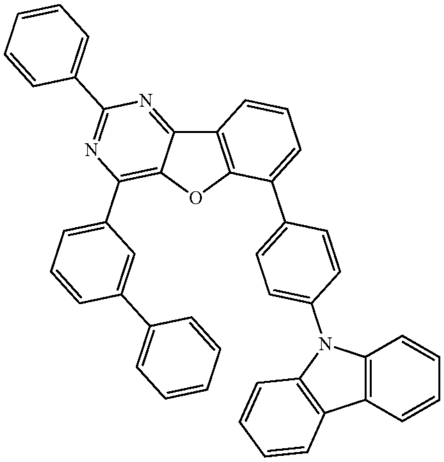
251
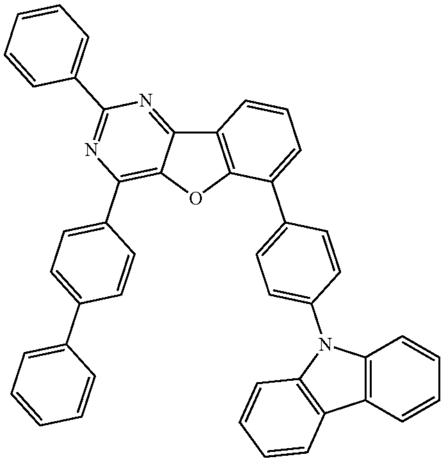

252
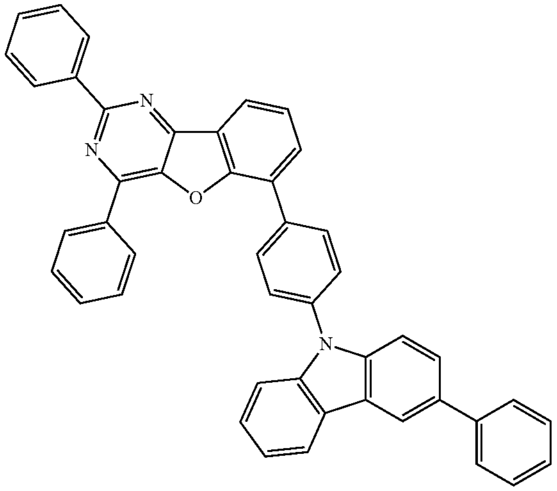
253
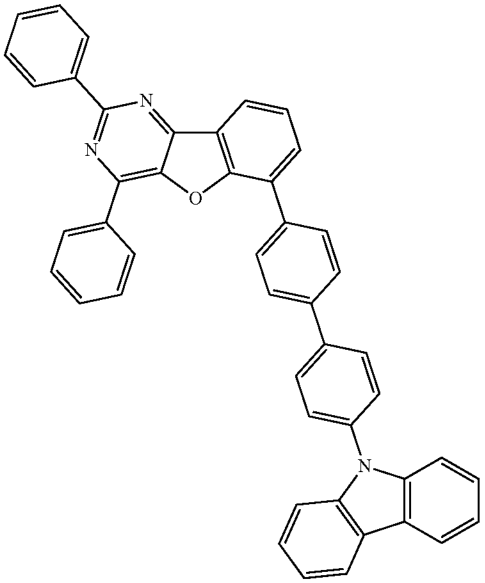
254
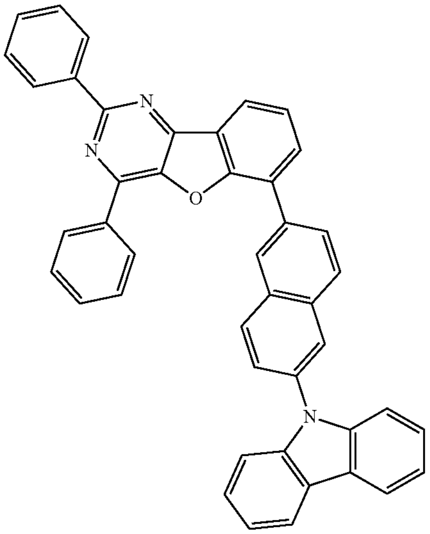
255
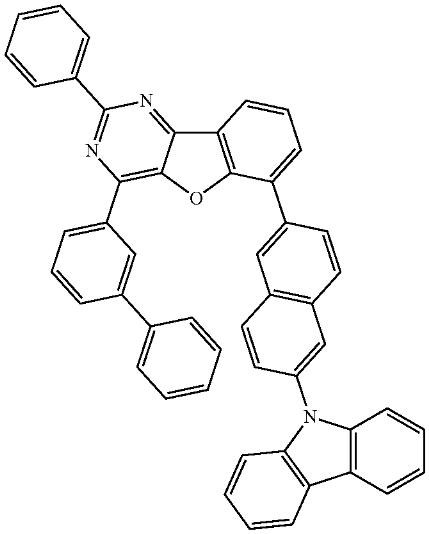
256
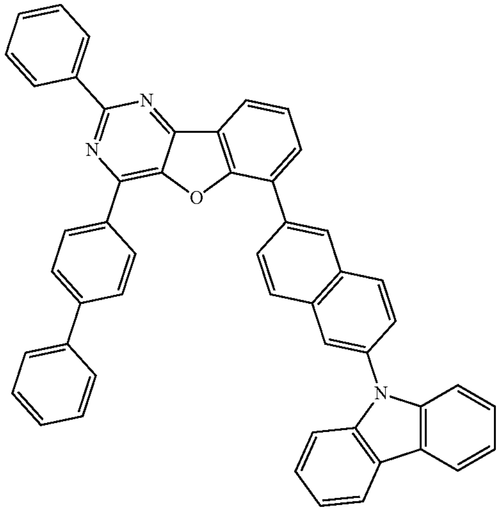
257
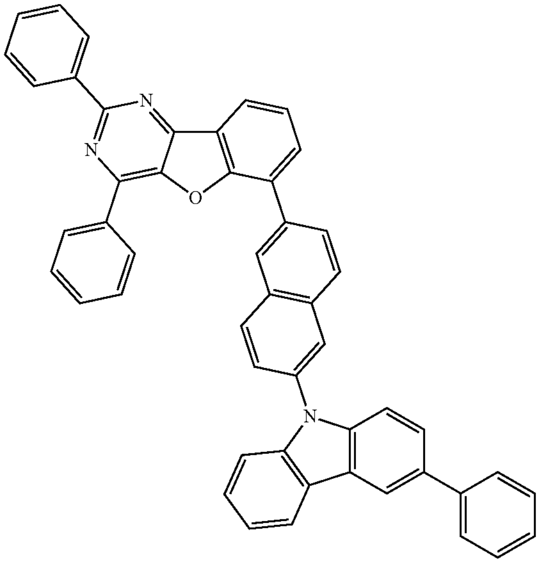

-continued
258
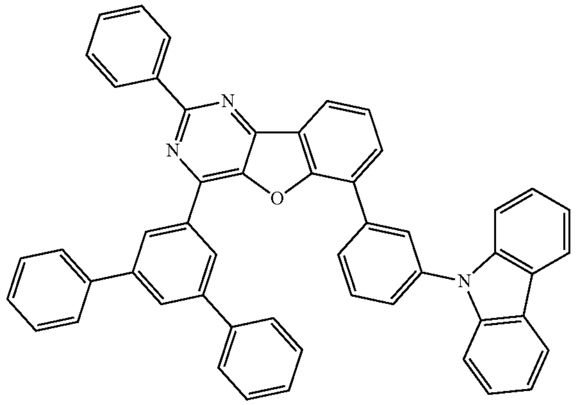
259
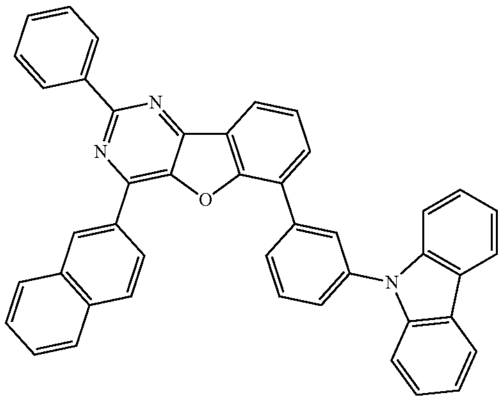
260
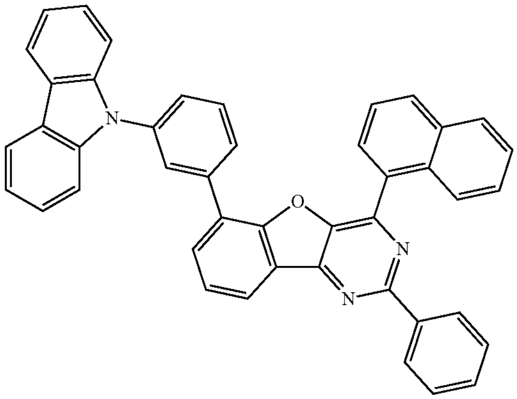
-continued
261
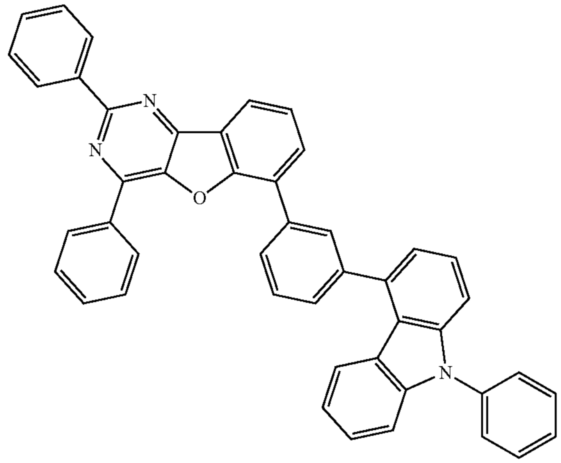
262
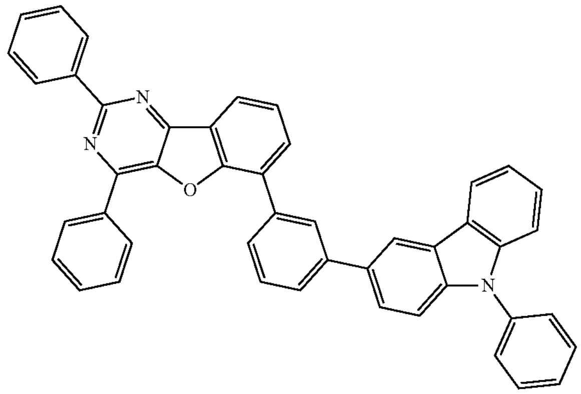
263
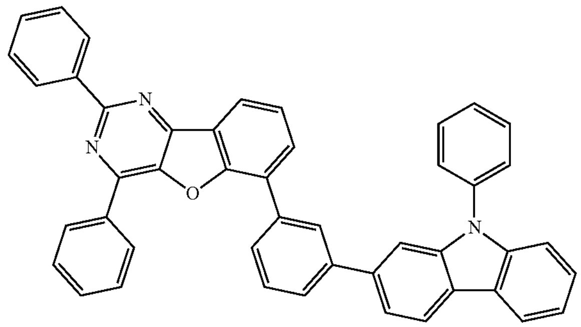

-continued
264
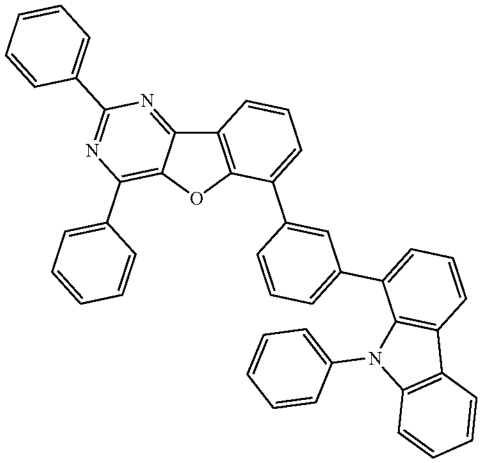
265
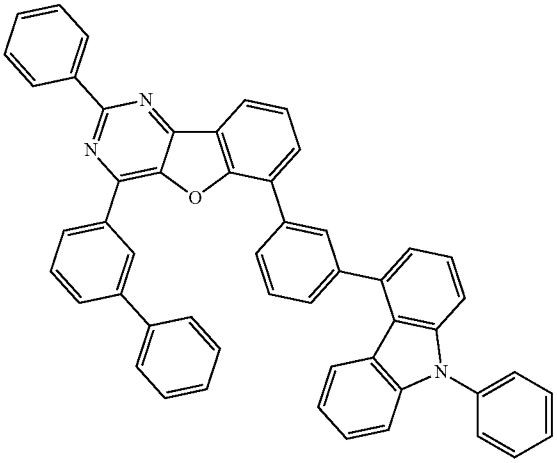
266
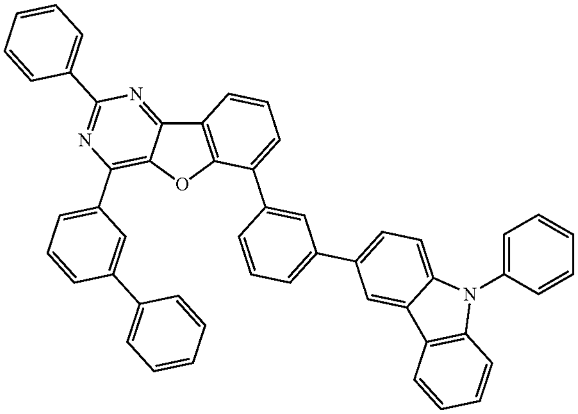
-continued
267
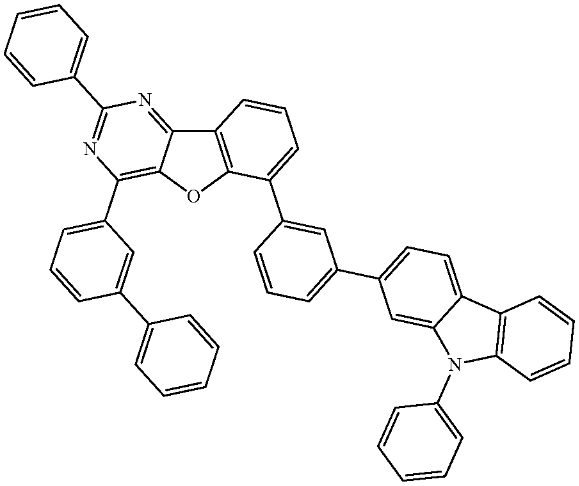
268
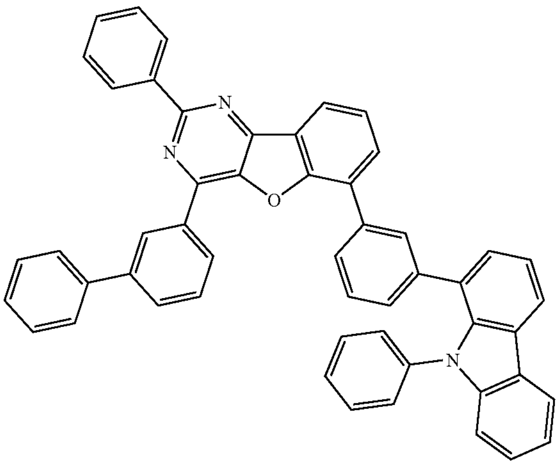
269
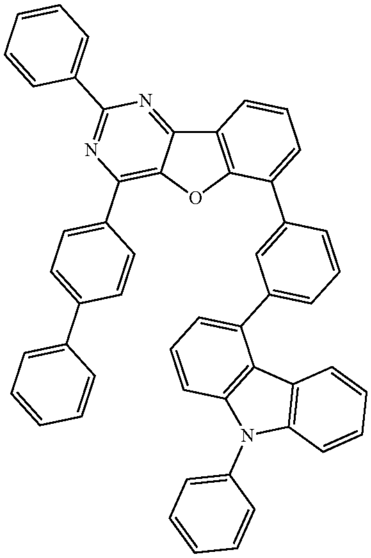

-continued
270
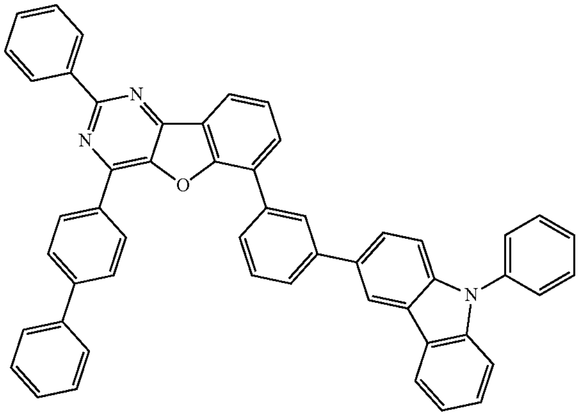
271
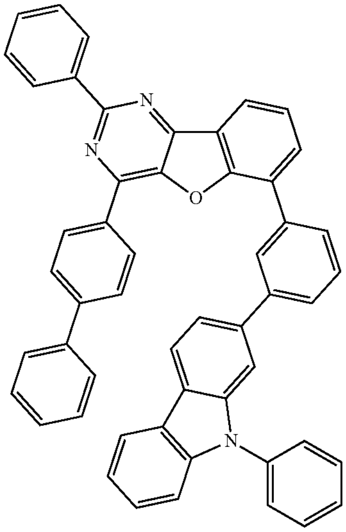
272
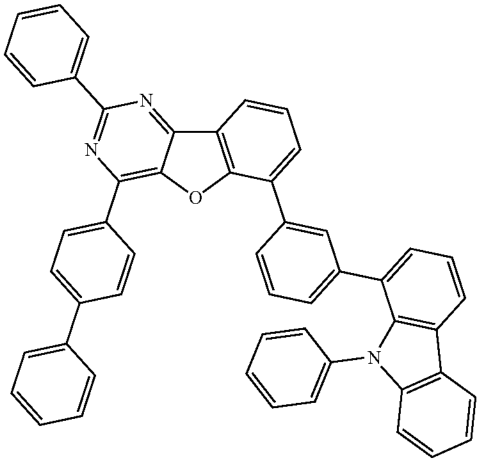
-continued
273
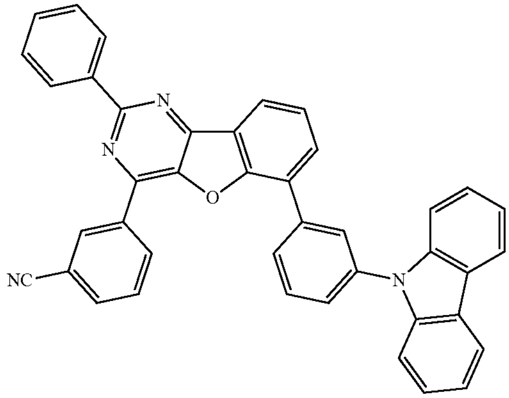
274
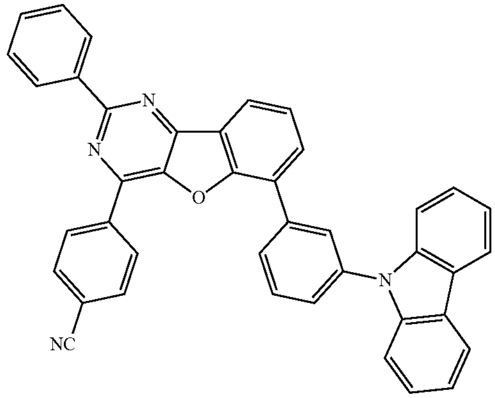
275
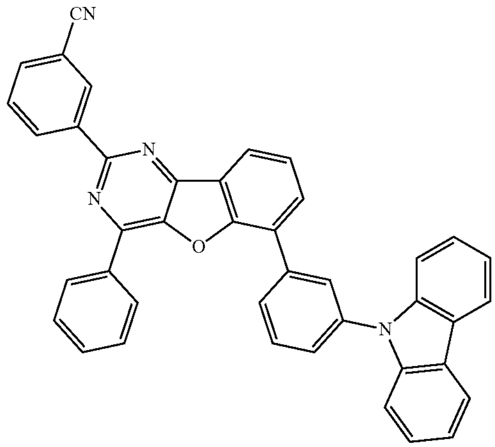

-continued
276
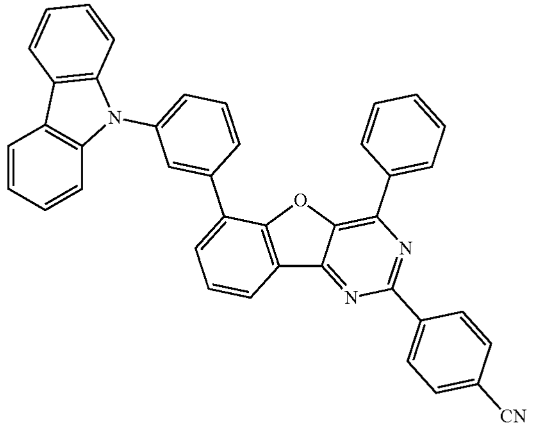
277
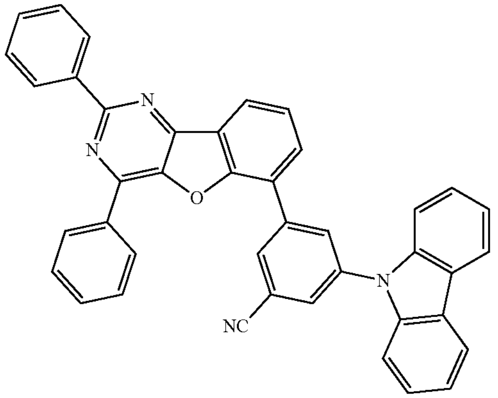
278
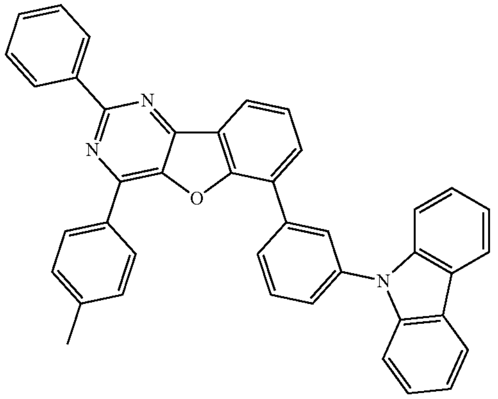
-continued
279
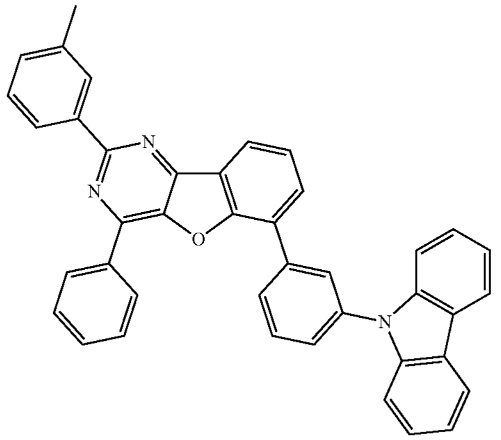
280
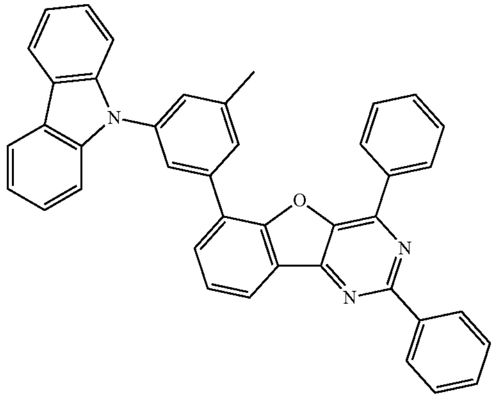
281
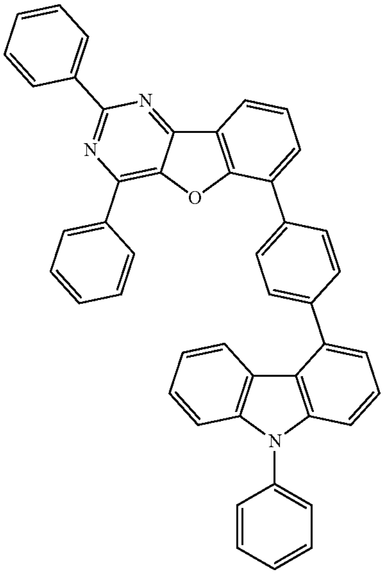

-continued
282
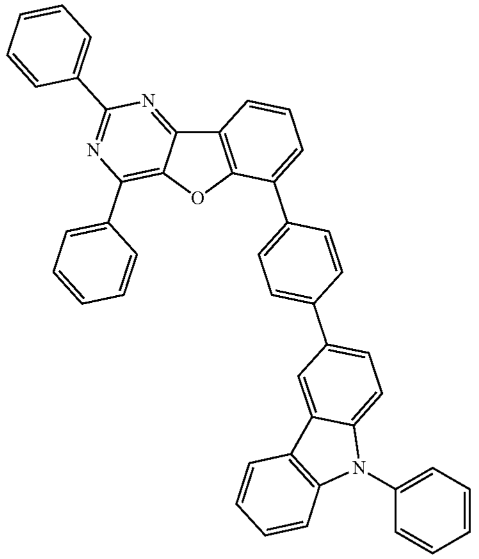
285
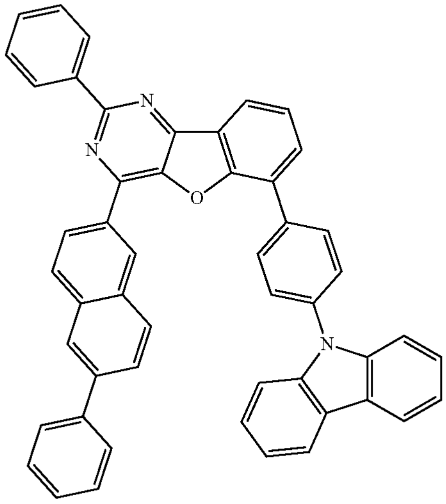
283
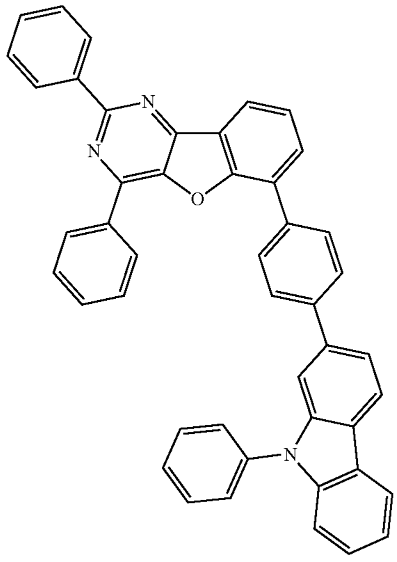
286
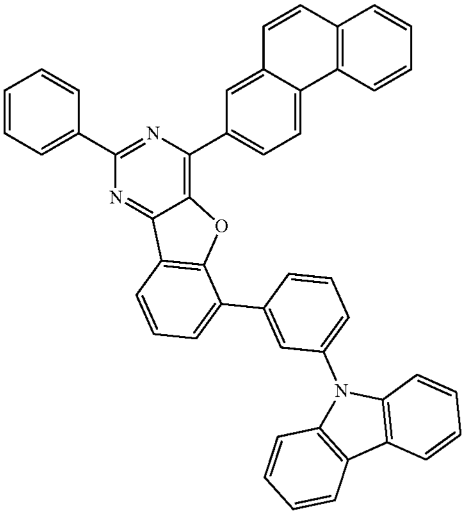
284
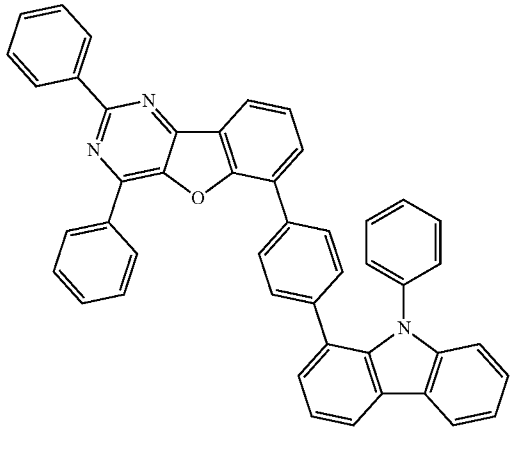
287
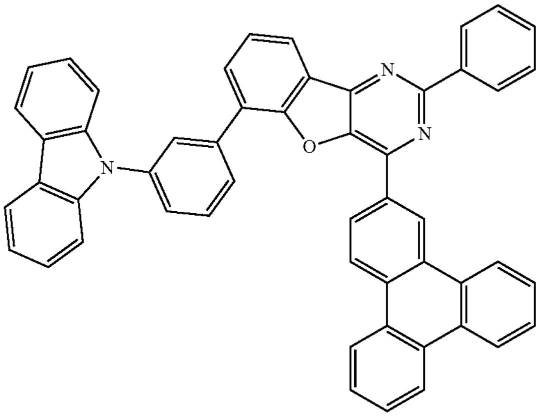

288
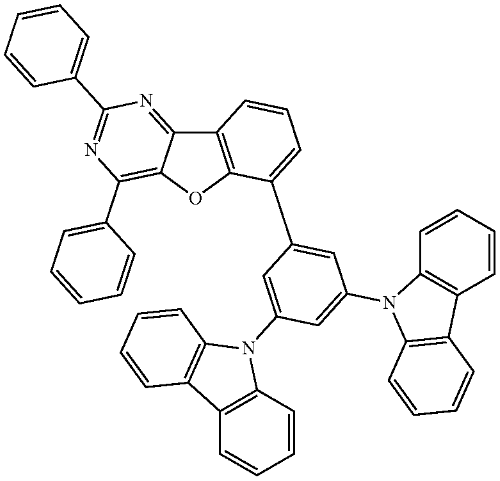
289
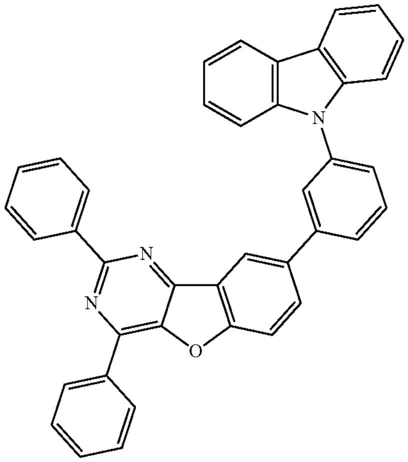
290
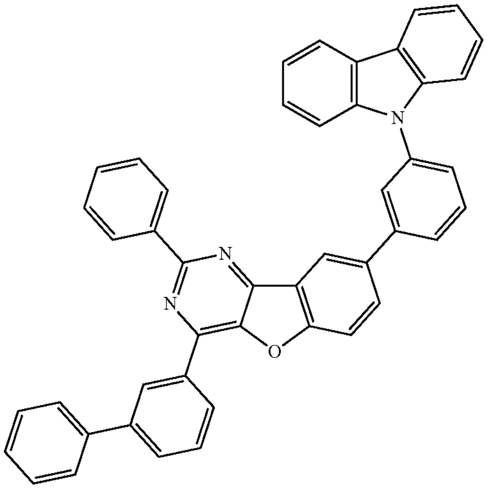
291
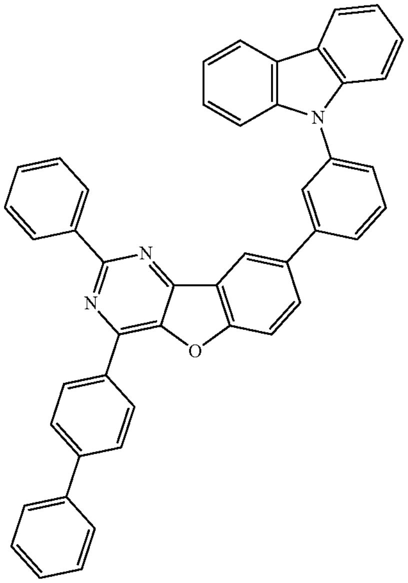
292
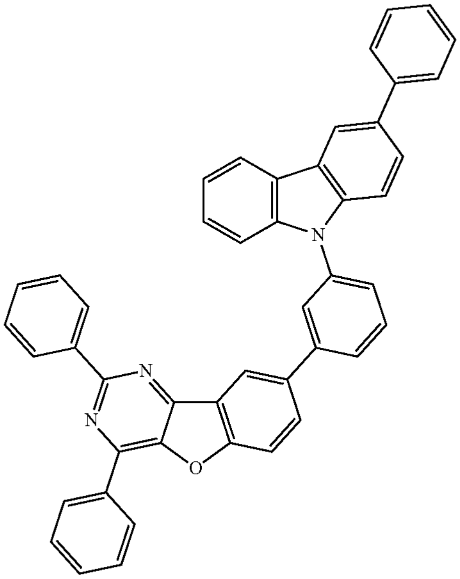
293
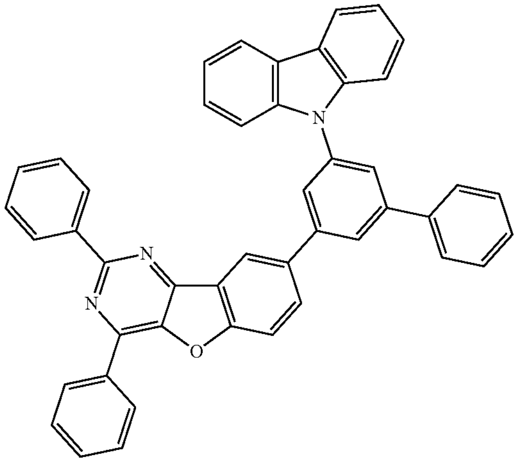

-continued
294
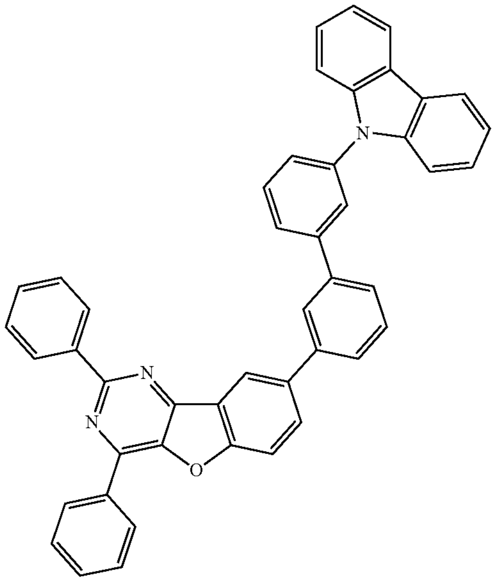
295
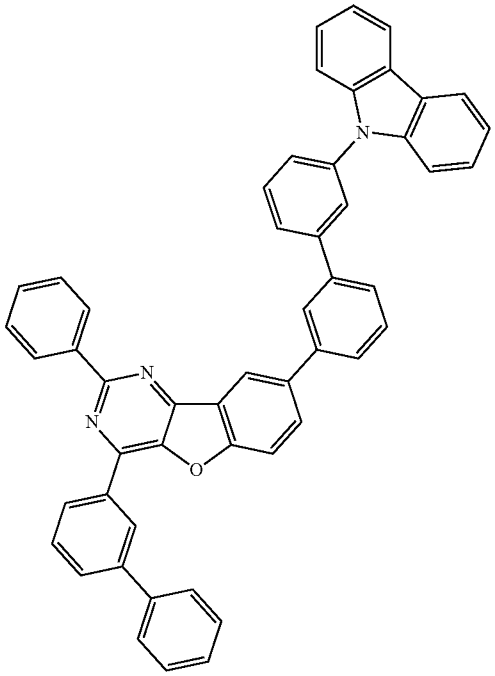
-continued
296
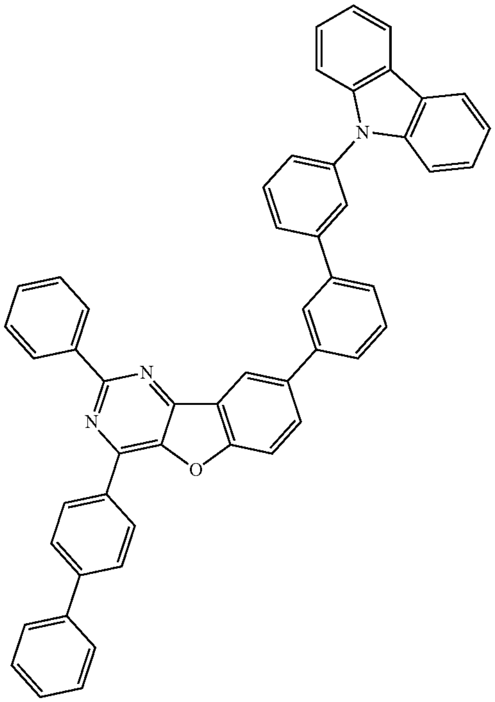
297
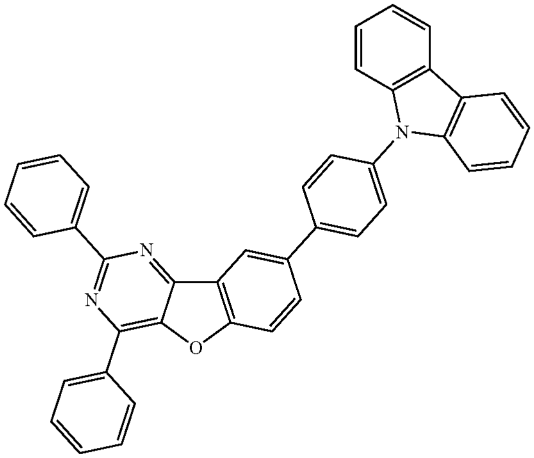

-continued
298
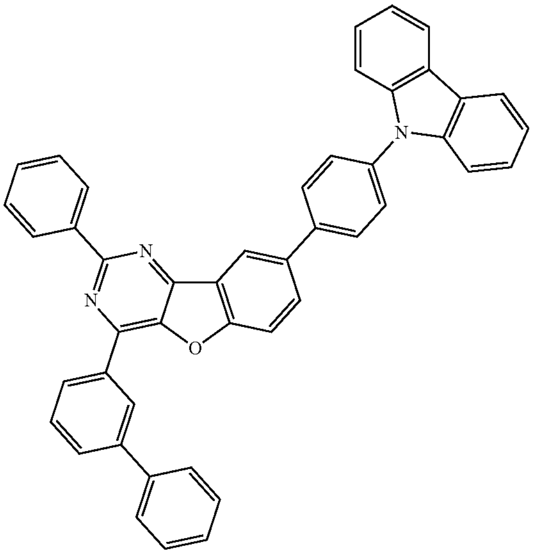
299
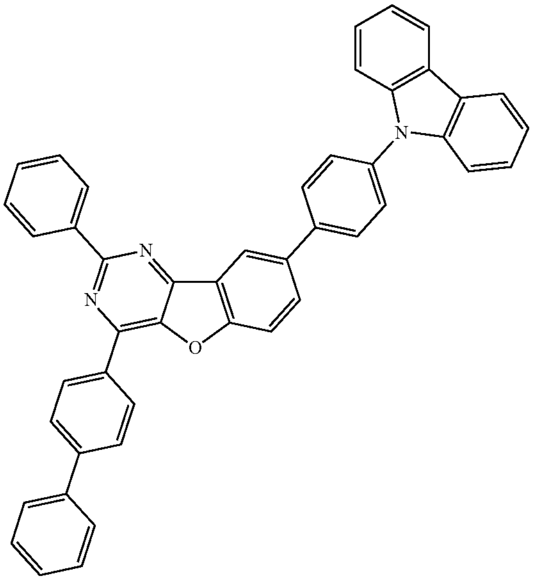
-continued
300
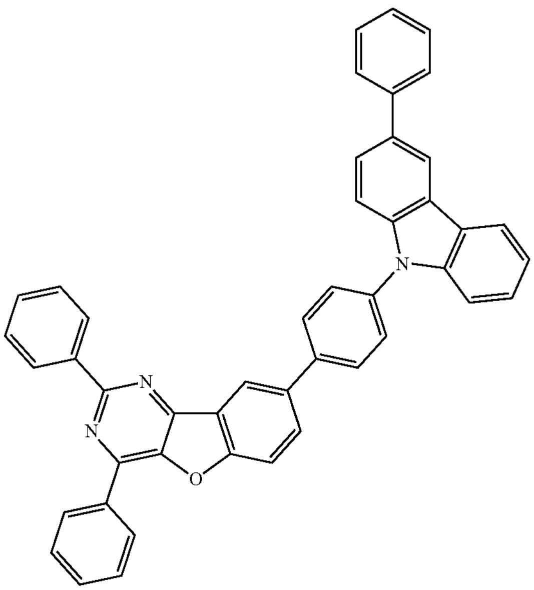
301
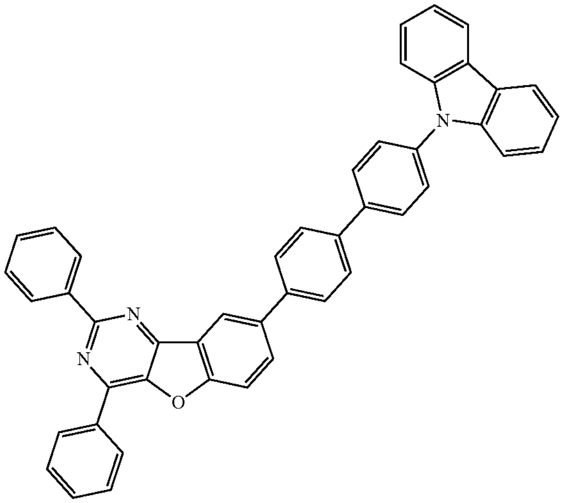
302
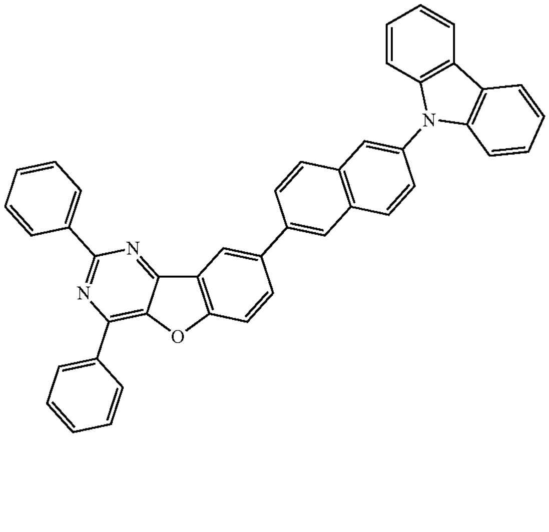

-continued
303
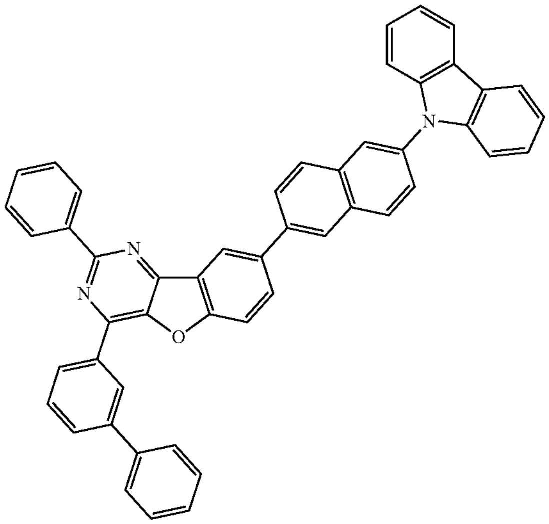
304
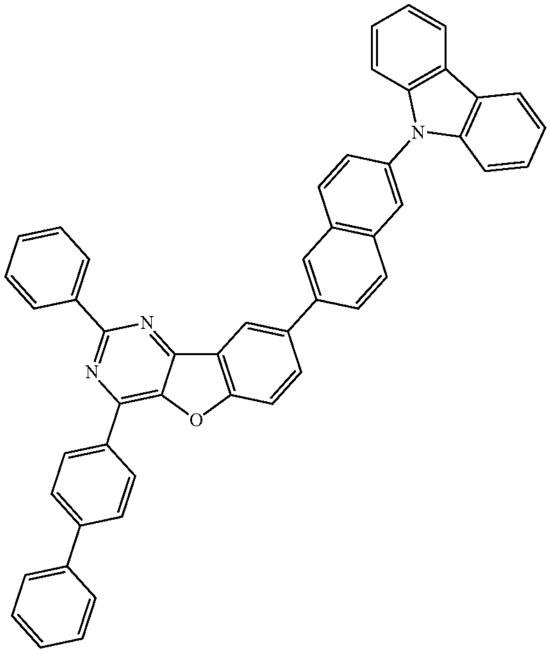
-continued
305
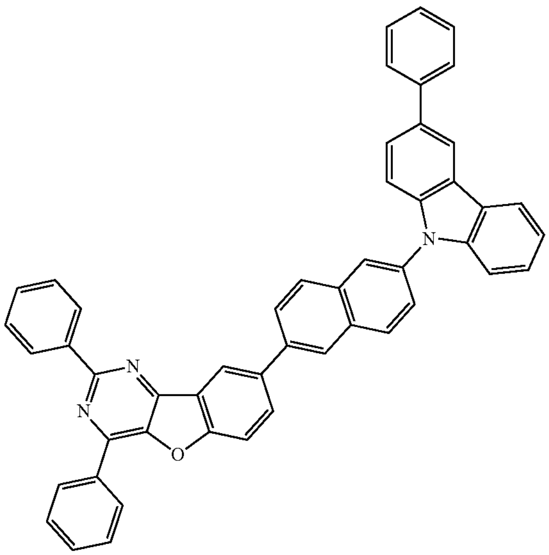
306
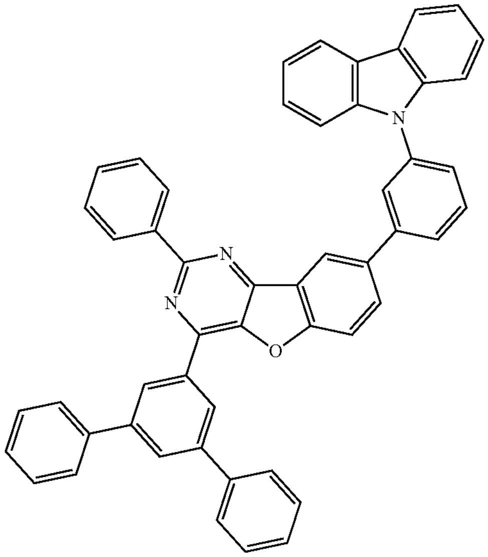
307
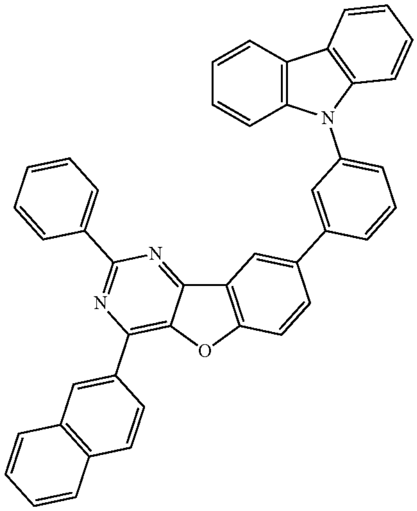

-continued
308
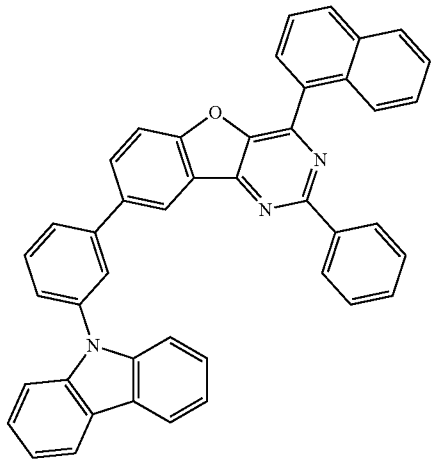
309
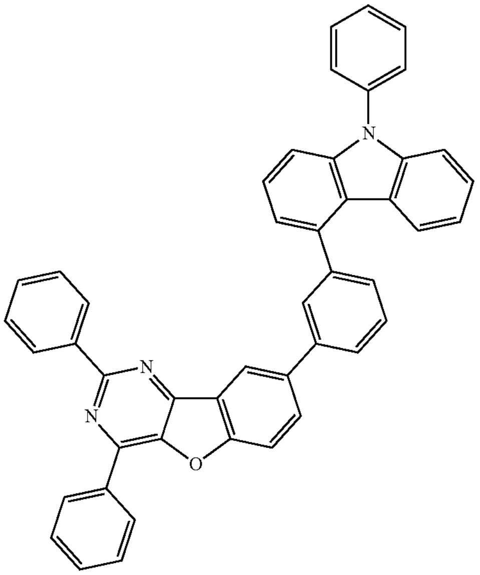
310
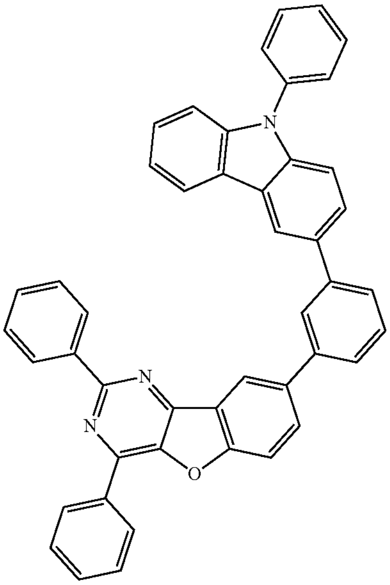
-continued
311
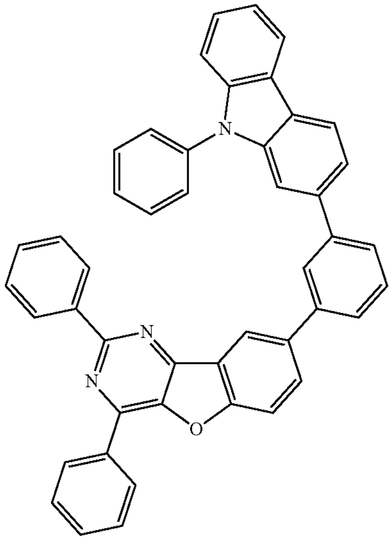
312
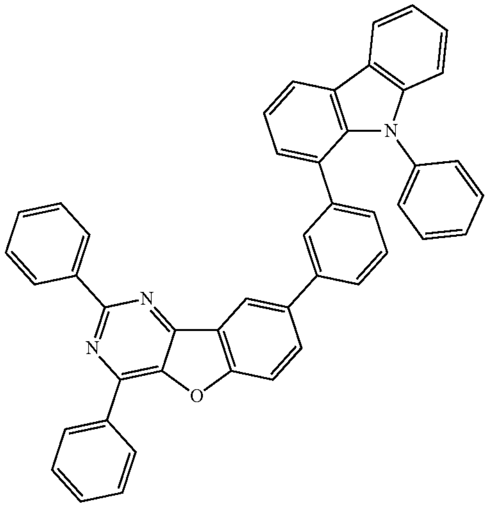

-continued
313
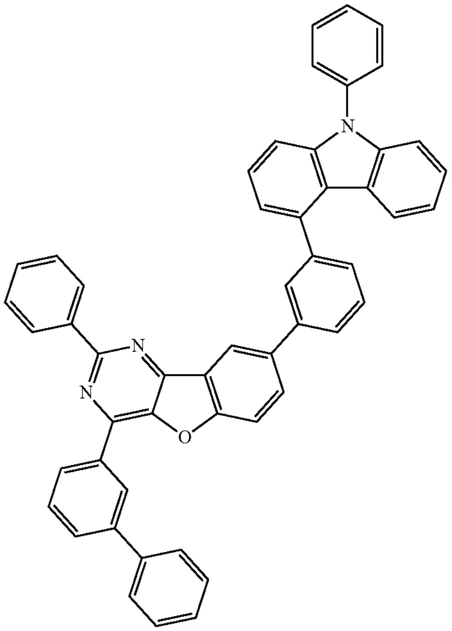
314
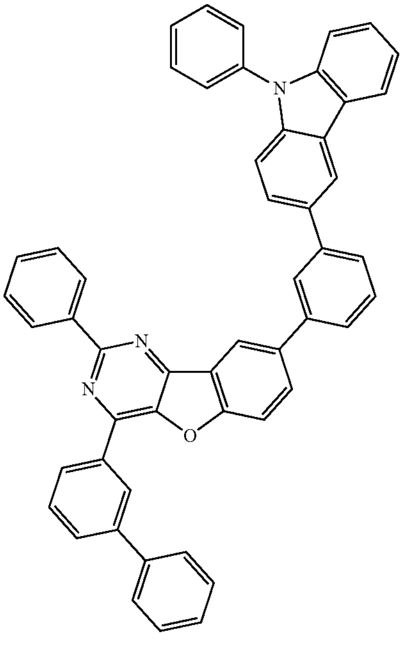
-continued
315
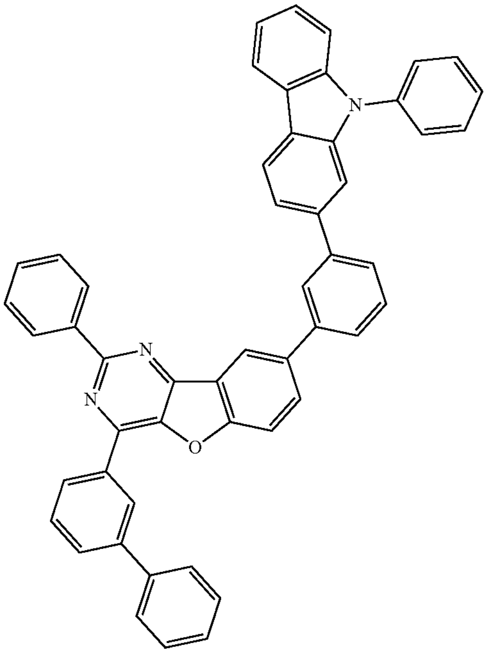
316
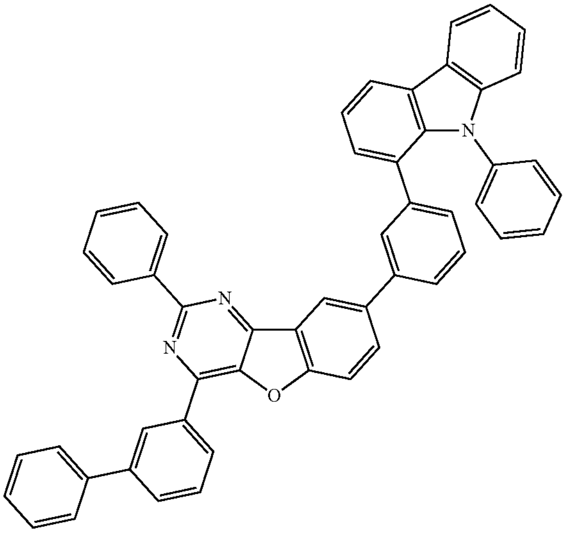

-continued
317
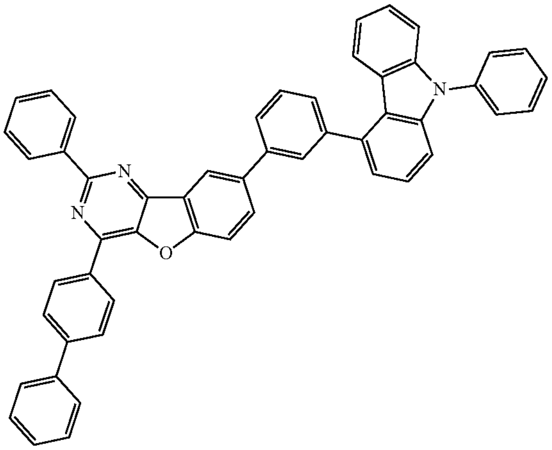
318
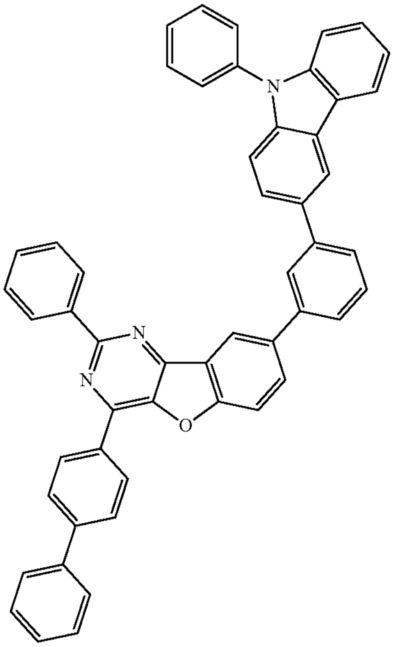
319
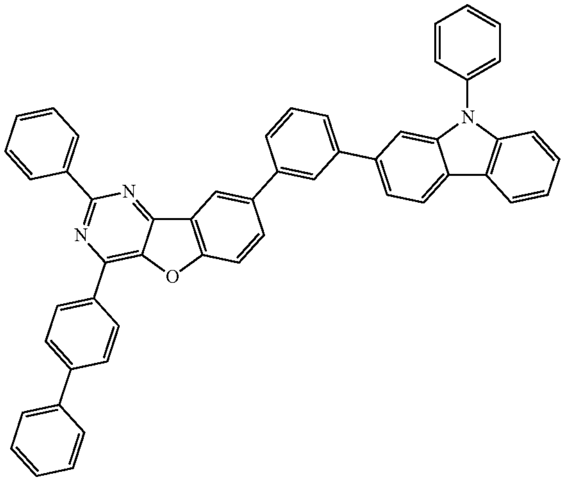
-continued
320
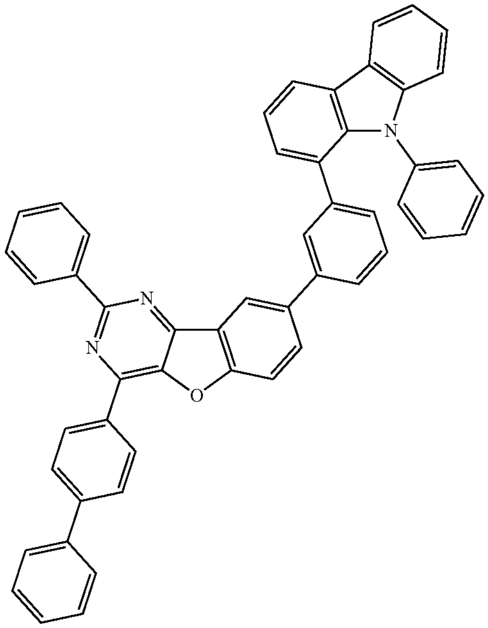
321
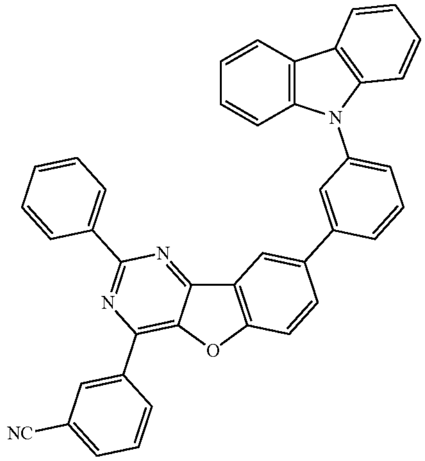
322
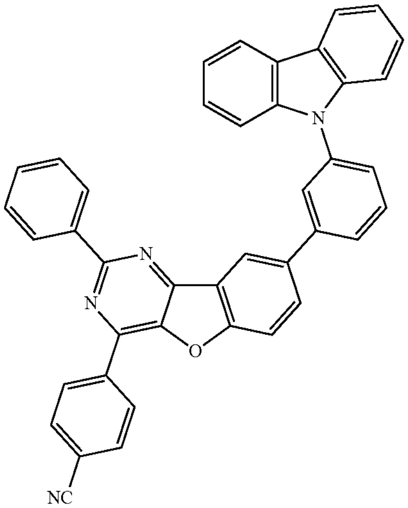

-continued
323
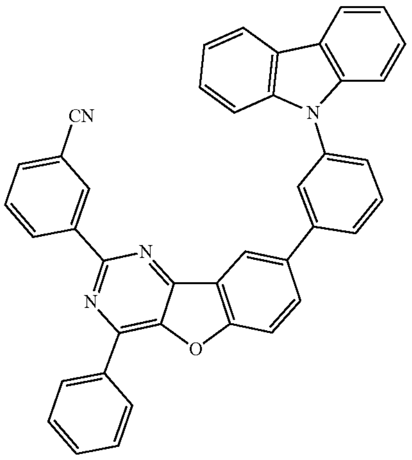
324
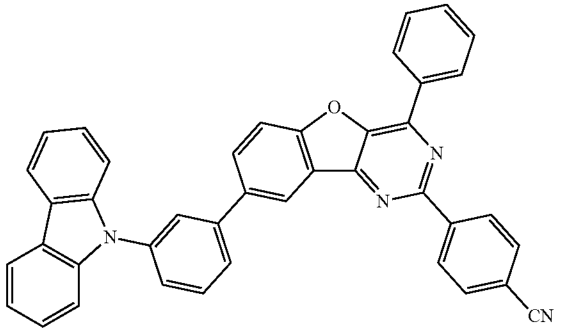
325
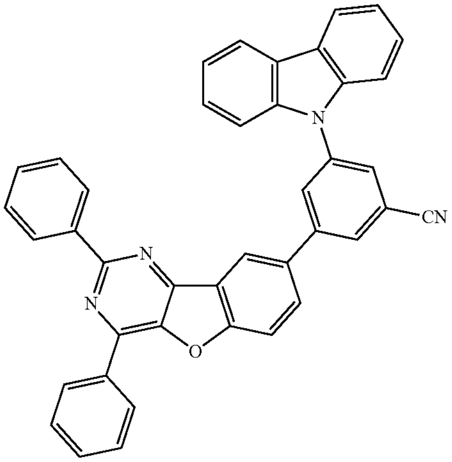
-continued
326
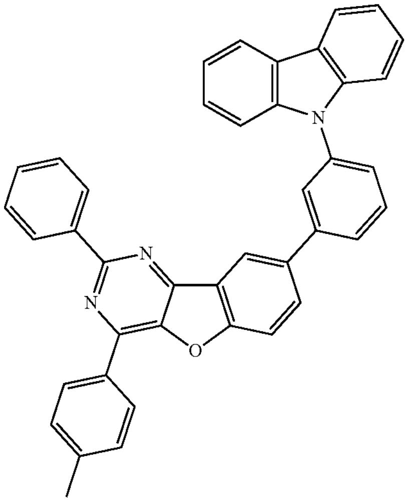
327
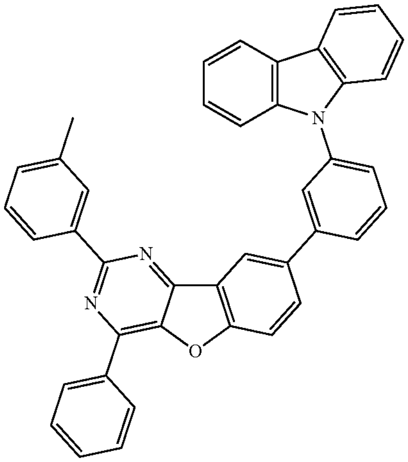
328
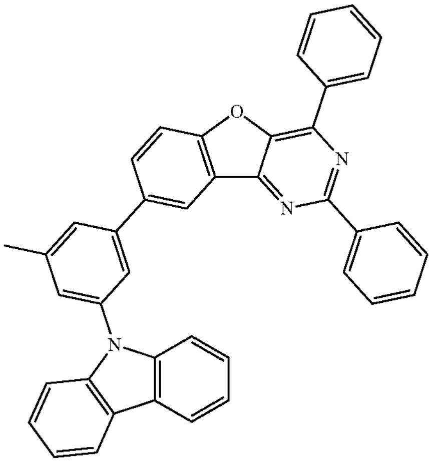

-continued
329
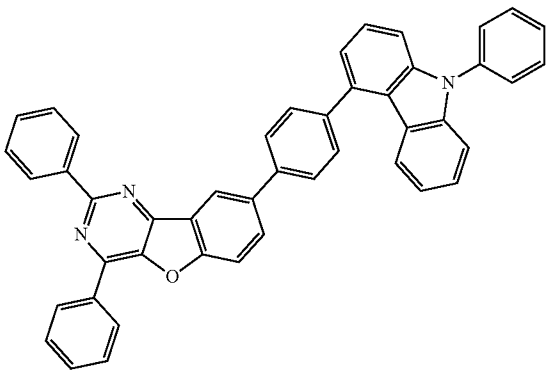
330
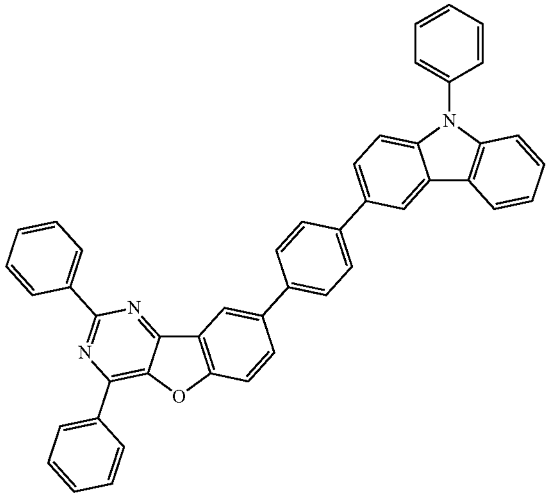
331
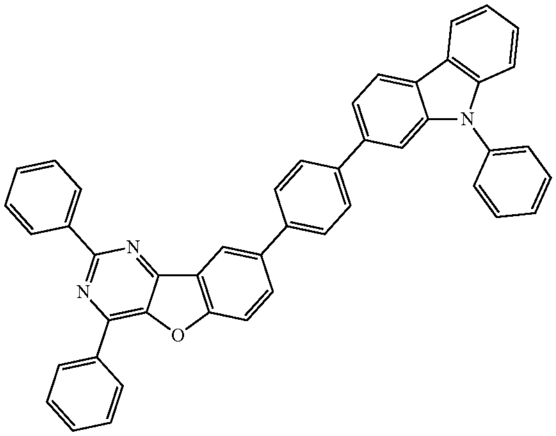
-continued
332
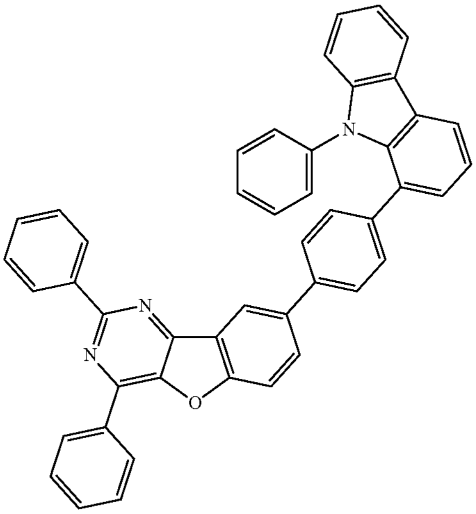
333
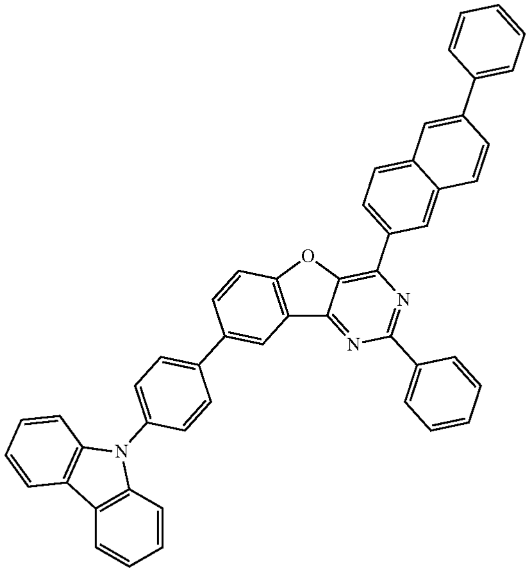
334
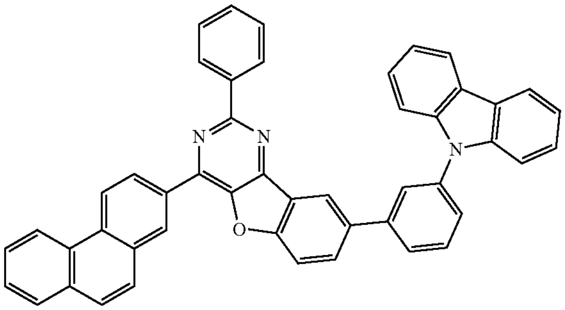

-continued
335
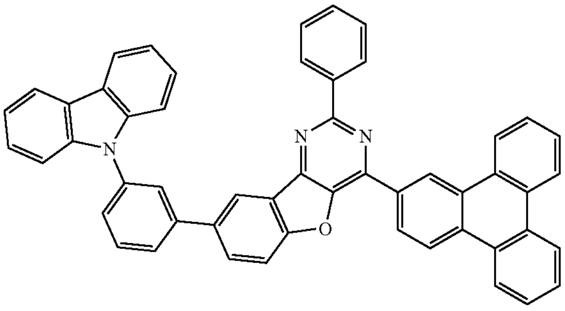
336
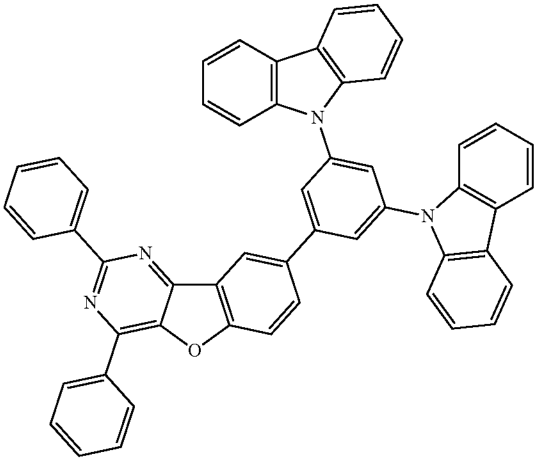
337
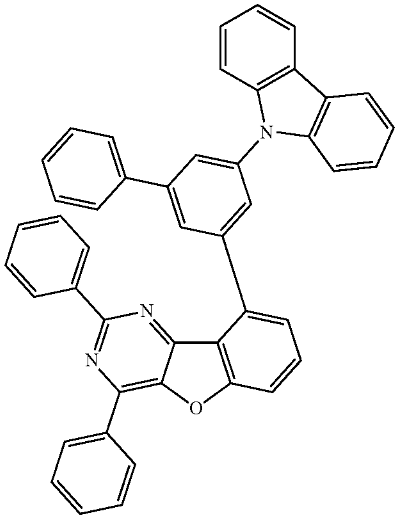
-continued
338
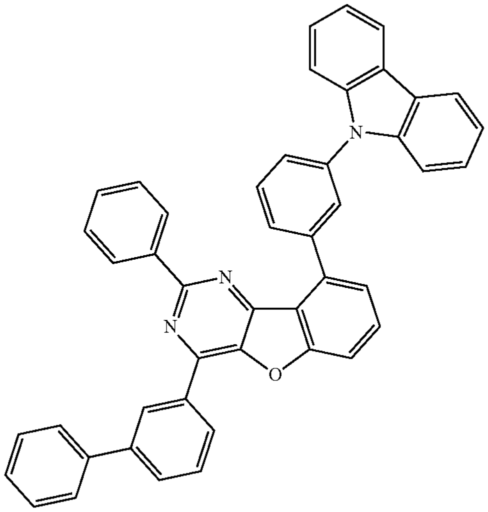
339
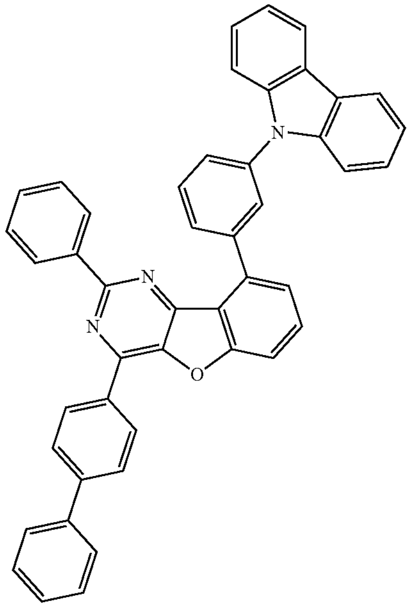
340
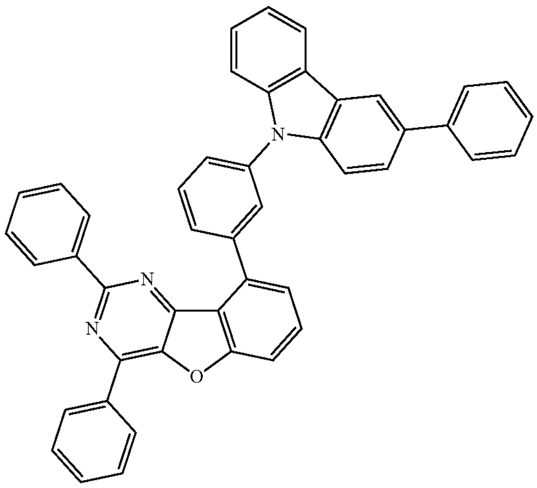

-continued
341
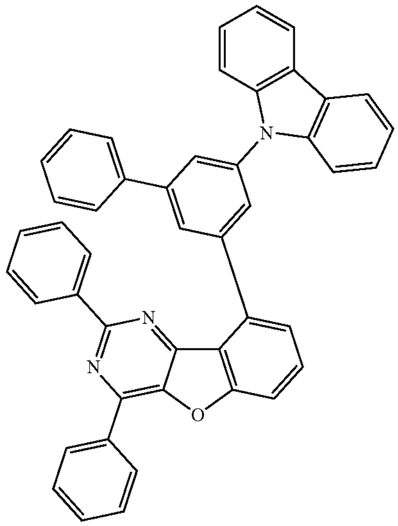
342
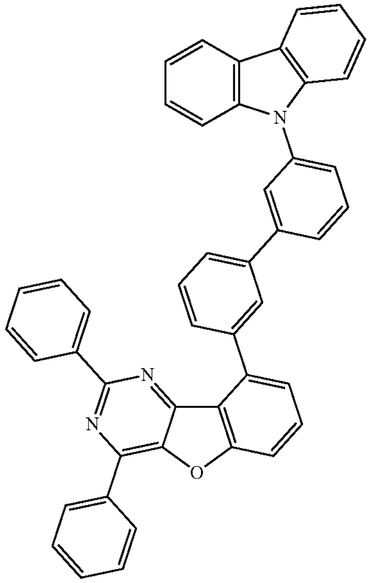
-continued
343
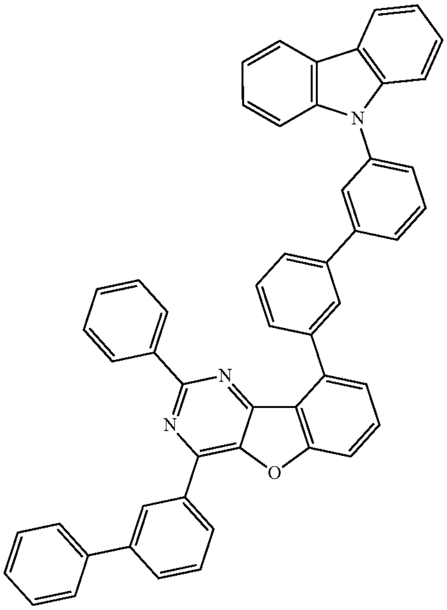
344
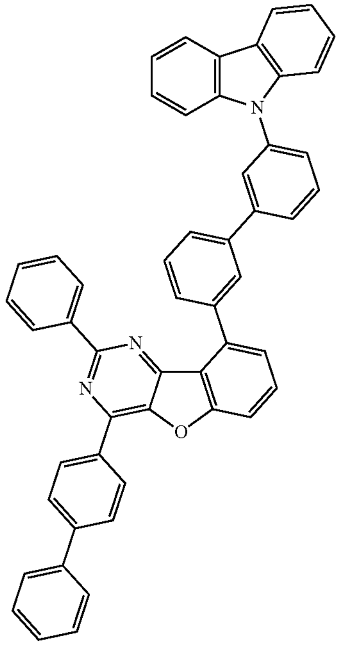

-continued
345
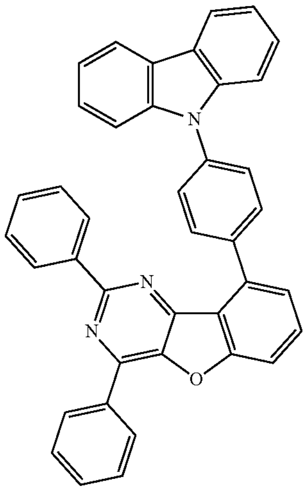
346
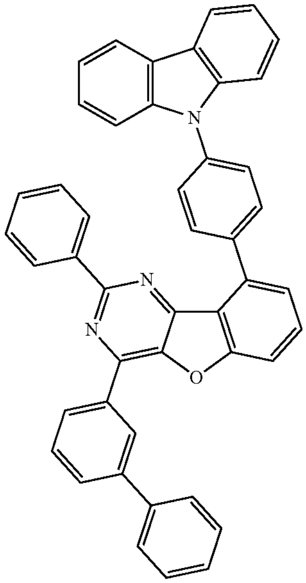
-continued
347
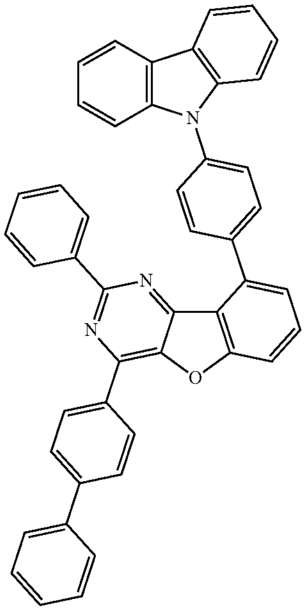
348
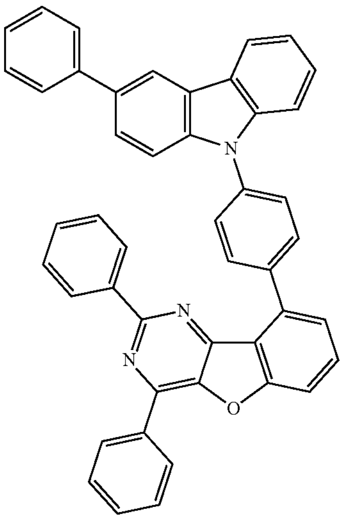

349
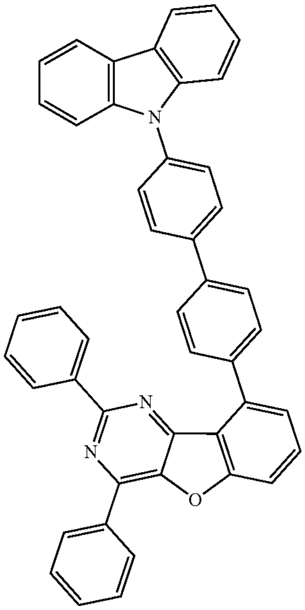
350
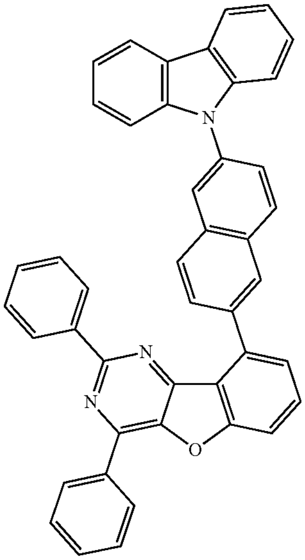
351
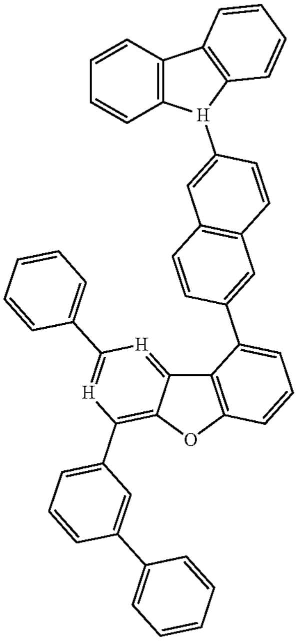
352
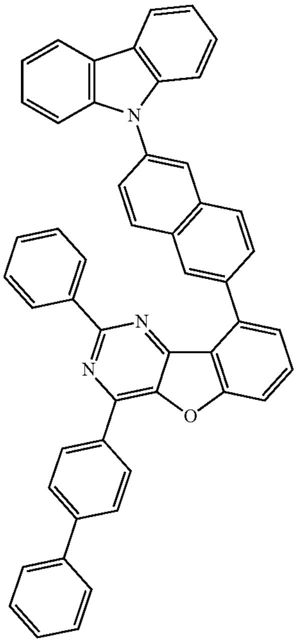

-continued
353
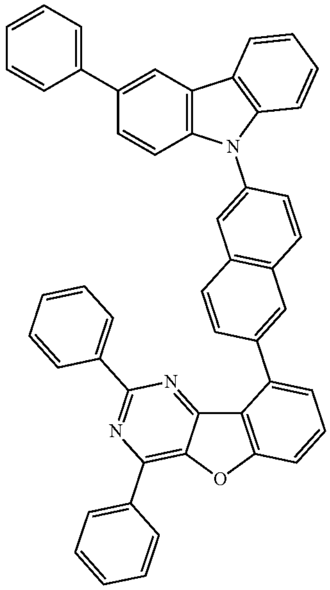
354
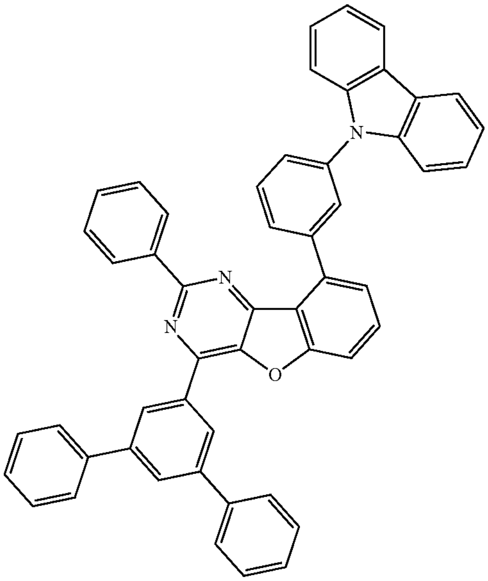
-continued
355
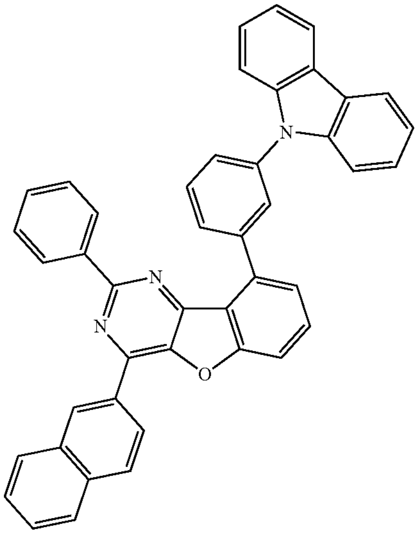
356
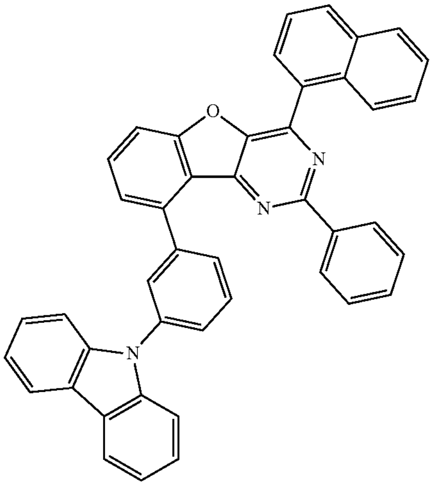
357
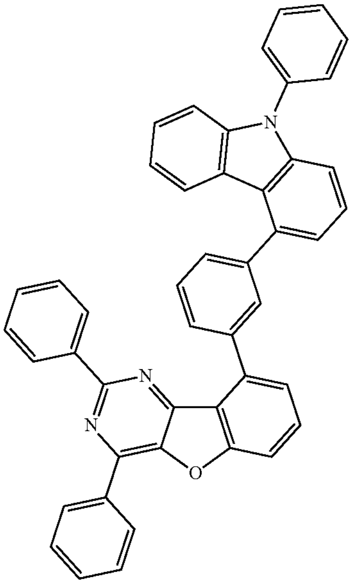

-continued
358
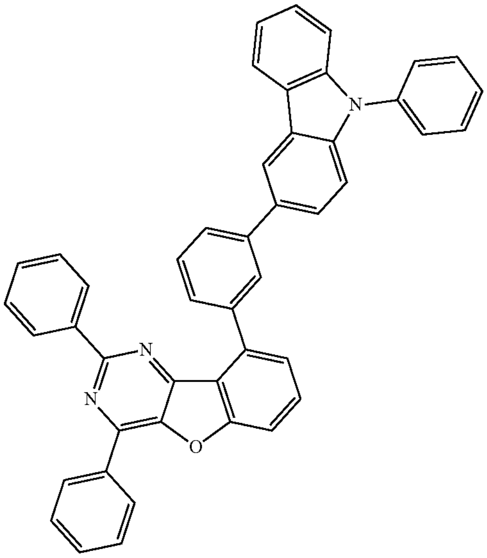
359
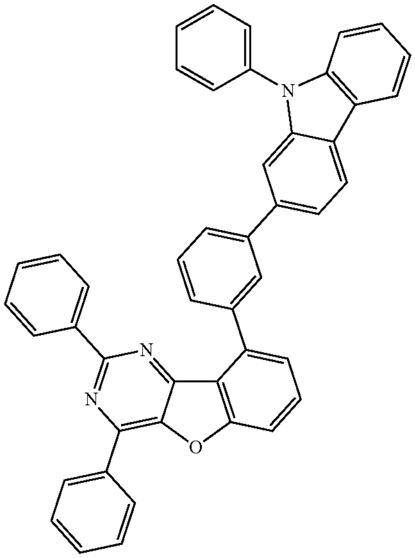
360
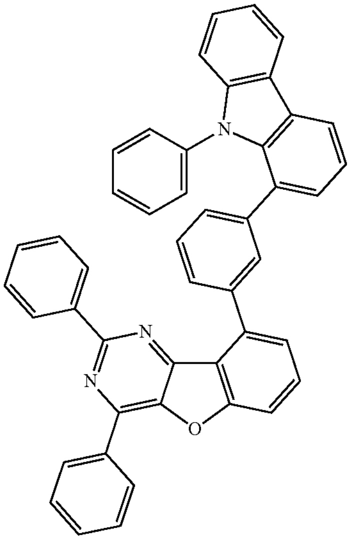
-continued
361
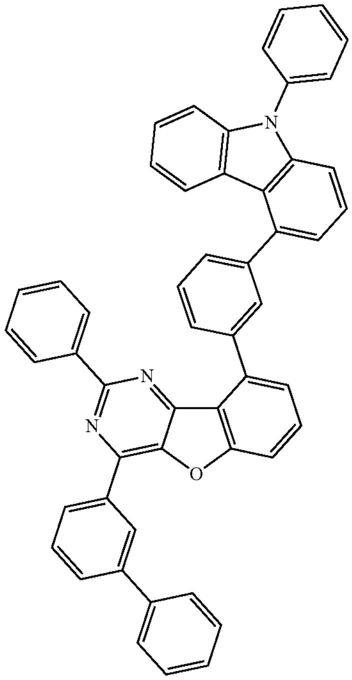
362
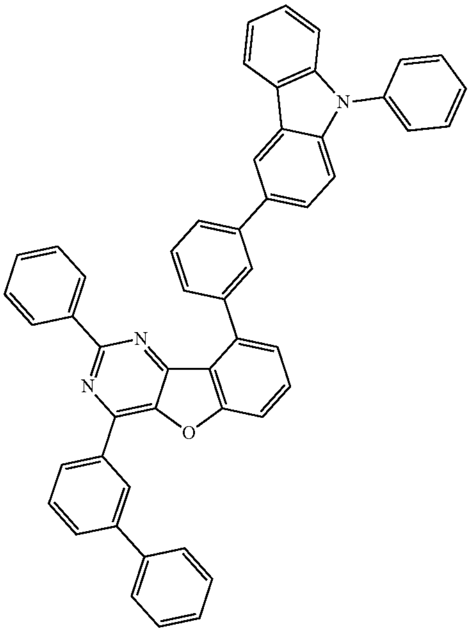

-continued
363
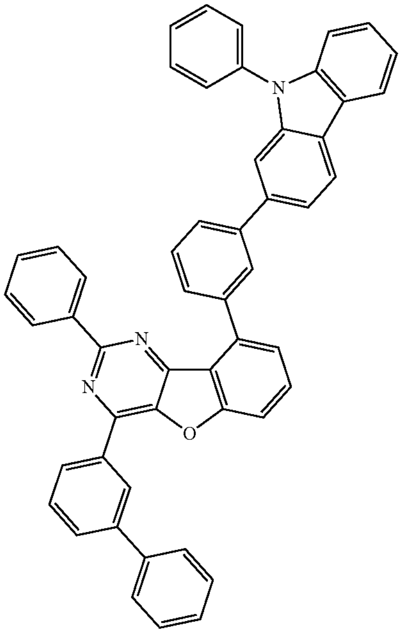
365
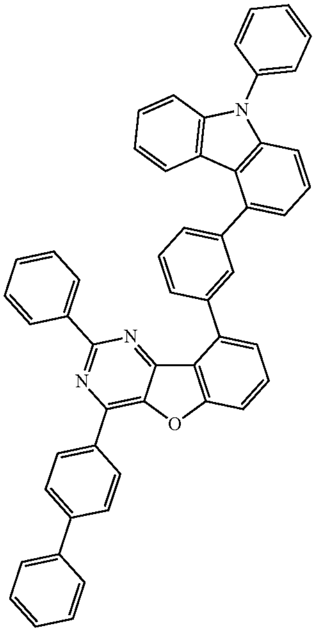
364
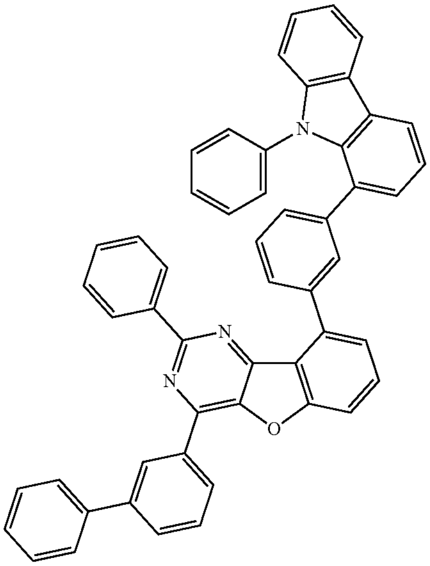
366
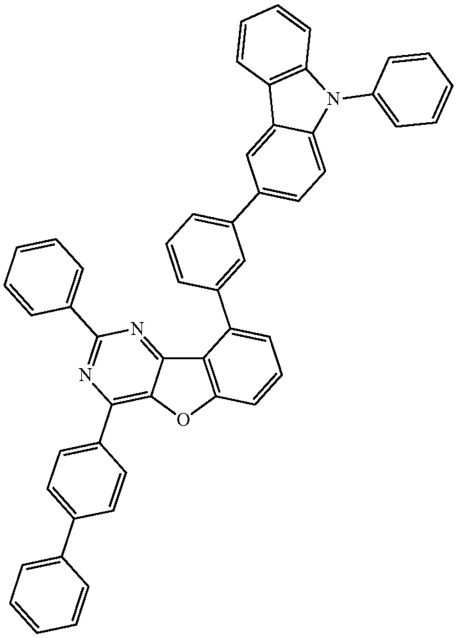

-continued
367
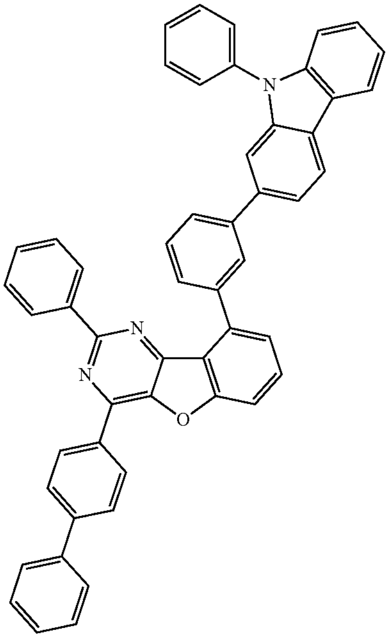
368
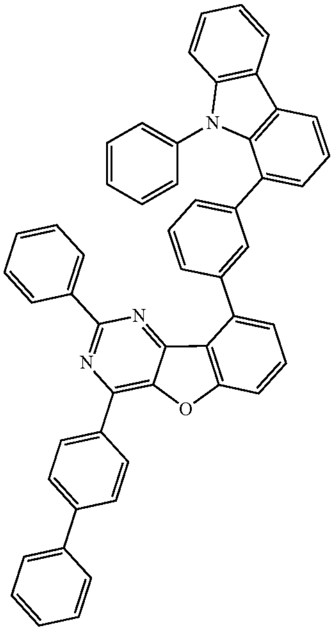
-continued
369
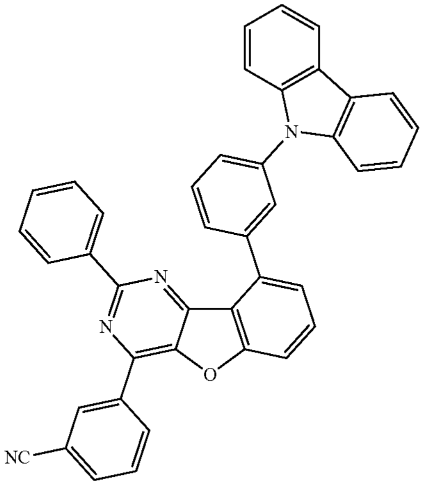
370
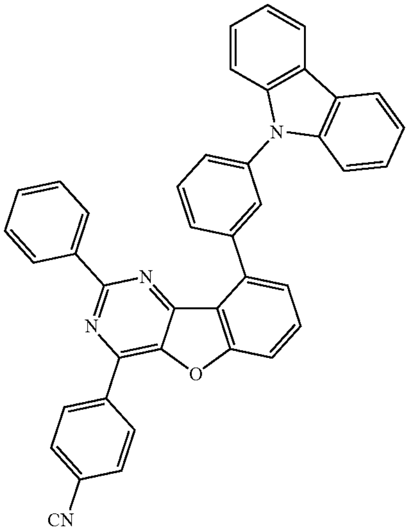
371
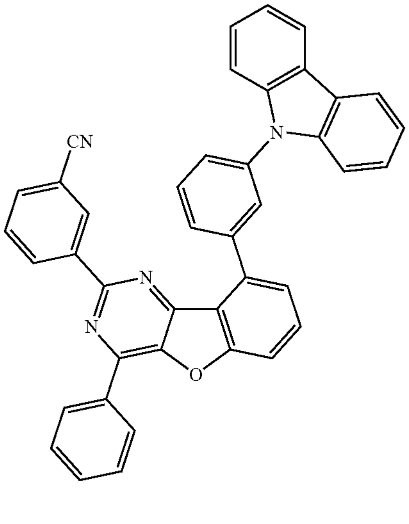

-continued
372
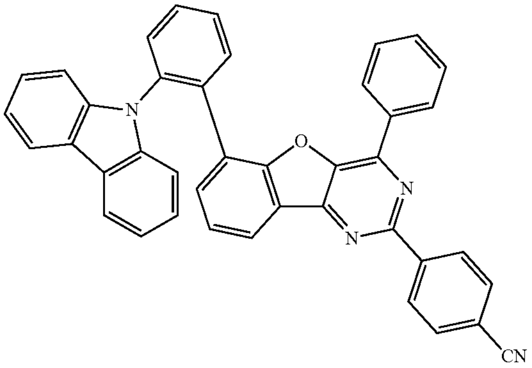
373
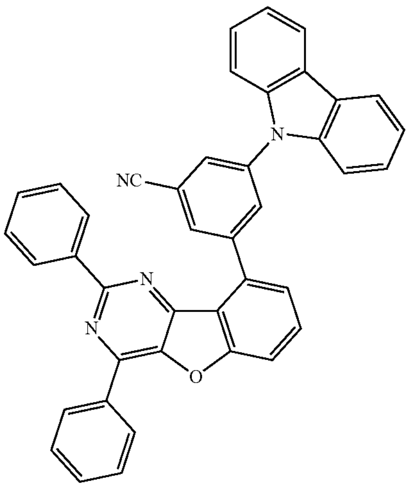
374
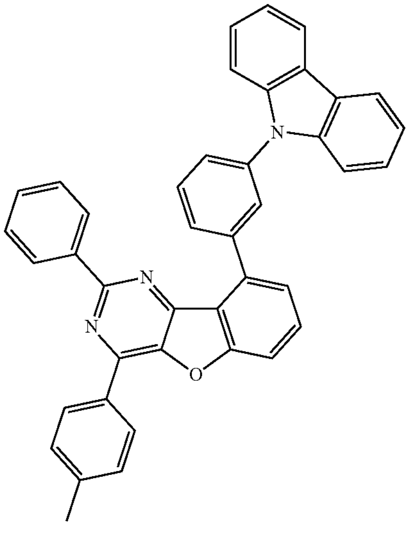
-continued
375
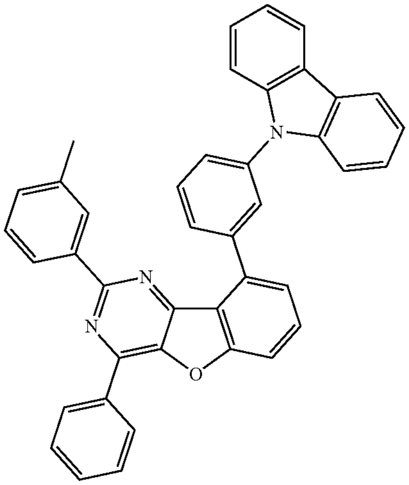
376
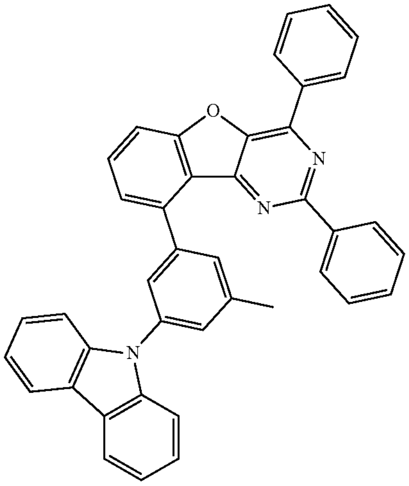
377
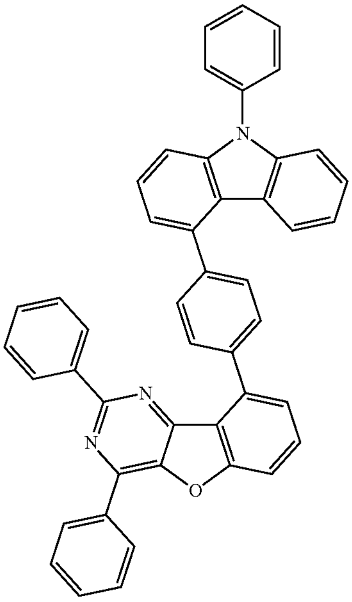

-continued
378
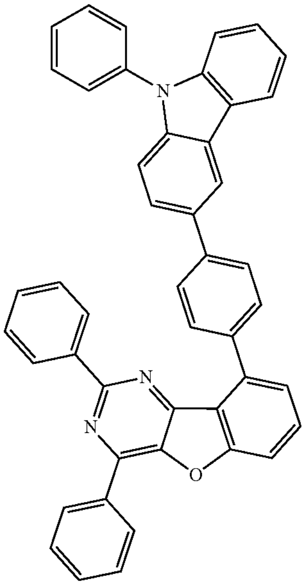
-continued
380
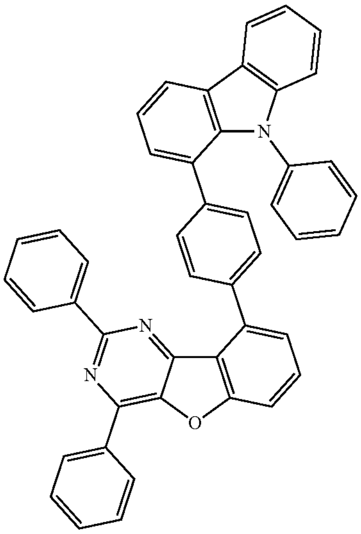
379
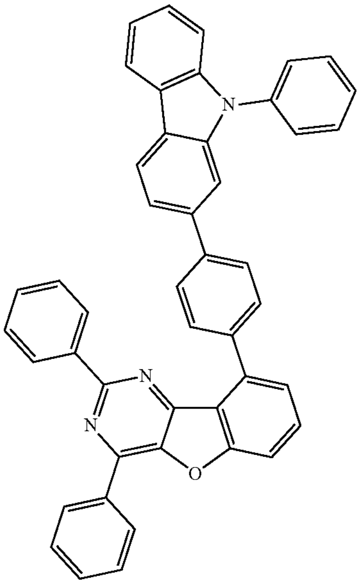
381
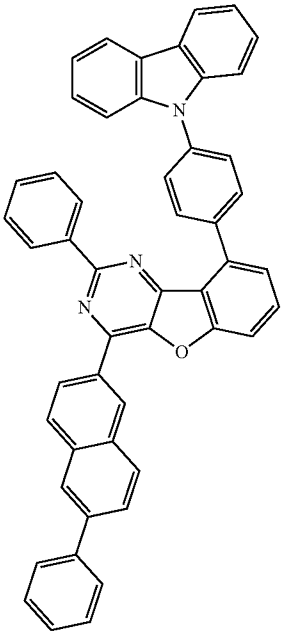

-continued

382

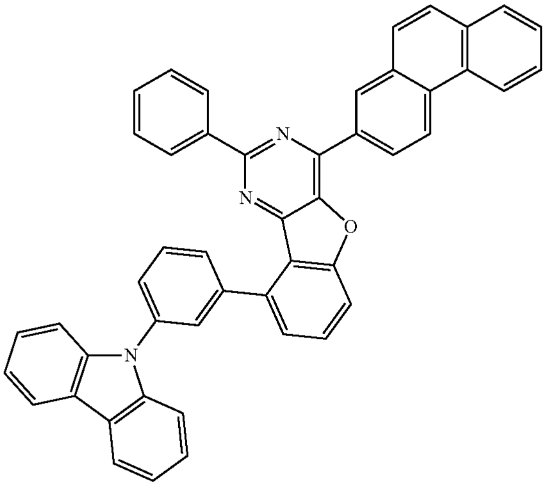

383

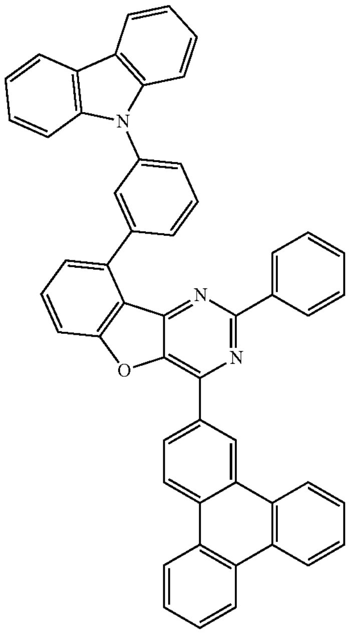

or

-continued

384

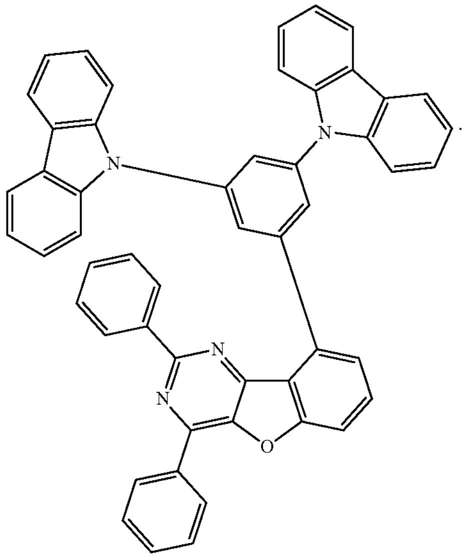

11. An organic optoelectronic device, comprising an anode and a cathode facing each other, and an organic layer disposed between the anode and the cathode, wherein the organic layer comprises the composition of claim 1.

12. The organic optoelectronic device of claim 11, wherein the organic layer further comprises a light emitting layer, and the light emitting layer includes the composition as a host.

13. A display device comprising the organic optoelectronic device of claim 11.

* * * * *